US006546074B1

(12) United States Patent
Blundell et al.

(10) Patent No.: US 6,546,074 B1
(45) Date of Patent: Apr. 8, 2003

(54) PROTEIN CRYSTAL STRUCTURE AND METHOD FOR IDENTIFYING PROTEIN MODULATORS

(75) Inventors: Tom L. Blundell, Royston (GB); Chris Abell, Cambridge (GB); Frank Von Delft, La Jolla, CA (US)

(73) Assignee: Astex Technology Limited, Cambridge (GB)

( * ) Notice: Subject to any disclaimer, the term of this patent is extended or adjusted under 35 U.S.C. 154(b) by 62 days.

(21) Appl. No.: 09/812,957

(22) Filed: Mar. 27, 2001

(51) Int. Cl.[7] ............................................. G01N 23/207
(52) U.S. Cl. ........................................ 378/73; 435/106
(58) Field of Search ..................... 378/70, 73; 435/106, 435/109, 116

(56) References Cited

U.S. PATENT DOCUMENTS

| 4,650,755 | A | * | 3/1987 | Wood et al. | .................. | 435/43 |
| 4,732,851 | A | * | 3/1988 | Wood et al. | .................. | 435/43 |
| 5,116,743 | A | * | 5/1992 | Goto et al. | ................. | 435/116 |
| 2002/0081674 | A1 | * | 6/2002 | Moeckel et al. | ............ | 435/115 |

OTHER PUBLICATIONS

Albert et al, *Nature Structural Biology*, 5, (1998), 289–293.
Bohacek et al, *Medicinal Research Reviews*, 16, (1996), 3–50.
Greer et al, *J. of Medicinal Chemistry*, 37, (1994), 1035–1054.
Jones et al in *Current Opinion in BiotechnologyCurrent Opinion in Biotechnology*, 6, (1995), 652–656.
Ramjee et al, *J. Biochem.*, 323, (1997), 661–669.
Williamson et al, *J. Biol. Chem.*, 254, (1979), 8074–8082.

* cited by examiner

*Primary Examiner*—David V. Bruce
(74) *Attorney, Agent, or Firm*—Nixon & Vanderhye P.C.

(57) ABSTRACT

A method of identifying an agent compound (such as an inhibitor) which modulates asparate decarboxylase (ADC) activity. The method comprises the steps of:
  a) providing a model of a binding cavity of ADC, said model including at least one of binding site nos. 1 and 9 defined by Table 2;
  b) providing the structure of said agent compound;
  c) fitting the candidate agent compound to said binding cavity, including determining the interactions between the candidate agent compound and at least one of binding site nos. 1 and 9; and
  d) selecting the candidate agent compound.

11 Claims, 17 Drawing Sheets

Fig. 3a L-Aspartate (Sbst)　　　　Imine Species
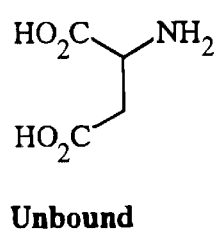
Unbound
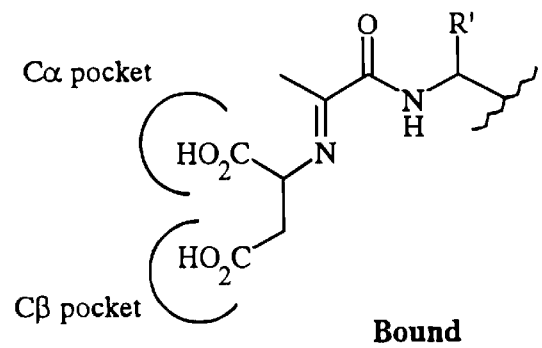
Bound
Fig. 3b β-Alanine (Prod)　　　　Imine Species
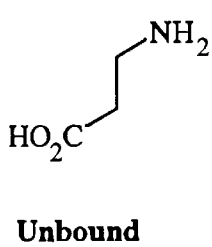
Unbound
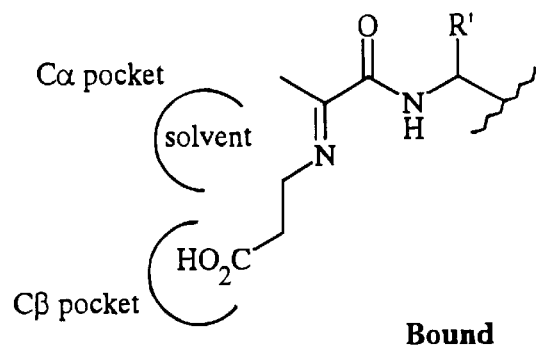
Bound
Fig. 3c Reductively Bound　　　Reduced Imine Species
β-Alanine (rβAla)
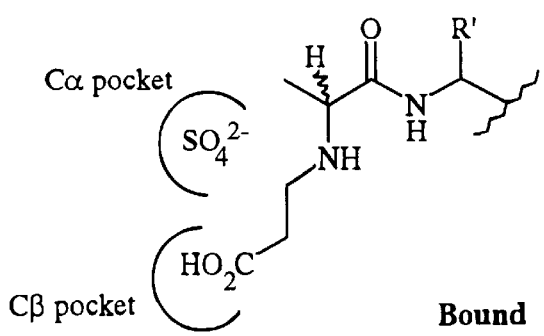
Bound

Fig. 3d α-Methyl Aspartate (MeAsp)    Imine Species
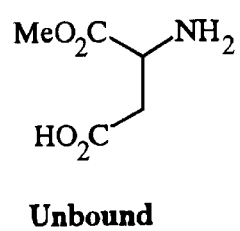
Unbound
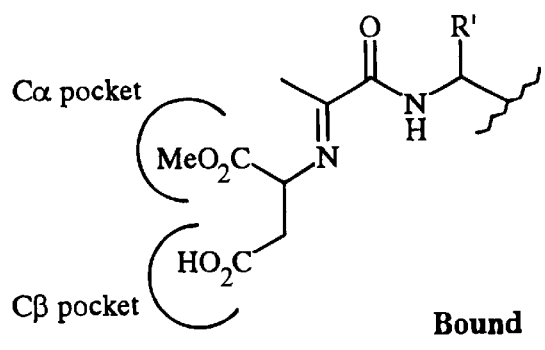
Bound
Fig. 3e β-Isopropyl-β-alanine (IsoA)    Imine Species
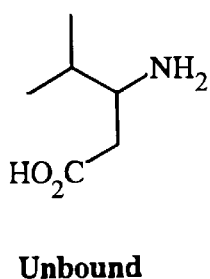
Unbound
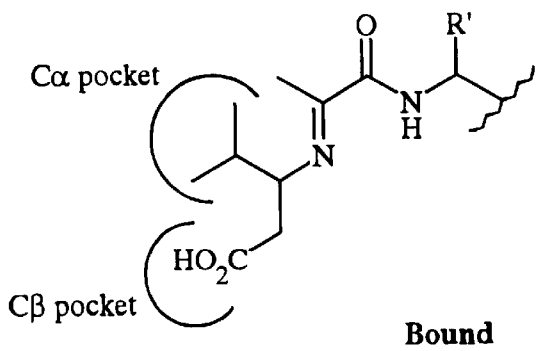
Bound

PROTEIN CRYSTAL STRUCTURE AND METHOD FOR IDENTIFYING PROTEIN MODULATORS

FIELD OF THE INVENTION

The present invention relates to the enzyme aspartate decarboxylase, and in particular the use of its crystal structure for drug discovery.

BACKGROUND OF THE INVENTION

Pantothenic acid (vitamin $B_5$) is found in coenzyme A (CoA) and the acyl carrier protein (ACP), both of which are involved in fatty acid metabolism.

Pantothenic acid can be synthesised by plants and microorganisms but animals are apparently unable to make the vitamin, and require it in their diet. However, all organisms are able to convert pantothenic acid to its metabolically active form, coenzyme A.

The pathway for the synthesis of pantothenic acid in bacteria is shown in FIG. 1. It provides a potential target for the treatment of infectious disease, since inhibitors of the pathway should be damaging to microorganisms but not to human or animal subjects infected by microorganisms.

Of specific interest is aspartate decarboxylase (L-aspartate-α-decarboxylase (EC 4.1.1.1)). This enzyme catalyses the decarboxylation of L-aspartate to β-alanine, which then goes on to form pantothenate in a condensation reaction with D-pantoate. Inhibitors (whether competitive, non-competitive, uncompetitive or irreversible) of aspartate decarboxylase (ADC) would be of significant technical and commercial interest.

ADC was first isolated from *Escherichia coli* by Williamson et al. (*J. Biol. Chem.*, 254, (1979), 8074–8082), who found indications that the protein was present in different processed states. The unprocessed enzyme is referred to as the n-chain and has 126 residues. Processing (see FIG. 2) splits the n-chain at the Gly24-Ser25 peptide bond into a larger C-terminal chain and a smaller N-terminal chain. A pyruvol group (for convenience termed Pv125) is generated from the serine residue (Ser25) at the end of the C-chain, and a carboxylate group is formed at the end of the glycine residue (Gly24) of the smaller N-terminal chain. Williamson et al. found that only a proportion of the enzyme chains were processed in this way.

Purification to homogeneity of overexpressed, recombinant ADC was achieved by Ramjee et al. (*J. Biochem.*, 323, (1997), 661–669). The purified enzyme was found to be a tetramer which, after processing, contained three processed chains and one chain which was not fully processed.

Albert et al. (*Nature Structural Biology*, 5, (1998), 289–293) used X-ray crystallography to determine the structure of ADC to 2.2 Å resolution. They showed that the enzyme studied by Ramjee et al. has pseudo-fourfold rotational symmetry, each of the four tetramer subunits (each subunit or corresponding to a n-chain labelled A, B, C or D) having a six-stranded β-barrel capped by small α-helices at each end. The binding cavities for aspartate decarboxylation are located between adjacent subunits. Three of the binding cavities have catalytic pyruvol groups resulting from respective processed n-chains. The other binding cavity has an ester which appears to be an intermediate in the processing reaction. The evidence points to an autocatalytic self-processing mechanism which did not lead to full processing of all the n-chains. The coordinates of the crystal structure determined by Albert et al. are available from the Protein Data Bank (Berman et al., *Nucleic Acids Research*, 28, (2000), 235–242) under access code 1AW8.

Albert et al. proposed a model of L-asparate binding, but did not suggest a mechanism by which ADC accomplishes aspartate decarboxylation. Until now very little was known about the enzyme's role in catalysis. This has impeded the development of ADC inhibitors via structure-based drug design methodologies. Knowledge of the mechanism would significantly assist the rational design of novel therapeutics based on ADC inhibitors.

DEFINITIONS

Specific residues are denoted herein by their conventional acronyms (e.g. Gly for glycine), and numbers corresponding to their position in the unprocessed n-chain counting from the N-terminal of the n-chain (e.g. Gly24). Moreover, because each binding cavity is formed from the residues of two n-chains, each residue is further denoted by a letter corresponding to the respective one of the n-chains (e.g. Gly24A or Lys9D). Below, we have used D and A to denote the two n-chains of a binding cavity, but in a tetramer with four equivalent binding cavities and subunits labelled A, B, C and D one could equally use A and B, B and C, or C and D instead.

In the following by "binding site" we mean a site, such as an atom or functional group of an amino acid residue, in the ADC binding cavity which may bind to an agent compound such as a candidate inhibitor. Depending on the particular molecule in the cavity, sites may exhibit attractive or repulsive binding interactions, brought about by charge, steric considerations and the like.

By "fitting", is meant determining by automatic, or semi-automatic means, interactions between one or more atoms of an agent molecule and one or more atoms or binding sites of the ADC, and determining the extent to which such interactions are stable. Various computer-based methods for fitting are described further herein.

By "fully processed" ADC we mean a composition comprising an amount of ADC in which pyruvoyl groups are generated from at least 90%, preferably at least 95%, and more preferably at least 99% of the ADC Ser25 residues.

By "root mean square deviation" we mean the square root of the arithmetic mean of the squares of the deviations from the mean.

By a "computer system" we mean the hardware means, software means and data storage means used to analyse atomic coordinate data. The minimum hardware means of the computer-based systems of the present invention comprises a central processing unit (CPU), input means, output means and data storage means. Desirably a monitor is provided to visualise structure data. The data storage means may be RAM or means for accessing computer readable media of the invention. Examples of such systems are microcomputer workstations available from Silicon Graphics Incorporated and Sun Microsystems running Unix based, Windows NT or IBM OS/2 operating systems.

By "computer readable media" we mean any media which can be read and accessed directly by a computer e.g. so that the media is suitable for use in the above-mentioned computer system. The media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

SUMMARY OF THE INVENTION

The present invention is at least partly based on overcoming several technical hurdles: we have (i) produced fully processed crystals of ADC of suitable quality for performing X-ray diffraction analyses, (ii) formed ADC-ligand complexes by soaking the crystals in appropriate soaking solutions, (iii) collected X-ray diffraction data from the ADC-ligand complexes, (iv) determined the three-dimensional structures of the complexes, (v) identified regions of ADC which undergo conformational changes upon ligand binding and decarboxylation, and (vi) determined the likely mechanism by which ADC accomplishes aspartate decarboxylation.

In general aspects, the present invention is concerned with identifying or obtaining agent compounds (especially inhibitors of ADC) for modulating ADC activity, and in preferred embodiments identifying or obtaining actual agent compounds/inhibitors. Crystal structure information presented herein as useful in designing potential inhibitors and modelling them or their potential interaction with the ADC binding cavity. Potential inhibitors may be brought into contact with ADC to test for ability to interact with the ADC binding cavity. Actual inhibitors may be identified from among potential inhibitors synthesized following design and model work performed in silico. An inhibitor identified using the present invention may be formulated into a composition, for instance a composition comprising a pharmaceutically acceptable excipient, and may be used in the manufacture of a medicament for use in a method of treatment. These and other aspects and embodiments of the present invention are discussed below.

A first aspect of the invention provides a crystal of fully processed ADC having a hexagonal space group $P6_122$, and unit cell dimensions of a=71.1 Å, and c=215.8 Å, or more generally a=71.1±0.2 Å, and c=215.8±0.2 Å.

Alternatively or additionally, the crystal has the three dimensional atomic coordinates of Table 1. An advantageous feature of the structural data according to Table 1 are that they have a high resolution of about 1.55 Å.

The coordinates of Table 1 provide a measure of atomic location in Angstroms, to a first decimal place. The coordinates are a relative set of positions that define a shape in three dimensions. It is possible that an entirely different set of coordinates having a different origin and/or axes could define a similar or identical shape. Furthermore, varying the relative atomic positions of the atoms of the structure so that the root mean square deviation of the conserved residue backbone atoms (i.e. the nitrogen-carbon-carbon backbone atoms of the protein amino acid residues) is less than 1.5 Å (preferably less than 1.0 Å and more preferably less than 0.5 Å) when superimposed on the coordinates provided in Table 1 for the conserved residue backbone atoms, will generally result in a structure which is substantially the same as the structure of Table 1 in terms of both its structural characteristics and potency for structure-based drug design of ADC inhibitors. Likewise changing the number and/or positions of the water molecules of Table 1 will not generally affect the potency of the structure for structure-based drug design of ADC inhibitors. Thus for the purposes described herein as being aspects of the present invention, it is within the scope of the invention if: the Table 1 coordinates are transposed to a different origin and/or axes; the relative atomic positions of the atoms of the structure are varied so that the root mean square deviation of conserved residue backbone atoms is less than 1.5 Å (preferably less than 1.0 Å and more preferably less than 0.5 Å) when superimposed on the coordinates provided in Table 1 for the conserved residue backbone atoms; and/or the number and/or positions of water molecules is varied. Reference herein to the coordinates of Table 1 thus includes the coordinates in which one or more individual values of the Table are varied in this way.

Also, modifications in the ADC crystal structure due to e.g. mutations, additions, substitutions, and/or deletions of amino acid residues (including the deletion of one or more tetramer subunits) could account for variations in the ADC atomic coordinates. However, atomic coordinate data of ADC modified so that a ligand that bound to one or more binding sites of ADC would also be expected to bind to the corresponding binding sites of the modified ADC are, for the purposes described herein as being aspects of the present invention, also within the scope of the invention. Reference herein to the coordinates of Table 1 thus includes the coordinates modified in this way. Preferably, the modified coordinate data define at least one ADC binding cavity.

We have been able to produce and isolate for the first time fully-processed ADC, in which the binding cavities of substantially all the ADC molecules are identical and each binding cavity has a catalytic pyruvol group. This has been made possible by the identification of conditions which allow the processing reaction to proceed to completion.

A second aspect of the invention provides a method of fully processing ADC comprising the step of forming a solution of ADC, the solution having a pH in the range 6.5–8.5 (preferably 7.0–8.0) and an ADC concentration in the range 1–50 mg/ml (preferably 4–20 mg/ml).

The method may further comprise the step of crystallising the dissolved ADC to form a crystal of fully processed ADC.

In a third aspect, the invention provides a method of testing a candidate agent compound (such as a candidate inhibitor of ADC) for ability to modulate ADC activity comprising the step of contacting the candidate agent compound with fully processed ADC (produced e.g. according to the method of the second aspect) to determine the ability of the candidate agent compound to interact with ADC.

Preferably, the candidate agent compound is contacted with ADC in the presence of L-aspartate, and typically a buffer.

By using fully processed ADC for forming ADC-ligand complexes more candidate agent compound molecules per molecule of ADC are exposed to fully processed binding cavities, thereby increasing the sensitivity of e.g. chemical assays based on such complexes.

In fourth aspect, the invention provides a method of analysing a fully processed ADC-ligand complex comprising the step of employing (i) X-ray crystallographic diffraction data from the fully processed ADC-ligand complex and (ii) a three-dimensional structure of fully processed ADC, to generate a difference Fourier electron density map of the complex, the three-dimensional structure being defined by atomic coordinate data according to Table 1.

Electron density maps can be calculated using programs such as those from the CCP4 computing package (Collaborative Computational Project 4. The-CCP4 Suite: Programs for Protein Crystallography, *Acta Crystallographica*, D50, (1994), 760–763.). For map visualisation and model building programs such as O (Jones et al., *Acta Crystallograhy*, A47, (1991), 110–119) can be used.

In a fifth aspect, the invention provides a method of identifying an agent compound (such as an inhibitor of ADC) which modulates ADC activity comprising the steps of:

a) providing a candidate agent compound;
b) forming a complex of fully processed ADC (produced e.g. according to the method of the second aspect) and the candidate agent compound; and
c) analysing said complex by X-ray crystallography (e.g. according to the method of the fourth aspect) or by NMR spectroscopy to determine the ability of said candidate agent compound to interact with ADC. Detailed structural information can then be obtained about the binding of the agent compound to ADC, and in the light of this information adjustments can be made to the structure or functionality of the agent compound, e.g. to improve binding to the binding cavity. Steps b) and c) may be repeated and re-repeated as necessary. For X-ray crystallographic analysis, the complex may be formed by crystal soaking or co-crystallisation.

Therefore, compared to partially processed ADC, X-ray crystallographic data from the binding cavities of fully processed ADC-ligand complexes can be interpreted more easily because all the binding cavities are identical. That is, the data are not complicated by reflections from binding sites containing esters instead of pyruvol groups. Likewise the interpretation of NMR spectra is simplified.

In a sixth aspect, the present invention provides a method of identifying an agent compound (such as an inhibitor of ADC) which modulates ADC activity, comprising the steps of:

a) providing a model of a binding cavity of ADC, said model including at least one (and preferably both) of binding site nos. 1 and 9 defined by Table 2;
b) providing the structure of a candidate agent compound;
c) fitting the candidate agent compound to said binding cavity, including determining the interactions between the candidate agent compound and at least one (and preferably both) of binding site nos. 1 and 9; and
d) selecting the fitted candidate agent compound.

Without wishing to be held to any particular theory, we believe that, in the appropriate context (e.g. in the complexes described below in the "Detailed Description of the Invention"), one or more of the binding sites of Table 2 provides the corresponding binding interaction of Table 2 to an agent compound. However, the binding interactions of Table 2 are not intended to be exhaustive, and it is within the scope of this aspect of the invention that any of the binding sites may exhibit an interaction which is not listed in Table 2.

Varying the relative positions of the binding sites of Table 2 by relatively small amounts generally results in arrangements of binding sites which are substantially identical to the arrangement of Table 2 in terms of expected interactions with the agent compound. Consequently, the scope of this aspect of the invention includes a binding cavity in which the root mean square deviation of the conserved residue backbone atoms of the residues of column 2 of Table 2 is less than 1.5 Å (preferably less than 1.0 Å and more preferably less than 0.5 Å) when superimposed on the coordinates provided in Table 1 for the conserved residue backbone atoms of the residues of column 2 of Table 2.

The smaller N-terminal β-chain has a tail (hereafter called Tail24A) formed when the n-chain cleaves at the Gly24-Ser25 peptide bond and consisting of the four residues His2A, Tyr22A, Glu23A, and Gly24A (as discussed above, Gly24A having a carboxylate end group). We have found that Tail24A shifts between an "open" and a "closed" position via a "half-closed" position (which we call the O-state, C-state and H-state respectively) during aspartate decarboxylation. In the C-state Tail24A obstructs the binding cavity, while the O-state allows access thereto. These states are characterised by increased disorder in the measured position of Tail24A as it shifts from the C-state to the O-state.

Binding site no. 1 is associated with the hydrophobic phenyl ring of Tyr22A which in turn belongs to Tail24A. Hence binding site no. 1 is closely involved with the C-, H- and O-states of Tail24.

The $NH_3^+$ group (binding site no. 9) of the Lys9D side chain is a potential hydrogen bond donor when Tail24A is in the O- and H-states. However, we have found that in the C-state the Gly24A carboxylate end group forms a salt bridge or hydrogen bond with the $NH_3^+$ group of the Lys9D side chain. This prevents the $NH_3^+$ group from being a potential hydrogen bond donor to the agent compound in the C-state.

The modelling may include generating the cavity (and optionally the agent compound) on a computer screen for visual inspection.

In practice, it is desirable to model a sufficient number of atoms of the ADC as defined by the coordinates of Table 1. Thus, in this aspect of the invention, there will preferably be provided the coordinates of at least 5, preferably at least 10, more preferably at least 50 and even more preferably at least 100 atoms of the ADC structure.

Preferred candidate agent compounds bind with at least two, three, four, five, six or seven of the binding sites defined by Table 2. In general, the agent compound binds better as the strength and number of binding interactions increases. The candidate agent compound may have a molecular weight of up to about 600.

Binding interactions may be mediated by e.g. water or other solvent molecules.

Candidate inhibitors identified according to the method are characterised by their suitability for binding to a particular binding site or sites. The binding cavity can therefore be regarded as a type of binding site framework or negative template with which the candidate inhibitors correlate in the manner described above.

More specifically, a potential modulator of ADC activity can be examined through the use of computer modelling using a docking program such as GRAM, DOCK, or AUTODOCK (see Walters et al., *Drug Discovery Today*, Vol.3, No.4, (1998), 160–178, and Dunbrack et al., *Folding and Design*, 2, (1997), 27–42) to identify candidate inhibitors of ADC. This procedure can include computer fitting of candidate inhibitors to ADC to ascertain how well the shape and the chemical structure of the candidate inhibitor will bind to the enzyme.

Computer programs can be employed to estimate the interactions between the ADC and the agent compound. The more specificity in the design of a candidate drug, the more likely it is that the drug will not interact with other proteins as well. This will tend to minimise side-effects due to unwanted interactions with other proteins.

Alternatively, step b) of the method may involve selecting the candidate agent compound by computationally screening a database of compounds for interaction with the binding cavity. For example, the model resulting from step a) may be used to interrogate the compound database, a candidate inhibitor being a compound that has a good match to the features of the model. In effect, the model is a type of virtual pharmacophore.

If one or more additional ADC binding cavities are characterised and a plurality of respective compounds are designed or selected, the candidate inhibitor may be formed by linking the respective compounds into a larger compound which maintains the relative positions and orientations of the respective compounds at the binding cavities. The larger compound may be formed as a real molecule or by computer modelling.

Having determined possible binding partners, these can then be obtained or synthesised and screened for activity. Consequently, the method preferably comprises the further step of:

e) contacting the candidate agent compound with ADC to determine the ability of the candidate agent compound to interact with ADC.

Preferably, in step e) the candidate agent compound is contacted with ADC in the presence of L-aspartate, and typically a buffer.

Instead of, or in addition to, performing a chemical assay, the method may comprise the further steps of:

e) forming a complex of ADC and said candidate agent compound; and f) analysing said complex by X-ray crystallography (e.g. according to the method of the fourth aspect) or by NMR spectroscopy to determine the ability of said candidate agent compound to interact with ADC. Detailed structural information can then be obtained about the binding of the candidate agent compound to ADC, and in the light of this information adjustments can be made to the structure or functionality of the candidate agent compound, e.g. to improve binding to the binding cavity. Steps e) and f) may then be repeated and re-repeated as necessary. For X-ray crystallographic analysis, the complex may be formed by crystal soaking or co-crystallisation.

In another aspect, the invention includes a compound which is identified as an agent compound (such as an inhibitor of ADC) for modulating ADC activity by the method of one the previous aspects.

Following identification of an agent compound it may be manufactured and/or used in preparation, i.e. manufacture or formulation, of a composition such as a medicament, pharmaceutical composition or drug. These may be administered to individuals.

Thus, the present invention extends in various aspects not only to an agent compound as provided by the invention, but also a pharmaceutical composition, medicament, drug or other composition comprising such an agent compound e.g. for treatment (which may include preventative treatment) of a disease such as a microbial infection; a method comprising administration of such a composition to a patient, e.g. for treatment of a disease such as a microbial infection; use of such an agent compound in the manufacture of a composition for administration, e.g. for treatment of a disease such as a microbial infection; and a method of making a pharmaceutical composition comprising admixing such an agent compound with a pharmaceutically acceptable excipient, vehicle or carrier, and optionally other ingredients.

In another aspect, the present invention provides a system, particularly a computer system, intended to generate structures and/or perform rational drug design for ADC or ADC ligand complexes, the system containing either (a) atomic coordinate data according to Table 1, said data defining the three-dimensional structure of fully-processed ADC, or (b) structure factor data for fully-processed ADC, said structure factor data being derivable from the atomic coordinate data of Table 1.

In a further aspect, the present invention provides computer readable media with either (a) atomic coordinate data according to Table 1 recorded thereon, said data defining the three-dimensional structure of fully-processed ADC, or (b) structure factor data for fully-processed ADC recorded thereon, the structure factor data being derivable from the atomic coordinate data of Table 1.

By providing such computer readable media, the atomic coordinate data can be routinely accessed to model fully-processed ADC. For example, RASMOL (Sayle et al., *Trends in Biochemical Sciences*, Vol. 20, (1995), 374) is a publicly available computer software package which allows access and analysis of atomic coordinate data for structure determination and/or rational drug design.

On the other hand, structure factor data, which are derivable from atomic coordinate data (see e.g. Blundell et al., *Protein Crystallography*, Academic Press, New York, London and San Francisco, (1976)), are particularly useful for calculating e.g. difference Fourier electron density maps.

BRIEF DESCRIPTION OF THE DRAWINGS

FIGS. 3a to e show the respective structures of ADC ligands and also show how the ligands interact with three significant functional regions of the ADC binding cavity, i.e. the $C_\alpha$ and $C_\beta$ pockets and the Pv125A/imine species: the $C_\alpha$ and $C_\beta$ pockets are shown schematically, whereas the Pv125A/imine species is given in chemical notation.

in FIG. 6a the ligand is α-methyl aspartate and Tail24A is in the C-state, in FIG. 6b the ligand is L-aspartate and Tail24A is in the H-state, and in FIG. 6c the ligand is reductively bound β-alanine and Tail24A is in the O-state. Also shown in wire-frame in FIG. 6b is an observed negative difference density which appears over the ligand atoms after refinement of the complete structure and which was modelled as three water molecules. The prominent wire-frame density in FIG. 6c between the ligand and Gly24A was modelled as sulphate.

DETAILED DESCRIPTION OF THE INVENTION

The present invention is founded at least partly on the production of fully processed ADC, the characterisation of the ADC binding cavity and the determination of a likely mechanism for aspartate decarboxylation.

In order to determine this mechanism and the binding site interactions the structures of several ADC-ligand complexes were solved. The ligands which were studied were: L-aspartate (hereinafter referred to as Sbst), β-alanine (Prod), reductively bound β-alanine (rβAla), α-methyl aspartate (MeAsp), 3-amino-4-methylpentanoic acid (i.e. β-isopropyl-β-alanine, isoA). The structures of the respective ligands are shown in FIGS. 3a to e. The structure of the uncomplexed protein (Nat) was also solved under identical conditions to those used for the ligand complexes, to enable better structural comparison with the complexes.

Figure 1:
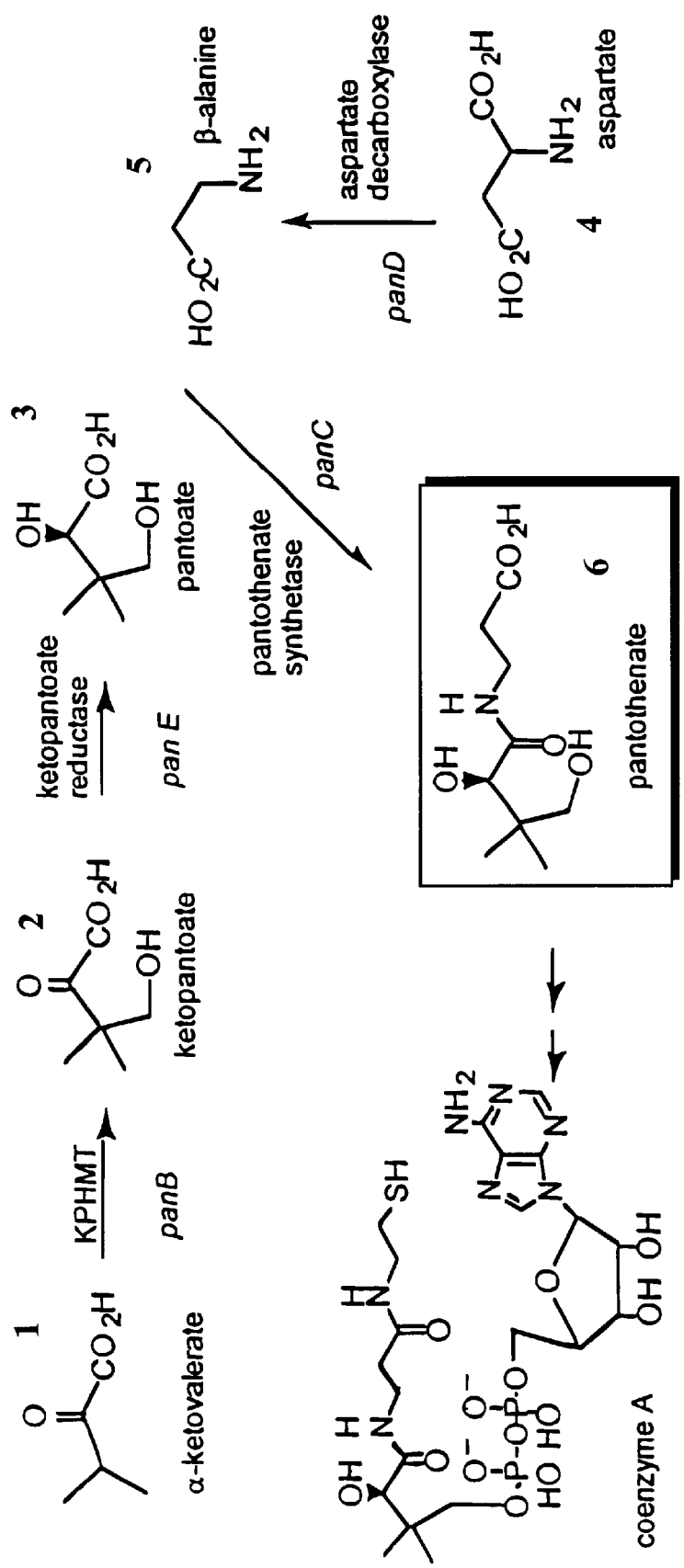
FIG. 1 shows schematically the pathway for the biosynthesis of pantothenic acid.
Figure 2:
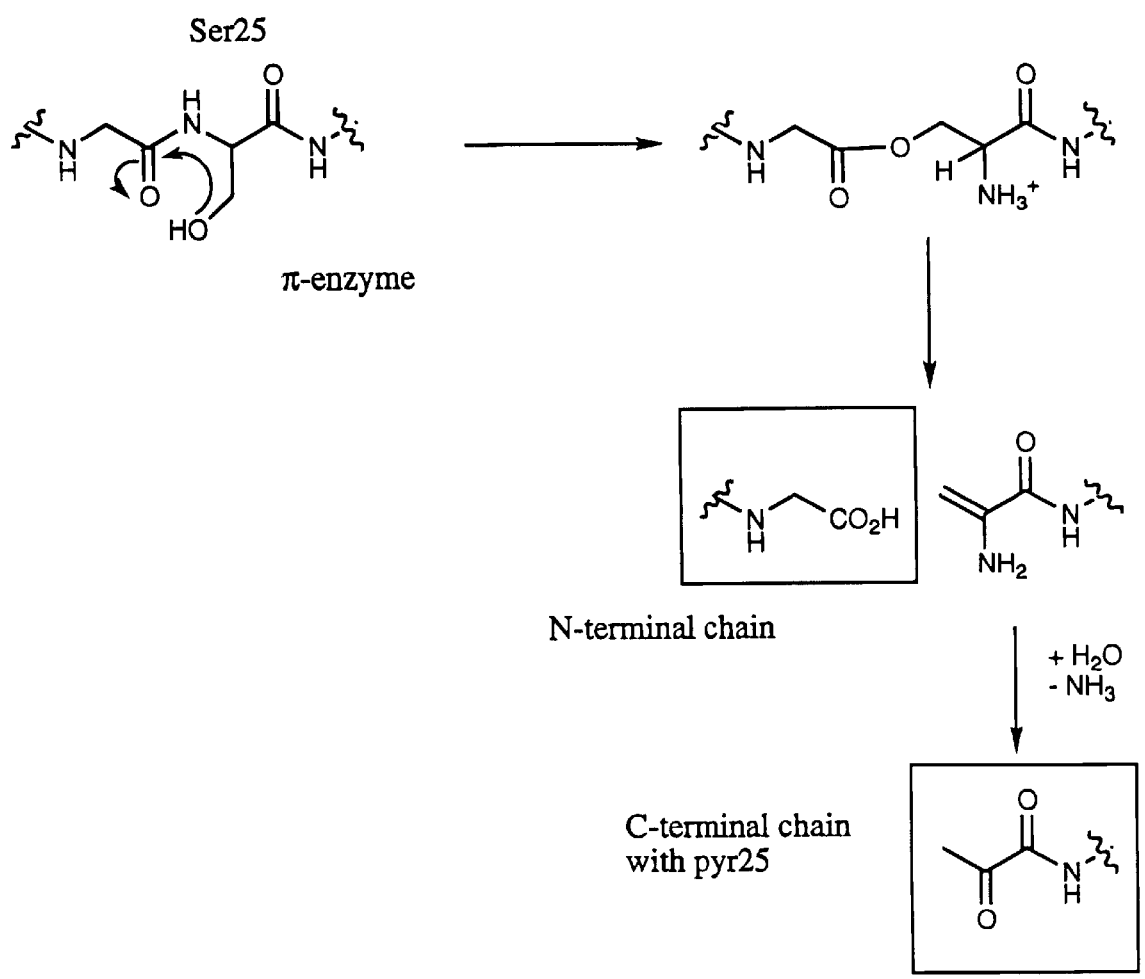
FIG. 2 shows schematically the mechanism for the processing of ADC.
Figure 4:
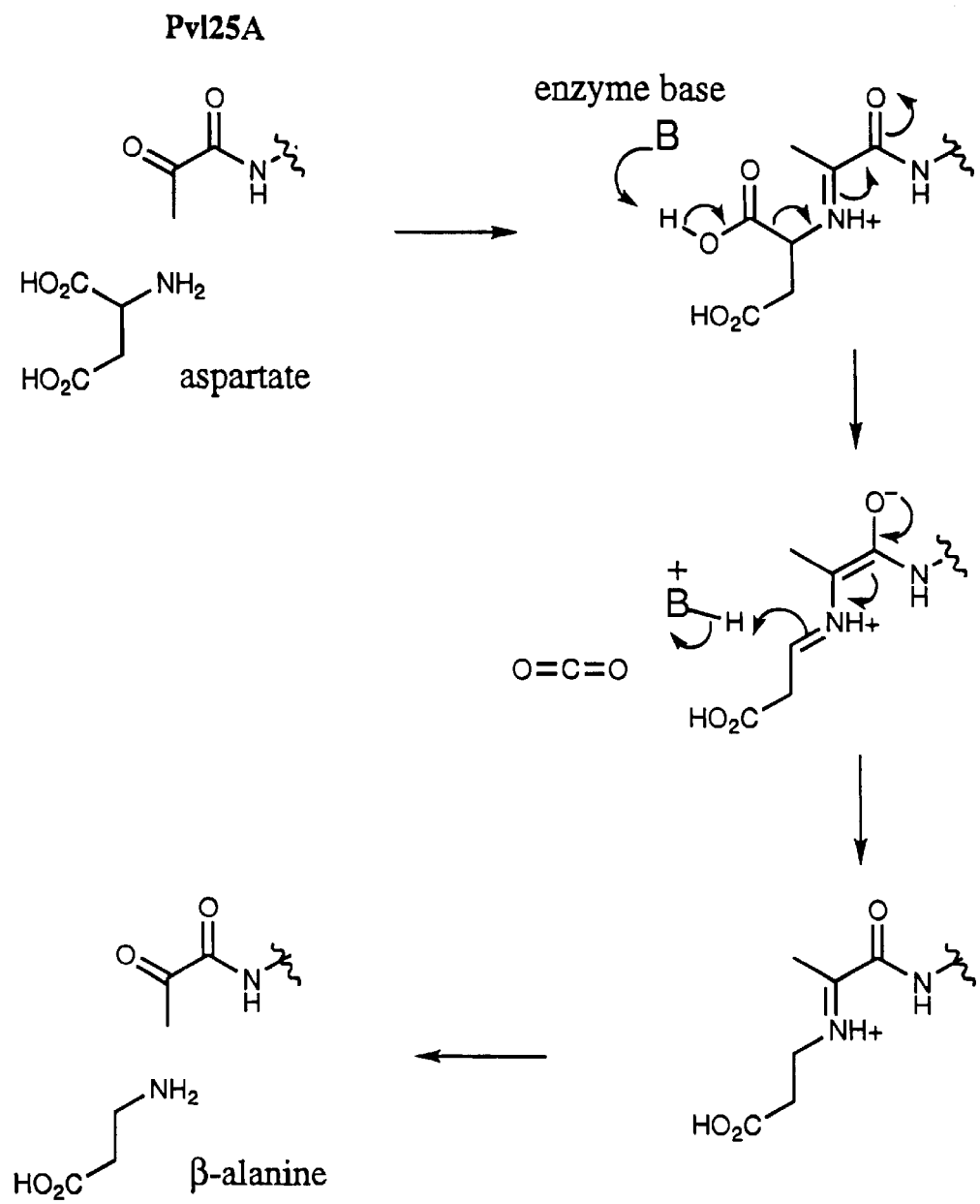
FIG. 4 shows the previously proposed (Ramjee et al.) catalytic mechanism of ADC.

We have found that elements of the model of aspartate binding originally proposed by Albert et al. are correct: Sbst $βCO_2$ (i.e. the L-aspartate carboxylate group furthest from the amine group, $αCO_2$ being the other L-aspartate carboxylate group) is in a well-defined pocket and forms a salt-bridge with the guanidyl group of Arg54D, the salt-bridge being stacked over the aromatic ring of Trp47D; Sbst $αCO_2$ is situated in another well-defined pocket; while an imine bond formed from the Sbst amine group and the Pv125A ketone closest to the split in the n-chain group results in an imine-amide intermediate. FIG. 4, which shows the previously proposed (Ramjee et al.) catalytic mechanism, illustrates the imine-amide intermediate. Three significant functional regions of the binding cavity may be identified: (i) Pv125A which is needed to form the imine species, (ii) a binding pocket for Sbst $βCO_2$, and (iii) a binding pocket for Sbst $αCO_2$. These regions are illustrated in FIGS. 4a to f which also show schematically how the ligands interact with these regions.

However, contrary to expectation, the $βCO_2$-guanidyl salt bridge is significantly non-planar, although an approximate plane may be constructed (RMS deviation between 0.16 and 0.23 Å). Also, although the atoms of the imine species in the four complexes formed respectively from MeAsp, IsoA, Prod and Sbst are nearly planar (the RMS deviation is between 0.02 and 0.06 Å), even this species does not appear completely planar, but has a slight rotational deviation (175–178°) around the imine-amide C—C bond (i.e. what was previously the pyruvoyl inter-oxygen C—C bond).

A significant advance over the model proposed by Albert et al. relates to the residues of Tail24A. Not only have we been able to determine the positions of these residues (except for Glu23A which was disordered in all the structures we studied as well as in the structure reported by Albert et al.) for Nat and the various ADC-ligand complexes, but we have determined the crucial role Tail24A plays in aspartate decarboxylation.

Solving the Crystal Structures
1. Abbreviations

IPTG, isopropyl-β-D-thioglactopyranoside; SeMet, L-selenomethionine; DTT, dithaiothreitol; ATP, adenosine triphosphate; PMSF, phenylmethylsulphonyl fluoride; HEPES, N-2-hydroxyethylpiperazine N'-2-ethanesulphonic acid; $PEG_{400/4000/8000}$, polyethylene glycol average MW 400/4000/8000; MPD, 2-methyl-2,4-pentanediol.

2. Materials and Methods

All the compounds used were obtained from Sigma, P.O.Box 14508 St. Louis, Mo. 63178, USA, with the following exceptions. Liquid and solid LB medium, Yeast Extract, Bactotryptone, Agar and the DIFCO Amino Acid Assay Medium were obtained from DIFCO Laboratories, Detroit, Mich. 48232–7058, USA. IPTG, HEPES and DTT were obtained from Melford Laboratories Ltd., Chelsworth, Suffolk IP7 7LE, UK. $PEG_{4000}$, $PEG_{9000}$, and MPD were purchased from Fluka Chemie AG, Messerschmidt Strasse 17, D-89231, Neu-Ulm, Germany. Ethanol and ethylene glycol were obtained from Fischer Scientific UK Ltd., LE11 5RG, UK. 3-Amino-4-methyl-pentanoic acid was obtained from ACROS, N.J., USA. α-methyl aspartate was synthesised in-house. All chromatography matrices were obtained from Pharmacia Biotech (now Amersham Pharmacia Biotech), Uppsala, Sweden.

Chromatography at 4° C. was performed using a Pharmacia FPLC system. At 37° C. the Pharmacia Äkta Explorer system was used. Concentrators were either (for volumes below 4 ml) Ultrafree™ centrifugal concentrators from Millipore Corporation, Bedford, Mass. 01730, USA; or (for larger volumes) the Amicon™ Ultrafiltration Cell, manufactured by Amicon Inc., Beverley, Mass. 01915, USA. Linbro™ plates were obtained from ICN Biomedicals Inc., 1263 South Chillicothe Rd., Aurora, Ohio, 44202. Qplate II™ and CrystalCap™ accessories were supplied by Hampton Research, 27632 El Lazo Road, Suite 100, Laguna Niguel, Calif. 92677–3913, USA.

To prepare the ADC, a glycerol stock of *E. coli* SJ16::pDKS1 (Ramjee et al.) was used to seed 1l of Terrific Broth containing 60 mg/ml ampicillin and 80 mg/ml IPTG. Growth was continued for 16 hours and approximately 6 g of stationary phase cells were harvested by centrifugation at 4000 g for 15 minutes, resuspended in 15 ml of buffer containing 10 mM Tris pH 8.0 and lysed by two passages through a French Press.

The crude lysate was centrifuged at 10 000 g for 30 minutes and filtered using 0.22 micrometer nitrocellulose before loading at 1 ml/min onto a Q-Sepharose Fast Flow column (Pharmacia 17–0510–01, 10×2 cm diameter, 30 ml matrix volume). The column was washed with 25 ml of 10 mM Tris pH 8.0. Protein was eluted using the same buffer with a zero to 1 M gradient of KCl and 2.5 ml fractions collected.

Fractions containing ADC were identified using Tricine SDS-PAGE (Schagger et al., *Analytical Biochemistry*, 166, (1987), 368–379), pooled and dialysed for 16 hours and 2 hours in 5 l of buffer containing 10 mM Tris pH 6.8. Pooled fractions were loaded onto a hydroxyapatite column (5 g Bio Rad HTP Hydroxyapatite No. 130–0420, in a 2.5×3.6 cm matrix volume) and eluted with a gradient of 10 to 500 mM $KH_2PO_4$ pH 7.0. Fractions containing ADC were identified using SDS-PAGE as before, pooled, and concentrated by ultrafiltration (Amicon centriprep 10 concentrators repeatedly centrifuged at 3000 g for 20 min) to approximately 10 mg/ml purified ADC. Approximately 5 mg ADC was obtained per gram of cells.

The ADC was stored at 4° C. for several weeks during which time autocatalytic processing occurred to form fully processed ADC with four binding site pyruvoyl groups per tetramer.

3. Protein Crystallisation

The protein was transferred to 25 mM HEPES buffer at pH 7.5 by repeated dilution and concentration using an Ultrafree™ filter. The final protein concentration was between 6 and 10 mg/ml, as judged by its theoretical extinction coefficient $e_{280}$=1.09 ml/mg (see Gill et al., *Analytical Biochemistry*, 182, (1989), 319–326). The crystallising solution was unbuffered $(NH_4)_2SO_4$ at concentrations of between 1.6 and 2.4 M. Equal volumes of protein and crystallisation solutions (2–10 ml) were placed on siliconised cover slides and sealed in wells containing the crystallisation solution (1 ml), in Linbro™ or Qplate II™ plates for vapour diffusion crystallisation as hanging or sitting drops respectively (as described by Sawyer et al., in *Crystallization of Nucleic Acids and Proteins*, ed. Ducroix and Giege, 225–289, John Wiley & Sons, New York, 1992). The protein crystallised both at 4 and 19° C., although the volume ratio of crystallisation to protein solution needed changing to 2:1 when at 4° C. Crystals formed within 1–7 days, depending on temperature and component concentrations. Typical crystals were clear hexagonal pyramids, but frequently grew on a surface so that the pyramid was only half formed. Crystals as long as 0.6 mm were grown. Growth in sitting drops or alternatively at 4° C. yielded the largest crystals.

The condition used here differed substantially from those used by Albert et al., where $PEG_{4000}$ was used with acetate buffer at pH 4.8. The pH of the HEPES buffer protein solution and the protein concentration was apparently significant in enabling the crystallisation of fully processed ADC in the present method.

4. Preparation of Crystals of ADC-Ligand Complexes

Six different ligands were used for ADC-ligand complexes.

The crystals of ADC were robust and appeared to withstand high solution concentrations of the ligands.

Sbst: Protein crystals were transferred to a crystallisation solution (1.9 M $(NH_4)_2SO_4$) containing 0.5 M Sbst. The solution was buffered to pH 4.5 with 50 mM NaAcetate. The soaking time was 10 minutes prior to mounting.

Prod: Protein crystals were transferred to a crystallisation solution (1.9 M $(NH_4)_2SO_4$) containing 0.5 M Prod. The soaking time was 10 minutes prior to mounting.

rβAla: Prod was reductively bound to ADC in solution using $NaCNBH_3$, using the method described by Ramjee et al., but substituting β-alanine for L-aspartate. The adduct was concentrated and crystallised as for the native protein.

MeAsp, isoA: These compounds were added in solid form to separate drops containing crystals of ADC, and left for 10–20 minutes before mounting.

The Nat and complex crystals were placed in crystallisation solution containing 25% glycerol for between 10–300 seconds. Each crystal was then scooped up in a cryoloop smaller than the crystal using the CrystalCap™ system (Hampton Research) Within 3 seconds the crystal was either plunged into liquid nitrogen, or flash-cooled in a stream of nitrogen gas at 100 K, and kept at low temperature (<110 K) until after data collection.

5. Data Collection

All the ligand-complex data were collected with a Raxis IV detector using copper $K_\alpha$ radiation from a Rigaku rotating anode generator, with crystals cooled to 100 K. The native dataset was collected on Station 9.6 at the Daresbury Laboratory Synchrotron Radiation Source with an ADSC Quantum 4 detector. Reflections were integrated with either DENZO (Otwinwski et al., Processing of X-ray diffraction data collected in oscillation mode, in *Methods in Enzymology*, Vol. 276, ed. Carter and Sweet, Academic Press, 1997) or MOSFLM (Leslie, *Joint CCP4 and EESF-EACMB Newsletter on Protein Crystallography*, Vol.26, Daresbury Laboratory, UK); data were scaled and merged using either SCALEPACK (Otwinwski et al.) or SCALA (Collaborative Computational Project 4—CCP4. The CCP4 Suite: Programs for Protein Crystallography, *Acta Crystallographica*, D50, (1994), 760–763); and intensities were converted to amplitudes using TRUNCATE (CCP4). Data quality statistics are given in Table 3.

During data collections from MeAsp, rβAla, Prod, and Sbst, the 2θ-angle (Table 3) needed changing from the standard 0° setting to enable recording of the high angle data on the 30 cm detector surface while allowing a crystal-detector separation where reflections did not overlap due to the long crystallographic c-axis, high mosaicity, and large beam divergence of the home X-ray source. In spite of the high symmetry of the reciprocal lattice (6/mmm), such a detector setting required the collection of oscillation data from at least two crystal orientations to enable acceptable (but even then not complete) coverage of reciprocal space. The data for Sbst were the least complete due to premature crystal destruction.

6. Refinement and Model Building

Refinement was performed similarly for all crystal structures. The crystallographic cell parameters agreed closely with those of the published structure of Albert et al., which was therefore intially used directly in the refinement, thereby avoiding an explicit molecular replacement search. The MeAsp structure was solved relatively early in this way and for some of the later complexes the MeAsp structure was used as the starting model. Tail24A and Pv125A were excluded from the initial rigid-body refinement and 12 cycles of restrained isotropic refinement with REFMAC (Murshudov et al., *Acta Crystallographica*, D53, (1997), 24–255). Using map coefficients generated by REFMAC, $\sigma_A$-weighted (Read, *Acta Crystallographica*, A42, (1986), 140–149) $2mF_o-DF_c$ and difference maps were calculated and manipulated using CCP4 and Uppsala Software Factory (G. J. Kleywegt, Dept. of Cell and Molecular Biology, Uppsala University, Biomedical Centre, Box 596, SE-75124 Uppsala, Sweden) programs, and examined in O (Jones et al., *Acta Crystallography*, A47, (1991), 110–119), which was used for all model rebuilding. The ligand species were built into the clearly identifiable difference density, and errors corrected in the rest of the model. At this stage the residues of Tail24A were only built, where possible, after a further round of refinement, and ordered solvent molecules were automatically added by alternating cycles of ARP (Perrakis et al., *Acta Crystallographica*, D55, (1999), 1765–1770) and REFMAC until convergence of the $R_{free}$ model-data residual (Brunger et al., *Acta Crystallographica*, D54, (1992), 905–921).

For each model, omit maps for Tail24A were recalculated using the program BUSTER (Bricogne, *Methods in Enzymology*, 276, (1993), 361–423) in its implementation with TNT (Tronrud, *Methods in Enzymology*, 277, (1997), 306–319). The refined structure from REFMAC, with Tail24A omitted along with any solvent molecules in the area, was briefly re-refined with optimised bulk solvent parameters, followed by Maximum Entropy partial structure completion and calculation of $\sigma_A$-weighted $mF_o-DF_c$ difference maps. Tail24A was modelled into all structures (in the absence of good density then by comparison with well-ordered structures) and refined to convergence with BUSTER/TNT. The refinement convergence and some model quality indicators are summarised in Table 4.

The standard Engh & Huber (Engh et al., *Acta Crystallographica*, A47, (1991) 392–400) parameters were used as geometric restraints for the ligands, where available. All structures, apart from the rβAla and MeSuc complexes and Nat, were defined to contain a planar imine-amide species, which is not represented in those parameters, and the relevant bond-lengths and angles were taken from the Cambridge Structural Database (CSD, Allen et al., *J. of Chemical Information and Computer Sciences*, 31, (1991), 187–204). The pyruvoyl in Nat was modelled in the cis conformation.

The different models agreed closely (between 0.1 and 0.2 Å RMS deviation over all $C_\alpha$-atoms), with differences limited to the binding cavity. The various soaked ligands did bind and were clearly visible.

Structural Characterisation

1. Nat

Tail24A residues were very well ordered, along with a solvent molecule between Tyr22A and Pv125A. There was a prominent density of uncertain origin deeper in the binding cavity in the substrate $\beta CO_2$ pocket between Pv125A and Arg54D. It was modelled as solvent. Table 1 provides the atomic coordinates of the Nat structure.

Unlike the partially processed enzyme (which only has a pseudo-fourfold rotation axis and at most three binding cavities), the fully processed ADC tetramer has a crystallographic fourfold rotation axis and four binding cavities. This significantly simplifies the analysis of X-ray experiments (e.g. for the determination of the structures of the complexes discussed below), the higher symmetry of the fully processed tetramer facilitating the interpretation of diffraction data and the additional binding cavity increasing the intensity of reflections from binding cavities.

Figure 5A:
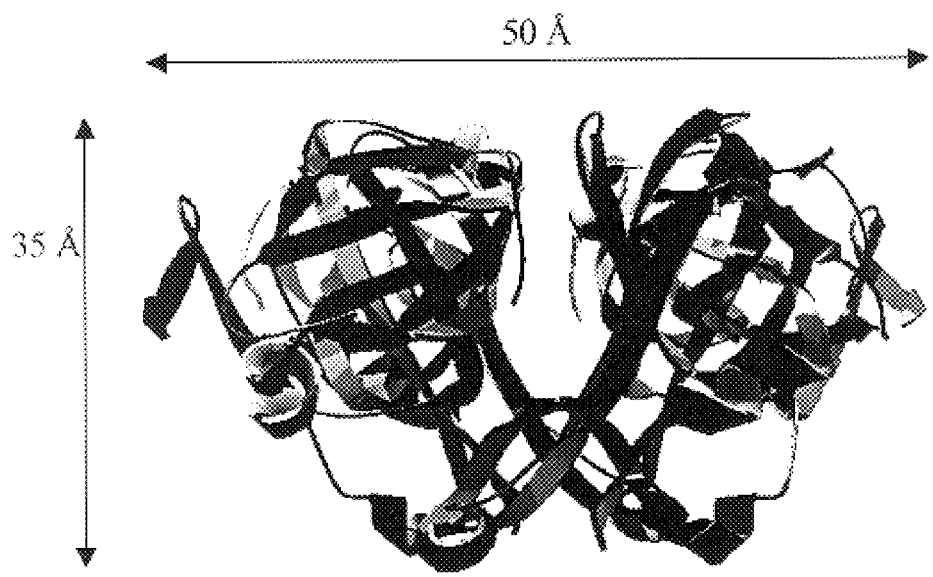
FIGS. 5a and b show respectively ribbon representations of fully processed ADC tetramer viewed perpendicularly to and along its fourfold axis.
Figure 5B:
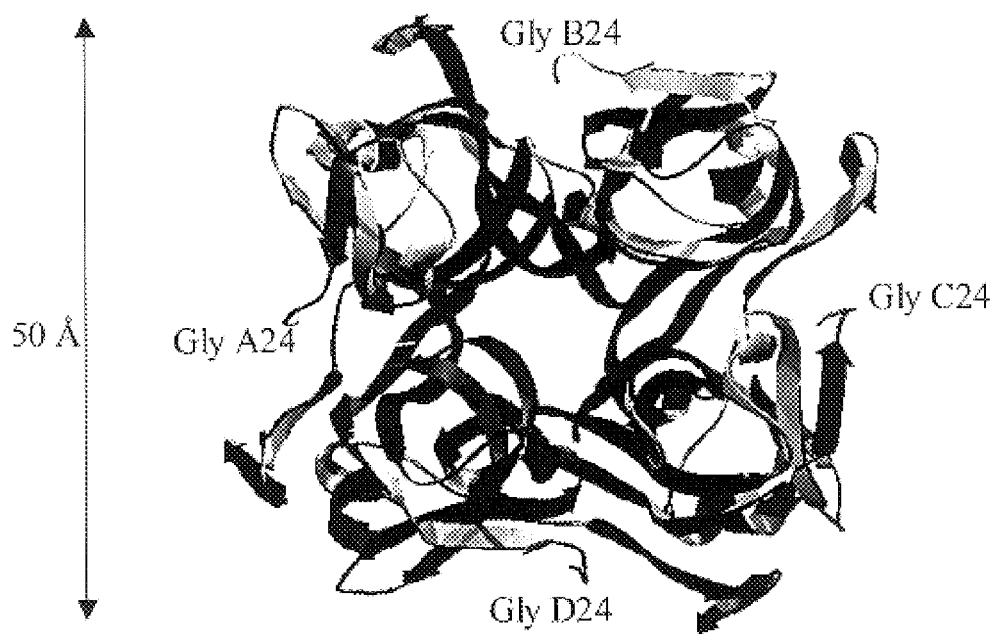

A ribbon representation of the fully processed tetramer is shown viewed perpendicularly to the four-fold axis in FIG. 5a and along the fourfold axis in FIG. 5b.

2. MeAsp, IsoA, Prod

These complexes had the cleanest density. The ligand positions were evident, and Tail24A was very well ordered, with no spurious density peaks. In Prod, there was a solvent molecule between Tyr22A and the Pv125A/ligand adduct, in the same position as the $\alpha CO_2 Me$ and isopropyl groups of MeAsp and IsoA. This position corresponds to the substrate $\alpha CO_2$ pocket.

3. r$\beta$Ala

The reduced $\beta$-alanine was located with ease, however Tail24A appeared more disordered. Only His21A and Tyr22A were defined, but by very weak densities. In the substrate $\alpha CO_2$ pocket there was a very prominent difference density feature. There is a significant likelihood that it is due to a sulphate ion—a crystallisation precipitant which has bound in this site. Sulphate matched the density reasonably well, and (at occupancy =0.5) refined to B-factors of around 47 and 37 $\text{Å}^2$ in the respective A and D subunits, which compared favourably with some of the less well-ordered parts of the structure. The two negative sulphate charges would be accommodated by $N_{ZLys9D}$ and the reduced nitrogen of the ligand ($N_{Lig}$), both of would be protonated and positive at the pH of crystallisation. The absence of such a sulphate in Prod may be explained by the different orientation of $N_{Lig}$, which in r$\beta$Ala, points towards the putative sulphate, but in Prod towards the Asn72A mainchain.

4. Sbst

Contrary to the other complexes, two crystallographically unique conformations, Y and Z, of ADC were observed in the asymmetric unit (with respect to the respective tetramer n-chains, conformation Y was observed in binding cavities D/A and B/C, and conformation Z in cavities A/B and C/D). These two conformations showed distinct differences in their respective binding cavities and appeared to correspond to different stages of decarboxylation. The difference densities for the ligands showed that neither conformation was as well ordered as ADC in the complexes with the other ligands. In both conformations there were breaks in the observed electron densities, but this may be a crystallographic artifact caused by incompleteness of the Sbst dataset. Of course, in view of the fact that Sbst undergoes decarboxylation by ADC it is not surprising that well-defined densities were not obtained.

Tail24A differed between the conformations, but in both it was visible only at low map contour levels and therefore accompanied by much spurious density which is unsurprising, since we expect to see a superposition of reaction states in the Sbst complex. With conformation Z, density is relatively convincing; while with conformation Y, it is significantly less well ordered, with a break in the $C_\alpha$ density of Tyr22A and a poorly defined Gly24A. The orientation of the terminal carboxylate group of Tail24A with conformation Y is different from that of the other structures, pointing out of the binding cavity rather than down at the amino group of Lys9D. A large difference density feature around Lys9D and Tyr58A was seen, at a higher map contour level, to consist of three separated peaks, and was therefore modelled as three water molecules.

So three states of Tail24A may be distinguished: the C- (closed), O- (open), and H- (half-closed) states. The C-state (seen in complexes with Nat, MeAsp, IsoA, and Prod is a conformation in which Tail24A blocks off the binding cavity and is well ordered, the terminal carboxylate of Gly24A interacting with Lys9D. In the O-state (seen in the complex with r$\beta$Ala) Tail24A is largely disordered and the binding cavity is exposed. In the H-state (seen with ADC conformation Y in the complex with Sbst) most of Tail24A has the C-state conformation, except the terminal carboxylate of Gly24A which does not interact with Lys9D.

Figure 6A:
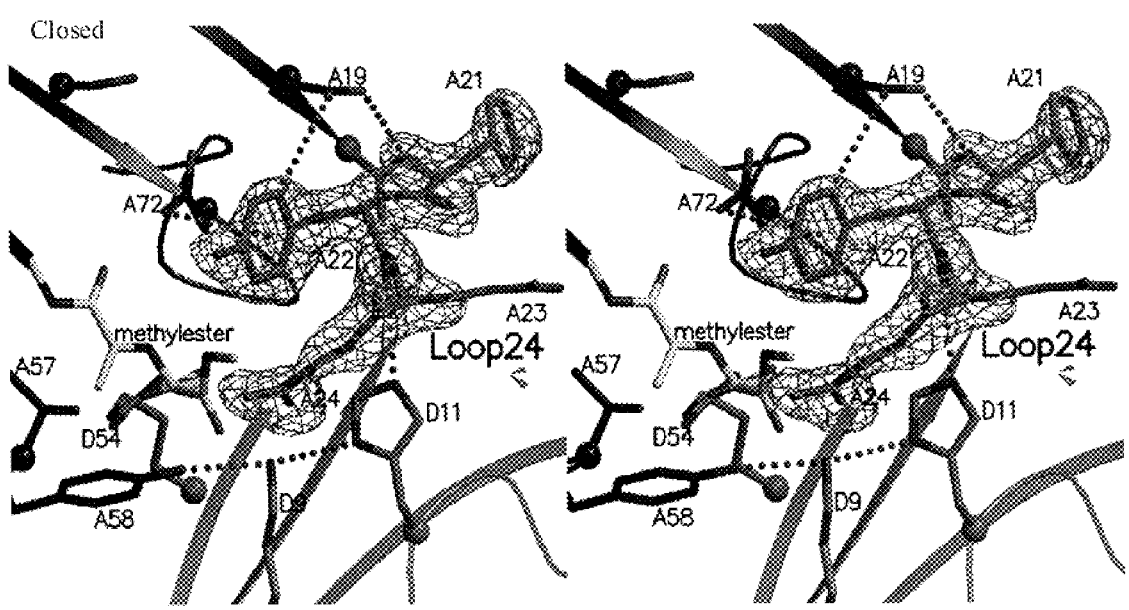
FIGS. 6a to c show stick model stereo representations of the ADC binding cavity and respective bound ligands, with the observed electron densities of Tail24A in wire-frame.
Figure 6B:
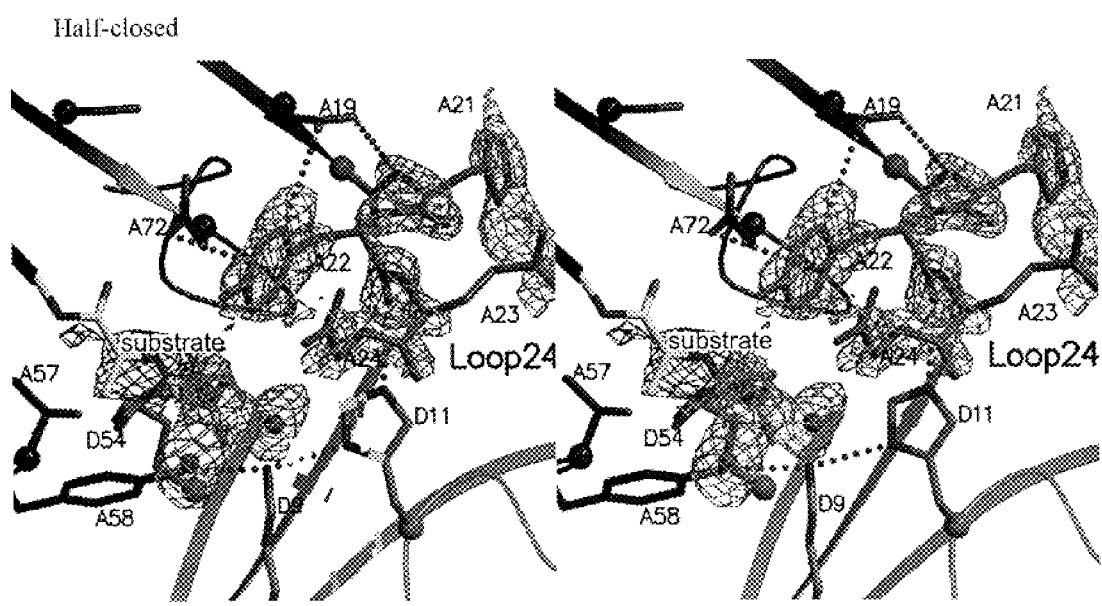
Figure 6C:
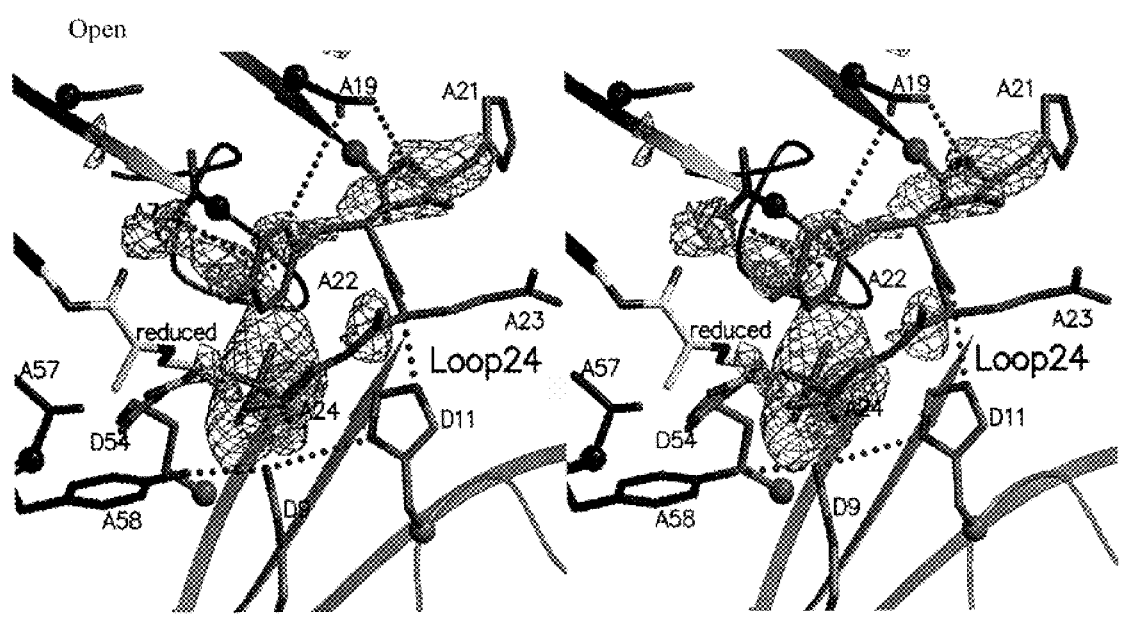

Table 2 (see below) provides the coordinates and binding interactions of binding sites within the binding cavity. The C-, H- and O-states are respectively illustrated in FIGS. 6a to c which show stereo representations of the binding cavity together with the observed electron density of Tail24A. In FIG. 6a the ligand is MeAsp, in FIG. 6b it is Sbst (in the complex with ADC conformation Y), and in FIG. 6c it is r$\beta$Ala.

Figure 7A:
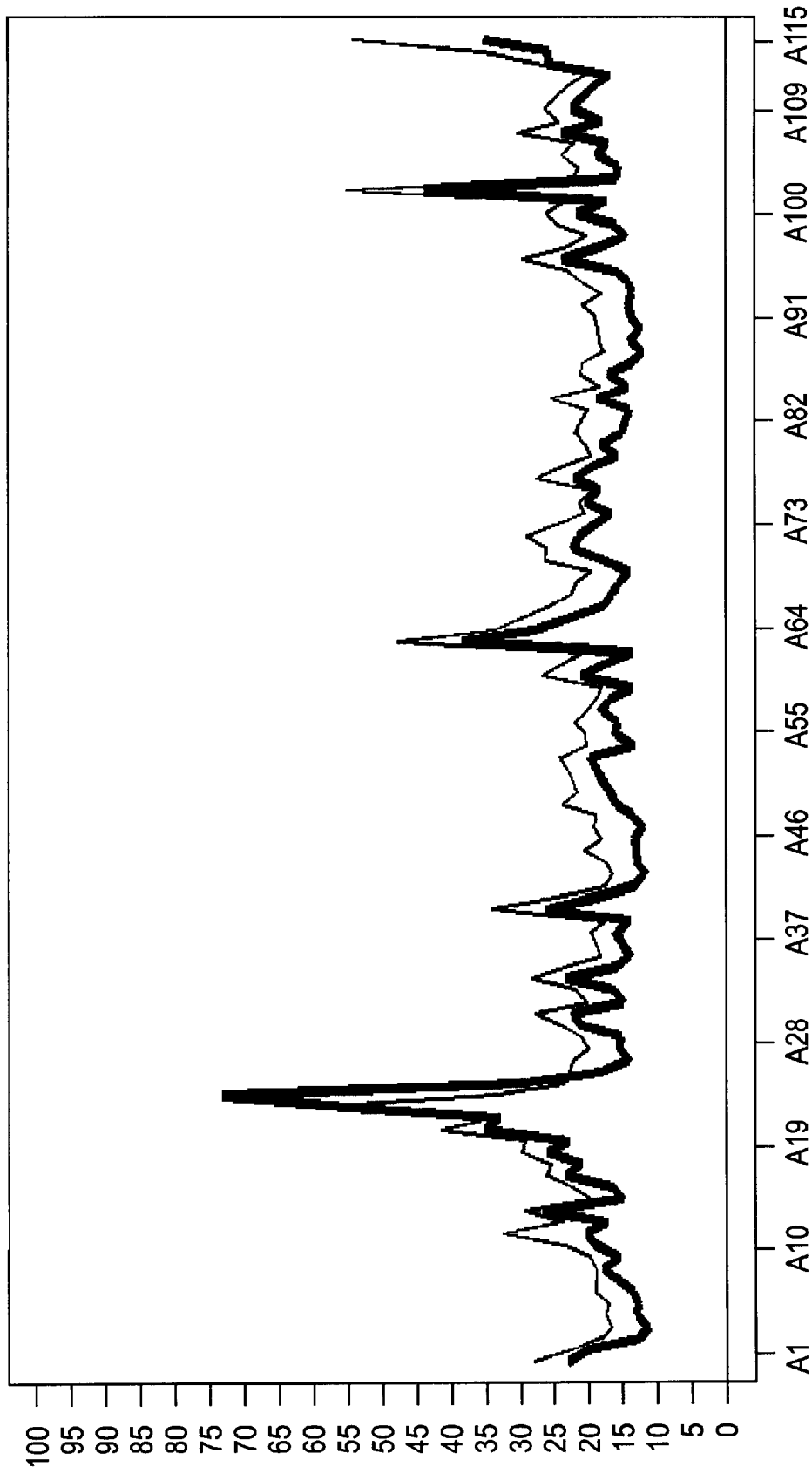
FIGS. 7a to c show plots (in thin line) of side chain temperature factor for the subunit A residues of respectively the α-methyl aspartate, L-aspartate and reductively bound β-alanine complexes. For reference, in each case the native side chain temperature factor is also plotted (in thick line).
Figure 7B:
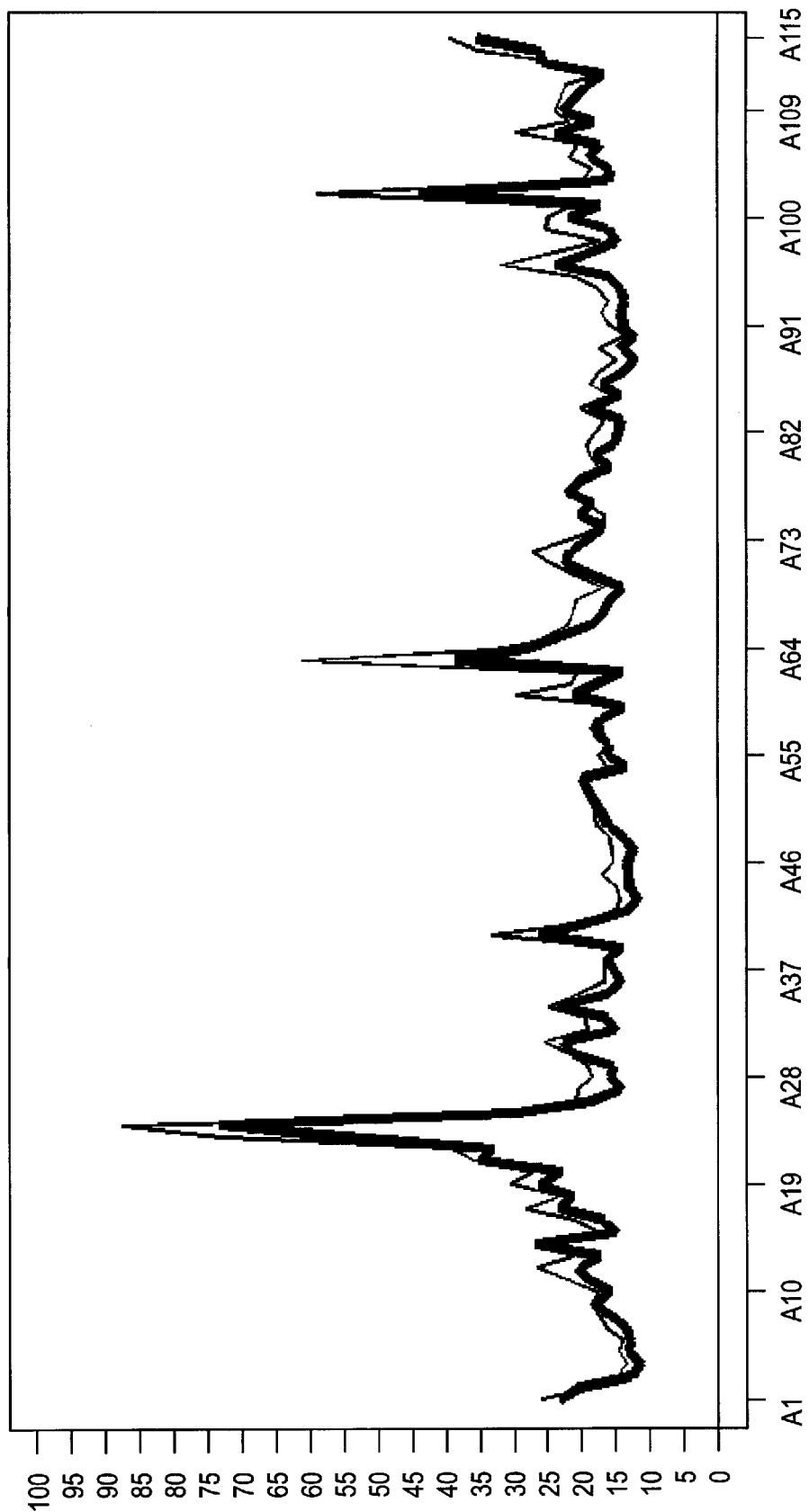
Figure 7C:
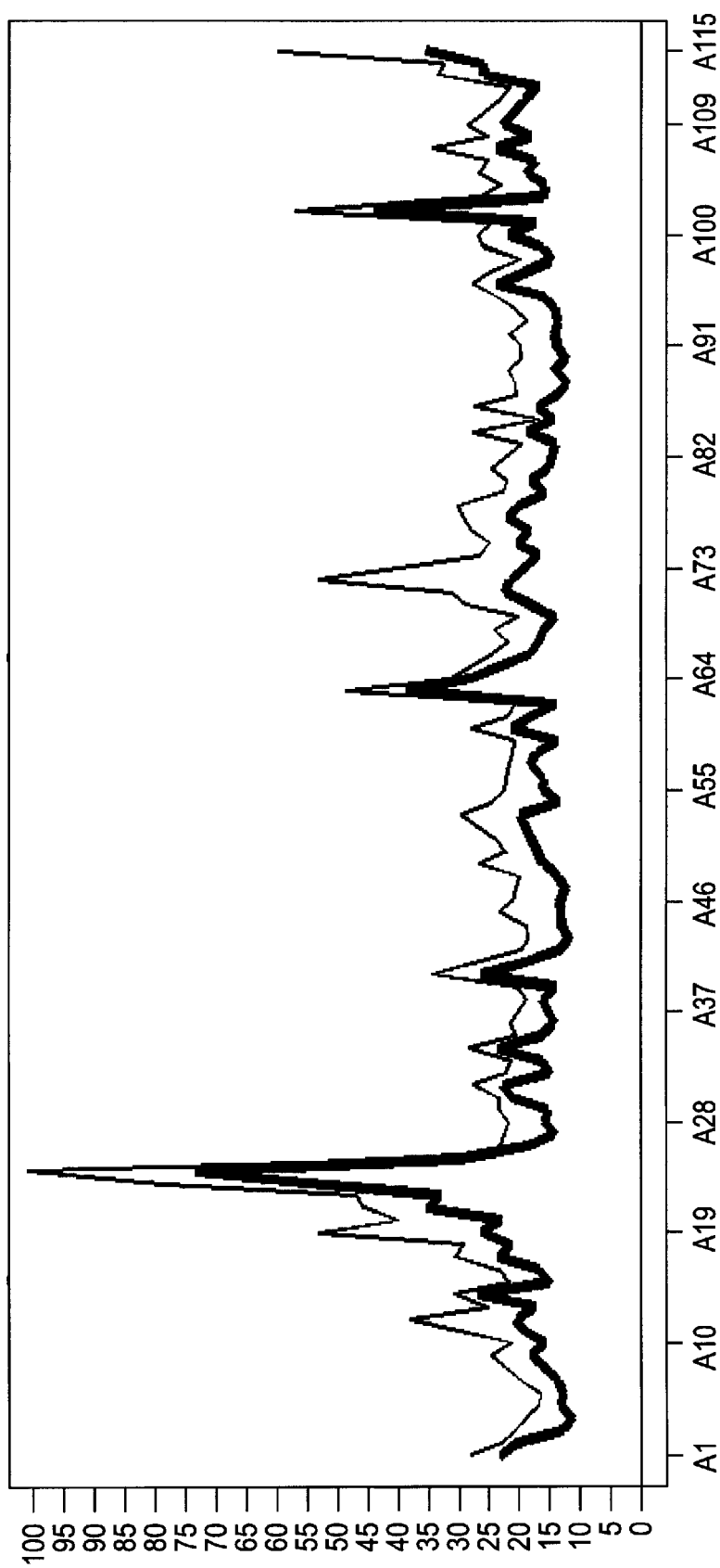

FIGS. 7a to c show plots (in thin line) of side chain temperature factor (B in Table 4) for the subunit A residues of respectively the MeAsp, Sbst and r$\beta$Ala complexes, i.e. the C-, H-, and O-states. For reference, in each case the Nat side chain temperature factor is also plotted (in thick line). Significant is the height of the main peak (corresponding to the residues of Tail24A) which increases in height as Tail24A progresses from the C-state to the O-state. This implies that in the O-state Tail24A is less strongly constrained to a particular conformation, i.e. Tail24A is more mobile. So although complexes having the respective states may be modelled by refined structures in which Tail24A adopts similar conformations, the higher B-factors allotted to the side chains of Tail-24A in the O-state are evidence of an increased indeterminacy in the position of Tail24A. This is consistent with increased exposure of the binding cavity in the O-state.

Aspartate Decarboxylation

Figure 8:
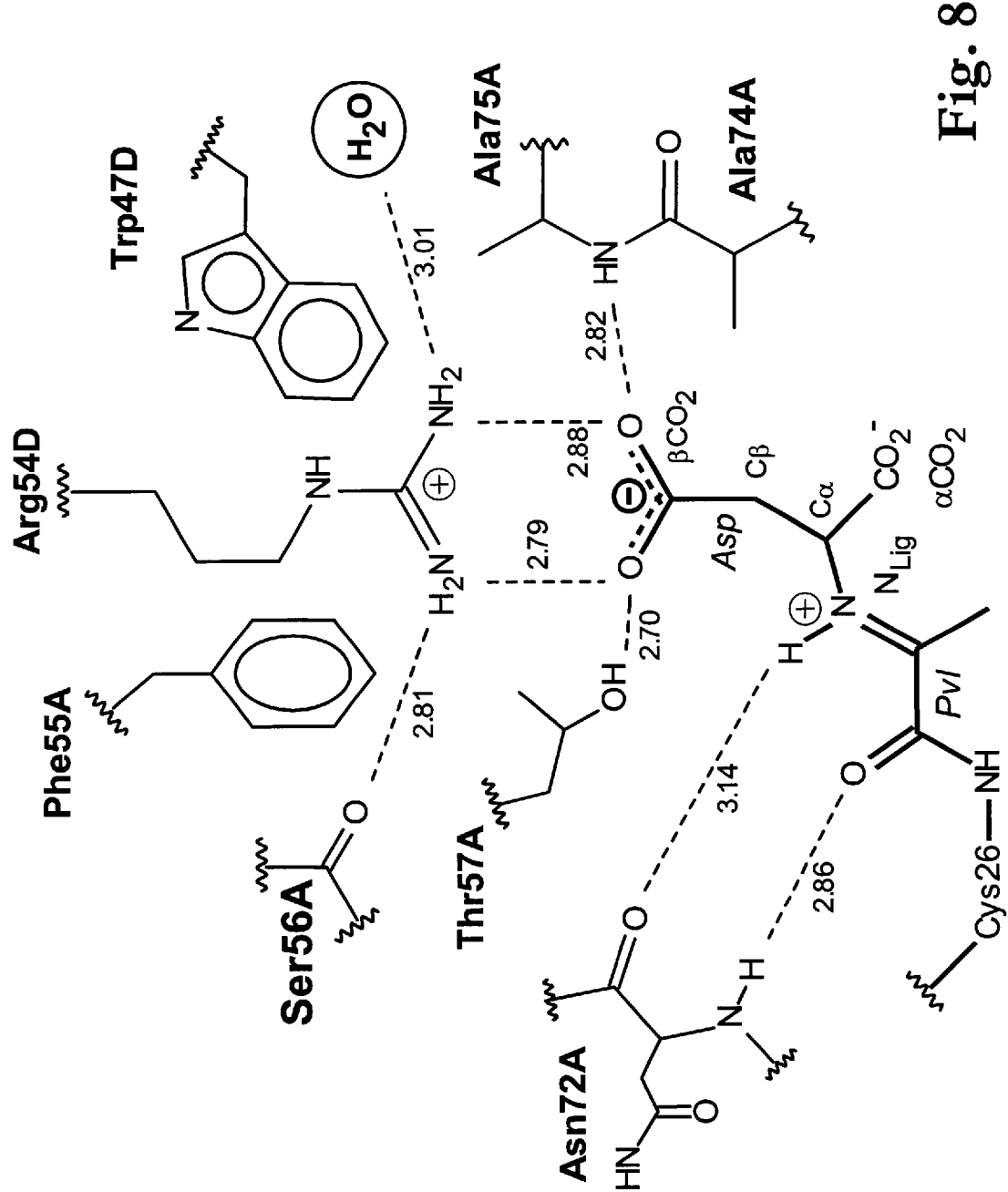
FIG. 8 shows schematically the residues and interactions of the $\beta CO_2$ binding pocket (interatomic distances are in Å)
Figure 9A:
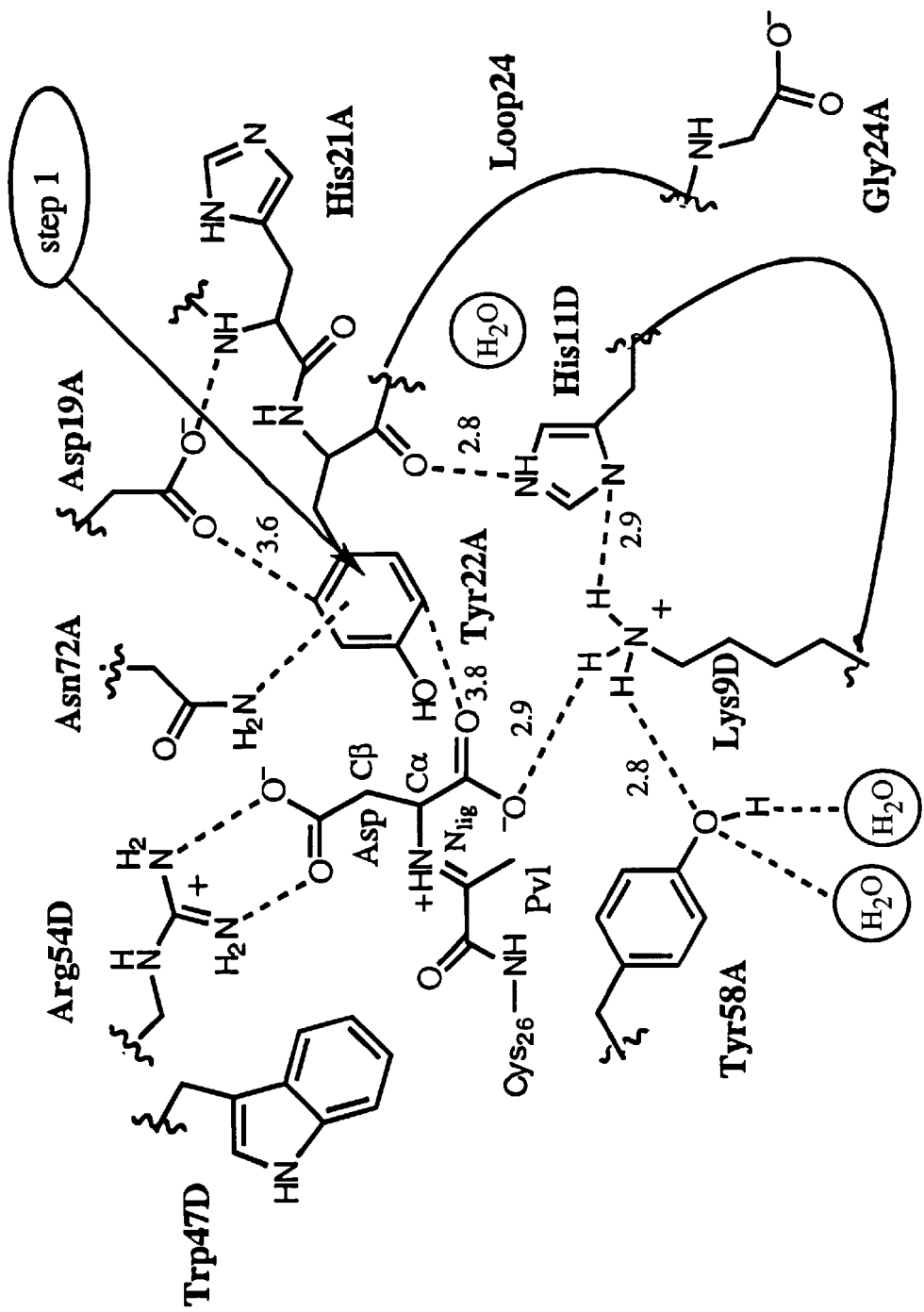
FIGS. 9a to d show schematically the four steps in the proposed decarboxylation catalytic process (interatomic distances are in Å).
Figure 9B:
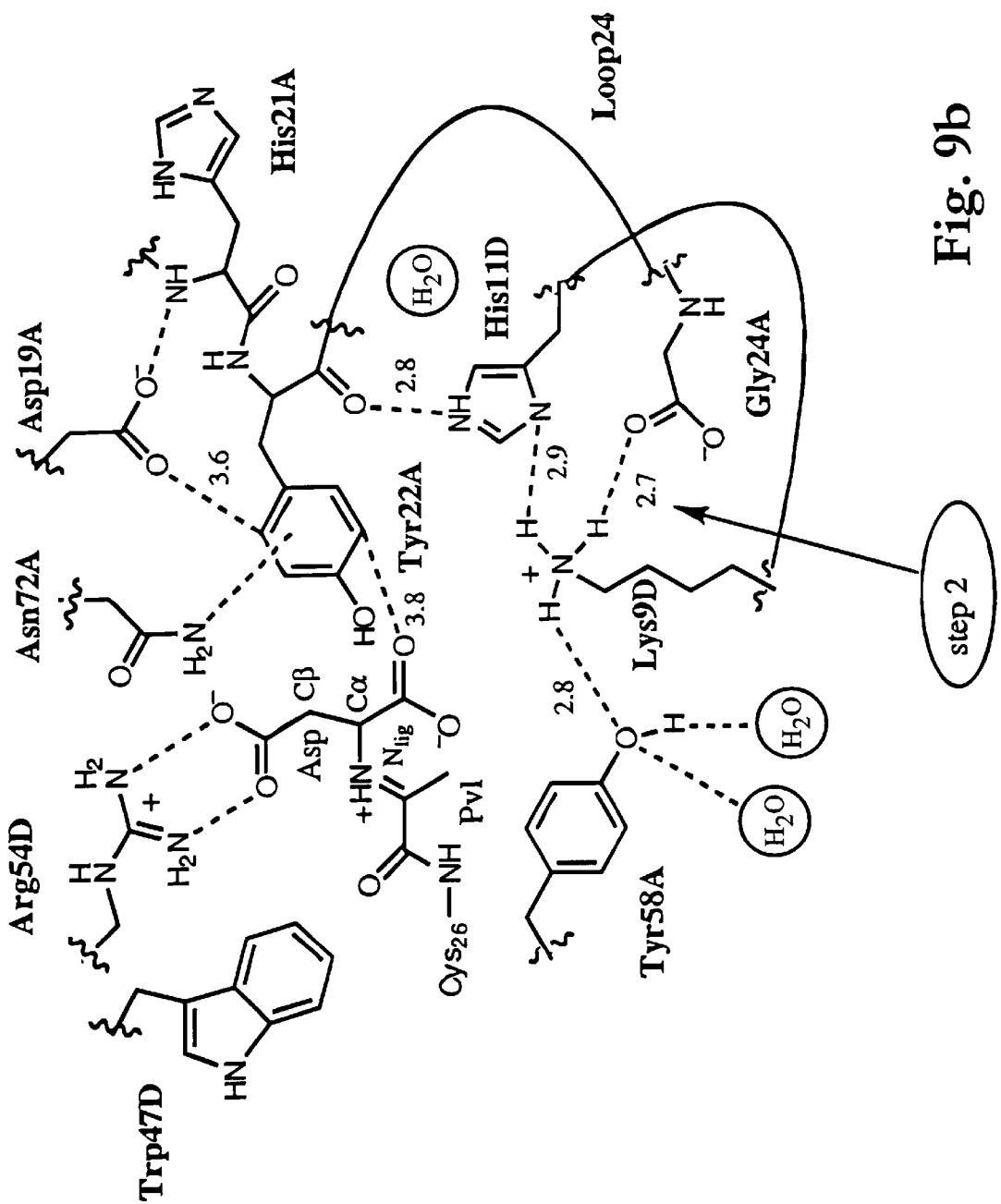
Figure 9C:
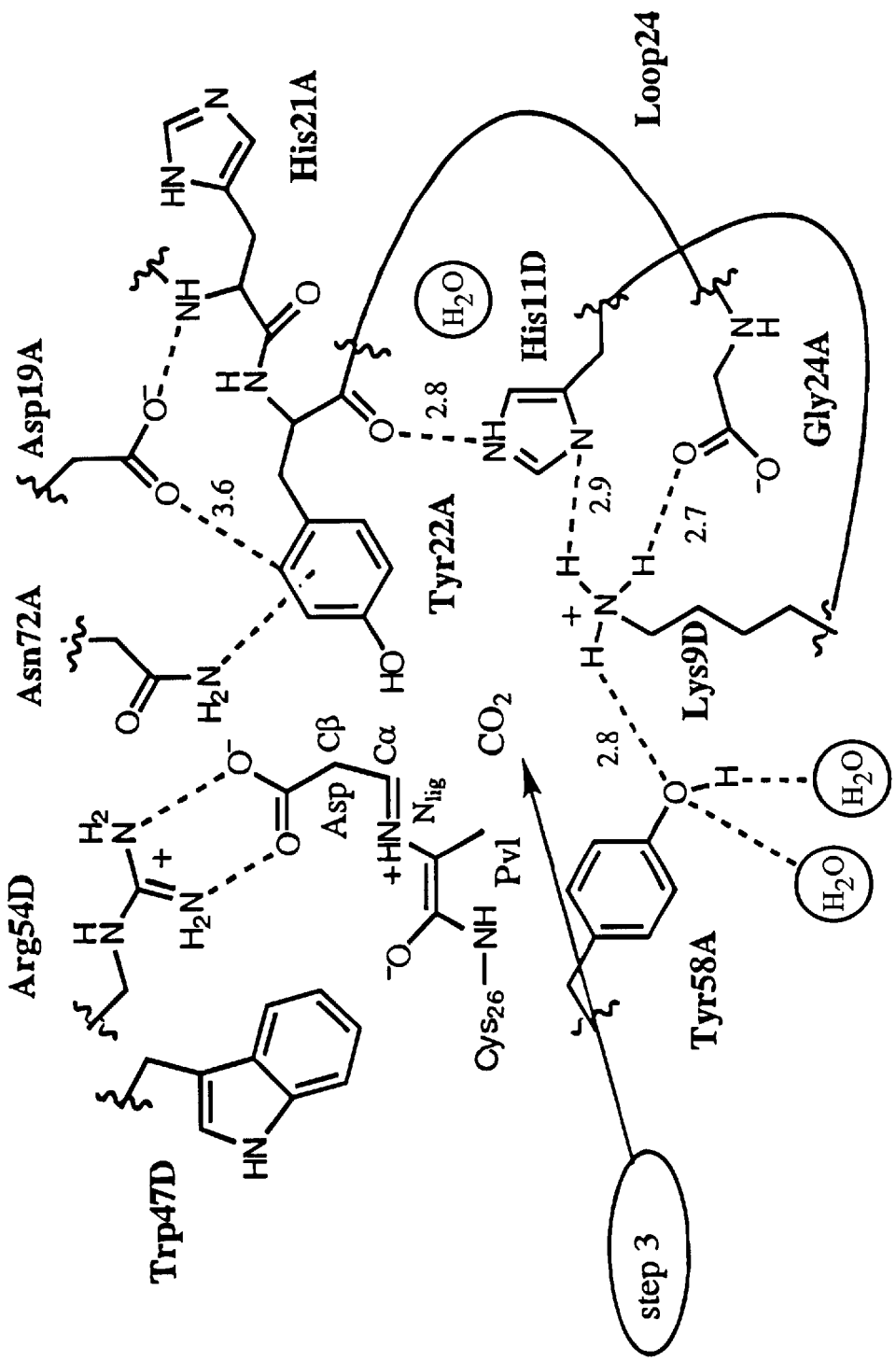
Figure 9D:
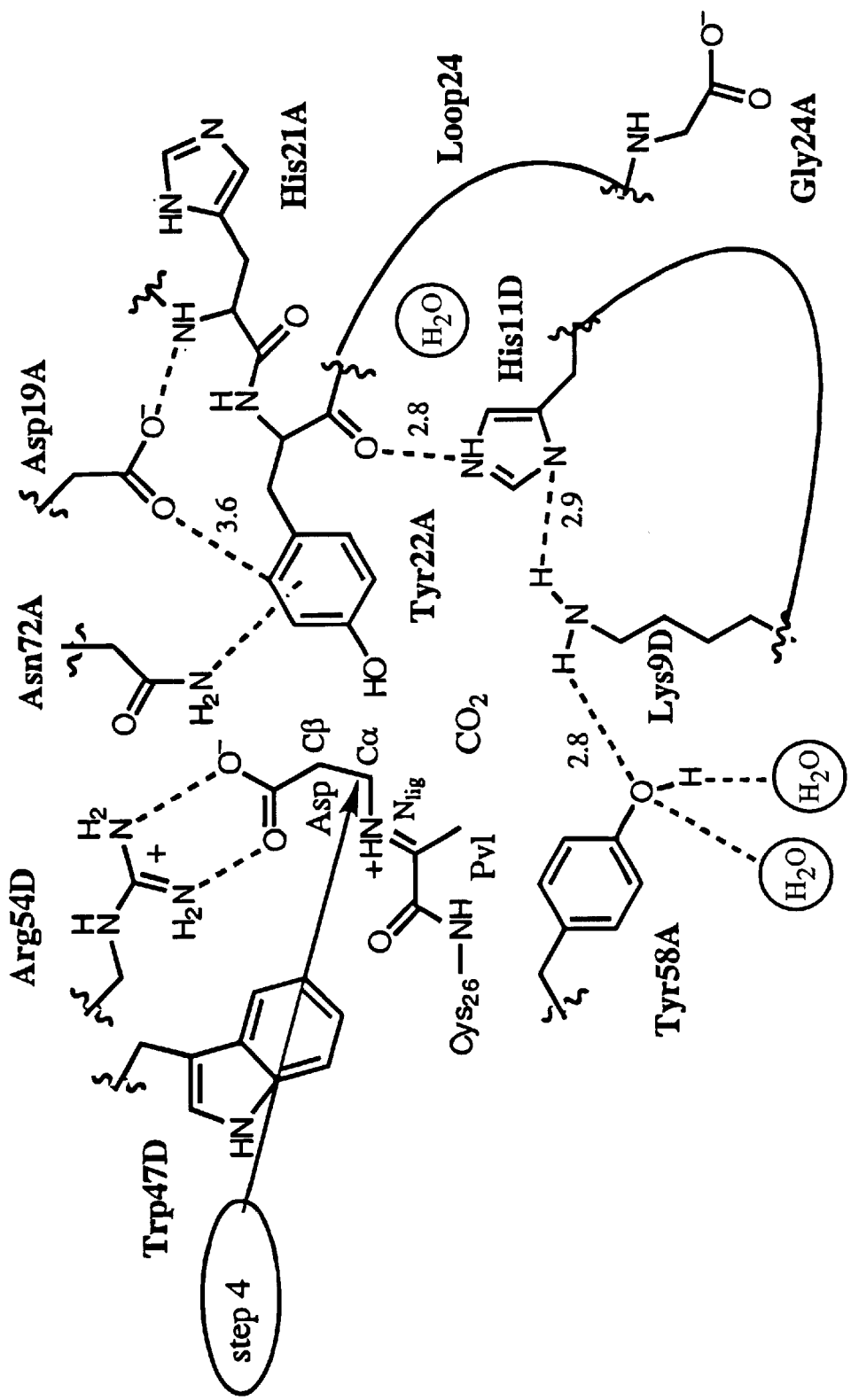

An elaborated version of the Albert et al. explanation for initial binding of the substrate into the binding cavity requires only minimal distortion of the residues of the two adjacent n-chain subunits. The guanidyl group of Arg54D is ideally positioned in a deep, hydrophobic pocket (Trp47D, Phe55A, Ala75A) to form a strong, directed salt bridge with the negatively charged aspartate $\beta CO_2$ group. The resulting aromatic stacking with Trp47D is known to be a favourable type of interaction (Westhead et al., Trends in Biochemical sciences, 23, (1998), 35–36). The $\beta CO_2$ binding pocket is shown schematically in FIG. 8.

$N_{Lig}$ (i.e. in this case the L-aspartate nitrogen atom) is thus placed at a suitable distance for imine formation above the Pv125A ketone closest to the split in the n-chain. The substrate $\alpha CO_2$ group is then positioned above the plane of the newly-formed imine-amide group in the hydrophobic environment of Tyr22A, Tyr58A and Ile60A, and the Pv125A methyl group. This provides the non-polar incentive to neutralise the negatively-charged substrate $\alpha CO_2$ and drive decarboxylation; the resulting negative charge on the adjacent ($C_\alpha$) substrate carbon being dispersed over the planar imine-amide group and beyond via hydrogen bonding between the oxygen of the remaining Pv125A ketone and strands β5 and β1 of subunit A and solvent molecules. The negative charge is finally neutralised by protonation of the substrate $C_\alpha$ carbanion.

However, this mechanism does not explain how the base, which must be available to protonate the $C_\alpha$ carbanion, is earlier prevented from stabilising the negatively-charged substrate $\alpha CO_2$; thereby preventing decarboxylation. Also, the position of the Tyr22A group varies with the position of Tail24A, and so is only available to provide a hydrophobic environment for the $\alpha CO_2$ group in certain positions of Tail24A.

We therefore propose the following four-step catalytic process which takes account of these factors:

(1) Tail24A flips from the C- to the O-state to allow the substrate molecule to enter the binding cavity. The substrate $\beta CO_2$ positions itself in the Trp47D, Phe55A, Ala75A hydrophobic pocket and $N_{Lig}$ reacts with Pv125A to form the imine-amide group, as described above. Tail24A then undergoes an O- to H-state transition whereby Tyr22A completes the hydrophobic pocket around the substrate $\alpha CO_2$ group.

(2) Tail24A undergoes an H- to C-state transition whereby the terminal carboxylate group of Gly24A neutralises the positive charge on Lys9D which had previously stabilised the substrate $\alpha CO_2$ group.

(3) The substrate $\alpha CO_2$ group undergoes decarboxylation.

(4) The decarboxylated substrate $C_\alpha$ carbanion is protonated and Tail24A opens to allow the carbon dioxide molecule to escape.

Steps (1) to (4) are illustrated schematically in FIGS. 9a to d, and are described in more detail below.

Step (1)

The detailed mechanism by which Tail24A flips from the C-to the O-state to allow the substrate molecule to enter the binding cavity, is not entirely clear. Possibly the steric and electrical presence of the substrate molecule is sufficient to force away the aromatic hydrophobic Tyr22A sidechain (and thus the rest of Tail24A) in the same way that the sulphate ion in the rβAla complex apparently forces Tail24A into the O-state. Note the position of Asp19A means that it is not possible simply to rotate the Tyr22A sidechain out of the binding cavity while maintaining the Tail24A mainchain in the C-state; the whole of Tail24A has to move away.

In any event, once the substrate is completely bound, through both $\beta CO_2$ and the imine species, the position and orientation of $\alpha CO_2$ induce the H-state. There are four interactions which fix Tyr22A into this conformation, one to the substrate, three within the enzyme: $O_{Tyr22A}$ hydrogen bonds to His11D, and the Tyr22A sidechain bonds with Asp19A and Asn72A. These two interactions arise from the electric dipole of the Tyr22A phenyl n-bond system which carries a fractional negative charge above, and a fractional positive charge equatorial to, the ring: the protons of the Asn72A sidechain amide interact with the former, the negative charge on Asp19A with the latter. The same effect allows the fourth Tyr22A interaction, which is the approach of the hydrophobic phenyl ring to the negatively charged substrate $\alpha CO_2$ group. This completes around $\alpha CO_2$ the hydrophobic pocket consisting of Tyr22A, Tyr58A, Ile60A (not shown in FIGS. 9a to d) and the pyruvoyl methyl carbon.

The $\alpha CO_2$ group also forms a hydrogen bridge to the positively charged Lys9D, forming the latter's third hydrogen bond (along with Tyr58A and His11D). At this stage, the negative Gly24A terminal carboxylate does not bind to Lys9D, and instead it has to adopt the conformation seen in conformation Y.

The two equatorial phenyl-carboxylate interactions (substrate $\alpha CO_2$ and Asp19A) involve the formally uncharged (see FIG. 8a) oxygens of the carboxylates, since the charged oxygens interact with $N_{ZLys9D}$ and $N_{His21A}$ respectively, both of which are better able to accommodate the negative charge than the only fractionally positive charge on the aromatic ring.

Step (2)

Because of its linkage to Tyr22A, the negatively charged Gly24A carboxylate is drawn into forming a salt bridge with the closest positive charge, which is that on $N_{ZLys9D}$. Tail24A is now in the C-state. The differing observations in the two ADC conformations with Sbst illustrate this competition for $N_{ZLys9D}$: in conformation Y, the substrate appears to be more clearly present than in Z, which suggests that Y represents a less advanced stage in the catalytic process. This is also consistent with Gly24A being relatively poorly ordered and not bound to $N_{ZLys9D}$ (i.e. the H-state) with conformation Y, whereas Gly24A is more ordered and Tail24A is more nearly in the C-state with Z.

The formation of the C-state observed with MeAsp and IsoA is also consistent with this step of the proposed mechanism. Like Sbst, MeAsp and IsoA are held in the binding cavity by the formation of the imine species and the favourable positioning of their carboxylate groups in the substrate $\beta CO_2$ binding pocket. However, unlike Sbst, neither MeAsp nor IsoA has a decarboxylatable $\alpha CO_2$ group. Instead each has a relatively hydrophobic group (respectively $\alpha CO_2 Me$ and 1isopropyl) which is stable in the $\alpha CO_2$ hydrophobic binding pocket and does not hydrogen bond to $N_{ZLys9D}$. Consequently, the $N_{ZLys9D}$-$Gly^{24}A$ carboxylate salt bridge is favoured and Tail24A is immobilised in the C-state.

Prod, like MeAsp and IsoA, is held in the binding cavity by the formation of a imine species and the favourable positioning of its carboxylate group into the $\beta CO_2$ binding pocket. However, with Prod the $N_{ZLys9D}$-Gly24A carboxylate salt bridge is favoured and Tail24A is held in the C-state because Prod lacks a group to interact significantly with the $\alpha CO_2$ binding pocket (a solvent molecule occupies this pocket in Prod). Similarly, in Nat there is no competition from any part of a bound ligand for $N_{ZLys9D}$, and so Tail24A favours the C-state.

Step (3)

The effect of the previous two steps was first to enclose $\alpha CO_2$ with hydrophobic residues, and next to remove the remaining stabilising interaction with the positive $N_{ZLys9D}$. This leaves the negative charge on $\alpha CO_2$ unstabilised and in an unfavourable environment, and thus provides the "push" required to drive decarboxylation. The fractional positive charge equatorial to the Tyr22A sidechain is not sufficient to stabilise the negative charge. Indirect evidence of this comes from the MeAsp complex, in which the MeAsp $\alpha CO_2 Me$ hydrophobic methyl group is oriented towards the aromatic ring of Tyr22A despite the electric dipole of the Tyr22A phenyl n-bond system.

The source of the "pull" effect, which is required to stabilise the charged, decarboxylated species, is also confirmed by the orientation of the oxygen of the remaining pyruvol ketone, which allows it to form H-bonds to the peptide bond groups between residues Val71A-Asn72A and Ala18A-Asp19A on parallel β-strands β5 and β1 of n-chain A. The negative charge which remains on the reaction intermediate after decarboxylation is dispersed over the planar imine species, which stabilises the intermediate. This creates a net negative charge on the electrophilic oxygen of the remaining pyruvol ketone, which in turn induces electric dipoles in the delocalised n-electrons of the two parallel amide bond systems to which it is H-bonded. This results in a stabilising dielectric effect which is further enhanced by the solvent which surrounds the amide bond between Ala18A and Asp19A. Overall the energy of the charged reaction intermediate is lowered and the reaction therefore accelerated.

Step(4)

The final step is protonation of $C_\alpha$, which probably occurs rapidly before the release of $CO_2$ from the cavity. His11D is unlikely to be the proton donor, since both of its N-atoms are involved in H-bonds. So the remaining candidates are Tyr58A and Lys9D, both of which are within 5 Å of $C_\alpha$, are part of the same H-bonding system and are exposed to solvent.

The most plausible mechanism involves both Lys9D and Tyr58A. Initially all three protons on $N_{ZLys9D}$ are used in H-bonds (to Tyr58A, His11D and Gly24A) and are therefore unavailable. The $OH_{Tyr58A}$ proton from Tyr58A, however, is available, because the proton for the H-bond between $OH_{Tyr58A}$ and $N_{ZLys9D}$ is provided by $N_{ZLys9D}$. Therefore the $OH_{Tyr58A}$ proton is transferred to the $C_\alpha$, and the resulting negative charge created on $OH_{Tyr58A}$ is stabilised by the neighbouring positive charge on $N_{ZLys9}$. This charge is then neutralised by transfer of the H-bonding proton from $N_{ZLys9D}$ which therefore loses its positive charge. Because of this the Gly24A terminal carboxylate group debonds from $N_{ZLys9D}$ and Tail24A adopts the H-or O-state, allowing the $CO_2$ molecule to escape from the binding cavity.

Of course, the O-state was observed with rβAla, but in this case the apparent reason that the Gly24A terminal carboxylate group was not bound to $N_{ZLys9D}$ (thereby releasing Tail24A from the C-state) was the steric and/or electrical effect of a sulphate ion in the $\alpha CO_2$ pocket. Such an ion may be a more preferred binding partner for $N_{ZLys9D}$ compared with the Gly24A terminal carboxylate.

The distance between C, and $OH_{Tyr58A}$ is about 4.5 Å. This may be close enough for a direct proton transfer after some side chain movement from $OH_{Tyr58A}$ to $C_\alpha$, or alternatively the $CO_2$ molecule may play a significant role, by transiently binding the proton during its transfer to $C_\alpha$.

To summarise, a function of the somewhat elaborate Tail24A mechanism is apparently to prevent Lys9D from interfering with the process of decarboxylation until Lys9D is needed for protonation.

Structure-Based Drug Design

Determination of the mechanism of aspartate decarboxylation by ADC, and in particular the recognition of the crucial role of Tail24A, provides important information for rational design of ADC inhibitors, e.g. via computational techniques which identify possible binding ligands for the binding cavity. These techniques are discussed in more detail below.

Greer et al. (*J. of Medicinal Chemistry*, 37, (1994), 1035–1054) described an iterative approach to ligand design based on repeated sequences of computer modelling, protein-ligand complex formation and X-ray crystallographic or NMR spectroscopic analysis. Thus novel thymidylate synthase inhibitor series were designed de novo by Greer et al., and ADC inhibitors may also be designed in the this way. More specifically, using e.g. GRID (Goodford, *J of Medicinal Chemistry*, 28, (1985), 849–857.) on the solved 3D structure of ADC, a ligand (e.g. a candidate inhibitor) for ADC may be designed that complements the functionalities of the ADC binding site. The ligand can then be synthesised, formed into a complex with ADC, and the complex then analysed by X-ray crystallography to identify the actual position of the bound ligand. The structure and/or functional groups of the ligand can then be adjusted, if necessary, in view of the results of the X-ray analysis, and the synthesis and analysis sequence repeated until an optimised ligand is obtained. Related approaches to structure-based drug design are also discussed in Bohacek et al., *Medicinal Research Reviews*, 16, (1996), 3–50.

As a result of the determination of the mechanism of aspartate decarboxylation, more purely computational techniques for rational drug design may also be used to design ADC inhibitors (for an overview of these techniques see e.g. Walters et al. mentioned above). For example, automated ligand-receptor docking programs (discussed e.g. by Jones et al. in *Current Opinion in Biotechnology*, 6, (1995), 652–656) which require accurate information on the atomic coordinates of target receptors may be used to design candidate ADC inhibitors.

The approaches to structure-based drug design described above all require initial identification of possible compounds for interaction with target bio-molecule (in this case ADC). Sometimes these compounds are known e.g. from the research literature. However, when they are not, or when novel compounds are wanted, a first stage of the drug design program may involve computer-based in silico screening of compound databases (such as the Cambridge Structural Database) with the aim of identifying compounds which interact with the binding cavity or sites of the target bio-molecule. Screening selection criteria may be based on pharmacokinetic properties such as metabolic stability and toxicity. However, determination of the mechanism of aspartate decarboxylation allows the architecture and chemical nature of the ADC binding site to be better defined, which in turn allows the geometric and functional constraints of a descriptor for the candidate inhibitor to be derived more accurately. The descriptor is, therefore, a type of virtual 3-D pharmacophore, which can also be used as selection criteria or filter for database screening.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention.

TABLE 1

Atomic structure of fully-processed native ADC

| CRYST1 | 71.080 | 71.080 | 215.781 | 90.00 | 90.00 | 120.00 |
|---|---|---|---|---|---|---|
| ORIGX1 | 1.000000 | 0.000000 | 0.000000 | 0.00000 | | |
| ORIGX2 | 0.000000 | 1.000000 | 0.000000 | 0.00000 | | |
| ORIGX3 | 0.000000 | 0.000000 | 1.000000 | 0.00000 | | |
| SCALE1 | 0.014069 | 0.008123 | 0.000000 | 0.00000 | | |
| SCALE2 | 0.000000 | 0.016245 | 0.000000 | 0.00000 | | |
| SCALE3 | 0.000000 | 0.000000 | 0.004634 | 0.00000 | | |

Remarks

Atoms of tetramer subunits A and B and their associated water molecules (which are designated G) are numbered from 1 to 2075. Tetramer subunits C and D were generated by symmetry from subunits A and B, and hence the atoms of subunits C and D and their associated water molecules (which are designated H) are also numbered from 1 to 2075.

Due to lack of measured electron density, C-terminal residues 116 to 126 were not modelled for any of the tetramer subunits. Hence atoms of residues 116 to 126 do not appear in the following data lists.

The atomic coordinates provided below are for orthogonal, right-handed axes. The following data lists provide:

| Column 2: | Atom no. |
|---|---|
| Column 3: | Atom type |

-continued

| Column 4: | Residue type |
|---|---|
| Column 5: | Tetramer subunit |
| Column 6: | Residue no. |
| Column 7: | x coordinate of atom (Å) |
| Column 8: | y coordinate of atom (Å) |
| Column 9: | z coordinate of atom (Å) |
| Column 10: | Occupancy |
| Column 11: | B-factor (Å$^2$) |

N.B. For water molecules, column 4 reads "WAT", column 5 reads G or H, column 6 is the no. of the water molecule, and the atomic coordinates of columns 7–9 are the coordinates of the water oxygen atoms.

Data Lists

| ATOM | 1 | N | MET | A | 1 | 42.243 | 31.537 | 9.436 | 1.00 | 25.25 |
|---|---|---|---|---|---|---|---|---|---|---|
| ATOM | 2 | CA | MET | A | 1 | 43.570 | 31.458 | 10.034 | 1.00 | 23.37 |
| ATOM | 3 | C | MET | A | 1 | 43.641 | 32.211 | 11.324 | 1.00 | 22.04 |
| ATOM | 4 | O | MET | A | 1 | 42.712 | 32.932 | 11.694 | 1.00 | 22.16 |
| ATOM | 5 | CB | MET | A | 1 | 44.716 | 31.746 | 9.121 | 1.00 | 26.58 |
| ATOM | 6 | CG | MET | A | 1 | 44.484 | 32.827 | 8.276 | 1.00 | 29.48 |
| ATOM | 7 | SD | MET | A | 1 | 44.383 | 34.380 | 9.083 | 1.00 | 32.96 |
| ATOM | 8 | CE | MET | A | 1 | 44.525 | 35.278 | 7.559 | 1.00 | 23.68 |
| ATOM | 9 | N | ILE | A | 2 | 44.751 | 32.014 | 11.983 | 1.00 | 14.33 |
| ATOM | 10 | CA | ILE | A | 2 | 44.972 | 32.564 | 13.345 | 1.00 | 12.86 |
| ATOM | 11 | C | ILE | A | 2 | 45.982 | 33.682 | 13.386 | 1.00 | 13.27 |
| ATOM | 12 | O | ILE | A | 2 | 47.126 | 33.561 | 12.838 | 1.00 | 12.60 |
| ATOM | 13 | CB | ILE | A | 2 | 45.444 | 31.363 | 14.210 | 1.00 | 15.76 |
| ATOM | 14 | CG1 | ILE | A | 2 | 44.358 | 30.267 | 14.277 | 1.00 | 18.95 |
| ATOM | 15 | CG2 | ILE | A | 2 | 45.853 | 31.814 | 15.631 | 1.00 | 15.91 |
| ATOM | 16 | CD1 | ILE | A | 2 | 43.131 | 30.698 | 14.977 | 1.00 | 30.84 |
| ATOM | 17 | N | ARG | A | 3 | 45.597 | 34.790 | 14.035 | 1.00 | 11.28 |
| ATOM | 18 | CA | ARG | A | 3 | 46.492 | 35.952 | 14.142 | 1.00 | 10.27 |
| ATOM | 19 | C | ARG | A | 3 | 47.228 | 36.039 | 15.491 | 1.00 | 12.97 |
| ATOM | 20 | O | ARG | A | 3 | 46.698 | 35.499 | 16.473 | 1.00 | 11.98 |
| ATOM | 21 | CB | ARG | A | 3 | 45.661 | 37.245 | 14.103 | 1.00 | 11.24 |
| ATOM | 22 | CG | ARG | A | 3 | 44.872 | 37.472 | 12.729 | 1.00 | 11.07 |
| ATOM | 23 | CD | ARG | A | 3 | 45.819 | 38.078 | 11.695 | 1.00 | 14.19 |
| ATOM | 24 | NE | ARG | A | 3 | 44.929 | 38.442 | 10.562 | 1.00 | 12.85 |
| ATOM | 25 | CZ | ARG | A | 3 | 45.343 | 39.206 | 9.551 | 1.00 | 13.01 |
| ATOM | 26 | NH1 | ARG | A | 3 | 46.582 | 39.576 | 9.415 | 1.00 | 11.87 |
| ATOM | 27 | NH2 | ARG | A | 3 | 44.406 | 39.516 | 8.613 | 1.00 | 15.42 |
| ATOM | 28 | N | THR | A | 4 | 48.373 | 36.698 | 15.491 | 1.00 | 10.90 |
| ATOM | 29 | CA | THR | A | 4 | 49.176 | 36.964 | 16.738 | 1.00 | 8.73 |
| ATOM | 30 | C | THR | A | 4 | 48.907 | 38.466 | 16.993 | 1.00 | 12.54 |
| ATOM | 31 | O | THR | A | 4 | 49.309 | 39.358 | 16.137 | 1.00 | 11.96 |
| ATOM | 32 | CB | THR | A | 4 | 50.623 | 36.684 | 16.549 | 1.00 | 10.20 |
| ATOM | 33 | OG1 | THR | A | 4 | 50.780 | 35.288 | 16.296 | 1.00 | 12.29 |
| ATOM | 34 | CG2 | THR | A | 4 | 51.479 | 37.146 | 17.856 | 1.00 | 12.13 |
| ATOM | 35 | N | MET | A | 5 | 48.224 | 38.786 | 18.149 | 1.00 | 10.12 |
| ATOM | 36 | CA | MET | A | 5 | 47.846 | 40.130 | 18.437 | 1.00 | 10.31 |
| ATOM | 37 | C | MET | A | 5 | 48.386 | 40.604 | 19.771 | 1.00 | 13.52 |
| ATOM | 38 | O | MET | A | 5 | 48.563 | 39.767 | 20.674 | 1.00 | 14.15 |
| ATOM | 39 | CB | MET | A | 5 | 46.316 | 40.208 | 18.572 | 1.00 | 13.06 |
| ATOM | 40 | CG | MET | A | 5 | 45.503 | 39.690 | 17.370 | 1.00 | 11.30 |
| ATOM | 41 | SD | MET | A | 5 | 45.827 | 40.706 | 15.868 | 1.00 | 13.37 |
| ATOM | 42 | CE | MET | A | 5 | 45.032 | 42.250 | 16.304 | 1.00 | 14.97 |
| ATOM | 43 | N | LEU | A | 6 | 48.622 | 41.904 | 19.871 | 1.00 | 10.44 |
| ATOM | 44 | CA | LEU | A | 6 | 49.081 | 42.499 | 21.181 | 1.00 | 11.49 |
| ATOM | 45 | C | LEU | A | 6 | 47.929 | 42.257 | 22.147 | 1.00 | 13.65 |
| ATOM | 46 | O | LEU | A | 6 | 46.795 | 42.770 | 21.986 | 1.00 | 12.95 |
| ATOM | 47 | CB | LEU | A | 6 | 49.255 | 43.989 | 21.000 | 1.00 | 11.43 |
| ATOM | 48 | CG | LEU | A | 6 | 49.699 | 44.732 | 22.302 | 1.00 | 12.67 |
| ATOM | 49 | CD1 | LEU | A | 6 | 51.156 | 44.411 | 22.585 | 1.00 | 13.37 |
| ATOM | 50 | CD2 | LEU | A | 6 | 49.593 | 46.238 | 22.044 | 1.00 | 14.36 |
| ATOM | 51 | N | GLN | A | 7 | 48.226 | 41.496 | 23.234 | 1.00 | 12.16 |
| ATOM | 52 | CA | GLN | A | 7 | 47.239 | 41.216 | 24.275 | 1.00 | 11.30 |
| ATOM | 53 | C | GLN | A | 7 | 47.141 | 42.451 | 25.220 | 1.00 | 12.23 |
| ATOM | 54 | O | GLN | A | 7 | 46.041 | 42.846 | 25.650 | 1.00 | 11.94 |

-continued

Data Lists

| ATOM | 55 | CB | GLN | A | 7 | 47.746 | 40.036 | 25.107 | 1.00 | 12.62 |
|------|----|-----|-----|---|----|--------|--------|--------|------|-------|
| ATOM | 56 | CG | GLN | A | 7 | 46.732 | 39.520 | 26.148 | 1.00 | 14.99 |
| ATOM | 57 | CD | GLN | A | 7 | 46.688 | 40.421 | 27.435 | 1.00 | 12.25 |
| ATOM | 58 | OE1 | GLN | A | 7 | 45.546 | 40.719 | 27.921 | 1.00 | 14.42 |
| ATOM | 59 | NE2 | GLN | A | 7 | 47.842 | 40.852 | 27.955 | 1.00 | 13.59 |
| ATOM | 60 | N | GLY | A | 8 | 48.310 | 43.015 | 25.491 | 1.00 | 12.10 |
| ATOM | 61 | CA | GLY | A | 8 | 48.374 | 44.194 | 26.380 | 1.00 | 12.14 |
| ATOM | 62 | C | GLY | A | 8 | 49.811 | 44.596 | 26.605 | 1.00 | 11.21 |
| ATOM | 63 | O | GLY | A | 8 | 50.775 | 43.898 | 26.221 | 1.00 | 12.25 |
| ATOM | 64 | N | LYS | A | 9 | 49.985 | 45.756 | 27.260 | 1.00 | 11.80 |
| ATOM | 65 | CA | LYS | A | 9 | 51.337 | 46.214 | 27.515 | 1.00 | 12.75 |
| ATOM | 66 | C | LYS | A | 9 | 51.410 | 47.227 | 28.669 | 1.00 | 12.69 |
| ATOM | 67 | O | LYS | A | 9 | 50.401 | 47.872 | 29.006 | 1.00 | 14.09 |
| ATOM | 68 | CB | LYS | A | 9 | 51.969 | 46.897 | 26.258 | 1.00 | 16.31 |
| ATOM | 69 | CG | LYS | A | 9 | 51.366 | 48.231 | 25.859 | 1.00 | 16.10 |
| ATOM | 70 | CD | LYS | A | 9 | 52.132 | 48.984 | 24.727 | 1.00 | 15.95 |
| ATOM | 71 | CE | LYS | A | 9 | 51.406 | 50.282 | 24.423 | 1.00 | 20.48 |
| ATOM | 72 | NZ | LYS | A | 9 | 52.258 | 51.132 | 23.526 | 1.00 | 22.05 |
| ATOM | 73 | N | LEU | A | 10 | 52.615 | 47.337 | 29.208 | 1.00 | 13.44 |
| ATOM | 74 | CA | LEU | A | 10 | 52.927 | 48.310 | 30.283 | 1.00 | 13.72 |
| ATOM | 75 | C | LEU | A | 10 | 53.805 | 49.288 | 29.528 | 1.00 | 14.03 |
| ATOM | 76 | O | LEU | A | 10 | 54.917 | 48.961 | 29.125 | 1.00 | 15.46 |
| ATOM | 77 | CB | LEU | A | 10 | 53.733 | 47.627 | 31.422 | 1.00 | 13.59 |
| ATOM | 78 | CG | LEU | A | 10 | 52.977 | 46.504 | 32.112 | 1.00 | 14.77 |
| ATOM | 79 | CD1 | LEU | A | 10 | 53.870 | 45.742 | 33.134 | 1.00 | 18.67 |
| ATOM | 80 | CD2 | LEU | A | 10 | 51.669 | 47.010 | 32.829 | 1.00 | 15.75 |
| ATOM | 81 | N | HIS | A | 11 | 53.306 | 50.476 | 29.335 | 1.00 | 14.06 |
| ATOM | 82 | CA | HIS | A | 11 | 54.009 | 51.485 | 28.542 | 1.00 | 14.41 |
| ATOM | 83 | C | HIS | A | 11 | 54.833 | 52.488 | 29.338 | 1.00 | 18.20 |
| ATOM | 84 | O | HIS | A | 11 | 54.265 | 53.263 | 30.102 | 1.00 | 16.24 |
| ATOM | 85 | CB | HIS | A | 11 | 53.007 | 52.202 | 27.614 | 1.00 | 17.29 |
| ATOM | 86 | CG | HIS | A | 11 | 53.650 | 53.095 | 26.601 | 1.00 | 18.36 |
| ATOM | 87 | ND1 | HIS | A | 11 | 54.118 | 52.627 | 25.381 | 1.00 | 20.19 |
| ATOM | 88 | CD2 | HIS | A | 11 | 53.902 | 54.430 | 26.612 | 1.00 | 19.36 |
| ATOM | 89 | CE1 | HIS | A | 11 | 54.652 | 53.629 | 24.711 | 1.00 | 19.59 |
| ATOM | 90 | NE2 | HIS | A | 11 | 54.530 | 54.737 | 25.432 | 1.00 | 18.93 |
| ATOM | 91 | N | ARG | A | 12 | 56.146 | 52.442 | 29.124 | 1.00 | 15.16 |
| ATOM | 92 | CA | ARG | A | 12 | 57.097 | 53.308 | 29.757 | 1.00 | 15.13 |
| ATOM | 93 | C | ARG | A | 12 | 57.204 | 53.130 | 31.261 | 1.00 | 16.37 |
| ATOM | 94 | O | ARG | A | 12 | 57.175 | 54.135 | 32.023 | 1.00 | 18.19 |
| ATOM | 95 | CB | ARG | A | 12 | 56.873 | 54.756 | 29.408 | 1.00 | 15.43 |
| ATOM | 96 | CG | ARG | A | 12 | 57.151 | 55.048 | 27.918 | 1.00 | 17.33 |
| ATOM | 97 | CD | ARG | A | 12 | 56.884 | 56.522 | 27.538 | 1.00 | 17.26 |
| ATOM | 98 | NE | ARG | A | 12 | 57.737 | 57.412 | 28.332 | 1.00 | 19.17 |
| ATOM | 99 | CZ | ARG | A | 12 | 58.961 | 57.793 | 28.026 | 1.00 | 24.65 |
| ATOM | 100 | NH1 | ARG | A | 12 | 59.545 | 57.416 | 26.907 | 1.00 | 21.82 |
| ATOM | 101 | NH2 | ARG | A | 12 | 59.630 | 58.580 | 28.874 | 1.00 | 28.03 |
| ATOM | 102 | N | VAL | A | 13 | 57.315 | 51.908 | 31.667 | 1.00 | 15.70 |
| ATOM | 103 | CA | VAL | A | 13 | 57.545 | 51.669 | 33.106 | 1.00 | 14.78 |
| ATOM | 104 | C | VAL | A | 13 | 59.069 | 51.826 | 33.262 | 1.00 | 18.42 |
| ATOM | 105 | O | VAL | A | 13 | 59.877 | 51.698 | 32.280 | 1.00 | 15.58 |
| ATOM | 106 | CB | VAL | A | 13 | 57.146 | 50.312 | 33.603 | 1.00 | 16.79 |
| ATOM | 107 | CG1 | VAL | A | 13 | 55.661 | 50.217 | 33.766 | 1.00 | 18.88 |
| ATOM | 108 | CG2 | VAL | A | 13 | 57.768 | 49.142 | 32.719 | 1.00 | 16.41 |
| ATOM | 109 | N | LYS | A | 14 | 59.524 | 52.096 | 34.513 | 1.00 | 15.68 |
| ATOM | 110 | CA | LYS | A | 14 | 60.941 | 52.258 | 34.789 | 1.00 | 16.45 |
| ATOM | 111 | C | LYS | A | 14 | 61.497 | 51.036 | 35.528 | 1.00 | 16.56 |
| ATOM | 112 | O | LYS | A | 14 | 60.817 | 50.471 | 36.456 | 1.00 | 16.75 |
| ATOM | 113 | CB | LYS | A | 14 | 61.161 | 53.498 | 35.659 | 1.00 | 17.97 |
| ATOM | 114 | CG | LYS | A | 14 | 62.639 | 53.803 | 35.880 | 1.00 | 20.97 |
| ATOM | 115 | CD | LYS | A | 14 | 62.866 | 55.127 | 36.574 | 1.00 | 29.18 |
| ATOM | 116 | CE | LYS | A | 14 | 62.630 | 56.291 | 35.666 | 1.00 | 32.48 |
| ATOM | 117 | NZ | LYS | A | 14 | 62.715 | 57.533 | 36.483 | 1.00 | 33.64 |
| ATOM | 118 | N | VAL | A | 15 | 62.708 | 50.585 | 35.121 | 1.00 | 13.79 |
| ATOM | 119 | CA | VAL | A | 15 | 63.339 | 49.420 | 35.746 | 1.00 | 14.02 |
| ATOM | 120 | C | VAL | A | 15 | 63.786 | 49.854 | 37.179 | 1.00 | 14.49 |
| ATOM | 121 | O | VAL | A | 15 | 64.448 | 50.872 | 37.322 | 1.00 | 14.91 |
| ATOM | 122 | CB | VAL | A | 15 | 64.579 | 48.948 | 34.960 | 1.00 | 14.72 |
| ATOM | 123 | CG1 | VAL | A | 15 | 65.246 | 47.816 | 35.695 | 1.00 | 15.47 |
| ATOM | 124 | CG2 | VAL | A | 15 | 64.092 | 48.461 | 33.499 | 1.00 | 15.44 |
| ATOM | 125 | N | THR | A | 16 | 63.327 | 49.098 | 38.172 | 1.00 | 14.68 |
| ATOM | 126 | CA | THR | A | 16 | 63.637 | 49.433 | 39.582 | 1.00 | 16.18 |
| ATOM | 127 | C | THR | A | 16 | 64.731 | 48.629 | 40.230 | 1.00 | 19.63 |
| ATOM | 128 | O | THR | A | 16 | 65.282 | 49.078 | 41.258 | 1.00 | 18.35 |
| ATOM | 129 | CB | THR | A | 16 | 62.365 | 49.292 | 40.416 | 1.00 | 14.13 |
| ATOM | 130 | OG1 | THR | A | 16 | 61.976 | 47.947 | 40.564 | 1.00 | 17.95 |
| ATOM | 131 | CG2 | THR | A | 16 | 61.253 | 50.204 | 39.873 | 1.00 | 18.04 |

-continued

Data Lists

| | | | | | | | | | |
|---|---|---|---|---|---|---|---|---|---|
| ATOM | 132 | N | HIS | A | 17 | 65.056 | 47.469 | 39.699 | 1.00 | 14.05 |
| ATOM | 133 | CA | HIS | A | 17 | 66.089 | 46.613 | 40.242 | 1.00 | 15.34 |
| ATOM | 134 | C | HIS | A | 17 | 66.664 | 45.687 | 39.129 | 1.00 | 19.86 |
| ATOM | 135 | O | HIS | A | 17 | 65.947 | 45.353 | 38.137 | 1.00 | 17.90 |
| ATOM | 136 | CB | HIS | A | 17 | 65.422 | 45.752 | 41.340 | 1.00 | 18.53 |
| ATOM | 137 | CG | HIS | A | 17 | 66.361 | 44.834 | 42.079 | 1.00 | 22.33 |
| ATOM | 138 | ND1 | HIS | A | 17 | 66.377 | 43.473 | 41.869 | 1.00 | 25.17 |
| ATOM | 139 | CD2 | HIS | A | 17 | 67.273 | 45.068 | 43.071 | 1.00 | 24.77 |
| ATOM | 140 | CE1 | HIS | A | 17 | 67.278 | 42.908 | 42.651 | 1.00 | 25.62 |
| ATOM | 141 | NE2 | HIS | A | 17 | 67.835 | 43.847 | 43.396 | 1.00 | 24.55 |
| ATOM | 142 | N | ALA | A | 18 | 67.902 | 45.246 | 39.301 | 1.00 | 16.82 |
| ATOM | 143 | CA | ALA | A | 18 | 68.552 | 44.311 | 38.349 | 1.00 | 18.95 |
| ATOM | 144 | C | ALA | A | 18 | 69.265 | 43.234 | 39.190 | 1.00 | 25.44 |
| ATOM | 145 | O | ALA | A | 18 | 69.873 | 43.546 | 40.228 | 1.00 | 26.69 |
| ATOM | 146 | CB | ALA | A | 18 | 69.508 | 45.039 | 37.431 | 1.00 | 21.19 |
| ATOM | 147 | N | ASP | A | 19 | 69.136 | 41.983 | 38.815 | 1.00 | 21.26 |
| ATOM | 148 | CA | ASP | A | 19 | 69.749 | 40.895 | 39.580 | 1.00 | 20.78 |
| ATOM | 149 | C | ASP | A | 19 | 70.278 | 39.807 | 38.655 | 1.00 | 21.60 |
| ATOM | 150 | O | ASP | A | 19 | 69.620 | 38.802 | 38.420 | 1.00 | 20.10 |
| ATOM | 151 | CB | ASP | A | 19 | 68.685 | 40.329 | 40.553 | 1.00 | 21.77 |
| ATOM | 152 | CG | ASP | A | 19 | 69.255 | 39.335 | 41.584 | 1.00 | 27.20 |
| ATOM | 153 | OD1 | ASP | A | 19 | 70.469 | 39.097 | 41.617 | 1.00 | 27.06 |
| ATOM | 154 | OD2 | ASP | A | 19 | 68.416 | 38.772 | 42.356 | 1.00 | 28.93 |
| ATOM | 155 | N | LEU | A | 20 | 71.500 | 40.003 | 38.200 | 1.00 | 21.47 |
| ATOM | 156 | CA | LEU | A | 20 | 72.137 | 39.036 | 37.337 | 1.00 | 21.15 |
| ATOM | 157 | C | LEU | A | 20 | 72.212 | 37.654 | 37.924 | 1.00 | 25.20 |
| ATOM | 158 | O | LEU | A | 20 | 72.017 | 36.677 | 37.212 | 1.00 | 24.39 |
| ATOM | 159 | CB | LEU | A | 20 | 73.557 | 39.513 | 36.967 | 1.00 | 21.58 |
| ATOM | 160 | CG | LEU | A | 20 | 74.383 | 38.693 | 35.995 | 1.00 | 24.50 |
| ATOM | 161 | CD1 | LEU | A | 20 | 73.751 | 38.833 | 34.550 | 1.00 | 22.31 |
| ATOM | 162 | CD2 | LEU | A | 20 | 75.811 | 39.297 | 36.010 | 1.00 | 24.07 |
| ATOM | 163 | N | HIS | A | 21 | 72.509 | 37.565 | 39.234 | 1.00 | 23.99 |
| ATOM | 164 | CA | HIS | A | 21 | 72.638 | 36.275 | 39.933 | 1.00 | 26.08 |
| ATOM | 165 | C | HIS | A | 21 | 71.407 | 35.687 | 40.499 | 1.00 | 29.17 |
| ATOM | 166 | O | HIS | A | 21 | 71.493 | 34.758 | 41.302 | 1.00 | 29.91 |
| ATOM | 167 | CB | HIS | A | 21 | 73.769 | 36.384 | 40.973 | 1.00 | 29.07 |
| ATOM | 168 | CG | HIS | A | 21 | 75.006 | 36.943 | 40.395 | 1.00 | 34.17 |
| ATOM | 169 | ND1 | HIS | A | 21 | 75.647 | 36.327 | 39.347 | 1.00 | 37.06 |
| ATOM | 170 | CD2 | HIS | A | 21 | 75.663 | 38.112 | 40.605 | 1.00 | 37.54 |
| ATOM | 171 | CE1 | HIS | A | 21 | 76.679 | 37.059 | 38.967 | 1.00 | 36.64 |
| ATOM | 172 | NE2 | HIS | A | 21 | 76.712 | 38.150 | 39.712 | 1.00 | 37.19 |
| ATOM | 173 | N | TYR | A | 22 | 70.251 | 36.223 | 40.095 | 1.00 | 26.33 |
| ATOM | 174 | CA | TYR | A | 22 | 68.964 | 35.717 | 40.583 | 1.00 | 27.04 |
| ATOM | 175 | C | TYR | A | 22 | 68.951 | 34.193 | 40.565 | 1.00 | 33.24 |
| ATOM | 176 | O | TYR | A | 22 | 69.325 | 33.541 | 39.561 | 1.00 | 26.75 |
| ATOM | 177 | CB | TYR | A | 22 | 67.847 | 36.225 | 39.676 | 1.00 | 28.34 |
| ATOM | 178 | CG | TYR | A | 22 | 66.437 | 35.946 | 40.154 | 1.00 | 30.64 |
| ATOM | 179 | CD1 | TYR | A | 22 | 65.983 | 36.448 | 41.367 | 1.00 | 31.96 |
| ATOM | 180 | CD2 | TYR | A | 22 | 65.562 | 35.230 | 39.361 | 1.00 | 32.31 |
| ATOM | 181 | CE1 | TYR | A | 22 | 64.671 | 36.214 | 41.795 | 1.00 | 32.16 |
| ATOM | 182 | CE2 | TYR | A | 22 | 64.261 | 34.978 | 39.779 | 1.00 | 32.82 |
| ATOM | 183 | CZ | TYR | A | 22 | 63.820 | 35.486 | 40.987 | 1.00 | 36.63 |
| ATOM | 184 | OH | TYR | A | 22 | 62.518 | 35.229 | 41.408 | 1.00 | 38.85 |
| ATOM | 185 | N | GLU | A | 23 | 68.550 | 33.606 | 41.669 | 1.00 | 34.58 |
| ATOM | 186 | CA | GLU | A | 23 | 68.528 | 32.182 | 41.739 | 1.00 | 37.52 |
| ATOM | 187 | C | GLU | A | 23 | 67.204 | 31.479 | 41.529 | 1.00 | 42.30 |
| ATOM | 188 | O | GLU | A | 23 | 67.151 | 30.280 | 41.645 | 1.00 | 40.71 |
| ATOM | 189 | CB | GLU | A | 23 | 69.228 | 31.682 | 43.000 | 1.00 | 39.74 |
| ATOM | 190 | CG | GLU | A | 23 | 70.712 | 32.011 | 43.019 | 1.00 | 50.28 |
| ATOM | 191 | CD | GLU | A | 23 | 71.564 | 30.874 | 42.477 | 1.00 | 61.64 |
| ATOM | 192 | OE1 | GLU | A | 23 | 71.007 | 29.955 | 41.832 | 1.00 | 62.40 |
| ATOM | 193 | OE2 | GLU | A | 23 | 72.796 | 30.894 | 42.709 | 1.00 | 61.54 |
| ATOM | 194 | N | GLY | A | 24 | 66.124 | 32.210 | 41.224 | 1.00 | 39.86 |
| ATOM | 195 | CA | GLY | A | 24 | 64.810 | 31.560 | 41.008 | 1.00 | 43.77 |
| ATOM | 196 | C | GLY | A | 24 | 64.377 | 31.624 | 39.535 | 1.00 | 49.67 |
| ATOM | 197 | O | GLY | A | 24 | 63.254 | 31.166 | 39.188 | 1.00 | 54.64 |
| ATOM | 198 | OH | GLY | A | 24 | 65.142 | 32.147 | 38.706 | 1.00 | 73.31 |
| ATOM | 199 | C | PVL | A | 25 | 62.860 | 38.226 | 34.454 | 1.00 | 17.73 |
| ATOM | 200 | O | PVL | A | 25 | 63.759 | 39.046 | 34.586 | 1.00 | 21.35 |
| ATOM | 201 | CA | PVL | A | 25 | 63.200 | 36.796 | 34.251 | 1.00 | 26.99 |
| ATOM | 202 | CB | PVL | A | 25 | 62.057 | 35.810 | 34.157 | 1.00 | 26.50 |
| ATOM | 203 | ON | PVL | A | 25 | 64.375 | 36.432 | 34.017 | 1.00 | 32.90 |
| ATOM | 204 | N | CYS | A | 26 | 61.544 | 38.621 | 34.583 | 1.00 | 13.65 |
| ATOM | 205 | CA | CYS | A | 26 | 61.178 | 39.997 | 34.916 | 1.00 | 13.69 |
| ATOM | 206 | CB | CYS | A | 26 | 60.770 | 40.866 | 33.674 | 1.00 | 19.50 |
| ATOM | 207 | SG | CYS | A | 26 | 60.527 | 42.598 | 34.108 | 1.00 | 17.42 |
| ATOM | 208 | C | CYS | A | 26 | 60.046 | 39.977 | 35.926 | 1.00 | 17.14 |

-continued

| | | | | | | | | | | |
|---|---|---|---|---|---|---|---|---|---|---|
| ATOM | 209 | O | CYS | A | 26 | 58.943 | 39.511 | 35.648 | 1.00 | 16.98 |
| ATOM | 210 | N | ALA | A | 27 | 60.356 | 40.411 | 37.200 | 1.00 | 14.97 |
| ATOM | 211 | CA | ALA | A | 27 | 59.366 | 40.425 | 38.264 | 1.00 | 14.51 |
| ATOM | 212 | C | ALA | A | 27 | 58.675 | 41.765 | 38.202 | 1.00 | 11.29 |
| ATOM | 213 | O | ALA | A | 27 | 59.305 | 42.828 | 38.099 | 1.00 | 13.77 |
| ATOM | 214 | CB | ALA | A | 27 | 60.106 | 40.243 | 39.609 | 1.00 | 14.33 |
| ATOM | 215 | N | ILE | A | 28 | 57.353 | 41.694 | 38.222 | 1.00 | 12.96 |
| ATOM | 216 | CA | ILE | A | 28 | 56.491 | 42.816 | 38.054 | 1.00 | 12.54 |
| ATOM | 217 | C | ILE | A | 28 | 55.302 | 42.854 | 39.067 | 1.00 | 13.11 |
| ATOM | 218 | O | ILE | A | 28 | 54.648 | 41.858 | 39.298 | 1.00 | 14.34 |
| ATOM | 219 | CB | ILE | A | 28 | 55.815 | 42.718 | 36.559 | 1.00 | 13.91 |
| ATOM | 220 | CG1 | ILE | A | 28 | 56.920 | 42.696 | 35.525 | 1.00 | 15.23 |
| ATOM | 221 | CG2 | ILE | A | 28 | 54.794 | 43.867 | 36.283 | 1.00 | 16.36 |
| ATOM | 222 | CD1 | ILE | A | 28 | 56.376 | 42.100 | 34.149 | 1.00 | 17.00 |
| ATOM | 223 | N | ASP | A | 29 | 55.127 | 44.025 | 39.651 | 1.00 | 15.10 |
| ATOM | 224 | CA | ASP | A | 29 | 54.022 | 44.252 | 40.636 | 1.00 | 14.57 |
| ATOM | 225 | C | ASP | A | 29 | 52.732 | 43.607 | 40.074 | 1.00 | 17.57 |
| ATOM | 226 | O | ASP | A | 29 | 52.315 | 43.902 | 38.916 | 1.00 | 15.63 |
| ATOM | 227 | CB | ASP | A | 29 | 53.864 | 45.728 | 40.818 | 1.00 | 14.77 |
| ATOM | 228 | CG | ASP | A | 29 | 52.748 | 46.139 | 41.788 | 1.00 | 14.70 |
| ATOM | 229 | OD1 | ASP | A | 29 | 51.750 | 45.420 | 41.984 | 1.00 | 15.75 |
| ATOM | 230 | OD2 | ASP | A | 29 | 52.843 | 47.278 | 42.239 | 1.00 | 16.77 |
| ATOM | 231 | N | GLN | A | 30 | 52.123 | 42.710 | 40.841 | 1.00 | 15.71 |
| ATOM | 232 | CA | GLN | A | 30 | 50.878 | 42.040 | 40.414 | 1.00 | 16.19 |
| ATOM | 233 | C | GLN | A | 30 | 49.797 | 43.037 | 39.938 | 1.00 | 17.73 |
| ATOM | 234 | O | GLN | A | 30 | 48.961 | 42.704 | 39.057 | 1.00 | 17.08 |
| ATOM | 235 | CB | GLN | A | 30 | 50.256 | 41.249 | 41.594 | 1.00 | 17.85 |
| ATOM | 236 | CG | GLN | A | 30 | 49.002 | 40.506 | 41.200 | 1.00 | 23.42 |
| ATOM | 237 | CD | GLN | A | 30 | 49.272 | 39.438 | 40.148 | 1.00 | 23.06 |
| ATOM | 238 | OE1 | GLN | A | 30 | 50.062 | 38.487 | 40.361 | 1.00 | 21.11 |
| ATOM | 239 | NE2 | GLN | A | 30 | 48.588 | 39.584 | 38.958 | 1.00 | 20.59 |
| ATOM | 240 | N | ASP | A | 31 | 49.716 | 44.238 | 40.516 | 1.00 | 16.44 |
| ATOM | 241 | CA | ASP | A | 31 | 48.714 | 45.223 | 40.100 | 1.00 | 16.57 |
| ATOM | 242 | C | ASP | A | 31 | 48.977 | 45.579 | 38.606 | 1.00 | 17.31 |
| ATOM | 243 | O | ASP | A | 31 | 47.995 | 45.769 | 37.843 | 1.00 | 17.32 |
| ATOM | 244 | CB | ASP | A | 31 | 48.805 | 46.539 | 40.892 | 1.00 | 19.02 |
| ATOM | 245 | CG | ASP | A | 31 | 48.138 | 46.456 | 42.294 | 1.00 | 24.47 |
| ATOM | 246 | OD1 | ASP | A | 31 | 47.188 | 45.655 | 42.488 | 1.00 | 24.53 |
| ATOM | 247 | OD2 | ASP | A | 31 | 48.596 | 47.257 | 43.166 | 1.00 | 22.76 |
| ATOM | 248 | N | PHE | A | 32 | 50.254 | 45.715 | 38.254 | 1.00 | 14.02 |
| ATOM | 249 | CA | PHE | A | 32 | 50.643 | 46.073 | 36.861 | 1.00 | 13.65 |
| ATOM | 250 | C | PHE | A | 32 | 50.244 | 44.926 | 35.950 | 1.00 | 16.12 |
| ATOM | 251 | O | PHE | A | 32 | 49.661 | 45.197 | 34.838 | 1.00 | 14.39 |
| ATOM | 252 | CB | PHE | A | 32 | 52.130 | 46.329 | 36.726 | 1.00 | 13.80 |
| ATOM | 253 | CG | PHE | A | 32 | 52.665 | 47.491 | 37.522 | 1.00 | 14.18 |
| ATOM | 254 | CD1 | PHE | A | 32 | 51.860 | 48.378 | 38.248 | 1.00 | 15.47 |
| ATOM | 255 | CD2 | PHE | A | 32 | 54.035 | 47.687 | 37.517 | 1.00 | 15.29 |
| ATOM | 256 | CE1 | PHE | A | 32 | 52.485 | 49.495 | 38.988 | 1.00 | 16.12 |
| ATOM | 257 | CE2 | PHE | A | 32 | 54.634 | 48.727 | 38.238 | 1.00 | 16.29 |
| ATOM | 258 | CZ | PHE | A | 32 | 53.855 | 49.634 | 38.963 | 1.00 | 15.53 |
| ATOM | 259 | N | LEU | A | 33 | 50.530 | 43.696 | 36.347 | 1.00 | 15.49 |
| ATOM | 260 | CA | LEU | A | 33 | 50.165 | 42.499 | 35.561 | 1.00 | 13.34 |
| ATOM | 261 | C | LEU | A | 33 | 48.648 | 42.564 | 35.331 | 1.00 | 17.57 |
| ATOM | 262 | O | LEU | A | 33 | 48.144 | 42.392 | 34.195 | 1.00 | 16.65 |
| ATOM | 263 | CB | LEU | A | 33 | 50.522 | 41.184 | 36.282 | 1.00 | 14.40 |
| ATOM | 264 | CG | LEU | A | 33 | 52.018 | 40.976 | 36.508 | 1.00 | 17.89 |
| ATOM | 265 | CD1 | LEU | A | 33 | 52.222 | 39.608 | 37.204 | 1.00 | 15.16 |
| ATOM | 266 | CD2 | LEU | A | 33 | 52.716 | 40.953 | 35.093 | 1.00 | 17.59 |
| ATOM | 267 | N | ASP | A | 34 | 47.856 | 42.816 | 36.382 | 1.00 | 15.41 |
| ATOM | 268 | CA | ASP | A | 34 | 46.391 | 42.861 | 36.217 | 1.00 | 16.06 |
| ATOM | 269 | C | ASP | A | 34 | 45.967 | 43.918 | 35.169 | 1.00 | 18.00 |
| ATOM | 270 | O | ASP | A | 34 | 45.067 | 43.667 | 34.353 | 1.00 | 18.35 |
| ATOM | 271 | CB | ASP | A | 34 | 45.717 | 43.339 | 37.556 | 1.00 | 18.61 |
| ATOM | 272 | CG | ASP | A | 34 | 45.731 | 42.290 | 38.661 | 1.00 | 24.34 |
| ATOM | 273 | OD1 | ASP | A | 34 | 46.077 | 41.121 | 38.437 | 1.00 | 22.17 |
| ATOM | 274 | OD2 | ASP | A | 34 | 45.349 | 42.715 | 39.815 | 1.00 | 28.71 |
| ATOM | 275 | N | ALA | A | 35 | 46.538 | 45.111 | 35.239 | 1.00 | 13.94 |
| ATOM | 276 | CA | ALA | A | 35 | 46.146 | 46.214 | 34.349 | 1.00 | 15.72 |
| ATOM | 277 | C | ALA | A | 35 | 46.430 | 45.899 | 32.899 | 1.00 | 17.50 |
| ATOM | 278 | O | ALA | A | 35 | 45.652 | 46.304 | 32.003 | 1.00 | 18.53 |
| ATOM | 279 | CB | ALA | A | 35 | 46.816 | 47.504 | 34.742 | 1.00 | 16.40 |
| ATOM | 280 | N | ALA | A | 36 | 47.547 | 45.207 | 32.677 | 1.00 | 13.80 |
| ATOM | 281 | CA | ALA | A | 36 | 47.926 | 44.876 | 31.274 | 1.00 | 14.07 |
| ATOM | 282 | C | ALA | A | 36 | 47.370 | 43.515 | 30.855 | 1.00 | 16.21 |
| ATOM | 283 | O | ALA | A | 36 | 47.595 | 43.085 | 29.690 | 1.00 | 16.15 |
| ATOM | 284 | CB | ALA | A | 36 | 49.461 | 44.944 | 31.064 | 1.00 | 14.23 |
| ATOM | 285 | N | GLY | A | 37 | 46.670 | 42.809 | 31.719 | 1.00 | 14.27 |

-continued

Data Lists

| | | | | | | | | | |
|---|---|---|---|---|---|---|---|---|---|
| ATOM | 286 | CA  | GLY | A | 37 | 46.126 | 41.505 | 31.411 | 1.00 | 12.78 |
| ATOM | 287 | C   | GLY | A | 37 | 47.249 | 40.412 | 31.271 | 1.00 | 11.55 |
| ATOM | 288 | O   | GLY | A | 37 | 46.960 | 39.297 | 30.764 | 1.00 | 13.36 |
| ATOM | 289 | N   | ILE | A | 38 | 48.469 | 40.675 | 31.788 | 1.00 | 13.57 |
| ATOM | 290 | CA  | ILE | A | 38 | 49.602 | 39.753 | 31.728 | 1.00 | 13.98 |
| ATOM | 291 | C   | ILE | A | 38 | 49.525 | 38.785 | 32.878 | 1.00 | 16.32 |
| ATOM | 292 | O   | ILE | A | 38 | 49.168 | 39.208 | 34.022 | 1.00 | 16.77 |
| ATOM | 293 | CB  | ILE | A | 38 | 50.930 | 40.521 | 31.729 | 1.00 | 15.34 |
| ATOM | 294 | CG1 | ILE | A | 38 | 50.976 | 41.423 | 30.470 | 1.00 | 14.55 |
| ATOM | 295 | CG2 | ILE | A | 38 | 52.146 | 39.592 | 31.688 | 1.00 | 15.27 |
| ATOM | 296 | CD1 | ILE | A | 38 | 52.162 | 42.332 | 30.393 | 1.00 | 19.63 |
| ATOM | 297 | N   | LEU | A | 39 | 49.805 | 37.537 | 32.591 | 1.00 | 12.96 |
| ATOM | 298 | CA  | LEU | A | 39 | 49.759 | 36.442 | 33.598 | 1.00 | 11.40 |
| ATOM | 299 | C   | LEU | A | 39 | 51.134 | 36.053 | 34.101 | 1.00 | 14.26 |
| ATOM | 300 | O   | LEU | A | 39 | 52.138 | 36.122 | 33.435 | 1.00 | 13.15 |
| ATOM | 301 | CB  | LEU | A | 39 | 49.109 | 35.177 | 33.041 | 1.00 | 12.16 |
| ATOM | 302 | CG  | LEU | A | 39 | 47.752 | 35.258 | 32.327 | 1.00 | 13.32 |
| ATOM | 303 | CD1 | LEU | A | 39 | 47.245 | 33.957 | 31.795 | 1.00 | 13.99 |
| ATOM | 304 | CD2 | LEU | A | 39 | 46.722 | 35.899 | 33.344 | 1.00 | 17.01 |
| ATOM | 305 | N   | GLU | A | 40 | 51.183 | 35.619 | 35.385 | 1.00 | 14.46 |
| ATOM | 306 | CA  | GLU | A | 40 | 52.460 | 35.148 | 35.863 | 1.00 | 15.39 |
| ATOM | 307 | C   | GLU | A | 40 | 52.828 | 33.894 | 34.973 | 1.00 | 13.93 |
| ATOM | 308 | O   | GLU | A | 40 | 51.988 | 33.067 | 34.640 | 1.00 | 13.92 |
| ATOM | 309 | CB  | GLU | A | 40 | 52.292 | 34.646 | 37.350 | 1.00 | 17.33 |
| ATOM | 310 | CG  | GLU | A | 40 | 53.617 | 34.054 | 37.878 | 1.00 | 22.86 |
| ATOM | 311 | CD  | GLU | A | 40 | 53.773 | 34.134 | 39.395 | 1.00 | 37.57 |
| ATOM | 312 | OE1 | GLU | A | 40 | 52.744 | 33.891 | 40.044 | 1.00 | 29.60 |
| ATOM | 313 | OE2 | GLU | A | 40 | 54.908 | 34.446 | 39.887 | 1.00 | 24.74 |
| ATOM | 314 | N   | ASN | A | 41 | 54.108 | 33.828 | 34.623 | 1.00 | 12.53 |
| ATOM | 315 | CA  | ASN | A | 41 | 54.739 | 32.808 | 33.826 | 1.00 | 12.52 |
| ATOM | 316 | C   | ASN | A | 41 | 54.433 | 33.020 | 32.318 | 1.00 | 13.84 |
| ATOM | 317 | O   | ASN | A | 41 | 54.806 | 32.130 | 31.523 | 1.00 | 13.31 |
| ATOM | 318 | CB  | ASN | A | 41 | 54.390 | 31.431 | 34.223 | 1.00 | 14.21 |
| ATOM | 319 | CG  | ASN | A | 41 | 54.886 | 31.102 | 35.690 | 1.00 | 18.26 |
| ATOM | 320 | OD1 | ASN | A | 41 | 56.030 | 31.307 | 36.004 | 1.00 | 19.96 |
| ATOM | 321 | ND2 | ASN | A | 41 | 53.970 | 30.620 | 36.521 | 1.00 | 23.65 |
| ATOM | 322 | N   | GLU | A | 42 | 53.772 | 34.119 | 31.971 | 1.00 | 12.49 |
| ATOM | 323 | CA  | GLU | A | 42 | 53.479 | 34.350 | 30.505 | 1.00 | 11.09 |
| ATOM | 324 | C   | GLU | A | 42 | 54.733 | 34.843 | 29.866 | 1.00 | 12.61 |
| ATOM | 325 | O   | GLU | A | 42 | 55.513 | 35.612 | 30.413 | 1.00 | 13.32 |
| ATOM | 326 | CB  | GLU | A | 42 | 52.425 | 35.399 | 30.378 | 1.00 | 11.37 |
| ATOM | 327 | CG  | GLU | A | 42 | 51.952 | 35.601 | 28.887 | 1.00 | 13.79 |
| ATOM | 328 | CD  | GLU | A | 42 | 50.768 | 36.534 | 28.828 | 1.00 | 16.86 |
| ATOM | 329 | OE1 | GLU | A | 42 | 50.420 | 37.221 | 29.808 | 1.00 | 14.48 |
| ATOM | 330 | OE2 | GLU | A | 42 | 50.126 | 36.672 | 27.703 | 1.00 | 11.57 |
| ATOM | 331 | N   | ALA | A | 43 | 54.906 | 34.509 | 28.554 | 1.00 | 11.23 |
| ATOM | 332 | CA  | ALA | A | 43 | 56.007 | 35.047 | 27.813 | 1.00 | 11.52 |
| ATOM | 333 | C   | ALA | A | 43 | 55.751 | 36.568 | 27.567 | 1.00 | 12.62 |
| ATOM | 334 | O   | ALA | A | 43 | 54.597 | 37.005 | 27.290 | 1.00 | 11.29 |
| ATOM | 335 | CB  | ALA | A | 43 | 56.006 | 34.370 | 26.420 | 1.00 | 11.84 |
| ATOM | 336 | N   | ILE | A | 44 | 56.805 | 37.359 | 27.702 | 1.00 | 10.61 |
| ATOM | 337 | CA  | ILE | A | 44 | 56.733 | 38.810 | 27.493 | 1.00 |  9.63 |
| ATOM | 338 | C   | ILE | A | 44 | 57.918 | 39.296 | 26.651 | 1.00 | 11.21 |
| ATOM | 339 | O   | ILE | A | 44 | 59.026 | 38.712 | 26.696 | 1.00 | 11.77 |
| ATOM | 340 | CB  | ILE | A | 44 | 56.682 | 39.604 | 28.857 | 1.00 | 11.13 |
| ATOM | 341 | CG1 | ILE | A | 44 | 57.879 | 39.178 | 29.734 | 1.00 | 12.75 |
| ATOM | 342 | CG2 | ILE | A | 44 | 55.328 | 39.346 | 29.486 | 1.00 | 11.62 |
| ATOM | 343 | CD1 | ILE | A | 44 | 58.019 | 40.058 | 31.041 | 1.00 | 16.57 |
| ATOM | 344 | N   | ASP | A | 45 | 57.676 | 40.362 | 25.894 | 1.00 | 11.18 |
| ATOM | 345 | CA  | ASP | A | 45 | 58.716 | 40.991 | 25.140 | 1.00 | 10.11 |
| ATOM | 346 | C   | ASP | A | 45 | 59.008 | 42.359 | 25.805 | 1.00 | 11.65 |
| ATOM | 347 | O   | ASP | A | 45 | 58.063 | 43.075 | 26.222 | 1.00 | 12.76 |
| ATOM | 348 | CB  | ASP | A | 45 | 58.208 | 41.256 | 23.682 | 1.00 | 11.49 |
| ATOM | 349 | CG  | ASP | A | 45 | 57.941 | 39.984 | 22.954 | 1.00 | 12.09 |
| ATOM | 350 | OD1 | ASP | A | 45 | 58.610 | 38.923 | 23.143 | 1.00 | 13.27 |
| ATOM | 351 | OD2 | ASP | A | 45 | 56.942 | 40.040 | 22.120 | 1.00 | 16.15 |
| ATOM | 352 | N   | ILE | A | 46 | 60.287 | 42.698 | 25.967 | 1.00 | 12.45 |
| ATOM | 353 | CA  | ILE | A | 46 | 60.676 | 43.964 | 26.617 | 1.00 | 11.69 |
| ATOM | 354 | C   | ILE | A | 46 | 61.478 | 44.752 | 25.640 | 1.00 | 13.15 |
| ATOM | 355 | O   | ILE | A | 46 | 62.482 | 44.255 | 25.076 | 1.00 | 13.26 |
| ATOM | 356 | CB  | ILE | A | 46 | 61.482 | 43.643 | 27.903 | 1.00 | 13.14 |
| ATOM | 357 | CG1 | ILE | A | 46 | 60.601 | 42.768 | 28.783 | 1.00 | 12.28 |
| ATOM | 358 | CG2 | ILE | A | 46 | 61.923 | 44.987 | 28.578 | 1.00 | 13.37 |
| ATOM | 359 | CD1 | ILE | A | 46 | 61.243 | 42.613 | 30.298 | 1.00 | 14.34 |
| ATOM | 360 | N   | TRP | A | 47 | 61.006 | 45.980 | 25.380 | 1.00 | 12.56 |
| ATOM | 361 | CA  | TRP | A | 47 | 61.641 | 46.875 | 24.399 | 1.00 | 11.59 |
| ATOM | 362 | C   | TRP | A | 47 | 62.178 | 48.069 | 25.241 | 1.00 | 12.65 |

-continued

Data Lists

| ATOM | 363 | O   | TRP | A | 47 | 61.400 | 48.793 | 25.849 | 1.00 | 13.30 |
| ATOM | 364 | CB  | TRP | A | 47 | 60.568 | 47.322 | 23.405 | 1.00 | 11.85 |
| ATOM | 365 | CG  | TRP | A | 47 | 59.929 | 46.134 | 22.708 | 1.00 | 11.21 |
| ATOM | 366 | CD1 | TRP | A | 47 | 60.560 | 45.005 | 22.299 | 1.00 | 12.57 |
| ATOM | 367 | CD2 | TRP | A | 47 | 58.558 | 46.012 | 22.330 | 1.00 | 12.14 |
| ATOM | 368 | NE1 | TRP | A | 47 | 59.646 | 44.145 | 21.663 | 1.00 | 11.88 |
| ATOM | 369 | CE2 | TRP | A | 47 | 58.417 | 44.748 | 21.674 | 1.00 | 10.79 |
| ATOM | 370 | CE3 | TRP | A | 47 | 57.437 | 46.819 | 22.525 | 1.00 | 14.11 |
| ATOM | 371 | CZ2 | TRP | A | 47 | 57.169 | 44.279 | 21.207 | 1.00 | 11.66 |
| ATOM | 372 | CZ3 | TRP | A | 47 | 56.173 | 46.361 | 22.020 | 1.00 | 14.28 |
| ATOM | 373 | CH2 | TRP | A | 47 | 56.091 | 45.074 | 21.376 | 1.00 | 14.15 |
| ATOM | 374 | N   | ASN | A | 48 | 63.480 | 48.235 | 25.209 | 1.00 | 12.67 |
| ATOM | 375 | CA  | ASN | A | 48 | 64.154 | 49.253 | 26.002 | 1.00 | 14.84 |
| ATOM | 376 | C   | ASN | A | 48 | 64.201 | 50.575 | 25.283 | 1.00 | 14.53 |
| ATOM | 377 | O   | ASN | A | 48 | 65.004 | 50.755 | 24.291 | 1.00 | 15.46 |
| ATOM | 378 | CB  | ASN | A | 48 | 65.526 | 48.733 | 26.416 | 1.00 | 13.17 |
| ATOM | 379 | CG  | ASN | A | 48 | 66.157 | 49.544 | 27.555 | 1.00 | 12.09 |
| ATOM | 380 | OD1 | ASN | A | 48 | 66.120 | 50.736 | 27.534 | 1.00 | 14.55 |
| ATOM | 381 | ND2 | ASN | A | 48 | 66.861 | 48.842 | 28.433 | 1.00 | 14.53 |
| ATOM | 382 | N   | VAL | A | 49 | 63.389 | 51.514 | 25.726 | 1.00 | 13.24 |
| ATOM | 383 | CA  | VAL | A | 49 | 63.372 | 52.806 | 25.119 | 1.00 | 13.19 |
| ATOM | 384 | C   | VAL | A | 49 | 64.680 | 53.581 | 25.322 | 1.00 | 18.14 |
| ATOM | 385 | O   | VAL | A | 49 | 65.121 | 54.385 | 24.480 | 1.00 | 19.15 |
| ATOM | 386 | CB  | VAL | A | 49 | 62.180 | 53.670 | 25.631 | 1.00 | 15.64 |
| ATOM | 387 | CG1 | VAL | A | 49 | 62.151 | 55.015 | 24.907 | 1.00 | 17.34 |
| ATOM | 388 | CG2 | VAL | A | 49 | 60.838 | 52.930 | 25.473 | 1.00 | 15.21 |
| ATOM | 389 | N   | THR | A | 50 | 65.328 | 53.372 | 26.474 | 1.00 | 14.80 |
| ATOM | 390 | CA  | THR | A | 50 | 66.553 | 54.086 | 26.727 | 1.00 | 14.70 |
| ATOM | 391 | C   | THR | A | 50 | 67.756 | 53.642 | 25.869 | 1.00 | 15.83 |
| ATOM | 392 | O   | THR | A | 50 | 68.460 | 54.508 | 25.322 | 1.00 | 18.87 |
| ATOM | 393 | CB  | THR | A | 50 | 66.910 | 53.985 | 28.265 | 1.00 | 18.21 |
| ATOM | 394 | OG1 | THR | A | 50 | 65.832 | 54.538 | 28.996 | 1.00 | 15.78 |
| ATOM | 395 | CG2 | THR | A | 50 | 68.159 | 54.773 | 28.550 | 1.00 | 16.82 |
| ATOM | 396 | N   | ASN | A | 51 | 67.997 | 52.351 | 25.772 | 1.00 | 14.06 |
| ATOM | 397 | CA  | ASN | A | 51 | 69.160 | 51.861 | 25.010 | 1.00 | 15.31 |
| ATOM | 398 | C   | ASN | A | 51 | 68.884 | 51.123 | 23.688 | 1.00 | 17.85 |
| ATOM | 399 | O   | ASN | A | 51 | 69.816 | 50.692 | 23.031 | 1.00 | 17.40 |
| ATOM | 400 | CB  | ASN | A | 51 | 70.089 | 51.021 | 25.909 | 1.00 | 18.14 |
| ATOM | 401 | CG  | ASN | A | 51 | 69.476 | 49.674 | 26.309 | 1.00 | 20.44 |
| ATOM | 402 | OD1 | ASN | A | 51 | 68.497 | 49.227 | 25.701 | 1.00 | 16.68 |
| ATOM | 403 | ND2 | ASN | A | 51 | 70.059 | 48.998 | 27.332 | 1.00 | 16.78 |
| ATOM | 404 | N   | GLY | A | 52 | 67.609 | 50.981 | 23.350 | 1.00 | 15.39 |
| ATOM | 405 | CA  | GLY | A | 52 | 67.235 | 50.290 | 22.093 | 1.00 | 16.35 |
| ATOM | 406 | C   | GLY | A | 52 | 67.255 | 48.776 | 22.108 | 1.00 | 18.04 |
| ATOM | 407 | O   | GLY | A | 52 | 66.818 | 48.153 | 21.106 | 1.00 | 15.14 |
| ATOM | 408 | N   | LYS | A | 53 | 67.728 | 48.111 | 23.180 | 1.00 | 13.62 |
| ATOM | 409 | CA  | LYS | A | 53 | 67.752 | 46.655 | 23.215 | 1.00 | 13.33 |
| ATOM | 410 | C   | LYS | A | 53 | 66.349 | 46.078 | 23.261 | 1.00 | 13.70 |
| ATOM | 411 | O   | LYS | A | 53 | 65.429 | 46.699 | 23.798 | 1.00 | 13.57 |
| ATOM | 412 | CB  | LYS | A | 53 | 68.618 | 46.094 | 24.379 | 1.00 | 15.27 |
| ATOM | 413 | CG  | LYS | A | 53 | 70.012 | 46.653 | 24.326 | 1.00 | 16.18 |
| ATOM | 414 | CD  | LYS | A | 53 | 70.885 | 45.950 | 25.341 | 1.00 | 18.83 |
| ATOM | 415 | CE  | LYS | A | 53 | 72.239 | 46.673 | 25.454 | 1.00 | 24.88 |
| ATOM | 416 | NZ  | LYS | A | 53 | 73.095 | 46.121 | 26.635 | 1.00 | 24.28 |
| ATOM | 417 | N   | ARG | A | 54 | 66.162 | 44.891 | 22.656 | 1.00 | 12.69 |
| ATOM | 418 | CA  | ARG | A | 54 | 64.873 | 44.207 | 22.584 | 1.00 | 11.88 |
| ATOM | 419 | C   | ARG | A | 54 | 65.109 | 42.735 | 22.949 | 1.00 | 14.37 |
| ATOM | 420 | O   | ARG | A | 54 | 65.984 | 42.067 | 22.418 | 1.00 | 13.79 |
| ATOM | 421 | CB  | ARG | A | 54 | 64.308 | 44.294 | 21.128 | 1.00 | 11.58 |
| ATOM | 422 | CG  | ARG | A | 54 | 64.188 | 45.704 | 20.705 | 1.00 | 12.91 |
| ATOM | 423 | CD  | ARG | A | 54 | 63.609 | 45.807 | 19.209 | 1.00 | 13.98 |
| ATOM | 424 | NE  | ARG | A | 54 | 62.173 | 45.652 | 19.138 | 1.00 | 15.65 |
| ATOM | 425 | CZ  | ARG | A | 54 | 61.300 | 46.628 | 19.354 | 1.00 | 13.20 |
| ATOM | 426 | NH1 | ARG | A | 54 | 61.742 | 47.863 | 19.705 | 1.00 | 13.97 |
| ATOM | 427 | NH2 | ARG | A | 54 | 59.988 | 46.434 | 19.232 | 1.00 | 12.47 |
| ATOM | 428 | N   | PHE | A | 55 | 64.333 | 42.196 | 23.889 | 1.00 | 13.21 |
| ATOM | 429 | CA  | PHE | A | 55 | 64.532 | 40.807 | 24.304 | 1.00 | 11.72 |
| ATOM | 430 | C   | PHE | A | 55 | 63.205 | 40.203 | 24.780 | 1.00 | 12.09 |
| ATOM | 431 | O   | PHE | A | 55 | 62.219 | 40.972 | 25.049 | 1.00 | 14.53 |
| ATOM | 432 | CB  | PHE | A | 55 | 65.612 | 40.693 | 25.418 | 1.00 | 12.81 |
| ATOM | 433 | CG  | PHE | A | 55 | 65.290 | 41.475 | 26.699 | 1.00 | 14.26 |
| ATOM | 434 | CD1 | PHE | A | 55 | 65.511 | 42.830 | 26.778 | 1.00 | 15.91 |
| ATOM | 435 | CD2 | PHE | A | 55 | 64.851 | 40.799 | 27.810 | 1.00 | 16.89 |
| ATOM | 436 | CE1 | PHE | A | 55 | 65.256 | 43.541 | 27.972 | 1.00 | 18.73 |
| ATOM | 437 | CE2 | PHE | A | 55 | 64.603 | 41.504 | 28.989 | 1.00 | 18.14 |
| ATOM | 438 | CZ  | PHE | A | 55 | 64.803 | 42.824 | 29.062 | 1.00 | 16.81 |
| ATOM | 439 | N   | SER | A | 56 | 63.195 | 38.884 | 24.887 | 1.00 | 12.30 |

-continued

Data Lists

| ATOM | 440 | CA | SER | A | 56 | 62.000 | 38.137 | 25.279 | 1.00 | 11.60 |
| ATOM | 441 | C | SER | A | 56 | 62.321 | 37.267 | 26.506 | 1.00 | 13.08 |
| ATOM | 442 | O | SER | A | 56 | 63.361 | 36.664 | 26.570 | 1.00 | 12.92 |
| ATOM | 443 | CB | SER | A | 56 | 61.485 | 37.268 | 24.140 | 1.00 | 14.04 |
| ATOM | 444 | OG | SER | A | 56 | 61.166 | 38.129 | 23.026 | 1.00 | 17.74 |
| ATOM | 445 | N | THR | A | 57 | 61.408 | 37.272 | 27.461 | 1.00 | 12.51 |
| ATOM | 446 | CA | THR | A | 57 | 61.598 | 36.500 | 28.703 | 1.00 | 15.14 |
| ATOM | 447 | C | THR | A | 57 | 60.206 | 36.070 | 29.208 | 1.00 | 16.57 |
| ATOM | 448 | O | THR | A | 57 | 59.313 | 35.793 | 28.389 | 1.00 | 13.36 |
| ATOM | 449 | CB | THR | A | 57 | 62.368 | 37.331 | 29.719 | 1.00 | 17.35 |
| ATOM | 450 | OG1 | THR | A | 57 | 62.652 | 36.502 | 30.862 | 1.00 | 17.51 |
| ATOM | 451 | CG2 | THR | A | 57 | 61.695 | 38.645 | 30.120 | 1.00 | 19.79 |
| ATOM | 452 | N | TYR | A | 58 | 59.971 | 35.950 | 30.539 | 1.00 | 13.07 |
| ATOM | 453 | CA | TYR | A | 58 | 58.641 | 35.565 | 31.042 | 1.00 | 11.86 |
| ATOM | 454 | C | TYR | A | 58 | 58.405 | 36.396 | 32.333 | 1.00 | 14.46 |
| ATOM | 455 | O | TYR | A | 58 | 59.351 | 36.898 | 32.907 | 1.00 | 14.80 |
| ATOM | 456 | CB | TYR | A | 58 | 58.474 | 34.094 | 31.314 | 1.00 | 11.64 |
| ATOM | 457 | CG | TYR | A | 58 | 59.412 | 33.543 | 32.372 | 1.00 | 14.08 |
| ATOM | 458 | CD1 | TYR | A | 58 | 60.722 | 33.204 | 32.057 | 1.00 | 14.47 |
| ATOM | 459 | CD2 | TYR | A | 58 | 58.962 | 33.402 | 33.703 | 1.00 | 16.79 |
| ATOM | 460 | CE1 | TYR | A | 58 | 61.591 | 32.711 | 33.019 | 1.00 | 19.79 |
| ATOM | 461 | CE2 | TYR | A | 58 | 59.850 | 32.890 | 34.685 | 1.00 | 15.79 |
| ATOM | 462 | CZ | TYR | A | 58 | 61.134 | 32.569 | 34.321 | 1.00 | 22.24 |
| ATOM | 463 | OH | TYR | A | 58 | 61.935 | 32.108 | 35.380 | 1.00 | 23.11 |
| ATOM | 464 | N | ALA | A | 59 | 57.139 | 36.566 | 32.673 | 1.00 | 11.72 |
| ATOM | 465 | CA | ALA | A | 59 | 56.764 | 37.373 | 33.834 | 1.00 | 12.72 |
| ATOM | 466 | C | ALA | A | 59 | 56.719 | 36.582 | 35.105 | 1.00 | 12.49 |
| ATOM | 467 | O | ALA | A | 59 | 56.191 | 35.479 | 35.157 | 1.00 | 13.37 |
| ATOM | 468 | CB | ALA | A | 59 | 55.325 | 37.956 | 33.607 | 1.00 | 13.81 |
| ATOM | 469 | N | ILE | A | 60 | 57.259 | 37.249 | 36.146 | 1.00 | 15.14 |
| ATOM | 470 | CA | ILE | A | 60 | 57.221 | 36.693 | 37.546 | 1.00 | 16.33 |
| ATOM | 471 | C | ILE | A | 60 | 56.402 | 37.733 | 38.349 | 1.00 | 16.77 |
| ATOM | 472 | O | ILE | A | 60 | 56.575 | 38.937 | 38.182 | 1.00 | 14.68 |
| ATOM | 473 | CB | ILE | A | 60 | 58.619 | 36.674 | 38.126 | 1.00 | 18.30 |
| ATOM | 474 | CG1 | ILE | A | 60 | 59.497 | 35.633 | 37.421 | 1.00 | 19.09 |
| ATOM | 475 | CG2 | ILE | A | 60 | 58.553 | 36.414 | 39.697 | 1.00 | 21.06 |
| ATOM | 476 | CD1 | ILE | A | 60 | 60.986 | 35.801 | 37.681 | 1.00 | 26.31 |
| ATOM | 477 | N | ALA | A | 61 | 55.480 | 37.268 | 39.208 | 1.00 | 15.66 |
| ATOM | 478 | CA | ALA | A | 61 | 54.713 | 38.264 | 39.966 | 1.00 | 15.73 |
| ATOM | 479 | C | ALA | A | 61 | 55.517 | 38.764 | 41.199 | 1.00 | 18.47 |
| ATOM | 480 | O | ALA | A | 61 | 56.163 | 37.978 | 41.882 | 1.00 | 23.19 |
| ATOM | 481 | CB | ALA | A | 61 | 53.384 | 37.696 | 40.428 | 1.00 | 17.99 |
| ATOM | 482 | N | ALA | A | 62 | 55.470 | 40.063 | 41.393 | 1.00 | 14.95 |
| ATOM | 483 | CA | ALA | A | 62 | 56.093 | 40.757 | 42.560 | 1.00 | 14.55 |
| ATOM | 484 | C | ALA | A | 62 | 54.872 | 41.146 | 43.391 | 1.00 | 18.92 |
| ATOM | 485 | O | ALA | A | 62 | 53.715 | 41.217 | 42.964 | 1.00 | 17.86 |
| ATOM | 486 | CB | ALA | A | 62 | 56.883 | 42.004 | 42.189 | 1.00 | 13.98 |
| ATOM | 487 | N | GLU | A | 63 | 55.159 | 41.391 | 44.690 | 1.00 | 17.78 |
| ATOM | 488 | CA | GLU | A | 63 | 54.108 | 41.762 | 45.620 | 1.00 | 19.52 |
| ATOM | 489 | C | GLU | A | 63 | 53.226 | 42.917 | 45.151 | 1.00 | 19.81 |
| ATOM | 490 | O | GLU | A | 63 | 53.728 | 43.915 | 44.654 | 1.00 | 17.13 |
| ATOM | 491 | CB | GLU | A | 63 | 54.809 | 42.221 | 46.926 | 1.00 | 21.37 |
| ATOM | 492 | CG | GLU | A | 63 | 53.838 | 42.563 | 48.082 | 1.00 | 29.86 |
| ATOM | 493 | CD | GLU | A | 63 | 54.387 | 43.633 | 49.041 | 1.00 | 53.22 |
| ATOM | 494 | OE1 | GLU | A | 63 | 55.572 | 44.035 | 48.935 | 1.00 | 44.04 |
| ATOM | 495 | OE2 | GLU | A | 63 | 53.610 | 44.064 | 49.915 | 1.00 | 43.79 |
| ATOM | 496 | N | ARG | A | 64 | 51.924 | 42.783 | 45.347 | 1.00 | 16.26 |
| ATOM | 497 | CA | ARG | A | 64 | 50.979 | 43.805 | 44.987 | 1.00 | 16.34 |
| ATOM | 498 | C | ARG | A | 64 | 51.297 | 45.121 | 45.697 | 1.00 | 21.13 |
| ATOM | 499 | O | ARG | A | 64 | 51.433 | 45.142 | 46.954 | 1.00 | 20.36 |
| ATOM | 500 | CB | ARG | A | 64 | 49.552 | 43.360 | 45.289 | 1.00 | 19.26 |
| ATOM | 501 | CG | ARG | A | 64 | 48.544 | 44.299 | 44.749 | 1.00 | 26.38 |
| ATOM | 502 | CD | ARG | A | 64 | 47.108 | 43.842 | 44.982 | 1.00 | 27.64 |
| ATOM | 503 | NE | ARG | A | 64 | 46.789 | 42.467 | 44.605 | 1.00 | 26.53 |
| ATOM | 504 | CZ | ARG | A | 64 | 46.420 | 42.092 | 43.371 | 1.00 | 41.54 |
| ATOM | 505 | NH1 | ARG | A | 64 | 46.373 | 42.981 | 42.364 | 1.00 | 23.51 |
| ATOM | 506 | NH2 | ARG | A | 64 | 46.122 | 40.831 | 43.137 | 1.00 | 30.75 |
| ATOM | 507 | N | GLY | A | 65 | 51.430 | 46.204 | 44.963 | 1.00 | 17.09 |
| ATOM | 508 | CA | GLY | A | 65 | 51.707 | 47.513 | 45.507 | 1.00 | 17.60 |
| ATOM | 509 | C | GLY | A | 65 | 53.195 | 47.853 | 45.639 | 1.00 | 18.83 |
| ATOM | 510 | O | GLY | A | 65 | 53.551 | 48.980 | 46.004 | 1.00 | 20.21 |
| ATOM | 511 | N | SER | A | 66 | 54.074 | 46.897 | 45.329 | 1.00 | 16.18 |
| ATOM | 512 | CA | SER | A | 66 | 55.502 | 47.099 | 45.413 | 1.00 | 15.57 |
| ATOM | 513 | C | SER | A | 66 | 56.089 | 47.993 | 44.302 | 1.00 | 19.13 |
| ATOM | 514 | O | SER | A | 66 | 57.144 | 48.615 | 44.440 | 1.00 | 18.34 |
| ATOM | 515 | CB | SER | A | 66 | 56.223 | 45.788 | 45.382 | 1.00 | 18.61 |
| ATOM | 516 | OG | SER | A | 66 | 56.092 | 45.139 | 44.066 | 1.00 | 17.83 |

-continued

Data Lists

| | | | | | | | | | | |
|---|---|---|---|---|---|---|---|---|---|---|
| ATOM | 517 | N | ARG | A | 67 | 55.339 | 48.040 | 43.176 | 1.00 | 16.53 |
| ATOM | 518 | CA | ARG | A | 67 | 55.762 | 48.826 | 41.973 | 1.00 | 17.76 |
| ATOM | 519 | C | ARG | A | 67 | 57.111 | 48.346 | 41.419 | 1.00 | 14.93 |
| ATOM | 520 | O | ARG | A | 67 | 57.803 | 49.101 | 40.784 | 1.00 | 16.56 |
| ATOM | 521 | CB | ARG | A | 67 | 55.791 | 50.324 | 42.242 | 1.00 | 15.58 |
| ATOM | 522 | CG | ARG | A | 67 | 54.431 | 50.904 | 42.651 | 1.00 | 14.91 |
| ATOM | 523 | CD | ARG | A | 67 | 54.376 | 52.362 | 42.553 | 1.00 | 13.81 |
| ATOM | 524 | NE | ARG | A | 67 | 53.069 | 52.872 | 43.035 | 1.00 | 16.78 |
| ATOM | 525 | CZ | ARG | A | 67 | 52.677 | 54.135 | 42.909 | 1.00 | 18.26 |
| ATOM | 526 | NH1 | ARG | A | 67 | 53.438 | 55.053 | 42.332 | 1.00 | 18.16 |
| ATOM | 527 | NH2 | ARG | A | 67 | 51.487 | 54.504 | 43.395 | 1.00 | 19.31 |
| ATOM | 528 | N | ILE | A | 68 | 57.444 | 47.091 | 41.670 | 1.00 | 13.92 |
| ATOM | 529 | CA | ILE | A | 68 | 58.720 | 46.535 | 41.233 | 1.00 | 13.11 |
| ATOM | 530 | C | ILE | A | 68 | 58.661 | 46.183 | 39.704 | 1.00 | 14.96 |
| ATOM | 531 | O | ILE | A | 68 | 57.632 | 45.692 | 39.216 | 1.00 | 16.08 |
| ATOM | 532 | CB | ILE | A | 68 | 59.009 | 45.237 | 42.014 | 1.00 | 16.07 |
| ATOM | 533 | CG1 | ILE | A | 68 | 59.387 | 45.593 | 43.529 | 1.00 | 15.43 |
| ATOM | 534 | CG2 | ILE | A | 68 | 60.143 | 44.394 | 41.325 | 1.00 | 14.91 |
| ATOM | 535 | CD1 | ILE | A | 68 | 59.427 | 44.398 | 44.371 | 1.00 | 17.12 |
| ATOM | 536 | N | ILE | A | 69 | 59.782 | 46.449 | 39.064 | 1.00 | 15.79 |
| ATOM | 537 | CA | ILE | A | 69 | 60.095 | 46.043 | 37.673 | 1.00 | 14.43 |
| ATOM | 538 | C | ILE | A | 69 | 61.570 | 45.598 | 37.885 | 1.00 | 12.91 |
| ATOM | 539 | O | ILE | A | 69 | 62.494 | 46.446 | 37.839 | 1.00 | 16.10 |
| ATOM | 540 | CB | ILE | A | 69 | 60.003 | 47.141 | 36.653 | 1.00 | 14.38 |
| ATOM | 541 | CG1 | ILE | A | 69 | 58.579 | 47.740 | 36.528 | 1.00 | 14.18 |
| ATOM | 542 | CG2 | ILE | A | 69 | 60.415 | 46.555 | 35.241 | 1.00 | 14.77 |
| ATOM | 543 | CD1 | ILE | A | 69 | 57.484 | 46.764 | 35.993 | 1.00 | 13.25 |
| ATOM | 544 | N | SER | A | 70 | 61.794 | 44.306 | 38.101 | 1.00 | 12.61 |
| ATOM | 545 | CA | SER | A | 70 | 63.124 | 43.778 | 38.331 | 1.00 | 12.79 |
| ATOM | 546 | C | SER | A | 70 | 63.559 | 42.861 | 37.151 | 1.00 | 16.65 |
| ATOM | 547 | O | SER | A | 70 | 62.929 | 41.846 | 36.887 | 1.00 | 16.44 |
| ATOM | 548 | CB | SER | A | 70 | 63.136 | 42.977 | 39.663 | 1.00 | 17.19 |
| ATOM | 549 | OG | SER | A | 70 | 64.479 | 42.512 | 39.964 | 1.00 | 19.28 |
| ATOM | 550 | N | VAL | A | 71 | 64.653 | 43.229 | 36.521 | 1.00 | 16.77 |
| ATOM | 551 | CA | VAL | A | 71 | 65.194 | 42.443 | 35.375 | 1.00 | 16.54 |
| ATOM | 552 | C | VAL | A | 71 | 66.231 | 41.490 | 36.002 | 1.00 | 18.47 |
| ATOM | 553 | O | VAL | A | 71 | 67.253 | 41.930 | 36.571 | 1.00 | 20.32 |
| ATOM | 554 | CB | VAL | A | 71 | 65.746 | 43.437 | 34.301 | 1.00 | 21.34 |
| ATOM | 555 | CG1 | VAL | A | 71 | 66.394 | 42.692 | 33.158 | 1.00 | 23.85 |
| ATOM | 556 | CG2 | VAL | A | 71 | 64.618 | 44.286 | 33.711 | 1.00 | 21.90 |
| ATOM | 557 | N | ASN | A | 72 | 65.953 | 40.204 | 35.942 | 1.00 | 17.21 |
| ATOM | 558 | CA | ASN | A | 72 | 66.764 | 39.178 | 36.560 | 1.00 | 18.06 |
| ATOM | 559 | C | ASN | A | 72 | 67.441 | 38.224 | 35.601 | 1.00 | 22.03 |
| ATOM | 560 | C | ASN | A | 72 | 67.039 | 38.141 | 34.422 | 1.00 | 20.77 |
| ATOM | 561 | CB | ASN | A | 72 | 65.847 | 38.323 | 37.470 | 1.00 | 15.71 |
| ATOM | 562 | CG | ASN | A | 72 | 65.116 | 39.170 | 38.557 | 1.00 | 21.14 |
| ATOM | 563 | OD1 | ASN | A | 72 | 65.574 | 40.229 | 38.928 | 1.00 | 22.76 |
| ATOM | 564 | ND2 | ASN | A | 72 | 63.951 | 38.678 | 38.978 | 1.00 | 26.84 |
| ATOM | 565 | N | GLY | A | 73 | 68.433 | 37.487 | 36.082 | 1.00 | 17.96 |
| ATOM | 566 | CA | GLY | A | 73 | 69.132 | 36.519 | 35.239 | 1.00 | 17.13 |
| ATOM | 567 | C | GLY | A | 73 | 69.886 | 37.193 | 34.124 | 1.00 | 17.10 |
| ATOM | 568 | O | GLY | A | 73 | 70.357 | 38.314 | 34.238 | 1.00 | 17.56 |
| ATOM | 569 | N | ALA | A | 74 | 69.996 | 36.475 | 33.003 | 1.00 | 16.81 |
| ATOM | 570 | CA | ALA | A | 74 | 70.743 | 37.040 | 31.860 | 1.00 | 16.63 |
| ATOM | 571 | C | ALA | A | 74 | 70.172 | 38.361 | 31.377 | 1.00 | 17.98 |
| ATOM | 572 | O | ALA | A | 74 | 70.911 | 39.200 | 30.838 | 1.00 | 17.87 |
| ATOM | 573 | CB | ALA | A | 74 | 70.760 | 36.034 | 30.703 | 1.00 | 16.76 |
| ATOM | 574 | N | ALA | A | 75 | 68.859 | 38.568 | 31.576 | 1.00 | 16.77 |
| ATOM | 575 | CA | ALA | A | 75 | 68.214 | 39.834 | 31.160 | 1.00 | 17.69 |
| ATOM | 576 | C | ALA | A | 75 | 68.855 | 41.099 | 31.787 | 1.00 | 17.68 |
| ATOM | 577 | O | ALA | A | 75 | 68.716 | 42.194 | 31.279 | 1.00 | 16.79 |
| ATOM | 578 | CB | ALA | A | 75 | 66.761 | 39.816 | 31.504 | 1.00 | 20.55 |
| ATOM | 579 | N | ALA | A | 76 | 69.556 | 40.921 | 32.930 | 1.00 | 16.67 |
| ATOM | 580 | CA | ALA | A | 76 | 70.183 | 42.082 | 33.556 | 1.00 | 17.52 |
| ATOM | 581 | C | ALA | A | 76 | 71.296 | 42.721 | 32.665 | 1.00 | 17.22 |
| ATOM | 582 | O | ALA | A | 76 | 71.738 | 43.846 | 32.900 | 1.00 | 18.09 |
| ATOM | 583 | CB | ALA | A | 76 | 70.695 | 41.726 | 34.989 | 1.00 | 18.29 |
| ATOM | 584 | N | HIS | A | 77 | 71.713 | 42.004 | 31.593 | 1.00 | 15.19 |
| ATOM | 585 | CA | HIS | A | 77 | 72.705 | 42.553 | 30.666 | 1.00 | 16.72 |
| ATOM | 586 | C | HIS | A | 77 | 71.996 | 43.452 | 29.623 | 1.00 | 16.17 |
| ATOM | 587 | O | HIS | A | 77 | 72.681 | 44.164 | 28.872 | 1.00 | 18.25 |
| ATOM | 588 | CB | HIS | A | 77 | 73.300 | 41.399 | 29.823 | 1.00 | 18.31 |
| ATOM | 589 | CG | HIS | A | 77 | 74.342 | 40.606 | 30.525 | 1.00 | 21.21 |
| ATOM | 590 | ND1 | HIS | A | 77 | 75.625 | 41.057 | 30.668 | 1.00 | 25.21 |
| ATOM | 591 | CD2 | HIS | A | 77 | 74.303 | 39.384 | 31.099 | 1.00 | 22.31 |
| ATOM | 592 | CE1 | HIS | A | 77 | 76.336 | 40.153 | 31.323 | 1.00 | 23.74 |
| ATOM | 593 | NE2 | HIS | A | 77 | 75.564 | 39.124 | 31.586 | 1.00 | 22.33 |

-continued

Data Lists

| ATOM | 594 | N | CYS | A | 78 | 70.666 | 43.404 | 29.585 | 1.00 | 14.86 |
|------|-----|-----|-----|---|----|--------|--------|--------|------|-------|
| ATOM | 595 | CA | CYS | A | 78 | 69.896 | 44.162 | 28.587 | 1.00 | 16.42 |
| ATOM | 596 | C | CYS | A | 78 | 69.145 | 45.376 | 29.085 | 1.00 | 16.96 |
| ATOM | 597 | O | CYS | A | 78 | 68.579 | 46.190 | 28.270 | 1.00 | 16.97 |
| ATOM | 598 | CB | CYS | A | 78 | 68.863 | 43.235 | 27.909 | 1.00 | 16.76 |
| ATOM | 599 | SG | CYS | A | 78 | 69.588 | 41.704 | 27.164 | 1.00 | 22.74 |
| ATOM | 600 | N | ALA | A | 79 | 69.075 | 45.549 | 30.440 | 1.00 | 14.78 |
| ATOM | 601 | CA | ALA | A | 79 | 68.366 | 46.701 | 30.991 | 1.00 | 14.85 |
| ATOM | 602 | C | ALA | A | 79 | 69.025 | 46.988 | 32.351 | 1.00 | 15.30 |
| ATOM | 603 | O | ALA | A | 79 | 69.567 | 46.065 | 32.964 | 1.00 | 16.51 |
| ATOM | 604 | CB | ALA | A | 79 | 66.885 | 46.431 | 31.178 | 1.00 | 15.77 |
| ATOM | 605 | N | SER | A | 80 | 68.971 | 48.263 | 32.704 | 1.00 | 13.90 |
| ATOM | 606 | CA | SER | A | 80 | 69.558 | 48.764 | 33.982 | 1.00 | 13.46 |
| ATOM | 607 | C | SER | A | 80 | 68.547 | 49.548 | 34.747 | 1.00 | 17.54 |
| ATOM | 608 | O | SER | A | 80 | 67.589 | 50.071 | 34.213 | 1.00 | 16.85 |
| ATOM | 609 | CB | SER | A | 80 | 70.739 | 49.652 | 33.656 | 1.00 | 17.79 |
| ATOM | 610 | OG | SER | A | 80 | 71.725 | 48.905 | 32.934 | 1.00 | 18.84 |
| ATOM | 611 | N | VAL | A | 81 | 68.788 | 49.664 | 36.076 | 1.00 | 15.99 |
| ATOM | 612 | CA | VAL | A | 81 | 67.897 | 50.448 | 36.907 | 1.00 | 14.74 |
| ATOM | 613 | C | VAL | A | 81 | 67.879 | 51.877 | 36.357 | 1.00 | 14.78 |
| ATOM | 614 | O | VAL | A | 81 | 68.899 | 52.500 | 36.103 | 1.00 | 15.81 |
| ATOM | 615 | CB | VAL | A | 81 | 68.468 | 50.470 | 38.409 | 1.00 | 14.01 |
| ATOM | 616 | CG1 | VAL | A | 81 | 67.606 | 51.444 | 39.242 | 1.00 | 15.95 |
| ATOM | 617 | CG2 | VAL | A | 81 | 68.363 | 49.104 | 39.020 | 1.00 | 15.67 |
| ATOM | 618 | N | GLY | A | 82 | 66.689 | 52.420 | 36.132 | 1.00 | 14.65 |
| ATOM | 619 | CA | GLY | A | 82 | 66.551 | 53.734 | 35.586 | 1.00 | 14.30 |
| ATOM | 620 | C | GLY | A | 82 | 66.072 | 53.721 | 34.113 | 1.00 | 16.91 |
| ATOM | 621 | O | GLY | A | 82 | 65.494 | 54.699 | 33.664 | 1.00 | 15.50 |
| ATOM | 622 | N | ASP | A | 83 | 66.347 | 52.624 | 33.431 | 1.00 | 14.93 |
| ATOM | 623 | CA | ASP | A | 83 | 65.911 | 52.551 | 31.994 | 1.00 | 13.74 |
| ATOM | 624 | C | ASP | A | 83 | 64.391 | 52.545 | 31.907 | 1.00 | 14.63 |
| ATOM | 625 | O | ASP | A | 83 | 63.687 | 51.980 | 32.775 | 1.00 | 15.91 |
| ATOM | 626 | CB | ASP | A | 83 | 66.421 | 51.242 | 31.319 | 1.00 | 13.28 |
| ATOM | 627 | CG | ASP | A | 83 | 67.917 | 51.248 | 31.004 | 1.00 | 12.11 |
| ATOM | 628 | OD1 | ASP | A | 83 | 68.614 | 52.301 | 31.107 | 1.00 | 15.32 |
| ATOM | 629 | OD2 | ASP | A | 83 | 68.382 | 50.116 | 30.667 | 1.00 | 15.76 |
| ATOM | 630 | N | ILE | A | 84 | 63.879 | 53.153 | 30.818 | 1.00 | 14.29 |
| ATOM | 631 | CA | ILE | A | 84 | 62.442 | 53.204 | 30.547 | 1.00 | 13.65 |
| ATOM | 632 | C | ILE | A | 84 | 62.169 | 52.078 | 29.504 | 1.00 | 13.60 |
| ATOM | 633 | O | ILE | A | 84 | 62.896 | 51.987 | 28.514 | 1.00 | 15.62 |
| ATOM | 634 | CB | ILE | A | 84 | 62.092 | 54.551 | 29.873 | 1.00 | 16.83 |
| ATOM | 635 | CG1 | ILE | A | 84 | 62.350 | 55.760 | 30.847 | 1.00 | 17.52 |
| ATOM | 636 | CG2 | ILE | A | 84 | 60.633 | 54.554 | 29.440 | 1.00 | 19.25 |
| ATOM | 637 | CD1 | ILE | A | 84 | 61.480 | 55.706 | 32.107 | 1.00 | 21.07 |
| ATOM | 638 | N | VAL | A | 85 | 61.212 | 51.235 | 29.785 | 1.00 | 12.41 |
| ATOM | 639 | CA | VAL | A | 85 | 60.934 | 50.112 | 28.876 | 1.00 | 12.94 |
| ATOM | 640 | C | VAL | A | 85 | 59.475 | 49.946 | 28.633 | 1.00 | 15.89 |
| ATOM | 641 | O | VAL | A | 85 | 58.583 | 50.517 | 29.317 | 1.00 | 14.01 |
| ATOM | 642 | CB | VAL | A | 85 | 61.466 | 48.783 | 29.474 | 1.00 | 14.37 |
| ATOM | 643 | CG1 | VAL | A | 85 | 62.960 | 48.870 | 29.885 | 1.00 | 13.95 |
| ATOM | 644 | CG2 | VAL | A | 85 | 60.649 | 48.332 | 30.741 | 1.00 | 14.77 |
| ATOM | 645 | N | ILE | A | 86 | 59.162 | 49.117 | 27.608 | 1.00 | 13.28 |
| ATOM | 646 | CA | ILE | A | 86 | 57.778 | 48.809 | 27.263 | 1.00 | 13.39 |
| ATOM | 647 | C | ILE | A | 86 | 57.723 | 47.283 | 27.366 | 1.00 | 14.02 |
| ATOM | 648 | O | ILE | A | 86 | 58.586 | 46.593 | 26.825 | 1.00 | 13.98 |
| ATOM | 649 | CB | ILE | A | 86 | 57.418 | 49.286 | 25.801 | 1.00 | 13.99 |
| ATOM | 650 | CG1 | ILE | A | 86 | 57.347 | 50.842 | 25.764 | 1.00 | 17.59 |
| ATOM | 651 | CG2 | ILE | A | 86 | 56.067 | 48.669 | 25.419 | 1.00 | 15.22 |
| ATOM | 652 | CD1 | ILE | A | 86 | 57.543 | 51.448 | 24.363 | 1.00 | 22.03 |
| ATOM | 653 | N | ILE | A | 87 | 56.779 | 46.734 | 28.149 | 1.00 | 12.05 |
| ATOM | 654 | CA | ILE | A | 87 | 56.654 | 45.304 | 28.337 | 1.00 | 11.27 |
| ATOM | 655 | C | ILE | A | 87 | 55.336 | 44.865 | 27.730 | 1.00 | 12.08 |
| ATOM | 656 | O | ILE | A | 87 | 54.252 | 45.364 | 28.075 | 1.00 | 13.19 |
| ATOM | 657 | CB | ILE | A | 87 | 56.693 | 44.934 | 29.905 | 1.00 | 12.91 |
| ATOM | 658 | CG1 | ILE | A | 87 | 57.972 | 45.491 | 30.455 | 1.00 | 14.33 |
| ATOM | 659 | CG2 | ILE | A | 87 | 56.572 | 43.438 | 30.062 | 1.00 | 14.68 |
| ATOM | 660 | CD1 | ILE | A | 87 | 58.085 | 45.263 | 32.060 | 1.00 | 14.91 |
| ATOM | 661 | N | ALA | A | 88 | 55.416 | 43.891 | 26.782 | 1.00 | 11.17 |
| ATOM | 662 | CA | ALA | A | 88 | 54.209 | 43.441 | 26.124 | 1.00 | 11.51 |
| ATOM | 663 | C | ALA | A | 88 | 53.978 | 41.975 | 26.112 | 1.00 | 11.06 |
| ATOM | 664 | O | ALA | A | 88 | 54.949 | 41.191 | 26.190 | 1.00 | 12.85 |
| ATOM | 665 | CB | ALA | A | 88 | 54.372 | 43.905 | 24.582 | 1.00 | 12.18 |
| ATOM | 666 | N | SER | A | 89 | 52.719 | 41.526 | 25.953 | 1.00 | 11.32 |
| ATOM | 667 | CA | SER | A | 89 | 52.459 | 40.087 | 25.769 | 1.00 | 11.17 |
| ATOM | 668 | C | SER | A | 89 | 51.547 | 39.992 | 24.538 | 1.00 | 11.44 |
| ATOM | 669 | O | SER | A | 89 | 50.833 | 40.964 | 24.213 | 1.00 | 11.04 |
| ATOM | 670 | CB | SER | A | 89 | 51.858 | 39.327 | 26.979 | 1.00 | 14.68 |

-continued

Data Lists

| | | | | | | | | | |
|---|---|---|---|---|---|---|---|---|---|
| ATOM | 671 | OG | SER | A | 89 | 50.438 | 39.480 | 27.037 | 1.00 | 13.56 |
| ATOM | 672 | N | PHE | A | 90 | 51.691 | 38.849 | 23.860 | 1.00 | 11.58 |
| ATOM | 673 | CA | PHE | A | 90 | 50.894 | 38.604 | 22.632 | 1.00 | 10.03 |
| ATOM | 674 | C | PHE | A | 90 | 50.125 | 37.331 | 22.780 | 1.00 | 11.41 |
| ATOM | 675 | O | PHE | A | 90 | 50.615 | 36.342 | 23.436 | 1.00 | 12.95 |
| ATOM | 676 | CB | PHE | A | 90 | 51.867 | 38.480 | 21.438 | 1.00 | 10.86 |
| ATOM | 677 | CG | PHE | A | 90 | 52.457 | 39.784 | 21.010 | 1.00 | 11.25 |
| ATOM | 678 | CD1 | PHE | A | 90 | 53.611 | 40.322 | 21.617 | 1.00 | 12.54 |
| ATOM | 679 | CD2 | PHE | A | 90 | 51.824 | 40.536 | 19.976 | 1.00 | 13.88 |
| ATOM | 680 | CE1 | PHE | A | 90 | 54.134 | 41.602 | 21.173 | 1.00 | 12.35 |
| ATOM | 681 | CE2 | PHE | A | 90 | 52.304 | 41.729 | 19.539 | 1.00 | 13.61 |
| ATOM | 682 | CZ | PHE | A | 90 | 53.459 | 42.314 | 20.114 | 1.00 | 12.98 |
| ATOM | 683 | N | VAL | A | 91 | 48.928 | 37.303 | 22.178 | 1.00 | 9.83 |
| ATOM | 684 | CA | VAL | A | 91 | 48.073 | 36.118 | 22.213 | 1.00 | 10.22 |
| ATOM | 685 | C | VAL | A | 91 | 47.588 | 35.798 | 20.793 | 1.00 | 14.03 |
| ATOM | 686 | O | VAL | A | 91 | 47.690 | 36.675 | 19.893 | 1.00 | 13.50 |
| ATOM | 687 | CB | VAL | A | 91 | 46.803 | 36.261 | 23.098 | 1.00 | 13.62 |
| ATOM | 688 | CG1 | VAL | A | 91 | 47.217 | 36.266 | 24.596 | 1.00 | 15.08 |
| ATOM | 689 | CG2 | VAL | A | 91 | 45.999 | 37.507 | 22.722 | 1.00 | 13.05 |
| ATOM | 690 | N | THR | A | 92 | 47.154 | 34.586 | 20.611 | 1.00 | 12.76 |
| ATOM | 691 | CA | THR | A | 92 | 46.628 | 34.182 | 19.275 | 1.00 | 11.56 |
| ATOM | 692 | C | THR | A | 92 | 45.132 | 33.971 | 19.349 | 1.00 | 13.31 |
| ATOM | 693 | O | THR | A | 92 | 44.530 | 33.582 | 20.391 | 1.00 | 13.08 |
| ATOM | 694 | CB | THR | A | 92 | 47.340 | 32.987 | 18.626 | 1.00 | 12.64 |
| ATOM | 695 | OG1 | THR | A | 92 | 47.132 | 31.797 | 19.427 | 1.00 | 16.06 |
| ATOM | 696 | CG2 | THR | A | 92 | 48.849 | 33.212 | 18.472 | 1.00 | 13.80 |
| ATOM | 697 | N | MET | A | 93 | 44.412 | 34.267 | 18.224 | 1.00 | 11.69 |
| ATOM | 698 | CA | MET | A | 93 | 42.951 | 34.108 | 18.147 | 1.00 | 11.35 |
| ATOM | 699 | C | MET | A | 93 | 42.609 | 34.143 | 16.641 | 1.00 | 14.45 |
| ATOM | 700 | O | MET | A | 93 | 43.429 | 34.572 | 15.835 | 1.00 | 13.44 |
| ATOM | 701 | CB | MET | A | 93 | 42.224 | 35.317 | 18.831 | 1.00 | 12.85 |
| ATOM | 702 | CG | MET | A | 93 | 42.628 | 36.660 | 18.178 | 1.00 | 13.91 |
| ATOM | 703 | SD | MET | A | 93 | 42.084 | 38.126 | 19.099 | 1.00 | 14.46 |
| ATOM | 704 | CE | MET | A | 93 | 43.261 | 37.982 | 20.500 | 1.00 | 14.10 |
| ATOM | 705 | N | PRO | A | 94 | 41.440 | 33.664 | 16.331 | 1.00 | 12.36 |
| ATOM | 706 | CA | PRO | A | 94 | 40.994 | 33.662 | 14.921 | 1.00 | 12.35 |
| ATOM | 707 | C | PRO | A | 94 | 40.927 | 35.119 | 14.384 | 1.00 | 15.66 |
| ATOM | 708 | O | PRO | A | 94 | 40.708 | 36.116 | 15.069 | 1.00 | 14.35 |
| ATOM | 709 | CB | PRO | A | 94 | 39.592 | 33.150 | 15.005 | 1.00 | 13.86 |
| ATOM | 710 | CG | PRO | A | 94 | 39.606 | 32.186 | 16.204 | 1.00 | 15.72 |
| ATOM | 711 | CD | PRO | A | 94 | 40.405 | 33.060 | 17.191 | 1.00 | 12.82 |
| ATOM | 712 | N | ASP | A | 95 | 41.040 | 35.223 | 13.035 | 1.00 | 14.03 |
| ATOM | 713 | CA | ASP | A | 95 | 40.966 | 36.538 | 12.434 | 1.00 | 15.39 |
| ATOM | 714 | C | ASP | A | 95 | 39.760 | 37.423 | 12.789 | 1.00 | 16.06 |
| ATOM | 715 | O | ASP | A | 95 | 39.886 | 38.651 | 12.959 | 1.00 | 16.29 |
| ATOM | 716 | CB | ASP | A | 95 | 40.998 | 36.355 | 10.903 | 1.00 | 15.44 |
| ATOM | 717 | CG | ASP | A | 95 | 41.147 | 37.685 | 10.168 | 1.00 | 15.85 |
| ATOM | 718 | CD1 | ASP | A | 95 | 42.199 | 38.354 | 10.289 | 1.00 | 14.33 |
| ATOM | 719 | OD2 | ASP | A | 95 | 40.178 | 38.088 | 9.441 | 1.00 | 18.70 |
| ATOM | 720 | N | GLU | A | 96 | 38.571 | 36.831 | 12.864 | 1.00 | 15.70 |
| ATOM | 721 | CA | GLU | A | 96 | 37.389 | 37.631 | 13.182 | 1.00 | 14.32 |
| ATOM | 722 | C | GLU | A | 96 | 37.468 | 38.304 | 14.550 | 1.00 | 18.35 |
| ATOM | 723 | O | GLU | A | 96 | 37.196 | 39.487 | 14.686 | 1.00 | 17.78 |
| ATOM | 724 | CB | GLU | A | 96 | 36.102 | 36.828 | 12.995 | 1.00 | 16.31 |
| ATOM | 725 | CG | GLU | A | 96 | 34.860 | 37.623 | 13.365 | 1.00 | 22.63 |
| ATOM | 726 | CD | GLU | A | 96 | 33.526 | 36.880 | 13.068 | 1.00 | 23.98 |
| ATOM | 727 | CE1 | GLU | A | 96 | 33.559 | 35.704 | 12.706 | 1.00 | 25.84 |
| ATOM | 728 | OE2 | GLU | A | 96 | 32.461 | 37.497 | 13.246 | 1.00 | 30.53 |
| ATOM | 729 | N | GLU | A | 97 | 37.863 | 37.514 | 15.545 | 1.00 | 15.16 |
| ATOM | 730 | CA | GLU | A | 97 | 37.999 | 38.111 | 16.875 | 1.00 | 15.52 |
| ATOM | 731 | C | GLU | A | 97 | 39.128 | 39.177 | 16.850 | 1.00 | 13.99 |
| ATOM | 732 | O | GLU | A | 97 | 39.028 | 40.206 | 17.493 | 1.00 | 16.67 |
| ATOM | 733 | CB | GLU | A | 97 | 38.338 | 36.990 | 17.857 | 1.00 | 15.35 |
| ATOM | 734 | OG | GLU | A | 97 | 38.566 | 37.525 | 19.290 | 1.00 | 17.59 |
| ATOM | 735 | CD | GLU | A | 97 | 38.814 | 36.394 | 20.261 | 1.00 | 22.36 |
| ATOM | 736 | CE1 | GLU | A | 97 | 38.899 | 35.209 | 19.850 | 1.00 | 17.71 |
| ATOM | 737 | OE2 | GLU | A | 97 | 38.890 | 36.747 | 21.481 | 1.00 | 22.62 |
| ATOM | 738 | N | ALA | A | 98 | 40.228 | 38.917 | 16.123 | 1.00 | 13.03 |
| ATOM | 739 | CA | ALA | A | 98 | 41.349 | 39.850 | 16.036 | 1.00 | 12.71 |
| ATOM | 740 | C | ALA | A | 98 | 40.957 | 41.219 | 15.463 | 1.00 | 15.63 |
| ATOM | 741 | O | ALA | A | 98 | 41.496 | 42.253 | 15.834 | 1.00 | 14.36 |
| ATOM | 742 | CB | ALA | A | 98 | 42.463 | 39.223 | 15.190 | 1.00 | 14.85 |
| ATOM | 743 | N | ARG | A | 99 | 39.959 | 41.235 | 14.534 | 1.00 | 14.05 |
| ATOM | 744 | CA | ARG | A | 99 | 39.565 | 42.490 | 13.944 | 1.00 | 15.96 |
| ATOM | 745 | C | ARG | A | 99 | 38.883 | 43.474 | 14.862 | 1.00 | 17.44 |
| ATOM | 746 | O | ARG | A | 99 | 38.845 | 44.666 | 14.535 | 1.00 | 21.21 |
| ATOM | 747 | CB | ARG | A | 99 | 38.743 | 42.259 | 12.633 | 1.00 | 17.37 |

-continued

| | | | | | | | | | |
|---|---|---|---|---|---|---|---|---|---|
| | | | Data Lists | | | | | | |
| ATOM | 748 | CG | ARG | A | 99 | 39.630 | 41.725 | 11.515 | 1.00 | 16.32 |
| ATOM | 749 | CD | ARG | A | 99 | 38.869 | 41.511 | 10.154 | 1.00 | 16.45 |
| ATOM | 750 | NE | ARG | A | 99 | 38.150 | 40.252 | 10.074 | 1.00 | 14.75 |
| ATOM | 751 | CZ | ARG | A | 99 | 36.851 | 40.106 | 10.202 | 1.00 | 13.61 |
| ATOM | 752 | NH1 | ARG | A | 99 | 36.084 | 41.162 | 10.415 | 1.00 | 16.09 |
| ATOM | 753 | NH2 | ARG | A | 99 | 36.306 | 38.906 | 10.083 | 1.00 | 18.40 |
| ATOM | 754 | N | THR | A | 100 | 38.364 | 43.021 | 15.998 | 1.00 | 16.42 |
| ATOM | 755 | CA | THR | A | 100 | 37.753 | 43.988 | 16.917 | 1.00 | 16.33 |
| ATOM | 756 | C | THR | A | 100 | 38.350 | 43.803 | 18.317 | 1.00 | 19.97 |
| ATOM | 757 | O | THR | A | 100 | 37.735 | 44.220 | 19.329 | 1.00 | 20.03 |
| ATOM | 758 | CB | THR | A | 100 | 36.246 | 43.908 | 17.014 | 1.00 | 21.91 |
| ATOM | 759 | OG1 | THR | A | 100 | 35.822 | 42.556 | 17.266 | 1.00 | 20.66 |
| ATOM | 760 | CG2 | THR | A | 100 | 35.626 | 44.354 | 15.658 | 1.00 | 22.68 |
| ATOM | 761 | N | TRP | A | 101 | 39.533 | 43.203 | 18.349 | 1.00 | 17.87 |
| ATOM | 762 | CA | TRP | A | 101 | 40.199 | 42.981 | 19.671 | 1.00 | 16.71 |
| ATOM | 763 | C | TRP | A | 101 | 40.710 | 44.288 | 20.258 | 1.00 | 19.04 |
| ATOM | 764 | O | TRP | A | 101 | 41.247 | 45.135 | 19.540 | 1.00 | 17.05 |
| ATOM | 765 | CB | TRP | A | 101 | 41.390 | 42.038 | 19.455 | 1.00 | 14.65 |
| ATOM | 766 | CG | TRP | A | 101 | 42.311 | 41.932 | 20.694 | 1.00 | 14.16 |
| ATOM | 767 | CD1 | TRP | A | 101 | 43.528 | 42.444 | 20.800 | 1.00 | 16.31 |
| ATOM | 768 | CD2 | TRP | A | 101 | 42.034 | 41.196 | 21.899 | 1.00 | 16.31 |
| ATOM | 769 | NE1 | TRP | A | 101 | 44.070 | 42.124 | 22.085 | 1.00 | 15.49 |
| ATOM | 770 | CE2 | TRP | A | 101 | 43.151 | 41.365 | 22.743 | 1.00 | 17.23 |
| ATOM | 771 | CE3 | TRP | A | 101 | 40.944 | 40.448 | 22.362 | 1.00 | 19.60 |
| ATOM | 772 | CZ2 | TRP | A | 101 | 43.211 | 40.796 | 24.037 | 1.00 | 18.02 |
| ATOM | 773 | CZ3 | TRP | A | 101 | 41.013 | 39.854 | 23.639 | 1.00 | 21.23 |
| ATOM | 774 | CH2 | TRP | A | 101 | 42.136 | 40.045 | 24.443 | 1.00 | 21.41 |
| ATOM | 775 | N | ARG | A | 102 | 40.563 | 44.465 | 21.612 | 1.00 | 15.76 |
| ATOM | 776 | CA | ARG | A | 102 | 41.070 | 45.703 | 22.235 | 1.00 | 16.64 |
| ATOM | 777 | C | ARG | A | 102 | 42.180 | 45.344 | 23.275 | 1.00 | 14.79 |
| ATOM | 778 | O | ARG | A | 102 | 41.838 | 44.748 | 24.316 | 1.00 | 17.03 |
| ATOM | 779 | CB | ARG | A | 102 | 39.943 | 46.431 | 22.963 | 1.00 | 17.42 |
| ATOM | 780 | CG | ARG | A | 102 | 38.775 | 46.821 | 22.058 | 1.00 | 24.67 |
| ATOM | 781 | CD | ARG | A | 102 | 39.285 | 47.662 | 20.922 | 1.00 | 40.94 |
| ATOM | 782 | NE | ARG | A | 102 | 38.215 | 47.967 | 19.971 | 1.00 | 58.76 |
| ATOM | 783 | CZ | ARG | A | 102 | 38.246 | 47.668 | 18.668 | 1.00 | 65.94 |
| ATOM | 784 | NH1 | ARG | A | 102 | 39.307 | 47.043 | 18.135 | 1.00 | 46.00 |
| ATOM | 785 | NH2 | ARG | A | 102 | 37.211 | 47.987 | 17.896 | 1.00 | 52.57 |
| ATOM | 786 | N | PRO | A | 103 | 43.422 | 45.671 | 22.999 | 1.00 | 15.12 |
| ATOM | 787 | CA | PRO | A | 103 | 44.515 | 45.313 | 23.948 | 1.00 | 13.53 |
| ATOM | 788 | C | PRO | A | 103 | 44.329 | 46.058 | 25.274 | 1.00 | 15.29 |
| ATOM | 789 | O | PRO | A | 103 | 43.749 | 47.117 | 25.309 | 1.00 | 16.02 |
| ATOM | 790 | CB | PRO | A | 103 | 45.770 | 45.786 | 23.270 | 1.00 | 14.34 |
| ATOM | 791 | CG | PRO | A | 103 | 45.386 | 45.801 | 21.717 | 1.00 | 18.46 |
| ATOM | 792 | CD | PRO | A | 103 | 43.942 | 46.250 | 21.748 | 1.00 | 15.59 |
| ATOM | 793 | N | ASN | A | 104 | 44.884 | 45.445 | 26.347 | 1.00 | 14.28 |
| ATOM | 794 | CA | ASN | A | 104 | 44.836 | 46.034 | 27.698 | 1.00 | 13.04 |
| ATOM | 795 | C | ASN | A | 104 | 46.119 | 46.863 | 27.862 | 1.00 | 14.43 |
| ATOM | 796 | O | ASN | A | 104 | 47.217 | 46.296 | 28.125 | 1.00 | 13.98 |
| ATOM | 797 | CB | ASN | A | 104 | 44.760 | 44.875 | 28.655 | 1.00 | 12.98 |
| ATOM | 798 | CG | ASN | A | 104 | 43.490 | 44.121 | 28.510 | 1.00 | 15.09 |
| ATOM | 799 | OD1 | ASN | A | 104 | 42.398 | 44.706 | 28.655 | 1.00 | 17.92 |
| ATOM | 800 | ND2 | ASN | A | 104 | 43.569 | 42.842 | 28.158 | 1.00 | 16.93 |
| ATOM | 801 | N | VAL | A | 105 | 46.019 | 48.179 | 27.673 | 1.00 | 14.40 |
| ATOM | 802 | CA | VAL | A | 105 | 47.150 | 49.048 | 27.734 | 1.00 | 15.19 |
| ATOM | 803 | C | VAL | A | 105 | 47.164 | 49.895 | 28.992 | 1.00 | 18.79 |
| ATOM | 804 | O | VAL | A | 105 | 46.172 | 50.559 | 29.309 | 1.00 | 20.46 |
| ATOM | 805 | CB | VAL | A | 105 | 47.188 | 50.005 | 26.534 | 1.00 | 18.28 |
| ATOM | 806 | CG1 | VAL | A | 105 | 48.423 | 50.904 | 26.591 | 1.00 | 20.67 |
| ATOM | 807 | CG2 | VAL | A | 105 | 47.223 | 49.166 | 25.186 | 1.00 | 17.51 |
| ATOM | 808 | N | ALA | A | 106 | 48.297 | 49.853 | 29.683 | 1.00 | 16.66 |
| ATOM | 809 | CA | ALA | A | 106 | 48.457 | 50.694 | 30.921 | 1.00 | 16.75 |
| ATOM | 810 | C | ALA | A | 106 | 49.647 | 51.596 | 30.665 | 1.00 | 15.84 |
| ATOM | 811 | O | ALA | A | 106 | 50.711 | 51.115 | 30.266 | 1.00 | 16.27 |
| ATOM | 812 | CB | ALA | A | 106 | 48.672 | 49.807 | 32.141 | 1.00 | 17.32 |
| ATOM | 813 | N | TYR | A | 107 | 49.475 | 52.911 | 30.905 | 1.00 | 15.99 |
| ATOM | 814 | CA | TYR | A | 107 | 50.474 | 53.931 | 30.697 | 1.00 | 15.93 |
| ATOM | 815 | C | TYR | A | 107 | 51.037 | 54.390 | 32.046 | 1.00 | 18.71 |
| ATOM | 816 | O | TYR | A | 107 | 50.287 | 54.506 | 33.007 | 1.00 | 20.84 |
| ATOM | 817 | CB | TYR | A | 107 | 49.901 | 55.154 | 29.951 | 1.00 | 19.26 |
| ATOM | 818 | CG | TYR | A | 107 | 49.419 | 54.812 | 28.533 | 1.00 | 21.14 |
| ATOM | 819 | CD1 | TYR | A | 107 | 50.291 | 54.819 | 27.490 | 1.00 | 21.91 |
| ATOM | 820 | CD2 | TYR | A | 107 | 48.106 | 54.510 | 28.307 | 1.00 | 23.16 |
| ATOM | 821 | CE1 | TYR | A | 107 | 49.861 | 54.497 | 26.190 | 1.00 | 24.59 |
| ATOM | 822 | CE2 | TYR | A | 107 | 47.672 | 54.182 | 27.007 | 1.00 | 24.09 |
| ATOM | 823 | CZ | TYR | A | 107 | 48.571 | 54.197 | 25.992 | 1.00 | 27.50 |
| ATOM | 824 | OH | TYR | A | 107 | 48.200 | 53.880 | 24.685 | 1.00 | 29.66 |

-continued

| | | | | | | | | | |
|---|---|---|---|---|---|---|---|---|---|
| ATOM | 825 | N | PHE | A | 108 | 52.340 | 54.609 | 32.042 | 1.00 | 15.42 |
| ATOM | 826 | CA | PHE | A | 108 | 53.049 | 55.012 | 33.297 | 1.00 | 15.71 |
| ATOM | 827 | C | PHE | A | 108 | 53.868 | 56.249 | 33.162 | 1.00 | 19.91 |
| ATOM | 828 | O | PHE | A | 108 | 54.268 | 56.703 | 32.071 | 1.00 | 19.12 |
| ATOM | 829 | CB | PHE | A | 108 | 53.974 | 53.876 | 33.723 | 1.00 | 16.87 |
| ATOM | 830 | CG | PHE | A | 108 | 53.258 | 52.651 | 34.125 | 1.00 | 16.76 |
| ATOM | 831 | CD1 | PHE | A | 108 | 52.842 | 51.702 | 33.160 | 1.00 | 17.17 |
| ATOM | 832 | CD2 | PHE | A | 108 | 52.940 | 52.381 | 35.481 | 1.00 | 17.45 |
| ATOM | 833 | CE1 | PHE | A | 108 | 52.147 | 50.577 | 33.546 | 1.00 | 19.62 |
| ATOM | 834 | CE2 | PHE | A | 108 | 52.242 | 51.243 | 35.867 | 1.00 | 20.41 |
| ATOM | 835 | CZ | PHE | A | 108 | 51.838 | 50.301 | 34.901 | 1.00 | 19.54 |
| ATOM | 836 | N | GLU | A | 109 | 54.193 | 56.830 | 34.342 | 1.00 | 17.02 |
| ATOM | 837 | CA | GLU | A | 109 | 55.053 | 58.009 | 34.382 | 1.00 | 17.21 |
| ATOM | 838 | C | GLU | A | 109 | 55.561 | 58.104 | 35.858 | 1.00 | 15.89 |
| ATOM | 839 | O | GLU | A | 109 | 55.062 | 57.376 | 36.696 | 1.00 | 16.10 |
| ATOM | 840 | CB | GLU | A | 109 | 54.259 | 59.300 | 34.091 | 1.00 | 18.77 |
| ATOM | 841 | CG | GLU | A | 109 | 53.234 | 59.595 | 35.166 | 1.00 | 19.64 |
| ATOM | 842 | CD | GLU | A | 109 | 52.394 | 60.875 | 34.948 | 1.00 | 21.63 |
| ATOM | 843 | OE1 | GLU | A | 109 | 52.761 | 61.761 | 34.165 | 1.00 | 24.76 |
| ATOM | 844 | OE2 | GLU | A | 109 | 51.361 | 60.960 | 35.616 | 1.00 | 28.24 |
| ATOM | 845 | N | GLY | A | 110 | 56.507 | 59.001 | 36.063 | 1.00 | 15.85 |
| ATOM | 846 | CA | GLY | A | 110 | 57.054 | 59.240 | 37.466 | 1.00 | 17.20 |
| ATOM | 847 | C | GLY | A | 110 | 57.499 | 57.968 | 38.164 | 1.00 | 16.93 |
| ATOM | 848 | O | GLY | A | 110 | 58.272 | 57.157 | 37.598 | 1.00 | 16.26 |
| ATOM | 849 | N | ASP | A | 111 | 57.047 | 57.749 | 39.423 | 1.00 | 14.38 |
| ATOM | 850 | CA | ASP | A | 111 | 57.455 | 56.568 | 40.177 | 1.00 | 14.84 |
| ATOM | 851 | C | ASP | A | 111 | 56.588 | 55.369 | 39.865 | 1.00 | 14.72 |
| ATOM | 852 | O | ASP | A | 111 | 55.888 | 54.753 | 40.690 | 1.00 | 14.34 |
| ATOM | 853 | CB | ASP | A | 111 | 57.356 | 56.953 | 41.689 | 1.00 | 17.05 |
| ATOM | 854 | CG | ASP | A | 111 | 57.812 | 55.841 | 42.614 | 1.00 | 19.59 |
| ATOM | 855 | OD1 | ASP | A | 111 | 58.707 | 55.034 | 42.277 | 1.00 | 20.52 |
| ATOM | 856 | OD2 | ASP | A | 111 | 57.219 | 55.731 | 43.714 | 1.00 | 19.81 |
| ATOM | 857 | N | ASN | A | 112 | 56.617 | 54.987 | 38.573 | 1.00 | 14.68 |
| ATOM | 858 | CA | ASN | A | 112 | 55.763 | 53.835 | 38.157 | 1.00 | 16.14 |
| ATOM | 859 | C | ASN | A | 112 | 54.291 | 54.049 | 38.569 | 1.00 | 13.02 |
| ATOM | 860 | O | ASN | A | 112 | 53.609 | 53.111 | 39.049 | 1.00 | 14.89 |
| ATOM | 861 | CB | ASN | A | 112 | 56.322 | 52.431 | 38.503 | 1.00 | 16.17 |
| ATOM | 862 | CG | ASN | A | 112 | 57.541 | 52.089 | 37.656 | 1.00 | 18.78 |
| ATOM | 863 | OD1 | ASN | A | 112 | 57.742 | 52.728 | 36.605 | 1.00 | 17.25 |
| ATOM | 864 | ND2 | ASN | A | 112 | 58.332 | 51.112 | 38.079 | 1.00 | 15.61 |
| ATOM | 865 | N | GLU | A | 113 | 53.814 | 55.286 | 38.317 | 1.00 | 14.05 |
| ATOM | 866 | CA | GLU | A | 113 | 52.440 | 55.685 | 38.605 | 1.00 | 15.74 |
| ATOM | 867 | C | GLU | A | 113 | 51.602 | 55.432 | 37.349 | 1.00 | 18.95 |
| ATOM | 868 | O | GLU | A | 113 | 51.844 | 56.053 | 36.325 | 1.00 | 19.58 |
| ATOM | 869 | CB | GLU | A | 113 | 52.402 | 57.167 | 38.952 | 1.00 | 17.38 |
| ATOM | 870 | CG | GLU | A | 113 | 51.034 | 57.648 | 39.454 | 1.00 | 20.91 |
| ATOM | 871 | CD | GLU | A | 113 | 50.594 | 57.002 | 40.802 | 1.00 | 24.09 |
| ATOM | 872 | OE1 | GLU | A | 113 | 51.358 | 56.979 | 41.779 | 1.00 | 30.10 |
| ATOM | 873 | OE2 | GLU | A | 113 | 49.450 | 56.530 | 40.862 | 1.00 | 36.71 |
| ATOM | 874 | N | MET | A | 114 | 50.624 | 54.554 | 37.470 | 1.00 | 18.64 |
| ATOM | 875 | CA | MET | A | 114 | 49.757 | 54.212 | 36.305 | 1.00 | 20.88 |
| ATOM | 876 | C | MET | A | 114 | 48.811 | 55.341 | 36.028 | 1.00 | 27.67 |
| ATOM | 877 | O | MET | A | 114 | 48.090 | 55.775 | 36.930 | 1.00 | 27.90 |
| ATOM | 878 | CB | MET | A | 114 | 48.991 | 52.925 | 36.584 | 1.00 | 23.89 |
| ATOM | 879 | CG | MET | A | 114 | 48.173 | 52.424 | 35.345 | 1.00 | 26.69 |
| ATOM | 880 | SD | MET | A | 114 | 47.345 | 50.879 | 35.650 | 1.00 | 29.33 |
| ATOM | 881 | CE | MET | A | 114 | 48.738 | 49.883 | 36.101 | 1.00 | 23.75 |
| ATOM | 882 | N | LYS | A | 115 | 48.790 | 55.846 | 34.789 | 1.00 | 25.26 |
| ATOM | 883 | CA | LYS | A | 115 | 47.883 | 56.943 | 34.440 | 1.00 | 30.27 |
| ATOM | 884 | C | LYS | A | 115 | 46.430 | 56.485 | 34.405 | 1.00 | 36.08 |
| ATOM | 885 | O | LYS | A | 115 | 45.545 | 57.363 | 34.605 | 1.00 | 41.29 |
| ATOM | 886 | CB | LYS | A | 115 | 48.251 | 57.602 | 33.112 | 1.00 | 31.52 |
| ATOM | 887 | CG | LYS | A | 115 | 49.665 | 58.100 | 32.995 | 1.00 | 29.39 |
| ATOM | 888 | CD | LYS | A | 115 | 49.830 | 58.930 | 31.710 | 1.00 | 35.11 |
| ATOM | 889 | CE | LYS | A | 115 | 51.281 | 59.149 | 31.351 | 1.00 | 39.16 |
| ATOM | 890 | NZ | LYS | A | 115 | 51.445 | 60.206 | 30.288 | 1.00 | 41.83 |
| ATOM | 892 | N | MET | B | 1 | 49.295 | 18.983 | 11.961 | 1.00 | 17.87 |
| ATOM | 893 | CA | MET | B | 1 | 50.088 | 19.983 | 12.674 | 1.00 | 15.77 |
| ATOM | 894 | C | MET | B | 1 | 49.867 | 21.364 | 12.128 | 1.00 | 18.38 |
| ATOM | 895 | O | MET | B | 1 | 49.270 | 21.493 | 11.014 | 1.00 | 16.03 |
| ATOM | 896 | CB | MET | B | 1 | 51.505 | 19.597 | 12.960 | 1.00 | 18.15 |
| ATOM | 897 | CG | MET | B | 1 | 52.312 | 19.036 | 11.858 | 1.00 | 21.69 |
| ATOM | 898 | SD | MET | B | 1 | 52.465 | 20.286 | 10.552 | 1.00 | 24.50 |
| ATOM | 899 | CE | MET | B | 1 | 53.497 | 19.234 | 9.256 | 1.00 | 19.90 |
| ATOM | 900 | N | ILE | B | 2 | 50.273 | 22.378 | 12.874 | 1.00 | 13.90 |
| ATOM | 901 | CA | ILE | B | 2 | 50.019 | 23.771 | 12.510 | 1.00 | 12.73 |
| ATOM | 902 | C | ILE | B | 2 | 51.265 | 24.482 | 12.069 | 1.00 | 15.11 |

-continued

Data Lists

| | | | | | | | | | |
|---|---|---|---|---|---|---|---|---|---|
| ATOM | 903 | O | ILE | B | 2 | 52.322 | 24.450 | 12.698 | 1.00 | 13.08 |
| ATOM | 904 | CB | ILE | B | 2 | 49.400 | 24.499 | 13.757 | 1.00 | 12.91 |
| ATOM | 905 | CG1 | ILE | B | 2 | 48.119 | 23.792 | 14.267 | 1.00 | 14.95 |
| ATOM | 906 | CG2 | ILE | B | 2 | 49.218 | 25.945 | 13.547 | 1.00 | 13.31 |
| ATOM | 907 | CD1 | ILE | B | 2 | 46.943 | 23.904 | 13.276 | 1.00 | 19.87 |
| ATOM | 908 | N | ARG | B | 3 | 51.138 | 25.131 | 10.910 | 1.00 | 11.64 |
| ATOM | 909 | CA | ARG | B | 3 | 52.229 | 25.868 | 10.327 | 1.00 | 9.38 |
| ATOM | 910 | C | ARG | B | 3 | 52.150 | 27.383 | 10.524 | 1.00 | 8.16 |
| ATOM | 911 | O | ARG | B | 3 | 51.039 | 27.931 | 10.673 | 1.00 | 9.82 |
| ATOM | 912 | CB | ARG | B | 3 | 52.082 | 25.697 | 8.760 | 1.00 | 11.91 |
| ATOM | 913 | CG | ARG | B | 3 | 52.248 | 24.258 | 8.287 | 1.00 | 12.07 |
| ATOM | 914 | CD | ARG | B | 3 | 53.705 | 23.876 | 8.003 | 1.00 | 12.41 |
| ATOM | 915 | NE | ARG | B | 3 | 53.758 | 22.596 | 7.334 | 1.00 | 12.53 |
| ATOM | 916 | CZ | ARG | B | 3 | 54.867 | 21.986 | 6.901 | 1.00 | 11.34 |
| ATOM | 917 | NH1 | ARG | B | 3 | 56.094 | 22.483 | 7.125 | 1.00 | 11.49 |
| ATOM | 918 | NH2 | ARG | B | 3 | 54.748 | 20.841 | 6.167 | 1.00 | 11.64 |
| ATOM | 919 | N | THR | B | 4 | 53.317 | 28.048 | 10.501 | 1.00 | 11.35 |
| ATOM | 920 | CA | THR | B | 4 | 53.417 | 29.519 | 10.576 | 1.00 | 10.99 |
| ATOM | 921 | C | THR | B | 4 | 53.769 | 29.941 | 9.093 | 1.00 | 9.80 |
| ATOM | 922 | O | THR | B | 4 | 54.789 | 29.551 | 8.631 | 1.00 | 10.46 |
| ATOM | 923 | CB | THR | B | 4 | 54.502 | 29.963 | 11.507 | 1.00 | 13.30 |
| ATOM | 924 | OG1 | THR | B | 4 | 54.145 | 29.451 | 12.826 | 1.00 | 12.86 |
| ATOM | 925 | CG2 | THR | B | 4 | 54.597 | 31.446 | 11.593 | 1.00 | 11.07 |
| ATOM | 926 | N | MET | B | 5 | 52.897 | 30.764 | 8.525 | 1.00 | 10.61 |
| ATOM | 927 | CA | MET | B | 5 | 53.045 | 31.215 | 7.092 | 1.00 | 10.17 |
| ATOM | 928 | C | MET | B | 5 | 53.023 | 32.709 | 6.987 | 1.00 | 13.79 |
| ATOM | 929 | O | MET | B | 5 | 52.333 | 33.412 | 7.759 | 1.00 | 12.14 |
| ATOM | 930 | CB | MET | B | 5 | 51.799 | 30.698 | 6.391 | 1.00 | 10.85 |
| ATOM | 931 | CG | MET | B | 5 | 51.655 | 29.138 | 6.389 | 1.00 | 13.35 |
| ATOM | 932 | SD | MET | B | 5 | 52.937 | 28.173 | 5.793 | 1.00 | 12.31 |
| ATOM | 933 | CE | MET | B | 5 | 52.760 | 28.465 | 3.924 | 1.00 | 9.06 |
| ATOM | 934 | N | LEU | B | 6 | 53.705 | 33.229 | 5.939 | 1.00 | 11.48 |
| ATOM | 935 | CA | LEU | B | 6 | 53.676 | 34.675 | 5.698 | 1.00 | 11.70 |
| ATOM | 936 | C | LEU | B | 6 | 52.227 | 35.093 | 5.344 | 1.00 | 15.58 |
| ATOM | 937 | O | LEU | B | 6 | 51.621 | 34.549 | 4.376 | 1.00 | 12.84 |
| ATOM | 938 | CB | LEU | B | 6 | 54.595 | 34.999 | 4.516 | 1.00 | 11.07 |
| ATOM | 939 | CG | LEU | B | 6 | 54.561 | 36.468 | 4.141 | 1.00 | 10.79 |
| ATOM | 940 | CD1 | LEU | B | 6 | 55.327 | 37.415 | 5.158 | 1.00 | 12.32 |
| ATOM | 941 | CD2 | LEU | B | 6 | 55.228 | 36.692 | 2.748 | 1.00 | 12.20 |
| ATOM | 942 | N | GLN | B | 7 | 51.608 | 36.000 | 6.115 | 1.00 | 11.50 |
| ATOM | 943 | CA | GLN | B | 7 | 50.275 | 36.439 | 5.854 | 1.00 | 12.08 |
| ATOM | 944 | C | GLN | B | 7 | 50.283 | 37.543 | 4.772 | 1.00 | 13.00 |
| ATOM | 945 | O | GLN | B | 7 | 49.368 | 37.573 | 3.878 | 1.00 | 13.76 |
| ATOM | 946 | CB | GLN | B | 7 | 49.614 | 37.046 | 7.144 | 1.00 | 13.70 |
| ATOM | 947 | CG | GLN | B | 7 | 48.181 | 37.402 | 7.017 | 1.00 | 13.52 |
| ATOM | 948 | CD | GLN | B | 7 | 47.882 | 38.740 | 6.256 | 1.00 | 15.62 |
| ATOM | 949 | OE1 | GLN | B | 7 | 46.810 | 38.816 | 5.553 | 1.00 | 14.96 |
| ATOM | 950 | NE2 | GLN | B | 7 | 48.745 | 39.780 | 6.431 | 1.00 | 13.51 |
| ATOM | 951 | N | GLY | B | 8 | 51.235 | 38.442 | 4.850 | 1.00 | 12.82 |
| ATOM | 952 | CA | GLY | B | 8 | 51.318 | 39.567 | 3.907 | 1.00 | 13.57 |
| ATOM | 953 | C | GLY | B | 8 | 52.519 | 40.435 | 4.210 | 1.00 | 17.33 |
| ATOM | 954 | O | GLY | B | 8 | 53.154 | 40.314 | 5.278 | 1.00 | 16.12 |
| ATOM | 955 | N | LYS | B | 9 | 52.917 | 41.301 | 3.271 | 1.00 | 13.73 |
| ATOM | 956 | CA | LYS | B | 9 | 54.045 | 42.162 | 3.517 | 1.00 | 14.09 |
| ATOM | 957 | C | LYS | B | 9 | 53.980 | 43.423 | 2.693 | 1.00 | 17.41 |
| ATOM | 958 | O | LYS | B | 9 | 53.290 | 43.474 | 1.636 | 1.00 | 16.23 |
| ATOM | 959 | CB | LYS | B | 9 | 55.357 | 41.484 | 3.338 | 1.00 | 17.25 |
| ATOM | 960 | CG | LYS | B | 9 | 55.685 | 41.165 | 1.849 | 1.00 | 16.41 |
| ATOM | 961 | CD | LYS | B | 9 | 57.128 | 40.757 | 1.590 | 1.00 | 16.11 |
| ATOM | 962 | CE | LYS | B | 9 | 57.413 | 40.363 | 0.083 | 1.00 | 20.64 |
| ATOM | 963 | NZ | LYS | B | 9 | 58.845 | 40.122 | −0.219 | 1.00 | 24.09 |
| ATOM | 964 | N | LEU | B | 10 | 54.623 | 44.438 | 3.206 | 1.00 | 14.37 |
| ATOM | 965 | CA | LEU | B | 10 | 54.793 | 45.753 | 2.541 | 1.00 | 13.07 |
| ATOM | 966 | C | LEU | B | 10 | 56.264 | 45.671 | 2.117 | 1.00 | 17.74 |
| ATOM | 967 | O | LEU | B | 10 | 57.211 | 45.651 | 2.922 | 1.00 | 15.88 |
| ATOM | 968 | CB | LEU | B | 10 | 54.531 | 46.942 | 3.473 | 1.00 | 12.64 |
| ATOM | 969 | CG | LEU | B | 10 | 53.125 | 47.012 | 4.065 | 1.00 | 16.69 |
| ATOM | 970 | CD1 | LEU | B | 10 | 52.972 | 48.183 | 5.050 | 1.00 | 19.95 |
| ATOM | 971 | CD2 | LEU | B | 10 | 51.998 | 47.113 | 2.952 | 1.00 | 18.21 |
| ATOM | 972 | N | HIS | B | 11 | 56.532 | 45.559 | 0.795 | 1.00 | 15.41 |
| ATOM | 973 | CA | HIS | B | 11 | 57.852 | 45.410 | 0.342 | 1.00 | 15.54 |
| ATOM | 974 | C | HIS | B | 11 | 58.554 | 46.680 | −0.107 | 1.00 | 20.36 |
| ATOM | 975 | O | HIS | B | 11 | 58.088 | 47.329 | −1.109 | 1.00 | 19.27 |
| ATOM | 976 | CB | HIS | B | 11 | 57.855 | 44.396 | −0.897 | 1.00 | 17.02 |
| ATOM | 977 | CG | HIS | B | 11 | 59.222 | 43.925 | −1.277 | 1.00 | 20.52 |
| ATOM | 978 | ND1 | HIS | B | 11 | 59.891 | 42.946 | −0.575 | 1.00 | 23.10 |
| ATOM | 979 | CD2 | HIS | B | 11 | 60.067 | 44.321 | −2.265 | 1.00 | 23.01 |

-continued

Data Lists

| | | | | | | | | | |
|---|---|---|---|---|---|---|---|---|---|
| ATOM | 980 | CE1 | HIS | B | 11 | 61.084 | 42.750 | −1.109 | 1.00 | 22.29 |
| ATOM | 981 | NE2 | HIS | B | 11 | 61.218 | 43.579 | −2.141 | 1.00 | 22.03 |
| ATOM | 982 | N | ARG | B | 12 | 59.636 | 47.041 | 0.577 | 1.00 | 17.66 |
| ATOM | 983 | CA | ARG | B | 12 | 60.427 | 48.202 | 0.273 | 1.00 | 17.87 |
| ATOM | 984 | C | ARG | B | 12 | 59.755 | 49.542 | 0.461 | 1.00 | 21.36 |
| ATOM | 985 | O | ARG | B | 12 | 59.858 | 50.465 | −0.401 | 1.00 | 21.72 |
| ATOM | 986 | CB | ARG | B | 12 | 61.185 | 48.082 | −1.105 | 1.00 | 17.27 |
| ATOM | 987 | CG | ARG | B | 12 | 62.150 | 46.920 | −1.155 | 1.00 | 16.85 |
| ATOM | 988 | CD | ARG | B | 12 | 62.849 | 46.746 | −2.537 | 1.00 | 21.64 |
| ATOM | 989 | NE | ARG | B | 12 | 63.541 | 47.993 | −2.907 | 1.00 | 26.91 |
| ATOM | 990 | CZ | ARG | B | 12 | 64.818 | 48.252 | −2.642 | 1.00 | 32.28 |
| ATOM | 991 | NH1 | ARG | B | 12 | 65.345 | 49.421 | −3.011 | 1.00 | 32.70 |
| ATOM | 992 | NH2 | ARG | B | 12 | 65.573 | 47.367 | −2.015 | 1.00 | 23.04 |
| ATOM | 993 | N | VAL | B | 13 | 59.082 | 49.737 | 1.613 | 1.00 | 16.36 |
| ATOM | 994 | CA | VAL | B | 13 | 58.476 | 51.010 | 1.919 | 1.00 | 16.81 |
| ATOM | 995 | C | VAL | B | 13 | 59.568 | 51.825 | 2.625 | 1.00 | 19.79 |
| ATOM | 996 | O | VAL | B | 13 | 60.555 | 51.259 | 3.103 | 1.00 | 21.56 |
| ATOM | 997 | CB | VAL | B | 13 | 57.262 | 50.903 | 2.868 | 1.00 | 20.87 |
| ATOM | 998 | CG1 | VAL | B | 13 | 56.117 | 50.340 | 2.233 | 1.00 | 22.00 |
| ATOM | 999 | CG2 | VAL | B | 13 | 57.614 | 50.095 | 4.174 | 1.00 | 19.93 |
| ATOM | 1000 | N | LYS | B | 14 | 59.429 | 53.148 | 2.658 | 1.00 | 17.58 |
| ATOM | 1001 | CA | LYS | B | 14 | 60.462 | 53.955 | 3.313 | 1.00 | 18.29 |
| ATOM | 1002 | C | LYS | B | 14 | 59.955 | 54.558 | 4.631 | 1.00 | 17.32 |
| ATOM | 1003 | O | LYS | B | 14 | 58.811 | 54.965 | 4.720 | 1.00 | 17.18 |
| ATOM | 1004 | CB | LYS | B | 14 | 60.958 | 55.077 | 2.370 | 1.00 | 21.96 |
| ATOM | 1005 | CG | LYS | B | 14 | 61.928 | 54.568 | 1.327 | 1.00 | 29.69 |
| ATOM | 1006 | CD | LYS | B | 14 | 62.379 | 55.718 | 0.374 | 1.00 | 27.98 |
| ATOM | 1007 | CE | LYS | B | 14 | 63.251 | 55.192 | −0.769 | 1.00 | 33.09 |
| ATOM | 1008 | NZ | LYS | B | 14 | 62.422 | 54.676 | −1.901 | 1.00 | 36.70 |
| ATOM | 1009 | N | VAL | B | 15 | 60.836 | 54.550 | 5.641 | 1.00 | 17.61 |
| ATOM | 1010 | CA | VAL | B | 15 | 60.462 | 55.122 | 6.942 | 1.00 | 15.98 |
| ATOM | 1011 | C | VAL | B | 15 | 60.291 | 56.648 | 6.751 | 1.00 | 18.36 |
| ATOM | 1012 | O | VAL | B | 15 | 61.155 | 57.284 | 6.183 | 1.00 | 20.10 |
| ATOM | 1013 | CB | VAL | B | 15 | 61.537 | 54.823 | 7.986 | 1.00 | 18.17 |
| ATOM | 1014 | CG1 | VAL | B | 15 | 61.172 | 55.554 | 9.332 | 1.00 | 19.48 |
| ATOM | 1015 | CG2 | VAL | B | 15 | 61.579 | 53.284 | 8.219 | 1.00 | 18.97 |
| ATOM | 1016 | N | THR | B | 16 | 59.195 | 57.208 | 7.241 | 1.00 | 16.59 |
| ATOM | 1017 | CA | THR | B | 16 | 58.949 | 58.657 | 7.071 | 1.00 | 18.46 |
| ATOM | 1018 | C | THR | B | 16 | 59.061 | 59.479 | 8.337 | 1.00 | 23.98 |
| ATOM | 1019 | O | THR | B | 16 | 59.187 | 60.728 | 8.286 | 1.00 | 23.98 |
| ATOM | 1020 | CB | THR | B | 16 | 57.537 | 58.906 | 6.438 | 1.00 | 20.68 |
| ATOM | 1021 | OG1 | THR | B | 16 | 56.495 | 58.483 | 7.322 | 1.00 | 20.66 |
| ATOM | 1022 | CG2 | THR | B | 16 | 57.407 | 58.134 | 5.067 | 1.00 | 20.82 |
| ATOM | 1023 | N | HIS | B | 17 | 59.034 | 58.811 | 9.484 | 1.00 | 21.79 |
| ATOM | 1024 | CA | HIS | B | 17 | 59.102 | 59.539 | 10.776 | 1.00 | 23.09 |
| ATOM | 1025 | C | HIS | B | 17 | 59.580 | 58.582 | 11.852 | 1.00 | 25.64 |
| ATOM | 1026 | O | HIS | B | 17 | 59.398 | 57.358 | 11.739 | 1.00 | 20.59 |
| ATOM | 1027 | CB | HIS | B | 17 | 57.630 | 59.960 | 11.101 | 1.00 | 25.73 |
| ATOM | 1028 | CG | HIS | B | 17 | 57.436 | 60.783 | 12.353 | 1.00 | 31.57 |
| ATOM | 1029 | ND1 | HIS | B | 17 | 56.596 | 60.377 | 13.379 | 1.00 | 34.88 |
| ATOM | 1030 | CD2 | HIS | B | 17 | 57.919 | 62.000 | 12.724 | 1.00 | 34.96 |
| ATOM | 1031 | CE1 | HIS | B | 17 | 56.589 | 61.293 | 14.335 | 1.00 | 35.01 |
| ATOM | 1032 | NE2 | HIS | B | 17 | 57.383 | 62.290 | 13.966 | 1.00 | 35.08 |
| ATOM | 1033 | N | ALA | B | 18 | 60.189 | 59.139 | 12.893 | 1.00 | 25.07 |
| ATOM | 1034 | CA | ALA | B | 18 | 60.673 | 58.327 | 14.027 | 1.00 | 25.93 |
| ATOM | 1035 | C | ALA | B | 18 | 60.235 | 59.122 | 15.285 | 1.00 | 31.11 |
| ATOM | 1036 | O | ALA | B | 18 | 60.376 | 60.360 | 15.314 | 1.00 | 33.50 |
| ATOM | 1037 | CB | ALA | B | 18 | 62.157 | 58.146 | 13.972 | 1.00 | 27.54 |
| ATOM | 1038 | N | ASP | B | 19 | 59.643 | 58.456 | 16.281 | 1.00 | 24.42 |
| ATOM | 1039 | CA | ASP | B | 19 | 59.162 | 59.161 | 17.502 | 1.00 | 24.78 |
| ATOM | 1040 | C | ASP | B | 19 | 59.503 | 58.342 | 18.739 | 1.00 | 27.05 |
| ATOM | 1041 | O | ASP | B | 19 | 58.658 | 57.595 | 19.257 | 1.00 | 24.71 |
| ATOM | 1042 | CB | ASP | B | 19 | 57.647 | 59.409 | 17.384 | 1.00 | 25.96 |
| ATOM | 1043 | CG | ASP | B | 19 | 57.052 | 60.183 | 18.572 | 1.00 | 34.10 |
| ATOM | 1044 | OD1 | ASP | B | 19 | 57.807 | 60.624 | 19.466 | 1.00 | 34.04 |
| ATOM | 1045 | OD2 | ASP | B | 19 | 55.800 | 60.351 | 18.593 | 1.00 | 38.22 |
| ATOM | 1046 | N | LEU | B | 20 | 60.742 | 58.494 | 19.199 | 1.00 | 25.80 |
| ATOM | 1047 | CA | LEU | B | 20 | 61.238 | 57.779 | 20.364 | 1.00 | 24.85 |
| ATOM | 1048 | C | LEU | B | 20 | 60.390 | 57.962 | 21.616 | 1.00 | 27.59 |
| ATOM | 1049 | O | LEU | B | 20 | 60.129 | 56.981 | 22.335 | 1.00 | 26.06 |
| ATOM | 1050 | CB | LEU | B | 20 | 62.689 | 58.208 | 20.666 | 1.00 | 25.72 |
| ATOM | 1051 | CG | LEU | B | 20 | 63.459 | 57.525 | 21.809 | 1.00 | 29.24 |
| ATOM | 1052 | CD1 | LEU | B | 20 | 63.844 | 56.100 | 21.431 | 1.00 | 28.84 |
| ATOM | 1053 | CD2 | LEU | B | 20 | 64.720 | 58.345 | 22.159 | 1.00 | 29.15 |
| ATOM | 1054 | N | HIS | B | 21 | 59.981 | 59.207 | 21.878 | 1.00 | 28.61 |
| ATOM | 1055 | CA | HIS | B | 21 | 59.155 | 59.572 | 23.074 | 1.00 | 30.90 |
| ATOM | 1056 | C | HIS | B | 21 | 57.680 | 59.351 | 23.007 | 1.00 | 36.12 |

-continued

| | | | | | | | | | |
|---|---|---|---|---|---|---|---|---|---|
| ATOM | 1057 | O | HIS | B | 21 | 56.915 | 59.806 | 23.896 | 1.00 | 35.00 |
| ATOM | 1058 | CB | HIS | B | 21 | 59.509 | 60.991 | 23.549 | 1.00 | 32.76 |
| ATOM | 1059 | CG | HIS | B | 21 | 60.950 | 61.157 | 23.845 | 1.00 | 36.81 |
| ATOM | 1060 | ND1 | HIS | B | 21 | 61.792 | 61.941 | 23.086 | 1.00 | 39.48 |
| ATOM | 1061 | CD2 | HIS | B | 21 | 61.731 | 60.556 | 24.776 | 1.00 | 38.76 |
| ATOM | 1062 | CE1 | HIS | B | 21 | 63.025 | 61.847 | 23.564 | 1.00 | 38.26 |
| ATOM | 1063 | NE2 | HIS | B | 21 | 63.014 | 61.014 | 24.588 | 1.00 | 38.36 |
| ATOM | 1064 | N | TYR | B | 22 | 57.270 | 58.641 | 21.975 | 1.00 | 33.13 |
| ATOM | 1065 | CA | TYR | B | 22 | 55.874 | 58.333 | 21.767 | 1.00 | 33.14 |
| ATOM | 1066 | C | TYR | B | 22 | 55.136 | 57.743 | 22.985 | 1.00 | 37.60 |
| ATOM | 1067 | O | TYR | B | 22 | 55.697 | 56.936 | 23.774 | 1.00 | 32.76 |
| ATOM | 1068 | CB | TYR | B | 22 | 55.794 | 57.254 | 20.681 | 1.00 | 33.35 |
| ATOM | 1069 | CG | TYR | B | 22 | 54.410 | 57.005 | 20.169 | 1.00 | 35.03 |
| ATOM | 1070 | CD1 | TYR | B | 22 | 53.728 | 58.003 | 19.481 | 1.00 | 36.82 |
| ATOM | 1071 | CD2 | TYR | B | 22 | 53.772 | 55.794 | 20.385 | 1.00 | 35.58 |
| ATOM | 1072 | CE1 | TYR | B | 22 | 52.442 | 57.795 | 19.013 | 1.00 | 37.35 |
| ATOM | 1073 | CE2 | TYR | B | 22 | 52.491 | 55.577 | 19.914 | 1.00 | 36.01 |
| ATOM | 1074 | CZ | TYR | B | 22 | 51.834 | 56.569 | 19.229 | 1.00 | 42.70 |
| ATOM | 1075 | OH | TYR | B | 22 | 50.542 | 56.288 | 18.772 | 1.00 | 46.65 |
| ATOM | 1076 | N | GLU | B | 23 | 53.877 | 58.126 | 23.092 | 1.00 | 39.24 |
| ATOM | 1077 | CA | GLU | B | 23 | 52.991 | 57.636 | 24.122 | 1.00 | 42.44 |
| ATOM | 1078 | C | GLU | B | 23 | 51.673 | 57.203 | 23.428 | 1.00 | 47.01 |
| ATOM | 1079 | O | GLU | B | 23 | 50.884 | 58.032 | 23.017 | 1.00 | 48.53 |
| ATOM | 1080 | CB | GLU | B | 23 | 52.723 | 58.677 | 25.211 | 1.00 | 44.81 |
| ATOM | 1081 | CG | GLU | B | 23 | 51.620 | 58.234 | 26.155 | 1.00 | 53.00 |
| ATOM | 1082 | CD | GLU | B | 23 | 51.690 | 58.900 | 27.515 | 1.00 | 63.57 |
| ATOM | 1083 | OE1 | GLU | B | 23 | 52.173 | 60.058 | 27.596 | 1.00 | 70.57 |
| ATOM | 1084 | OE2 | GLU | B | 23 | 51.237 | 58.268 | 28.501 | 1.00 | 49.95 |
| ATOM | 1085 | N | GLY | B | 24 | 51.453 | 55.900 | 23.305 | 1.00 | 43.35 |
| ATOM | 1086 | CA | GLY | B | 24 | 50.234 | 55.411 | 22.678 | 1.00 | 47.63 |
| ATOM | 1087 | C | GLY | B | 24 | 50.321 | 53.939 | 22.257 | 1.00 | 49.81 |
| ATOM | 1088 | O | GLY | B | 24 | 50.860 | 53.127 | 23.028 | 1.00 | 43.71 |
| ATOM | 1089 | OH | GLY | B | 24 | 49.852 | 53.595 | 21.143 | 1.00 | 78.26 |
| ATOM | 1090 | C | PVL | B | 25 | 55.590 | 51.160 | 16.243 | 1.00 | 18.29 |
| ATOM | 1091 | O | PVL | B | 25 | 56.587 | 51.766 | 16.023 | 1.00 | 21.21 |
| ATOM | 1092 | CA | PVL | B | 25 | 55.340 | 50.687 | 17.625 | 1.00 | 27.46 |
| ATOM | 1093 | CB | PVL | B | 25 | 54.143 | 49.829 | 17.834 | 1.00 | 25.35 |
| ATOM | 1094 | ON | PVL | B | 25 | 56.135 | 50.957 | 18.541 | 1.00 | 33.71 |
| ATOM | 1095 | N | CYS | B | 26 | 54.735 | 50.714 | 15.217 | 1.00 | 15.60 |
| ATOM | 1096 | CA | CYS | B | 26 | 54.985 | 51.203 | 13.855 | 1.00 | 16.64 |
| ATOM | 1097 | CB | CYS | B | 26 | 55.756 | 50.146 | 13.029 | 1.00 | 14.30 |
| ATOM | 1098 | SG | CYS | B | 26 | 56.010 | 50.798 | 11.325 | 1.00 | 18.05 |
| ATOM | 1099 | C | CYS | B | 26 | 53.636 | 51.600 | 13.281 | 1.00 | 14.55 |
| ATOM | 1100 | O | CYS | B | 26 | 52.716 | 50.778 | 13.121 | 1.00 | 16.28 |
| ATOM | 1101 | N | ALA | B | 27 | 53.472 | 52.925 | 13.012 | 1.00 | 15.46 |
| ATOM | 1102 | CA | ALA | B | 27 | 52.197 | 53.479 | 12.457 | 1.00 | 15.63 |
| ATOM | 1103 | C | ALA | B | 27 | 52.328 | 53.470 | 10.917 | 1.00 | 15.10 |
| ATOM | 1104 | O | ALA | B | 27 | 53.303 | 53.924 | 10.380 | 1.00 | 15.77 |
| ATOM | 1105 | CB | ALA | B | 27 | 51.919 | 54.908 | 12.948 | 1.00 | 16.71 |
| ATOM | 1106 | N | ILE | B | 28 | 51.301 | 52.924 | 10.300 | 1.00 | 14.23 |
| ATOM | 1107 | CA | ILE | B | 28 | 51.286 | 52.712 | 8.846 | 1.00 | 14.71 |
| ATOM | 1108 | C | ILE | B | 28 | 49.989 | 53.151 | 8.224 | 1.00 | 17.41 |
| ATOM | 1109 | O | ILE | B | 28 | 48.913 | 52.880 | 8.714 | 1.00 | 16.90 |
| ATOM | 1110 | CB | ILE | B | 28 | 51.404 | 51.141 | 8.665 | 1.00 | 16.58 |
| ATOM | 1111 | CG1 | ILE | B | 28 | 52.699 | 50.640 | 9.314 | 1.00 | 16.36 |
| ATOM | 1112 | CG2 | ILE | B | 28 | 51.329 | 50.765 | 7.154 | 1.00 | 15.52 |
| ATOM | 1113 | CD1 | ILE | B | 28 | 52.708 | 49.114 | 9.667 | 1.00 | 18.68 |
| ATOM | 1114 | N | ASP | B | 29 | 50.128 | 53.872 | 7.090 | 1.00 | 16.97 |
| ATOM | 1115 | CA | ASP | B | 29 | 48.943 | 54.364 | 6.337 | 1.00 | 18.01 |
| ATOM | 1116 | C | ASP | B | 29 | 47.927 | 53.186 | 6.186 | 1.00 | 17.51 |
| ATOM | 1117 | O | ASP | B | 29 | 48.339 | 52.095 | 5.725 | 1.00 | 15.93 |
| ATOM | 1118 | CB | ASP | B | 29 | 49.481 | 54.766 | 4.949 | 1.00 | 18.64 |
| ATOM | 1119 | CG | ASP | B | 29 | 48.383 | 55.304 | 3.960 | 1.00 | 21.55 |
| ATOM | 1120 | OD1 | ASP | B | 29 | 47.171 | 55.003 | 4.082 | 1.00 | 21.30 |
| ATOM | 1121 | OD2 | ASP | B | 29 | 48.831 | 56.051 | 3.034 | 1.00 | 22.85 |
| ATOM | 1122 | N | GLN | B | 30 | 46.665 | 53.404 | 6.579 | 1.00 | 17.64 |
| ATOM | 1123 | CA | GLN | B | 30 | 45.593 | 52.389 | 6.498 | 1.00 | 16.64 |
| ATOM | 1124 | C | GLN | B | 30 | 45.497 | 51.773 | 5.101 | 1.00 | 20.42 |
| ATOM | 1125 | O | GLN | B | 30 | 45.212 | 50.578 | 4.991 | 1.00 | 19.64 |
| ATOM | 1126 | CB | GLN | B | 30 | 44.231 | 52.918 | 6.947 | 1.00 | 19.10 |
| ATOM | 1127 | CG | GLN | B | 30 | 43.138 | 51.881 | 6.990 | 1.00 | 20.18 |
| ATOM | 1128 | CD | GLN | B | 30 | 43.422 | 50.807 | 8.020 | 1.00 | 24.27 |
| ATOM | 1129 | CE1 | GLN | B | 30 | 43.624 | 51.129 | 9.221 | 1.00 | 20.83 |
| ATOM | 1130 | NE2 | GLN | B | 30 | 43.418 | 49.525 | 7.584 | 1.00 | 20.72 |
| ATOM | 1131 | N | ASP | B | 31 | 45.765 | 52.541 | 4.034 | 1.00 | 19.98 |
| ATOM | 1132 | CA | ASP | B | 31 | 45.692 | 51.922 | 2.700 | 1.00 | 20.52 |
| ATOM | 1133 | C | ASP | B | 31 | 46.711 | 50.794 | 2.519 | 1.00 | 19.87 |

-continued

Data Lists

| | | | | | | | | | |
|---|---|---|---|---|---|---|---|---|---|
| ATOM | 1134 | O | ASP | B | 31 | 46.458 | 49.781 | 1.783 | 1.00 | 20.49 |
| ATOM | 1135 | CB | ASP | B | 31 | 45.971 | 52.970 | 1.621 | 1.00 | 20.56 |
| ATOM | 1136 | CG | ASP | B | 31 | 44.751 | 53.787 | 1.281 | 1.00 | 27.59 |
| ATOM | 1137 | CD1 | ASP | B | 31 | 43.596 | 53.382 | 1.538 | 1.00 | 27.63 |
| ATOM | 1138 | CD2 | ASP | B | 31 | 44.990 | 54.926 | 0.798 | 1.00 | 25.47 |
| ATOM | 1139 | N | PHE | B | 32 | 47.886 | 50.935 | 3.170 | 1.00 | 17.26 |
| ATOM | 1140 | CA | PHE | B | 32 | 48.951 | 49.962 | 3.088 | 1.00 | 16.13 |
| ATOM | 1141 | C | PHE | B | 32 | 48.525 | 48.723 | 3.890 | 1.00 | 15.84 |
| ATOM | 1142 | O | PHE | B | 32 | 48.690 | 47.554 | 3.430 | 1.00 | 15.43 |
| ATOM | 1143 | CB | PHE | B | 32 | 50.278 | 50.479 | 3.670 | 1.00 | 17.62 |
| ATOM | 1144 | CG | PHE | B | 32 | 50.847 | 51.723 | 2.976 | 1.00 | 18.64 |
| ATOM | 1145 | CD1 | PHE | B | 32 | 50.236 | 52.299 | 1.842 | 1.00 | 20.38 |
| ATOM | 1146 | CD2 | PHE | B | 32 | 52.019 | 52.292 | 3.473 | 1.00 | 21.28 |
| ATOM | 1147 | CE1 | PHE | B | 32 | 50.828 | 53.473 | 1.249 | 1.00 | 21.62 |
| ATOM | 1148 | CE2 | PHE | B | 32 | 52.587 | 53.413 | 2.908 | 1.00 | 24.06 |
| ATOM | 1149 | CZ | PHE | B | 32 | 51.988 | 54.006 | 1.779 | 1.00 | 22.14 |
| ATOM | 1150 | N | LEU | B | 33 | 47.989 | 48.981 | 5.086 | 1.00 | 15.62 |
| ATOM | 1151 | CA | LEU | B | 33 | 47.526 | 47.856 | 5.919 | 1.00 | 15.62 |
| ATOM | 1152 | C | LEU | B | 33 | 46.481 | 47.031 | 5.124 | 1.00 | 14.56 |
| ATOM | 1153 | O | LEU | B | 33 | 46.534 | 45.810 | 5.106 | 1.00 | 15.50 |
| ATOM | 1154 | CB | LEU | B | 33 | 46.899 | 48.361 | 7.221 | 1.00 | 15.46 |
| ATOM | 1155 | CG | LEU | B | 33 | 47.899 | 49.072 | 8.189 | 1.00 | 17.68 |
| ATOM | 1156 | CD1 | LEU | B | 33 | 47.114 | 49.554 | 9.450 | 1.00 | 18.11 |
| ATOM | 1157 | CD2 | LEU | B | 33 | 48.993 | 48.086 | 8.627 | 1.00 | 17.59 |
| ATOM | 1158 | N | ASP | B | 34 | 45.530 | 47.724 | 4.466 | 1.00 | 15.47 |
| ATOM | 1159 | CA | ASP | B | 34 | 44.461 | 47.090 | 3.695 | 1.00 | 15.42 |
| ATOM | 1160 | C | ASP | B | 34 | 45.018 | 46.177 | 2.609 | 1.00 | 15.50 |
| ATOM | 1161 | O | ASP | B | 34 | 44.542 | 45.082 | 2.444 | 1.00 | 16.94 |
| ATOM | 1162 | CB | ASP | B | 34 | 43.604 | 48.177 | 3.031 | 1.00 | 16.78 |
| ATOM | 1163 | CG | ASP | B | 34 | 42.649 | 48.846 | 3.990 | 1.00 | 21.53 |
| ATOM | 1164 | OD1 | ASP | B | 34 | 42.574 | 48.461 | 5.192 | 1.00 | 22.41 |
| ATOM | 1165 | OD2 | ASP | B | 34 | 41.944 | 49.809 | 3.549 | 1.00 | 24.39 |
| ATOM | 1166 | N | ALA | B | 35 | 46.013 | 46.650 | 1.875 | 1.00 | 15.30 |
| ATOM | 1167 | CA | ALA | B | 35 | 46.623 | 45.864 | 0.804 | 1.00 | 16.57 |
| ATOM | 1168 | C | ALA | B | 35 | 47.378 | 44.636 | 1.289 | 1.00 | 18.73 |
| ATOM | 1169 | O | ALA | B | 35 | 47.387 | 43.587 | 0.644 | 1.00 | 19.02 |
| ATOM | 1170 | CB | ALA | B | 35 | 47.576 | 46.726 | −0.042 | 1.00 | 18.18 |
| ATOM | 1171 | N | ALA | B | 36 | 48.063 | 44.784 | 2.448 | 1.00 | 15.77 |
| ATOM | 1172 | CA | ALA | B | 36 | 48.818 | 43.688 | 2.949 | 1.00 | 14.01 |
| ATOM | 1173 | C | ALA | B | 36 | 48.015 | 42.756 | 3.920 | 1.00 | 12.66 |
| ATOM | 1174 | O | ALA | B | 36 | 48.612 | 41.710 | 4.327 | 1.00 | 15.97 |
| ATOM | 1175 | CB | ALA | B | 36 | 50.083 | 44.221 | 3.681 | 1.00 | 15.98 |
| ATOM | 1176 | N | GLY | B | 37 | 46.798 | 43.130 | 4.266 | 1.00 | 12.31 |
| ATOM | 1177 | CA | GLY | B | 37 | 45.973 | 42.352 | 5.150 | 1.00 | 12.99 |
| ATOM | 1178 | C | GLY | B | 37 | 46.496 | 42.432 | 6.606 | 1.00 | 13.99 |
| ATOM | 1179 | O | GLY | B | 37 | 46.069 | 41.557 | 7.415 | 1.00 | 13.49 |
| ATOM | 1180 | N | ILE | B | 38 | 47.307 | 43.444 | 6.904 | 1.00 | 13.30 |
| ATOM | 1181 | CA | ILE | B | 38 | 47.864 | 43.618 | 8.310 | 1.00 | 11.90 |
| ATOM | 1182 | C | ILE | B | 38 | 46.839 | 44.382 | 9.121 | 1.00 | 13.73 |
| ATOM | 1183 | O | ILE | B | 38 | 46.308 | 45.399 | 8.700 | 1.00 | 13.87 |
| ATOM | 1184 | CB | ILE | B | 38 | 49.184 | 44.279 | 8.258 | 1.00 | 12.06 |
| ATOM | 1185 | CG1 | ILE | B | 38 | 50.228 | 43.360 | 7.542 | 1.00 | 13.02 |
| ATOM | 1186 | CG2 | ILE | B | 38 | 49.697 | 44.582 | 9.755 | 1.00 | 11.46 |
| ATOM | 1187 | CD1 | ILE | B | 38 | 51.570 | 43.996 | 7.284 | 1.00 | 14.92 |
| ATOM | 1188 | N | LEU | B | 39 | 46.564 | 43.916 | 10.371 | 1.00 | 11.75 |
| ATOM | 1189 | CA | LEU | B | 39 | 45.578 | 44.546 | 11.229 | 1.00 | 11.57 |
| ATOM | 1190 | C | LEU | B | 39 | 46.194 | 45.436 | 12.297 | 1.00 | 13.60 |
| ATOM | 1191 | O | LEU | B | 39 | 47.314 | 45.212 | 12.681 | 1.00 | 12.83 |
| ATOM | 1192 | CB | LEU | B | 39 | 44.793 | 43.478 | 11.979 | 1.00 | 11.62 |
| ATOM | 1193 | CG | LEU | B | 39 | 44.184 | 42.300 | 11.176 | 1.00 | 13.66 |
| ATOM | 1194 | CD1 | LEU | B | 39 | 43.446 | 41.373 | 12.104 | 1.00 | 15.79 |
| ATOM | 1195 | CD2 | LEU | B | 39 | 43.241 | 42.956 | 10.120 | 1.00 | 15.29 |
| ATOM | 1196 | N | GLU | B | 40 | 45.452 | 46.455 | 12.667 | 1.00 | 14.52 |
| ATOM | 1197 | CA | GLU | B | 40 | 45.908 | 47.316 | 13.786 | 1.00 | 14.56 |
| ATOM | 1198 | C | GLU | B | 40 | 46.034 | 46.318 | 14.996 | 1.00 | 14.90 |
| ATOM | 1199 | O | GLU | B | 40 | 45.194 | 45.428 | 15.204 | 1.00 | 13.14 |
| ATOM | 1200 | CB | GLU | B | 40 | 44.819 | 48.341 | 14.096 | 1.00 | 17.43 |
| ATOM | 1201 | CG | GLU | B | 40 | 45.175 | 49.769 | 13.693 | 1.00 | 36.71 |
| ATOM | 1202 | CD | GLU | B | 40 | 44.728 | 50.776 | 14.770 | 1.00 | 43.99 |
| ATOM | 1203 | OE1 | GLU | B | 40 | 43.514 | 50.732 | 15.112 | 1.00 | 33.64 |
| ATOM | 1204 | OE2 | GLU | B | 40 | 45.573 | 51.603 | 15.285 | 1.00 | 23.74 |
| ATOM | 1205 | N | ASN | B | 41 | 47.136 | 46.514 | 15.758 | 1.00 | 12.38 |
| ATOM | 1206 | CA | ASN | B | 41 | 47.457 | 45.691 | 16.951 | 1.00 | 12.93 |
| ATOM | 1207 | C | ASN | B | 41 | 48.019 | 44.334 | 16.656 | 1.00 | 15.81 |
| ATOM | 1208 | O | ASN | B | 41 | 48.283 | 43.527 | 17.534 | 1.00 | 13.21 |
| ATOM | 1209 | CB | ASN | B | 41 | 46.298 | 45.648 | 17.922 | 1.00 | 14.28 |
| ATOM | 1210 | CG | ASN | B | 41 | 45.966 | 47.041 | 18.493 | 1.00 | 12.10 |

-continued

| | | | | | | | | | |
|---|---|---|---|---|---|---|---|---|---|
| ATOM | 1211 | OD1 | ASN | B | 41 | 46.860 | 47.804 | 18.856 | 1.00 | 16.64 |
| ATOM | 1212 | ND2 | ASN | B | 41 | 44.680 | 47.382 | 18.491 | 1.00 | 15.27 |
| ATOM | 1213 | N | GLU | B | 42 | 48.244 | 44.017 | 15.384 | 1.00 | 10.98 |
| ATOM | 1214 | CA | GLU | B | 42 | 48.831 | 42.744 | 15.033 | 1.00 | 9.74 |
| ATOM | 1215 | C | GLU | B | 42 | 50.356 | 42.767 | 15.148 | 1.00 | 9.74 |
| ATOM | 1216 | O | GLU | B | 42 | 51.026 | 43.784 | 14.869 | 1.00 | 10.17 |
| ATOM | 1217 | CB | GLU | B | 42 | 48.499 | 42.388 | 13.482 | 1.00 | 10.40 |
| ATOM | 1218 | CG | GLU | B | 42 | 48.990 | 40.990 | 13.056 | 1.00 | 10.03 |
| ATOM | 1219 | CD | GLU | B | 42 | 48.652 | 40.661 | 11.573 | 1.00 | 13.25 |
| ATOM | 1220 | OE1 | GLU | B | 42 | 48.260 | 41.628 | 10.893 | 1.00 | 15.16 |
| ATOM | 1221 | OE2 | GLU | B | 42 | 48.788 | 39.493 | 11.198 | 1.00 | 12.03 |
| ATOM | 1222 | N | ALA | B | 43 | 50.947 | 41.634 | 15.574 | 1.00 | 9.51 |
| ATOM | 1223 | CA | ALA | B | 43 | 52.384 | 41.493 | 15.647 | 1.00 | 10.88 |
| ATOM | 1224 | C | ALA | B | 43 | 52.996 | 41.666 | 14.214 | 1.00 | 10.85 |
| ATOM | 1225 | O | ALA | B | 43 | 52.435 | 41.054 | 13.263 | 1.00 | 11.54 |
| ATOM | 1226 | CB | ALA | B | 43 | 52.772 | 40.069 | 16.175 | 1.00 | 12.49 |
| ATOM | 1227 | N | ILE | B | 44 | 54.041 | 42.408 | 14.075 | 1.00 | 11.86 |
| ATOM | 1228 | CA | ILE | B | 44 | 54.719 | 42.557 | 12.737 | 1.00 | 11.02 |
| ATOM | 1229 | C | ILE | B | 44 | 56.251 | 42.437 | 12.901 | 1.00 | 13.51 |
| ATOM | 1230 | O | ILE | B | 44 | 56.824 | 42.780 | 13.996 | 1.00 | 13.63 |
| ATOM | 1231 | CB | ILE | B | 44 | 54.386 | 43.905 | 12.029 | 1.00 | 12.21 |
| ATOM | 1232 | CG1 | ILE | B | 44 | 54.727 | 45.106 | 12.987 | 1.00 | 12.04 |
| ATOM | 1233 | CG2 | ILE | B | 44 | 52.925 | 43.894 | 11.585 | 1.00 | 14.58 |
| ATOM | 1234 | CD1 | ILE | B | 44 | 54.477 | 46.487 | 12.346 | 1.00 | 12.27 |
| ATOM | 1235 | N | ASP | B | 45 | 56.970 | 41.986 | 11.865 | 1.00 | 10.42 |
| ATOM | 1236 | CA | ASP | B | 45 | 58.401 | 41.882 | 11.844 | 1.00 | 10.06 |
| ATOM | 1237 | C | ASP | B | 45 | 58.826 | 42.973 | 10.843 | 1.00 | 14.23 |
| ATOM | 1238 | O | ASP | B | 45 | 58.174 | 43.130 | 9.772 | 1.00 | 14.99 |
| ATOM | 1239 | CB | ASP | B | 45 | 58.893 | 40.494 | 11.379 | 1.00 | 12.39 |
| ATOM | 1240 | CG | ASP | B | 45 | 58.410 | 39.394 | 12.277 | 1.00 | 15.51 |
| ATOM | 1241 | OD1 | ASP | B | 45 | 58.325 | 39.655 | 13.536 | 1.00 | 15.80 |
| ATOM | 1242 | OD2 | ASP | B | 45 | 58.044 | 38.297 | 11.812 | 1.00 | 15.67 |
| ATOM | 1243 | N | ILE | B | 46 | 59.874 | 43.711 | 11.152 | 1.00 | 10.63 |
| ATOM | 1244 | CA | ILE | B | 46 | 60.402 | 44.798 | 10.315 | 1.00 | 10.58 |
| ATOM | 1245 | C | ILE | B | 46 | 61.845 | 44.462 | 10.039 | 1.00 | 14.80 |
| ATOM | 1246 | O | ILE | B | 46 | 62.670 | 44.242 | 10.926 | 1.00 | 13.14 |
| ATOM | 1247 | CB | ILE | B | 46 | 60.237 | 46.173 | 10.981 | 1.00 | 12.68 |
| ATOM | 1248 | CG1 | ILE | B | 46 | 58.759 | 46.398 | 11.267 | 1.00 | 11.97 |
| ATOM | 1249 | CG2 | ILE | B | 46 | 60.843 | 47.266 | 10.035 | 1.00 | 14.01 |
| ATOM | 1250 | CD1 | ILE | B | 46 | 58.431 | 47.842 | 11.715 | 1.00 | 17.51 |
| ATOM | 1251 | N | TRP | B | 47 | 62.185 | 44.361 | 8.719 | 1.00 | 11.09 |
| ATOM | 1252 | CA | TRP | B | 47 | 63.488 | 43.982 | 8.256 | 1.00 | 12.91 |
| ATOM | 1253 | C | TRP | B | 47 | 64.025 | 45.208 | 7.488 | 1.00 | 18.14 |
| ATOM | 1254 | O | TRP | B | 47 | 63.436 | 45.628 | 6.467 | 1.00 | 16.83 |
| ATOM | 1255 | CB | TRP | B | 47 | 63.352 | 42.731 | 7.340 | 1.00 | 12.75 |
| ATOM | 1256 | CG | TRP | B | 47 | 62.711 | 41.546 | 8.024 | 1.00 | 12.68 |
| ATOM | 1257 | CD1 | TRP | B | 47 | 62.891 | 41.157 | 9.370 | 1.00 | 13.80 |
| ATOM | 1258 | CD2 | TRP | B | 47 | 61.810 | 40.606 | 7.470 | 1.00 | 12.97 |
| ATOM | 1259 | NE1 | TRP | B | 47 | 62.133 | 40.068 | 9.635 | 1.00 | 12.97 |
| ATOM | 1260 | CE2 | TRP | B | 47 | 61.449 | 39.686 | 8.500 | 1.00 | 14.42 |
| ATOM | 1261 | CE3 | TRP | B | 47 | 61.195 | 40.476 | 6.207 | 1.00 | 14.96 |
| ATOM | 1262 | CZ2 | TRP | B | 47 | 60.573 | 38.635 | 8.298 | 1.00 | 14.53 |
| ATOM | 1263 | CZ3 | TRP | B | 47 | 60.351 | 39.440 | 5.994 | 1.00 | 16.02 |
| ATOM | 1264 | CH2 | TRP | B | 47 | 60.033 | 38.509 | 7.012 | 1.00 | 16.49 |
| ATOM | 1265 | N | ASN | B | 48 | 65.081 | 45.816 | 8.024 | 1.00 | 15.37 |
| ATOM | 1266 | CA | ASN | B | 48 | 65.648 | 47.056 | 7.466 | 1.00 | 15.56 |
| ATOM | 1267 | C | ASN | B | 48 | 66.662 | 46.765 | 6.393 | 1.00 | 16.84 |
| ATOM | 1268 | O | ASN | B | 48 | 67.746 | 46.284 | 6.662 | 1.00 | 15.08 |
| ATOM | 1269 | CB | ASN | B | 48 | 66.293 | 47.841 | 8.654 | 1.00 | 14.22 |
| ATOM | 1270 | CG | ASN | B | 48 | 66.594 | 49.267 | 8.309 | 1.00 | 19.83 |
| ATOM | 1271 | OD1 | ASN | B | 48 | 67.100 | 49.532 | 7.211 | 1.00 | 17.68 |
| ATOM | 1272 | ND2 | ASN | B | 48 | 66.291 | 50.207 | 9.205 | 1.00 | 18.60 |
| ATOM | 1273 | N | VAL | B | 49 | 66.292 | 47.051 | 5.125 | 1.00 | 16.35 |
| ATOM | 1274 | CA | VAL | B | 49 | 67.188 | 46.806 | 4.002 | 1.00 | 16.91 |
| ATOM | 1275 | C | VAL | B | 49 | 68.418 | 47.753 | 4.002 | 1.00 | 18.54 |
| ATOM | 1276 | O | VAL | B | 49 | 69.539 | 47.390 | 3.566 | 1.00 | 19.45 |
| ATOM | 1277 | CB | VAL | B | 49 | 66.442 | 47.003 | 2.694 | 1.00 | 20.06 |
| ATOM | 1278 | CG1 | VAL | B | 49 | 67.380 | 46.691 | 1.524 | 1.00 | 21.67 |
| ATOM | 1279 | CG2 | VAL | B | 49 | 65.196 | 46.106 | 2.650 | 1.00 | 18.68 |
| ATOM | 1280 | N | THR | B | 50 | 68.196 | 48.964 | 4.504 | 1.00 | 17.72 |
| ATOM | 1281 | CA | THR | B | 50 | 69.290 | 49.926 | 4.552 | 1.00 | 18.92 |
| ATOM | 1282 | C | THR | B | 50 | 70.403 | 49.565 | 5.528 | 1.00 | 20.97 |
| ATOM | 1283 | O | THR | B | 50 | 71.593 | 49.537 | 5.172 | 1.00 | 20.06 |
| ATOM | 1284 | CB | THR | B | 50 | 68.764 | 51.325 | 4.851 | 1.00 | 19.40 |
| ATOM | 1285 | OG1 | THR | B | 50 | 67.798 | 51.708 | 3.856 | 1.00 | 19.82 |
| ATOM | 1286 | CG2 | THR | B | 50 | 69.931 | 52.390 | 4.950 | 1.00 | 21.30 |
| ATOM | 1287 | N | ASN | B | 51 | 70.022 | 49.279 | 6.788 | 1.00 | 17.46 |

-continued

| | | | | | | | | | |
|---|---|---|---|---|---|---|---|---|---|
| ATOM | 1288 | CA | ASN | B | 51 | 71.032 | 48.962 | 7.814 | 1.00 | 18.39 |
| ATOM | 1289 | C | ASN | B | 51 | 71.132 | 47.525 | 8.327 | 1.00 | 19.48 |
| ATOM | 1290 | O | ASN | B | 51 | 71.970 | 47.226 | 9.183 | 1.00 | 19.00 |
| ATOM | 1291 | CB | ASN | B | 51 | 70.913 | 49.949 | 8.998 | 1.00 | 18.51 |
| ATOM | 1292 | CG | ASN | B | 51 | 69.679 | 49.690 | 9.874 | 1.00 | 22.35 |
| ATOM | 1293 | OD1 | ASN | B | 51 | 69.028 | 48.659 | 9.772 | 1.00 | 17.21 |
| ATOM | 1294 | ND2 | ASN | B | 51 | 69.349 | 50.649 | 10.715 | 1.00 | 21.24 |
| ATOM | 1295 | N | GLY | B | 52 | 70.282 | 46.636 | 7.807 | 1.00 | 15.50 |
| ATOM | 1296 | CA | GLY | B | 52 | 70.231 | 45.232 | 8.164 | 1.00 | 14.95 |
| ATOM | 1297 | C | GLY | B | 52 | 69.601 | 44.846 | 9.523 | 1.00 | 14.04 |
| ATOM | 1298 | O | GLY | B | 52 | 69.541 | 43.629 | 9.815 | 1.00 | 16.62 |
| ATOM | 1299 | N | LYS | B | 53 | 69.153 | 45.837 | 10.279 | 1.00 | 14.08 |
| ATOM | 1300 | CA | LYS | B | 53 | 68.540 | 45.457 | 11.593 | 1.00 | 14.38 |
| ATOM | 1301 | C | LYS | B | 53 | 67.239 | 44.729 | 11.349 | 1.00 | 15.94 |
| ATOM | 1302 | O | LYS | B | 53 | 66.565 | 44.973 | 10.344 | 1.00 | 16.45 |
| ATOM | 1303 | CB | LYS | B | 53 | 68.311 | 46.698 | 12.463 | 1.00 | 14.22 |
| ATOM | 1304 | CG | LYS | B | 53 | 69.654 | 47.303 | 12.877 | 1.00 | 16.49 |
| ATOM | 1305 | CD | LYS | B | 53 | 69.457 | 48.540 | 13.748 | 1.00 | 19.28 |
| ATOM | 1306 | CE | LYS | B | 53 | 70.801 | 49.177 | 14.108 | 1.00 | 26.70 |
| ATOM | 1307 | NZ | LYS | B | 53 | 70.585 | 50.475 | 14.799 | 1.00 | 29.14 |
| ATOM | 1308 | N | ARG | B | 54 | 66.839 | 43.849 | 12.303 | 1.00 | 12.88 |
| ATOM | 1309 | CA | ARG | B | 54 | 65.612 | 43.091 | 12.229 | 1.00 | 11.93 |
| ATOM | 1310 | C | ARG | B | 54 | 64.954 | 43.162 | 13.592 | 1.00 | 14.91 |
| ATOM | 1311 | O | ARG | B | 54 | 65.646 | 42.907 | 14.590 | 1.00 | 15.98 |
| ATOM | 1312 | CB | ARG | B | 54 | 65.862 | 41.628 | 11.855 | 1.00 | 13.59 |
| ATOM | 1313 | CG | ARG | B | 54 | 66.751 | 41.516 | 10.564 | 1.00 | 14.24 |
| ATOM | 1314 | CD | ARG | B | 54 | 67.058 | 40.054 | 10.159 | 1.00 | 13.75 |
| ATOM | 1315 | NE | ARG | B | 54 | 65.931 | 39.313 | 9.621 | 1.00 | 13.94 |
| ATOM | 1316 | CZ | ARG | B | 54 | 65.562 | 39.372 | 8.330 | 1.00 | 16.69 |
| ATOM | 1317 | NH1 | ARG | B | 54 | 66.281 | 40.180 | 7.510 | 1.00 | 13.80 |
| ATOM | 1318 | NH2 | ARG | B | 54 | 64.520 | 38.644 | 7.857 | 1.00 | 13.52 |
| ATOM | 1319 | N | PHE | B | 55 | 63.707 | 43.548 | 13.634 | 1.00 | 12.40 |
| ATOM | 1320 | CA | PHE | B | 55 | 63.013 | 43.648 | 14.924 | 1.00 | 13.30 |
| ATOM | 1321 | C | PHE | B | 55 | 61.564 | 43.314 | 14.815 | 1.00 | 18.51 |
| ATOM | 1322 | O | PHE | B | 55 | 61.017 | 43.231 | 13.703 | 1.00 | 16.08 |
| ATOM | 1323 | CB | PHE | B | 55 | 63.302 | 44.986 | 15.586 | 1.00 | 13.02 |
| ATOM | 1324 | CG | PHE | B | 55 | 62.735 | 46.165 | 14.864 | 1.00 | 14.95 |
| ATOM | 1325 | CD1 | PHE | B | 55 | 63.436 | 46.742 | 13.782 | 1.00 | 15.75 |
| ATOM | 1326 | CD2 | PHE | B | 55 | 61.514 | 46.740 | 15.273 | 1.00 | 15.13 |
| ATOM | 1327 | CE1 | PHE | B | 55 | 62.892 | 47.912 | 13.106 | 1.00 | 17.56 |
| ATOM | 1328 | CE2 | PHE | B | 55 | 60.996 | 47.844 | 14.615 | 1.00 | 17.23 |
| ATOM | 1329 | CZ | PHE | B | 55 | 61.713 | 48.427 | 13.528 | 1.00 | 16.09 |
| ATOM | 1330 | N | SER | B | 56 | 60.880 | 43.095 | 15.940 | 1.00 | 12.78 |
| ATOM | 1331 | CA | SER | B | 56 | 59.482 | 42.752 | 15.962 | 1.00 | 12.18 |
| ATOM | 1332 | C | SER | B | 56 | 58.741 | 43.706 | 16.846 | 1.00 | 15.48 |
| ATOM | 1333 | O | SER | B | 56 | 59.258 | 44.045 | 17.916 | 1.00 | 14.26 |
| ATOM | 1334 | CB | SER | B | 56 | 59.222 | 41.336 | 16.394 | 1.00 | 13.68 |
| ATOM | 1335 | OG | SER | B | 56 | 59.880 | 40.377 | 15.532 | 1.00 | 18.10 |
| ATOM | 1336 | N | THR | B | 57 | 57.570 | 44.140 | 16.428 | 1.00 | 11.29 |
| ATOM | 1337 | CA | THR | B | 57 | 56.749 | 45.129 | 17.169 | 1.00 | 11.02 |
| ATOM | 1338 | C | THR | B | 57 | 55.256 | 44.860 | 16.831 | 1.00 | 11.10 |
| ATOM | 1339 | O | THR | B | 57 | 54.854 | 43.697 | 16.649 | 1.00 | 10.41 |
| ATOM | 1340 | CB | THR | B | 57 | 57.270 | 46.560 | 16.849 | 1.00 | 13.63 |
| ATOM | 1341 | OG1 | THR | B | 57 | 56.492 | 47.529 | 17.575 | 1.00 | 16.82 |
| ATOM | 1342 | CG2 | THR | B | 57 | 57.073 | 46.896 | 15.328 | 1.00 | 16.40 |
| ATOM | 1343 | N | TYR | B | 58 | 54.424 | 45.890 | 16.747 | 1.00 | 11.85 |
| ATOM | 1344 | CA | TYR | B | 58 | 52.995 | 45.709 | 16.405 | 1.00 | 11.66 |
| ATOM | 1345 | C | TYR | B | 58 | 52.572 | 46.896 | 15.567 | 1.00 | 14.10 |
| ATOM | 1346 | O | TYR | B | 58 | 53.194 | 47.962 | 15.639 | 1.00 | 12.80 |
| ATOM | 1347 | CB | TYR | B | 58 | 52.072 | 45.475 | 17.632 | 1.00 | 13.66 |
| ATOM | 1348 | CG | TYR | B | 58 | 51.879 | 46.659 | 18.537 | 1.00 | 14.03 |
| ATOM | 1349 | CD1 | TYR | B | 58 | 52.768 | 46.908 | 19.611 | 1.00 | 14.60 |
| ATOM | 1350 | CD2 | TYR | B | 58 | 50.836 | 47.529 | 18.362 | 1.00 | 14.69 |
| ATOM | 1351 | CE1 | TYR | B | 58 | 52.596 | 48.015 | 20.420 | 1.00 | 14.59 |
| ATOM | 1352 | CE2 | TYR | B | 58 | 50.645 | 48.649 | 19.199 | 1.00 | 16.85 |
| ATOM | 1353 | CZ | TYR | B | 58 | 51.546 | 48.875 | 20.222 | 1.00 | 21.58 |
| ATOM | 1354 | OH | TYR | B | 58 | 51.493 | 49.934 | 21.108 | 1.00 | 22.59 |
| ATOM | 1355 | N | ALA | B | 59 | 51.536 | 46.705 | 14.748 | 1.00 | 12.25 |
| ATOM | 1356 | CA | ALA | B | 59 | 51.078 | 47.769 | 13.891 | 1.00 | 12.10 |
| ATOM | 1357 | C | ALA | B | 59 | 50.067 | 48.702 | 14.494 | 1.00 | 14.08 |
| ATOM | 1358 | O | ALA | B | 59 | 49.190 | 48.297 | 15.241 | 1.00 | 13.85 |
| ATOM | 1359 | CB | ALA | B | 59 | 50.435 | 47.110 | 12.626 | 1.00 | 13.24 |
| ATOM | 1360 | N | ILE | B | 60 | 50.148 | 49.990 | 14.096 | 1.00 | 15.08 |
| ATOM | 1361 | CA | ILE | B | 60 | 49.231 | 51.025 | 14.514 | 1.00 | 17.01 |
| ATOM | 1362 | C | ILE | B | 60 | 48.729 | 51.687 | 13.195 | 1.00 | 16.03 |
| ATOM | 1363 | O | ILE | B | 60 | 49.522 | 51.850 | 12.286 | 1.00 | 16.17 |
| ATOM | 1364 | CB | ILE | B | 60 | 50.004 | 52.105 | 15.349 | 1.00 | 20.97 |

-continued

Data Lists

| | | | | | | | | | |
|---|---|---|---|---|---|---|---|---|---|
| ATOM | 1365 | CG1 | ILE | B | 60 | 50.363 | 51.533 | 16.724 | 1.00 | 23.49 |
| ATOM | 1366 | CG2 | ILE | B | 60 | 49.155 | 53.362 | 15.569 | 1.00 | 23.18 |
| ATOM | 1367 | CD1 | ILE | B | 60 | 51.454 | 52.337 | 17.451 | 1.00 | 26.91 |
| ATOM | 1368 | N | ALA | B | 61 | 47.449 | 52.016 | 13.107 | 1.00 | 16.21 |
| ATOM | 1369 | CA | ALA | B | 61 | 46.948 | 52.655 | 11.878 | 1.00 | 17.99 |
| ATOM | 1370 | C | ALA | B | 61 | 47.328 | 54.129 | 11.847 | 1.00 | 20.83 |
| ATOM | 1371 | O | ALA | B | 61 | 47.221 | 54.819 | 12.875 | 1.00 | 20.99 |
| ATOM | 1372 | CB | ALA | B | 61 | 45.481 | 52.541 | 11.804 | 1.00 | 19.35 |
| ATOM | 1373 | N | ALA | B | 62 | 47.721 | 54.613 | 10.665 | 1.00 | 17.91 |
| ATOM | 1374 | CA | ALA | B | 62 | 48.040 | 56.043 | 10.407 | 1.00 | 17.67 |
| ATOM | 1375 | C | ALA | B | 62 | 46.962 | 56.453 | 9.380 | 1.00 | 23.91 |
| ATOM | 1376 | O | ALA | B | 62 | 46.335 | 55.614 | 8.745 | 1.00 | 22.36 |
| ATOM | 1377 | CB | ALA | B | 62 | 49.400 | 56.238 | 9.833 | 1.00 | 13.45 |
| ATOM | 1378 | N | GLU | B | 63 | 46.756 | 57.756 | 9.246 | 1.00 | 22.90 |
| ATOM | 1379 | CA | GLU | B | 63 | 45.759 | 58.312 | 8.358 | 1.00 | 23.71 |
| ATOM | 1380 | C | GLU | B | 63 | 45.824 | 57.781 | 6.943 | 1.00 | 23.19 |
| ATOM | 1381 | O | GLU | B | 63 | 46.894 | 57.737 | 6.345 | 1.00 | 22.01 |
| ATOM | 1382 | CB | GLU | B | 63 | 45.919 | 59.835 | 8.343 | 1.00 | 25.20 |
| ATOM | 1333 | CG | GLU | B | 63 | 44.902 | 60.517 | 7.444 | 1.00 | 31.69 |
| ATOM | 1384 | CD | GLU | B | 63 | 44.852 | 61.991 | 7.708 | 1.00 | 54.65 |
| ATOM | 1385 | OE1 | GLU | B | 63 | 44.033 | 62.414 | 8.559 | 1.00 | 50.68 |
| ATOM | 1386 | OE2 | GLU | B | 63 | 45.642 | 62.719 | 7.072 | 1.00 | 49.85 |
| ATOM | 1387 | N | ARG | B | 64 | 44.657 | 57.412 | 6.411 | 1.00 | 23.54 |
| ATOM | 1388 | CA | ARG | B | 64 | 44.564 | 56.896 | 5.065 | 1.00 | 24.49 |
| ATOM | 1389 | C | ARG | B | 64 | 45.068 | 57.940 | 4.059 | 1.00 | 29.91 |
| ATOM | 1390 | O | ARG | B | 64 | 44.635 | 59.103 | 4.101 | 1.00 | 30.10 |
| ATOM | 1391 | CB | ARG | B | 64 | 43.116 | 56.548 | 4.739 | 1.00 | 24.54 |
| ATOM | 1392 | CG | ARG | B | 64 | 42.977 | 55.708 | 3.502 | 1.00 | 33.44 |
| ATOM | 1393 | CD | ARG | B | 64 | 41.521 | 55.461 | 3.169 | 1.00 | 30.76 |
| ATOM | 1394 | NE | ARG | B | 64 | 40.824 | 54.612 | 4.127 | 1.00 | 27.92 |
| ATOM | 1395 | CZ | ARG | B | 64 | 41.003 | 53.288 | 4.241 | 1.00 | 30.52 |
| ATOM | 1396 | NH1 | ARG | B | 64 | 41.878 | 52.653 | 3.470 | 1.00 | 26.37 |
| ATOM | 1397 | NH2 | ARG | B | 64 | 40.302 | 52.609 | 5.131 | 1.00 | 30.42 |
| ATOM | 1398 | N | GLY | B | 65 | 45.967 | 57.544 | 3.177 | 1.00 | 27.07 |
| ATOM | 1399 | CA | GLY | B | 65 | 46.485 | 58.475 | 2.170 | 1.00 | 26.85 |
| ATOM | 1400 | C | GLY | B | 65 | 47.687 | 59.292 | 2.603 | 1.00 | 30.69 |
| ATOM | 1401 | O | GLY | B | 65 | 48.287 | 59.983 | 1.789 | 1.00 | 31.19 |
| ATOM | 1402 | N | SER | B | 66 | 48.069 | 59.183 | 3.874 | 1.00 | 25.88 |
| ATOM | 1403 | CA | SER | B | 66 | 49.215 | 59.916 | 4.387 | 1.00 | 24.31 |
| ATOM | 1404 | C | SER | B | 66 | 50.565 | 59.353 | 3.903 | 1.00 | 28.10 |
| ATOM | 1405 | O | SER | B | 66 | 51.589 | 60.044 | 3.898 | 1.00 | 29.06 |
| ATOM | 1406 | CB | SER | B | 66 | 49.182 | 59.888 | 5.929 | 1.00 | 25.33 |
| ATOM | 1407 | OG | SER | B | 66 | 49.450 | 58.548 | 6.422 | 1.00 | 25.27 |
| ATOM | 1408 | N | ARG | B | 67 | 50.576 | 58.055 | 3.539 | 1.00 | 21.92 |
| ATOM | 1409 | CA | ARG | B | 67 | 51.780 | 57.368 | 3.106 | 1.00 | 20.64 |
| ATOM | 1410 | C | ARG | B | 67 | 52.867 | 57.306 | 4.205 | 1.00 | 21.33 |
| ATOM | 1411 | O | ARG | B | 67 | 54.033 | 57.113 | 3.932 | 1.00 | 23.88 |
| ATOM | 1412 | CB | ARG | B | 67 | 52.272 | 57.896 | 1.753 | 1.00 | 24.90 |
| ATOM | 1413 | CG | ARG | B | 67 | 51.094 | 57.832 | 0.749 | 1.00 | 34.18 |
| ATOM | 1414 | CD | ARG | B | 67 | 51.498 | 57.942 | −0.692 | 1.00 | 41.97 |
| ATOM | 1415 | NE | ARG | B | 67 | 51.642 | 59.344 | −1.083 | 1.00 | 42.73 |
| ATOM | 1416 | CZ | ARG | B | 67 | 50.665 | 60.252 | −1.300 | 1.00 | 50.11 |
| ATOM | 1417 | NH1 | ARG | B | 67 | 49.347 | 60.005 | −1.191 | 1.00 | 32.87 |
| ATOM | 1418 | NH2 | ARG | B | 67 | 51.053 | 61.472 | −1.652 | 1.00 | 35.89 |
| ATOM | 1419 | N | ILE | B | 68 | 52.404 | 57.413 | 5.449 | 1.00 | 20.99 |
| ATOM | 1420 | CA | ILE | B | 68 | 53.313 | 57.374 | 6.590 | 1.00 | 19.82 |
| ATOM | 1421 | C | ILE | B | 68 | 53.722 | 55.943 | 7.025 | 1.00 | 18.74 |
| ATOM | 1422 | O | ILE | B | 68 | 52.928 | 54.964 | 6.944 | 1.00 | 18.59 |
| ATOM | 1423 | CB | ILE | B | 68 | 52.613 | 58.021 | 7.843 | 1.00 | 22.72 |
| ATOM | 1424 | CG1 | ILE | B | 68 | 52.569 | 59.567 | 7.775 | 1.00 | 22.79 |
| ATOM | 1425 | CG2 | ILE | B | 68 | 53.272 | 57.570 | 9.182 | 1.00 | 23.66 |
| ATOM | 1426 | CD1 | ILE | B | 68 | 51.511 | 60.133 | 8.696 | 1.00 | 24.22 |
| ATOM | 1427 | N | ILE | B | 69 | 54.953 | 55.877 | 7.455 | 1.00 | 17.03 |
| ATOM | 1428 | CA | ILE | B | 69 | 55.592 | 54.662 | 8.057 | 1.00 | 16.07 |
| ATOM | 1429 | C | ILE | B | 69 | 56.398 | 55.328 | 9.218 | 1.00 | 18.47 |
| ATOM | 1430 | O | ILE | B | 69 | 57.495 | 55.875 | 9.001 | 1.00 | 19.41 |
| ATOM | 1431 | CB | ILE | B | 69 | 56.579 | 53.927 | 7.167 | 1.00 | 17.97 |
| ATOM | 1432 | CG1 | ILE | B | 69 | 55.861 | 53.307 | 5.925 | 1.00 | 17.84 |
| ATOM | 1433 | CG2 | ILE | B | 69 | 57.274 | 52.750 | 7.990 | 1.00 | 14.87 |
| ATOM | 1434 | CD1 | ILE | B | 69 | 54.757 | 52.283 | 6.267 | 1.00 | 16.76 |
| ATOM | 1435 | N | SER | B | 70 | 55.833 | 55.293 | 10.427 | 1.00 | 16.82 |
| ATOM | 1436 | CA | SER | B | 70 | 56.501 | 55.939 | 11.600 | 1.00 | 16.67 |
| ATOM | 1437 | C | SER | B | 70 | 56.965 | 54.905 | 12.627 | 1.00 | 16.91 |
| ATOM | 1438 | O | SER | B | 70 | 56.147 | 54.102 | 13.128 | 1.00 | 17.58 |
| ATOM | 1439 | CB | SER | B | 70 | 55.507 | 56.879 | 12.249 | 1.00 | 19.85 |
| ATOM | 1440 | OG | SER | B | 70 | 56.106 | 57.626 | 13.304 | 1.00 | 22.39 |
| ATOM | 1441 | N | VAL | B | 71 | 58.251 | 54.930 | 12.921 | 1.00 | 16.01 |

-continued

Data Lists

| | | | | | | | | | |
|---|---|---|---|---|---|---|---|---|---|
| ATOM | 1442 | CA | VAL | B | 71 | 58.827 | 53.962 | 13.933 | 1.00 | 17.80 |
| ATOM | 1443 | C | VAL | B | 71 | 58.832 | 54.719 | 15.270 | 1.00 | 22.32 |
| ATOM | 1444 | O | VAL | B | 71 | 59.512 | 55.723 | 15.417 | 1.00 | 23.49 |
| ATOM | 1445 | CB | VAL | B | 71 | 60.163 | 53.404 | 13.523 | 1.00 | 22.83 |
| ATOM | 1446 | CG1 | VAL | B | 71 | 59.967 | 52.567 | 12.214 | 1.00 | 21.98 |
| ATOM | 1447 | CG2 | VAL | B | 71 | 61.222 | 54.501 | 13.387 | 1.00 | 24.06 |
| ATOM | 1448 | N | ASN | B | 72 | 58.010 | 54.232 | 16.202 | 1.00 | 20.48 |
| ATOM | 1449 | CA | ASN | B | 72 | 57.806 | 54.878 | 17.519 | 1.00 | 20.13 |
| ATOM | 1450 | C | ASN | B | 72 | 58.320 | 54.086 | 18.687 | 1.00 | 22.39 |
| ATOM | 1451 | O | ASN | B | 72 | 58.488 | 52.863 | 18.621 | 1.00 | 22.18 |
| ATOM | 1452 | CB | ASN | B | 72 | 56.296 | 55.038 | 17.753 | 1.00 | 21.77 |
| ATOM | 1453 | CG | ASN | B | 72 | 55.591 | 55.775 | 16.621 | 1.00 | 30.59 |
| ATOM | 1454 | OD1 | ASN | B | 72 | 56.228 | 56.530 | 15.869 | 1.00 | 25.69 |
| ATOM | 1455 | ND2 | ASN | B | 72 | 54.279 | 55.529 | 16.469 | 1.00 | 26.90 |
| ATOM | 1456 | N | GLY | B | 73 | 58.520 | 54.790 | 19.792 | 1.00 | 20.53 |
| ATOM | 1457 | CA | GLY | B | 73 | 58.998 | 54.092 | 20.992 | 1.00 | 19.66 |
| ATOM | 1458 | C | GLY | B | 73 | 60.428 | 53.605 | 20.792 | 1.00 | 20.18 |
| ATOM | 1459 | O | GLY | B | 73 | 61.239 | 54.232 | 20.080 | 1.00 | 19.03 |
| ATOM | 1460 | N | ALA | B | 74 | 60.758 | 52.473 | 21.443 | 1.00 | 16.73 |
| ATOM | 1461 | CA | ALA | B | 74 | 62.107 | 51.908 | 21.352 | 1.00 | 16.27 |
| ATOM | 1462 | C | ALA | B | 74 | 62.580 | 51.614 | 19.912 | 1.00 | 17.37 |
| ATOM | 1463 | O | ALA | B | 74 | 63.776 | 51.649 | 19.637 | 1.00 | 18.06 |
| ATOM | 1464 | CB | ALA | B | 74 | 62.278 | 50.633 | 22.256 | 1.00 | 17.59 |
| ATOM | 1465 | N | ALA | B | 75 | 61.592 | 51.305 | 19.057 | 1.00 | 17.95 |
| ATOM | 1466 | CA | ALA | B | 75 | 61.873 | 50.961 | 17.639 | 1.00 | 17.42 |
| ATOM | 1467 | C | ALA | B | 75 | 62.567 | 52.115 | 16.916 | 1.00 | 19.91 |
| ATOM | 1468 | O | ALA | B | 75 | 63.215 | 51.889 | 15.889 | 1.00 | 19.81 |
| ATOM | 1469 | CB | ALA | B | 75 | 60.630 | 50.577 | 16.959 | 1.00 | 18.30 |
| ATOM | 1470 | N | ALA | B | 76 | 62.467 | 53.348 | 17.441 | 1.00 | 16.78 |
| ATOM | 1471 | CA | ALA | B | 76 | 63.152 | 54.470 | 16.804 | 1.00 | 18.31 |
| ATOM | 1472 | C | ALA | B | 76 | 64.688 | 54.276 | 16.795 | 1.00 | 18.92 |
| ATOM | 1473 | O | ALA | B | 76 | 65.409 | 54.921 | 16.046 | 1.00 | 19.50 |
| ATOM | 1474 | CB | ALA | B | 76 | 62.747 | 55.786 | 17.477 | 1.00 | 19.95 |
| ATOM | 1475 | N | HIS | B | 77 | 65.225 | 53.369 | 17.637 | 1.00 | 16.41 |
| ATOM | 1476 | CA | HIS | B | 77 | 66.629 | 53.103 | 17.671 | 1.00 | 17.43 |
| ATOM | 1477 | C | HIS | B | 77 | 67.082 | 52.158 | 16.543 | 1.00 | 18.10 |
| ATOM | 1478 | O | HIS | B | 77 | 68.280 | 51.967 | 16.351 | 1.00 | 20.06 |
| ATOM | 1479 | CB | HIS | B | 77 | 66.975 | 52.307 | 18.995 | 1.00 | 19.37 |
| ATOM | 1480 | CG | HIS | B | 77 | 67.026 | 53.149 | 20.241 | 1.00 | 22.65 |
| ATOM | 1481 | ND1 | HIS | B | 77 | 68.174 | 53.787 | 20.649 | 1.00 | 25.27 |
| ATOM | 1482 | CD2 | HIS | B | 77 | 66.090 | 53.421 | 21.181 | 1.00 | 22.98 |
| ATOM | 1483 | CE1 | HIS | B | 77 | 67.944 | 54.431 | 21.784 | 1.00 | 24.52 |
| ATOM | 1484 | NE2 | HIS | B | 77 | 66.688 | 54.230 | 22.129 | 1.00 | 23.17 |
| ATOM | 1485 | N | CYS | B | 78 | 66.107 | 51.548 | 15.846 | 1.00 | 17.70 |
| ATOM | 1486 | CA | CYS | B | 78 | 66.400 | 50.536 | 14.812 | 1.00 | 18.05 |
| ATOM | 1487 | C | CYS | B | 78 | 66.195 | 50.986 | 13.386 | 1.00 | 21.51 |
| ATOM | 1488 | O | CYS | B | 78 | 66.497 | 50.233 | 12.465 | 1.00 | 21.14 |
| ATOM | 1489 | CB | CYS | B | 78 | 65.489 | 49.332 | 15.033 | 1.00 | 19.61 |
| ATOM | 1490 | SG | CYS | B | 78 | 65.663 | 48.553 | 16.688 | 1.00 | 25.07 |
| ATOM | 1491 | N | ALA | B | 79 | 65.673 | 52.190 | 13.200 | 1.00 | 20.09 |
| ATOM | 1492 | CA | ALA | B | 79 | 65.471 | 52.690 | 11.843 | 1.00 | 19.73 |
| ATOM | 1493 | C | ALA | B | 79 | 65.477 | 54.201 | 11.864 | 1.00 | 25.47 |
| ATOM | 1494 | O | ALA | B | 79 | 65.094 | 54.811 | 12.852 | 1.00 | 23.97 |
| ATOM | 1495 | CB | ALA | B | 79 | 64.173 | 52.190 | 11.274 | 1.00 | 20.06 |
| ATOM | 1496 | N | SER | B | 80 | 65.895 | 54.802 | 10.750 | 1.00 | 21.56 |
| ATOM | 1497 | CA | SER | B | 80 | 65.935 | 56.270 | 10.595 | 1.00 | 22.17 |
| ATOM | 1498 | C | SER | B | 80 | 65.082 | 56.677 | 9.407 | 1.00 | 23.37 |
| ATOM | 1499 | O | SER | B | 80 | 64.831 | 55.862 | 8.511 | 1.00 | 21.62 |
| ATOM | 1500 | CB | SER | B | 80 | 67.335 | 56.763 | 10.301 | 1.00 | 25.03 |
| ATOM | 1501 | OG | SER | B | 80 | 68.302 | 56.327 | 11.243 | 1.00 | 28.26 |
| ATOM | 1502 | N | VAL | B | 81 | 64.652 | 57.936 | 9.398 | 1.00 | 18.88 |
| ATOM | 1503 | CA | VAL | B | 81 | 63.839 | 58.463 | 8.295 | 1.00 | 19.13 |
| ATOM | 1504 | C | VAL | B | 81 | 64.647 | 58.216 | 7.017 | 1.00 | 21.75 |
| ATOM | 1505 | O | VAL | B | 81 | 65.878 | 58.452 | 6.967 | 1.00 | 20.90 |
| ATOM | 1506 | CB | VAL | B | 81 | 63.576 | 59.970 | 8.514 | 1.00 | 21.73 |
| ATOM | 1507 | CG1 | VAL | B | 81 | 63.015 | 60.599 | 7.224 | 1.00 | 22.57 |
| ATOM | 1508 | CG2 | VAL | B | 81 | 62.555 | 60.148 | 9.631 | 1.00 | 21.80 |
| ATOM | 1509 | N | GLY | B | 82 | 63.961 | 57.728 | 5.988 | 1.00 | 18.71 |
| ATOM | 1510 | CA | GLY | B | 82 | 64.654 | 57.428 | 4.731 | 1.00 | 18.70 |
| ATOM | 1511 | C | GLY | B | 82 | 65.071 | 55.972 | 4.552 | 1.00 | 22.87 |
| ATOM | 1512 | O | GLY | B | 82 | 65.361 | 55.545 | 3.448 | 1.00 | 22.78 |
| ATOM | 1513 | N | ASP | B | 83 | 65.157 | 55.182 | 5.641 | 1.00 | 16.66 |
| ATOM | 1514 | CA | ASP | B | 83 | 65.546 | 53.791 | 5.481 | 1.00 | 16.76 |
| ATOM | 1515 | C | ASP | B | 83 | 64.461 | 53.003 | 4.716 | 1.00 | 16.77 |
| ATOM | 1516 | O | ASP | B | 83 | 63.257 | 53.256 | 4.890 | 1.00 | 17.18 |
| ATOM | 1517 | CB | ASP | B | 83 | 65.668 | 53.149 | 6.878 | 1.00 | 18.79 |
| ATOM | 1518 | CG | ASP | B | 83 | 66.945 | 53.556 | 7.622 | 1.00 | 22.59 |

-continued

Data Lists

| | | | | | | | | | |
|---|---|---|---|---|---|---|---|---|---|
| ATOM | 1519 | OD1 | ASP | B | 83 | 67.788 | 54.320 | 7.106 | 1.00 | 20.93 |
| ATOM | 1520 | OD2 | ASP | B | 83 | 67.141 | 53.058 | 8.771 | 1.00 | 21.88 |
| ATOM | 1521 | N | ILE | B | 84 | 64.912 | 52.031 | 3.926 | 1.00 | 17.58 |
| ATOM | 1522 | CA | ILE | B | 84 | 63.979 | 51.167 | 3.183 | 1.00 | 17.77 |
| ATOM | 1523 | C | ILE | B | 84 | 63.804 | 49.904 | 4.035 | 1.00 | 17.52 |
| ATOM | 1524 | O | ILE | B | 84 | 64.819 | 49.318 | 4.435 | 1.00 | 16.51 |
| ATOM | 1525 | CB | ILE | B | 84 | 64.627 | 50.788 | 1.851 | 1.00 | 21.87 |
| ATOM | 1526 | CG1 | ILE | B | 84 | 64.840 | 52.071 | 1.020 | 1.00 | 22.20 |
| ATOM | 1527 | CG2 | ILE | B | 84 | 63.771 | 49.760 | 1.060 | 1.00 | 22.70 |
| ATOM | 1528 | CD1 | ILE | B | 84 | 65.694 | 51.766 | −0.225 | 1.00 | 27.68 |
| ATOM | 1529 | N | VAL | B | 85 | 62.549 | 49.558 | 4.289 | 1.00 | 16.68 |
| ATOM | 1530 | CA | VAL | B | 85 | 62.253 | 48.361 | 5.100 | 1.00 | 14.93 |
| ATOM | 1531 | C | VAL | B | 85 | 61.196 | 47.462 | 4.460 | 1.00 | 18.77 |
| ATOM | 1532 | O | VAL | B | 85 | 60.487 | 47.874 | 3.522 | 1.00 | 18.51 |
| ATOM | 1533 | CB | VAL | B | 85 | 61.774 | 48.796 | 6.520 | 1.00 | 15.49 |
| ATOM | 1534 | CG1 | VAL | B | 85 | 61.754 | 49.740 | 7.159 | 1.00 | 16.44 |
| ATOM | 1535 | CG2 | VAL | B | 85 | 60.456 | 49.420 | 6.480 | 1.00 | 14.40 |
| ATOM | 1536 | N | ILE | B | 86 | 61.088 | 46.220 | 4.979 | 1.00 | 14.77 |
| ATOM | 1537 | CA | ILE | B | 86 | 60.101 | 45.258 | 4.557 | 1.00 | 15.52 |
| ATOM | 1538 | C | ILE | B | 86 | 59.318 | 44.987 | 5.853 | 1.00 | 15.28 |
| ATOM | 1539 | O | ILE | B | 86 | 59.977 | 44.736 | 6.887 | 1.00 | 15.56 |
| ATOM | 1540 | CB | ILE | B | 86 | 60.708 | 43.982 | 4.000 | 1.00 | 18.22 |
| ATOM | 1541 | CG1 | ILE | B | 86 | 61.392 | 44.270 | 2.628 | 1.00 | 19.52 |
| ATOM | 1542 | CG2 | ILE | B | 86 | 59.635 | 42.934 | 3.810 | 1.00 | 18.36 |
| ATOM | 1543 | CD1 | ILE | B | 86 | 62.446 | 43.260 | 2.291 | 1.00 | 25.25 |
| ATOM | 1544 | N | ILE | B | 87 | 58.027 | 45.119 | 5.832 | 1.00 | 11.80 |
| ATOM | 1545 | CA | ILE | B | 87 | 57.150 | 44.909 | 7.039 | 1.00 | 11.37 |
| ATOM | 1546 | C | ILE | B | 87 | 56.294 | 43.697 | 6.765 | 1.00 | 16.80 |
| ATOM | 1547 | O | ILE | B | 87 | 55.535 | 43.669 | 5.743 | 1.00 | 15.75 |
| ATOM | 1548 | CB | ILE | B | 87 | 56.290 | 46.133 | 7.310 | 1.00 | 14.04 |
| ATOM | 1549 | CG1 | ILE | B | 87 | 57.201 | 47.385 | 7.461 | 1.00 | 14.68 |
| ATOM | 1550 | CG2 | ILE | B | 87 | 55.352 | 45.915 | 8.585 | 1.00 | 16.46 |
| ATOM | 1551 | CD1 | ILE | B | 87 | 56.479 | 48.706 | 7.825 | 1.00 | 16.93 |
| ATOM | 1552 | N | ALA | B | 88 | 56.344 | 42.673 | 7.625 | 1.00 | 13.54 |
| ATOM | 1553 | CA | ALA | B | 88 | 55.573 | 41.433 | 7.389 | 1.00 | 12.01 |
| ATOM | 1554 | C | ALA | B | 88 | 54.747 | 40.989 | 8.570 | 1.00 | 15.27 |
| ATOM | 1555 | O | ALA | B | 88 | 55.124 | 41.315 | 9.709 | 1.00 | 14.13 |
| ATOM | 1556 | CB | ALA | B | 88 | 56.578 | 40.310 | 7.103 | 1.00 | 12.68 |
| ATOM | 1557 | N | SER | B | 89 | 53.681 | 40.257 | 8.354 | 1.00 | 11.75 |
| ATOM | 1558 | CA | SER | B | 89 | 52.915 | 39.648 | 9.450 | 1.00 | 9.22 |
| ATOM | 1559 | C | SER | B | 89 | 52.832 | 38.161 | 9.095 | 1.00 | 13.85 |
| ATOM | 1560 | O | SER | B | 89 | 52.842 | 37.761 | 7.892 | 1.00 | 12.02 |
| ATOM | 1561 | CB | SER | B | 89 | 51.576 | 40.264 | 9.748 | 1.00 | 13.00 |
| ATOM | 1562 | OG | SER | B | 89 | 50.496 | 39.710 | 8.999 | 1.00 | 13.68 |
| ATOM | 1563 | N | PHE | B | 90 | 52.719 | 37.289 | 10.096 | 1.00 | 9.51 |
| ATOM | 1564 | CA | PHE | B | 90 | 52.623 | 35.844 | 9.949 | 1.00 | 10.69 |
| ATOM | 1565 | C | PHE | B | 90 | 51.374 | 35.318 | 10.617 | 1.00 | 14.12 |
| ATOM | 1566 | O | PHE | B | 90 | 50.966 | 35.838 | 11.662 | 1.00 | 13.43 |
| ATOM | 1567 | CB | PHE | B | 90 | 53.867 | 35.159 | 10.575 | 1.00 | 9.99 |
| ATOM | 1568 | CG | PHE | B | 90 | 55.113 | 35.353 | 9.734 | 1.00 | 8.63 |
| ATOM | 1569 | CD1 | PHE | B | 90 | 55.859 | 36.535 | 9.814 | 1.00 | 12.75 |
| ATOM | 1570 | CD2 | PHE | B | 90 | 55.522 | 34.331 | 8.843 | 1.00 | 9.84 |
| ATOM | 1571 | CE1 | PHE | B | 90 | 57.025 | 36.701 | 9.041 | 1.00 | 12.66 |
| ATOM | 1572 | CE2 | PHE | B | 90 | 56.641 | 34.530 | 8.034 | 1.00 | 11.34 |
| ATOM | 1573 | CZ | PHE | B | 90 | 57.402 | 35.653 | 8.117 | 1.00 | 11.79 |
| ATOM | 1574 | N | VAL | B | 91 | 50.758 | 34.290 | 10.053 | 1.00 | 11.04 |
| ATOM | 1575 | CA | VAL | B | 91 | 49.550 | 33.671 | 10.631 | 1.00 | 8.97 |
| ATOM | 1576 | C | VAL | B | 91 | 49.759 | 32.182 | 10.733 | 1.00 | 12.88 |
| ATOM | 1577 | O | VAL | B | 91 | 50.664 | 31.609 | 10.051 | 1.00 | 13.37 |
| ATOM | 1578 | CB | VAL | B | 91 | 48.248 | 33.943 | 9.847 | 1.00 | 11.62 |
| ATOM | 1579 | CG1 | VAL | B | 91 | 47.808 | 35.362 | 9.981 | 1.00 | 11.91 |
| ATOM | 1580 | CG2 | VAL | B | 91 | 48.467 | 33.557 | 8.297 | 1.00 | 13.43 |
| ATOM | 1581 | N | THR | B | 92 | 48.950 | 31.506 | 11.576 | 1.00 | 11.67 |
| ATOM | 1582 | CA | THR | B | 92 | 49.050 | 30.076 | 11.700 | 1.00 | 9.61 |
| ATOM | 1583 | C | THR | B | 92 | 47.768 | 29.379 | 11.153 | 1.00 | 8.31 |
| ATOM | 1584 | O | THR | B | 92 | 46.695 | 29.929 | 11.140 | 1.00 | 11.35 |
| ATOM | 1585 | CB | THR | B | 92 | 49.410 | 29.637 | 13.156 | 1.00 | 12.02 |
| ATOM | 1586 | OG1 | THR | B | 92 | 48.375 | 30.148 | 14.048 | 1.00 | 17.42 |
| ATOM | 1587 | CG2 | THR | B | 92 | 50.764 | 30.137 | 13.517 | 1.00 | 11.07 |
| ATOM | 1588 | N | MET | B | 93 | 47.931 | 28.135 | 10.727 | 1.00 | 10.31 |
| ATOM | 1589 | CA | MET | B | 93 | 46.813 | 27.363 | 10.119 | 1.00 | 10.55 |
| ATOM | 1590 | C | MET | B | 93 | 47.283 | 25.922 | 9.940 | 1.00 | 10.55 |
| ATOM | 1591 | O | MET | B | 93 | 48.489 | 25.635 | 9.886 | 1.00 | 11.69 |
| ATOM | 1592 | CB | MET | B | 93 | 46.433 | 27.950 | 8.677 | 1.00 | 11.27 |
| ATOM | 1593 | CG | MET | B | 93 | 47.606 | 27.775 | 7.732 | 1.00 | 11.07 |
| ATOM | 1594 | SD | MET | B | 93 | 47.367 | 28.740 | 6.145 | 1.00 | 13.35 |
| ATOM | 1595 | CE | MET | B | 93 | 47.673 | 30.365 | 6.821 | 1.00 | 13.30 |

-continued

| | | | | | | | | | |
|---|---|---|---|---|---|---|---|---|---|
| \multicolumn{10}{c}{Data Lists} |

| | | | | | | | | | |
|---|---|---|---|---|---|---|---|---|---|
| ATOM | 1596 | N | PRO | B | 94 | 46.310 | 25.017 | 9.819 | 1.00 | 10.89 |
| ATOM | 1597 | CA | PRO | B | 94 | 46.643 | 23.597 | 9.614 | 1.00 | 10.92 |
| ATOM | 1598 | C | PRO | B | 94 | 47.476 | 23.350 | 8.341 | 1.00 | 13.89 |
| ATOM | 1599 | O | PRO | B | 94 | 47.320 | 24.098 | 7.342 | 1.00 | 13.64 |
| ATOM | 1600 | CB | PRO | B | 94 | 45.279 | 22.924 | 9.495 | 1.00 | 15.15 |
| ATOM | 1601 | CG | PRO | B | 94 | 44.323 | 23.877 | 10.157 | 1.00 | 18.73 |
| ATOM | 1602 | CD | PRO | B | 94 | 44.883 | 25.258 | 9.963 | 1.00 | 13.59 |
| ATOM | 1603 | N | ASP | B | 95 | 48.342 | 22.360 | 8.373 | 1.00 | 12.77 |
| ATOM | 1604 | CA | ASP | B | 95 | 49.212 | 22.008 | 7.262 | 1.00 | 11.85 |
| ATOM | 1605 | C | ASP | B | 95 | 48.393 | 21.914 | 5.939 | 1.00 | 12.73 |
| ATOM | 1606 | O | ASP | B | 95 | 48.870 | 22.437 | 4.868 | 1.00 | 14.23 |
| ATOM | 1607 | CB | ASP | B | 95 | 49.866 | 20.644 | 7.529 | 1.00 | 13.88 |
| ATOM | 1608 | CG | ASP | B | 95 | 50.845 | 20.258 | 6.464 | 1.00 | 16.93 |
| ATOM | 1609 | OD1 | ASP | B | 95 | 51.845 | 20.951 | 6.229 | 1.00 | 15.12 |
| ATOM | 1610 | OD2 | ASP | B | 95 | 50.556 | 19.245 | 5.782 | 1.00 | 25.27 |
| ATOM | 1611 | N | GLU | B | 96 | 47.243 | 21.265 | 6.009 | 1.00 | 11.92 |
| ATOM | 1612 | CA | GLU | B | 96 | 46.390 | 21.080 | 4.780 | 1.00 | 13.09 |
| ATOM | 1613 | C | GLU | B | 96 | 46.038 | 22.401 | 4.116 | 1.00 | 17.50 |
| ATOM | 1614 | O | GLU | B | 96 | 46.007 | 22.470 | 2.870 | 1.00 | 17.59 |
| ATOM | 1615 | CB | GLU | B | 96 | 45.127 | 20.359 | 5.163 | 1.00 | 15.73 |
| ATOM | 1616 | CG | GLU | B | 96 | 44.284 | 19.936 | 3.967 | 1.00 | 27.44 |
| ATOM | 1617 | CD | GLU | B | 96 | 43.202 | 20.920 | 3.636 | 1.00 | 46.48 |
| ATOM | 1618 | OE1 | GLU | B | 96 | 42.841 | 21.740 | 4.488 | 1.00 | 32.53 |
| ATOM | 1619 | OE2 | GLU | B | 96 | 42.694 | 20.865 | 2.486 | 1.00 | 50.29 |
| ATOM | 1620 | N | GLU | B | 97 | 45.759 | 23.446 | 4.888 | 1.00 | 13.12 |
| ATOM | 1621 | CA | GLU | B | 97 | 45.427 | 24.755 | 4.311 | 1.00 | 11.58 |
| ATOM | 1622 | C | GLU | B | 97 | 46.740 | 25.459 | 3.880 | 1.00 | 14.13 |
| ATOM | 1623 | O | GLU | B | 97 | 46.819 | 26.229 | 2.912 | 1.00 | 14.05 |
| ATOM | 1624 | CB | GLU | B | 97 | 44.687 | 25.646 | 5.357 | 1.00 | 10.79 |
| ATOM | 1625 | CG | GLU | B | 97 | 43.358 | 25.155 | 5.736 | 1.00 | 12.84 |
| ATOM | 1626 | CD | GLU | B | 97 | 42.625 | 26.039 | 6.749 | 1.00 | 16.10 |
| ATOM | 1627 | OE1 | GLU | B | 97 | 43.205 | 27.015 | 7.351 | 1.00 | 17.56 |
| ATOM | 1628 | OE2 | GLU | B | 97 | 41.424 | 25.785 | 6.889 | 1.00 | 19.58 |
| ATOM | 1629 | N | ALA | B | 98 | 47.825 | 25.307 | 4.639 | 1.00 | 11.26 |
| ATOM | 1630 | CA | ALA | B | 98 | 49.073 | 25.952 | 4.345 | 1.00 | 12.13 |
| ATOM | 1631 | C | ALA | B | 98 | 49.676 | 25.620 | 2.956 | 1.00 | 12.78 |
| ATOM | 1632 | O | ALA | B | 98 | 50.385 | 26.476 | 2.363 | 1.00 | 12.87 |
| ATOM | 1633 | CB | ALA | B | 98 | 50.090 | 25.538 | 5.483 | 1.00 | 13.93 |
| ATOM | 1634 | N | ARG | B | 99 | 49.379 | 24.371 | 2.518 | 1.00 | 13.12 |
| ATOM | 1635 | CA | ARG | B | 99 | 49.910 | 23.918 | 1.252 | 1.00 | 13.91 |
| ATOM | 1636 | C | ARG | B | 99 | 49.405 | 24.782 | 0.094 | 1.00 | 15.52 |
| ATOM | 1637 | O | ARG | B | 99 | 50.124 | 24.819 | −0.929 | 1.00 | 16.74 |
| ATOM | 1638 | CB | ARG | B | 99 | 49.565 | 22.459 | 1.069 | 1.00 | 13.81 |
| ATOM | 1639 | CG | ARG | B | 99 | 50.400 | 21.628 | 2.049 | 1.00 | 21.54 |
| ATOM | 1640 | CD | ARG | B | 99 | 50.114 | 20.193 | 2.018 | 1.00 | 31.31 |
| ATOM | 1641 | NE | ARG | B | 99 | 50.922 | 19.539 | 3.049 | 1.00 | 34.14 |
| ATOM | 1642 | CZ | ARG | B | 99 | 52.233 | 19.293 | 2.966 | 1.00 | 39.78 |
| ATOM | 1643 | NH1 | ARG | B | 99 | 52.927 | 19.613 | 1.874 | 1.00 | 39.29 |
| ATOM | 1644 | NH2 | ARG | B | 99 | 52.860 | 18.698 | 3.965 | 1.00 | 34.68 |
| ATOM | 1645 | N | THR | B | 100 | 48.273 | 25.465 | 0.233 | 1.00 | 12.99 |
| ATOM | 1646 | CA | THR | B | 100 | 47.765 | 26.311 | −0.888 | 1.00 | 13.08 |
| ATOM | 1647 | C | THR | B | 100 | 47.681 | 27.801 | −0.521 | 1.00 | 15.62 |
| ATOM | 1648 | O | THR | B | 100 | 47.191 | 28.652 | −1.282 | 1.00 | 16.66 |
| ATOM | 1649 | CB | THR | B | 100 | 46.391 | 25.798 | −1.313 | 1.00 | 15.79 |
| ATOM | 1650 | OG1 | THR | B | 100 | 45.503 | 25.711 | −0.202 | 1.00 | 14.58 |
| ATOM | 1651 | CG2 | THR | B | 100 | 46.501 | 24.357 | −1.922 | 1.00 | 15.05 |
| ATOM | 1652 | N | TRP | B | 101 | 48.179 | 28.176 | 0.681 | 1.00 | 14.25 |
| ATOM | 1653 | CA | TRP | B | 101 | 48.083 | 29.565 | 1.087 | 1.00 | 13.12 |
| ATOM | 1654 | C | TRP | B | 101 | 48.843 | 30.513 | 0.232 | 1.00 | 15.17 |
| ATOM | 1655 | O | TRP | B | 101 | 49.947 | 30.182 | −0.256 | 1.00 | 16.82 |
| ATOM | 1656 | CB | TRP | B | 101 | 48.617 | 29.632 | 2.595 | 1.00 | 11.79 |
| ATOM | 1657 | CG | TRP | B | 101 | 48.657 | 31.026 | 3.110 | 1.00 | 10.50 |
| ATOM | 1658 | CD1 | TRP | B | 101 | 49.734 | 31.812 | 3.259 | 1.00 | 12.40 |
| ATOM | 1659 | CD2 | TRP | B | 101 | 47.519 | 31.822 | 3.403 | 1.00 | 12.89 |
| ATOM | 1660 | NE1 | TRP | B | 101 | 49.344 | 33.048 | 3.665 | 1.00 | 12.65 |
| ATOM | 1661 | CE2 | TRP | B | 101 | 47.998 | 33.095 | 3.786 | 1.00 | 13.88 |
| ATOM | 1662 | CE3 | TRP | B | 101 | 46.141 | 31.580 | 3.424 | 1.00 | 15.74 |
| ATOM | 1663 | CZ2 | TRP | B | 101 | 47.158 | 34.140 | 4.162 | 1.00 | 16.20 |
| ATOM | 1664 | CZ3 | TRP | B | 101 | 45.272 | 32.635 | 3.777 | 1.00 | 19.25 |
| ATOM | 1665 | CH2 | TRP | B | 101 | 45.792 | 33.914 | 4.137 | 1.00 | 19.62 |
| ATOM | 1666 | N | ARG | B | 102 | 48.283 | 31.722 | 0.072 | 1.00 | 15.08 |
| ATOM | 1667 | CA | ARG | B | 102 | 48.934 | 32.768 | −0.695 | 1.00 | 15.90 |
| ATOM | 1668 | C | ARG | B | 102 | 48.968 | 34.063 | 0.149 | 1.00 | 11.33 |
| ATOM | 1669 | O | ARG | B | 102 | 47.928 | 34.506 | 0.584 | 1.00 | 14.41 |
| ATOM | 1670 | CB | ARG | B | 102 | 48.114 | 33.078 | −1.993 | 1.00 | 18.89 |
| ATOM | 1671 | CG | ARG | B | 102 | 48.011 | 31.878 | −2.994 | 1.00 | 24.40 |
| ATOM | 1672 | CD | ARG | B | 102 | 47.276 | 32.241 | −4.310 | 1.00 | 22.77 |

-continued

| | | | | | | | | | |
|---|---|---|---|---|---|---|---|---|---|
| | | | Data Lists | | | | | | |
| ATOM | 1673 | NE   | ARG | B | 102 | 47.968 | 33.268 | −5.060 | 1.00 | 27.18 |
| ATOM | 1674 | CZ   | ARG | B | 102 | 48.980 | 33.060 | −5.903 | 1.00 | 28.35 |
| ATOM | 1675 | NH1  | ARG | B | 102 | 49.464 | 31.849 | −6.107 | 1.00 | 23.60 |
| ATOM | 1676 | NH2  | ARG | B | 102 | 49.523 | 34.086 | −6.528 | 1.00 | 31.92 |
| ATOM | 1677 | N    | PRO | B | 103 | 50.154 | 34.655 | 0.289  | 1.00 | 12.26 |
| ATOM | 1678 | CA   | PRO | B | 103 | 50.259 | 35.917 | 0.065  | 1.00 | 13.54 |
| ATOM | 1679 | C    | PRO | B | 103 | 49.796 | 37.123 | 0.286  | 1.00 | 17.32 |
| ATOM | 1680 | O    | PRO | B | 103 | 49.731 | 37.056 | −1.006 | 1.00 | 16.83 |
| ATOM | 1681 | CB   | PRO | B | 103 | 51.763 | 36.065 | 1.280  | 1.00 | 14.38 |
| ATOM | 1682 | CG   | PRO | B | 103 | 52.386 | 35.452 | 0.019  | 1.00 | 22.25 |
| ATOM | 1683 | CD   | PRO | B | 103 | 51.461 | 34.218 | −0.225 | 1.00 | 16.38 |
| ATOM | 1684 | N    | ASN | B | 104 | 49.507 | 38.228 | 1.005  | 1.00 | 13.82 |
| ATOM | 1685 | CA   | ASN | B | 104 | 49.083 | 39.495 | 0.409  | 1.00 | 12.48 |
| ATOM | 1686 | C    | ASN | B | 104 | 50.317 | 40.372 | 0.282  | 1.00 | 19.52 |
| ATOM | 1687 | O    | ASN | B | 104 | 50.868 | 40.809 | 1.326  | 1.00 | 16.91 |
| ATOM | 1688 | CB   | ASN | B | 104 | 48.000 | 40.183 | 1.247  | 1.00 | 13.72 |
| ATOM | 1689 | CG   | ASN | B | 104 | 46.823 | 39.329 | 1.441  | 1.00 | 19.91 |
| ATOM | 1690 | OD1  | ASN | B | 104 | 46.218 | 38.875 | 0.448  | 1.00 | 17.05 |
| ATOM | 1691 | ND2  | ASN | B | 104 | 46.460 | 39.032 | 2.699  | 1.00 | 20.70 |
| ATOM | 1692 | N    | VAL | B | 105 | 50.789 | 40.668 | −0.936 | 1.00 | 17.67 |
| ATOM | 1693 | CA   | VAL | B | 105 | 51.984 | 41.447 | −1.064 | 1.00 | 16.36 |
| ATOM | 1694 | C    | VAL | B | 105 | 51.762 | 42.755 | −1.760 | 1.00 | 21.93 |
| ATOM | 1695 | O    | VAL | B | 105 | 51.102 | 42.783 | −2.816 | 1.00 | 22.45 |
| ATOM | 1696 | CB   | VAL | B | 105 | 53.090 | 40.681 | −1.848 | 1.00 | 18.76 |
| ATOM | 1697 | CG1  | VAL | B | 105 | 54.343 | 41.495 | −1.957 | 1.00 | 19.86 |
| ATOM | 1698 | CG2  | VAL | B | 105 | 53.336 | 39.231 | −1.253 | 1.00 | 19.00 |
| ATOM | 1699 | N    | ALA | B | 106 | 52.287 | 43.832 | −1.188 | 1.00 | 20.08 |
| ATOM | 1700 | CA   | ALA | B | 106 | 52.199 | 45.188 | −1.794 | 1.00 | 19.28 |
| ATOM | 1701 | C    | ALA | B | 106 | 53.617 | 45.637 | −2.080 | 1.00 | 22.54 |
| ATOM | 1702 | O    | ALA | B | 106 | 54.491 | 45.558 | −1.214 | 1.00 | 20.02 |
| ATOM | 1703 | CB   | ALA | B | 106 | 51.533 | 46.151 | −0.903 | 1.00 | 19.59 |
| ATOM | 1704 | N    | TYR | B | 107 | 53.895 | 46.128 | −3.312 | 1.00 | 21.77 |
| ATOM | 1705 | CA   | TYR | B | 107 | 55.244 | 46.571 | −3.683 | 1.00 | 22.90 |
| ATOM | 1706 | C    | TYR | B | 107 | 55.292 | 48.084 | −3.760 | 1.00 | 25.98 |
| ATOM | 1707 | O    | TYR | B | 107 | 54.300 | 48.712 | −4.096 | 1.00 | 25.22 |
| ATOM | 1708 | CB   | TYR | B | 107 | 55.668 | 45.972 | −5.032 | 1.00 | 25.00 |
| ATOM | 1709 | CG   | TYR | B | 107 | 55.904 | 44.492 | −4.966 | 1.00 | 24.25 |
| ATOM | 1710 | CD1  | TYR | B | 107 | 57.129 | 43.980 | −4.544 | 1.00 | 26.30 |
| ATOM | 1711 | CD2  | TYR | B | 107 | 54.888 | 43.600 | −5.316 | 1.00 | 25.93 |
| ATOM | 1712 | CE1  | TYR | B | 107 | 57.342 | 42.629 | −4.484 | 1.00 | 29.13 |
| ATOM | 1713 | CE2  | TYR | B | 107 | 55.100 | 42.234 | −5.270 | 1.00 | 25.26 |
| ATOM | 1714 | CZ   | TYR | B | 107 | 56.326 | 41.757 | −4.872 | 1.00 | 31.88 |
| ATOM | 1715 | OH   | TYR | B | 107 | 56.524 | 40.388 | −4.808 | 1.00 | 35.96 |
| ATOM | 1716 | N    | PHE | B | 108 | 56.446 | 48.652 | −3.408 | 1.00 | 26.53 |
| ATOM | 1717 | CA   | PHE | B | 108 | 56.584 | 50.098 | −3.399 | 1.00 | 25.71 |
| ATOM | 1718 | C    | PHE | B | 108 | 57.894 | 50.568 | −4.005 | 1.00 | 31.22 |
| ATOM | 1719 | O    | PHE | B | 108 | 58.893 | 49.844 | −4.074 | 1.00 | 28.62 |
| ATOM | 1720 | CB   | PHE | B | 108 | 56.572 | 50.645 | −1.933 | 1.00 | 25.29 |
| ATOM | 1721 | CG   | PHE | B | 108 | 55.293 | 50.411 | −1.188 | 1.00 | 21.78 |
| ATOM | 1722 | CD1  | PHE | B | 108 | 55.033 | 49.174 | −0.571 | 1.00 | 19.05 |
| ATOM | 1723 | CD2  | PHE | B | 108 | 54.354 | 51.421 | −1.064 | 1.00 | 20.20 |
| ATOM | 1724 | CE1  | PHE | B | 108 | 53.856 | 48.967 | 0.111  | 1.00 | 19.07 |
| ATOM | 1725 | CE2  | PHE | B | 108 | 53.187 | 51.237 | −0.377 | 1.00 | 22.77 |
| ATOM | 1726 | CZ   | PHE | B | 108 | 52.950 | 49.952 | 0.240  | 1.00 | 20.24 |
| ATOM | 1727 | N    | GLU | B | 109 | 57.864 | 51.828 | −4.412 | 1.00 | 30.97 |
| ATOM | 1728 | CA   | GLU | B | 109 | 59.012 | 52.499 | −5.011 | 1.00 | 32.90 |
| ATOM | 1729 | C    | GLU | B | 109 | 58.921 | 53.977 | −4.680 | 1.00 | 33.93 |
| ATOM | 1730 | O    | GLU | B | 109 | 57.889 | 54.468 | −4.269 | 1.00 | 30.42 |
| ATOM | 1731 | CB   | GLU | B | 109 | 58.916 | 52.388 | −6.540 | 1.00 | 35.17 |
| ATOM | 1732 | CG   | GLU | B | 109 | 57.721 | 53.172 | −7.089 | 1.00 | 44.89 |
| ATOM | 1733 | CD   | GLU | B | 109 | 57.496 | 52.955 | −8.566 | 1.00 | 68.70 |
| ATOM | 1734 | OE1  | GLU | B | 109 | 58.416 | 52.425 | −9.234 | 1.00 | 58.38 |
| ATOM | 1735 | OE2  | GLU | B | 109 | 56.391 | 53.305 | −9.056 | 1.00 | 66.11 |
| ATOM | 1736 | N    | GLY | B | 110 | 60.008 | 54.705 | −4.916 | 1.00 | 33.06 |
| ATOM | 1737 | CA   | GLY | B | 110 | 60.007 | 56.135 | −4.668 | 1.00 | 32.35 |
| ATOM | 1738 | C    | GLY | B | 110 | 59.545 | 56.486 | −3.270 | 1.00 | 35.50 |
| ATOM | 1739 | O    | GLY | B | 110 | 60.045 | 55.920 | −2.286 | 1.00 | 35.53 |
| ATOM | 1740 | N    | ASP | B | 111 | 58.646 | 57.449 | −3.185 | 1.00 | 29.97 |
| ATOM | 1741 | CA   | ASP | B | 111 | 58.151 | 57.917 | −1.907 | 1.00 | 31.05 |
| ATOM | 1742 | C    | ASP | B | 111 | 56.884 | 57.180 | −1.499 | 1.00 | 30.82 |
| ATOM | 1743 | O    | ASP | B | 111 | 55.761 | 57.743 | −1.439 | 1.00 | 28.67 |
| ATOM | 1744 | CB   | ASP | B | 111 | 57.984 | 59.438 | −1.931 | 1.00 | 33.49 |
| ATOM | 1745 | CG   | ASP | B | 111 | 57.207 | 59.966 | −0.755 | 1.00 | 44.31 |
| ATOM | 1746 | OD1  | ASP | B | 111 | 57.431 | 59.473 | 0.386  | 1.00 | 46.12 |
| ATOM | 1747 | OD2  | ASP | B | 111 | 56.359 | 60.857 | −0.974 | 1.00 | 41.60 |
| ATOM | 1748 | N    | ASN | B | 112 | 57.084 | 55.909 | −1.181 | 1.00 | 27.75 |
| ATOM | 1749 | CA   | ASN | B | 112 | 55.987 | 55.068 | −0.770 | 1.00 | 25.85 |

-continued

Data Lists

| | | | | | | | | |
|---|---|---|---|---|---|---|---|---|
| ATOM | 1750 | C | ASN | B | 112 | 54.870 | 55.008 | −1.770 | 1.00 | 28.56 |
| ATOM | 1751 | O | ASN | B | 112 | 53.695 | 55.087 | −1.425 | 1.00 | 24.07 |
| ATOM | 1752 | CB | ASN | B | 112 | 55.512 | 55.413 | 0.637 | 1.00 | 25.14 |
| ATOM | 1753 | CG | ASN | B | 112 | 56.544 | 55.084 | 1.628 | 1.00 | 19.48 |
| ATOM | 1754 | OD1 | ASN | B | 112 | 57.512 | 54.410 | 1.275 | 1.00 | 22.70 |
| ATOM | 1755 | ND2 | ASN | B | 112 | 56.399 | 55.582 | 2.868 | 1.00 | 21.36 |
| ATOM | 1756 | N | GLU | B | 113 | 55.271 | 54.857 | −3.032 | 1.00 | 27.11 |
| ATOM | 1757 | CA | GLU | B | 113 | 54.288 | 54.748 | −4.114 | 1.00 | 28.84 |
| ATOM | 1758 | C | GLU | B | 113 | 54.071 | 53.286 | −4.361 | 1.00 | 27.72 |
| ATOM | 1759 | O | GLU | B | 113 | 55.024 | 52.572 | −4.769 | 1.00 | 26.82 |
| ATOM | 1760 | CB | GLU | B | 113 | 54.752 | 55.441 | −5.391 | 1.00 | 30.87 |
| ATOM | 1761 | CG | GLU | B | 113 | 54.797 | 56.958 | −5.306 | 1.00 | 37.93 |
| ATOM | 1762 | CD | GLU | B | 113 | 53.442 | 57.703 | −5.230 | 1.00 | 59.74 |
| ATOM | 1763 | OE1 | GLU | B | 113 | 52.345 | 57.089 | −5.096 | 1.00 | 46.50 |
| ATOM | 1764 | OE2 | GLU | B | 113 | 53.517 | 58.956 | −5.296 | 1.00 | 59.60 |
| ATOM | 1765 | N | MET | B | 114 | 52.842 | 52.856 | −4.080 | 1.00 | 27.25 |
| ATOM | 1766 | CA | MET | B | 114 | 52.436 | 51.459 | −4.226 | 1.00 | 32.32 |
| ATOM | 1767 | C | MET | B | 114 | 52.272 | 51.103 | −5.666 | 1.00 | 39.86 |
| ATOM | 1768 | O | MET | B | 114 | 51.463 | 51.727 | −6.359 | 1.00 | 40.94 |
| ATOM | 1769 | CB | MET | B | 114 | 51.094 | 51.203 | −3.533 | 1.00 | 34.33 |
| ATOM | 1770 | CG | MET | B | 114 | 50.808 | 49.728 | −3.412 | 1.00 | 36.77 |
| ATOM | 1771 | SD | MET | B | 114 | 49.151 | 49.352 | −2.940 | 1.00 | 39.76 |
| ATOM | 1772 | CE | MET | B | 114 | 49.252 | 49.698 | −1.017 | 1.00 | 31.31 |
| ATOM | 1773 | N | LYS | B | 115 | 53.006 | 50.104 | −6.129 | 1.00 | 37.37 |
| ATOM | 1774 | CA | LYS | B | 115 | 52.918 | 49.687 | −7.538 | 1.00 | 38.95 |
| ATOM | 1775 | C | LYS | B | 115 | 51.644 | 48.899 | −7.836 | 1.00 | 54.19 |
| ATOM | 1776 | O | LYS | B | 115 | 51.157 | 48.178 | −6.919 | 1.00 | 51.66 |
| ATOM | 1777 | CB | LYS | B | 115 | 54.114 | 48.851 | −7.929 | 1.00 | 41.43 |
| ATOM | 1778 | CG | LYS | B | 115 | 55.452 | 49.572 | −7.954 | 1.00 | 47.27 |
| ATOM | 1779 | CD | LYS | B | 115 | 56.543 | 48.571 | −8.255 | 1.00 | 43.78 |
| ATOM | 1780 | CE | LYS | B | 115 | 57.915 | 49.055 | −7.874 | 1.00 | 55.99 |
| ATOM | 1781 | NZ | LYS | B | 115 | 58.975 | 48.255 | −8.577 | 1.00 | 62.59 |
| ATOM | 1 | N | MET | C | 1 | 48.433 | 20.814 | 26.350 | 1.00 | 25.25 |
| ATOM | 2 | CA | MET | C | 1 | 49.028 | 22.003 | 25.752 | 1.00 | 23.37 |
| ATOM | 3 | C | MET | C | 1 | 49.715 | 21.688 | 24.462 | 1.00 | 22.04 |
| ATOM | 4 | O | MET | C | 1 | 49.875 | 20.523 | 24.092 | 1.00 | 22.16 |
| ATOM | 5 | CB | MET | C | 1 | 49.850 | 22.851 | 26.665 | 1.00 | 26.58 |
| ATOM | 6 | CG | MET | C | 1 | 50.670 | 22.110 | 27.510 | 1.00 | 29.48 |
| ATOM | 7 | SD | MET | C | 1 | 51.965 | 21.246 | 26.703 | 1.00 | 32.96 |
| ATOM | 8 | CE | MET | C | 1 | 52.813 | 20.920 | 28.227 | 1.00 | 23.68 |
| ATOM | 9 | N | ILE | C | 2 | 50.100 | 22.747 | 23.803 | 1.00 | 14.33 |
| ATOM | 10 | CA | ILE | C | 2 | 50.686 | 22.664 | 22.441 | 1.00 | 12.86 |
| ATOM | 11 | C | ILE | C | 2 | 52.160 | 22.979 | 22.400 | 1.00 | 13.27 |
| ATOM | 12 | O | ILE | C | 2 | 52.627 | 24.031 | 22.948 | 1.00 | 12.60 |
| ATOM | 13 | CB | ILE | C | 2 | 49.882 | 23.673 | 21.576 | 1.00 | 15.76 |
| ATOM | 14 | CG1 | ILE | C | 2 | 48.390 | 23.281 | 21.509 | 1.00 | 18.95 |
| ATOM | 15 | CG2 | ILE | C | 2 | 50.477 | 23.802 | 20.155 | 1.00 | 15.91 |
| ATOM | 16 | CD1 | ILE | C | 2 | 48.150 | 22.002 | 20.809 | 1.00 | 30.84 |
| ATOM | 17 | N | ARG | C | 3 | 52.927 | 22.092 | 21.751 | 1.00 | 11.28 |
| ATOM | 18 | CA | ARG | C | 3 | 54.380 | 22.286 | 21.644 | 1.00 | 10.27 |
| ATOM | 19 | C | ARG | C | 3 | 54.824 | 22.880 | 20.295 | 1.00 | 12.97 |
| ATOM | 20 | O | ARG | C | 3 | 54.091 | 22.691 | 19.313 | 1.00 | 11.98 |
| ATOM | 21 | CB | ARG | C | 3 | 55.085 | 20.920 | 21.683 | 1.00 | 11.24 |
| ATOM | 22 | CG | ARG | C | 3 | 54.887 | 20.123 | 23.057 | 1.00 | 11.07 |
| ATOM | 23 | CD | ARG | C | 3 | 55.885 | 20.640 | 24.091 | 1.00 | 14.19 |
| ATOM | 24 | NE | ARG | C | 3 | 55.755 | 19.688 | 25.224 | 1.00 | 12.85 |
| ATOM | 25 | CZ | ARG | C | 3 | 56.624 | 19.664 | 26.235 | 1.00 | 13.01 |
| ATOM | 26 | NH1 | ARG | C | 3 | 57.564 | 20.552 | 26.371 | 1.00 | 11.87 |
| ATOM | 27 | NH2 | ARG | C | 3 | 56.424 | 18.698 | 27.173 | 1.00 | 15.42 |
| ATOM | 28 | N | THR | C | 4 | 55.967 | 23.542 | 20.295 | 1.00 | 10.90 |
| ATOM | 29 | CA | THR | C | 4 | 56.599 | 24.104 | 19.048 | 1.00 | 8.73 |
| ATOM | 30 | C | THR | C | 4 | 57.765 | 23.120 | 18.793 | 1.00 | 12.54 |
| ATOM | 31 | O | THR | C | 4 | 58.739 | 23.023 | 19.649 | 1.00 | 11.96 |
| ATOM | 32 | CB | THR | C | 4 | 57.080 | 25.498 | 19.237 | 1.00 | 10.20 |
| ATOM | 33 | OG1 | THR | C | 4 | 55.949 | 26.331 | 19.490 | 1.00 | 12.29 |
| ATOM | 34 | CG2 | THR | C | 4 | 57.908 | 26.008 | 17.930 | 1.00 | 12.13 |
| ATOM | 35 | N | MET | C | 5 | 57.701 | 22.369 | 17.637 | 1.00 | 10.12 |
| ATOM | 36 | CA | MET | C | 5 | 58.676 | 21.370 | 17.349 | 1.00 | 10.31 |
| ATOM | 37 | C | MET | C | 5 | 59.356 | 21.600 | 16.015 | 1.00 | 13.52 |
| ATOM | 38 | O | MET | C | 5 | 58.720 | 22.172 | 15.112 | 1.00 | 14.15 |
| ATOM | 39 | CB | MET | C | 5 | 57.978 | 20.006 | 17.214 | 1.00 | 13.06 |
| ATOM | 40 | CG | MET | C | 5 | 57.123 | 19.561 | 18.416 | 1.00 | 11.30 |
| ATOM | 41 | SD | MET | C | 5 | 58.165 | 19.333 | 19.918 | 1.00 | 13.37 |
| ATOM | 42 | CE | MET | C | 5 | 59.104 | 17.873 | 19.482 | 1.00 | 14.97 |
| ATOM | 43 | N | LEU | C | 6 | 60.600 | 21.155 | 15.915 | 1.00 | 10.44 |
| ATOM | 44 | CA | LEU | C | 6 | 61.345 | 21.255 | 14.605 | 1.00 | 11.49 |
| ATOM | 45 | C | LEU | C | 6 | 60.559 | 20.378 | 13.639 | 1.00 | 13.65 |

-continued

Data Lists

| | | | | | | | | | |
|---|---|---|---|---|---|---|---|---|---|
| ATOM | 46 | O | LEU | C | 6 | 60.436 | 19.139 | 13.800 | 1.00 | 12.95 |
| ATOM | 47 | CB | LEU | C | 6 | 62.722 | 20.660 | 14.786 | 1.00 | 11.43 |
| ATOM | 48 | CG | LEU | C | 6 | 63.587 | 20.673 | 13.484 | 1.00 | 12.67 |
| ATOM | 49 | CD1 | LEU | C | 6 | 64.038 | 22.096 | 13.201 | 1.00 | 13.37 |
| ATOM | 50 | CD2 | LEU | C | 6 | 64.839 | 19.829 | 13.742 | 1.00 | 14.36 |
| ATOM | 51 | N | GLN | C | 7 | 60.049 | 21.016 | 12.552 | 1.00 | 12.16 |
| ATOM | 52 | CA | GLN | C | 7 | 59.313 | 20.301 | 11.511 | 1.00 | 11.30 |
| ATOM | 53 | C | GLN | C | 7 | 60.333 | 19.599 | 10.566 | 1.00 | 12.23 |
| ATOM | 54 | O | GLN | C | 7 | 60.125 | 18.449 | 10.136 | 1.00 | 11.94 |
| ATOM | 55 | CB | GLN | C | 7 | 58.544 | 21.330 | 10.679 | 1.00 | 12.62 |
| ATOM | 56 | CG | GLN | C | 7 | 57.590 | 20.710 | 9.638 | 1.00 | 14.99 |
| ATOM | 57 | CD | GLN | C | 7 | 58.349 | 20.221 | 8.351 | 1.00 | 12.25 |
| ATOM | 58 | OE1 | GLN | C | 7 | 58.036 | 19.083 | 7.865 | 1.00 | 14.42 |
| ATOM | 59 | NE2 | GLN | C | 7 | 59.299 | 21.005 | 7.831 | 1.00 | 13.59 |
| ATOM | 60 | N | GLY | C | 8 | 61.406 | 20.329 | 10.295 | 1.00 | 12.10 |
| ATOM | 61 | CA | GLY | C | 8 | 62.459 | 19.795 | 9.406 | 1.00 | 12.14 |
| ATOM | 62 | C | GLY | C | 8 | 63.526 | 20.838 | 9.181 | 1.00 | 11.21 |
| ATOM | 63 | O | GLY | C | 8 | 63.403 | 22.022 | 9.565 | 1.00 | 12.25 |
| ATOM | 64 | N | LYS | C | 9 | 64.617 | 20.409 | 8.526 | 1.00 | 11.80 |
| ATOM | 65 | CA | LYS | C | 9 | 65.690 | 21.351 | 8.271 | 1.00 | 12.75 |
| ATOM | 66 | C | LYS | C | 9 | 66.604 | 20.908 | 7.117 | 1.00 | 12.69 |
| ATOM | 67 | O | LYS | C | 9 | 66.658 | 19.711 | 6.780 | 1.00 | 14.09 |
| ATOM | 68 | CB | LYS | C | 9 | 66.597 | 21.557 | 9.528 | 1.00 | 16.31 |
| ATOM | 69 | CG | LYS | C | 9 | 67.451 | 20.367 | 9.927 | 1.00 | 16.10 |
| ATOM | 70 | CD | LYS | C | 9 | 68.486 | 20.654 | 11.059 | 1.00 | 15.95 |
| ATOM | 71 | CE | LYS | C | 9 | 69.247 | 19.377 | 11.363 | 1.00 | 20.48 |
| ATOM | 72 | NZ | LYS | C | 9 | 70.409 | 19.689 | 12.260 | 1.00 | 22.05 |
| ATOM | 73 | N | LEU | C | 10 | 67.301 | 21.896 | 6.578 | 1.00 | 13.44 |
| ATOM | 74 | CA | LEU | C | 10 | 68.300 | 21.680 | 5.503 | 1.00 | 13.72 |
| ATOM | 75 | C | LEU | C | 10 | 69.586 | 21.951 | 6.258 | 1.00 | 14.03 |
| ATOM | 76 | O | LEU | C | 10 | 69.859 | 23.078 | 6.661 | 1.00 | 15.46 |
| ATOM | 77 | CB | LEU | C | 10 | 68.111 | 22.719 | 4.364 | 1.00 | 13.59 |
| ATOM | 78 | CC | LEU | C | 10 | 66.761 | 22.626 | 3.674 | 1.00 | 14.77 |
| ATOM | 79 | CD1 | LEU | C | 10 | 66.548 | 23.780 | 2.652 | 1.00 | 18.67 |
| ATOM | 80 | CD2 | LEU | C | 10 | 66.545 | 21.240 | 2.957 | 1.00 | 15.75 |
| ATOM | 81 | N | HIS | C | 11 | 70.365 | 20.925 | 6.451 | 1.00 | 14.06 |
| ATOM | 82 | CA | HIS | C | 11 | 71.591 | 21.029 | 7.244 | 1.00 | 14.41 |
| ATOM | 83 | C | HIS | C | 11 | 72.871 | 21.241 | 6.448 | 1.00 | 18.20 |
| ATOM | 84 | O | HIS | C | 11 | 73.258 | 20.362 | 5.684 | 1.00 | 16.24 |
| ATOM | 85 | CB | HIS | C | 11 | 71.710 | 19.803 | 8.172 | 1.00 | 17.29 |
| ATOM | 86 | CG | HIS | C | 11 | 72.805 | 19.913 | 9.185 | 1.00 | 18.36 |
| ATOM | 87 | ND1 | HIS | C | 11 | 72.634 | 20.553 | 10.405 | 1.00 | 20.19 |
| ATOM | 88 | CD2 | HIS | C | 11 | 74.087 | 19.464 | 9.174 | 1.00 | 19.36 |
| ATOM | 89 | CE1 | HIS | C | 11 | 73.769 | 20.514 | 11.075 | 1.00 | 19.59 |
| ATOM | 90 | NE2 | HIS | C | 11 | 74.667 | 19.854 | 10.354 | 1.00 | 18.93 |
| ATOM | 91 | N | ARG | C | 12 | 73.488 | 22.401 | 6.662 | 1.00 | 15.16 |
| ATOM | 92 | CA | ARG | C | 12 | 74.713 | 22.792 | 6.029 | 1.00 | 15.13 |
| ATOM | 93 | C | ARG | C | 12 | 74.613 | 22.974 | 4.525 | 1.00 | 16.37 |
| ATOM | 94 | O | ARG | C | 12 | 75.468 | 22.446 | 3.763 | 1.00 | 18.19 |
| ATOM | 95 | CB | ARG | C | 12 | 75.855 | 21.874 | 6.378 | 1.00 | 15.43 |
| ATOM | 96 | CG | ARG | C | 12 | 76.247 | 21.969 | 7.868 | 1.00 | 17.33 |
| ATOM | 97 | CD | ARG | C | 12 | 77.390 | 21.001 | 8.248 | 1.00 | 17.26 |
| ATOM | 98 | NE | ARG | C | 12 | 78.587 | 21.294 | 7.454 | 1.00 | 19.17 |
| ATOM | 99 | CZ | ARG | C | 12 | 79.529 | 22.164 | 7.760 | 1.00 | 24.65 |
| ATOM | 100 | NH1 | ARG | C | 12 | 79.495 | 22.858 | 8.879 | 1.00 | 21.82 |
| ATOM | 101 | NH2 | ARG | C | 12 | 80.545 | 22.350 | 6.912 | 1.00 | 28.03 |
| ATOM | 102 | N | VAL | C | 13 | 73.610 | 23.681 | 4.119 | 1.00 | 15.70 |
| ATOM | 103 | CA | VAL | C | 13 | 73.518 | 23.999 | 2.680 | 1.00 | 14.78 |
| ATOM | 104 | C | VAL | C | 13 | 74.416 | 25.241 | 2.524 | 1.00 | 18.42 |
| ATOM | 105 | O | VAL | C | 13 | 74.709 | 26.004 | 3.506 | 1.00 | 15.58 |
| ATOM | 106 | CB | VAL | C | 13 | 72.143 | 24.332 | 2.183 | 1.00 | 16.79 |
| ATOM | 107 | CG1 | VAL | C | 13 | 71.318 | 23.094 | 2.020 | 1.00 | 18.88 |
| ATOM | 108 | CG2 | VAL | C | 13 | 71.441 | 25.456 | 3.067 | 1.00 | 16.41 |
| ATOM | 109 | N | LYS | C | 14 | 74.877 | 25.500 | 1.273 | 1.00 | 15.68 |
| ATOM | 110 | CA | LYS | C | 14 | 75.726 | 26.646 | 0.997 | 1.00 | 16.45 |
| ATOM | 111 | C | LYS | C | 14 | 74.946 | 27.738 | 0.258 | 1.00 | 16.56 |
| ATOM | 112 | O | LYS | C | 14 | 74.116 | 27.432 | −0.670 | 1.00 | 16.75 |
| ATOM | 113 | CB | LYS | C | 14 | 76.910 | 26.216 | 0.127 | 1.00 | 17.97 |
| ATOM | 114 | CG | LYS | C | 14 | 77.913 | 27.344 | −0.094 | 1.00 | 20.97 |
| ATOM | 115 | CD | LYS | C | 14 | 79.173 | 26.878 | −0.788 | 1.00 | 29.18 |
| ATOM | 116 | CE | LYS | C | 14 | 80.063 | 26.092 | 0.120 | 1.00 | 32.48 |
| ATOM | 117 | NZ | LYS | C | 14 | 81.181 | 25.545 | −0.697 | 1.00 | 33.64 |
| ATOM | 118 | N | VAL | C | 15 | 75.161 | 29.013 | 0.665 | 1.00 | 13.79 |
| ATOM | 119 | CA | VAL | C | 15 | 74.467 | 30.142 | 0.040 | 1.00 | 14.02 |
| ATOM | 120 | C | VAL | C | 15 | 75.067 | 30.312 | −1.393 | 1.00 | 14.49 |
| ATOM | 121 | O | VAL | C | 15 | 76.279 | 30.376 | −1.536 | 1.00 | 14.91 |
| ATOM | 122 | CB | VAL | C | 15 | 74.678 | 31.451 | 0.826 | 1.00 | 14.72 |

-continued

Data Lists

| | | | | | | | | | |
|---|---|---|---|---|---|---|---|---|---|
| ATOM | 123 | CG1 | VAL | C | 15 | 74.032 | 32.595 | 0.091 | 1.00 | 15.47 |
| ATOM | 124 | CG2 | VAL | C | 15 | 74.013 | 31.273 | 2.287 | 1.00 | 15.44 |
| ATOM | 125 | N | THR | C | 16 | 74.182 | 30.292 | −2.386 | 1.00 | 14.68 |
| ATOM | 126 | CA | THR | C | 16 | 74.627 | 30.393 | −3.796 | 1.00 | 16.18 |
| ATOM | 127 | C | THR | C | 16 | 74.478 | 31.743 | −4.444 | 1.00 | 19.63 |
| ATOM | 128 | O | THR | C | 16 | 75.143 | 31.995 | −5.472 | 1.00 | 18.35 |
| ATOM | 129 | CB | THR | C | 16 | 73.869 | 29.362 | −4.630 | 1.00 | 14.13 |
| ATOM | 130 | OG1 | THR | C | 16 | 72.510 | 29.698 | −4.778 | 1.00 | 17.95 |
| ATOM | 131 | CG2 | THR | C | 16 | 74.103 | 27.943 | −4.087 | 1.00 | 18.04 |
| ATOM | 132 | N | HIS | C | 17 | 73.636 | 32.604 | −3.913 | 1.00 | 14.05 |
| ATOM | 133 | CA | HIS | C | 17 | 73.411 | 33.927 | −4.456 | 1.00 | 15.34 |
| ATOM | 134 | C | HIS | C | 17 | 72.897 | 34.888 | −3.343 | 1.00 | 19.86 |
| ATOM | 135 | O | HIS | C | 17 | 72.249 | 34.434 | −2.351 | 1.00 | 17.90 |
| ATOM | 136 | CB | HIS | C | 17 | 72.332 | 33.779 | −5.554 | 1.00 | 18.53 |
| ATOM | 137 | CG | HIS | C | 17 | 72.007 | 35.052 | −6.293 | 1.00 | 22.33 |
| ATOM | 138 | ND1 | HIS | C | 17 | 70.836 | 35.746 | −6.083 | 1.00 | 25.17 |
| ATOM | 139 | CD2 | HIS | C | 17 | 72.665 | 35.724 | −7.285 | 1.00 | 24.77 |
| ATOM | 140 | CE1 | HIS | C | 17 | 70.797 | 36.809 | −6.865 | 1.00 | 25.62 |
| ATOM | 141 | NE2 | HIS | C | 17 | 71.889 | 36.822 | −7.610 | 1.00 | 24.55 |
| ATOM | 142 | N | ALA | C | 18 | 73.134 | 36.180 | −3.515 | 1.00 | 16.82 |
| ATOM | 143 | CA | ALA | C | 18 | 72.649 | 37.211 | −2.563 | 1.00 | 18.95 |
| ATOM | 144 | C | ALA | C | 18 | 72.073 | 38.366 | −3.404 | 1.00 | 25.44 |
| ATOM | 145 | O | ALA | C | 18 | 72.647 | 38.737 | −4.442 | 1.00 | 26.69 |
| ATOM | 146 | CB | ALA | C | 18 | 73.758 | 37.674 | −1.645 | 1.00 | 21.19 |
| ATOM | 147 | N | ASP | C | 19 | 70.925 | 38.880 | −3.029 | 1.00 | 21.26 |
| ATOM | 148 | CA | ASP | C | 19 | 70.290 | 39.955 | −3.794 | 1.00 | 20.73 |
| ATOM | 149 | C | ASP | C | 19 | 69.612 | 40.957 | −2.869 | 1.00 | 21.60 |
| ATOM | 150 | O | ASP | C | 19 | 68.413 | 40.890 | −2.634 | 1.00 | 20.10 |
| ATOM | 151 | CB | ASP | C | 19 | 69.267 | 39.317 | −4.767 | 1.00 | 21.77 |
| ATOM | 152 | CG | ASP | C | 19 | 68.692 | 40.307 | −5.798 | 1.00 | 27.20 |
| ATOM | 153 | OD1 | ASP | C | 19 | 69.092 | 41.478 | −5.831 | 1.00 | 27.06 |
| ATOM | 154 | OD2 | ASP | C | 19 | 67.785 | 39.862 | −6.570 | 1.00 | 28.93 |
| ATOM | 155 | N | LEU | C | 20 | 70.393 | 41.917 | −2.414 | 1.00 | 21.47 |
| ATOM | 156 | CA | LEU | C | 20 | 69.874 | 42.953 | −1.551 | 1.00 | 21.15 |
| ATOM | 157 | C | LEU | C | 20 | 68.714 | 43.709 | −2.138 | 1.00 | 25.20 |
| ATOM | 158 | O | LEU | C | 20 | 67.771 | 44.028 | −1.426 | 1.00 | 24.39 |
| ATOM | 159 | CB | LEU | C | 20 | 70.997 | 43.944 | −1.181 | 1.00 | 21.58 |
| ATOM | 160 | CG | LEU | C | 20 | 70.700 | 45.069 | −0.209 | 1.00 | 24.50 |
| ATOM | 161 | CD1 | LEU | C | 20 | 70.505 | 44.452 | 1.236 | 1.00 | 22.31 |
| ATOM | 162 | CD2 | LEU | C | 20 | 71.937 | 46.004 | −0.224 | 1.00 | 24.07 |
| ATOM | 163 | N | HIS | C | 21 | 68.786 | 44.010 | −3.448 | 1.00 | 23.99 |
| ATOM | 164 | CA | HIS | C | 21 | 67.733 | 44.767 | −4.147 | 1.00 | 26.08 |
| ATOM | 165 | C | HIS | C | 21 | 66.608 | 43.995 | −4.713 | 1.00 | 29.17 |
| ATOM | 166 | O | HIS | C | 21 | 65.847 | 44.534 | −5.516 | 1.00 | 29.91 |
| ATOM | 167 | CB | HIS | C | 21 | 68.393 | 45.692 | −5.187 | 1.00 | 29.07 |
| ATOM | 168 | CG | HIS | C | 21 | 69.496 | 46.484 | −4.609 | 1.00 | 34.17 |
| ATOM | 169 | ND1 | HIS | C | 21 | 69.283 | 47.347 | −3.561 | 1.00 | 37.06 |
| ATOM | 170 | CD2 | HIS | C | 21 | 70.836 | 46.468 | −4.819 | 1.00 | 37.54 |
| ATOM | 171 | CE1 | HIS | C | 21 | 70.433 | 47.875 | −3.181 | 1.00 | 36.64 |
| ATOM | 172 | NE2 | HIS | C | 21 | 71.394 | 47.358 | −3.926 | 1.00 | 37.19 |
| ATOM | 173 | N | TYR | C | 22 | 66.495 | 42.726 | −4.309 | 1.00 | 26.33 |
| ATOM | 174 | CA | TYR | C | 22 | 65.413 | 41.864 | −4.797 | 1.00 | 27.04 |
| ATOM | 175 | C | TYR | C | 22 | 64.087 | 42.615 | −4.779 | 1.00 | 33.24 |
| ATOM | 176 | O | TYR | C | 22 | 63.709 | 43.265 | −3.775 | 1.00 | 26.75 |
| ATOM | 177 | CB | TYR | C | 22 | 65.294 | 40.643 | −3.890 | 1.00 | 28.34 |
| ATOM | 178 | CG | TYR | C | 22 | 64.348 | 39.561 | −4.368 | 1.00 | 30.64 |
| ATOM | 179 | CD1 | TYR | C | 22 | 64.555 | 38.917 | −5.581 | 1.00 | 31.96 |
| ATOM | 180 | CD2 | TYR | C | 22 | 63.290 | 39.162 | −3.575 | 1.00 | 32.31 |
| ATOM | 181 | CE1 | TYR | C | 22 | 63.697 | 37.898 | −6.009 | 1.00 | 32.16 |
| ATOM | 182 | CE2 | TYR | C | 22 | 62.421 | 38.161 | −3.993 | 1.00 | 32.82 |
| ATOM | 183 | CZ | TYR | C | 22 | 62.641 | 37.525 | −5.201 | 1.00 | 36.63 |
| ATOM | 184 | OH | TYR | C | 22 | 61.767 | 36.526 | −5.622 | 1.00 | 38.85 |
| ATOM | 185 | N | GLU | C | 23 | 63.378 | 42.561 | −5.883 | 1.00 | 34.58 |
| ATOM | 186 | CA | GLU | C | 23 | 62.134 | 43.254 | −5.953 | 1.00 | 37.52 |
| ATOM | 187 | C | GLU | C | 23 | 60.863 | 42.459 | −5.743 | 1.00 | 42.30 |
| ATOM | 188 | O | GLU | C | 23 | 59.798 | 43.013 | −5.859 | 1.00 | 40.71 |
| ATOM | 189 | CB | GLU | C | 23 | 62.051 | 44.110 | −7.214 | 1.00 | 39.74 |
| ATOM | 190 | CG | GLU | C | 23 | 63.078 | 45.231 | −7.233 | 1.00 | 50.28 |
| ATOM | 191 | CD | GLU | C | 23 | 62.519 | 46.537 | −6.691 | 1.00 | 61.64 |
| ATOM | 192 | OE1 | GLU | C | 23 | 61.445 | 46.515 | −6.046 | 1.00 | 62.40 |
| ATOM | 193 | OE2 | GLU | C | 23 | 63.152 | 47.594 | −6.923 | 1.00 | 61.54 |
| ATOM | 194 | N | GLY | C | 24 | 60.956 | 41.158 | −5.438 | 1.00 | 39.86 |
| ATOM | 195 | CA | GLY | C | 24 | 59.736 | 40.345 | −5.222 | 1.00 | 43.77 |
| ATOM | 196 | C | GLY | C | 24 | 59.575 | 39.938 | −3.749 | 1.00 | 49.67 |
| ATOM | 197 | O | GLY | C | 24 | 58.617 | 39.195 | −3.402 | 1.00 | 54.64 |
| ATOM | 198 | OH | GLY | C | 24 | 60.410 | 40.339 | −2.920 | 1.00 | 73.31 |
| ATOM | 199 | C | PVL | C | 25 | 64.534 | 35.324 | 1.332 | 1.00 | 17.73 |

-continued

Data Lists

| ATOM | 200 | O | PVL | C | 25 | 65.693 | 35.692 | 1.200 | 1.00 | 21.35 |
|---|---|---|---|---|---|---|---|---|---|---|
| ATOM | 201 | CA | PVL | C | 25 | 63.465 | 36.333 | 1.535 | 1.00 | 26.99 |
| ATOM | 202 | CB | PVL | C | 25 | 62.040 | 35.836 | 1.629 | 1.00 | 26.50 |
| ATOM | 203 | ON | PVL | C | 25 | 63.738 | 37.533 | 1.769 | 1.00 | 32.90 |
| ATOM | 204 | N | CYS | C | 26 | 64.218 | 33.987 | 1.203 | 1.00 | 13.65 |
| ATOM | 205 | CA | CYS | C | 26 | 65.226 | 32.982 | 0.870 | 1.00 | 13.69 |
| ATOM | 206 | CB | CYS | C | 26 | 65.775 | 32.194 | 2.112 | 1.00 | 19.50 |
| ATOM | 207 | SG | CYS | C | 26 | 67.153 | 31.117 | 1.678 | 1.00 | 17.42 |
| ATOM | 208 | C | CYS | C | 26 | 64.643 | 32.011 | −0.140 | 1.00 | 17.14 |
| ATOM | 209 | O | CYS | C | 26 | 63.688 | 31.289 | 0.138 | 1.00 | 16.98 |
| ATOM | 210 | N | ALA | C | 27 | 65.174 | 32.063 | −1.414 | 1.00 | 14.97 |
| ATOM | 211 | CA | ALA | C | 27 | 64.691 | 31.198 | −2.478 | 1.00 | 14.51 |
| ATOM | 212 | C | ALA | C | 27 | 65.506 | 29.930 | −2.416 | 1.00 | 11.29 |
| ATOM | 213 | O | ALA | C | 27 | 66.742 | 29.944 | −2.313 | 1.00 | 13.77 |
| ATOM | 214 | CB | ALA | C | 27 | 64.903 | 31.930 | −3.823 | 1.00 | 14.33 |
| ATOM | 215 | N | ILE | C | 28 | 64.784 | 28.821 | −2.436 | 1.00 | 12.96 |
| ATOM | 216 | CA | ILE | C | 28 | 65.324 | 27.513 | −2.268 | 1.00 | 12.54 |
| ATOM | 217 | C | ILE | C | 28 | 64.763 | 26.465 | −3.281 | 1.00 | 13.11 |
| ATOM | 218 | O | ILE | C | 28 | 63.573 | 26.396 | −3.512 | 1.00 | 14.34 |
| ATOM | 219 | CB | ILE | C | 28 | 64.901 | 26.977 | −0.773 | 1.00 | 13.91 |
| ATOM | 220 | CG1 | ILE | C | 28 | 65.435 | 27.945 | 0.261 | 1.00 | 15.23 |
| ATOM | 221 | CG2 | ILE | C | 28 | 65.386 | 25.518 | −0.497 | 1.00 | 16.36 |
| ATOM | 222 | CD1 | ILE | C | 28 | 64.647 | 27.772 | 1.637 | 1.00 | 17.00 |
| ATOM | 223 | N | ASP | C | 29 | 65.689 | 25.727 | −3.865 | 1.00 | 15.10 |
| ATOM | 224 | CA | ASP | C | 29 | 65.333 | 24.657 | −4.850 | 1.00 | 14.57 |
| ATOM | 225 | C | ASP | C | 29 | 64.130 | 23.862 | −4.288 | 1.00 | 17.57 |
| ATOM | 226 | O | ASP | C | 29 | 64.177 | 23.354 | −3.130 | 1.00 | 15.63 |
| ATOM | 227 | CB | ASP | C | 29 | 66.532 | 23.782 | −5.032 | 1.00 | 14.77 |
| ATOM | 228 | CG | ASP | C | 29 | 66.330 | 22.610 | −6.002 | 1.00 | 14.70 |
| ATOM | 229 | OD1 | ASP | C | 29 | 65.209 | 22.105 | −6.198 | 1.00 | 15.75 |
| ATOM | 230 | OD2 | ASP | C | 29 | 67.364 | 22.123 | −6.453 | 1.00 | 16.77 |
| ATOM | 231 | N | GLN | C | 30 | 63.048 | 23.784 | −5.055 | 1.00 | 15.71 |
| ATOM | 232 | CA | GLN | C | 30 | 61.846 | 23.040 | −4.628 | 1.00 | 16.19 |
| ATOM | 233 | C | GLN | C | 30 | 62.169 | 21.606 | −4.152 | 1.00 | 17.73 |
| ATOM | 234 | O | GLN | C | 30 | 61.462 | 21.048 | −3.271 | 1.00 | 17.08 |
| ATOM | 235 | CB | GLN | C | 30 | 60.850 | 22.897 | −5.808 | 1.00 | 17.85 |
| ATOM | 236 | CG | GLN | C | 30 | 59.579 | 22.183 | −5.414 | 1.00 | 23.42 |
| ATOM | 237 | CD | GLN | C | 30 | 58.789 | 22.951 | −4.362 | 1.00 | 23.06 |
| ATOM | 238 | OE1 | GLN | C | 30 | 58.361 | 24.110 | −4.575 | 1.00 | 21.11 |
| ATOM | 239 | NE2 | GLN | C | 30 | 58.574 | 22.285 | −3.172 | 1.00 | 20.59 |
| ATOM | 240 | N | ASP | C | 31 | 63.168 | 20.935 | −4.730 | 1.00 | 16.44 |
| ATOM | 241 | CA | ASP | C | 31 | 63.520 | 19.575 | −4.314 | 1.00 | 16.57 |
| ATOM | 242 | C | ASP | C | 31 | 63.960 | 19.625 | −2.820 | 1.00 | 17.31 |
| ATOM | 243 | O | ASP | C | 31 | 63.633 | 18.679 | −2.057 | 1.00 | 17.32 |
| ATOM | 244 | CB | ASP | C | 31 | 64.705 | 18.996 | −5.106 | 1.00 | 19.02 |
| ATOM | 245 | CG | ASP | C | 31 | 64.300 | 18.460 | −6.508 | 1.00 | 24.47 |
| ATOM | 246 | OD1 | ASP | C | 31 | 63.131 | 18.037 | −6.702 | 1.00 | 24.53 |
| ATOM | 247 | OD2 | ASP | C | 31 | 65.223 | 18.456 | −7.380 | 1.00 | 22.76 |
| ATOM | 248 | N | PHE | C | 32 | 64.716 | 20.662 | −2.468 | 1.00 | 14.02 |
| ATOM | 249 | CA | PHE | C | 32 | 65.221 | 20.820 | −1.075 | 1.00 | 13.65 |
| ATOM | 250 | C | PHE | C | 32 | 64.028 | 21.048 | −0.164 | 1.00 | 16.12 |
| ATOM | 251 | O | PHE | C | 32 | 63.971 | 20.408 | 0.948 | 1.00 | 14.39 |
| ATOM | 252 | CB | PHE | C | 32 | 66.186 | 21.980 | −0.940 | 1.00 | 13.80 |
| ATOM | 253 | CG | PHE | C | 32 | 67.460 | 21.862 | −1.736 | 1.00 | 14.18 |
| ATOM | 254 | CD1 | PHE | C | 32 | 67.825 | 20.722 | −2.462 | 1.00 | 15.47 |
| ATOM | 255 | CD2 | PHE | C | 32 | 68.314 | 22.951 | −1.731 | 1.00 | 15.29 |
| ATOM | 256 | CE1 | PHE | C | 32 | 69.105 | 20.705 | −3.202 | 1.00 | 16.12 |
| ATOM | 257 | CE2 | PHE | C | 32 | 69.515 | 22.950 | −2.452 | 1.00 | 16.29 |
| ATOM | 258 | CZ | PHE | C | 32 | 69.911 | 21.821 | −3.177 | 1.00 | 15.53 |
| ATOM | 259 | N | LEU | C | 33 | 63.106 | 21.911 | −0.561 | 1.00 | 15.49 |
| ATOM | 260 | CA | LEU | C | 33 | 61.887 | 22.193 | 0.225 | 1.00 | 13.34 |
| ATOM | 261 | C | LEU | C | 33 | 61.184 | 20.847 | 0.455 | 1.00 | 17.57 |
| ATOM | 262 | O | LEU | C | 33 | 60.783 | 20.497 | 1.591 | 1.00 | 16.65 |
| ATOM | 263 | CB | LEU | C | 33 | 60.926 | 23.160 | −0.496 | 1.00 | 14.40 |
| ATOM | 264 | CG | LEU | C | 33 | 61.494 | 24.560 | −0.722 | 1.00 | 17.89 |
| ATOM | 265 | CD1 | LEU | C | 33 | 60.412 | 25.420 | −1.418 | 1.00 | 15.16 |
| ATOM | 266 | CD2 | LEU | C | 33 | 61.823 | 25.176 | 0.693 | 1.00 | 17.59 |
| ATOM | 267 | N | ASP | C | 34 | 61.007 | 20.035 | −0.596 | 1.00 | 15.41 |
| ATOM | 268 | CA | ASP | C | 34 | 60.313 | 18.744 | −0.431 | 1.00 | 16.06 |
| ATOM | 269 | C | ASP | C | 34 | 61.016 | 17.848 | 0.617 | 1.00 | 18.00 |
| ATOM | 270 | O | ASP | C | 34 | 60.349 | 17.195 | 1.433 | 1.00 | 18.35 |
| ATOM | 271 | CB | ASP | C | 34 | 60.390 | 17.921 | −1.770 | 1.00 | 18.61 |
| ATOM | 272 | CG | ASP | C | 34 | 59.489 | 18.458 | −2.875 | 1.00 | 24.34 |
| ATOM | 273 | OD1 | ASP | C | 34 | 58.649 | 19.342 | −2.651 | 1.00 | 22.17 |
| ATOM | 274 | OD2 | ASP | C | 34 | 59.666 | 17.915 | −4.029 | 1.00 | 28.71 |
| ATOM | 275 | N | ALA | C | 35 | 62.335 | 17.746 | 0.547 | 1.00 | 13.94 |
| ATOM | 276 | CA | ALA | C | 35 | 63.094 | 16.855 | 1.437 | 1.00 | 15.72 |

-continued

Data Lists

| ATOM | 277 | C | ALA | C | 35 | 62.964 | 17.259 | 2.887 | 1.00 | 17.50 |
|------|-----|-----|-----|---|----|--------|--------|-------|------|-------|
| ATOM | 278 | O | ALA | C | 35 | 62.925 | 16.383 | 3.783 | 1.00 | 18.53 |
| ATOM | 279 | CB | ALA | C | 35 | 64.546 | 16.791 | 1.044 | 1.00 | 16.40 |
| ATOM | 280 | N | ALA | C | 36 | 62.923 | 18.572 | 3.109 | 1.00 | 13.80 |
| ATOM | 281 | CA | ALA | C | 36 | 62.826 | 19.066 | 4.512 | 1.00 | 14.07 |
| ATOM | 282 | C | ALA | C | 36 | 61.369 | 19.265 | 4.931 | 1.00 | 16.21 |
| ATOM | 283 | O | ALA | C | 36 | 61.109 | 19.675 | 6.096 | 1.00 | 16.15 |
| ATOM | 284 | CB | ALA | C | 36 | 63.652 | 20.361 | 4.722 | 1.00 | 14.23 |
| ATOM | 285 | N | GLY | C | 37 | 60.408 | 19.012 | 4.067 | 1.00 | 14.27 |
| ATOM | 286 | CA | GLY | C | 37 | 59.006 | 19.193 | 4.375 | 1.00 | 12.78 |
| ATOM | 287 | C | GLY | C | 37 | 58.621 | 20.712 | 4.515 | 1.00 | 11.55 |
| ATOM | 288 | O | GLY | C | 37 | 57.511 | 21.019 | 5.022 | 1.00 | 13.36 |
| ATOM | 289 | N | ILE | C | 38 | 59.459 | 21.637 | 3.998 | 1.00 | 13.57 |
| ATOM | 290 | CA | ILE | C | 38 | 59.227 | 23.079 | 4.058 | 1.00 | 13.98 |
| ATOM | 291 | C | ILE | C | 38 | 58.350 | 23.496 | 2.908 | 1.00 | 16.32 |
| ATOM | 292 | O | ILE | C | 38 | 58.538 | 22.975 | 1.764 | 1.00 | 16.77 |
| ATOM | 293 | CB | ILE | C | 38 | 60.556 | 23.845 | 4.057 | 1.00 | 15.34 |
| ATOM | 294 | CG1 | ILE | C | 38 | 61.360 | 23.434 | 5.316 | 1.00 | 14.55 |
| ATOM | 295 | CG2 | ILE | C | 38 | 60.360 | 25.362 | 4.098 | 1.00 | 15.27 |
| ATOM | 296 | CD1 | ILE | C | 38 | 62.741 | 24.006 | 5.393 | 1.00 | 19.63 |
| ATOM | 297 | N | LEU | C | 39 | 57.410 | 24.363 | 3.195 | 1.00 | 12.96 |
| ATOM | 298 | CA | LEU | C | 39 | 56.438 | 24.870 | 2.188 | 1.00 | 11.40 |
| ATOM | 299 | C | LEU | C | 39 | 56.789 | 26.256 | 1.685 | 1.00 | 14.26 |
| ATOM | 300 | O | LEU | C | 39 | 57.351 | 27.091 | 2.351 | 1.00 | 13.15 |
| ATOM | 301 | CB | LEU | C | 39 | 55.018 | 24.940 | 2.745 | 1.00 | 12.16 |
| ATOM | 302 | CG | LEU | C | 39 | 54.409 | 23.724 | 3.459 | 1.00 | 13.32 |
| ATOM | 303 | CD1 | LEU | C | 39 | 53.029 | 23.936 | 3.991 | 1.00 | 13.99 |
| ATOM | 304 | CD2 | LEU | C | 39 | 54.450 | 22.512 | 2.442 | 1.00 | 17.01 |
| ATOM | 305 | N | GLU | C | 40 | 56.438 | 26.515 | 0.401 | 1.00 | 14.46 |
| ATOM | 306 | CA | GLU | C | 40 | 56.668 | 27.856 | -0.077 | 1.00 | 15.39 |
| ATOM | 307 | C | GLU | C | 40 | 55.766 | 28.802 | 0.813 | 1.00 | 13.93 |
| ATOM | 308 | O | GLU | C | 40 | 54.630 | 28.488 | 1.146 | 1.00 | 13.92 |
| ATOM | 309 | CB | GLU | C | 40 | 56.149 | 27.962 | -1.564 | 1.00 | 17.33 |
| ATOM | 310 | CG | GLU | C | 40 | 56.299 | 29.405 | -2.092 | 1.00 | 22.86 |
| ATOM | 311 | CD | GLU | C | 40 | 56.447 | 29.500 | -3.609 | 1.00 | 37.57 |
| ATOM | 312 | OE1 | GLU | C | 40 | 55.722 | 28.731 | -4.258 | 1.00 | 29.60 |
| ATOM | 313 | OE2 | GLU | C | 40 | 57.284 | 30.327 | -4.101 | 1.00 | 24.74 |
| ATOM | 314 | N | ASN | C | 41 | 56.349 | 29.944 | 1.163 | 1.00 | 12.53 |
| ATOM | 315 | CA | ASN | C | 41 | 55.781 | 31.000 | 1.960 | 1.00 | 12.52 |
| ATOM | 316 | C | ASN | C | 41 | 55.812 | 30.629 | 3.468 | 1.00 | 13.84 |
| ATOM | 317 | O | ASN | C | 41 | 55.228 | 31.397 | 4.263 | 1.00 | 13.31 |
| ATOM | 318 | CB | ASN | C | 41 | 54.414 | 31.386 | 1.563 | 1.00 | 14.21 |
| ATOM | 319 | CG | ASN | C | 41 | 54.377 | 31.980 | 0.096 | 1.00 | 18.26 |
| ATOM | 320 | OD1 | ASN | C | 41 | 55.127 | 32.868 | -0.218 | 1.00 | 19.96 |
| ATOM | 321 | ND2 | ASN | C | 41 | 53.502 | 31.428 | -0.735 | 1.00 | 23.65 |
| ATOM | 322 | N | GLU | C | 42 | 56.433 | 29.507 | 3.815 | 1.00 | 12.49 |
| ATOM | 323 | CA | GLU | C | 42 | 56.487 | 29.138 | 5.281 | 1.00 | 11.09 |
| ATOM | 324 | C | GLU | C | 42 | 57.541 | 29.977 | 5.920 | 1.00 | 12.61 |
| ATOM | 325 | O | GLU | C | 42 | 58.596 | 30.268 | 5.373 | 1.00 | 13.32 |
| ATOM | 326 | CB | GLU | C | 42 | 56.868 | 27.701 | 5.408 | 1.00 | 11.37 |
| ATOM | 327 | CG | GLU | C | 42 | 56.806 | 27.190 | 6.899 | 1.00 | 13.79 |
| ATOM | 328 | CD | GLU | C | 42 | 57.022 | 25.698 | 6.958 | 1.00 | 16.86 |
| ATOM | 329 | OE1 | GLU | C | 42 | 57.443 | 25.053 | 5.978 | 1.00 | 14.48 |
| ATOM | 330 | OE2 | GLU | C | 42 | 56.821 | 25.073 | 8.083 | 1.00 | 11.57 |
| ATOM | 331 | N | ALA | C | 43 | 57.338 | 30.294 | 7.232 | 1.00 | 11.23 |
| ATOM | 332 | CA | ALA | C | 43 | 58.354 | 30.979 | 7.973 | 1.00 | 11.52 |
| ATOM | 333 | C | ALA | C | 43 | 59.543 | 29.996 | 8.219 | 1.00 | 12.62 |
| ATOM | 334 | O | ALA | C | 43 | 59.345 | 28.779 | 8.496 | 1.00 | 11.29 |
| ATOM | 335 | CB | ALA | C | 43 | 57.767 | 31.316 | 9.366 | 1.00 | 11.84 |
| ATOM | 336 | N | ILE | C | 44 | 60.755 | 30.514 | 8.084 | 1.00 | 10.61 |
| ATOM | 337 | CA | ILE | C | 44 | 61.976 | 29.726 | 8.293 | 1.00 | 9.63 |
| ATOM | 338 | C | ILE | C | 44 | 62.989 | 30.509 | 9.135 | 1.00 | 11.21 |
| ATOM | 339 | O | ILE | C | 44 | 63.038 | 31.761 | 9.090 | 1.00 | 11.77 |
| ATOM | 340 | CB | ILE | C | 44 | 62.638 | 29.285 | 6.929 | 1.00 | 11.13 |
| ATOM | 341 | CG1 | ILE | C | 44 | 62.868 | 30.534 | 6.052 | 1.00 | 12.75 |
| ATOM | 342 | CG2 | ILE | C | 44 | 61.738 | 28.241 | 6.300 | 1.00 | 11.62 |
| ATOM | 343 | CD1 | ILE | C | 44 | 63.700 | 30.215 | 4.745 | 1.00 | 16.57 |
| ATOM | 344 | N | ASP | C | 45 | 63.791 | 29.766 | 9.892 | 1.00 | 11.18 |
| ATOM | 345 | CA | ASP | C | 45 | 64.856 | 30.353 | 10.646 | 1.00 | 10.11 |
| ATOM | 346 | C | ASP | C | 45 | 66.187 | 29.921 | 9.981 | 1.00 | 11.65 |
| ATOM | 347 | O | ASP | C | 45 | 66.334 | 28.745 | 9.564 | 1.00 | 12.76 |
| ATOM | 348 | CB | ASP | C | 45 | 64.832 | 29.780 | 12.104 | 1.00 | 11.49 |
| ATOM | 349 | CG | ASP | C | 45 | 63.597 | 30.185 | 12.832 | 1.00 | 12.09 |
| ATOM | 350 | OD1 | ASP | C | 45 | 63.012 | 31.295 | 12.643 | 1.00 | 13.27 |
| ATOM | 351 | OD2 | ASP | C | 45 | 63.146 | 29.292 | 13.666 | 1.00 | 16.15 |
| ATOM | 352 | N | ILE | C | 46 | 67.120 | 30.860 | 9.819 | 1.00 | 12.45 |
| ATOM | 353 | CA | ILE | C | 46 | 68.411 | 30.563 | 9.169 | 1.00 | 11.69 |

-continued

Data Lists

| | | | | | | | | | |
|---|---|---|---|---|---|---|---|---|---|
| ATOM | 354 | C | ILE | C | 46 | 69.494 | 30.864 | 10.146 | 1.00 | 13.15 |
| ATOM | 355 | O | ILE | C | 46 | 69.566 | 31.982 | 10.710 | 1.00 | 13.26 |
| ATOM | 356 | CB | ILE | C | 46 | 68.536 | 31.422 | 7.883 | 1.00 | 13.14 |
| ATOM | 357 | CG1 | ILE | C | 46 | 67.338 | 31.096 | 7.003 | 1.00 | 12.28 |
| ATOM | 358 | CG2 | ILE | C | 46 | 69.920 | 31.132 | 7.208 | 1.00 | 13.37 |
| ATOM | 359 | CD1 | ILE | C | 46 | 67.524 | 31.730 | 5.488 | 1.00 | 14.34 |
| ATOM | 360 | N | TRP | C | 47 | 70.322 | 29.841 | 10.406 | 1.00 | 12.56 |
| ATOM | 361 | CA | TRP | C | 47 | 71.414 | 29.944 | 11.387 | 1.00 | 11.59 |
| ATOM | 362 | C | TRP | C | 47 | 72.717 | 29.812 | 10.545 | 1.00 | 12.65 |
| ATOM | 363 | O | TRP | C | 47 | 72.955 | 28.776 | 9.937 | 1.00 | 13.30 |
| ATOM | 364 | CB | TRP | C | 47 | 71.265 | 28.791 | 12.381 | 1.00 | 11.85 |
| ATOM | 365 | CG | TRP | C | 47 | 69.917 | 28.832 | 13.078 | 1.00 | 11.21 |
| ATOM | 366 | CD1 | TRP | C | 47 | 69.254 | 29.942 | 13.487 | 1.00 | 12.57 |
| ATOM | 367 | CD2 | TRP | C | 47 | 69.125 | 27.705 | 13.456 | 1.00 | 12.14 |
| ATOM | 368 | NE1 | TRP | C | 47 | 68.053 | 29.581 | 14.123 | 1.00 | 11.88 |
| ATOM | 369 | CE2 | TRP | C | 47 | 67.960 | 28.215 | 14.112 | 1.00 | 10.79 |
| ATOM | 370 | CE3 | TRP | C | 47 | 69.264 | 26.331 | 13.261 | 1.00 | 14.11 |
| ATOM | 371 | CZ2 | TRP | C | 47 | 66.930 | 27.369 | 14.579 | 1.00 | 11.66 |
| ATOM | 372 | CZ3 | TRP | C | 47 | 68.235 | 25.465 | 13.766 | 1.00 | 14.28 |
| ATOM | 373 | CH2 | TRP | C | 47 | 67.080 | 26.038 | 14.410 | 1.00 | 14.15 |
| ATOM | 374 | N | ASN | C | 48 | 73.512 | 30.856 | 10.577 | 1.00 | 12.67 |
| ATOM | 375 | CA | ASN | C | 48 | 74.730 | 30.931 | 9.784 | 1.00 | 14.84 |
| ATOM | 376 | C | ASN | C | 48 | 75.898 | 30.311 | 10.503 | 1.00 | 14.53 |
| ATOM | 377 | O | ASN | C | 48 | 76.456 | 30.916 | 11.495 | 1.00 | 15.46 |
| ATOM | 378 | CB | ASN | C | 48 | 74.966 | 32.379 | 9.370 | 1.00 | 13.17 |
| ATOM | 379 | CG | ASN | C | 48 | 75.984 | 32.520 | 8.231 | 1.00 | 12.09 |
| ATOM | 380 | OD1 | ASN | C | 48 | 76.997 | 31.892 | 8.252 | 1.00 | 14.55 |
| ATOM | 381 | ND2 | ASN | C | 48 | 75.728 | 33.481 | 7.353 | 1.00 | 14.53 |
| ATOM | 382 | N | VAL | C | 49 | 76.306 | 29.138 | 10.060 | 1.00 | 13.24 |
| ATOM | 383 | CA | VAL | C | 49 | 77.416 | 28.477 | 10.667 | 1.00 | 13.19 |
| ATOM | 384 | C | VAL | C | 49 | 78.741 | 29.222 | 10.464 | 1.00 | 18.14 |
| ATOM | 385 | O | VAL | C | 49 | 79.658 | 29.202 | 11.306 | 1.00 | 19.15 |
| ATOM | 386 | CB | VAL | C | 49 | 77.568 | 27.013 | 10.155 | 1.00 | 15.64 |
| ATOM | 387 | CG1 | VAL | C | 49 | 78.718 | 26.315 | 10.879 | 1.00 | 17.34 |
| ATOM | 388 | CG2 | VAL | C | 49 | 76.256 | 26.221 | 10.313 | 1.00 | 15.21 |
| ATOM | 389 | N | THR | C | 50 | 78.884 | 29.888 | 9.312 | 1.00 | 14.80 |
| ATOM | 390 | CA | THR | C | 50 | 80.115 | 30.592 | 9.059 | 1.00 | 14.70 |
| ATOM | 391 | C | THR | C | 50 | 80.332 | 31.856 | 9.917 | 1.00 | 15.83 |
| ATOM | 392 | O | THR | C | 50 | 81.434 | 32.032 | 10.464 | 1.00 | 18.87 |
| ATOM | 393 | CB | THR | C | 50 | 80.206 | 30.952 | 7.521 | 1.00 | 18.21 |
| ATOM | 394 | OG1 | THR | C | 50 | 80.146 | 29.742 | 6.790 | 1.00 | 15.78 |
| ATOM | 395 | CG2 | THR | C | 50 | 81.513 | 31.639 | 7.236 | 1.00 | 16.82 |
| ATOM | 396 | N | ASN | C | 51 | 79.334 | 32.710 | 10.014 | 1.00 | 14.06 |
| ATOM | 397 | CA | ASN | C | 51 | 79.492 | 33.962 | 10.776 | 1.00 | 15.31 |
| ATOM | 398 | C | ASN | C | 51 | 78.715 | 34.092 | 12.098 | 1.00 | 17.85 |
| ATOM | 399 | O | ASN | C | 51 | 78.807 | 35.115 | 12.755 | 1.00 | 17.40 |
| ATOM | 400 | CB | ASN | C | 51 | 79.229 | 35.187 | 9.877 | 1.00 | 18.14 |
| ATOM | 401 | CG | ASN | C | 51 | 77.756 | 35.329 | 9.477 | 1.00 | 20.44 |
| ATOM | 402 | OD1 | ASN | C | 51 | 76.879 | 34.705 | 10.085 | 1.00 | 16.68 |
| ATOM | 403 | ND2 | ASN | C | 51 | 77.462 | 36.172 | 8.454 | 1.00 | 16.78 |
| ATOM | 404 | N | GLY | C | 52 | 77.954 | 33.059 | 12.436 | 1.00 | 15.39 |
| ATOM | 405 | CA | GLY | C | 52 | 77.169 | 33.081 | 13.693 | 1.00 | 16.35 |
| ATOM | 406 | C | GLY | C | 52 | 75.868 | 33.855 | 13.678 | 1.00 | 18.04 |
| ATOM | 407 | O | GLY | C | 52 | 75.109 | 33.788 | 14.680 | 1.00 | 15.14 |
| ATOM | 408 | N | LYS | C | 53 | 75.528 | 34.597 | 12.606 | 1.00 | 13.62 |
| ATOM | 409 | CA | LYS | C | 53 | 74.279 | 35.346 | 12.571 | 1.00 | 13.33 |
| ATOM | 410 | C | LYS | C | 53 | 73.078 | 34.419 | 12.525 | 1.00 | 13.70 |
| ATOM | 411 | O | LYS | C | 53 | 73.156 | 33.312 | 11.988 | 1.00 | 13.57 |
| ATOM | 412 | CB | LYS | C | 53 | 74.226 | 36.376 | 11.407 | 1.00 | 15.27 |
| ATOM | 413 | CG | LYS | C | 53 | 75.408 | 37.304 | 11.460 | 1.00 | 16.18 |
| ATOM | 414 | CD | LYS | C | 53 | 75.235 | 38.411 | 10.445 | 1.00 | 18.83 |
| ATOM | 415 | CE | LYS | C | 53 | 76.538 | 39.222 | 10.332 | 1.00 | 24.88 |
| ATOM | 416 | NZ | LYS | C | 53 | 76.488 | 40.240 | 9.151 | 1.00 | 24.28 |
| ATOM | 417 | N | ARG | C | 54 | 71.957 | 34.851 | 13.130 | 1.00 | 12.69 |
| ATOM | 418 | CA | ARG | C | 54 | 70.720 | 34.077 | 13.202 | 1.00 | 11.88 |
| ATOM | 419 | C | ARG | C | 54 | 69.563 | 35.017 | 12.837 | 1.00 | 14.37 |
| ATOM | 420 | O | ARG | C | 54 | 69.422 | 36.109 | 13.368 | 1.00 | 13.79 |
| ATOM | 421 | CB | ARG | C | 54 | 70.513 | 33.544 | 14.658 | 1.00 | 11.58 |
| ATOM | 422 | CG | ARG | C | 54 | 71.674 | 32.735 | 15.081 | 1.00 | 12.91 |
| ATOM | 423 | CD | ARG | C | 54 | 71.473 | 32.182 | 16.577 | 1.00 | 13.98 |
| ATOM | 424 | NE | ARG | C | 54 | 70.621 | 31.016 | 16.648 | 1.00 | 15.65 |
| ATOM | 425 | CZ | ARG | C | 54 | 71.030 | 29.772 | 16.432 | 1.00 | 13.20 |
| ATOM | 426 | NH1 | ARG | C | 54 | 72.320 | 29.537 | 16.081 | 1.00 | 13.97 |
| ATOM | 427 | NH2 | ARG | C | 54 | 70.206 | 28.733 | 16.554 | 1.00 | 12.47 |
| ATOM | 428 | N | PHE | C | 55 | 68.708 | 34.614 | 11.897 | 1.00 | 13.21 |
| ATOM | 429 | CA | PHE | C | 55 | 67.605 | 35.481 | 11.482 | 1.00 | 11.72 |
| ATOM | 430 | C | PHE | C | 55 | 66.418 | 34.634 | 11.006 | 1.00 | 12.09 |

-continued

Data Lists

| | | | | | | | | | |
|---|---|---|---|---|---|---|---|---|---|
| ATOM | 431 | O | PHE | C | 55 | 66.591 | 33.396 | 10.737 | 1.00 | 14.53 |
| ATOM | 432 | CB | PHE | C | 55 | 68.046 | 36.473 | 10.368 | 1.00 | 12.81 |
| ATOM | 433 | CG | PHE | C | 55 | 68.562 | 35.804 | 9.087 | 1.00 | 14.26 |
| ATOM | 434 | CD1 | PHE | C | 55 | 69.846 | 35.318 | 9.008 | 1.00 | 15.91 |
| ATOM | 435 | CD2 | PHE | C | 55 | 67.757 | 35.761 | 7.976 | 1.00 | 16.89 |
| ATOM | 436 | CE1 | PHE | C | 55 | 70.335 | 34.741 | 7.814 | 1.00 | 18.73 |
| ATOM | 437 | CE2 | PHE | C | 55 | 68.244 | 35.194 | 6.797 | 1.00 | 18.14 |
| ATOM | 438 | CZ | PHE | C | 55 | 69.487 | 34.707 | 6.724 | 1.00 | 16.81 |
| ATOM | 439 | N | SER | C | 56 | 65.271 | 35.285 | 10.899 | 1.00 | 12.30 |
| ATOM | 440 | CA | SER | C | 56 | 64.027 | 34.624 | 10.507 | 1.00 | 11.60 |
| ATOM | 441 | C | SER | C | 56 | 63.434 | 35.336 | 9.280 | 1.00 | 13.08 |
| ATOM | 442 | O | SER | C | 56 | 63.432 | 36.539 | 9.216 | 1.00 | 12.92 |
| ATOM | 443 | CB | SER | C | 56 | 63.017 | 34.612 | 11.646 | 1.00 | 14.04 |
| ATOM | 444 | OG | SER | C | 56 | 63.603 | 33.905 | 12.760 | 1.00 | 17.74 |
| ATOM | 445 | N | THR | C | 57 | 62.982 | 34.543 | 8.325 | 1.00 | 12.51 |
| ATOM | 446 | CA | THR | C | 57 | 62.408 | 35.094 | 7.083 | 1.00 | 15.14 |
| ATOM | 447 | C | THR | C | 57 | 61.340 | 34.103 | 6.578 | 1.00 | 16.57 |
| ATOM | 448 | O | THR | C | 57 | 60.653 | 33.469 | 7.397 | 1.00 | 13.36 |
| ATOM | 449 | CB | THR | C | 57 | 63.513 | 35.345 | 6.067 | 1.00 | 17.35 |
| ATOM | 450 | OG1 | THR | C | 57 | 62.937 | 36.006 | 4.924 | 1.00 | 17.51 |
| ATOM | 451 | CG2 | THR | C | 57 | 64.314 | 34.105 | 5.666 | 1.00 | 19.79 |
| ATOM | 452 | N | TYR | C | 58 | 61.118 | 33.960 | 5.247 | 1.00 | 13.07 |
| ATOM | 453 | CA | TYR | C | 58 | 60.120 | 33.001 | 4.744 | 1.00 | 11.86 |
| ATOM | 454 | C | TYR | C | 58 | 60.721 | 32.381 | 3.453 | 1.00 | 14.46 |
| ATOM | 455 | O | TYR | C | 58 | 61.629 | 32.949 | 2.879 | 1.00 | 14.80 |
| ATOM | 456 | CB | TYR | C | 58 | 58.762 | 33.591 | 4.472 | 1.00 | 11.64 |
| ATOM | 457 | CG | TYR | C | 58 | 58.754 | 34.679 | 3.414 | 1.00 | 14.08 |
| ATOM | 458 | CD1 | TYR | C | 58 | 59.116 | 35.983 | 3.729 | 1.00 | 14.47 |
| ATOM | 459 | CD2 | TYR | C | 58 | 58.407 | 34.360 | 2.083 | 1.00 | 16.79 |
| ATOM | 460 | CE1 | TYR | C | 58 | 59.123 | 36.982 | 2.767 | 1.00 | 19.79 |
| ATOM | 461 | CE2 | TYR | C | 58 | 58.408 | 35.385 | 1.101 | 1.00 | 15.79 |
| ATOM | 462 | CZ | TYR | C | 58 | 58.772 | 36.658 | 1.465 | 1.00 | 22.24 |
| ATOM | 463 | OH | TYR | C | 58 | 58.773 | 37.582 | 0.406 | 1.00 | 23.11 |
| ATOM | 464 | N | ALA | C | 59 | 60.236 | 31.199 | 3.113 | 1.00 | 11.72 |
| ATOM | 465 | CA | ALA | C | 59 | 60.747 | 30.471 | 1.952 | 1.00 | 12.72 |
| ATOM | 466 | C | ALA | C | 59 | 60.040 | 30.828 | 0.681 | 1.00 | 12.49 |
| ATOM | 467 | O | ALA | C | 59 | 58.820 | 30.922 | 0.629 | 1.00 | 13.37 |
| ATOM | 468 | CB | ALA | C | 59 | 60.532 | 28.933 | 2.179 | 1.00 | 13.81 |
| ATOM | 469 | N | ILE | C | 60 | 60.887 | 30.962 | −0.360 | 1.00 | 15.14 |
| ATOM | 470 | CA | ILE | C | 60 | 60.387 | 31.207 | −1.760 | 1.00 | 16.33 |
| ATOM | 471 | C | ILE | C | 60 | 60.878 | 29.978 | −2.563 | 1.00 | 16.77 |
| ATOM | 472 | O | ILE | C | 60 | 62.007 | 29.525 | −2.396 | 1.00 | 14.68 |
| ATOM | 473 | CB | ILE | C | 60 | 61.069 | 32.427 | −2.340 | 1.00 | 18.30 |
| ATOM | 474 | CG1 | ILE | C | 60 | 60.607 | 33.708 | −1.635 | 1.00 | 19.09 |
| ATOM | 475 | CG2 | ILE | C | 60 | 60.811 | 32.500 | −3.911 | 1.00 | 21.06 |
| ATOM | 476 | CD1 | ILE | C | 60 | 61.497 | 34.913 | −1.895 | 1.00 | 26.31 |
| ATOM | 477 | N | ALA | C | 61 | 60.014 | 29.412 | −3.422 | 1.00 | 15.66 |
| ATOM | 478 | CA | ALA | C | 61 | 60.493 | 28.249 | −4.180 | 1.00 | 15.73 |
| ATOM | 479 | C | ALA | C | 61 | 61.328 | 28.696 | −5.413 | 1.00 | 18.47 |
| ATOM | 480 | O | ALA | C | 61 | 60.970 | 29.648 | −6.096 | 1.00 | 23.19 |
| ATOM | 481 | CB | ALA | C | 61 | 59.337 | 27.383 | −4.642 | 1.00 | 17.99 |
| ATOM | 482 | N | ALA | C | 62 | 62.430 | 28.006 | −5.607 | 1.00 | 14.95 |
| ATOM | 483 | CA | ALA | C | 62 | 63.342 | 28.198 | −6.774 | 1.00 | 14.55 |
| ATOM | 484 | C | ALA | C | 62 | 63.068 | 26.946 | −7.605 | 1.00 | 18.92 |
| ATOM | 485 | O | ALA | C | 62 | 62.551 | 25.909 | −7.178 | 1.00 | 17.86 |
| ATOM | 486 | CB | ALA | C | 62 | 64.817 | 28.259 | −6.403 | 1.00 | 13.98 |
| ATOM | 487 | N | GLU | C | 63 | 63.424 | 27.072 | −8.904 | 1.00 | 17.78 |
| ATOM | 488 | CA | GLU | C | 63 | 63.220 | 25.977 | −9.834 | 1.00 | 19.52 |
| ATOM | 489 | C | GLU | C | 63 | 63.779 | 24.635 | −9.365 | 1.00 | 19.81 |
| ATOM | 490 | O | GLU | C | 63 | 64.894 | 24.571 | −8.868 | 1.00 | 17.13 |
| ATOM | 491 | CB | GLU | C | 63 | 63.968 | 26.354 | −11.140 | 1.00 | 21.37 |
| ATOM | 492 | CG | GLU | C | 63 | 63.779 | 25.342 | −12.296 | 1.00 | 29.86 |
| ATOM | 493 | CD | GLU | C | 63 | 64.980 | 25.283 | −13.255 | 1.00 | 53.22 |
| ATOM | 494 | OE1 | GLU | C | 63 | 65.920 | 26.108 | −13.149 | 1.00 | 44.04 |
| ATOM | 495 | OE2 | GLU | C | 63 | 64.964 | 24.394 | −14.129 | 1.00 | 43.79 |
| ATOM | 496 | N | ARG | C | 64 | 63.012 | 23.575 | −9.561 | 1.00 | 16.26 |
| ATOM | 497 | CA | ARG | C | 64 | 63.425 | 22.245 | −9.201 | 1.00 | 16.34 |
| ATOM | 498 | C | ARG | C | 64 | 64.723 | 21.863 | −9.911 | 1.00 | 21.13 |
| ATOM | 499 | O | ARG | C | 64 | 64.809 | 21.970 | −11.168 | 1.00 | 20.36 |
| ATOM | 500 | CB | ARG | C | 64 | 62.326 | 21.232 | −9.503 | 1.00 | 19.26 |
| ATOM | 501 | CG | ARG | C | 64 | 62.635 | 19.890 | −8.963 | 1.00 | 26.38 |
| ATOM | 502 | CD | ARG | C | 64 | 61.521 | 18.875 | −9.196 | 1.00 | 27.64 |
| ATOM | 503 | NE | ARG | C | 64 | 60.171 | 19.286 | −8.819 | 1.00 | 26.53 |
| ATOM | 504 | CZ | ARG | C | 64 | 59.662 | 19.154 | −7.585 | 1.00 | 41.54 |
| ATOM | 505 | NH1 | ARG | C | 64 | 60.408 | 18.669 | −6.578 | 1.00 | 23.51 |
| ATOM | 506 | NH2 | ARG | C | 64 | 58.421 | 19.526 | −7.351 | 1.00 | 30.75 |
| ATOM | 507 | N | GLY | C | 65 | 65.728 | 21.436 | −9.177 | 1.00 | 17.09 |

-continued

Data Lists

| | | | | | | | | | |
|---|---|---|---|---|---|---|---|---|---|
| ATOM | 508 | CA | GLY | C | 65 | 67.000 | 21.022 | −9.721 | 1.00 | 17.60 |
| ATOM | 509 | C | GLY | C | 65 | 68.038 | 22.140 | −9.853 | 1.00 | 18.83 |
| ATOM | 510 | O | GLY | C | 65 | 69.192 | 21.885 | −10.218 | 1.00 | 20.21 |
| ATOM | 511 | N | SER | C | 66 | 67.650 | 23.380 | −9.543 | 1.00 | 16.18 |
| ATOM | 512 | CA | SER | C | 66 | 68.539 | 24.515 | −9.627 | 1.00 | 15.57 |
| ATOM | 513 | C | SER | C | 66 | 69.606 | 24.577 | −8.516 | 1.00 | 19.13 |
| ATOM | 514 | O | SER | C | 66 | 70.673 | 25.179 | −8.654 | 1.00 | 18.34 |
| ATOM | 515 | CB | SER | C | 66 | 67.764 | 25.795 | −9.596 | 1.00 | 18.61 |
| ATOM | 516 | OG | SER | C | 66 | 67.136 | 26.006 | −8.280 | 1.00 | 17.83 |
| ATOM | 517 | N | ARG | C | 67 | 69.272 | 23.904 | −7.390 | 1.00 | 16.53 |
| ATOM | 518 | CA | ARG | C | 67 | 70.164 | 23.877 | −6.187 | 1.00 | 17.76 |
| ATOM | 519 | C | ARG | C | 67 | 70.423 | 25.285 | −5.633 | 1.00 | 14.93 |
| ATOM | 520 | O | ARG | C | 67 | 71.423 | 25.507 | −4.998 | 1.00 | 16.56 |
| ATOM | 521 | CB | ARG | C | 67 | 71.476 | 23.153 | −6.456 | 1.00 | 15.58 |
| ATOM | 522 | CG | ARG | C | 67 | 71.298 | 21.685 | −6.865 | 1.00 | 14.91 |
| ATOM | 523 | CD | ARG | C | 67 | 72.533 | 20.909 | −6.767 | 1.00 | 13.81 |
| ATOM | 524 | NE | ARG | C | 67 | 72.322 | 19.522 | −7.249 | 1.00 | 16.78 |
| ATOM | 525 | CZ | ARG | C | 67 | 73.219 | 18.551 | −7.123 | 1.00 | 18.26 |
| ATOM | 526 | NH1 | ARG | C | 67 | 74.395 | 18.751 | −6.546 | 1.00 | 18.16 |
| ATOM | 527 | NH2 | ARG | C | 67 | 72.944 | 17.336 | −7.609 | 1.00 | 19.31 |
| ATOM | 528 | N | ILE | C | 68 | 69.503 | 26.201 | −5.884 | 1.00 | 13.92 |
| ATOM | 529 | CA | ILE | C | 68 | 69.659 | 27.584 | −5.447 | 1.00 | 13.11 |
| ATOM | 530 | C | ILE | C | 68 | 69.325 | 27.709 | −3.918 | 1.00 | 14.96 |
| ATOM | 531 | O | ILE | C | 68 | 68.385 | 27.063 | −3.430 | 1.00 | 16.08 |
| ATOM | 532 | CB | ILE | C | 68 | 68.680 | 28.483 | −6.228 | 1.00 | 16.07 |
| ATOM | 533 | CG1 | ILE | C | 68 | 69.177 | 28.633 | −7.743 | 1.00 | 15.43 |
| ATOM | 534 | CG2 | ILE | C | 68 | 68.517 | 29.887 | −5.539 | 1.00 | 14.91 |
| ATOM | 535 | CD1 | ILE | C | 68 | 68.162 | 29.265 | −8.585 | 1.00 | 17.12 |
| ATOM | 536 | N | ILE | C | 69 | 70.116 | 28.547 | −3.278 | 1.00 | 15.79 |
| ATOM | 537 | CA | ILE | C | 69 | 69.921 | 29.021 | −1.887 | 1.00 | 14.43 |
| ATOM | 538 | C | ILE | C | 69 | 70.273 | 30.521 | −2.099 | 1.00 | 12.91 |
| ATOM | 539 | O | ILE | C | 69 | 71.469 | 30.897 | −2.053 | 1.00 | 16.10 |
| ATOM | 540 | CB | ILE | C | 69 | 70.826 | 28.392 | −0.867 | 1.00 | 14.38 |
| ATOM | 541 | CG1 | ILE | C | 69 | 70.632 | 26.859 | −0.742 | 1.00 | 14.18 |
| ATOM | 542 | CG2 | ILE | C | 69 | 70.524 | 29.042 | 0.545 | 1.00 | 14.77 |
| ATOM | 543 | CD1 | ILE | C | 69 | 69.240 | 26.399 | −0.207 | 1.00 | 13.25 |
| ATOM | 544 | N | SER | C | 70 | 69.266 | 31.361 | −2.315 | 1.00 | 12.61 |
| ATOM | 545 | CA | SER | C | 70 | 69.474 | 32.776 | −2.545 | 1.00 | 12.79 |
| ATOM | 546 | C | SER | C | 70 | 68.897 | 33.612 | −1.365 | 1.00 | 16.65 |
| ATOM | 547 | O | SER | C | 70 | 67.703 | 33.574 | −1.101 | 1.00 | 16.44 |
| ATOM | 548 | CB | SER | C | 70 | 68.786 | 33.187 | −3.877 | 1.00 | 17.19 |
| ATOM | 549 | OG | SER | C | 70 | 69.055 | 34.583 | −4.178 | 1.00 | 19.28 |
| ATOM | 550 | N | VAL | C | 71 | 69.763 | 34.375 | −0.735 | 1.00 | 16.77 |
| ATOM | 551 | CA | VAL | C | 71 | 69.353 | 35.237 | 0.411 | 1.00 | 16.54 |
| ATOM | 552 | C | VAL | C | 71 | 69.046 | 36.611 | −0.216 | 1.00 | 18.47 |
| ATOM | 553 | O | VAL | C | 71 | 69.938 | 37.276 | −0.785 | 1.00 | 20.32 |
| ATOM | 554 | CB | VAL | C | 71 | 70.489 | 35.218 | 1.485 | 1.00 | 21.34 |
| ATOM | 555 | CG1 | VAL | C | 71 | 70.168 | 36.151 | 2.628 | 1.00 | 23.85 |
| ATOM | 556 | CG2 | VAL | C | 71 | 70.601 | 33.816 | 2.075 | 1.00 | 21.90 |
| ATOM | 557 | N | ASN | C | 72 | 67.793 | 37.013 | −0.156 | 1.00 | 17.21 |
| ATOM | 558 | CA | ASN | C | 72 | 67.310 | 38.229 | −0.774 | 1.00 | 18.06 |
| ATOM | 559 | C | ASN | C | 72 | 66.822 | 39.292 | 0.185 | 1.00 | 22.03 |
| ATOM | 560 | O | ASN | C | 72 | 66.550 | 38.985 | 1.364 | 1.00 | 20.77 |
| ATOM | 561 | CB | ASN | C | 72 | 66.111 | 37.862 | −1.684 | 1.00 | 15.71 |
| ATOM | 562 | CG | ASN | C | 72 | 66.479 | 36.805 | −2.771 | 1.00 | 21.14 |
| ATOM | 563 | OD1 | ASN | C | 72 | 67.625 | 36.673 | −3.142 | 1.00 | 22.76 |
| ATOM | 564 | ND2 | ASN | C | 72 | 65.471 | 36.043 | −3.192 | 1.00 | 26.84 |
| ATOM | 565 | N | GLY | C | 73 | 66.680 | 40.519 | −0.296 | 1.00 | 17.96 |
| ATOM | 566 | CA | GLY | C | 73 | 66.191 | 41.609 | 0.547 | 1.00 | 17.13 |
| ATOM | 567 | C | GLY | C | 73 | 67.152 | 41.925 | 1.662 | 1.00 | 17.10 |
| ATOM | 568 | O | GLY | C | 73 | 68.358 | 41.772 | 1.548 | 1.00 | 17.56 |
| ATOM | 569 | N | ALA | C | 74 | 66.585 | 42.379 | 2.783 | 1.00 | 16.81 |
| ATOM | 570 | CA | ALA | C | 74 | 67.448 | 42.743 | 3.926 | 1.00 | 16.63 |
| ATOM | 571 | C | ALA | C | 74 | 68.307 | 41.588 | 4.409 | 1.00 | 17.98 |
| ATOM | 572 | O | ALA | C | 74 | 69.403 | 41.809 | 4.948 | 1.00 | 17.87 |
| ATOM | 573 | CB | ALA | C | 74 | 66.585 | 43.261 | 5.083 | 1.00 | 16.76 |
| ATOM | 574 | N | ALA | C | 75 | 67.829 | 40.348 | 4.210 | 1.00 | 16.77 |
| ATOM | 575 | CA | ALA | C | 75 | 68.603 | 39.156 | 4.626 | 1.00 | 17.69 |
| ATOM | 576 | C | ALA | C | 75 | 70.019 | 39.079 | 3.999 | 1.00 | 17.68 |
| ATOM | 577 | O | ALA | C | 75 | 70.898 | 38.411 | 4.507 | 1.00 | 16.79 |
| ATOM | 578 | CB | ALA | C | 75 | 67.861 | 37.907 | 4.282 | 1.00 | 20.55 |
| ATOM | 579 | N | ALA | C | 76 | 70.216 | 39.775 | 2.856 | 1.00 | 16.67 |
| ATOM | 580 | CA | ALA | C | 76 | 71.535 | 39.737 | 2.230 | 1.00 | 17.52 |
| ATOM | 581 | C | ALA | C | 76 | 72.644 | 40.382 | 3.121 | 1.00 | 17.22 |
| ATOM | 582 | O | ALA | C | 76 | 73.840 | 40.202 | 2.886 | 1.00 | 18.09 |
| ATOM | 583 | CB | ALA | C | 76 | 71.482 | 40.359 | 0.797 | 1.00 | 18.29 |
| ATOM | 584 | N | HIS | C | 77 | 72.232 | 41.101 | 4.193 | 1.00 | 15.19 |

-continued

Data Lists

| | | | | | | | | | |
|---|---|---|---|---|---|---|---|---|---|
| ATOM | 585 | CA | HIS | C | 77 | 73.203 | 41.686 | 5.120 | 1.00 | 16.72 |
| ATOM | 586 | C | HIS | C | 77 | 73.627 | 40.623 | 6.163 | 1.00 | 16.17 |
| ATOM | 587 | O | HIS | C | 77 | 74.587 | 40.860 | 6.914 | 1.00 | 18.25 |
| ATOM | 588 | CB | HIS | C | 77 | 72.502 | 42.778 | 5.963 | 1.00 | 18.31 |
| ATOM | 589 | CG | HIS | C | 77 | 72.336 | 44.077 | 5.261 | 1.00 | 21.21 |
| ATOM | 590 | ND1 | HIS | C | 77 | 73.368 | 44.963 | 5.118 | 1.00 | 25.21 |
| ATOM | 591 | CD2 | HIS | C | 77 | 71.258 | 44.654 | 4.687 | 1.00 | 22.31 |
| ATOM | 592 | CE1 | HIS | C | 77 | 72.940 | 46.030 | 4.463 | 1.00 | 23.74 |
| ATOM | 593 | NE2 | HIS | C | 77 | 71.663 | 45.876 | 4.200 | 1.00 | 22.33 |
| ATOM | 594 | N | CYS | C | 78 | 72.921 | 39.495 | 6.201 | 1.00 | 14.86 |
| ATOM | 595 | CA | CYS | C | 78 | 73.192 | 38.449 | 7.199 | 1.00 | 16.42 |
| ATOM | 596 | C | CYS | C | 78 | 73.868 | 37.192 | 6.701 | 1.00 | 16.96 |
| ATOM | 597 | O | CYS | C | 78 | 74.290 | 36.294 | 7.516 | 1.00 | 16.97 |
| ATOM | 598 | CB | CYS | C | 78 | 71.873 | 38.018 | 7.877 | 1.00 | 16.76 |
| ATOM | 599 | SG | CYS | C | 78 | 70.910 | 39.411 | 8.622 | 1.00 | 22.74 |
| ATOM | 600 | N | ALA | C | 79 | 73.983 | 37.044 | 5.346 | 1.00 | 14.78 |
| ATOM | 601 | CA | ALA | C | 79 | 74.626 | 35.854 | 4.795 | 1.00 | 14.85 |
| ATOM | 602 | C | ALA | C | 79 | 75.204 | 36.282 | 3.435 | 1.00 | 15.30 |
| ATOM | 603 | O | ALA | C | 79 | 74.676 | 37.213 | 2.822 | 1.00 | 16.51 |
| ATOM | 604 | CB | ALA | C | 79 | 73.652 | 34.707 | 4.608 | 1.00 | 15.77 |
| ATOM | 605 | N | SER | C | 80 | 76.281 | 35.597 | 3.082 | 1.00 | 13.90 |
| ATOM | 606 | CA | SER | C | 80 | 77.009 | 35.855 | 1.804 | 1.00 | 13.46 |
| ATOM | 607 | C | SER | C | 80 | 77.182 | 34.588 | 1.039 | 1.00 | 17.54 |
| ATOM | 608 | O | SER | C | 80 | 77.156 | 33.497 | 1.573 | 1.00 | 16.85 |
| ATOM | 609 | CB | SER | C | 80 | 78.368 | 36.434 | 2.130 | 1.00 | 17.79 |
| ATOM | 610 | OG | SER | C | 80 | 78.214 | 37.661 | 2.852 | 1.00 | 18.84 |
| ATOM | 611 | N | VAL | C | 81 | 77.403 | 34.738 | −0.290 | 1.00 | 15.99 |
| ATOM | 612 | CA | VAL | C | 81 | 77.636 | 33.575 | −1.121 | 1.00 | 14.74 |
| ATOM | 613 | C | VAL | C | 81 | 78.865 | 32.845 | −0.571 | 1.00 | 14.78 |
| ATOM | 614 | O | VAL | C | 81 | 79.915 | 33.417 | −0.317 | 1.00 | 15.81 |
| ATOM | 615 | CB | VAL | C | 81 | 77.941 | 34.058 | −2.623 | 1.00 | 14.01 |
| ATOM | 616 | CG1 | VAL | C | 81 | 78.354 | 32.825 | −3.456 | 1.00 | 15.95 |
| ATOM | 617 | CG2 | VAL | C | 81 | 76.706 | 34.650 | −3.234 | 1.00 | 15.67 |
| ATOM | 618 | N | GLY | C | 82 | 78.740 | 31.543 | −0.346 | 1.00 | 14.65 |
| ATOM | 619 | CA | GLY | C | 82 | 79.809 | 30.766 | 0.200 | 1.00 | 14.30 |
| ATOM | 620 | C | GLY | C | 82 | 79.558 | 30.358 | 1.673 | 1.00 | 16.91 |
| ATOM | 621 | O | GLY | C | 82 | 80.116 | 29.368 | 2.122 | 1.00 | 15.50 |
| ATOM | 622 | N | ASP | C | 83 | 78.746 | 31.145 | 2.355 | 1.00 | 14.93 |
| ATOM | 623 | CA | ASP | C | 83 | 78.465 | 30.803 | 3.792 | 1.00 | 13.74 |
| ATOM | 624 | C | ASP | C | 83 | 77.699 | 29.490 | 3.879 | 1.00 | 14.63 |
| ATOM | 625 | O | ASP | C | 83 | 76.858 | 29.163 | 3.011 | 1.00 | 15.91 |
| ATOM | 626 | CB | ASP | C | 83 | 77.586 | 31.900 | 4.467 | 1.00 | 13.28 |
| ATOM | 627 | CG | ASP | C | 83 | 78.339 | 33.192 | 4.782 | 1.00 | 12.11 |
| ATOM | 628 | OD1 | ASP | C | 83 | 79.600 | 33.269 | 4.679 | 1.00 | 15.32 |
| ATOM | 629 | OD2 | ASP | C | 83 | 77.591 | 34.161 | 5.119 | 1.00 | 15.76 |
| ATOM | 630 | N | ILE | C | 84 | 77.970 | 28.743 | 4.968 | 1.00 | 14.29 |
| ATOM | 631 | CA | ILE | C | 84 | 77.296 | 27.473 | 5.239 | 1.00 | 13.65 |
| ATOM | 632 | C | ILE | C | 84 | 76.184 | 27.799 | 6.282 | 1.00 | 13.60 |
| ATOM | 633 | O | ILE | C | 84 | 76.469 | 28.474 | 7.272 | 1.00 | 15.62 |
| ATOM | 634 | CB | ILE | C | 84 | 78.287 | 26.496 | 5.913 | 1.00 | 16.83 |
| ATOM | 635 | CG1 | ILE | C | 84 | 79.463 | 26.115 | 4.939 | 1.00 | 17.52 |
| ATOM | 636 | CG2 | ILE | C | 84 | 77.560 | 25.231 | 6.346 | 1.00 | 19.25 |
| ATOM | 637 | CD1 | ILE | C | 84 | 78.981 | 25.389 | 3.679 | 1.00 | 21.07 |
| ATOM | 638 | N | VAL | C | 85 | 74.976 | 27.392 | 6.001 | 1.00 | 12.41 |
| ATOM | 639 | CA | VAL | C | 85 | 73.864 | 27.713 | 6.910 | 1.00 | 12.94 |
| ATOM | 640 | C | VAL | C | 85 | 72.991 | 26.532 | 7.153 | 1.00 | 15.89 |
| ATOM | 641 | O | VAL | C | 85 | 73.039 | 25.474 | 6.469 | 1.00 | 14.01 |
| ATOM | 642 | CB | VAL | C | 85 | 72.979 | 28.838 | 6.312 | 1.00 | 14.37 |
| ATOM | 643 | CG1 | VAL | C | 85 | 73.501 | 30.088 | 5.901 | 1.00 | 13.95 |
| ATOM | 644 | CG2 | VAL | C | 85 | 72.180 | 28.356 | 5.045 | 1.00 | 14.77 |
| ATOM | 645 | N | ILE | C | 86 | 72.116 | 26.676 | 8.178 | 1.00 | 13.28 |
| ATOM | 646 | CA | ILE | C | 86 | 71.158 | 25.631 | 8.523 | 1.00 | 13.39 |
| ATOM | 647 | C | ILE | C | 86 | 69.809 | 26.347 | 8.420 | 1.00 | 14.02 |
| ATOM | 648 | O | ILE | C | 86 | 69.643 | 27.39 | 8.961 | 1.00 | 13.98 |
| ATOM | 649 | CB | ILE | C | 86 | 71.391 | 25.081 | 9.985 | 1.00 | 13.99 |
| ATOM | 650 | CG1 | ILE | C | 86 | 72.703 | 24.242 | 10.022 | 1.00 | 17.59 |
| ATOM | 651 | CG2 | ILE | C | 86 | 70.181 | 24.220 | 10.367 | 1.00 | 15.22 |
| ATOM | 652 | CD1 | ILE | C | 86 | 73.325 | 24.108 | 11.423 | 1.00 | 22.03 |
| ATOM | 653 | N | ILE | C | 87 | 68.861 | 25.804 | 7.637 | 1.00 | 12.05 |
| ATOM | 654 | CA | ILE | C | 87 | 67.560 | 26.410 | 7.449 | 1.00 | 11.27 |
| ATOM | 655 | C | ILE | C | 87 | 66.521 | 25.488 | 8.056 | 1.00 | 12.08 |
| ATOM | 656 | O | ILE | C | 87 | 66.411 | 24.300 | 7.711 | 1.00 | 13.19 |
| ATOM | 657 | CB | ILE | C | 87 | 67.259 | 26.629 | 5.881 | 1.00 | 12.91 |
| ATOM | 658 | CG1 | ILE | C | 87 | 68.381 | 27.458 | 5.331 | 1.00 | 14.33 |
| ATOM | 659 | CG2 | ILE | C | 87 | 65.903 | 27.272 | 5.724 | 1.00 | 14.68 |
| ATOM | 660 | CD1 | ILE | C | 87 | 68.240 | 27.670 | 3.726 | 1.00 | 14.91 |
| ATOM | 661 | N | ALA | C | 88 | 65.718 | 26.045 | 9.004 | 1.00 | 11.17 |

-continued

Data Lists

| | | | | | | | | | |
|---|---|---|---|---|---|---|---|---|---|
| ATOM | 662 | CA | ALA | C | 88 | 64.724 | 25.224 | 9.662 | 1.00 | 11.51 |
| ATOM | 663 | C | ALA | C | 88 | 63.339 | 25.757 | 9.674 | 1.00 | 11.06 |
| ATOM | 664 | O | ALA | C | 88 | 63.146 | 26.990 | 9.596 | 1.00 | 12.85 |
| ATOM | 665 | CB | ALA | C | 88 | 65.208 | 25.134 | 11.204 | 1.00 | 12.18 |
| ATOM | 666 | N | SER | C | 89 | 62.321 | 24.892 | 9.833 | 1.00 | 11.32 |
| ATOM | 667 | CA | SER | C | 89 | 60.945 | 25.386 | 10.017 | 1.00 | 11.17 |
| ATOM | 668 | C | SER | C | 89 | 60.407 | 24.644 | 11.248 | 1.00 | 11.44 |
| ATOM | 669 | O | SER | C | 89 | 60.891 | 23.539 | 11.573 | 1.00 | 11.04 |
| ATOM | 670 | CB | SER | C | 89 | 59.986 | 25.246 | 8.807 | 1.00 | 14.68 |
| ATOM | 671 | OG | SER | C | 89 | 59.409 | 23.939 | 8.749 | 1.00 | 13.56 |
| ATOM | 672 | N | PHE | C | 90 | 59.489 | 25.340 | 11.926 | 1.00 | 11.58 |
| ATOM | 673 | CA | PHE | C | 90 | 58.878 | 24.772 | 13.154 | 1.00 | 10.03 |
| ATOM | 674 | C | PHE | C | 90 | 57.391 | 24.743 | 13.006 | 1.00 | 11.41 |
| ATOM | 675 | O | PHE | C | 90 | 56.780 | 25.662 | 12.350 | 1.00 | 12.95 |
| ATOM | 676 | CB | PHE | C | 90 | 59.257 | 25.677 | 14.348 | 1.00 | 10.86 |
| ATOM | 677 | CG | PHE | C | 90 | 60.681 | 25.536 | 14.776 | 1.00 | 11.25 |
| ATOM | 678 | CD1 | PHE | C | 90 | 61.724 | 26.266 | 14.169 | 1.00 | 12.54 |
| ATOM | 679 | CD2 | PHE | C | 90 | 61.016 | 24.612 | 15.810 | 1.00 | 13.88 |
| ATOM | 680 | CE1 | PHE | C | 90 | 63.094 | 26.079 | 14.613 | 1.00 | 12.35 |
| ATOM | 681 | CE2 | PHE | C | 90 | 62.289 | 24.431 | 16.247 | 1.00 | 13.61 |
| ATOM | 682 | CZ | PHE | C | 90 | 63.373 | 25.138 | 15.672 | 1.00 | 12.98 |
| ATOM | 683 | N | VAL | C | 91 | 56.768 | 23.720 | 13.608 | 1.00 | 9.83 |
| ATOM | 684 | CA | VAL | C | 91 | 55.315 | 23.572 | 13.573 | 1.00 | 10.22 |
| ATOM | 685 | C | VAL | C | 91 | 54.795 | 23.312 | 14.993 | 1.00 | 14.03 |
| ATOM | 686 | O | VAL | C | 91 | 55.606 | 22.962 | 15.893 | 1.00 | 13.50 |
| ATOM | 687 | CB | VAL | C | 91 | 54.804 | 22.401 | 12.688 | 1.00 | 13.62 |
| ATOM | 688 | CG1 | VAL | C | 91 | 55.015 | 22.757 | 11.190 | 1.00 | 15.08 |
| ATOM | 689 | CG2 | VAL | C | 91 | 55.481 | 21.082 | 13.064 | 1.00 | 13.05 |
| ATOM | 690 | N | THR | C | 92 | 53.528 | 23.542 | 15.175 | 1.00 | 12.76 |
| ATOM | 691 | CA | THR | C | 92 | 52.916 | 23.289 | 16.511 | 1.00 | 11.56 |
| ATOM | 692 | C | THR | C | 92 | 51.985 | 22.099 | 16.437 | 1.00 | 13.31 |
| ATOM | 693 | O | THR | C | 92 | 51.347 | 21.772 | 15.395 | 1.00 | 13.08 |
| ATOM | 694 | CB | THR | C | 92 | 52.237 | 24.503 | 17.160 | 1.00 | 12.64 |
| ATOM | 695 | OG1 | THR | C | 92 | 51.102 | 24.918 | 16.359 | 1.00 | 16.06 |
| ATOM | 696 | CG2 | THR | C | 92 | 53.186 | 25.697 | 17.314 | 1.00 | 13.80 |
| ATOM | 697 | N | MET | C | 93 | 51.881 | 21.327 | 17.562 | 1.00 | 11.69 |
| ATOM | 698 | CA | MET | C | 93 | 51.013 | 20.142 | 17.639 | 1.00 | 11.35 |
| ATOM | 699 | C | MET | C | 93 | 50.872 | 19.828 | 19.145 | 1.00 | 14.45 |
| ATOM | 700 | O | MET | C | 93 | 51.654 | 20.324 | 19.951 | 1.00 | 13.44 |
| ATOM | 701 | CB | MET | C | 93 | 51.697 | 18.907 | 16.955 | 1.00 | 12.85 |
| ATOM | 702 | CG | MET | C | 93 | 53.062 | 18.586 | 17.608 | 1.00 | 13.91 |
| ATOM | 703 | SD | MET | C | 93 | 54.059 | 17.382 | 16.687 | 1.00 | 14.46 |
| ATOM | 704 | CE | MET | C | 93 | 54.523 | 18.473 | 15.286 | 1.00 | 14.10 |
| ATOM | 705 | N | PRO | C | 94 | 49.873 | 19.055 | 19.455 | 1.00 | 12.36 |
| ATOM | 706 | CA | PRO | C | 94 | 49.648 | 18.670 | 20.865 | 1.00 | 12.35 |
| ATOM | 707 | C | PRO | C | 94 | 50.877 | 17.883 | 21.402 | 1.00 | 15.66 |
| ATOM | 708 | O | PRO | C | 94 | 51.630 | 17.195 | 20.717 | 1.00 | 14.35 |
| ATOM | 709 | CB | PRO | C | 94 | 48.504 | 17.712 | 20.781 | 1.00 | 13.86 |
| ATOM | 710 | CG | PRO | C | 94 | 47.676 | 18.206 | 19.582 | 1.00 | 15.72 |
| ATOM | 711 | CD | PRO | C | 94 | 48.832 | 18.461 | 18.595 | 1.00 | 12.82 |
| ATOM | 712 | N | ASP | C | 95 | 51.023 | 17.929 | 22.751 | 1.00 | 14.03 |
| ATOM | 713 | CA | ASP | C | 95 | 52.125 | 17.208 | 23.352 | 1.00 | 15.39 |
| ATOM | 714 | C | ASP | C | 95 | 52.288 | 15.721 | 22.997 | 1.00 | 16.06 |
| ATOM | 715 | O | ASP | C | 95 | 53.415 | 15.216 | 22.827 | 1.00 | 16.29 |
| ATOM | 716 | CB | ASP | C | 95 | 51.982 | 17.327 | 24.883 | 1.00 | 15.44 |
| ATOM | 717 | CG | ASP | C | 95 | 53.209 | 16.791 | 25.618 | 1.00 | 15.85 |
| ATOM | 718 | OD1 | ASP | C | 95 | 54.314 | 17.367 | 25.497 | 1.00 | 14.33 |
| ATOM | 719 | OD2 | ASP | C | 95 | 53.073 | 15.750 | 26.345 | 1.00 | 18.70 |
| ATOM | 720 | N | GLU | C | 96 | 51.181 | 14.987 | 22.922 | 1.00 | 15.70 |
| ATOM | 721 | CA | GLU | C | 96 | 51.283 | 13.563 | 22.604 | 1.00 | 14.32 |
| ATOM | 722 | C | GLU | C | 96 | 51.905 | 13.295 | 21.236 | 1.00 | 18.35 |
| ATOM | 723 | O | GLU | C | 96 | 52.794 | 12.468 | 21.100 | 1.00 | 17.78 |
| ATOM | 724 | CB | GLU | C | 96 | 49.944 | 12.850 | 22.791 | 1.00 | 16.31 |
| ATOM | 725 | CG | GLU | C | 96 | 50.012 | 11.377 | 22.421 | 1.00 | 22.63 |
| ATOM | 726 | CD | GLU | C | 96 | 48.701 | 10.594 | 22.718 | 1.00 | 23.98 |
| ATOM | 727 | OE1 | GLU | C | 96 | 47.699 | 11.210 | 23.080 | 1.00 | 25.84 |
| ATOM | 728 | OE2 | GLU | C | 96 | 48.703 | 9.363 | 22.540 | 1.00 | 30.53 |
| ATOM | 729 | N | GLU | C | 97 | 51.419 | 14.032 | 20.241 | 1.00 | 15.16 |
| ATOM | 730 | CA | GLU | C | 97 | 52.004 | 13.852 | 18.911 | 1.00 | 15.52 |
| ATOM | 731 | C | GLU | C | 97 | 53.491 | 14.296 | 18.936 | 1.00 | 13.99 |
| ATOM | 732 | O | GLU | C | 97 | 54.332 | 13.695 | 18.293 | 1.00 | 16.67 |
| ATOM | 733 | CB | GLU | C | 97 | 51.202 | 14.706 | 17.929 | 1.00 | 15.35 |
| ATOM | 734 | CG | GLU | C | 97 | 51.780 | 14.636 | 16.496 | 1.00 | 17.59 |
| ATOM | 735 | CD | GLU | C | 97 | 50.924 | 15.416 | 15.525 | 1.00 | 22.36 |
| ATOM | 736 | OE1 | GLU | C | 97 | 43.940 | 16.082 | 15.936 | 1.00 | 17.71 |
| ATOM | 737 | OE2 | GLU | C | 97 | 51.268 | 15.305 | 14.305 | 1.00 | 22.62 |
| ATOM | 738 | N | ALA | C | 98 | 53.816 | 15.379 | 19.663 | 1.00 | 13.03 |

-continued

| | | | | | | | | | |
|---|---|---|---|---|---|---|---|---|---|
| ATOM | 739 | CA | ALA | C | 98 | 55.185 | 15.883 | 19.750 | 1.00 | 12.71 |
| ATOM | 740 | C | ALA | C | 98 | 56.174 | 14.859 | 20.323 | 1.00 | 15.63 |
| ATOM | 741 | O | ALA | C | 98 | 57.339 | 14.809 | 19.952 | 1.00 | 14.36 |
| ATOM | 742 | CB | ALA | C | 98 | 55.199 | 17.161 | 20.596 | 1.00 | 14.85 |
| ATOM | 743 | N | ARG | C | 99 | 55.689 | 13.987 | 21.252 | 1.00 | 14.05 |
| ATOM | 744 | CA | ARG | C | 99 | 56.579 | 13.018 | 21.842 | 1.00 | 15.96 |
| ATOM | 745 | C | ARG | C | 99 | 57.090 | 11.936 | 20.924 | 1.00 | 17.44 |
| ATOM | 746 | O | ARG | C | 99 | 58.103 | 11.307 | 21.251 | 1.00 | 21.21 |
| ATOM | 747 | CB | ARG | C | 99 | 55.968 | 12.422 | 23.153 | 1.00 | 17.37 |
| ATOM | 748 | CG | ARG | C | 99 | 55.949 | 13.457 | 24.271 | 1.00 | 16.32 |
| ATOM | 749 | CD | ARG | C | 99 | 55.383 | 12.905 | 25.632 | 1.00 | 16.45 |
| ATOM | 750 | NE | ARG | C | 99 | 53.933 | 12.912 | 25.712 | 1.00 | 14.75 |
| ATOM | 751 | CZ | ARG | C | 99 | 53.157 | 11.860 | 25.584 | 1.00 | 13.61 |
| ATOM | 752 | NH1 | ARG | C | 99 | 53.688 | 10.668 | 25.371 | 1.00 | 16.09 |
| ATOM | 753 | NH2 | ARG | C | 99 | 51.846 | 11.988 | 25.703 | 1.00 | 18.40 |
| ATOM | 754 | N | THR | C | 100 | 56.438 | 11.713 | 19.788 | 1.00 | 16.42 |
| ATOM | 755 | CA | THR | C | 100 | 56.970 | 10.700 | 18.869 | 1.00 | 16.33 |
| ATOM | 756 | C | THR | C | 100 | 57.108 | 11.310 | 17.469 | 1.00 | 19.97 |
| ATOM | 757 | O | THR | C | 100 | 57.162 | 10.569 | 16.457 | 1.00 | 20.03 |
| ATOM | 758 | CB | THR | C | 100 | 56.147 | 9.435 | 18.772 | 1.00 | 21.91 |
| ATOM | 759 | OG1 | THR | C | 100 | 54.764 | 9.744 | 18.520 | 1.00 | 20.66 |
| ATOM | 760 | CG2 | THR | C | 100 | 56.224 | 8.675 | 20.128 | 1.00 | 22.68 |
| ATOM | 761 | N | TRP | C | 101 | 57.180 | 12.634 | 17.437 | 1.00 | 17.87 |
| ATOM | 762 | CA | TRP | C | 101 | 57.321 | 13.322 | 16.115 | 1.00 | 16.71 |
| ATOM | 763 | C | TRP | C | 101 | 58.708 | 13.111 | 15.528 | 1.00 | 19.04 |
| ATOM | 764 | O | TRP | C | 101 | 59.710 | 13.152 | 16.246 | 1.00 | 17.05 |
| ATOM | 765 | CB | TRP | C | 101 | 57.100 | 14.825 | 16.331 | 1.00 | 14.65 |
| ATOM | 766 | CG | TRP | C | 101 | 57.469 | 15.675 | 15.092 | 1.00 | 14.16 |
| ATOM | 767 | CD1 | TRP | C | 101 | 58.521 | 16.473 | 14.986 | 1.00 | 16.31 |
| ATOM | 768 | CD2 | TRP | C | 101 | 56.693 | 15.803 | 13.887 | 1.00 | 16.31 |
| ATOM | 769 | NE1 | TRP | C | 101 | 58.514 | 17.103 | 13.701 | 1.00 | 15.49 |
| ATOM | 770 | CE2 | TRP | C | 101 | 57.398 | 16.686 | 13.043 | 1.00 | 17.23 |
| ATOM | 771 | CE3 | TRP | C | 101 | 55.500 | 15.234 | 13.424 | 1.00 | 19.60 |
| ATOM | 772 | CZ2 | TRP | C | 101 | 56.935 | 17.023 | 11.749 | 1.00 | 18.02 |
| ATOM | 773 | CZ3 | TRP | C | 101 | 55.020 | 15.590 | 12.147 | 1.00 | 21.23 |
| ATOM | 774 | CH2 | TRP | C | 101 | 55.747 | 16.467 | 11.343 | 1.00 | 21.41 |
| ATOM | 775 | N | ARG | C | 102 | 58.788 | 12.895 | 14.174 | 1.00 | 15.76 |
| ATOM | 776 | CA | ARG | C | 102 | 60.114 | 12.715 | 13.551 | 1.00 | 16.64 |
| ATOM | 777 | C | ARG | C | 102 | 60.358 | 13.856 | 12.511 | 1.00 | 14.79 |
| ATOM | 778 | O | ARG | C | 102 | 59.671 | 13.858 | 11.470 | 1.00 | 17.03 |
| ATOM | 779 | CB | ARG | C | 102 | 60.181 | 11.375 | 12.823 | 1.00 | 17.42 |
| ATOM | 780 | CG | ARG | C | 102 | 59.934 | 10.169 | 13.728 | 1.00 | 24.67 |
| ATOM | 781 | CD | ARG | C | 102 | 60.918 | 10.190 | 14.864 | 1.00 | 40.94 |
| ATOM | 782 | NE | ARG | C | 102 | 60.647 | 9.111 | 15.815 | 1.00 | 58.76 |
| ATOM | 783 | CZ | ARG | C | 102 | 60.403 | 9.287 | 17.118 | 1.00 | 65.94 |
| ATOM | 784 | NH1 | ARG | C | 102 | 60.393 | 10.518 | 17.651 | 1.00 | 46.00 |
| ATOM | 785 | NH2 | ARG | C | 102 | 60.162 | 8.231 | 17.890 | 1.00 | 52.57 |
| ATOM | 786 | N | PRO | C | 103 | 61.262 | 14.768 | 12.787 | 1.00 | 15.12 |
| ATOM | 787 | CA | PRO | C | 103 | 61.499 | 15.893 | 11.838 | 1.00 | 13.53 |
| ATOM | 788 | C | PRO | C | 103 | 62.051 | 15.360 | 10.512 | 1.00 | 15.29 |
| ATOM | 789 | O | PRO | C | 103 | 62.678 | 14.328 | 10.477 | 1.00 | 16.02 |
| ATOM | 790 | CB | PRO | C | 103 | 62.536 | 16.744 | 12.516 | 1.00 | 14.34 |
| ATOM | 791 | CG | PRO | C | 103 | 62.357 | 16.404 | 14.069 | 1.00 | 18.46 |
| ATOM | 792 | CD | PRO | C | 103 | 62.024 | 14.929 | 14.038 | 1.00 | 15.59 |
| ATOM | 793 | N | ASN | C | 104 | 61.797 | 16.147 | 9.439 | 1.00 | 14.28 |
| ATOM | 794 | CA | ASN | C | 104 | 62.283 | 15.811 | 8.088 | 1.00 | 13.04 |
| ATOM | 795 | C | ASN | C | 104 | 63.643 | 16.508 | 7.924 | 1.00 | 14.43 |
| ATOM | 796 | O | ASN | C | 104 | 63.701 | 17.742 | 7.661 | 1.00 | 13.98 |
| ATOM | 797 | CB | ASN | C | 104 | 61.242 | 16.325 | 7.131 | 1.00 | 12.98 |
| ATOM | 798 | CG | ASN | C | 104 | 59.954 | 15.602 | 7.276 | 1.00 | 15.09 |
| ATOM | 799 | OD1 | ASN | C | 104 | 59.914 | 14.364 | 7.131 | 1.00 | 17.92 |
| ATOM | 800 | ND2 | ASN | C | 104 | 58.886 | 16.310 | 7.628 | 1.00 | 16.93 |
| ATOM | 801 | N | VAL | C | 105 | 64.733 | 15.763 | 8.113 | 1.00 | 14.40 |
| ATOM | 802 | CA | VAL | C | 105 | 66.051 | 16.308 | 8.052 | 1.00 | 15.19 |
| ATOM | 803 | C | VAL | C | 105 | 66.791 | 15.897 | 6.794 | 1.00 | 18.79 |
| ATOM | 804 | O | VAL | C | 105 | 66.870 | 14.705 | 6.477 | 1.00 | 20.46 |
| ATOM | 805 | CB | VAL | C | 105 | 66.898 | 15.862 | 9.252 | 1.00 | 18.28 |
| ATOM | 806 | CG1 | VAL | C | 105 | 68.294 | 16.482 | 9.195 | 1.00 | 20.67 |
| ATOM | 807 | CG2 | VAL | C | 105 | 66.189 | 16.312 | 10.600 | 1.00 | 17.51 |
| ATOM | 808 | N | ALA | C | 106 | 67.321 | 16.899 | 6.103 | 1.00 | 16.66 |
| ATOM | 809 | CA | ALA | C | 106 | 68.130 | 16.617 | 4.865 | 1.00 | 16.75 |
| ATOM | 810 | C | ALA | C | 106 | 69.506 | 17.196 | 5.121 | 1.00 | 15.84 |
| ATOM | 811 | O | ALA | C | 106 | 69.621 | 18.358 | 5.520 | 1.00 | 16.27 |
| ATOM | 812 | CB | ALA | C | 106 | 67.469 | 17.246 | 3.645 | 1.00 | 17.32 |
| ATOM | 813 | N | TYR | C | 107 | 70.558 | 16.390 | 4.881 | 1.00 | 15.99 |
| ATOM | 814 | CA | TYR | C | 107 | 71.941 | 16.745 | 5.089 | 1.00 | 15.93 |
| ATOM | 815 | C | TYR | C | 107 | 72.620 | 17.003 | 3.740 | 1.00 | 18.71 |

-continued

Data Lists

| ATOM | 816 | O | TYR | C | 107 | 72.346 | 16.296 | 2.779 | 1.00 | 20.84 |
| ATOM | 817 | CB | TYR | C | 107 | 72.714 | 15.637 | 5.835 | 1.00 | 19.26 |
| ATOM | 818 | CG | TYR | C | 107 | 72.177 | 15.391 | 7.253 | 1.00 | 21.14 |
| ATOM | 819 | CD1 | TYR | C | 107 | 72.619 | 16.143 | 8.296 | 1.00 | 21.91 |
| ATOM | 820 | CD2 | TYR | C | 107 | 71.259 | 14.405 | 7.479 | 1.00 | 23.16 |
| ATOM | 821 | CE1 | TYR | C | 107 | 72.125 | 15.931 | 9.596 | 1.00 | 24.59 |
| ATOM | 822 | CE2 | TYR | C | 107 | 70.758 | 14.193 | 8.779 | 1.00 | 24.09 |
| ATOM | 823 | CZ | TYR | C | 107 | 71.220 | 14.964 | 9.794 | 1.00 | 27.50 |
| ATOM | 824 | OH | TYR | C | 107 | 70.760 | 14.801 | 11.101 | 1.00 | 29.66 |
| ATOM | 825 | N | PHE | C | 108 | 73.461 | 18.022 | 3.744 | 1.00 | 15.42 |
| ATOM | 826 | CA | PHE | C | 108 | 74.165 | 18.434 | 2.489 | 1.00 | 15.71 |
| ATOM | 827 | C | PHE | C | 108 | 75.646 | 18.525 | 2.624 | 1.00 | 19.91 |
| ATOM | 828 | O | PHE | C | 108 | 76.239 | 18.645 | 3.715 | 1.00 | 19.12 |
| ATOM | 829 | CB | PHE | C | 108 | 73.644 | 19.803 | 2.063 | 1.00 | 16.87 |
| ATOM | 830 | CG | PHE | C | 108 | 72.225 | 19.796 | 1.661 | 1.00 | 16.76 |
| ATOM | 831 | CD1 | PHE | C | 108 | 71.195 | 19.910 | 2.626 | 1.00 | 17.17 |
| ATOM | 832 | CD2 | PHE | C | 108 | 71.832 | 19.656 | 0.305 | 1.00 | 17.45 |
| ATOM | 833 | CE1 | PHE | C | 108 | 69.873 | 19.871 | 2.240 | 1.00 | 19.62 |
| ATOM | 834 | CE2 | PHE | C | 108 | 70.497 | 19.620 | −0.081 | 1.00 | 20.41 |
| ATOM | 835 | CZ | PHE | C | 108 | 69.480 | 19.741 | 0.885 | 1.00 | 19.54 |
| ATOM | 836 | N | GLU | C | 109 | 76.311 | 18.516 | 1.444 | 1.00 | 17.02 |
| ATOM | 837 | CA | GLU | C | 109 | 77.762 | 18.671 | 1.404 | 1.00 | 17.21 |
| ATOM | 838 | C | GLU | C | 109 | 78.099 | 19.064 | −0.072 | 1.00 | 15.89 |
| ATOM | 839 | O | GLU | C | 109 | 77.219 | 18.996 | −0.910 | 1.00 | 16.10 |
| ATOM | 840 | CB | GLU | C | 109 | 78.483 | 17.338 | 1.695 | 1.00 | 18.77 |
| ATOM | 841 | CG | GLU | C | 109 | 78.226 | 16.303 | 0.620 | 1.00 | 19.64 |
| ATOM | 842 | CD | GLU | C | 109 | 78.915 | 14.936 | 0.838 | 1.00 | 21.63 |
| ATOM | 843 | OE1 | GLU | C | 109 | 79.866 | 14.811 | 1.621 | 1.00 | 24.76 |
| ATOM | 844 | OE2 | GLU | C | 109 | 78.472 | 13.999 | 0.170 | 1.00 | 28.24 |
| ATOM | 845 | N | GLY | C | 110 | 79.348 | 19.435 | −0.277 | 1.00 | 15.85 |
| ATOM | 846 | CA | GLY | C | 110 | 79.829 | 19.789 | −1.680 | 1.00 | 17.20 |
| ATOM | 847 | C | GLY | C | 110 | 78.950 | 20.810 | −2.378 | 1.00 | 16.93 |
| ATOM | 848 | O | GLY | C | 110 | 78.634 | 21.885 | −1.812 | 1.00 | 16.26 |
| ATOM | 849 | N | ASP | C | 111 | 78.534 | 20.528 | −3.637 | 1.00 | 14.38 |
| ATOM | 850 | CA | ASP | C | 111 | 77.715 | 21.472 | −4.391 | 1.00 | 14.84 |
| ATOM | 851 | C | ASP | C | 111 | 76.244 | 21.321 | −4.079 | 1.00 | 14.72 |
| ATOM | 852 | O | ASP | C | 111 | 75.360 | 21.023 | −4.904 | 1.00 | 14.34 |
| ATOM | 853 | CB | ASP | C | 111 | 77.999 | 21.194 | −5.903 | 1.00 | 17.05 |
| ATOM | 854 | CG | ASP | C | 111 | 77.264 | 22.145 | −6.828 | 1.00 | 19.59 |
| ATOM | 855 | OD1 | ASP | C | 111 | 77.013 | 23.323 | −6.491 | 1.00 | 20.52 |
| ATOM | 856 | OD2 | ASP | C | 111 | 76.873 | 21.686 | −7.928 | 1.00 | 19.81 |
| ATOM | 857 | N | ASN | C | 112 | 75.927 | 21.537 | −2.787 | 1.00 | 14.68 |
| ATOM | 858 | CA | ASN | C | 112 | 74.503 | 21.373 | −2.371 | 1.00 | 16.14 |
| ATOM | 859 | C | ASN | C | 112 | 73.952 | 19.992 | −2.783 | 1.00 | 13.02 |
| ATOM | 860 | O | ASN | C | 112 | 72.799 | 19.870 | −3.263 | 1.00 | 14.89 |
| ATOM | 861 | CB | ASN | C | 112 | 73.566 | 22.559 | −2.717 | 1.00 | 16.17 |
| ATOM | 862 | CG | ASN | C | 112 | 73.880 | 23.786 | −1.870 | 1.00 | 18.78 |
| ATOM | 863 | OD1 | ASN | C | 112 | 74.533 | 23.641 | −0.819 | 1.00 | 17.25 |
| ATOM | 864 | ND2 | ASN | C | 112 | 73.429 | 24.960 | −2.293 | 1.00 | 15.61 |
| ATOM | 865 | N | GLU | C | 113 | 74.785 | 18.960 | −2.531 | 1.00 | 14.05 |
| ATOM | 866 | CA | GLU | C | 113 | 74.443 | 17.571 | −2.819 | 1.00 | 15.74 |
| ATOM | 867 | C | GLU | C | 113 | 73.805 | 16.971 | −1.563 | 1.00 | 18.95 |
| ATOM | 868 | O | GLU | C | 113 | 74.464 | 16.870 | −0.539 | 1.00 | 19.58 |
| ATOM | 869 | CB | GLU | C | 113 | 75.708 | 16.797 | −3.166 | 1.00 | 17.38 |
| ATOM | 870 | CG | GLU | C | 113 | 75.440 | 15.371 | −3.668 | 1.00 | 20.91 |
| ATOM | 871 | CD | GLU | C | 113 | 74.661 | 15.313 | −5.016 | 1.00 | 24.09 |
| ATOM | 872 | OE1 | GLU | C | 113 | 75.023 | 15.987 | −5.993 | 1.00 | 30.10 |
| ATOM | 873 | OE2 | GLU | C | 113 | 73.680 | 14.559 | −5.076 | 1.00 | 36.71 |
| ATOM | 874 | N | MET | C | 114 | 72.556 | 16.563 | −1.684 | 1.00 | 18.64 |
| ATOM | 875 | CA | MET | C | 114 | 71.826 | 15.984 | −0.519 | 1.00 | 20.88 |
| ATOM | 876 | C | MET | C | 114 | 72.331 | 14.600 | −0.242 | 1.00 | 27.67 |
| ATOM | 877 | O | MET | C | 114 | 72.346 | 13.758 | −1.144 | 1.00 | 27.90 |
| ATOM | 878 | CB | MET | C | 114 | 70.329 | 15.964 | −0.798 | 1.00 | 23.89 |
| ATOM | 879 | CG | MET | C | 114 | 69.486 | 15.506 | 0.441 | 1.00 | 26.69 |
| ATOM | 880 | SD | MET | C | 114 | 67.734 | 15.561 | 0.136 | 1.00 | 29.33 |
| ATOM | 881 | CE | MET | C | 114 | 67.568 | 17.266 | −0.315 | 1.00 | 23.75 |
| ATOM | 882 | N | LYS | C | 115 | 72.758 | 14.329 | 0.997 | 1.00 | 25.26 |
| ATOM | 883 | CA | LYS | C | 115 | 73.254 | 12.995 | 1.346 | 1.00 | 30.27 |
| ATOM | 884 | C | LYS | C | 115 | 72.131 | 11.966 | 1.381 | 1.00 | 36.08 |
| ATOM | 885 | O | LYS | C | 115 | 72.449 | 10.760 | 1.181 | 1.00 | 41.29 |
| ATOM | 886 | CB | LYS | C | 115 | 74.009 | 12.984 | 2.674 | 1.00 | 31.52 |
| ATOM | 887 | CG | LYS | C | 115 | 75.147 | 13.960 | 2.791 | 1.00 | 29.39 |
| ATOM | 888 | CD | LYS | C | 115 | 75.948 | 13.688 | 4.076 | 1.00 | 35.11 |
| ATOM | 889 | CE | LYS | C | 115 | 76.864 | 14.835 | 4.435 | 1.00 | 39.16 |
| ATOM | 890 | NZ | LYS | C | 115 | 77.861 | 14.448 | 5.498 | 1.00 | 41.83 |
| ATOM | 892 | N | MET | D | 1 | 41.087 | 33.198 | 23.825 | 1.00 | 17.87 |
| ATOM | 893 | CA | MET | D | 1 | 42.349 | 33.385 | 23.112 | 1.00 | 15.77 |

-continued

Data Lists

| | | | | | | | | | |
|---|---|---|---|---|---|---|---|---|---|
| ATOM | 894 | C | MET | D | 1 | 43.435 | 32.503 | 23.658 | 1.00 | 18.38 |
| ATOM | 895 | O | MET | D | 1 | 43.248 | 31.921 | 24.772 | 1.00 | 16.03 |
| ATOM | 896 | CB | MET | D | 1 | 42.724 | 34.805 | 22.826 | 1.00 | 18.15 |
| ATOM | 897 | CG | MET | D | 1 | 42.641 | 35.784 | 23.928 | 1.00 | 21.69 |
| ATOM | 898 | SD | MET | D | 1 | 43.800 | 35.292 | 25.234 | 1.00 | 24.50 |
| ATOM | 899 | CE | MET | D | 1 | 43.405 | 36.711 | 26.530 | 1.00 | 19.90 |
| ATOM | 900 | N | ILE | D | 2 | 44.516 | 32.347 | 22.912 | 1.00 | 13.90 |
| ATOM | 901 | CA | ILE | D | 2 | 45.595 | 31.431 | 23.276 | 1.00 | 12.73 |
| ATOM | 902 | C | ILE | D | 2 | 46.834 | 32.154 | 23.717 | 1.00 | 15.11 |
| ATOM | 903 | O | ILE | D | 2 | 47.335 | 33.086 | 23.088 | 1.00 | 13.08 |
| ATOM | 904 | CB | ILE | D | 2 | 45.916 | 30.531 | 22.029 | 1.00 | 12.91 |
| ATOM | 905 | CG1 | ILE | D | 2 | 44.663 | 29.775 | 21.519 | 1.00 | 14.95 |
| ATOM | 906 | CG2 | ILE | D | 2 | 47.077 | 29.650 | 22.239 | 1.00 | 13.31 |
| ATOM | 907 | CD1 | ILE | D | 2 | 44.172 | 28.701 | 22.510 | 1.00 | 19.87 |
| ATOM | 908 | N | ARG | D | 3 | 47.332 | 31.720 | 24.876 | 1.00 | 11.64 |
| ATOM | 909 | CA | ARG | D | 3 | 48.516 | 32.296 | 25.459 | 1.00 | 9.38 |
| ATOM | 910 | C | ARG | D | 3 | 49.789 | 31.470 | 25.262 | 1.00 | 8.16 |
| ATOM | 911 | O | ARG | D | 3 | 49.708 | 30.234 | 25.113 | 1.00 | 9.82 |
| ATOM | 912 | CB | ARG | D | 3 | 48.295 | 32.255 | 27.026 | 1.00 | 11.91 |
| ATOM | 913 | CG | ARG | D | 3 | 47.131 | 33.118 | 27.499 | 1.00 | 12.07 |
| ATOM | 914 | CD | ARG | D | 3 | 47.529 | 34.571 | 27.783 | 1.00 | 12.41 |
| ATOM | 915 | NE | ARG | D | 3 | 46.447 | 35.256 | 28.452 | 1.00 | 12.53 |
| ATOM | 916 | CZ | ARG | D | 3 | 46.473 | 36.522 | 28.885 | 1.00 | 11.34 |
| ATOM | 917 | NH1 | ARG | D | 3 | 47.517 | 37.336 | 28.661 | 1.00 | 11.49 |
| ATOM | 918 | NH2 | ARG | D | 3 | 45.422 | 36.991 | 29.619 | 1.00 | 11.64 |
| ATOM | 919 | N | THR | D | 4 | 50.948 | 32.149 | 25.285 | 1.00 | 11.35 |
| ATOM | 920 | CA | THR | D | 4 | 52.272 | 31.500 | 25.210 | 1.00 | 10.99 |
| ATOM | 921 | C | THR | D | 4 | 52.813 | 31.593 | 26.693 | 1.00 | 9.80 |
| ATOM | 922 | O | THR | D | 4 | 52.986 | 32.672 | 27.155 | 1.00 | 10.46 |
| ATOM | 923 | CB | THR | D | 4 | 53.199 | 32.217 | 24.279 | 1.00 | 13.30 |
| ATOM | 924 | OG1 | THR | D | 4 | 52.577 | 32.164 | 22.960 | 1.00 | 12.86 |
| ATOM | 925 | CG2 | THR | D | 4 | 54.531 | 31.558 | 24.193 | 1.00 | 11.07 |
| ATOM | 926 | N | MET | D | 5 | 53.090 | 30.427 | 27.261 | 1.00 | 10.61 |
| ATOM | 927 | CA | MET | D | 5 | 53.555 | 30.329 | 28.694 | 1.00 | 10.17 |
| ATOM | 928 | C | MET | D | 5 | 54.837 | 29.563 | 28.799 | 1.00 | 13.79 |
| ATOM | 929 | O | MET | D | 5 | 55.101 | 28.614 | 28.027 | 1.00 | 12.14 |
| ATOM | 930 | CB | MET | D | 5 | 52.484 | 29.509 | 29.395 | 1.00 | 10.85 |
| ATOM | 931 | CG | MET | D | 5 | 51.061 | 30.164 | 29.397 | 1.00 | 13.35 |
| ATOM | 932 | SD | MET | D | 5 | 50.866 | 31.757 | 29.993 | 1.00 | 12.31 |
| ATOM | 933 | CE | MET | D | 5 | 51.031 | 31.458 | 31.862 | 1.00 | 9.06 |
| ATOM | 934 | N | LEU | D | 6 | 55.629 | 29.894 | 29.847 | 1.00 | 11.48 |
| ATOM | 935 | CA | LEU | D | 6 | 56.867 | 29.146 | 30.088 | 1.00 | 11.70 |
| ATOM | 936 | C | LEU | D | 6 | 56.504 | 27.682 | 30.442 | 1.00 | 15.58 |
| ATOM | 937 | O | LEU | D | 6 | 55.730 | 27.429 | 31.410 | 1.00 | 12.84 |
| ATOM | 938 | CB | LEU | D | 6 | 57.607 | 29.780 | 31.270 | 1.00 | 11.07 |
| ATOM | 939 | CG | LEU | D | 6 | 58.862 | 29.016 | 31.645 | 1.00 | 10.79 |
| ATOM | 940 | CD1 | LEU | D | 6 | 60.065 | 29.206 | 30.628 | 1.00 | 12.32 |
| ATOM | 941 | CD2 | LEU | D | 6 | 59.389 | 29.481 | 33.038 | 1.00 | 12.20 |
| ATOM | 942 | N | GLN | D | 7 | 56.980 | 26.693 | 29.671 | 1.00 | 11.50 |
| ATOM | 943 | CA | GLN | D | 7 | 56.694 | 25.319 | 29.932 | 1.00 | 12.08 |
| ATOM | 944 | C | GLN | D | 7 | 57.654 | 24.774 | 31.014 | 1.00 | 13.00 |
| ATOM | 945 | O | GLN | D | 7 | 57.222 | 23.966 | 31.908 | 1.00 | 13.76 |
| ATOM | 946 | CB | GLN | D | 7 | 56.889 | 24.443 | 28.642 | 1.00 | 13.70 |
| ATOM | 947 | CG | GLN | D | 7 | 56.481 | 23.024 | 28.769 | 1.00 | 13.52 |
| ATOM | 948 | CD | GLN | D | 7 | 57.490 | 22.096 | 29.530 | 1.00 | 15.62 |
| ATOM | 949 | OE1 | GLN | D | 7 | 57.020 | 21.129 | 30.233 | 1.00 | 14.96 |
| ATOM | 950 | NE2 | GLN | D | 7 | 58.822 | 22.323 | 29.355 | 1.00 | 13.51 |
| ATOM | 951 | N | GLY | D | 8 | 58.908 | 25.149 | 30.936 | 1.00 | 12.82 |
| ATOM | 952 | CA | GLY | D | 8 | 59.924 | 24.658 | 31.879 | 1.00 | 13.57 |
| ATOM | 953 | C | GLY | D | 8 | 61.276 | 25.264 | 31.576 | 1.00 | 17.33 |
| ATOM | 954 | O | GLY | D | 8 | 61.489 | 25.874 | 30.508 | 1.00 | 16.12 |
| ATOM | 955 | N | LYS | D | 9 | 62.225 | 25.176 | 32.515 | 1.00 | 13.73 |
| ATOM | 956 | CA | LYS | D | 9 | 63.535 | 25.722 | 32.269 | 1.00 | 14.09 |
| ATOM | 957 | C | LYS | D | 9 | 64.594 | 25.035 | 33.093 | 1.00 | 17.41 |
| ATOM | 958 | O | LYS | D | 9 | 64.293 | 24.412 | 34.150 | 1.00 | 16.23 |
| ATOM | 959 | CB | LYS | D | 9 | 63.604 | 27.197 | 32.448 | 1.00 | 17.25 |
| ATOM | 960 | CG | LYS | D | 9 | 63.491 | 27.641 | 33.937 | 1.00 | 16.41 |
| ATOM | 961 | CD | LYS | D | 9 | 63.860 | 29.094 | 34.196 | 1.00 | 16.11 |
| ATOM | 962 | CE | LYS | D | 9 | 63.661 | 29.538 | 35.703 | 1.00 | 20.64 |
| ATOM | 963 | NZ | LYS | D | 9 | 64.168 | 30.899 | 36.005 | 1.00 | 24.09 |
| ATOM | 964 | N | LEU | D | 10 | 65.795 | 25.085 | 32.580 | 1.00 | 14.37 |
| ATOM | 965 | CA | LEU | D | 10 | 67.019 | 24.574 | 33.245 | 1.00 | 13.07 |
| ATOM | 966 | C | LEU | D | 10 | 67.683 | 25.889 | 33.669 | 1.00 | 17.74 |
| ATOM | 967 | O | LEU | D | 10 | 68.139 | 26.719 | 32.864 | 1.00 | 15.88 |
| ATOM | 968 | CB | LEU | D | 10 | 67.917 | 23.753 | 32.313 | 1.00 | 12.64 |
| ATOM | 969 | CG | LEU | D | 10 | 67.275 | 22.500 | 31.721 | 1.00 | 16.69 |
| ATOM | 970 | CD1 | LEU | D | 10 | 68.212 | 21.782 | 30.736 | 1.00 | 19.95 |

-continued

Data Lists

| | | | | | | | | | |
|---|---|---|---|---|---|---|---|---|---|
| ATOM | 971 | CD2 | LEU | D | 10 | 66.799 | 21.474 | 32.834 | 1.00 | 18.21 |
| ATOM | 972 | N | HIS | D | 11 | 67.720 | 26.177 | 34.991 | 1.00 | 15.41 |
| ATOM | 973 | CA | HIS | D | 11 | 68.251 | 27.395 | 35.444 | 1.00 | 15.54 |
| ATOM | 974 | C | HIS | D | 11 | 69.702 | 27.368 | 35.893 | 1.00 | 20.36 |
| ATOM | 975 | O | HIS | D | 11 | 70.031 | 26.640 | 36.895 | 1.00 | 19.27 |
| ATOM | 976 | CB | HIS | D | 11 | 67.374 | 27.904 | 36.683 | 1.00 | 17.02 |
| ATOM | 977 | CG | HIS | D | 11 | 67.650 | 29.324 | 37.063 | 1.00 | 20.52 |
| ATOM | 978 | ND1 | HIS | D | 11 | 67.137 | 30.393 | 36.361 | 1.00 | 23.10 |
| ATOM | 979 | CD2 | HIS | D | 11 | 68.415 | 29.858 | 38.051 | 1.00 | 23.01 |
| ATOM | 980 | CE1 | HIS | D | 11 | 67.563 | 31.524 | 36.895 | 1.00 | 22.29 |
| ATOM | 981 | NE2 | HIS | D | 11 | 68.348 | 31.225 | 37.927 | 1.00 | 22.03 |
| ATOM | 982 | N | ARG | D | 12 | 70.556 | 28.124 | 35.209 | 1.00 | 17.66 |
| ATOM | 983 | CA | ARG | D | 12 | 71.956 | 28.229 | 35.513 | 1.00 | 17.87 |
| ATOM | 984 | C | ARG | D | 12 | 72.781 | 26.977 | 35.325 | 1.00 | 21.36 |
| ATOM | 985 | O | ARG | D | 12 | 73.632 | 26.605 | 36.187 | 1.00 | 21.72 |
| ATOM | 986 | CB | ARG | D | 12 | 72.232 | 28.945 | 36.891 | 1.00 | 17.27 |
| ATOM | 987 | CG | ARG | D | 12 | 71.708 | 30.362 | 36.941 | 1.00 | 16.85 |
| ATOM | 988 | CD | ARG | D | 12 | 71.907 | 31.054 | 38.323 | 1.00 | 21.64 |
| ATOM | 989 | NE | ARG | D | 12 | 73.332 | 31.030 | 38.693 | 1.00 | 26.91 |
| ATOM | 990 | CZ | ARG | D | 12 | 74.195 | 32.006 | 38.428 | 1.00 | 32.28 |
| ATOM | 991 | NH1 | ARG | D | 12 | 75.471 | 31.878 | 38.797 | 1.00 | 32.70 |
| ATOM | 992 | NH2 | ARG | D | 12 | 73.806 | 33.103 | 37.801 | 1.00 | 23.04 |
| ATOM | 993 | N | VAL | D | 13 | 72.613 | 26.297 | 34.173 | 1.00 | 16.36 |
| ATOM | 994 | CA | VAL | D | 13 | 73.413 | 25.135 | 33.867 | 1.00 | 16.81 |
| ATOM | 995 | C | VAL | D | 13 | 74.664 | 25.673 | 33.161 | 1.00 | 19.79 |
| ATOM | 996 | O | VAL | D | 13 | 74.668 | 26.811 | 32.683 | 1.00 | 21.56 |
| ATOM | 997 | CB | VAL | D | 13 | 72.713 | 24.137 | 32.918 | 1.00 | 20.87 |
| ATOM | 998 | CG1 | VAL | D | 13 | 71.653 | 23.427 | 33.553 | 1.00 | 22.00 |
| ATOM | 999 | CG2 | VAL | D | 13 | 72.189 | 24.846 | 31.612 | 1.00 | 19.93 |
| ATOM | 1000 | N | LYS | D | 14 | 75.741 | 24.892 | 33.128 | 1.00 | 17.58 |
| ATOM | 1001 | CA | LYS | D | 14 | 76.956 | 25.383 | 32.473 | 1.00 | 18.29 |
| ATOM | 1002 | C | LYS | D | 14 | 77.225 | 24.642 | 31.155 | 1.00 | 17.32 |
| ATOM | 1003 | O | LYS | D | 14 | 77.005 | 23.448 | 31.066 | 1.00 | 17.18 |
| ATOM | 1004 | CB | LYS | D | 14 | 78.176 | 25.251 | 33.416 | 1.00 | 21.96 |
| ATOM | 1005 | CG | LYS | D | 14 | 78.220 | 26.346 | 34.459 | 1.00 | 29.69 |
| ATOM | 1006 | CD | LYS | D | 14 | 79.441 | 26.161 | 35.412 | 1.00 | 27.98 |
| ATOM | 1007 | CE | LYS | D | 14 | 79.422 | 27.179 | 36.555 | 1.00 | 33.09 |
| ATOM | 1008 | NZ | LYS | D | 14 | 78.560 | 26.719 | 37.687 | 1.00 | 36.70 |
| ATOM | 1009 | N | VAL | D | 15 | 77.658 | 25.409 | 30.145 | 1.00 | 17.61 |
| ATOM | 1010 | CA | VAL | D | 15 | 77.967 | 24.799 | 28.844 | 1.00 | 15.98 |
| ATOM | 1011 | C | VAL | D | 15 | 79.203 | 23.888 | 29.035 | 1.00 | 18.36 |
| ATOM | 1012 | O | VAL | D | 15 | 80.185 | 24.318 | 29.603 | 1.00 | 20.10 |
| ATOM | 1013 | CB | VAL | D | 15 | 78.245 | 25.880 | 27.800 | 1.00 | 18.17 |
| ATOM | 1014 | CG1 | VAL | D | 15 | 78.696 | 25.198 | 26.454 | 1.00 | 19.48 |
| ATOM | 1015 | CG2 | VAL | D | 15 | 76.933 | 26.685 | 27.567 | 1.00 | 18.97 |
| ATOM | 1016 | N | THR | D | 16 | 79.140 | 22.659 | 28.545 | 1.00 | 16.59 |
| ATOM | 1017 | CA | THR | D | 16 | 80.271 | 21.721 | 28.715 | 1.00 | 18.46 |
| ATOM | 1018 | C | THR | D | 16 | 81.039 | 21.407 | 27.449 | 1.00 | 23.98 |
| ATOM | 1019 | O | THR | D | 16 | 82.184 | 20.892 | 27.500 | 1.00 | 23.98 |
| ATOM | 1020 | CB | THR | D | 16 | 79.781 | 20.374 | 29.348 | 1.00 | 20.68 |
| ATOM | 1021 | OG1 | THR | D | 16 | 78.894 | 19.683 | 28.464 | 1.00 | 20.66 |
| ATOM | 1022 | CG2 | THR | D | 16 | 79.048 | 20.647 | 30.719 | 1.00 | 20.82 |
| ATOM | 1023 | N | HIS | D | 17 | 80.447 | 21.718 | 26.302 | 1.00 | 21.79 |
| ATOM | 1024 | CA | HIS | D | 17 | 81.112 | 21.413 | 25.010 | 1.00 | 23.09 |
| ATOM | 1025 | C | HIS | D | 17 | 80.522 | 22.305 | 23.934 | 1.00 | 25.64 |
| ATOM | 1026 | O | HIS | D | 17 | 79.371 | 22.760 | 24.047 | 1.00 | 20.59 |
| ATOM | 1027 | CB | HIS | D | 17 | 80.740 | 19.928 | 24.685 | 1.00 | 25.73 |
| ATOM | 1028 | CG | HIS | D | 17 | 81.356 | 19.348 | 23.433 | 1.00 | 31.57 |
| ATOM | 1029 | ND1 | HIS | D | 17 | 80.584 | 18.824 | 22.407 | 1.00 | 34.88 |
| ATOM | 1030 | CD2 | HIS | D | 17 | 82.652 | 19.158 | 23.062 | 1.00 | 34.96 |
| ATOM | 1031 | CE1 | HIS | D | 17 | 81.374 | 18.360 | 21.451 | 1.00 | 35.01 |
| ATOM | 1032 | NE2 | HIS | D | 17 | 82.635 | 18.549 | 21.820 | 1.00 | 35.08 |
| ATOM | 1033 | N | ALA | D | 18 | 81.309 | 22.554 | 22.893 | 1.00 | 25.07 |
| ATOM | 1034 | CA | ALA | D | 18 | 80.848 | 23.379 | 21.759 | 1.00 | 25.93 |
| ATOM | 1035 | C | ALA | D | 18 | 81.317 | 22.603 | 20.201 | 1.00 | 31.11 |
| ATOM | 1036 | O | ALA | D | 18 | 82.460 | 22.106 | 20.472 | 1.00 | 33.50 |
| ATOM | 1037 | CB | ALA | D | 18 | 81.433 | 24.755 | 21.814 | 1.00 | 27.54 |
| ATOM | 1038 | N | ASP | D | 19 | 80.444 | 22.423 | 19.505 | 1.00 | 24.42 |
| ATOM | 1039 | CA | ASP | D | 19 | 80.814 | 21.654 | 18.284 | 1.00 | 24.78 |
| ATOM | 1040 | C | ASP | D | 19 | 80.276 | 22.359 | 17.047 | 1.00 | 27.05 |
| ATOM | 1041 | O | ASP | D | 19 | 79.206 | 22.000 | 16.529 | 1.00 | 24.71 |
| ATOM | 1042 | CB | ASP | D | 19 | 80.272 | 20.218 | 18.402 | 1.00 | 25.96 |
| ATOM | 1043 | CG | ASP | D | 19 | 80.644 | 19.316 | 17.214 | 1.00 | 34.10 |
| ATOM | 1044 | OD1 | ASP | D | 19 | 81.404 | 19.749 | 16.320 | 1.00 | 34.04 |
| ATOM | 1045 | OD2 | ASP | D | 19 | 80.164 | 18.147 | 17.193 | 1.00 | 38.22 |
| ATOM | 1046 | N | LEU | D | 20 | 81.027 | 23.356 | 16.587 | 1.00 | 25.80 |
| ATOM | 1047 | CA | LEU | D | 20 | 80.656 | 24.143 | 15.422 | 1.00 | 24.85 |

-continued

Data Lists

| | | | | | | | | | |
|---|---|---|---|---|---|---|---|---|---|
| ATOM | 1048 | C | LEU | D | 20 | 80.390 | 23.317 | 14.170 | 1.00 | 27.59 |
| ATOM | 1049 | O | LEU | D | 20 | 79.410 | 23.581 | 13.451 | 1.00 | 26.06 |
| ATOM | 1050 | CB | LEU | D | 20 | 81.753 | 25.185 | 15.120 | 1.00 | 25.72 |
| ATOM | 1051 | CG | LEU | D | 20 | 81.546 | 26.193 | 13.977 | 1.00 | 29.24 |
| ATOM | 1052 | CD1 | LEU | D | 20 | 80.505 | 27.239 | 14.355 | 1.00 | 28.84 |
| ATOM | 1053 | CD2 | LEU | D | 20 | 82.887 | 26.875 | 13.627 | 1.00 | 29.15 |
| ATOM | 1054 | N | HIS | D | 21 | 81.264 | 22.340 | 13.908 | 1.00 | 28.61 |
| ATOM | 1055 | CA | HIS | D | 21 | 81.167 | 21.442 | 12.712 | 1.00 | 30.90 |
| ATOM | 1056 | C | HIS | D | 21 | 80.238 | 20.275 | 12.779 | 1.00 | 36.12 |
| ATOM | 1057 | O | HIS | D | 21 | 80.249 | 19.385 | 11.890 | 1.00 | 35.00 |
| ATOM | 1058 | CB | HIS | D | 21 | 82.573 | 21.039 | 12.237 | 1.00 | 32.76 |
| ATOM | 1059 | CG | HIS | D | 21 | 83.437 | 22.204 | 11.941 | 1.00 | 36.81 |
| ATOM | 1060 | ND1 | HIS | D | 21 | 84.537 | 22.541 | 12.700 | 1.00 | 39.48 |
| ATOM | 1061 | CD2 | HIS | D | 21 | 83.307 | 23.151 | 11.010 | 1.00 | 38.76 |
| ATOM | 1062 | CE1 | HIS | D | 21 | 85.072 | 23.656 | 12.222 | 1.00 | 38.26 |
| ATOM | 1063 | NE2 | HIS | D | 21 | 84.345 | 24.063 | 11.198 | 1.00 | 38.36 |
| ATOM | 1064 | N | TYR | D | 22 | 79.418 | 20.275 | 13.811 | 1.00 | 33.13 |
| ATOM | 1065 | CA | TYR | D | 22 | 78.453 | 19.220 | 14.019 | 1.00 | 33.14 |
| ATOM | 1066 | C | TYR | D | 22 | 77.573 | 18.876 | 12.801 | 1.00 | 37.60 |
| ATOM | 1067 | O | TYR | D | 22 | 77.155 | 19.766 | 12.012 | 1.00 | 32.76 |
| ATOM | 1068 | CB | TYR | D | 22 | 77.479 | 19.691 | 15.105 | 1.00 | 33.35 |
| ATOM | 1069 | CG | TYR | D | 22 | 76.571 | 18.617 | 15.617 | 1.00 | 35.03 |
| ATOM | 1070 | CD1 | TYR | D | 22 | 77.095 | 17.527 | 16.305 | 1.00 | 36.82 |
| ATOM | 1071 | CD2 | TYR | D | 22 | 75.204 | 18.670 | 15.401 | 1.00 | 35.58 |
| ATOM | 1072 | CE1 | TYR | D | 22 | 76.271 | 16.517 | 16.773 | 1.00 | 37.35 |
| ATOM | 1073 | CE2 | TYR | D | 22 | 74.375 | 17.669 | 15.872 | 1.00 | 36.01 |
| ATOM | 1074 | CZ | TYR | D | 22 | 74.906 | 16.604 | 16.557 | 1.00 | 42.70 |
| ATOM | 1075 | OH | TYR | D | 22 | 74.016 | 15.625 | 17.014 | 1.00 | 46.65 |
| ATOM | 1076 | N | GLU | D | 23 | 77.276 | 17.594 | 12.694 | 1.00 | 39.24 |
| ATOM | 1077 | CA | GLU | D | 23 | 76.408 | 17.072 | 11.664 | 1.00 | 42.44 |
| ATOM | 1078 | C | GLU | D | 23 | 75.374 | 16.147 | 12.358 | 1.00 | 47.01 |
| ATOM | 1079 | O | GLU | D | 23 | 75.698 | 15.050 | 12.769 | 1.00 | 48.53 |
| ATOM | 1080 | CB | GLU | D | 23 | 77.176 | 16.320 | 10.575 | 1.00 | 44.81 |
| ATOM | 1081 | CG | GLU | D | 23 | 76.241 | 15.586 | 9.631 | 1.00 | 53.00 |
| ATOM | 1082 | CD | GLU | D | 23 | 76.852 | 15.314 | 8.271 | 1.00 | 63.57 |
| ATOM | 1083 | OE1 | GLU | D | 23 | 78.097 | 15.153 | 8.190 | 1.00 | 70.57 |
| ATOM | 1084 | OE2 | GLU | D | 23 | 76.079 | 15.237 | 7.285 | 1.00 | 49.95 |
| ATOM | 1085 | N | GLY | D | 24 | 74.136 | 16.608 | 12.481 | 1.00 | 43.35 |
| ATOM | 1086 | CA | GLY | D | 24 | 73.103 | 15.797 | 13.108 | 1.00 | 47.63 |
| ATOM | 1087 | C | GLY | D | 24 | 71.872 | 16.608 | 13.529 | 1.00 | 49.81 |
| ATOM | 1088 | O | GLY | D | 24 | 71.438 | 17.481 | 12.758 | 1.00 | 43.71 |
| ATOM | 1089 | OH | GLY | D | 24 | 71.339 | 16.374 | 14.643 | 1.00 | 78.26 |
| ATOM | 1090 | C | PVL | D | 25 | 72.100 | 22.561 | 19.543 | 1.00 | 18.29 |
| ATOM | 1091 | O | PVL | D | 25 | 73.123 | 23.121 | 19.763 | 1.00 | 21.21 |
| ATOM | 1092 | CA | PVL | D | 25 | 71.565 | 22.581 | 18.161 | 1.00 | 27.46 |
| ATOM | 1093 | CB | PVL | D | 25 | 70.223 | 21.973 | 17.952 | 1.00 | 25.35 |
| ATOM | 1094 | ON | PVL | D | 25 | 72.196 | 23.134 | 17.245 | 1.00 | 33.71 |
| ATOM | 1095 | N | CYS | D | 26 | 71.286 | 22.044 | 20.569 | 1.00 | 15.60 |
| ATOM | 1096 | CA | CYS | D | 26 | 71.834 | 22.016 | 21.931 | 1.00 | 16.64 |
| ATOM | 1097 | CB | CYS | D | 26 | 71.304 | 23.212 | 22.757 | 1.00 | 14.30 |
| ATOM | 1098 | SG | CYS | D | 26 | 71.996 | 23.106 | 24.461 | 1.00 | 18.05 |
| ATOM | 1099 | C | CYS | D | 26 | 71.504 | 20.649 | 22.505 | 1.00 | 14.55 |
| ATOM | 1100 | O | CYS | D | 26 | 70.332 | 20.263 | 22.665 | 1.00 | 16.28 |
| ATOM | 1101 | N | ALA | D | 27 | 72.569 | 19.844 | 22.774 | 1.00 | 15.46 |
| ATOM | 1102 | CA | ALA | D | 27 | 72.411 | 18.463 | 23.329 | 1.00 | 15.63 |
| ATOM | 1103 | C | ALA | D | 27 | 72.469 | 18.581 | 24.869 | 1.00 | 15.10 |
| ATOM | 1104 | O | ALA | D | 27 | 73.350 | 19.198 | 25.406 | 1.00 | 15.77 |
| ATOM | 1105 | CB | ALA | D | 27 | 73.510 | 17.508 | 22.838 | 1.00 | 16.71 |
| ATOM | 1106 | N | ILE | D | 28 | 71.483 | 17.965 | 25.486 | 1.00 | 14.23 |
| ATOM | 1107 | CA | ILE | D | 28 | 71.292 | 18.058 | 26.940 | 1.00 | 14.71 |
| ATOM | 1108 | C | ILE | D | 28 | 71.023 | 16.715 | 27.562 | 1.00 | 17.41 |
| ATOM | 1109 | O | ILE | D | 28 | 70.251 | 15.919 | 27.072 | 1.00 | 16.90 |
| ATOM | 1110 | CB | ILE | D | 28 | 69.990 | 18.945 | 27.121 | 1.00 | 16.58 |
| ATOM | 1111 | CG1 | ILE | D | 28 | 70.204 | 20.317 | 26.472 | 1.00 | 16.36 |
| ATOM | 1112 | CG2 | ILE | D | 28 | 69.627 | 19.068 | 28.632 | 1.00 | 15.52 |
| ATOM | 1113 | CD1 | ILE | D | 28 | 68.887 | 21.088 | 26.119 | 1.00 | 18.68 |
| ATOM | 1114 | N | ASP | D | 29 | 71.717 | 16.475 | 28.696 | 1.00 | 16.97 |
| ATOM | 1115 | CA | ASP | D | 29 | 71.551 | 15.203 | 29.449 | 1.00 | 18.01 |
| ATOM | 1116 | C | ASP | D | 29 | 70.023 | 14.912 | 29.600 | 1.00 | 17.51 |
| ATOM | 1117 | O | ASP | D | 29 | 69.284 | 15.814 | 30.061 | 1.00 | 15.93 |
| ATOM | 1118 | CB | ASP | D | 29 | 72.168 | 15.468 | 30.837 | 1.00 | 18.64 |
| ATOM | 1119 | CG | ASP | D | 29 | 72.085 | 14.248 | 31.826 | 1.00 | 21.55 |
| ATOM | 1120 | OD1 | ASP | D | 29 | 71.218 | 13.349 | 31.704 | 1.00 | 21.30 |
| ATOM | 1121 | OD2 | ASP | D | 29 | 72.956 | 14.262 | 32.752 | 1.00 | 22.85 |
| ATOM | 1122 | N | GLN | D | 30 | 69.580 | 13.710 | 29.207 | 1.00 | 17.64 |
| ATOM | 1123 | CA | GLN | D | 30 | 68.165 | 13.289 | 29.288 | 1.00 | 16.64 |
| ATOM | 1124 | C | GLN | D | 30 | 67.584 | 13.514 | 30.685 | 1.00 | 20.42 |

-continued

Data Lists

| | | | | | | | | | |
|---|---|---|---|---|---|---|---|---|---|
| ATOM | 1125 | O | GLN | D | 30 | 66.407 | 13.865 | 30.795 | 1.00 | 19.64 |
| ATOM | 1126 | CB | GLN | D | 30 | 67.942 | 11.845 | 28.839 | 1.00 | 19.10 |
| ATOM | 1127 | CG | GLN | D | 30 | 66.498 | 11.417 | 28.796 | 1.00 | 20.18 |
| ATOM | 1128 | CD | GLN | D | 30 | 65.710 | 12.200 | 27.766 | 1.00 | 24.27 |
| ATOM | 1129 | OE1 | GLN | D | 30 | 66.090 | 12.214 | 26.565 | 1.00 | 20.83 |
| ATOM | 1130 | NE2 | GLN | D | 30 | 64.598 | 12.837 | 28.202 | 1.00 | 20.72 |
| ATOM | 1131 | N | ASP | D | 31 | 68.383 | 13.362 | 31.752 | 1.00 | 19.98 |
| ATOM | 1132 | CA | ASP | D | 31 | 67.810 | 13.608 | 33.086 | 1.00 | 20.52 |
| ATOM | 1133 | C | ASP | D | 31 | 67.343 | 15.055 | 33.267 | 1.00 | 19.87 |
| ATOM | 1134 | O | ASP | D | 31 | 66.339 | 15.342 | 34.003 | 1.00 | 20.49 |
| ATOM | 1135 | CB | ASP | D | 31 | 68.858 | 13.326 | 34.165 | 1.00 | 20.56 |
| ATOM | 1136 | CG | ASP | D | 31 | 68.955 | 11.861 | 34.505 | 1.00 | 27.59 |
| ATOM | 1137 | OD1 | ASP | D | 31 | 68.027 | 11.063 | 34.248 | 1.00 | 27.63 |
| ATOM | 1138 | OD2 | ASP | D | 31 | 70.061 | 11.498 | 34.988 | 1.00 | 25.47 |
| ATOM | 1139 | N | PHE | D | 32 | 68.053 | 16.002 | 32.616 | 1.00 | 17.26 |
| ATOM | 1140 | CA | PHE | D | 32 | 67.743 | 17.411 | 32.698 | 1.00 | 16.13 |
| ATOM | 1141 | C | PHE | D | 32 | 66.457 | 17.661 | 31.896 | 1.00 | 15.84 |
| ATOM | 1142 | O | PHE | D | 32 | 65.527 | 18.389 | 32.356 | 1.00 | 15.43 |
| ATOM | 1143 | CB | PHE | D | 32 | 68.854 | 18.301 | 32.116 | 1.00 | 17.62 |
| ATOM | 1144 | CG | PHE | D | 32 | 70.216 | 18.172 | 32.810 | 1.00 | 18.64 |
| ATOM | 1145 | CD1 | PHE | D | 32 | 70.409 | 17.355 | 33.944 | 1.00 | 20.38 |
| ATOM | 1146 | CD2 | PHE | D | 32 | 71.294 | 18.902 | 32.313 | 1.00 | 21.28 |
| ATOM | 1147 | CE1 | PHE | D | 32 | 71.722 | 17.281 | 34.537 | 1.00 | 21.62 |
| ATOM | 1148 | CE2 | PHE | D | 32 | 72.549 | 18.834 | 32.878 | 1.00 | 24.06 |
| ATOM | 1149 | CZ | PHE | D | 32 | 72.763 | 18.019 | 34.007 | 1.00 | 22.14 |
| ATOM | 1150 | N | LEU | D | 33 | 66.412 | 17.068 | 30.700 | 1.00 | 15.62 |
| ATOM | 1151 | CA | LEU | D | 33 | 65.206 | 17.230 | 29.867 | 1.00 | 15.62 |
| ATOM | 1152 | C | LEU | D | 33 | 63.969 | 16.737 | 30.662 | 1.00 | 14.56 |
| ATOM | 1153 | O | LEU | D | 33 | 62.938 | 17.393 | 30.680 | 1.00 | 15.50 |
| ATOM | 1154 | CB | LEU | D | 33 | 65.330 | 16.434 | 28.565 | 1.00 | 15.46 |
| ATOM | 1155 | CG | LEU | D | 33 | 66.446 | 16.945 | 27.597 | 1.00 | 17.68 |
| ATOM | 1156 | CD1 | LEU | D | 33 | 66.471 | 16.024 | 26.336 | 1.00 | 18.11 |
| ATOM | 1157 | CD2 | LEU | D | 33 | 66.139 | 18.385 | 27.159 | 1.00 | 17.59 |
| ATOM | 1158 | N | ASP | D | 34 | 64.094 | 15.567 | 31.320 | 1.00 | 15.47 |
| ATOM | 1159 | CA | ASP | D | 34 | 63.010 | 14.958 | 32.091 | 1.00 | 15.42 |
| ATOM | 1160 | C | ASP | D | 34 | 62.498 | 15.897 | 33.177 | 1.00 | 15.50 |
| ATOM | 1161 | O | ASP | D | 34 | 61.312 | 16.032 | 33.342 | 1.00 | 16.94 |
| ATOM | 1162 | CB | ASP | D | 34 | 63.523 | 13.673 | 32.755 | 1.00 | 16.78 |
| ATOM | 1163 | CG | ASP | D | 34 | 63.625 | 12.511 | 31.796 | 1.00 | 21.53 |
| ATOM | 1164 | OD1 | ASP | D | 34 | 63.254 | 12.639 | 30.594 | 1.00 | 22.41 |
| ATOM | 1165 | OD2 | ASP | D | 34 | 64.107 | 11.419 | 32.237 | 1.00 | 24.39 |
| ATOM | 1166 | N | ALA | D | 35 | 63.405 | 16.522 | 33.911 | 1.00 | 15.30 |
| ATOM | 1167 | CA | ALA | D | 35 | 63.030 | 17.444 | 34.982 | 1.00 | 16.57 |
| ATOM | 1168 | C | ALA | D | 35 | 62.344 | 18.711 | 34.497 | 1.00 | 18.73 |
| ATOM | 1169 | O | ALA | D | 35 | 61.440 | 19.244 | 35.142 | 1.00 | 19.02 |
| ATOM | 1170 | CB | ALA | D | 35 | 64.253 | 17.838 | 35.828 | 1.00 | 18.18 |
| ATOM | 1171 | N | ALA | D | 36 | 62.814 | 19.231 | 33.338 | 1.00 | 15.77 |
| ATOM | 1172 | CA | ALA | D | 36 | 62.243 | 20.432 | 32.837 | 1.00 | 14.01 |
| ATOM | 1173 | C | ALA | D | 36 | 61.034 | 20.203 | 31.866 | 1.00 | 12.66 |
| ATOM | 1174 | O | ALA | D | 36 | 60.427 | 21.243 | 31.459 | 1.00 | 15.97 |
| ATOM | 1175 | CB | ALA | D | 36 | 63.337 | 21.261 | 32.105 | 1.00 | 15.98 |
| ATOM | 1176 | N | GLY | D | 37 | 60.750 | 18.962 | 31.520 | 1.00 | 12.31 |
| ATOM | 1177 | CA | GLY | D | 37 | 59.663 | 18.637 | 30.636 | 1.00 | 12.99 |
| ATOM | 1178 | C | GLY | D | 37 | 59.994 | 19.050 | 29.180 | 1.00 | 13.99 |
| ATOM | 1179 | O | GLY | D | 37 | 59.023 | 19.117 | 28.371 | 1.00 | 13.49 |
| ATOM | 1180 | N | ILE | D | 38 | 61.276 | 19.246 | 28.882 | 1.00 | 13.30 |
| ATOM | 1181 | CA | ILE | D | 38 | 61.705 | 19.641 | 27.476 | 1.00 | 11.90 |
| ATOM | 1182 | C | ILE | D | 38 | 61.854 | 18.372 | 26.665 | 1.00 | 13.73 |
| ATOM | 1183 | O | ILE | D | 38 | 62.470 | 17.403 | 27.086 | 1.00 | 13.87 |
| ATOM | 1184 | CB | ILE | D | 38 | 62.938 | 20.454 | 27.528 | 1.00 | 12.06 |
| ATOM | 1185 | CG1 | ILE | D | 38 | 62.664 | 21.817 | 28.244 | 1.00 | 13.02 |
| ATOM | 1186 | CG2 | ILE | D | 38 | 63.457 | 20.747 | 26.031 | 1.00 | 11.46 |
| ATOM | 1187 | CD1 | ILE | D | 38 | 63.886 | 22.662 | 28.502 | 1.00 | 14.92 |
| ATOM | 1188 | N | LEU | D | 39 | 61.313 | 18.366 | 25.415 | 1.00 | 11.75 |
| ATOM | 1189 | CA | LEU | D | 39 | 61.366 | 17.198 | 24.557 | 1.00 | 11.57 |
| ATOM | 1190 | C | LEU | D | 39 | 62.445 | 17.286 | 23.489 | 1.00 | 13.60 |
| ATOM | 1191 | O | LEU | D | 39 | 62.811 | 18.368 | 23.105 | 1.00 | 12.83 |
| ATOM | 1192 | CB | LEU | D | 39 | 60.048 | 17.052 | 23.807 | 1.00 | 11.62 |
| ATOM | 1193 | CG | LEU | D | 39 | 58.724 | 17.113 | 24.610 | 1.00 | 13.66 |
| ATOM | 1194 | CD1 | LEU | D | 39 | 57.552 | 16.938 | 23.682 | 1.00 | 15.79 |
| ATOM | 1195 | CD2 | LEU | D | 39 | 58.820 | 15.969 | 25.666 | 1.00 | 15.29 |
| ATOM | 1196 | N | GLU | D | 40 | 62.956 | 16.134 | 23.119 | 1.00 | 14.52 |
| ATOM | 1197 | CA | GLU | D | 40 | 63.930 | 16.098 | 22.000 | 1.00 | 14.56 |
| ATOM | 1198 | C | GLU | D | 40 | 63.128 | 16.706 | 20.790 | 1.00 | 14.90 |
| ATOM | 1199 | O | GLU | D | 40 | 61.938 | 16.424 | 20.582 | 1.00 | 13.14 |
| ATOM | 1200 | CB | GLU | D | 40 | 64.273 | 14.643 | 21.690 | 1.00 | 17.43 |
| ATOM | 1201 | CG | GLU | D | 40 | 65.687 | 14.237 | 22.093 | 1.00 | 36.71 |

-continued

| | | | | | | | | | |
|---|---|---|---|---|---|---|---|---|---|
| | Data Lists | | | | | | | | |
| ATOM | 1202 | CD | GLU | D | 40 | 66.336 | 13.346 | 21.016 | 1.00 | 43.99 |
| ATOM | 1203 | OE1 | GLU | D | 40 | 65.691 | 12.317 | 20.674 | 1.00 | 33.64 |
| ATOM | 1204 | OE2 | GLU | D | 40 | 67.475 | 13.665 | 20.501 | 1.00 | 23.74 |
| ATOM | 1205 | N | ASN | D | 41 | 63.849 | 17.563 | 20.028 | 1.00 | 12.38 |
| ATOM | 1206 | CA | ASN | D | 41 | 63.297 | 18.252 | 18.835 | 1.00 | 12.93 |
| ATOM | 1207 | C | ASN | D | 41 | 62.403 | 19.417 | 19.130 | 1.00 | 15.81 |
| ATOM | 1208 | O | ASN | D | 41 | 61.836 | 20.050 | 18.252 | 1.00 | 13.21 |
| ATOM | 1209 | CB | ASN | D | 41 | 62.680 | 17.270 | 17.864 | 1.00 | 14.28 |
| ATOM | 1210 | CG | ASN | D | 41 | 63.721 | 16.286 | 17.293 | 1.00 | 12.10 |
| ATOM | 1211 | OD1 | ASN | D | 41 | 64.828 | 16.679 | 16.930 | 1.00 | 16.64 |
| ATOM | 1212 | ND2 | ASN | D | 41 | 63.373 | 15.002 | 17.295 | 1.00 | 15.27 |
| ATOM | 1213 | N | GLU | D | 42 | 62.241 | 19.771 | 20.402 | 1.00 | 10.98 |
| ATOM | 1214 | CA | GLU | D | 42 | 61.432 | 20.916 | 20.753 | 1.00 | 9.74 |
| ATOM | 1215 | C | GLU | D | 42 | 62.214 | 22.225 | 20.638 | 1.00 | 9.74 |
| ATOM | 1216 | O | GLU | D | 42 | 63.430 | 22.297 | 20.917 | 1.00 | 10.17 |
| ATOM | 1217 | CB | GLU | D | 42 | 60.958 | 20.806 | 22.304 | 1.00 | 10.40 |
| ATOM | 1218 | CG | GLU | D | 42 | 59.992 | 21.930 | 22.730 | 1.00 | 10.03 |
| ATOM | 1219 | CD | GLU | D | 42 | 59.538 | 21.802 | 24.213 | 1.00 | 13.25 |
| ATOM | 1220 | OE1 | GLU | D | 42 | 60.180 | 20.979 | 24.893 | 1.00 | 15.16 |
| ATOM | 1221 | OE2 | GLU | D | 42 | 58.595 | 22.504 | 24.588 | 1.00 | 12.03 |
| ATOM | 1222 | N | ALA | D | 43 | 61.529 | 23.303 | 20.212 | 1.00 | 9.51 |
| ATOM | 1223 | CA | ALA | D | 43 | 62.125 | 24.618 | 20.139 | 1.00 | 10.88 |
| ATOM | 1224 | C | ALA | D | 43 | 62.581 | 25.062 | 21.572 | 1.00 | 10.85 |
| ATOM | 1225 | O | ALA | D | 43 | 61.770 | 24.882 | 22.523 | 1.00 | 11.54 |
| ATOM | 1226 | CB | ALA | D | 43 | 61.086 | 25.666 | 19.611 | 1.00 | 12.49 |
| ATOM | 1227 | N | ILE | D | 44 | 63.746 | 25.596 | 21.711 | 1.00 | 11.86 |
| ATOM | 1228 | CA | ILE | D | 44 | 64.214 | 26.108 | 23.049 | 1.00 | 11.02 |
| ATOM | 1229 | C | ILE | D | 44 | 64.876 | 27.495 | 22.885 | 1.00 | 13.51 |
| ATOM | 1230 | O | ILE | D | 44 | 65.459 | 27.820 | 21.790 | 1.00 | 13.63 |
| ATOM | 1231 | CB | ILE | D | 44 | 65.215 | 25.146 | 23.757 | 1.00 | 12.21 |
| ATOM | 1232 | CG1 | ILE | D | 44 | 66.425 | 24.841 | 22.799 | 1.00 | 12.04 |
| ATOM | 1233 | CG2 | ILE | D | 44 | 64.475 | 23.886 | 24.201 | 1.00 | 14.58 |
| ATOM | 1234 | CD1 | ILE | D | 44 | 67.496 | 23.934 | 23.440 | 1.00 | 12.27 |
| ATOM | 1235 | N | ASP | D | 45 | 64.845 | 28.343 | 23.921 | 1.00 | 10.42 |
| ATOM | 1236 | CA | ASP | D | 45 | 65.470 | 29.634 | 23.942 | 1.00 | 10.06 |
| ATOM | 1237 | C | ASP | D | 45 | 66.628 | 29.457 | 24.943 | 1.00 | 14.23 |
| ATOM | 1238 | O | ASP | D | 45 | 66.438 | 28.814 | 26.014 | 1.00 | 14.99 |
| ATOM | 1239 | CB | ASP | D | 45 | 64.514 | 30.754 | 24.407 | 1.00 | 12.39 |
| ATOM | 1240 | CG | ASP | D | 45 | 63.320 | 30.886 | 23.509 | 1.00 | 15.51 |
| ATOM | 1241 | OD1 | ASP | D | 45 | 63.504 | 30.682 | 22.250 | 1.00 | 15.80 |
| ATOM | 1242 | OD2 | ASP | D | 45 | 62.187 | 31.118 | 23.974 | 1.00 | 15.67 |
| ATOM | 1243 | N | ILE | D | 46 | 67.791 | 29.995 | 24.634 | 1.00 | 10.63 |
| ATOM | 1244 | CA | ILE | D | 46 | 68.996 | 29.909 | 25.471 | 1.00 | 10.58 |
| ATOM | 1245 | C | ILE | D | 46 | 69.427 | 31.327 | 25.747 | 1.00 | 14.80 |
| ATOM | 1246 | O | ILE | D | 46 | 69.649 | 32.151 | 24.860 | 1.00 | 13.14 |
| ATOM | 1247 | CB | ILE | D | 46 | 70.104 | 29.079 | 24.805 | 1.00 | 12.68 |
| ATOM | 1248 | CG1 | ILE | D | 46 | 69.560 | 27.686 | 24.519 | 1.00 | 11.97 |
| ATOM | 1249 | CG2 | ILE | D | 46 | 71.354 | 29.057 | 25.751 | 1.00 | 14.01 |
| ATOM | 1250 | CD1 | ILE | D | 46 | 70.647 | 26.680 | 24.071 | 1.00 | 17.51 |
| ATOM | 1251 | N | TRP | D | 47 | 69.509 | 31.672 | 27.067 | 1.00 | 11.09 |
| ATOM | 1252 | CA | TRP | D | 47 | 69.832 | 32.990 | 27.530 | 1.00 | 12.91 |
| ATOM | 1253 | C | TRP | D | 47 | 71.163 | 32.842 | 28.298 | 1.00 | 18.14 |
| ATOM | 1254 | O | TRP | D | 47 | 71.232 | 32.122 | 29.319 | 1.00 | 16.83 |
| ATOM | 1255 | CB | TRP | D | 47 | 68.681 | 33.497 | 28.446 | 1.00 | 12.75 |
| ATOM | 1256 | CG | TRP | D | 47 | 67.334 | 33.535 | 27.762 | 1.00 | 12.68 |
| ATOM | 1257 | CD1 | TRP | D | 47 | 67.087 | 33.885 | 26.416 | 1.00 | 13.80 |
| ATOM | 1258 | CD2 | TRP | D | 47 | 66.070 | 33.224 | 28.316 | 1.00 | 12.97 |
| ATOM | 1259 | NE1 | TRP | D | 47 | 65.765 | 33.773 | 26.151 | 1.00 | 12.97 |
| ATOM | 1260 | CE2 | TRP | D | 47 | 65.093 | 33.372 | 27.286 | 1.00 | 14.42 |
| ATOM | 1261 | CE3 | TRP | D | 47 | 65.650 | 32.757 | 29.579 | 1.00 | 14.96 |
| ATOM | 1262 | CZ2 | TRP | D | 47 | 63.744 | 33.139 | 27.488 | 1.00 | 14.53 |
| ATOM | 1263 | CZ3 | TRP | D | 47 | 64.331 | 32.544 | 29.792 | 1.00 | 16.02 |
| ATOM | 1264 | CH2 | TRP | D | 47 | 63.365 | 32.734 | 28.774 | 1.00 | 16.49 |
| ATOM | 1265 | N | ASN | D | 48 | 72.217 | 33.452 | 27.762 | 1.00 | 15.37 |
| ATOM | 1266 | CA | ASN | D | 48 | 73.574 | 33.323 | 28.320 | 1.00 | 15.56 |
| ATOM | 1267 | C | ASN | D | 48 | 73.829 | 34.347 | 29.393 | 1.00 | 16.84 |
| ATOM | 1268 | O | ASN | D | 48 | 73.955 | 35.526 | 29.124 | 1.00 | 15.08 |
| ATOM | 1269 | CB | ASN | D | 48 | 74.577 | 33.489 | 27.132 | 1.00 | 14.22 |
| ATOM | 1270 | CG | ASN | D | 48 | 75.962 | 33.037 | 27.477 | 1.00 | 19.83 |
| ATOM | 1271 | OD1 | ASN | D | 48 | 76.445 | 33.343 | 28.575 | 1.00 | 17.68 |
| ATOM | 1272 | ND2 | ASN | D | 48 | 76.625 | 32.305 | 26.581 | 1.00 | 18.60 |
| ATOM | 1273 | N | VAL | D | 49 | 73.892 | 33.883 | 30.661 | 1.00 | 16.35 |
| ATOM | 1274 | CA | VAL | D | 49 | 74.128 | 34.782 | 31.784 | 1.00 | 16.91 |
| ATOM | 1275 | C | VAL | D | 49 | 75.563 | 35.373 | 31.784 | 1.00 | 18.54 |
| ATOM | 1276 | O | VAL | D | 49 | 75.809 | 36.526 | 32.220 | 1.00 | 19.45 |
| ATOM | 1277 | CB | VAL | D | 49 | 73.926 | 34.037 | 33.092 | 1.00 | 20.06 |
| ATOM | 1278 | CG1 | VAL | D | 49 | 74.124 | 35.006 | 34.262 | 1.00 | 21.67 |

-continued

Data Lists

| | | | | | | | | | |
|---|---|---|---|---|---|---|---|---|---|
| ATOM | 1279 | CG2 | VAL | D | 49 | 72.526 | 33.407 | 33.136 | 1.00 | 18.68 |
| ATOM | 1280 | N | THR | D | 50 | 76.501 | 34.576 | 31.282 | 1.00 | 17.72 |
| ATOM | 1281 | CA | THR | D | 50 | 77.881 | 35.042 | 31.234 | 1.00 | 18.92 |
| ATOM | 1282 | C | THR | D | 50 | 78.125 | 36.187 | 30.258 | 1.00 | 20.97 |
| ATOM | 1283 | O | THR | D | 50 | 78.696 | 37.231 | 30.614 | 1.00 | 20.06 |
| ATOM | 1284 | CB | THR | D | 50 | 78.829 | 33.887 | 30.935 | 1.00 | 19.40 |
| ATOM | 1285 | OG1 | THR | D | 50 | 78.678 | 32.859 | 31.930 | 1.00 | 19.82 |
| ATOM | 1286 | CG2 | THR | D | 50 | 80.335 | 34.365 | 30.836 | 1.00 | 21.30 |
| ATOM | 1287 | N | ASN | D | 51 | 77.687 | 36.000 | 28.998 | 1.00 | 17.46 |
| ATOM | 1288 | CA | ASN | D | 51 | 77.917 | 37.033 | 27.972 | 1.00 | 18.39 |
| ATOM | 1289 | C | ASN | D | 51 | 76.723 | 37.838 | 27.459 | 1.00 | 19.48 |
| ATOM | 1290 | O | ASN | D | 51 | 76.883 | 38.713 | 26.603 | 1.00 | 19.00 |
| ATOM | 1291 | CB | ASN | D | 51 | 78.712 | 36.436 | 26.788 | 1.00 | 18.51 |
| ATOM | 1292 | CG | ASN | D | 51 | 77.871 | 35.497 | 25.912 | 1.00 | 22.35 |
| ATOM | 1293 | OD1 | ASN | D | 51 | 76.653 | 35.449 | 26.014 | 1.00 | 17.21 |
| ATOM | 1294 | ND2 | ASN | D | 51 | 78.537 | 34.732 | 25.071 | 1.00 | 21.24 |
| ATOM | 1295 | N | GLY | D | 52 | 75.528 | 37.546 | 27.979 | 1.00 | 15.50 |
| ATOM | 1296 | CA | GLY | D | 52 | 74.286 | 38.204 | 27.622 | 1.00 | 14.95 |
| ATOM | 1297 | C | GLY | D | 52 | 73.637 | 37.851 | 26.263 | 1.00 | 14.04 |
| ATOM | 1298 | O | GLY | D | 52 | 72.553 | 38.408 | 25.971 | 1.00 | 16.62 |
| ATOM | 1299 | N | LYS | D | 53 | 74.271 | 36.968 | 25.507 | 1.00 | 14.08 |
| ATOM | 1300 | CA | LYS | D | 53 | 73.636 | 36.627 | 24.193 | 1.00 | 14.38 |
| ATOM | 1301 | C | LYS | D | 53 | 72.355 | 35.864 | 24.437 | 1.00 | 15.94 |
| ATOM | 1302 | O | LYS | D | 53 | 72.229 | 35.159 | 25.442 | 1.00 | 16.45 |
| ATOM | 1303 | CB | LYS | D | 53 | 74.596 | 35.808 | 23.323 | 1.00 | 14.22 |
| ATOM | 1304 | CG | LYS | D | 53 | 75.791 | 36.669 | 22.909 | 1.00 | 16.49 |
| ATOM | 1305 | CD | LYS | D | 53 | 76.764 | 35.880 | 22.038 | 1.00 | 19.28 |
| ATOM | 1306 | CE | LYS | D | 53 | 77.988 | 36.725 | 21.678 | 1.00 | 26.70 |
| ATOM | 1307 | NZ | LYS | D | 53 | 79.004 | 35.889 | 20.987 | 1.00 | 29.14 |
| ATOM | 1308 | N | ARG | D | 54 | 71.393 | 35.958 | 23.483 | 1.00 | 12.88 |
| ATOM | 1309 | CA | ARG | D | 54 | 70.123 | 35.274 | 23.557 | 1.00 | 11.93 |
| ATOM | 1310 | C | ARG | D | 54 | 69.855 | 34.669 | 22.194 | 1.00 | 14.91 |
| ATOM | 1311 | O | ARG | D | 54 | 69.980 | 35.396 | 21.196 | 1.00 | 15.98 |
| ATOM | 1312 | CB | ARG | D | 54 | 68.981 | 36.222 | 23.931 | 1.00 | 13.59 |
| ATOM | 1313 | CG | ARG | D | 54 | 69.328 | 37.048 | 25.222 | 1.00 | 14.24 |
| ATOM | 1314 | CD | ARG | D | 54 | 68.216 | 38.045 | 25.627 | 1.00 | 13.75 |
| ATOM | 1315 | NE | ARG | D | 54 | 67.011 | 37.440 | 26.165 | 1.00 | 13.94 |
| ATOM | 1316 | CZ | ARG | D | 54 | 66.877 | 37.091 | 27.456 | 1.00 | 16.69 |
| ATOM | 1317 | NH1 | ARG | D | 54 | 67.936 | 37.309 | 28.276 | 1.00 | 13.80 |
| ATOM | 1318 | NH2 | ARG | D | 54 | 65.726 | 36.552 | 27.929 | 1.00 | 13.52 |
| ATOM | 1319 | N | PHE | D | 55 | 69.566 | 33.396 | 22.152 | 1.00 | 12.40 |
| ATOM | 1320 | CA | PHE | D | 55 | 69.306 | 32.745 | 20.862 | 1.00 | 13.30 |
| ATOM | 1321 | C | PHE | D | 55 | 68.292 | 31.657 | 20.971 | 1.00 | 18.51 |
| ATOM | 1322 | O | PHE | D | 55 | 67.947 | 31.225 | 22.083 | 1.00 | 16.08 |
| ATOM | 1323 | CB | PHE | D | 55 | 70.609 | 32.327 | 20.200 | 1.00 | 13.02 |
| ATOM | 1324 | CG | PHE | D | 55 | 71.346 | 31.246 | 20.922 | 1.00 | 14.95 |
| ATOM | 1325 | CD1 | PHE | D | 55 | 72.197 | 31.565 | 22.004 | 1.00 | 15.75 |
| ATOM | 1326 | CD2 | PHE | D | 55 | 71.234 | 29.901 | 20.513 | 1.00 | 15.13 |
| ATOM | 1327 | CE1 | PHE | D | 55 | 72.938 | 30.508 | 22.680 | 1.00 | 17.56 |
| ATOM | 1328 | CE2 | PHE | D | 55 | 71.931 | 28.901 | 21.171 | 1.00 | 17.23 |
| ATOM | 1329 | CZ | PHE | D | 55 | 72.794 | 29.230 | 22.258 | 1.00 | 16.09 |
| ATOM | 1330 | N | SER | D | 56 | 67.760 | 31.175 | 19.846 | 1.00 | 12.78 |
| ATOM | 1331 | CA | SER | D | 56 | 66.764 | 30.135 | 19.824 | 1.00 | 12.18 |
| ATOM | 1332 | C | SER | D | 56 | 67.220 | 29.017 | 18.940 | 1.00 | 15.48 |
| ATOM | 1333 | O | SER | D | 56 | 67.772 | 29.295 | 17.870 | 1.00 | 14.26 |
| ATOM | 1334 | CB | SER | D | 56 | 65.408 | 30.618 | 19.392 | 1.00 | 13.68 |
| ATOM | 1335 | OG | SER | D | 56 | 64.906 | 31.668 | 20.254 | 1.00 | 18.10 |
| ATOM | 1336 | N | THR | D | 57 | 67.010 | 27.786 | 19.358 | 1.00 | 11.29 |
| ATOM | 1337 | CA | THR | D | 57 | 67.456 | 26.580 | 18.617 | 1.00 | 11.02 |
| ATOM | 1338 | C | THR | D | 57 | 66.477 | 25.422 | 18.955 | 1.00 | 11.10 |
| ATOM | 1339 | O | THR | D | 57 | 65.269 | 25.655 | 19.137 | 1.00 | 10.41 |
| ATOM | 1340 | CB | THR | D | 57 | 68.956 | 26.316 | 18.937 | 1.00 | 13.63 |
| ATOM | 1341 | OG1 | THR | D | 57 | 69.406 | 25.158 | 18.211 | 1.00 | 16.82 |
| ATOM | 1342 | CG2 | THR | D | 57 | 69.148 | 25.977 | 20.458 | 1.00 | 16.40 |
| ATOM | 1343 | N | TYR | D | 58 | 66.953 | 24.186 | 19.039 | 1.00 | 11.85 |
| ATOM | 1344 | CA | TYR | D | 58 | 66.081 | 23.039 | 19.381 | 1.00 | 11.66 |
| ATOM | 1345 | C | TYR | D | 58 | 66.898 | 22.079 | 20.219 | 1.00 | 14.10 |
| ATOM | 1346 | O | TYR | D | 58 | 68.132 | 22.085 | 20.147 | 1.00 | 12.80 |
| ATOM | 1347 | CB | TYR | D | 58 | 65.417 | 22.357 | 18.154 | 1.00 | 13.66 |
| ATOM | 1348 | CG | TYR | D | 58 | 66.346 | 21.598 | 17.249 | 1.00 | 14.03 |
| ATOM | 1349 | CD1 | TYR | D | 58 | 67.006 | 22.243 | 16.175 | 1.00 | 14.60 |
| ATOM | 1350 | CD2 | TYR | D | 58 | 66.578 | 20.259 | 17.424 | 1.00 | 14.69 |
| ATOM | 1351 | CE1 | TYR | D | 58 | 67.879 | 21.541 | 15.366 | 1.00 | 14.59 |
| ATOM | 1352 | CE2 | TYR | D | 58 | 67.453 | 19.534 | 16.587 | 1.00 | 16.85 |
| ATOM | 1353 | CZ | TYR | D | 58 | 68.099 | 20.201 | 15.564 | 1.00 | 21.58 |
| ATOM | 1354 | OH | TYR | D | 58 | 68.989 | 19.626 | 14.678 | 1.00 | 22.59 |
| ATOM | 1355 | N | ALA | D | 59 | 66.215 | 21.278 | 21.038 | 1.00 | 12.25 |

-continued

Data Lists

| ATOM | 1356 | CA | ALA | D | 59 | 66.907 | 20.349 | 21.895 | 1.00 | 12.10 |
|---|---|---|---|---|---|---|---|---|---|---|
| ATOM | 1357 | C | ALA | D | 59 | 67.209 | 19.007 | 21.292 | 1.00 | 14.08 |
| ATOM | 1358 | O | ALA | D | 59 | 66.420 | 18.450 | 20.545 | 1.00 | 13.85 |
| ATOM | 1359 | CB | ALA | D | 59 | 66.015 | 20.122 | 23.160 | 1.00 | 13.24 |
| ATOM | 1360 | N | ILE | D | 60 | 68.365 | 18.433 | 21.690 | 1.00 | 15.08 |
| ATOM | 1361 | CA | ILE | D | 60 | 68.803 | 17.122 | 21.272 | 1.00 | 17.01 |
| ATOM | 1362 | C | ILE | D | 60 | 69.125 | 16.356 | 22.591 | 1.00 | 16.03 |
| ATOM | 1363 | O | ILE | D | 60 | 69.663 | 16.961 | 23.500 | 1.00 | 16.17 |
| ATOM | 1364 | CB | ILE | D | 60 | 70.125 | 17.251 | 20.437 | 1.00 | 20.97 |
| ATOM | 1365 | CG1 | ILE | D | 60 | 69.809 | 17.848 | 19.062 | 1.00 | 23.49 |
| ATOM | 1366 | CG2 | ILE | D | 60 | 70.789 | 15.887 | 20.217 | 1.00 | 23.18 |
| ATOM | 1367 | CD1 | ILE | D | 60 | 71.051 | 18.391 | 18.335 | 1.00 | 26.91 |
| ATOM | 1368 | N | ALA | D | 61 | 68.770 | 15.083 | 22.679 | 1.00 | 16.21 |
| ATOM | 1369 | CA | ALA | D | 61 | 69.073 | 14.329 | 23.908 | 1.00 | 17.99 |
| ATOM | 1370 | C | ALA | D | 61 | 70.540 | 13.922 | 23.939 | 1.00 | 20.83 |
| ATOM | 1371 | O | ALA | D | 61 | 71.084 | 13.484 | 22.911 | 1.00 | 20.99 |
| ATOM | 1372 | CB | ALA | D | 61 | 68.241 | 13.116 | 23.982 | 1.00 | 19.35 |
| ATOM | 1373 | N | ALA | D | 62 | 71.155 | 14.020 | 25.121 | 1.00 | 17.91 |
| ATOM | 1374 | CA | ALA | D | 62 | 72.553 | 13.581 | 25.379 | 1.00 | 17.67 |
| ATOM | 1375 | C | ALA | D | 62 | 72.369 | 12.443 | 26.406 | 1.00 | 23.91 |
| ATOM | 1376 | O | ALA | D | 62 | 71.329 | 12.319 | 27.041 | 1.00 | 22.36 |
| ATOM | 1377 | CB | ALA | D | 62 | 73.402 | 14.661 | 25.953 | 1.00 | 18.45 |
| ATOM | 1378 | N | GLU | D | 63 | 73.395 | 11.613 | 26.540 | 1.00 | 22.90 |
| ATOM | 1379 | CA | GLU | D | 63 | 73.378 | 10.471 | 27.428 | 1.00 | 23.71 |
| ATOM | 1380 | C | GLU | D | 63 | 72.950 | 10.793 | 28.843 | 1.00 | 23.19 |
| ATOM | 1381 | O | GLU | D | 63 | 73.447 | 11.742 | 29.441 | 1.00 | 22.01 |
| ATOM | 1382 | CB | GLU | D | 63 | 74.777 | 9.848 | 27.443 | 1.00 | 25.20 |
| ATOM | 1383 | CG | GLU | D | 63 | 74.859 | 8.627 | 28.342 | 1.00 | 31.69 |
| ATOM | 1384 | CD | GLU | D | 63 | 76.110 | 7.846 | 28.078 | 1.00 | 54.65 |
| ATOM | 1385 | OE1 | GLU | D | 63 | 76.067 | 6.926 | 27.227 | 1.00 | 50.68 |
| ATOM | 1386 | OE2 | GLU | D | 63 | 77.136 | 8.166 | 28.714 | 1.00 | 49.85 |
| ATOM | 1387 | N | ARG | D | 64 | 72.047 | 9.967 | 29.375 | 1.00 | 23.54 |
| ATOM | 1388 | CA | ARG | D | 64 | 71.554 | 10.144 | 30.721 | 1.00 | 24.49 |
| ATOM | 1389 | C | ARG | D | 64 | 72.710 | 10.059 | 31.727 | 1.00 | 29.91 |
| ATOM | 1390 | O | ARG | D | 64 | 73.501 | 9.102 | 31.685 | 1.00 | 30.10 |
| ATOM | 1391 | CB | ARG | D | 64 | 70.529 | 9.064 | 31.047 | 1.00 | 24.54 |
| ATOM | 1392 | CG | ARG | D | 64 | 69.732 | 9.364 | 32.284 | 1.00 | 33.44 |
| ATOM | 1393 | CD | ARG | D | 64 | 68.790 | 8.227 | 32.617 | 1.00 | 30.76 |
| ATOM | 1394 | NE | ARG | D | 64 | 67.706 | 8.048 | 31.659 | 1.00 | 27.92 |
| ATOM | 1395 | CZ | ARG | D | 64 | 66.649 | 8.865 | 31.545 | 1.00 | 30.52 |
| ATOM | 1396 | NH1 | ARG | D | 64 | 66.536 | 9.940 | 32.316 | 1.00 | 26.37 |
| ATOM | 1397 | NH2 | ARG | D | 64 | 65.710 | 8.597 | 30.655 | 1.00 | 30.42 |
| ATOM | 1398 | N | GLY | D | 65 | 72.817 | 11.035 | 32.609 | 1.00 | 27.07 |
| ATOM | 1399 | CA | GLY | D | 65 | 73.882 | 11.019 | 33.616 | 1.00 | 26.85 |
| ATOM | 1400 | C | GLY | D | 65 | 75.190 | 11.651 | 33.183 | 1.00 | 30.69 |
| ATOM | 1401 | O | GLY | D | 65 | 76.089 | 11.825 | 33.997 | 1.00 | 31.19 |
| ATOM | 1402 | N | SER | D | 66 | 75.287 | 12.036 | 31.912 | 1.00 | 25.88 |
| ATOM | 1403 | CA | SER | D | 66 | 76.495 | 12.662 | 31.399 | 1.00 | 24.31 |
| ATOM | 1404 | C | SER | D | 66 | 76.682 | 14.113 | 31.883 | 1.00 | 28.10 |
| ATOM | 1405 | O | SER | D | 66 | 77.793 | 14.654 | 31.888 | 1.00 | 29.06 |
| ATOM | 1406 | CB | SER | D | 66 | 76.454 | 12.648 | 29.857 | 1.00 | 25.33 |
| ATOM | 1407 | OG | SER | D | 66 | 75.428 | 13.550 | 29.364 | 1.00 | 25.27 |
| ATOM | 1408 | N | ARG | D | 67 | 75.564 | 14.771 | 32.247 | 1.00 | 21.92 |
| ATOM | 1409 | CA | ARG | D | 67 | 75.571 | 16.157 | 32.680 | 1.00 | 20.64 |
| ATOM | 1410 | C | ARG | D | 67 | 76.060 | 17.130 | 31.581 | 1.00 | 21.33 |
| ATOM | 1411 | O | ARG | D | 67 | 76.476 | 18.236 | 31.854 | 1.00 | 23.88 |
| ATOM | 1412 | CB | ARG | D | 67 | 76.274 | 16.320 | 34.033 | 1.00 | 24.90 |
| ATOM | 1413 | CG | ARG | D | 67 | 75.630 | 15.331 | 35.037 | 1.00 | 34.18 |
| ATOM | 1414 | CD | ARG | D | 67 | 75.927 | 15.626 | 36.478 | 1.00 | 41.97 |
| ATOM | 1415 | NE | ARG | D | 67 | 77.213 | 15.050 | 36.869 | 1.00 | 42.73 |
| ATOM | 1416 | CZ | ARG | D | 67 | 77.511 | 13.750 | 37.086 | 1.00 | 50.11 |
| ATOM | 1417 | NH1 | ARG | D | 67 | 76.638 | 12.732 | 36.977 | 1.00 | 32.87 |
| ATOM | 1418 | NH2 | ARG | D | 67 | 78.761 | 13.476 | 37.438 | 1.00 | 35.89 |
| ATOM | 1419 | N | ILE | D | 68 | 75.922 | 16.675 | 30.337 | 1.00 | 20.99 |
| ATOM | 1420 | CA | ILE | D | 68 | 76.342 | 17.482 | 29.196 | 1.00 | 19.82 |
| ATOM | 1421 | C | ILE | D | 68 | 75.308 | 18.552 | 28.761 | 1.00 | 18.74 |
| ATOM | 1422 | O | ILE | D | 68 | 74.063 | 18.354 | 28.842 | 1.00 | 18.59 |
| ATOM | 1423 | CB | ILE | D | 68 | 76.553 | 16.552 | 27.943 | 1.00 | 22.72 |
| ATOM | 1424 | CG1 | ILE | D | 68 | 77.870 | 15.741 | 28.011 | 1.00 | 22.79 |
| ATOM | 1425 | CG2 | ILE | D | 68 | 76.492 | 17.349 | 26.604 | 1.00 | 23.66 |
| ATOM | 1426 | CD1 | ILE | D | 68 | 77.831 | 14.542 | 27.090 | 1.00 | 24.22 |
| ATOM | 1427 | N | ILE | D | 69 | 75.866 | 19.651 | 28.331 | 1.00 | 17.03 |
| ATOM | 1428 | CA | ILE | D | 69 | 75.133 | 20.812 | 27.729 | 1.00 | 16.07 |
| ATOM | 1429 | C | ILE | D | 69 | 76.113 | 21.177 | 26.568 | 1.00 | 18.47 |
| ATOM | 1430 | O | ILE | D | 69 | 77.135 | 21.853 | 26.785 | 1.00 | 19.41 |
| ATOM | 1431 | CB | ILE | D | 69 | 74.990 | 22.034 | 28.619 | 1.00 | 17.97 |
| ATOM | 1432 | CG1 | ILE | D | 69 | 74.094 | 21.722 | 29.861 | 1.00 | 17.84 |

-continued

Data Lists

| ATOM | 1433 | CG2 | ILE | D | 69 | 74.318 | 23.224 | 27.796 | 1.00 | 14.87 |
| ATOM | 1434 | CD1 | ILE | D | 69 | 72.656 | 21.278 | 29.519 | 1.00 | 16.76 |
| ATOM | 1435 | N   | SER | D | 70 | 75.800 | 20.705 | 25.359 | 1.00 | 16.82 |
| ATOM | 1436 | CA  | SER | D | 70 | 76.694 | 20.960 | 24.186 | 1.00 | 16.67 |
| ATOM | 1437 | C   | SER | D | 70 | 76.030 | 21.879 | 23.159 | 1.00 | 16.91 |
| ATOM | 1438 | O   | SER | D | 70 | 74.926 | 21.572 | 22.658 | 1.00 | 17.58 |
| ATOM | 1439 | CB  | SER | D | 70 | 77.011 | 9.630  | 23.537 | 1.00 | 19.85 |
| ATOM | 1440 | OG  | SER | D | 70 | 77.957 | 19.775 | 22.482 | 1.00 | 22.39 |
| ATOM | 1441 | N   | VAL | D | 71 | 76.695 | 22.980 | 22.865 | 1.00 | 16.01 |
| ATOM | 1442 | CA  | VAL | D | 71 | 76.145 | 23.963 | 21.853 | 1.00 | 17.80 |
| ATOM | 1443 | C   | VAL | D | 71 | 76.803 | 23.589 | 20.516 | 1.00 | 22.32 |
| ATOM | 1444 | O   | VAL | D | 71 | 78.012 | 23.676 | 20.369 | 1.00 | 23.49 |
| ATOM | 1445 | CB  | VAL | D | 71 | 76.329 | 25.399 | 22.263 | 1.00 | 22.83 |
| ATOM | 1446 | CG1 | VAL | D | 71 | 75.507 | 25.648 | 23.572 | 1.00 | 21.98 |
| ATOM | 1447 | CG2 | VAL | D | 71 | 77.809 | 25.768 | 22.399 | 1.00 | 24.06 |
| ATOM | 1448 | N   | ASN | D | 72 | 75.970 | 23.121 | 19.584 | 1.00 | 20.48 |
| ATOM | 1449 | CA  | ASN | D | 72 | 76.427 | 22.621 | 18.267 | 1.00 | 20.13 |
| ATOM | 1450 | C   | ASN | D | 72 | 75.998 | 23.462 | 17.099 | 1.00 | 22.39 |
| ATOM | 1451 | O   | ASN | D | 72 | 75.023 | 24.219 | 17.165 | 1.00 | 22.18 |
| ATOM | 1452 | CB  | ASN | D | 72 | 75.811 | 21.233 | 18.033 | 1.00 | 21.77 |
| ATOM | 1453 | CG  | ASN | D | 72 | 76.097 | 20.254 | 19.165 | 1.00 | 30.59 |
| ATOM | 1454 | OD1 | ASN | D | 72 | 77.069 | 20.428 | 19.917 | 1.00 | 25.69 |
| ATOM | 1455 | ND2 | ASN | D | 72 | 75.228 | 19.241 | 19.317 | 1.00 | 26.90 |
| ATOM | 1456 | N   | GLY | D | 73 | 76.708 | 23.283 | 15.994 | 1.00 | 20.53 |
| ATOM | 1457 | CA  | GLY | D | 73 | 76.343 | 24.046 | 14.794 | 1.00 | 19.66 |
| ATOM | 1458 | C   | GLY | D | 73 | 76.636 | 25.528 | 14.994 | 1.00 | 20.18 |
| ATOM | 1459 | O   | GLY | D | 73 | 77.584 | 25.917 | 15.706 | 1.00 | 19.03 |
| ATOM | 1460 | N   | ALA | D | 74 | 75.821 | 26.380 | 14.343 | 1.00 | 16.73 |
| ATOM | 1461 | CA  | ALA | D | 74 | 76.006 | 27.831 | 14.434 | 1.00 | 16.27 |
| ATOM | 1462 | C   | ALA | D | 74 | 75.988 | 28.387 | 15.874 | 1.00 | 17.37 |
| ATOM | 1463 | O   | ALA | D | 74 | 76.616 | 29.406 | 16.149 | 1.00 | 18.06 |
| ATOM | 1464 | CB  | ALA | D | 74 | 74.987 | 28.616 | 13.530 | 1.00 | 17.59 |
| ATOM | 1465 | N   | ALA | D | 75 | 75.226 | 27.686 | 16.729 | 1.00 | 17.95 |
| ATOM | 1466 | CA  | ALA | D | 75 | 75.069 | 28.102 | 18.147 | 1.00 | 17.42 |
| ATOM | 1467 | C   | ALA | D | 75 | 76.415 | 28.126 | 18.870 | 1.00 | 19.91 |
| ATOM | 1468 | O   | ALA | D | 75 | 76.543 | 28.800 | 19.897 | 1.00 | 19.81 |
| ATOM | 1469 | CB  | ALA | D | 75 | 74.115 | 27.217 | 18.827 | 1.00 | 18.30 |
| ATOM | 1470 | N   | ALA | D | 76 | 77.433 | 27.422 | 18.345 | 1.00 | 16.78 |
| ATOM | 1471 | CA  | ALA | D | 76 | 78.747 | 27.455 | 18.982 | 1.00 | 18.31 |
| ATOM | 1472 | C   | ALA | D | 76 | 79.347 | 28.882 | 18.991 | 1.00 | 18.92 |
| ATOM | 1473 | O   | ALA | D | 76 | 80.266 | 29.184 | 19.740 | 1.00 | 19.50 |
| ATOM | 1474 | CB  | ALA | D | 76 | 79.684 | 26.446 | 18.309 | 1.00 | 19.95 |
| ATOM | 1475 | N   | HIS | D | 77 | 78.830 | 29.800 | 18.149 | 1.00 | 16.41 |
| ATOM | 1476 | CA  | HIS | D | 77 | 79.302 | 31.149 | 18.115 | 1.00 | 17.43 |
| ATOM | 1477 | C   | HIS | D | 77 | 78.710 | 32.014 | 19.243 | 1.00 | 18.10 |
| ATOM | 1478 | O   | HIS | D | 77 | 79.143 | 33.147 | 19.435 | 1.00 | 20.06 |
| ATOM | 1479 | CB  | HIS | D | 77 | 78.785 | 31.847 | 16.791 | 1.00 | 19.37 |
| ATOM | 1480 | CG  | HIS | D | 77 | 79.540 | 31.470 | 15.545 | 1.00 | 22.65 |
| ATOM | 1481 | ND1 | HIS | D | 77 | 80.667 | 32.145 | 15.137 | 1.00 | 25.27 |
| ATOM | 1482 | CD2 | HIS | D | 77 | 79.308 | 30.523 | 14.605 | 1.00 | 22.98 |
| ATOM | 1483 | CE1 | HIS | D | 77 | 81.109 | 31.624 | 14.002 | 1.00 | 24.52 |
| ATOM | 1484 | NE2 | HIS | D | 77 | 80.307 | 30.637 | 13.657 | 1.00 | 23.17 |
| ATOM | 1485 | N   | CYS | D | 78 | 77.694 | 31.475 | 19.940 | 1.00 | 17.70 |
| ATOM | 1486 | CA  | CYS | D | 78 | 76.964 | 32.234 | 20.974 | 1.00 | 18.05 |
| ATOM | 1487 | C   | CYS | D | 78 | 77.251 | 31.832 | 22.400 | 1.00 | 21.51 |
| ATOM | 1488 | O   | CYS | D | 78 | 76.750 | 32.470 | 23.321 | 1.00 | 21.14 |
| ATOM | 1489 | CB  | CYS | D | 78 | 75.466 | 32.047 | 20.753 | 1.00 | 19.61 |
| ATOM | 1490 | SG  | CYS | D | 78 | 74.878 | 32.588 | 19.098 | 1.00 | 25.07 |
| ATOM | 1491 | N   | ALA | D | 79 | 78.033 | 30.778 | 22.586 | 1.00 | 20.09 |
| ATOM | 1492 | CA  | ALA | D | 79 | 78.365 | 30.353 | 23.943 | 1.00 | 19.73 |
| ATOM | 1493 | C   | ALA | D | 79 | 79.677 | 29.603 | 23.922 | 1.00 | 25.47 |
| ATOM | 1494 | O   | ALA | D | 79 | 80.013 | 28.966 | 22.934 | 1.00 | 23.97 |
| ATOM | 1495 | CB  | ALA | D | 79 | 77.283 | 29.479 | 24.512 | 1.00 | 20.06 |
| ATOM | 1496 | N   | SER | D | 80 | 80.406 | 29.664 | 25.036 | 1.00 | 21.56 |
| ATOM | 1497 | CA  | SER | D | 80 | 81.697 | 28.965 | 25.191 | 1.00 | 22.17 |
| ATOM | 1498 | C   | SER | D | 80 | 81.623 | 28.023 | 26.379 | 1.00 | 23.37 |
| ATOM | 1499 | O   | SER | D | 80 | 80.792 | 28.213 | 27.275 | 1.00 | 21.62 |
| ATOM | 1500 | CB  | SER | D | 80 | 82.824 | 29.931 | 25.485 | 1.00 | 25.03 |
| ATOM | 1501 | OG  | SER | D | 80 | 82.930 | 30.986 | 24.543 | 1.00 | 28.26 |
| ATOM | 1502 | N   | VAL | D | 81 | 82.499 | 27.021 | 26.388 | 1.00 | 18.88 |
| ATOM | 1503 | CA  | VAL | D | 81 | 82.548 | 26.053 | 27.491 | 1.00 | 19.13 |
| ATOM | 1504 | C   | VAL | D | 81 | 82.739 | 26.876 | 28.769 | 1.00 | 21.75 |
| ATOM | 1505 | O   | VAL | D | 81 | 83.558 | 27.824 | 28.819 | 1.00 | 20.90 |
| ATOM | 1506 | CB  | VAL | D | 81 | 83.722 | 25.072 | 27.272 | 1.00 | 21.73 |
| ATOM | 1507 | CG1 | VAL | D | 81 | 83.986 | 24.271 | 28.562 | 1.00 | 22.57 |
| ATOM | 1508 | CG2 | VAL | D | 81 | 83.366 | 24.099 | 26.155 | 1.00 | 21.80 |
| ATOM | 1509 | N   | GLY | D | 82 | 81.973 | 26.526 | 29.798 | 1.00 | 18.71 |

-continued

| | | | | | | | | | |
|---|---|---|---|---|---|---|---|---|---|
| ATOM | 1510 | CA | GLY | D | 82 | 82.060 | 27.276 | 31.055 | 1.00 | 18.70 |
| ATOM | 1511 | C | GLY | D | 82 | 81.007 | 28.365 | 31.234 | 1.00 | 22.87 |
| ATOM | 1512 | O | GLY | D | 82 | 80.782 | 28.830 | 32.338 | 1.00 | 22.78 |
| ATOM | 1513 | N | ASP | D | 83 | 80.366 | 28.835 | 30.145 | 1.00 | 16.66 |
| ATOM | 1514 | CA | ASP | D | 83 | 79.356 | 29.867 | 30.305 | 1.00 | 16.76 |
| ATOM | 1515 | C | ASP | D | 83 | 78.131 | 29.322 | 31.070 | 1.00 | 16.77 |
| ATOM | 1516 | O | ASP | D | 83 | 77.748 | 28.153 | 30.896 | 1.00 | 17.18 |
| ATOM | 1517 | CB | ASP | D | 83 | 78.861 | 30.294 | 28.908 | 1.00 | 18.79 |
| ATOM | 1518 | CG | ASP | D | 83 | 79.852 | 31.196 | 28.164 | 1.00 | 22.59 |
| ATOM | 1519 | OD1 | ASP | D | 83 | 80.935 | 31.544 | 28.680 | 1.00 | 20.93 |
| ATOM | 1520 | OD2 | ASP | D | 83 | 79.519 | 31.615 | 27.015 | 1.00 | 21.88 |
| ATOM | 1521 | N | ILE | D | 84 | 77.515 | 30.198 | 31.860 | 1.00 | 17.58 |
| ATOM | 1522 | CA | ILE | D | 84 | 76.300 | 29.822 | 32.603 | 1.00 | 17.77 |
| ATOM | 1523 | C | ILE | D | 84 | 75.119 | 30.302 | 31.751 | 1.00 | 17.52 |
| ATOM | 1524 | O | ILE | D | 84 | 75.119 | 31.474 | 31.351 | 1.00 | 16.51 |
| ATOM | 1525 | CB | ILE | D | 84 | 76.296 | 30.573 | 33.935 | 1.00 | 21.87 |
| ATOM | 1526 | CG1 | ILE | D | 84 | 77.513 | 30.116 | 34.766 | 1.00 | 22.20 |
| ATOM | 1527 | CG2 | ILE | D | 84 | 74.978 | 30.346 | 34.726 | 1.00 | 22.70 |
| ATOM | 1528 | CD1 | ILE | D | 84 | 77.676 | 31.008 | 36.011 | 1.00 | 27.68 |
| ATOM | 1529 | N | VAL | D | 85 | 74.192 | 29.388 | 31.497 | 1.00 | 16.68 |
| ATOM | 1530 | CA | VAL | D | 85 | 73.007 | 29.731 | 30.686 | 1.00 | 14.93 |
| ATOM | 1531 | C | VAL | D | 85 | 71.700 | 29.265 | 31.326 | 1.00 | 18.77 |
| ATOM | 1532 | O | VAL | D | 85 | 71.702 | 28.445 | 32.264 | 1.00 | 18.51 |
| ATOM | 1533 | CB | VAL | D | 85 | 73.144 | 29.098 | 29.266 | 1.00 | 15.49 |
| ATOM | 1534 | CG1 | VAL | D | 85 | 74.452 | 29.475 | 28.627 | 1.00 | 16.44 |
| ATOM | 1535 | CG2 | VAL | D | 85 | 73.026 | 27.645 | 29.306 | 1.00 | 14.40 |
| ATOM | 1536 | N | ILE | D | 86 | 70.571 | 29.792 | 30.807 | 1.00 | 14.77 |
| ATOM | 1537 | CA | ILE | D | 86 | 69.244 | 29.418 | 31.229 | 1.00 | 15.52 |
| ATOM | 1538 | C | ILE | D | 86 | 68.618 | 28.876 | 29.933 | 1.00 | 15.28 |
| ATOM | 1539 | O | ILE | D | 86 | 68.730 | 29.572 | 28.899 | 1.00 | 15.56 |
| ATOM | 1540 | CB | ILE | D | 86 | 68.442 | 30.582 | 31.786 | 1.00 | 18.22 |
| ATOM | 1541 | CG1 | ILE | D | 86 | 69.034 | 31.030 | 33.158 | 1.00 | 19.52 |
| ATOM | 1542 | CG2 | ILE | D | 86 | 66.998 | 30.177 | 31.976 | 1.00 | 18.36 |
| ATOM | 1543 | CD1 | ILE | D | 86 | 68.686 | 32.448 | 33.495 | 1.00 | 25.25 |
| ATOM | 1544 | N | ILE | D | 87 | 68.087 | 27.692 | 29.954 | 1.00 | 11.80 |
| ATOM | 1545 | CA | ILE | D | 87 | 67.466 | 27.037 | 28.747 | 1.00 | 11.37 |
| ATOM | 1546 | C | ILE | D | 87 | 65.989 | 26.902 | 29.021 | 1.00 | 16.80 |
| ATOM | 1547 | O | ILE | D | 87 | 65.585 | 26.259 | 30.043 | 1.00 | 15.75 |
| ATOM | 1548 | CB | ILE | D | 87 | 68.096 | 25.681 | 28.476 | 1.00 | 14.04 |
| ATOM | 1549 | CG1 | ILE | D | 87 | 69.636 | 25.844 | 28.325 | 1.00 | 14.68 |
| ATOM | 1550 | CG2 | ILE | D | 87 | 67.438 | 24.977 | 27.201 | 1.00 | 16.46 |
| ATOM | 1551 | CD1 | ILE | D | 87 | 70.419 | 24.558 | 27.961 | 1.00 | 16.93 |
| ATOM | 1552 | N | ALA | D | 88 | 65.127 | 27.457 | 28.161 | 1.00 | 13.54 |
| ATOM | 1553 | CA | ALA | D | 88 | 63.667 | 27.410 | 28.397 | 1.00 | 12.01 |
| ATOM | 1554 | C | ALA | D | 88 | 62.870 | 26.916 | 27.216 | 1.00 | 15.27 |
| ATOM | 1555 | O | ALA | D | 88 | 63.341 | 27.080 | 26.077 | 1.00 | 14.13 |
| ATOM | 1556 | CB | ALA | D | 88 | 63.197 | 28.842 | 28.683 | 1.00 | 12.68 |
| ATOM | 1557 | N | SER | D | 89 | 61.703 | 26.359 | 27.432 | 1.00 | 11.75 |
| ATOM | 1558 | CA | SER | D | 89 | 60.793 | 26.000 | 26.336 | 1.00 | 9.22 |
| ATOM | 1559 | C | SER | D | 89 | 59.463 | 26.672 | 26.691 | 1.00 | 13.85 |
| ATOM | 1560 | O | SER | D | 89 | 59.122 | 26.881 | 27.894 | 1.00 | 12.02 |
| ATOM | 1561 | CB | SER | D | 89 | 60.657 | 24.533 | 26.038 | 1.00 | 13.00 |
| ATOM | 1562 | OG | SER | D | 89 | 59.637 | 23.875 | 26.787 | 1.00 | 13.68 |
| ATOM | 1563 | N | PHE | D | 90 | 58.652 | 27.010 | 25.690 | 1.00 | 9.51 |
| ATOM | 1564 | CA | PHE | D | 90 | 57.352 | 27.650 | 25.837 | 1.00 | 10.69 |
| ATOM | 1565 | C | PHE | D | 90 | 56.272 | 26.831 | 25.169 | 1.00 | 14.12 |
| ATOM | 1566 | O | PHE | D | 90 | 56.519 | 26.218 | 24.124 | 1.00 | 13.43 |
| ATOM | 1567 | CB | PHE | D | 90 | 57.381 | 29.069 | 25.211 | 1.00 | 9.99 |
| ATOM | 1568 | CG | PHE | D | 90 | 58.172 | 30.051 | 26.052 | 1.00 | 8.63 |
| ATOM | 1569 | CD1 | PHE | D | 90 | 59.569 | 30.106 | 25.972 | 1.00 | 12.75 |
| ATOM | 1570 | CD2 | PHE | D | 90 | 57.492 | 30.917 | 26.943 | 1.00 | 9.84 |
| ATOM | 1571 | CE1 | PHE | D | 90 | 60.296 | 31.033 | 26.745 | 1.00 | 12.66 |
| ATOM | 1572 | CE2 | PHE | D | 90 | 58.223 | 31.786 | 27.752 | 1.00 | 11.34 |
| ATOM | 1573 | CZ | PHE | D | 90 | 59.576 | 31.884 | 27.669 | 1.00 | 11.79 |
| ATOM | 1574 | N | VAL | D | 91 | 55.074 | 26.811 | 25.733 | 1.00 | 11.04 |
| ATOM | 1575 | CA | VAL | D | 91 | 53.934 | 26.075 | 25.155 | 1.00 | 8.97 |
| ATOM | 1576 | C | VAL | D | 91 | 52.749 | 27.000 | 25.053 | 1.00 | 12.88 |
| ATOM | 1577 | O | VAL | D | 91 | 52.705 | 28.071 | 25.735 | 1.00 | 13.37 |
| ATOM | 1578 | CB | VAL | D | 91 | 53.519 | 24.811 | 25.939 | 1.00 | 11.62 |
| ATOM | 1579 | CG1 | VAL | D | 91 | 54.527 | 23.721 | 25.805 | 1.00 | 11.91 |
| ATOM | 1580 | CG2 | VAL | D | 91 | 53.294 | 25.194 | 27.489 | 1.00 | 13.43 |
| ATOM | 1581 | N | THR | D | 92 | 51.759 | 26.638 | 24.210 | 1.00 | 11.67 |
| ATOM | 1582 | CA | THR | D | 92 | 50.571 | 27.439 | 24.086 | 1.00 | 9.61 |
| ATOM | 1583 | C | THR | D | 92 | 49.326 | 26.678 | 24.633 | 1.00 | 8.31 |
| ATOM | 1584 | O | THR | D | 92 | 49.266 | 25.473 | 24.646 | 1.00 | 11.35 |
| ATOM | 1585 | CB | THR | D | 92 | 50.371 | 27.971 | 22.630 | 1.00 | 12.02 |
| ATOM | 1586 | OG1 | THR | D | 92 | 50.296 | 26.819 | 21.738 | 1.00 | 17.42 |

-continued

Data Lists

| | | | | | | | | | |
|---|---|---|---|---|---|---|---|---|---|
| ATOM | 1587 | CG2 | THR | D | 92 | 51.481 | 28.893 | 22.269 | 1.00 | 11.07 |
| ATOM | 1588 | N | MET | D | 93 | 48.330 | 27.441 | 25.059 | 1.00 | 10.31 |
| ATOM | 1589 | CA | MET | D | 93 | 47.103 | 26.859 | 25.667 | 1.00 | 10.55 |
| ATOM | 1590 | C | MET | D | 93 | 46.090 | 27.986 | 25.846 | 1.00 | 10.55 |
| ATOM | 1591 | O | MET | D | 93 | 46.444 | 29.174 | 25.900 | 1.00 | 11.69 |
| ATOM | 1592 | CB | MET | D | 93 | 47.421 | 26.236 | 27.109 | 1.00 | 11.27 |
| ATOM | 1593 | CG | MET | D | 93 | 47.856 | 27.339 | 28.054 | 1.00 | 11.07 |
| ATOM | 1594 | SD | MET | D | 93 | 48.572 | 26.650 | 29.641 | 1.00 | 13.35 |
| ATOM | 1595 | CE | MET | D | 93 | 50.133 | 26.102 | 28.965 | 1.00 | 13.30 |
| ATOM | 1596 | N | PRO | D | 94 | 44.820 | 27.596 | 25.967 | 1.00 | 10.89 |
| ATOM | 1597 | CA | PRO | D | 94 | 43.757 | 28.594 | 26.172 | 1.00 | 10.92 |
| ATOM | 1598 | C | PRO | D | 94 | 43.959 | 29.439 | 27.445 | 1.00 | 13.89 |
| ATOM | 1599 | O | PRO | D | 94 | 44.529 | 28.930 | 28.444 | 1.00 | 13.64 |
| ATOM | 1600 | CB | PRO | D | 94 | 42.492 | 27.750 | 26.291 | 1.00 | 15.15 |
| ATOM | 1601 | CG | PRO | D | 94 | 42.839 | 26.445 | 25.629 | 1.00 | 18.73 |
| ATOM | 1602 | CD | PRO | D | 94 | 44.315 | 26.240 | 25.823 | 1.00 | 13.59 |
| ATOM | 1603 | N | ASP | D | 95 | 43.535 | 30.684 | 27.413 | 1.00 | 12.77 |
| ATOM | 1604 | CA | ASP | D | 95 | 43.665 | 31.614 | 28.524 | 1.00 | 11.85 |
| ATOM | 1605 | C | ASP | D | 95 | 43.174 | 30.951 | 29.847 | 1.00 | 12.73 |
| ATOM | 1606 | O | ASP | D | 95 | 43.865 | 31.103 | 30.918 | 1.00 | 14.23 |
| ATOM | 1607 | CB | ASP | D | 95 | 42.811 | 32.862 | 28.257 | 1.00 | 13.88 |
| ATOM | 1608 | CG | ASP | D | 95 | 42.966 | 33.903 | 29.322 | 1.00 | 16.93 |
| ATOM | 1609 | OD1 | ASP | D | 95 | 44.066 | 34.422 | 29.557 | 1.00 | 15.12 |
| ATOM | 1610 | OD2 | ASP | D | 95 | 41.944 | 34.159 | 30.004 | 1.00 | 25.27 |
| ATOM | 1611 | N | GLU | D | 96 | 42.037 | 30.280 | 29.777 | 1.00 | 11.92 |
| ATOM | 1612 | CA | GLU | D | 96 | 41.450 | 29.634 | 31.006 | 1.00 | 13.09 |
| ATOM | 1613 | C | GLU | D | 96 | 42.418 | 28.668 | 31.670 | 1.00 | 17.50 |
| ATOM | 1614 | O | GLU | D | 96 | 42.463 | 28.607 | 32.916 | 1.00 | 17.59 |
| ATOM | 1615 | CB | GLU | D | 96 | 40.194 | 28.900 | 30.623 | 1.00 | 15.73 |
| ATOM | 1616 | CG | GLU | D | 96 | 39.407 | 28.382 | 31.819 | 1.00 | 27.44 |
| ATOM | 1617 | CD | GLU | D | 96 | 39.718 | 26.953 | 32.150 | 1.00 | 46.48 |
| ATOM | 1618 | OE1 | GLU | D | 96 | 40.247 | 26.230 | 31.298 | 1.00 | 32.53 |
| ATOM | 1619 | OE2 | GLU | D | 96 | 39.416 | 26.541 | 33.300 | 1.00 | 50.29 |
| ATOM | 1620 | N | GLU | D | 97 | 43.184 | 27.904 | 30.898 | 1.00 | 13.12 |
| ATOM | 1621 | CA | GLU | D | 97 | 44.151 | 26.962 | 31.475 | 1.00 | 11.58 |
| ATOM | 1622 | C | GLU | D | 97 | 45.417 | 27.747 | 31.906 | 1.00 | 14.13 |
| ATOM | 1623 | O | GLU | D | 97 | 46.124 | 27.431 | 32.874 | 1.00 | 14.05 |
| ATOM | 1624 | CB | GLU | D | 97 | 44.553 | 25.876 | 30.429 | 1.00 | 10.79 |
| ATOM | 1625 | CG | GLU | D | 97 | 43.463 | 24.971 | 30.050 | 1.00 | 12.84 |
| ATOM | 1626 | CD | GLU | D | 97 | 43.862 | 23.894 | 29.037 | 1.00 | 16.10 |
| ATOM | 1627 | OE1 | GLU | D | 97 | 44.997 | 23.908 | 28.435 | 1.00 | 17.56 |
| ATOM | 1628 | OE2 | GLU | D | 97 | 43.042 | 22.981 | 28.897 | 1.00 | 19.58 |
| ATOM | 1629 | N | ALA | D | 98 | 45.828 | 28.763 | 31.147 | 1.00 | 11.26 |
| ATOM | 1630 | CA | ALA | D | 98 | 47.011 | 29.521 | 31.441 | 1.00 | 12.13 |
| ATOM | 1631 | C | ALA | D | 98 | 47.025 | 30.209 | 32.830 | 1.00 | 12.78 |
| ATOM | 1632 | O | ALA | D | 98 | 48.121 | 30.395 | 33.423 | 1.00 | 12.87 |
| ATOM | 1633 | CB | ALA | D | 98 | 47.161 | 30.609 | 30.303 | 1.00 | 13.93 |
| ATOM | 1634 | N | ARG | D | 99 | 45.795 | 30.577 | 33.268 | 1.00 | 13.12 |
| ATOM | 1635 | CA | ARG | D | 99 | 45.668 | 31.263 | 34.534 | 1.00 | 13.91 |
| ATOM | 1636 | C | ARG | D | 99 | 46.164 | 30.394 | 35.692 | 1.00 | 15.52 |
| ATOM | 1637 | O | ARG | D | 99 | 46.555 | 30.998 | 36.715 | 1.00 | 16.74 |
| ATOM | 1638 | CB | ARG | D | 99 | 44.232 | 31.694 | 34.717 | 1.00 | 13.81 |
| ATOM | 1639 | CG | ARG | D | 99 | 43.930 | 32.832 | 33.737 | 1.00 | 21.54 |
| ATOM | 1640 | CD | ARG | D | 99 | 42.544 | 33.302 | 33.768 | 1.00 | 31.31 |
| ATOM | 1641 | NE | ARG | D | 99 | 42.382 | 34.329 | 32.737 | 1.00 | 34.14 |
| ATOM | 1642 | CZ | ARG | D | 99 | 42.824 | 35.587 | 32.820 | 1.00 | 39.78 |
| ATOM | 1643 | NH1 | ARG | D | 99 | 43.448 | 36.028 | 33.912 | 1.00 | 39.29 |
| ATOM | 1644 | NH2 | ARG | D | 99 | 42.622 | 36.428 | 31.821 | 1.00 | 34.68 |
| ATOM | 1645 | N | THR | D | 100 | 46.189 | 29.072 | 35.553 | 1.00 | 12.99 |
| ATOM | 1646 | CA | THR | D | 100 | 46.668 | 28.209 | 36.674 | 1.00 | 13.08 |
| ATOM | 1647 | C | THR | D | 100 | 47.916 | 27.391 | 36.307 | 1.00 | 15.62 |
| ATOM | 1648 | O | THR | D | 100 | 48.408 | 26.541 | 37.068 | 1.00 | 16.66 |
| ATOM | 1649 | CB | THR | D | 100 | 45.537 | 27.276 | 37.099 | 1.00 | 15.79 |
| ATOM | 1650 | OG1 | THR | D | 100 | 45.017 | 26.550 | 35.988 | 1.00 | 14.58 |
| ATOM | 1651 | CG2 | THR | D | 100 | 44.344 | 28.091 | 37.708 | 1.00 | 15.05 |
| ATOM | 1652 | N | TRP | D | 101 | 48.490 | 27.635 | 35.105 | 1.00 | 14.25 |
| ATOM | 1653 | CA | TRP | D | 101 | 49.645 | 26.857 | 34.699 | 1.00 | 13.12 |
| ATOM | 1654 | C | TRP | D | 101 | 50.846 | 27.042 | 35.554 | 1.00 | 15.17 |
| ATOM | 1655 | O | TRP | D | 101 | 51.111 | 28.163 | 36.042 | 1.00 | 16.82 |
| ATOM | 1656 | CB | TRP | D | 101 | 49.970 | 27.286 | 33.191 | 1.00 | 11.79 |
| ATOM | 1657 | CG | TRP | D | 101 | 51.197 | 26.624 | 32.676 | 1.00 | 10.50 |
| ATOM | 1658 | CD1 | TRP | D | 101 | 52.416 | 27.164 | 32.527 | 1.00 | 12.40 |
| ATOM | 1659 | CD2 | TRP | D | 101 | 51.317 | 25.240 | 32.383 | 1.00 | 12.89 |
| ATOM | 1660 | NE1 | TRP | D | 101 | 53.292 | 26.208 | 32.121 | 1.00 | 12.65 |
| ATOM | 1661 | CE2 | TRP | D | 101 | 52.659 | 25.019 | 32.000 | 1.00 | 13.88 |
| ATOM | 1662 | CE3 | TRP | D | 101 | 50.419 | 24.168 | 32.362 | 1.00 | 15.74 |
| ATOM | 1663 | CZ2 | TRP | D | 101 | 53.144 | 23.769 | 31.624 | 1.00 | 16.20 |

-continued

Data Lists

| ATOM | 1664 | CZ3 | TRP | D | 101 | 50.898 | 22.888 | 32.009 | 1.00 | 19.25 |
| --- | --- | --- | --- | --- | --- | --- | --- | --- | --- | --- |
| ATOM | 1665 | CH2 | TRP | D | 101 | 52.266 | 22.699 | 31.649 | 1.00 | 19.62 |
| ATOM | 1666 | N | ARG | D | 102 | 51.613 | 25.952 | 35.714 | 1.00 | 15.08 |
| ATOM | 1667 | CA | ARG | D | 102 | 52.844 | 25.993 | 36.481 | 1.00 | 15.90 |
| ATOM | 1668 | C | ARG | D | 102 | 53.983 | 25.375 | 35.637 | 1.00 | 11.33 |
| ATOM | 1669 | O | ARG | D | 102 | 53.846 | 24.253 | 35.202 | 1.00 | 14.41 |
| ATOM | 1670 | CB | ARG | D | 102 | 52.703 | 25.128 | 37.779 | 1.00 | 18.89 |
| ATOM | 1671 | CG | ARG | D | 102 | 51.612 | 25.639 | 38.780 | 1.00 | 24.40 |
| ATOM | 1672 | CD | ARG | D | 102 | 51.559 | 24.821 | 40.096 | 1.00 | 22.77 |
| ATOM | 1673 | NE | ARG | D | 102 | 52.794 | 24.906 | 40.846 | 1.00 | 27.18 |
| ATOM | 1674 | CZ | ARG | D | 102 | 53.120 | 25.887 | 41.689 | 1.00 | 28.35 |
| ATOM | 1675 | NH1 | ARG | D | 102 | 52.313 | 26.911 | 41.893 | 1.00 | 23.60 |
| ATOM | 1676 | NH2 | ARG | D | 102 | 54.280 | 25.844 | 42.314 | 1.00 | 31.92 |
| ATOM | 1677 | N | PRO | D | 103 | 55.088 | 26.106 | 35.497 | 1.00 | 12.26 |
| ATOM | 1678 | CA | PRO | D | 103 | 56.234 | 25.566 | 34.721 | 1.00 | 13.54 |
| ATOM | 1679 | C | PRO | D | 103 | 57.047 | 24.562 | 35.500 | 1.00 | 17.32 |
| ATOM | 1680 | O | PRO | D | 103 | 56.956 | 24.539 | 36.792 | 1.00 | 16.83 |
| ATOM | 1681 | CB | PRO | D | 103 | 57.114 | 26.794 | 34.506 | 1.00 | 14.38 |
| ATOM | 1682 | CG | PRO | D | 103 | 56.894 | 27.640 | 35.767 | 1.00 | 22.25 |
| ATOM | 1683 | CD | PRO | D | 103 | 55.363 | 27.456 | 36.011 | 1.00 | 16.38 |
| ATOM | 1684 | N | ASN | D | 104 | 57.859 | 23.759 | 34.781 | 1.00 | 13.82 |
| ATOM | 1685 | CA | ASN | D | 104 | 58.744 | 22.758 | 35.377 | 1.00 | 12.48 |
| ATOM | 1686 | C | ASN | D | 104 | 60.121 | 23.389 | 35.504 | 1.00 | 19.52 |
| ATOM | 1687 | O | ASN | D | 104 | 60.775 | 23.647 | 34.460 | 1.00 | 16.91 |
| ATOM | 1688 | CB | ASN | D | 104 | 58.798 | 21.477 | 34.539 | 1.00 | 13.72 |
| ATOM | 1689 | CG | ASN | D | 104 | 57.470 | 20.884 | 34.345 | 1.00 | 19.91 |
| ATOM | 1690 | OD1 | ASN | D | 104 | 56.775 | 20.587 | 35.338 | 1.00 | 17.05 |
| ATOM | 1691 | ND2 | ASN | D | 104 | 57.032 | 20.718 | 33.087 | 1.00 | 20.70 |
| ATOM | 1692 | N | VAL | D | 105 | 60.613 | 23.649 | 36.722 | 1.00 | 17.67 |
| ATOM | 1693 | CA | VAL | D | 105 | 61.885 | 24.295 | 36.850 | 1.00 | 16.36 |
| ATOM | 1694 | C | VAL | D | 105 | 62.907 | 23.448 | 37.546 | 1.00 | 21.93 |
| ATOM | 1695 | O | VAL | D | 105 | 62.601 | 22.863 | 38.602 | 1.00 | 22.45 |
| ATOM | 1696 | CB | VAL | D | 105 | 61.775 | 25.635 | 37.634 | 1.00 | 18.76 |
| ATOM | 1697 | CG1 | VAL | D | 105 | 63.106 | 26.314 | 37.743 | 1.00 | 19.86 |
| ATOM | 1698 | CG2 | VAL | D | 105 | 60.642 | 26.573 | 37.039 | 1.00 | 19.00 |
| ATOM | 1699 | N | ALA | D | 106 | 64.102 | 23.365 | 36.974 | 1.00 | 20.08 |
| ATOM | 1700 | CA | ALA | D | 106 | 65.232 | 22.610 | 37.580 | 1.00 | 19.28 |
| ATOM | 1701 | C | ALA | D | 106 | 66.330 | 23.614 | 37.866 | 1.00 | 22.54 |
| ATOM | 1702 | O | ALA | D | 106 | 66.699 | 24.410 | 37.000 | 1.00 | 20.02 |
| ATOM | 1703 | CB | ALA | D | 106 | 65.733 | 21.552 | 36.689 | 1.00 | 19.59 |
| ATOM | 1704 | N | TYR | D | 107 | 66.894 | 23.609 | 39.098 | 1.00 | 21.77 |
| ATOM | 1705 | CA | TYR | D | 107 | 67.952 | 24.556 | 39.469 | 1.00 | 22.90 |
| ATOM | 1706 | C | TYR | D | 107 | 69.287 | 23.841 | 39.546 | 1.00 | 25.98 |
| ATOM | 1707 | O | TYR | D | 107 | 69.335 | 22.668 | 39.882 | 1.00 | 25.22 |
| ATOM | 1708 | CB | TYR | D | 107 | 67.646 | 25.222 | 40.818 | 1.00 | 25.00 |
| ATOM | 1709 | CG | TYR | D | 107 | 66.482 | 26.167 | 40.752 | 1.00 | 24.25 |
| ATOM | 1710 | CD1 | TYR | D | 107 | 66.651 | 27.484 | 40.330 | 1.00 | 26.30 |
| ATOM | 1711 | CD2 | TYR | D | 107 | 65.202 | 25.733 | 41.102 | 1.00 | 25.93 |
| ATOM | 1712 | CE1 | TYR | D | 107 | 65.588 | 28.344 | 40.270 | 1.00 | 29.13 |
| ATOM | 1713 | CE2 | TYR | D | 107 | 64.125 | 26.600 | 41.056 | 1.00 | 25.26 |
| ATOM | 1714 | CZ | TYR | D | 107 | 64.325 | 27.900 | 40.658 | 1.00 | 31.88 |
| ATOM | 1715 | OH | TYR | D | 107 | 63.238 | 28.756 | 40.594 | 1.00 | 35.96 |
| ATOM | 1716 | N | PHE | D | 108 | 70.356 | 24.556 | 39.194 | 1.00 | 26.53 |
| ATOM | 1717 | CA | PHE | D | 108 | 71.677 | 23.953 | 39.185 | 1.00 | 25.71 |
| ATOM | 1718 | C | PHE | D | 108 | 72.739 | 24.852 | 39.791 | 1.00 | 31.22 |
| ATOM | 1719 | O | PHE | D | 108 | 72.611 | 26.079 | 39.860 | 1.00 | 28.62 |
| ATOM | 1720 | CB | PHE | D | 108 | 72.145 | 23.669 | 37.719 | 1.00 | 25.29 |
| ATOM | 1721 | CG | PHE | D | 108 | 71.302 | 22.678 | 36.974 | 1.00 | 21.78 |
| ATOM | 1722 | CD1 | PHE | D | 108 | 70.101 | 23.072 | 36.357 | 1.00 | 19.05 |
| ATOM | 1723 | CD2 | PHE | D | 108 | 71.708 | 21.360 | 36.850 | 1.00 | 20.20 |
| ATOM | 1724 | CE1 | PHE | D | 108 | 69.333 | 22.156 | 35.675 | 1.00 | 19.07 |
| ATOM | 1725 | CE2 | PHE | D | 108 | 70.965 | 20.441 | 36.163 | 1.00 | 22.77 |
| ATOM | 1726 | CZ | PHE | D | 108 | 69.733 | 20.879 | 35.546 | 1.00 | 20.24 |
| ATOM | 1727 | N | GLU | D | 109 | 73.815 | 24.196 | 40.198 | 1.00 | 30.97 |
| ATOM | 1728 | CA | GLU | D | 109 | 74.970 | 24.855 | 40.797 | 1.00 | 32.90 |
| ATOM | 1729 | C | GLU | D | 109 | 76.205 | 24.037 | 40.466 | 1.00 | 33.93 |
| ATOM | 1730 | O | GLU | D | 109 | 76.114 | 22.898 | 40.055 | 1.00 | 30.42 |
| ATOM | 1731 | CB | GLU | D | 109 | 74.826 | 24.827 | 42.326 | 1.00 | 35.17 |
| ATOM | 1732 | CG | GLU | D | 109 | 74.907 | 23.400 | 42.875 | 1.00 | 44.89 |
| ATOM | 1733 | CD | GLU | D | 109 | 74.607 | 23.314 | 44.352 | 1.00 | 68.70 |
| ATOM | 1734 | OE1 | GLU | D | 109 | 74.608 | 24.376 | 45.020 | 1.00 | 58.38 |
| ATOM | 1735 | OE2 | GLU | D | 109 | 74.358 | 22.182 | 44.842 | 1.00 | 66.11 |
| ATOM | 1736 | N | GLY | D | 110 | 77.379 | 24.614 | 40.702 | 1.00 | 33.06 |
| ATOM | 1737 | CA | GLY | D | 110 | 78.616 | 23.899 | 40.454 | 1.00 | 32.35 |
| ATOM | 1738 | C | GLY | D | 110 | 78.689 | 23.323 | 39.056 | 1.00 | 35.50 |
| ATOM | 1739 | O | GLY | D | 110 | 78.449 | 24.039 | 38.072 | 1.00 | 35.53 |
| ATOM | 1740 | N | ASP | D | 111 | 79.074 | 22.063 | 38.971 | 1.00 | 29.97 |

-continued

Data Lists

| | | | | | | | | | |
|---|---|---|---|---|---|---|---|---|---|
| ATOM | 1741 | CA | ASP | D | 111 | 79.232 | 21.400 | 37.693 | 1.00 | 31.05 |
| ATOM | 1742 | C | ASP | D | 111 | 77.960 | 20.672 | 37.285 | 1.00 | 30.82 |
| ATOM | 1743 | O | ASP | D | 111 | 77.886 | 19.418 | 37.225 | 1.00 | 28.67 |
| ATOM | 1744 | CB | ASP | D | 111 | 80.465 | 20.495 | 37.717 | 1.00 | 33.49 |
| ATOM | 1745 | CG | ASP | D | 111 | 80.534 | 19.558 | 36.541 | 1.00 | 44.31 |
| ATOM | 1746 | OD1 | ASP | D | 111 | 80.219 | 19.999 | 35.400 | 1.00 | 46.12 |
| ATOM | 1747 | OD2 | ASP | D | 111 | 80.882 | 18.378 | 36.760 | 1.00 | 41.60 |
| ATOM | 1748 | N | ASN | D | 112 | 76.959 | 21.480 | 36.967 | 1.00 | 27.75 |
| ATOM | 1749 | CA | ASN | D | 112 | 75.682 | 20.951 | 36.556 | 1.00 | 25.85 |
| ATOM | 1750 | C | ASN | D | 112 | 75.072 | 20.013 | 37.556 | 1.00 | 28.56 |
| ATOM | 1751 | O | ASN | D | 112 | 74.553 | 18.956 | 37.211 | 1.00 | 24.07 |
| ATOM | 1752 | CB | ASN | D | 112 | 75.744 | 20.367 | 35.149 | 1.00 | 25.14 |
| ATOM | 1753 | CG | ASN | D | 112 | 75.975 | 21.425 | 34.158 | 1.00 | 19.48 |
| ATOM | 1754 | OD1 | ASN | D | 112 | 75.875 | 22.600 | 34.511 | 1.00 | 22.70 |
| ATOM | 1755 | ND2 | ASN | D | 112 | 76.334 | 21.051 | 32.918 | 1.00 | 21.36 |
| ATOM | 1756 | N | GLU | D | 413 | 75.142 | 20.436 | 38.818 | 1.00 | 27.11 |
| ATOM | 1757 | CA | GLU | D | 113 | 74.556 | 19.639 | 39.900 | 1.00 | 28.84 |
| ATOM | 1758 | C | GLU | D | 113 | 73.181 | 20.182 | 40.147 | 1.00 | 27.72 |
| ATOM | 1759 | O | GLU | D | 113 | 73.039 | 21.365 | 40.555 | 1.00 | 26.82 |
| ATOM | 1760 | CB | GLU | D | 113 | 75.388 | 19.695 | 41.177 | 1.00 | 30.87 |
| ATOM | 1761 | CG | GLU | D | 113 | 76.724 | 18.975 | 41.092 | 1.00 | 37.93 |
| ATOM | 1762 | CD | GLU | D | 113 | 76.692 | 17.429 | 41.016 | 1.00 | 59.74 |
| ATOM | 1763 | OE1 | GLU | D | 113 | 75.612 | 16.786 | 40.882 | 1.00 | 46.50 |
| ATOM | 1764 | OE2 | GLU | D | 113 | 77.814 | 16.868 | 41.082 | 1.00 | 59.60 |
| ATOM | 1765 | N | MET | D | 114 | 72.194 | 19.333 | 39.866 | 1.00 | 27.25 |
| ATOM | 1766 | CA | MET | D | 114 | 70.781 | 19.680 | 40.012 | 1.00 | 32.32 |
| ATOM | 1767 | C | MET | D | 114 | 70.391 | 19.716 | 41.452 | 1.00 | 39.86 |
| ATOM | 1768 | O | MET | D | 114 | 70.527 | 18.703 | 42.145 | 1.00 | 40.94 |
| ATOM | 1769 | CB | MET | D | 114 | 69.889 | 18.646 | 39.319 | 1.00 | 34.33 |
| ATOM | 1770 | CG | MET | D | 114 | 68.468 | 19.136 | 39.198 | 1.00 | 36.77 |
| ATOM | 1771 | SD | MET | D | 114 | 67.314 | 17.889 | 38.726 | 1.00 | 39.76 |
| ATOM | 1772 | CE | MET | D | 114 | 67.664 | 17.803 | 36.803 | 1.00 | 31.31 |
| ATOM | 1773 | N | LYS | D | 115 | 69.893 | 20.851 | 41.915 | 1.00 | 37.37 |
| ATOM | 1774 | CA | LYS | D | 115 | 69.488 | 20.983 | 43.324 | 1.00 | 38.95 |
| ATOM | 1775 | C | LYS | D | 115 | 68.169 | 20.274 | 43.622 | 1.00 | 54.19 |
| ATOM | 1776 | O | LYS | D | 115 | 67.301 | 20.213 | 42.705 | 1.00 | 51.66 |
| ATOM | 1777 | CB | LYS | D | 115 | 69.362 | 22.437 | 43.715 | 1.00 | 41.43 |
| ATOM | 1778 | CG | LYS | D | 115 | 70.655 | 23.235 | 43.740 | 1.00 | 47.27 |
| ATOM | 1779 | CD | LYS | D | 115 | 70.334 | 24.681 | 44.041 | 1.00 | 43.78 |
| ATOM | 1780 | CE | LYS | D | 115 | 71.439 | 25.627 | 43.660 | 1.00 | 55.99 |
| ATOM | 1781 | NZ | LYS | D | 115 | 71.276 | 26.945 | 44.363 | 1.00 | 62.59 |
| ATOM | 1783 | OW0 | WAT | G | 1 | 50.690 | 34.966 | 25.739 | 1.00 | 12.46 |
| ATOM | 1784 | OW0 | WAT | G | 2 | 65.358 | 37.341 | 23.976 | 1.00 | 14.50 |
| ATOM | 1785 | OW0 | WAT | G | 3 | 53.112 | 36.553 | 25.090 | 1.00 | 12.96 |
| ATOM | 1786 | OW0 | WAT | G | 4 | 59.501 | 34.869 | 25.680 | 1.00 | 16.21 |
| ATOM | 1787 | OW0 | WAT | G | 5 | 42.457 | 44.697 | 14.900 | 1.00 | 16.96 |
| ATOM | 1788 | OW0 | WAT | G | 6 | 62.264 | 42.848 | 18.466 | 1.00 | 12.78 |
| ATOM | 1789 | OW0 | WAT | G | 7 | 60.346 | 41.648 | 20.211 | 1.00 | 14.43 |
| ATOM | 1790 | OW0 | WAT | G | 8 | 49.376 | 37.618 | 12.957 | 1.00 | 11.87 |
| ATOM | 1791 | OW0 | WAT | G | 9 | 43.082 | 43.742 | 4.464 | 1.00 | 15.75 |
| ATOM | 1792 | OW0 | WAT | G | 10 | 57.736 | 40.739 | 19.570 | 1.00 | 18.14 |
| ATOM | 1793 | OW0 | WAT | G | 11 | 53.768 | 31.148 | 15.023 | 1.00 | 18.49 |
| ATOM | 1794 | OW0 | WAT | G | 12 | 46.397 | 19.640 | 8.284 | 1.00 | 20.49 |
| ATOM | 1795 | OW0 | WAT | G | 13 | 49.398 | 32.153 | 35.416 | 1.00 | 15.58 |
| ATOM | 1796 | OW0 | WAT | G | 14 | 52.292 | 38.335 | 12.919 | 1.00 | 12.77 |
| ATOM | 1797 | OW0 | WAT | G | 15 | 55.884 | 41.199 | 17.565 | 1.00 | 17.15 |
| ATOM | 1798 | OW0 | WAT | G | 16 | 68.646 | 41.874 | 7.890 | 1.00 | 18.45 |
| ATOM | 1799 | OW0 | WAT | G | 17 | 60.172 | 36.501 | 11.568 | 1.00 | 20.08 |
| ATOM | 1800 | OW0 | WAT | G | 18 | 52.295 | 33.705 | 18.070 | 1.00 | 19.24 |
| ATOM | 1801 | OW0 | WAT | G | 19 | 43.878 | 46.628 | 8.547 | 1.00 | 18.83 |
| ATOM | 1802 | OW0 | WAT | G | 20 | 44.503 | 23.424 | 0.796 | 1.00 | 17.45 |
| ATOM | 1803 | OW0 | WAT | G | 21 | 64.440 | 48.899 | 19.979 | 1.00 | 18.93 |
| ATOM | 1804 | OW0 | WAT | G | 22 | 71.193 | 48.088 | 36.959 | 1.00 | 16.89 |
| ATOM | 1805 | OW0 | WAT | G | 23 | 49.349 | 33.334 | 14.599 | 1.00 | 20.32 |
| ATOM | 1806 | OW0 | WAT | G | 24 | 71.024 | 49.740 | 30.410 | 1.00 | 19.88 |
| ATOM | 1807 | OW0 | WAT | G | 25 | 42.979 | 46.992 | 11.153 | 1.00 | 17.12 |
| ATOM | 1808 | OW0 | WAT | G | 26 | 38.559 | 42.979 | 23.184 | 1.00 | 21.81 |
| ATOM | 1809 | OW0 | WAT | G | 27 | 53.263 | 26.900 | 13.822 | 1.00 | 15.81 |
| ATOM | 1810 | OW0 | WAT | G | 28 | 71.768 | 47.157 | 29.190 | 1.00 | 21.31 |
| ATOM | 1811 | OW0 | WAT | G | 29 | 50.910 | 52.836 | 39.909 | 1.00 | 21.20 |
| ATOM | 1812 | OW0 | WAT | G | 30 | 51.612 | 34.739 | 20.749 | 1.00 | 21.50 |
| ATOM | 1813 | OW0 | WAT | G | 31 | 47.760 | 55.722 | 0.508 | 1.00 | 26.79 |
| ATOM | 1814 | OW0 | WAT | G | 32 | 57.250 | 54.959 | 34.792 | 1.00 | 18.33 |
| ATOM | 1815 | OW0 | WAT | G | 33 | 65.008 | 51.887 | 42.170 | 1.00 | 21.45 |
| ATOM | 1816 | OW0 | WAT | G | 34 | 71.716 | 46.104 | 34.998 | 1.00 | 19.77 |
| ATOM | 1817 | OW0 | WAT | G | 35 | 56.789 | 36.428 | 13.221 | 1.00 | 19.13 |
| ATOM | 1818 | OW0 | WAT | G | 36 | 69.004 | 52.586 | 13.271 | 1.00 | 25.88 |

-continued

Data Lists

| | | | | | | | | | |
|---|---|---|---|---|---|---|---|---|---|
| ATOM | 1819 | OW0 | WAT | G | 37 | 36.912 | 40.900 | 19.049 | 1.00 | 24.35 |
| ATOM | 1820 | OW0 | WAT | G | 38 | 37.939 | 34.172 | 11.858 | 1.00 | 21.53 |
| ATOM | 1821 | OW0 | WAT | G | 39 | 50.673 | 48.829 | 42.462 | 1.00 | 17.05 |
| ATOM | 1822 | OW0 | WAT | G | 40 | 40.211 | 49.838 | 5.952 | 1.00 | 26.29 |
| ATOM | 1823 | OW0 | WAT | G | 41 | 46.904 | 53.941 | 31.892 | 1.00 | 26.19 |
| ATOM | 1824 | OW0 | WAT | G | 42 | 69.397 | 54.598 | 32.144 | 1.00 | 21.59 |
| ATOM | 1825 | OW0 | WAT | G | 43 | 42.745 | 49.698 | 11.329 | 1.00 | 28.13 |
| ATOM | 1826 | OW0 | WAT | G | 44 | 69.038 | 43.121 | 14.087 | 1.00 | 27.79 |
| ATOM | 1827 | OW0 | WAT | G | 45 | 37.919 | 36.710 | 9.225 | 1.00 | 22.42 |
| ATOM | 1828 | OW0 | WAT | G | 46 | 62.878 | 47.097 | 42.928 | 1.00 | 24.58 |
| ATOM | 1829 | OW0 | WAT | G | 47 | 39.794 | 32.943 | 21.142 | 1.00 | 24.59 |
| ATOM | 1830 | OW0 | WAT | G | 48 | 45.700 | 54.348 | 15.115 | 1.00 | 34.46 |
| ATOM | 1831 | OW0 | WAT | G | 49 | 59.403 | 48.140 | 46.193 | 1.00 | 20.52 |
| ATOM | 1832 | OW0 | WAT | G | 50 | 60.684 | 31.160 | 37.777 | 1.00 | 29.82 |
| ATOM | 1833 | OW0 | WAT | G | 51 | 49.475 | 50.666 | 40.460 | 1.00 | 22.18 |
| ATOM | 1834 | OW0 | WAT | G | 52 | 39.653 | 24.604 | 5.289 | 1.00 | 17.35 |
| ATOM | 1835 | OW0 | WAT | G | 53 | 59.252 | 56.969 | 34.916 | 1.00 | 19.50 |
| ATOM | 1836 | OW0 | WAT | G | 54 | 69.096 | 53.771 | 10.568 | 1.00 | 27.87 |
| ATOM | 1837 | OW0 | WAT | G | 55 | 66.440 | 38.568 | 14.149 | 1.00 | 30.16 |
| ATOM | 1838 | OW0 | WAT | G | 56 | 65.406 | 57.383 | 14.154 | 1.00 | 26.01 |
| ATOM | 1839 | OW0 | WAT | G | 57 | 41.137 | 23.132 | 3.518 | 1.00 | 23.54 |
| ATOM | 1840 | OW0 | WAT | G | 58 | 49.156 | 50.953 | 21.456 | 1.00 | 30.99 |
| ATOM | 1841 | OW0 | WAT | G | 59 | 57.860 | 36.323 | 24.017 | 1.00 | 20.83 |
| ATOM | 1842 | OW0 | WAT | G | 60 | 57.496 | 33.962 | 11.899 | 1.00 | 21.39 |
| ATOM | 1843 | OW0 | WAT | G | 61 | 66.579 | 48.294 | 43.413 | 1.00 | 24.77 |
| ATOM | 1844 | OW0 | WAT | G | 62 | 54.871 | 38.598 | 18.657 | 1.00 | 25.45 |
| ATOM | 1845 | OW0 | WAT | G | 63 | 50.967 | 51.195 | 43.999 | 1.00 | 22.75 |
| ATOM | 1846 | OW0 | WAT | G | 64 | 44.140 | 29.593 | 6.643 | 1.00 | 21.96 |
| ATOM | 1847 | OW0 | WAT | G | 65 | 43.548 | 39.803 | 29.673 | 1.00 | 26.57 |
| ATOM | 1848 | OW0 | WAT | G | 66 | 36.492 | 44.150 | 10.666 | 1.00 | 24.57 |
| ATOM | 1849 | OW0 | WAT | G | 67 | 72.566 | 46.343 | 31.771 | 1.00 | 22.95 |
| ATOM | 1850 | OW0 | WAT | G | 68 | 48.293 | 59.724 | 10.894 | 1.00 | 26.76 |
| ATOM | 1851 | OW0 | WAT | G | 69 | 62.460 | 39.930 | 21.422 | 1.00 | 26.61 |
| ATOM | 1852 | OW0 | WAT | G | 70 | 56.208 | 39.397 | 15.274 | 1.00 | 20.01 |
| ATOM | 1853 | OW0 | WAT | G | 71 | 72.875 | 42.561 | 38.908 | 1.00 | 36.97 |
| ATOM | 1854 | OW0 | WAT | G | 72 | 68.365 | 44.087 | 20.849 | 1.00 | 29.26 |
| ATOM | 1855 | OW0 | WAT | G | 73 | 43.058 | 49.160 | 23.577 | 1.00 | 29.45 |
| ATOM | 1856 | OW0 | WAT | G | 74 | 70.366 | 27.891 | 40.490 | 1.00 | 33.14 |
| ATOM | 1857 | OW0 | WAT | G | 75 | 37.060 | 33.614 | 18.493 | 1.00 | 25.03 |
| ATOM | 1858 | OW0 | WAT | G | 76 | 43.652 | 50.031 | 19.379 | 1.00 | 36.34 |
| ATOM | 1859 | OW0 | WAT | G | 77 | 70.513 | 54.847 | 7.916 | 1.00 | 33.66 |
| ATOM | 1860 | OW0 | WAT | G | 78 | 74.648 | 42.946 | 34.418 | 1.00 | 46.06 |
| ATOM | 1861 | OW0 | WAT | G | 79 | 44.747 | 49.850 | −0.304 | 1.00 | 26.95 |
| ATOM | 1862 | OW0 | WAT | G | 80 | 40.824 | 41.298 | 27.887 | 1.00 | 25.17 |
| ATOM | 1863 | OW0 | WAT | G | 81 | 41.107 | 45.630 | 12.507 | 1.00 | 25.41 |
| ATOM | 1864 | OW0 | WAT | G | 82 | 57.806 | 41.126 | 45.667 | 1.00 | 28.19 |
| ATOM | 1865 | OW0 | WAT | G | 83 | 51.183 | 54.617 | −2.727 | 1.00 | 32.75 |
| ATOM | 1866 | OW0 | WAT | G | 84 | 43.186 | 49.347 | 27.882 | 1.00 | 28.33 |
| ATOM | 1867 | OW0 | WAT | G | 85 | 61.540 | 49.575 | −4.582 | 1.00 | 35.95 |
| ATOM | 1868 | OW0 | WAT | G | 86 | 50.267 | 17.542 | 8.910 | 1.00 | 30.16 |
| ATOM | 1869 | OW0 | WAT | G | 87 | 36.217 | 32.811 | 13.941 | 1.00 | 28.34 |
| ATOM | 1870 | OW0 | WAT | G | 88 | 72.058 | 52.836 | 10.622 | 1.00 | 45.57 |
| ATOM | 1871 | OW0 | WAT | G | 89 | 61.348 | 58.887 | 3.805 | 1.00 | 30.95 |
| ATOM | 1872 | OW0 | WAT | G | 90 | 48.622 | 56.983 | 14.003 | 1.00 | 31.75 |
| ATOM | 1873 | OW0 | WAT | G | 91 | 51.936 | 33.480 | 13.709 | 1.00 | 26.64 |
| ATOM | 1874 | OW0 | WAT | G | 92 | 51.875 | 46.258 | −5.376 | 1.00 | 34.61 |
| ATOM | 1875 | OW0 | WAT | G | 93 | 42.359 | 53.407 | 10.255 | 1.00 | 30.41 |
| ATOM | 1876 | OW0 | WAT | G | 94 | 52.890 | 57.749 | 15.136 | 1.00 | 30.22 |
| ATOM | 1877 | OW0 | WAT | G | 95 | 58.430 | 56.302 | 24.467 | 1.00 | 26.47 |
| ATOM | 1878 | OW0 | WAT | G | 96 | 37.197 | 41.147 | 21.811 | 1.00 | 24.52 |
| ATOM | 1879 | OW0 | WAT | G | 97 | 52.686 | 23.652 | −1.094 | 1.00 | 25.58 |
| ATOM | 1880 | OW0 | WAT | G | 98 | 43.317 | 41.529 | 34.451 | 1.00 | 35.83 |
| ATOM | 1881 | OW0 | WAT | G | 99 | 50.916 | 40.421 | 46.697 | 1.00 | 31.62 |
| ATOM | 1882 | OW0 | WAT | G | 100 | 59.444 | 53.045 | −1.297 | 1.00 | 35.13 |
| ATOM | 1883 | OW0 | WAT | G | 101 | 54.344 | 37.059 | 14.071 | 1.00 | 25.37 |
| ATOM | 1884 | OW0 | WAT | G | 102 | 39.161 | 35.171 | 23.645 | 1.00 | 22.49 |
| ATOM | 1885 | OW0 | WAT | G | 103 | 48.196 | 28.696 | 16.212 | 1.00 | 22.74 |
| ATOM | 1886 | OW0 | WAT | G | 104 | 51.803 | 31.025 | 19.010 | 1.00 | 23.17 |
| ATOM | 1887 | OW0 | WAT | G | 105 | 50.671 | 37.681 | 42.927 | 1.00 | 29.64 |
| ATOM | 1888 | OW0 | WAT | G | 106 | 62.180 | 51.664 | −1.624 | 1.00 | 34.04 |
| ATOM | 1889 | OW0 | WAT | G | 107 | 52.524 | 59.538 | 42.266 | 1.00 | 35.09 |
| ATOM | 1890 | OW0 | WAT | G | 108 | 46.932 | 49.006 | 21.391 | 1.00 | 25.94 |
| ATOM | 1891 | OW0 | WAT | G | 109 | 37.499 | 38.570 | 22.800 | 1.00 | 26.50 |
| ATOM | 1892 | OW0 | WAT | G | 110 | 72.898 | 50.305 | 27.829 | 1.00 | 30.56 |
| ATOM | 1893 | OW0 | WAT | G | 111 | 67.993 | 56.760 | 5.901 | 1.00 | 29.70 |
| ATOM | 1894 | OW0 | WAT | G | 112 | 48.644 | 53.571 | −1.398 | 1.00 | 35.84 |
| ATOM | 1895 | OW0 | WAT | G | 113 | 58.963 | 38.275 | 42.967 | 1.00 | 30.25 |

-continued

Data Lists

| | | | | | | | | | |
|---|---|---|---|---|---|---|---|---|---|
| ATOM | 1896 | OW0 | WAT | G | 114 | 48.644 | 29.728 | 18.792 | 1.00 | 30.45 |
| ATOM | 1897 | OW0 | WAT | G | 115 | 42.373 | 28.434 | 9.504 | 1.00 | 30.65 |
| ATOM | 1898 | OW0 | WAT | G | 116 | 48.337 | 17.998 | 4.927 | 1.00 | 26.85 |
| ATOM | 1899 | OW0 | WAT | G | 117 | 43.367 | 57.024 | 0.108 | 1.00 | 36.26 |
| ATOM | 1900 | OW0 | WAT | G | 118 | 55.991 | 35.183 | 42.088 | 1.00 | 33.36 |
| ATOM | 1901 | OW0 | WAT | G | 119 | 55.166 | 18.825 | 3.751 | 1.00 | 39.06 |
| ATOM | 1902 | OW0 | WAT | G | 120 | 36.538 | 34.658 | 16.002 | 1.00 | 23.39 |
| ATOM | 1903 | OW0 | WAT | G | 121 | 38.971 | 45.277 | 10.960 | 1.00 | 32.00 |
| ATOM | 1904 | OW0 | WAT | G | 122 | 45.394 | 39.705 | 40.673 | 1.00 | 28.95 |
| ATOM | 1905 | OW0 | WAT | G | 123 | 64.660 | 56.850 | 28.096 | 1.00 | 31.43 |
| ATOM | 1906 | OW0 | WAT | G | 124 | 31.495 | 39.706 | 12.940 | 1.00 | 30.11 |
| ATOM | 1907 | OW0 | WAT | G | 125 | 66.898 | 41.660 | 19.788 | 1.00 | 37.52 |
| ATOM | 1908 | OW0 | WAT | G | 126 | 59.279 | 62.353 | 6.022 | 1.00 | 30.85 |
| ATOM | 1909 | OW0 | WAT | G | 127 | 54.862 | 34.329 | 17.654 | 1.00 | 28.43 |
| ATOM | 1910 | OW0 | WAT | G | 128 | 46.944 | 36.876 | −2.147 | 1.00 | 28.17 |
| ATOM | 1911 | OW0 | WAT | G | 129 | 47.374 | 18.007 | 2.535 | 1.00 | 36.60 |
| ATOM | 1912 | OW0 | WAT | G | 130 | 44.808 | 50.361 | 22.031 | 1.00 | 29.95 |
| ATOM | 1913 | OW0 | WAT | G | 131 | 56.071 | 58.293 | 30.768 | 1.00 | 29.87 |
| ATOM | 1914 | OW0 | WAT | G | 132 | 39.948 | 33.299 | 8.889 | 1.00 | 43.00 |
| ATOM | 1917 | OW0 | WAT | G | 135 | 62.136 | 38.451 | 12.117 | 1.00 | 15.27 |
| ATOM | 1918 | OW0 | WAT | G | 136 | 57.446 | 61.036 | 34.612 | 1.00 | 23.04 |
| ATOM | 1919 | OW0 | WAT | G | 137 | 55.835 | 37.709 | 21.070 | 1.00 | 20.63 |
| ATOM | 1920 | OW0 | WAT | G | 138 | 62.428 | 40.009 | 14.530 | 1.00 | 34.20 |
| ATOM | 1921 | OW0 | WAT | G | 139 | 62.638 | 59.963 | 30.173 | 1.00 | 31.10 |
| ATOM | 1922 | OW0 | WAT | G | 140 | 55.220 | 36.878 | 16.564 | 1.00 | 26.78 |
| ATOM | 1923 | OW0 | WAT | G | 141 | 53.791 | 35.442 | 22.528 | 1.00 | 28.89 |
| ATOM | 1924 | OW0 | WAT | G | 142 | 64.950 | 39.916 | 20.459 | 1.00 | 30.25 |
| ATOM | 1925 | OW0 | WAT | G | 143 | 60.864 | 56.504 | 38.809 | 1.00 | 27.10 |
| ATOM | 1926 | OW0 | WAT | G | 144 | 50.834 | 36.062 | −3.236 | 1.00 | 24.20 |
| ATOM | 1927 | OW0 | WAT | G | 145 | 57.988 | 31.870 | 13.658 | 1.00 | 27.16 |
| ATOM | 1928 | OW0 | WAT | G | 146 | 59.420 | 50.371 | 43.012 | 1.00 | 27.11 |
| ATOM | 1929 | OW0 | WAT | G | 147 | 41.507 | 31.122 | 20.116 | 1.00 | 27.47 |
| ATOM | 1930 | OW0 | WAT | G | 148 | 60.586 | 52.675 | 43.032 | 1.00 | 29.71 |
| ATOM | 1931 | OW0 | WAT | G | 149 | 46.395 | 26.704 | 16.386 | 1.00 | 36.67 |
| ATOM | 1932 | OW0 | WAT | G | 150 | 65.273 | 33.456 | 33.695 | 1.00 | 30.16 |
| ATOM | 1933 | OW0 | WAT | G | 151 | 64.591 | 41.448 | 18.391 | 1.00 | 28.63 |
| ATOM | 1934 | OW0 | WAT | G | 152 | 48.864 | 29.166 | −5.087 | 1.00 | 26.64 |
| ATOM | 1935 | OW0 | WAT | G | 153 | 62.622 | 58.231 | 27.208 | 1.00 | 34.13 |
| ATOM | 1936 | OW0 | WAT | G | 154 | 61.506 | 38.693 | 18.376 | 1.00 | 48.10 |
| ATOM | 1937 | OW0 | WAT | G | 155 | 56.258 | 32.027 | 15.818 | 1.00 | 40.67 |
| ATOM | 1938 | OW0 | WAT | G | 156 | 58.824 | 38.296 | 18.235 | 1.00 | 34.94 |
| ATOM | 1939 | OW0 | WAT | G | 157 | 53.978 | 29.606 | 39.376 | 1.00 | 38.68 |
| ATOM | 1940 | OW0 | WAT | G | 158 | 53.182 | 56.416 | 29.461 | 1.00 | 25.79 |
| ATOM | 1941 | OW0 | WAT | G | 159 | 49.085 | 39.844 | −3.201 | 1.00 | 29.14 |
| ATOM | 1942 | OW0 | WAT | G | 160 | 60.344 | 34.232 | 21.770 | 1.00 | 38.25 |
| ATOM | 1943 | OW0 | WAT | G | 161 | 51.797 | 60.535 | −5.207 | 1.00 | 32.32 |
| ATOM | 1944 | OW0 | WAT | G | 162 | 48.186 | 38.211 | 36.506 | 1.00 | 28.29 |
| ATOM | 1945 | OW0 | WAT | G | 163 | 58.462 | 37.470 | 15.660 | 1.00 | 45.25 |
| ATOM | 1946 | OW0 | WAT | G | 164 | 45.851 | 29.690 | 18.302 | 1.00 | 28.59 |
| ATOM | 1947 | OW0 | WAT | G | 165 | 64.873 | 40.315 | 16.036 | 1.00 | 36.40 |
| ATOM | 1948 | OW0 | WAT | G | 166 | 59.897 | 58.114 | 1.470 | 1.00 | 36.57 |
| ATOM | 1949 | OW0 | WAT | G | 167 | 55.910 | 60.828 | 8.749 | 1.00 | 35.99 |
| ATOM | 1950 | OW0 | WAT | G | 168 | 58.826 | 36.800 | 21.280 | 1.00 | 46.77 |
| ATOM | 1951 | OW0 | WAT | G | 169 | 73.241 | 44.114 | 36.191 | 1.00 | 28.55 |
| ATOM | 1952 | OW0 | WAT | G | 170 | 62.716 | 53.030 | 41.277 | 1.00 | 28.32 |
| ATOM | 1953 | OW0 | WAT | G | 171 | 71.215 | 34.038 | 37.383 | 1.00 | 27.69 |
| ATOM | 1954 | OW0 | WAT | G | 172 | 62.192 | 37.635 | 14.596 | 1.00 | 50.53 |
| ATOM | 1955 | OW0 | WAT | G | 173 | 65.616 | 56.974 | 1.251 | 1.00 | 31.26 |
| ATOM | 1956 | OW0 | WAT | G | 174 | 76.080 | 34.843 | 37.370 | 1.00 | 35.85 |
| ATOM | 1957 | OW0 | WAT | G | 175 | 73.299 | 43.407 | 25.575 | 1.00 | 36.58 |
| ATOM | 1958 | OW0 | WAT | G | 176 | 65.884 | 43.263 | 17.413 | 1.00 | 40.37 |
| ATOM | 1959 | OW0 | WAT | G | 177 | 67.452 | 40.654 | 15.215 | 1.00 | 42.76 |
| ATOM | 1960 | OW0 | WAT | G | 178 | 54.648 | 62.290 | 32.413 | 1.00 | 53.70 |
| ATOM | 1961 | OW0 | WAT | G | 179 | 51.497 | 49.736 | 48.977 | 1.00 | 29.11 |
| ATOM | 1962 | OW0 | WAT | G | 180 | 44.613 | 37.553 | 5.661 | 1.00 | 33.03 |
| ATOM | 1963 | OW0 | WAT | G | 181 | 70.015 | 49.056 | 17.242 | 1.00 | 35.32 |
| ATOM | 1964 | OW0 | WAT | G | 182 | 67.847 | 54.823 | 14.616 | 1.00 | 27.00 |
| ATOM | 1965 | OW0 | WAT | G | 183 | 75.622 | 47.339 | 26.201 | 1.00 | 39.70 |
| ATOM | 1966 | OW0 | WAT | G | 184 | 58.156 | 30.750 | 37.764 | 1.00 | 43.06 |
| ATOM | 1967 | OW0 | WAT | G | 185 | 63.117 | 44.122 | 43.660 | 1.00 | 32.67 |
| ATOM | 1968 | OW0 | WAT | G | 186 | 70.428 | 46.037 | 20.380 | 1.00 | 37.29 |
| ATOM | 1969 | OW0 | WAT | G | 187 | 65.215 | 59.373 | 12.091 | 1.00 | 28.47 |
| ATOM | 1970 | OW0 | WAT | G | 188 | 67.748 | 44.609 | 18.032 | 1.00 | 53.73 |
| ATOM | 1971 | OW0 | WAT | G | 189 | 40.492 | 30.145 | 11.606 | 1.00 | 64.58 |
| ATOM | 1972 | OW0 | WAT | G | 190 | 67.625 | 60.042 | 8.441 | 1.00 | 33.03 |
| ATOM | 1973 | OW0 | WAT | G | 191 | 50.314 | 57.576 | 44.671 | 1.00 | 50.98 |
| ATOM | 1974 | OW0 | WAT | G | 192 | 52.073 | 26.847 | −2.175 | 1.00 | 30.83 |

-continued

Data Lists

| ATOM | 1975 | OW0 | WAT | G | 193 | 46.545 | 20.307 | 1.167 | 1.00 | 32.08 |
| --- | --- | --- | --- | --- | --- | --- | --- | --- | --- | --- |
| ATOM | 1976 | OW0 | WAT | G | 194 | 73.086 | 39.913 | 40.981 | 1.00 | 33.57 |
| ATOM | 1977 | OW0 | WAT | G | 195 | 45.430 | 39.245 | −2.273 | 1.00 | 37.02 |
| ATOM | 1978 | OW0 | WAT | G | 196 | 52.037 | 58.706 | 12.556 | 1.00 | 43.96 |
| ATOM | 1979 | OW0 | WAT | G | 197 | 57.543 | 61.063 | 30.828 | 1.00 | 37.03 |
| ATOM | 1980 | OW0 | WAT | G | 198 | 61.990 | 41.753 | 42.998 | 1.00 | 33.81 |
| ATOM | 1981 | OW0 | WAT | G | 199 | 43.339 | 30.612 | 18.051 | 1.00 | 41.32 |
| ATOM | 1982 | OW0 | WAT | G | 200 | 67.423 | 56.983 | 24.190 | 1.00 | 29.95 |
| ATOM | 1983 | OW0 | WAT | G | 201 | 63.945 | 61.652 | 12.824 | 1.00 | 34.11 |
| ATOM | 1984 | OW0 | WAT | G | 202 | 63.921 | 52.785 | 39.204 | 1.00 | 38.19 |
| ATOM | 1985 | OW0 | WAT | G | 203 | 52.495 | 20.862 | −0.923 | 1.00 | 33.05 |
| ATOM | 1986 | OW0 | WAT | G | 204 | 53.126 | 35.768 | −3.356 | 1.00 | 51.51 |
| ATOM | 1987 | OW0 | WAT | G | 205 | 42.327 | 41.556 | 31.448 | 1.00 | 30.36 |
| ATOM | 1988 | OW0 | WAT | G | 206 | 42.439 | 21.980 | 7.095 | 1.00 | 40.12 |
| ATOM | 1989 | OW0 | WAT | G | 207 | 72.241 | 46.621 | 16.496 | 1.00 | 54.53 |
| ATOM | 1990 | OW0 | WAT | G | 208 | 74.161 | 48.453 | 34.505 | 1.00 | 32.75 |
| ATOM | 1991 | OW0 | WAT | G | 209 | 48.098 | 26.277 | −4.627 | 1.00 | 41.33 |
| ATOM | 1992 | OW0 | WAT | G | 210 | 70.983 | 44.677 | 42.814 | 1.00 | 43.40 |
| ATOM | 1993 | OW0 | WAT | G | 211 | 47.557 | 20.513 | −1.605 | 1.00 | 40.08 |
| ATOM | 1994 | OW0 | WAT | G | 212 | 61.375 | 59.056 | −0.566 | 1.00 | 39.28 |
| ATOM | 1995 | OW0 | WAT | G | 213 | 72.365 | 48.660 | 2.612 | 1.00 | 35.85 |
| ATOM | 1996 | OW0 | WAT | G | 214 | 42.447 | 46.142 | 17.219 | 1.00 | 28.95 |
| ATOM | 1997 | OW0 | WAT | G | 215 | 70.417 | 41.828 | 12.236 | 1.00 | 60.99 |
| ATOM | 1998 | OW0 | WAT | G | 216 | 65.658 | 40.114 | 42.603 | 1.00 | 38.52 |
| ATOM | 1999 | OW0 | WAT | G | 217 | 61.676 | 48.645 | 44.176 | 1.00 | 39.02 |
| ATOM | 2000 | OW0 | WAT | G | 218 | 40.044 | 49.688 | 1.595 | 1.00 | 34.19 |
| ATOM | 2001 | OW0 | WAT | G | 219 | 40.202 | 42.880 | 25.589 | 1.00 | 32.08 |
| ATOM | 2002 | OW0 | WAT | G | 220 | 70.759 | 53.406 | 19.605 | 1.00 | 41.25 |
| ATOM | 2003 | OW0 | WAT | G | 221 | 34.228 | 33.047 | 11.879 | 1.00 | 38.87 |
| ATOM | 2004 | OW0 | WAT | G | 222 | 60.879 | 55.070 | 40.559 | 1.00 | 33.10 |
| ATOM | 2005 | OW0 | WAT | G | 223 | 58.520 | 33.967 | 42.655 | 1.00 | 52.56 |
| ATOM | 2006 | OW0 | WAT | G | 224 | 47.130 | 35.676 | −4.383 | 1.00 | 40.47 |
| ATOM | 2007 | OW0 | WAT | G | 225 | 42.291 | 57.764 | 7.951 | 1.00 | 34.20 |
| ATOM | 2008 | OW0 | WAT | G | 226 | 51.783 | 38.556 | −5.023 | 1.00 | 54.27 |
| ATOM | 2009 | OW0 | WAT | G | 227 | 63.204 | 39.780 | 41.589 | 1.00 | 26.92 |
| ATOM | 2010 | OW0 | WAT | G | 228 | 70.115 | 41.265 | 21.543 | 1.00 | 54.51 |
| ATOM | 2011 | OW0 | WAT | G | 229 | 35.142 | 41.094 | 15.033 | 1.00 | 26.43 |
| ATOM | 2012 | OW0 | WAT | G | 230 | 49.437 | 28.507 | −7.487 | 1.00 | 36.06 |
| ATOM | 2013 | OW0 | WAT | G | 231 | 48.186 | 58.600 | 27.989 | 1.00 | 47.86 |
| ATOM | 2014 | OW0 | WAT | G | 232 | 43.227 | 57.642 | 34.042 | 1.00 | 64.53 |
| ATOM | 2015 | OW0 | WAT | G | 233 | 44.435 | 45.324 | 40.354 | 1.00 | 38.94 |
| ATOM | 2016 | OW0 | WAT | G | 234 | 68.332 | 40.178 | 22.530 | 1.00 | 41.49 |
| ATOM | 2017 | OW0 | WAT | G | 235 | 41.021 | 47.384 | 26.519 | 1.00 | 32.18 |
| ATOM | 2018 | OW0 | WAT | G | 236 | 67.943 | 34.804 | 44.311 | 1.00 | 40.51 |
| ATOM | 2019 | OW0 | WAT | G | 237 | 54.009 | 33.505 | 14.576 | 1.00 | 38.62 |
| ATOM | 2020 | OW0 | WAT | G | 238 | 69.128 | 52.076 | 1.540 | 1.00 | 44.17 |
| ATOM | 2021 | OW0 | WAT | G | 239 | 48.173 | 55.704 | 43.334 | 1.00 | 38.16 |
| ATOM | 2022 | OW0 | WAT | G | 240 | 43.506 | 19.874 | 8.570 | 1.00 | 34.50 |
| ATOM | 2023 | OW0 | WAT | G | 241 | 46.783 | 19.606 | 10.993 | 1.00 | 33.70 |
| ATOM | 2024 | OW0 | WAT | G | 242 | 62.052 | 46.130 | 46.425 | 1.00 | 52.48 |
| ATOM | 2025 | OW0 | WAT | G | 243 | 34.174 | 43.821 | 10.769 | 1.00 | 40.93 |
| ATOM | 2026 | OW0 | WAT | G | 244 | 39.585 | 37.127 | 26.006 | 1.00 | 35.75 |
| ATOM | 2027 | OW0 | WAT | G | 245 | 70.915 | 52.471 | 29.511 | 1.00 | 46.35 |
| ATOM | 2028 | OW0 | WAT | G | 246 | 50.280 | 28.842 | −2.906 | 1.00 | 34.56 |
| ATOM | 2029 | OW0 | WAT | G | 247 | 45.574 | 23.804 | −6.012 | 1.00 | 54.66 |
| ATOM | 2030 | OW0 | WAT | G | 248 | 50.575 | 41.649 | −5.114 | 1.00 | 37.19 |
| ATOM | 2031 | OW0 | WAT | G | 249 | 46.284 | 60.877 | −0.658 | 1.00 | 48.34 |
| ATOM | 2032 | OW0 | WAT | G | 250 | 69.052 | 41.253 | 44.563 | 1.00 | 41.98 |
| ATOM | 2033 | OW0 | WAT | G | 251 | 76.192 | 44.065 | 31.740 | 1.00 | 39.19 |
| ATOM | 2034 | OW0 | WAT | G | 252 | 55.206 | 59.668 | 2.632 | 1.00 | 44.08 |
| ATOM | 2035 | OW0 | WAT | G | 253 | 46.669 | 36.720 | 40.608 | 1.00 | 50.14 |
| ATOM | 2036 | OW0 | WAT | G | 254 | 59.034 | 52.468 | 41.277 | 1.00 | 35.99 |
| ATOM | 2037 | OW0 | WAT | G | 255 | 52.334 | 63.688 | 32.421 | 1.00 | 64.26 |
| ATOM | 2038 | OW0 | WAT | G | 256 | 45.249 | 20.912 | 12.682 | 1.00 | 45.78 |
| ATOM | 2039 | OW0 | WAT | G | 257 | 45.580 | 47.063 | 38.611 | 1.00 | 32.72 |
| ATOM | 2040 | OW0 | WAT | G | 258 | 60.934 | 36.503 | 20.702 | 1.00 | 58.02 |
| ATOM | 2041 | OW0 | WAT | G | 259 | 47.948 | 47.662 | 45.709 | 1.00 | 33.97 |
| ATOM | 2042 | OW0 | WAT | G | 260 | 60.178 | 62.958 | 9.683 | 1.00 | 36.71 |
| ATOM | 2043 | OW0 | WAT | G | 261 | 55.919 | 30.766 | 39.029 | 1.00 | 61.42 |
| ATOM | 2044 | OW0 | WAT | G | 262 | 58.188 | 56.854 | 32.396 | 1.00 | 36.54 |
| ATOM | 2045 | OW0 | WAT | G | 263 | 56.797 | 37.074 | 18.930 | 1.00 | 61.43 |
| ATOM | 2046 | OW0 | WAT | G | 264 | 54.847 | 38.394 | −5.215 | 1.00 | 61.42 |
| ATOM | 2047 | OW0 | WAT | G | 265 | 74.299 | 44.365 | 9.183 | 1.00 | 48.11 |
| ATOM | 2048 | OW0 | WAT | G | 266 | 68.666 | 37.135 | 44.386 | 1.00 | 49.26 |
| ATOM | 2049 | OW0 | WAT | G | 267 | 48.423 | 62.166 | 9.434 | 1.00 | 37.66 |
| ATOM | 2050 | OW0 | WAT | G | 268 | 42.729 | 27.614 | 12.002 | 1.00 | 46.39 |
| ATOM | 2051 | OW0 | WAT | G | 269 | 53.863 | 61.181 | 11.430 | 1.00 | 60.41 |

-continued

Data Lists

| | | | | | | | | | |
|---|---|---|---|---|---|---|---|---|---|
| ATOM | 2052 | OW0 | WAT | G | 270 | 65.415 | 58.143 | 25.828 | 1.00 | 41.48 |
| ATOM | 2053 | OW0 | WAT | G | 271 | 51.875 | 32.393 | −8.603 | 1.00 | 53.80 |
| ATOM | 2054 | OW0 | WAT | G | 272 | 60.962 | 61.993 | 12.376 | 1.00 | 29.89 |
| ATOM | 2055 | OW0 | WAT | G | 273 | 40.308 | 32.786 | 11.451 | 1.00 | 35.54 |
| ATOM | 2056 | OW0 | WAT | G | 274 | 62.383 | 60.257 | 17.773 | 1.00 | 38.70 |
| ATOM | 2057 | OW0 | WAT | G | 275 | 37.093 | 30.464 | 14.199 | 1.00 | 47.27 |
| ATOM | 2058 | OW0 | WAT | G | 276 | 53.952 | 61.207 | −1.317 | 1.00 | 46.85 |
| ATOM | 2059 | OW0 | WAT | G | 277 | 51.860 | 29.501 | 0.746 | 1.00 | 37.36 |
| ATOM | 2060 | OW0 | WAT | G | 278 | 50.151 | 63.360 | 7.446 | 1.00 | 45.00 |
| ATOM | 2061 | OW0 | WAT | G | 279 | 69.694 | 43.050 | 22.397 | 1.00 | 68.19 |
| ATOM | 2062 | OW0 | WAT | G | 280 | 49.754 | 37.037 | −4.944 | 1.00 | 69.60 |
| ATOM | 2063 | OW0 | WAT | G | 281 | 50.342 | 25.060 | −3.761 | 1.00 | 44.24 |
| ATOM | 2064 | OW0 | WAT | G | 282 | 54.321 | 59.856 | 16.427 | 1.00 | 35.71 |
| ATOM | 2065 | OW0 | WAT | G | 283 | 63.746 | 59.693 | 0.468 | 1.00 | 55.15 |
| ATOM | 2066 | OW0 | WAT | G | 284 | 43.389 | 46.275 | 36.615 | 1.00 | 37.96 |
| ATOM | 2067 | OW0 | WAT | G | 285 | 59.808 | 40.715 | 43.590 | 1.00 | 33.32 |
| ATOM | 2068 | OW0 | WAT | G | 286 | 43.995 | 23.232 | 16.324 | 1.00 | 38.95 |
| ATOM | 2069 | OW0 | WAT | G | 287 | 43.552 | 24.401 | 13.416 | 1.00 | 61.34 |
| ATOM | 2070 | OW0 | WAT | G | 288 | 71.661 | 53.820 | 27.764 | 1.00 | 45.96 |
| ATOM | 2071 | OW0 | WAT | G | 289 | 48.871 | 35.713 | 37.068 | 1.00 | 21.32 |
| ATOM | 2072 | OW0 | WAT | G | 290 | 39.975 | 49.726 | 8.734 | 1.00 | 46.02 |
| ATOM | 2074 | OW0 | WAT | G | 292 | 65.526 | 33.873 | 35.894 | 1.00 | 37.27 |
| ATOM | 2075 | OW0 | WAT | G | 293 | 48.218 | 18.217 | 9.649 | 1.00 | 32.19 |
| ATOM | 1783 | OW0 | WAT | H | 1 | 55.626 | 26.415 | 10.047 | 1.00 | 12.46 |
| ATOM | 1784 | OW0 | WAT | H | 2 | 65.016 | 37.930 | 11.810 | 1.00 | 14.50 |
| ATOM | 1785 | OW0 | WAT | H | 3 | 58.211 | 27.718 | 10.696 | 1.00 | 12.96 |
| ATOM | 1786 | OW0 | WAT | H | 4 | 59.947 | 34.093 | 10.106 | 1.00 | 16.21 |
| ATOM | 1787 | OW0 | WAT | H | 5 | 59.936 | 14.419 | 20.886 | 1.00 | 16.96 |
| ATOM | 1788 | OW0 | WAT | H | 6 | 68.238 | 32.497 | 17.320 | 1.00 | 12.78 |
| ATOM | 1789 | OW0 | WAT | H | 7 | 66.240 | 31.436 | 15.575 | 1.00 | 14.43 |
| ATOM | 1790 | OW0 | WAT | H | 8 | 57.265 | 23.951 | 22.829 | 1.00 | 11.87 |
| ATOM | 1791 | OW0 | WAT | H | 9 | 59.422 | 15.438 | 31.322 | 1.00 | 15.75 |
| ATOM | 1792 | OW0 | WAT | H | 10 | 84.148 | 29.630 | 16.216 | 1.00 | 18.14 |
| ATOM | 1793 | OW0 | WAT | H | 11 | 53.858 | 30.989 | 20.763 | 1.00 | 18.49 |
| ATOM | 1794 | OW0 | WAT | H | 12 | 40.207 | 30.360 | 27.502 | 1.00 | 20.49 |
| ATOM | 1795 | OW0 | WAT | H | 13 | 52.543 | 26.702 | 0.370 | 1.00 | 15.58 |
| ATOM | 1796 | OW0 | WAT | H | 14 | 59.344 | 26.117 | 22.867 | 1.00 | 12.77 |
| ATOM | 1797 | OW0 | WAT | H | 15 | 63.620 | 27.796 | 18.221 | 1.00 | 17.15 |
| ATOM | 1798 | OW0 | WAT | H | 16 | 70.586 | 38.510 | 27.896 | 1.00 | 18.45 |
| ATOM | 1799 | OW0 | WAT | H | 17 | 61.696 | 33.858 | 24.218 | 1.00 | 20.08 |
| ATOM | 1800 | OW0 | WAT | H | 18 | 55.336 | 28.435 | 17.716 | 1.00 | 19.24 |
| ATOM | 1801 | OW0 | WAT | H | 19 | 62.319 | 14.684 | 27.239 | 1.00 | 18.83 |
| ATOM | 1802 | OW0 | WAT | H | 20 | 42.537 | 26.828 | 34.990 | 1.00 | 17.45 |
| ATOM | 1803 | OW0 | WAT | H | 21 | 74.567 | 31.356 | 15.807 | 1.00 | 18.93 |
| ATOM | 1804 | OW0 | WAT | H | 22 | 77.241 | 37.609 | −1.173 | 1.00 | 16.89 |
| ATOM | 1805 | OW0 | WAT | H | 23 | 53.542 | 26.069 | 21.187 | 1.00 | 20.32 |
| ATOM | 1806 | OW0 | WAT | H | 24 | 78.587 | 36.637 | 5.376 | 1.00 | 19.88 |
| ATOM | 1807 | OW0 | WAT | H | 25 | 62.185 | 13.724 | 24.633 | 1.00 | 17.12 |
| ATOM | 1808 | OW0 | WAT | H | 26 | 56.499 | 11.903 | 12.602 | 1.00 | 21.81 |
| ATOM | 1809 | OW0 | WAT | H | 27 | 49.927 | 32.676 | 21.964 | 1.00 | 15.81 |
| ATOM | 1810 | OW0 | WAT | H | 28 | 76.722 | 38.573 | 6.596 | 1.00 | 21.31 |
| ATOM | 1811 | OW0 | WAT | H | 29 | 71.211 | 17.670 | −4.123 | 1.00 | 21.20 |
| ATOM | 1812 | OW0 | WAT | H | 30 | 55.890 | 27.326 | 15.037 | 1.00 | 21.50 |
| ATOM | 1813 | OW0 | WAT | H | 31 | 72.135 | 13.499 | 35.278 | 1.00 | 26.79 |
| ATOM | 1814 | OW0 | WAT | H | 32 | 76.219 | 22.099 | 0.994 | 1.00 | 18.33 |
| ATOM | 1815 | OW0 | WAT | H | 33 | 77.438 | 30.353 | −6.384 | 1.00 | 21.45 |
| ATOM | 1816 | OW0 | WAT | H | 34 | 75.784 | 39.054 | 0.788 | 1.00 | 19.77 |
| ATOM | 1817 | OW0 | WAT | H | 35 | 59.941 | 30.965 | 22.565 | 1.00 | 19.13 |
| ATOM | 1818 | OW0 | WAT | H | 36 | 80.041 | 33.464 | 22.515 | 1.00 | 25.88 |
| ATOM | 1819 | OW0 | WAT | H | 37 | 53.875 | 11.516 | 16.737 | 1.00 | 24.35 |
| ATOM | 1820 | OW0 | WAT | H | 38 | 48.562 | 15.769 | 23.928 | 1.00 | 21.53 |
| ATOM | 1821 | OW0 | WAT | H | 39 | 67.622 | 19.468 | −6.676 | 1.00 | 17.05 |
| ATOM | 1822 | OW0 | WAT | H | 40 | 63.265 | 9.904 | 29.834 | 1.00 | 26.29 |
| ATOM | 1823 | OW0 | WAT | H | 41 | 70.165 | 13.648 | 3.894 | 1.00 | 26.19 |
| ATOM | 1824 | OW0 | WAT | H | 42 | 81.980 | 32.799 | 3.642 | 1.00 | 21.59 |
| ATOM | 1825 | OW0 | WAT | H | 43 | 64.411 | 12.168 | 24.457 | 1.00 | 28.13 |
| ATOM | 1826 | OW0 | WAT | H | 44 | 71.862 | 38.226 | 21.699 | 1.00 | 27.79 |
| ATOM | 1827 | OW0 | WAT | H | 45 | 50.750 | 14.483 | 26.561 | 1.00 | 22.42 |
| ATOM | 1828 | OW0 | WAT | H | 46 | 72.225 | 30.904 | −7.142 | 1.00 | 24.58 |
| ATOM | 1829 | OW0 | WAT | H | 47 | 48.426 | 17.990 | 14.644 | 1.00 | 24.59 |
| ATOM | 1830 | OW0 | WAT | H | 48 | 69.915 | 12.402 | 20.671 | 1.00 | 34.46 |
| ATOM | 1831 | OW0 | WAT | H | 49 | 71.391 | 27.373 | −10.407 | 1.00 | 20.52 |
| ATOM | 1832 | OW0 | WAT | H | 50 | 57.327 | 36.972 | −1.991 | 1.00 | 29.82 |
| ATOM | 1833 | OW0 | WAT | H | 51 | 68.614 | 17.512 | −4.674 | 1.00 | 22.18 |
| ATOM | 1834 | OW0 | WAT | H | 52 | 41.134 | 22.037 | 30.497 | 1.00 | 17.35 |
| ATOM | 1835 | OW0 | WAT | H | 53 | 78.961 | 22.828 | 0.870 | 1.00 | 19.50 |
| ATOM | 1836 | OW0 | WAT | H | 54 | 81.114 | 32.952 | 25.218 | 1.00 | 27.87 |

-continued

Data Lists

| | | | | | | | | | |
|---|---|---|---|---|---|---|---|---|---|
| ATOM | 1837 | OW0 | WAT | H | 55 | 66.620 | 38.253 | 21.637 | 1.00 | 30.16 |
| ATOM | 1838 | OW0 | WAT | H | 56 | 82.397 | 27.950 | 21.632 | 1.00 | 26.01 |
| ATOM | 1839 | OW0 | WAT | H | 57 | 40.601 | 24.059 | 32.268 | 1.00 | 23.54 |
| ATOM | 1840 | OW0 | WAT | H | 58 | 68.703 | 17.093 | 14.330 | 1.00 | 30.99 |
| ATOM | 1841 | OW0 | WAT | H | 59 | 60.386 | 31.945 | 11.769 | 1.00 | 20.83 |
| ATOM | 1842 | OW0 | WAT | H | 60 | 58.159 | 32.811 | 23.887 | 1.00 | 21.39 |
| ATOM | 1843 | OW0 | WAT | H | 61 | 75.112 | 33.510 | −7.627 | 1.00 | 24.77 |
| ATOM | 1844 | OW0 | WAT | H | 62 | 60.861 | 28.219 | 17.129 | 1.00 | 25.45 |
| ATOM | 1845 | OW0 | WAT | H | 63 | 69.818 | 18.540 | −8.213 | 1.00 | 22.75 |
| ATOM | 1846 | OW0 | WAT | H | 64 | 47.698 | 23.429 | 29.143 | 1.00 | 21.96 |
| ATOM | 1847 | OW0 | WAT | H | 65 | 56.243 | 17.811 | 6.113 | 1.00 | 26.57 |
| ATOM | 1848 | OW0 | WAT | H | 66 | 56.480 | 9.527 | 25.120 | 1.00 | 24.57 |
| ATOM | 1849 | OW0 | WAT | H | 67 | 76.416 | 39.671 | 4.015 | 1.00 | 22.95 |
| ATOM | 1850 | OW0 | WAT | H | 68 | 75.867 | 11.960 | 24.892 | 1.00 | 26.76 |
| ATOM | 1851 | OW0 | WAT | H | 69 | 65.809 | 34.125 | 14.364 | 1.00 | 26.61 |
| ATOM | 1852 | OW0 | WAT | H | 70 | 62.222 | 28.978 | 20.512 | 1.00 | 20.01 |
| ATOM | 1853 | OW0 | WAT | H | 71 | 73.295 | 41.829 | −3.122 | 1.00 | 36.97 |
| ATOM | 1854 | OW0 | WAT | H | 72 | 72.362 | 37.161 | 14.937 | 1.00 | 29.26 |
| ATOM | 1855 | OW0 | WAT | H | 73 | 64.102 | 12.708 | 12.209 | 1.00 | 29.45 |
| ATOM | 1856 | OW0 | WAT | H | 74 | 59.337 | 46.991 | −4.704 | 1.00 | 33.14 |
| ATOM | 1857 | OW0 | WAT | H | 75 | 47.640 | 15.287 | 17.293 | 1.00 | 25.03 |
| ATOM | 1858 | OW0 | WAT | H | 76 | 65.153 | 12.787 | 16.407 | 1.00 | 36.34 |
| ATOM | 1859 | OW0 | WAT | H | 77 | 82.754 | 33.641 | 27.870 | 1.00 | 33.66 |
| ATOM | 1860 | OW0 | WAT | H | 78 | 74.515 | 43.172 | 1.368 | 1.00 | 46.06 |
| ATOM | 1861 | OW0 | WAT | H | 79 | 65.544 | 13.826 | 36.090 | 1.00 | 26.95 |
| ATOM | 1862 | OW0 | WAT | H | 80 | 56.176 | 14.705 | 7.899 | 1.00 | 25.17 |
| ATOM | 1863 | OW0 | WAT | H | 81 | 60.069 | 12.784 | 23.279 | 1.00 | 25.41 |
| ATOM | 1864 | OW0 | WAT | H | 82 | 64.518 | 29.497 | −9.881 | 1.00 | 28.19 |
| ATOM | 1865 | OW0 | WAT | H | 83 | 72.890 | 17.016 | 38.513 | 1.00 | 32.75 |
| ATOM | 1866 | OW0 | WAT | H | 84 | 64.327 | 12.726 | 7.904 | 1.00 | 28.33 |
| ATOM | 1867 | OW0 | WAT | H | 85 | 73.702 | 28.506 | 40.368 | 1.00 | 35.95 |
| ATOM | 1868 | OW0 | WAT | H | 86 | 40.325 | 34.760 | 26.876 | 1.00 | 30.16 |
| ATOM | 1869 | OW0 | WAT | H | 87 | 46.523 | 14.958 | 21.845 | 1.00 | 28.34 |
| ATOM | 1870 | OW0 | WAT | H | 88 | 81.785 | 35.984 | 25.164 | 1.00 | 45.57 |
| ATOM | 1871 | OW0 | WAT | H | 89 | 81.670 | 23.684 | 31.981 | 1.00 | 30.95 |
| ATOM | 1872 | OW0 | WAT | H | 90 | 73.658 | 13.615 | 21.783 | 1.00 | 31.75 |
| ATOM | 1873 | OW0 | WAT | H | 91 | 54.962 | 28.237 | 22.077 | 1.00 | 26.64 |
| ATOM | 1874 | OW0 | WAT | H | 92 | 65.997 | 21.795 | 41.162 | 1.00 | 34.61 |
| ATOM | 1875 | OW0 | WAT | H | 93 | 67.430 | 9.979 | 25.531 | 1.00 | 30.41 |
| ATOM | 1876 | OW0 | WAT | H | 94 | 76.456 | 16.928 | 20.650 | 1.00 | 30.22 |
| ATOM | 1877 | OW0 | WAT | H | 95 | 77.973 | 22.449 | 11.319 | 1.00 | 26.47 |
| ATOM | 1878 | OW0 | WAT | H | 96 | 54.232 | 11.639 | 13.975 | 1.00 | 24.52 |
| ATOM | 1879 | OW0 | WAT | H | 97 | 46.826 | 33.800 | 36.880 | 1.00 | 25.58 |
| ATOM | 1880 | OW0 | WAT | H | 98 | 57.623 | 16.748 | 1.335 | 1.00 | 35.83 |
| ATOM | 1881 | OW0 | WAT | H | 99 | 60.463 | 23.883 | −10.911 | 1.00 | 31.62 |
| ATOM | 1882 | OW0 | WAT | H | 100 | 75.659 | 24.956 | 37.083 | 1.00 | 35.13 |
| ATOM | 1883 | OW0 | WAT | H | 101 | 59.265 | 28.532 | 21.715 | 1.00 | 25.37 |
| ATOM | 1884 | OW0 | WAT | H | 102 | 50.039 | 16.328 | 12.141 | 1.00 | 22.49 |
| ATOM | 1885 | OW0 | WAT | H | 103 | 48.949 | 27.390 | 19.574 | 1.00 | 22.74 |
| ATOM | 1886 | OW0 | WAT | H | 104 | 52.769 | 29.349 | 16.776 | 1.00 | 23.17 |
| ATOM | 1887 | OW0 | WAT | H | 105 | 57.967 | 25.041 | −7.141 | 1.00 | 29.64 |
| ATOM | 1888 | OW0 | WAT | H | 106 | 75.831 | 28.016 | 37.410 | 1.00 | 34.04 |
| ATOM | 1889 | OW0 | WAT | H | 107 | 77.822 | 15.717 | −6.480 | 1.00 | 35.09 |
| ATOM | 1890 | OW0 | WAT | H | 108 | 65.905 | 16.140 | 14.395 | 1.00 | 25.94 |
| ATOM | 1891 | OW0 | WAT | H | 109 | 52.151 | 13.189 | 12.986 | 1.00 | 26.50 |
| ATOM | 1892 | OW0 | WAT | H | 110 | 80.013 | 37.977 | 7.957 | 1.00 | 30.56 |
| ATOM | 1893 | OW0 | WAT | H | 111 | 83.151 | 30.502 | 29.885 | 1.00 | 29.70 |
| ATOM | 1894 | OW0 | WAT | H | 112 | 70.714 | 15.340 | 37.184 | 1.00 | 35.84 |
| ATOM | 1895 | OW0 | WAT | H | 113 | 62.628 | 31.924 | −7.181 | 1.00 | 30.25 |
| ATOM | 1896 | OW0 | WAT | H | 114 | 50.066 | 27.262 | 16.994 | 1.00 | 30.45 |
| ATOM | 1897 | OW0 | WAT | H | 115 | 45.810 | 22.478 | 26.282 | 1.00 | 30.65 |
| ATOM | 1898 | OW0 | WAT | H | 116 | 39.755 | 32.861 | 30.859 | 1.00 | 26.85 |
| ATOM | 1899 | OW0 | WAT | H | 117 | 71.066 | 9.044 | 35.678 | 1.00 | 36.26 |
| ATOM | 1900 | OW0 | WAT | H | 118 | 58.464 | 30.097 | −6.302 | 1.00 | 33.36 |
| ATOM | 1901 | OW0 | WAT | H | 119 | 43.885 | 38.361 | 32.035 | 1.00 | 39.06 |
| ATOM | 1902 | OW0 | WAT | H | 120 | 48.283 | 14.313 | 19.784 | 1.00 | 23.39 |
| ATOM | 1903 | OW0 | WAT | H | 121 | 58.695 | 11.110 | 24.826 | 1.00 | 32.00 |
| ATOM | 1904 | OW0 | WAT | H | 122 | 57.082 | 19.459 | −4.887 | 1.00 | 28.95 |
| ATOM | 1905 | OW0 | WAT | H | 123 | 81.562 | 27.571 | 7.690 | 1.00 | 31.43 |
| ATOM | 1906 | OW0 | WAT | H | 124 | 50.133 | 7.422 | 22.846 | 1.00 | 30.11 |
| ATOM | 1907 | OW0 | WAT | H | 125 | 69.527 | 37.104 | 15.998 | 1.00 | 37.52 |
| ATOM | 1908 | OW0 | WAT | H | 126 | 83.637 | 20.159 | 29.764 | 1.00 | 30.85 |
| ATOM | 1909 | OW0 | WAT | H | 127 | 57.160 | 30.346 | 18.132 | 1.00 | 28.43 |
| ATOM | 1910 | OW0 | WAT | H | 128 | 55.407 | 22.216 | 37.933 | 1.00 | 28.17 |
| ATOM | 1911 | OW0 | WAT | H | 129 | 39.281 | 32.022 | 33.251 | 1.00 | 36.60 |
| ATOM | 1912 | OW0 | WAT | H | 130 | 66.017 | 13.623 | 13.755 | 1.00 | 29.95 |
| ATOM | 1913 | OW0 | WAT | H | 131 | 78.517 | 19.411 | 5.018 | 1.00 | 29.87 |

-continued

Data Lists

| | | | | | | | | | |
|---|---|---|---|---|---|---|---|---|---|
| ATOM | 1914 | OW0 | WAT | H | 132 | 48.811 | 17.945 | 26.897 | 1.00 | 43.00 |
| ATOM | 1917 | OW0 | WAT | H | 135 | 64.367 | 34.584 | 23.669 | 1.00 | 15.27 |
| ATOM | 1918 | OW0 | WAT | H | 136 | 81.580 | 19.230 | 1.174 | 1.00 | 23.04 |
| ATOM | 1919 | OW0 | WAT | H | 137 | 60.573 | 29.499 | 14.716 | 1.00 | 20.63 |
| ATOM | 1920 | OW0 | WAT | H | 138 | 65.862 | 34.058 | 21.256 | 1.00 | 34.20 |
| ATOM | 1921 | OW0 | WAT | H | 139 | 83.247 | 24.263 | 5.613 | 1.00 | 31.10 |
| ATOM | 1922 | OW0 | WAT | H | 140 | 59.546 | 29.382 | 19.222 | 1.00 | 26.78 |
| ATOM | 1923 | OW0 | WAT | H | 141 | 57.588 | 28.862 | 13.258 | 1.00 | 28.89 |
| ATOM | 1924 | OW0 | WAT | H | 142 | 67.042 | 36.289 | 15.327 | 1.00 | 30.25 |
| ATOM | 1925 | OW0 | WAT | H | 143 | 79.364 | 24.456 | −3.023 | 1.00 | 27.10 |
| ATOM | 1926 | OW0 | WAT | H | 144 | 56.647 | 25.991 | 39.022 | 1.00 | 24.20 |
| ATOM | 1927 | OW0 | WAT | H | 145 | 56.593 | 34.283 | 22.128 | 1.00 | 27.16 |
| ATOM | 1928 | OW0 | WAT | H | 146 | 73.331 | 26.272 | −7.226 | 1.00 | 27.11 |
| ATOM | 1929 | OW0 | WAT | H | 147 | 47.705 | 20.384 | 15.670 | 1.00 | 27.47 |
| ATOM | 1930 | OW0 | WAT | H | 148 | 75.910 | 26.130 | −7.246 | 1.00 | 29.71 |
| ATOM | 1931 | OW0 | WAT | H | 149 | 46.323 | 26.826 | 19.400 | 1.00 | 36.67 |
| ATOM | 1932 | OW0 | WAT | H | 150 | 61.609 | 39.798 | 2.091 | 1.00 | 30.16 |
| ATOM | 1933 | OW0 | WAT | H | 151 | 68.189 | 35.212 | 17.395 | 1.00 | 28.63 |
| ATOM | 1934 | OW0 | WAT | H | 152 | 49.690 | 27.733 | 40.873 | 1.00 | 26.64 |
| ATOM | 1935 | OW0 | WAT | H | 153 | 81.739 | 25.115 | 8.578 | 1.00 | 34.13 |
| ATOM | 1936 | OW0 | WAT | H | 154 | 64.261 | 33.918 | 17.410 | 1.00 | 48.10 |
| ATOM | 1937 | OW0 | WAT | H | 155 | 55.864 | 32.706 | 19.968 | 1.00 | 40.67 |
| ATOM | 1938 | OW0 | WAT | H | 156 | 62.576 | 31.794 | 17.551 | 1.00 | 34.94 |
| ATOM | 1939 | OW0 | WAT | H | 157 | 52.628 | 31.942 | −3.590 | 1.00 | 38.68 |
| ATOM | 1940 | OW0 | WAT | H | 158 | 75.447 | 17.848 | 6.325 | 1.00 | 25.79 |
| ATOM | 1941 | OW0 | WAT | H | 159 | 59.047 | 22.586 | 38.987 | 1.00 | 29.14 |
| ATOM | 1942 | OW0 | WAT | H | 160 | 59.817 | 35.142 | 14.016 | 1.00 | 38.25 |
| ATOM | 1943 | OW0 | WAT | H | 161 | 78.322 | 14.589 | 40.993 | 1.00 | 32.32 |
| ATOM | 1944 | OW0 | WAT | H | 162 | 57.184 | 22.624 | −0.720 | 1.00 | 28.29 |
| ATOM | 1945 | OW0 | WAT | H | 163 | 61.680 | 31.893 | 20.126 | 1.00 | 45.25 |
| ATOM | 1946 | OW0 | WAT | H | 164 | 48.637 | 24.862 | 17.484 | 1.00 | 28.59 |
| ATOM | 1947 | OW0 | WAT | H | 165 | 67.349 | 36.023 | 19.750 | 1.00 | 36.40 |
| ATOM | 1948 | OW0 | WAT | H | 166 | 80.275 | 22.814 | 34.316 | 1.00 | 36.57 |
| ATOM | 1949 | OW0 | WAT | H | 167 | 80.632 | 18.004 | 27.037 | 1.00 | 35.99 |
| ATOM | 1950 | OW0 | WAT | H | 168 | 61.282 | 32.543 | 14.506 | 1.00 | 46.77 |
| ATOM | 1951 | OW0 | WAT | H | 169 | 74.823 | 41.370 | −0.405 | 1.00 | 28.55 |
| ATOM | 1952 | OW0 | WAT | H | 170 | 77.282 | 27.797 | −5.491 | 1.00 | 28.32 |
| ATOM | 1953 | OW0 | WAT | H | 171 | 65.084 | 44.653 | −1.597 | 1.00 | 27.69 |
| ATOM | 1954 | OW0 | WAT | H | 172 | 63.688 | 35.041 | 21.190 | 1.00 | 50.53 |
| ATOM | 1955 | OW0 | WAT | H | 173 | 82.147 | 28.336 | 34.535 | 1.00 | 31.26 |
| ATOM | 1956 | OW0 | WAT | H | 174 | 68.214 | 48.464 | −1.584 | 1.00 | 35.85 |
| ATOM | 1957 | OW0 | WAT | H | 175 | 74.240 | 41.773 | 10.211 | 1.00 | 36.58 |
| ATOM | 1958 | OW0 | WAT | H | 176 | 70.408 | 35.424 | 18.373 | 1.00 | 40.37 |
| ATOM | 1959 | OW0 | WAT | H | 177 | 68.932 | 38.086 | 20.571 | 1.00 | 42.76 |
| ATOM | 1960 | OW0 | WAT | H | 178 | 81.267 | 16.180 | 3.373 | 1.00 | 53.70 |
| ATOM | 1961 | OW0 | WAT | H | 179 | 68.820 | 19.728 | −13.191 | 1.00 | 29.11 |
| ATOM | 1962 | OW0 | WAT | H | 180 | 54.827 | 19.858 | 30.125 | 1.00 | 33.03 |
| ATOM | 1963 | OW0 | WAT | H | 181 | 77.490 | 36.105 | 18.544 | 1.00 | 35.32 |
| ATOM | 1964 | OW0 | WAT | H | 182 | 81.400 | 31.344 | 21.170 | 1.00 | 27.00 |
| ATOM | 1965 | OW0 | WAT | H | 183 | 78.807 | 41.819 | 9.585 | 1.00 | 39.70 |
| ATOM | 1966 | OW0 | WAT | H | 184 | 55.707 | 34.988 | −1.978 | 1.00 | 43.06 |
| ATOM | 1967 | OW0 | WAT | H | 185 | 69.768 | 32.598 | −7.874 | 1.00 | 32.67 |
| ATOM | 1968 | OW0 | WAT | H | 186 | 75.082 | 37.972 | 15.406 | 1.00 | 37.29 |
| ATOM | 1969 | OW0 | WAT | H | 187 | 84.025 | 26.790 | 23.695 | 1.00 | 28.47 |
| ATOM | 1970 | OW0 | WAT | H | 188 | 72.505 | 36.365 | 17.754 | 1.00 | 53.73 |
| ATOM | 1971 | OW0 | WAT | H | 189 | 46.352 | 19.994 | 24.180 | 1.00 | 64.58 |
| ATOM | 1972 | OW0 | WAT | H | 190 | 85.809 | 28.542 | 27.345 | 1.00 | 33.03 |
| ATOM | 1973 | OW0 | WAT | H | 191 | 75.018 | 14.784 | −8.885 | 1.00 | 50.98 |
| ATOM | 1974 | OW0 | WAT | H | 192 | 49.286 | 31.672 | 37.961 | 1.00 | 30.83 |
| ATOM | 1975 | OW0 | WAT | H | 193 | 40.858 | 30.154 | 34.619 | 1.00 | 32.08 |
| ATOM | 1976 | OW0 | WAT | H | 194 | 71.108 | 43.336 | −5.195 | 1.00 | 33.57 |
| ATOM | 1977 | OW0 | WAT | H | 195 | 56.701 | 19.720 | 38.059 | 1.00 | 37.02 |
| ATOM | 1978 | OW0 | WAT | H | 196 | 76.858 | 15.711 | 23.230 | 1.00 | 43.96 |
| ATOM | 1979 | OW0 | WAT | H | 197 | 81.652 | 19.301 | 4.958 | 1.00 | 37.03 |
| ATOM | 1980 | OW0 | WAT | H | 198 | 67.153 | 32.807 | −7.212 | 1.00 | 33.81 |
| ATOM | 1981 | OW0 | WAT | H | 199 | 48.179 | 22.226 | 17.735 | 1.00 | 41.32 |
| ATOM | 1982 | OW0 | WAT | H | 200 | 83.059 | 29.897 | 11.596 | 1.00 | 29.95 |
| ATOM | 1983 | OW0 | WAT | H | 201 | 85.363 | 24.550 | 22.962 | 1.00 | 34.11 |
| ATOM | 1984 | OW0 | WAT | H | 202 | 77.672 | 28.963 | −3.418 | 1.00 | 38.19 |
| ATOM | 1985 | OW0 | WAT | H | 203 | 44.314 | 35.030 | 36.709 | 1.00 | 33.05 |
| ATOM | 1986 | OW0 | WAT | H | 204 | 57.538 | 28.123 | 39.142 | 1.00 | 51.51 |
| ATOM | 1987 | OW0 | WAT | H | 205 | 57.151 | 15.877 | 4.338 | 1.00 | 30.36 |
| ATOM | 1988 | OW0 | WAT | H | 206 | 40.254 | 25.762 | 28.691 | 1.00 | 40.12 |
| ATOM | 1989 | OW0 | WAT | H | 207 | 76.494 | 39.250 | 19.290 | 1.00 | 54.53 |
| ATOM | 1990 | OW0 | WAT | H | 208 | 79.041 | 39.997 | 1.281 | 1.00 | 32.75 |
| ATOM | 1991 | OW0 | WAT | H | 209 | 46.805 | 28.514 | 40.413 | 1.00 | 41.33 |
| ATOM | 1992 | OW0 | WAT | H | 210 | 74.182 | 39.133 | −7.028 | 1.00 | 43.40 |

-continued

Data Lists

| | | | | | | | | | |
|---|---|---|---|---|---|---|---|---|---|
| ATOM | 1993 | OW0 | WAT | H | 211 | 41.543 | 30.928 | 37.391 | 1.00 | 40.08 |
| ATOM | 1994 | OW0 | WAT | H | 212 | 81.830 | 23.623 | 36.352 | 1.00 | 39.28 |
| ATOM | 1995 | OW0 | WAT | H | 213 | 78.322 | 38.338 | 33.174 | 1.00 | 35.85 |
| ATOM | 1996 | OW0 | WAT | H | 214 | 61.182 | 13.688 | 18.567 | 1.00 | 28.95 |
| ATOM | 1997 | OW0 | WAT | H | 215 | 71.432 | 40.067 | 23.550 | 1.00 | 60.99 |
| ATOM | 1998 | OW0 | WAT | H | 216 | 67.568 | 36.803 | −6.817 | 1.00 | 38.52 |
| ATOM | 1999 | OW0 | WAT | H | 217 | 72.965 | 29.089 | −8.390 | 1.00 | 39.02 |
| ATOM | 2000 | OW0 | WAT | H | 218 | 63.052 | 9.834 | 34.191 | 1.00 | 34.19 |
| ATOM | 2001 | OW0 | WAT | H | 219 | 57.235 | 13.375 | 10.197 | 1.00 | 32.08 |
| ATOM | 2002 | OW0 | WAT | H | 220 | 81.629 | 34.574 | 16.181 | 1.00 | 41.25 |
| ATOM | 2003 | OW0 | WAT | H | 221 | 45.733 | 13.118 | 23.907 | 1.00 | 38.87 |
| ATOM | 2004 | OW0 | WAT | H | 222 | 78.130 | 25.186 | −4.773 | 1.00 | 33.10 |
| ATOM | 2005 | OW0 | WAT | H | 223 | 58.675 | 33.695 | −6.869 | 1.00 | 52.56 |
| ATOM | 2006 | OW0 | WAT | H | 224 | 54.460 | 22.977 | 40.169 | 1.00 | 40.47 |
| ATOM | 2007 | OW0 | WAT | H | 225 | 71.169 | 7.742 | 27.835 | 1.00 | 34.20 |
| ATOM | 2008 | OW0 | WAT | H | 226 | 59.281 | 25.566 | 40.809 | 1.00 | 54.27 |
| ATOM | 2009 | OW0 | WAT | H | 227 | 66.051 | 34.845 | −5.803 | 1.00 | 26.92 |
| ATOM | 2010 | OW0 | WAT | H | 228 | 70.793 | 40.087 | 14.243 | 1.00 | 54.51 |
| ATOM | 2011 | OW0 | WAT | H | 229 | 53.158 | 9.886 | 20.753 | 1.00 | 26.43 |
| ATOM | 2012 | OW0 | WAT | H | 230 | 49.406 | 28.559 | 43.273 | 1.00 | 36.06 |
| ATOM | 2013 | OW0 | WAT | H | 231 | 74.841 | 12.429 | 7.797 | 1.00 | 47.86 |
| ATOM | 2014 | OW0 | WAT | H | 232 | 71.531 | 8.614 | 1.744 | 1.00 | 64.53 |
| ATOM | 2015 | OW0 | WAT | H | 233 | 61.468 | 15.819 | −4.568 | 1.00 | 38.94 |
| ATOM | 2016 | OW0 | WAT | H | 234 | 68.960 | 39.087 | 13.256 | 1.00 | 41.49 |
| ATOM | 2017 | OW0 | WAT | H | 235 | 61.545 | 11.832 | 9.267 | 1.00 | 32.18 |
| ATOM | 2018 | OW0 | WAT | H | 236 | 64.112 | 41.437 | −8.525 | 1.00 | 40.51 |
| ATOM | 2019 | OW0 | WAT | H | 237 | 56.020 | 30.019 | 21.210 | 1.00 | 38.62 |
| ATOM | 2020 | OW0 | WAT | H | 238 | 79.662 | 33.827 | 34.246 | 1.00 | 44.17 |
| ATOM | 2021 | OW0 | WAT | H | 239 | 72.326 | 13.866 | −7.548 | 1.00 | 38.16 |
| ATOM | 2022 | OW0 | WAT | H | 240 | 38.964 | 27.739 | 27.216 | 1.00 | 34.50 |
| ATOM | 2023 | OW0 | WAT | H | 241 | 40.370 | 30.711 | 24.793 | 1.00 | 33.70 |
| ATOM | 2024 | OW0 | WAT | H | 242 | 70.975 | 30.672 | −10.639 | 1.00 | 52.48 |
| ATOM | 2025 | OW0 | WAT | H | 243 | 55.036 | 7.684 | 25.017 | 1.00 | 40.93 |
| ATOM | 2026 | OW0 | WAT | H | 244 | 51.944 | 15.717 | 9.780 | 1.00 | 35.75 |
| ATOM | 2027 | OW0 | WAT | H | 245 | 80.897 | 35.177 | 6.275 | 1.00 | 46.35 |
| ATOM | 2028 | OW0 | WAT | H | 246 | 50.117 | 29.121 | 38.692 | 1.00 | 34.56 |
| ATOM | 2029 | OW0 | WAT | H | 247 | 43.401 | 27.565 | 41.798 | 1.00 | 54.66 |
| ATOM | 2030 | OW0 | WAT | H | 248 | 61.356 | 22.973 | 40.900 | 1.00 | 37.19 |
| ATOM | 2031 | OW0 | WAT | H | 249 | 75.861 | 9.643 | 36.444 | 1.00 | 48.34 |
| ATOM | 2032 | OW0 | WAT | H | 250 | 70.251 | 39.173 | −8.777 | 1.00 | 41.98 |
| ATOM | 2033 | OW0 | WAT | H | 251 | 76.256 | 43.950 | 4.046 | 1.00 | 39.19 |
| ATOM | 2034 | OW0 | WAT | H | 252 | 79.275 | 17.974 | 33.154 | 1.00 | 44.08 |
| ATOM | 2035 | OW0 | WAT | H | 253 | 55.134 | 22.055 | −4.822 | 1.00 | 50.14 |
| ATOM | 2036 | OW0 | WAT | H | 254 | 74.954 | 24.889 | −5.491 | 1.00 | 35.99 |
| ATOM | 2037 | OW0 | WAT | H | 255 | 81.321 | 13.477 | 3.365 | 1.00 | 64.26 |
| ATOM | 2038 | OW0 | WAT | H | 256 | 40.734 | 28.730 | 23.104 | 1.00 | 45.78 |
| ATOM | 2039 | OW0 | WAT | H | 257 | 63.547 | 15.941 | −2.825 | 1.00 | 32.72 |
| ATOM | 2040 | OW0 | WAT | H | 258 | 62.079 | 34.517 | 15.084 | 1.00 | 58.02 |
| ATOM | 2041 | OW0 | WAT | H | 259 | 65.249 | 17.692 | −9.923 | 1.00 | 33.97 |
| ATOM | 2042 | OW0 | WAT | H | 260 | 84.611 | 20.635 | 26.103 | 1.00 | 36.71 |
| ATOM | 2043 | OW0 | WAT | H | 261 | 54.603 | 33.043 | −3.243 | 1.00 | 61.42 |
| ATOM | 2044 | OW0 | WAT | H | 262 | 78.330 | 21.964 | 3.390 | 1.00 | 36.54 |
| ATOM | 2045 | OW0 | WAT | H | 263 | 60.505 | 30.649 | 16.856 | 1.00 | 61.43 |
| ATOM | 2046 | OW0 | WAT | H | 264 | 60.673 | 28.301 | 41.001 | 1.00 | 61.42 |
| ATOM | 2047 | OW0 | WAT | H | 265 | 75.570 | 42.160 | 26.603 | 1.00 | 48.11 |
| ATOM | 2048 | OW0 | WAT | H | 266 | 66.492 | 40.897 | −8.600 | 1.00 | 49.26 |
| ATOM | 2049 | OW0 | WAT | H | 267 | 78.047 | 10.851 | 26.352 | 1.00 | 37.66 |
| ATOM | 2050 | OW0 | WAT | H | 268 | 45.278 | 23.196 | 23.784 | 1.00 | 46.39 |
| ATOM | 2051 | OW0 | WAT | H | 269 | 79.914 | 16.055 | 24.356 | 1.00 | 60.41 |
| ATOM | 2052 | OW0 | WAT | H | 270 | 83.059 | 27.578 | 9.958 | 1.00 | 41.48 |
| ATOM | 2053 | OW0 | WAT | H | 271 | 53.990 | 28.727 | 44.389 | 1.00 | 53.80 |
| ATOM | 2054 | OW0 | WAT | H | 272 | 84.167 | 21.797 | 23.410 | 1.00 | 29.89 |
| ATOM | 2055 | OW0 | WAT | H | 273 | 48.547 | 18.514 | 24.335 | 1.00 | 35.54 |
| ATOM | 2056 | OW0 | WAT | H | 274 | 83.374 | 23.895 | 18.013 | 1.00 | 38.70 |
| ATOM | 2057 | OW0 | WAT | H | 275 | 44.928 | 16.891 | 21.587 | 1.00 | 47.27 |
| ATOM | 2058 | OW0 | WAT | H | 276 | 79.981 | 10.119 | 37.103 | 1.00 | 46.85 |
| ATOM | 2059 | OW0 | WAT | H | 277 | 51.478 | 30.160 | 35.040 | 1.00 | 37.36 |
| ATOM | 2060 | OW0 | WAT | H | 278 | 79.945 | 11.751 | 28.340 | 1.00 | 45.00 |
| ATOM | 2061 | OW0 | WAT | H | 279 | 72.128 | 38.830 | 13.389 | 1.00 | 68.19 |
| ATOM | 2062 | OW0 | WAT | H | 280 | 56.951 | 24.568 | 40.730 | 1.00 | 69.60 |
| ATOM | 2063 | OW0 | WAT | H | 281 | 46.873 | 31.066 | 39.547 | 1.00 | 44.24 |
| ATOM | 2064 | OW0 | WAT | H | 282 | 78.996 | 17.114 | 19.359 | 1.00 | 35.71 |
| ATOM | 2065 | OW0 | WAT | H | 283 | 83.567 | 25.358 | 35.318 | 1.00 | 55.15 |
| ATOM | 2066 | OW0 | WAT | H | 284 | 61.769 | 14.437 | −0.829 | 1.00 | 37.96 |
| ATOM | 2067 | OW0 | WAT | H | 285 | 65.163 | 31.436 | −7.804 | 1.00 | 33.32 |
| ATOM | 2068 | OW0 | WAT | H | 286 | 42.116 | 26.484 | 19.462 | 1.00 | 38.95 |
| ATOM | 2069 | OW0 | WAT | H | 287 | 42.907 | 25.516 | 22.370 | 1.00 | 61.34 |

-continued

Data Lists

| | | | | | | | | | |
|---|---|---|---|---|---|---|---|---|---|
| ATOM | 2070 | OW0 | WAT | H | 288 | 82.439 | 35.148 | 8.022 | 1.00 | 45.96 |
| ATOM | 2071 | OW0 | WAT | H | 289 | 55.363 | 24.466 | −1.282 | 1.00 | 21.32 |
| ATOM | 2072 | OW0 | WAT | H | 290 | 63.050 | 9.755 | 27.052 | 1.00 | 46.02 |
| ATOM | 2074 | OW0 | WAT | H | 292 | 62.097 | 39.809 | −0.108 | 1.00 | 37.27 |
| ATOM | 2075 | OW0 | WAT | H | 293 | 39.885 | 32.648 | 26.137 | 1.00 | 32.19 |
| ATOM | 661 | N | ALA | A | 88 | 55.416 | 43.891 | 26.782 | 1.00 | 11.17 |
| ATOM | 662 | CA | ALA | A | 88 | 54.209 | 43.441 | 26.124 | 1.00 | 11.51 |
| ATOM | 663 | C | ALA | A | 88 | 53.978 | 41.975 | 26.112 | 1.00 | 11.06 |
| ATOM | 664 | O | ALA | A | 88 | 54.949 | 41.191 | 26.190 | 1.00 | 12.85 |
| ATOM | 665 | CB | ALA | A | 88 | 54.372 | 43.905 | 24.582 | 1.00 | 12.18 |
| ATOM | 666 | N | SER | A | 89 | 52.719 | 41.526 | 25.953 | 1.00 | 11.32 |
| ATOM | 667 | CA | SER | A | 89 | 52.459 | 40.087 | 25.769 | 1.00 | 11.17 |
| ATOM | 668 | C | SER | A | 89 | 51.547 | 39.992 | 24.538 | 1.00 | 11.44 |
| ATOM | 669 | O | SER | A | 89 | 50.833 | 40.964 | 24.213 | 1.00 | 11.04 |
| ATOM | 670 | CB | SER | A | 89 | 51.858 | 39.327 | 26.979 | 1.00 | 14.68 |
| ATOM | 671 | OG | SER | A | 89 | 50.438 | 39.480 | 27.037 | 1.00 | 13.56 |
| ATOM | 672 | N | PHE | A | 90 | 51.691 | 38.849 | 23.860 | 1.00 | 11.58 |
| ATOM | 673 | CA | PHE | A | 90 | 50.894 | 38.604 | 22.632 | 1.00 | 10.03 |
| ATOM | 674 | C | PHE | A | 90 | 50.125 | 37.331 | 22.780 | 1.00 | 11.41 |
| ATOM | 675 | O | PHE | A | 90 | 50.615 | 36.342 | 23.436 | 1.00 | 12.95 |
| ATOM | 676 | CB | PHE | A | 90 | 51.867 | 38.480 | 21.438 | 1.00 | 10.86 |
| ATOM | 677 | CG | PHE | A | 90 | 52.457 | 39.784 | 21.010 | 1.00 | 11.25 |
| ATOM | 678 | CD1 | PHE | A | 90 | 53.611 | 40.322 | 21.617 | 1.00 | 12.54 |
| ATOM | 679 | CD2 | PHE | A | 90 | 51.824 | 40.536 | 19.976 | 1.00 | 13.88 |
| ATOM | 680 | CE1 | PHE | A | 90 | 54.134 | 41.602 | 21.173 | 1.00 | 12.35 |
| ATOM | 681 | CE2 | PHE | A | 90 | 52.304 | 41.729 | 19.539 | 1.00 | 13.61 |
| ATOM | 682 | CZ | PHE | A | 90 | 53.459 | 42.314 | 20.114 | 1.00 | 12.98 |
| ATOM | 683 | N | VAL | A | 91 | 48.928 | 37.303 | 22.178 | 1.00 | 9.83 |
| ATOM | 684 | CA | VAL | A | 91 | 48.073 | 36.118 | 22.213 | 1.00 | 10.22 |
| ATOM | 685 | C | VAL | A | 91 | 47.588 | 35.798 | 20.793 | 1.00 | 14.03 |
| ATOM | 686 | O | VAL | A | 91 | 47.690 | 36.675 | 19.893 | 1.00 | 13.50 |
| ATOM | 687 | CB | VAL | A | 91 | 46.803 | 36.261 | 23.098 | 1.00 | 13.62 |
| ATOM | 688 | CG1 | VAL | A | 91 | 47.217 | 36.266 | 24.596 | 1.00 | 15.08 |
| ATOM | 689 | CG2 | VAL | A | 91 | 45.999 | 37.507 | 22.722 | 1.00 | 13.05 |
| ATOM | 690 | N | THR | A | 92 | 47.154 | 34.586 | 20.611 | 1.00 | 12.76 |
| ATOM | 691 | CA | THR | A | 92 | 46.628 | 34.182 | 19.275 | 1.00 | 11.56 |
| ATOM | 692 | C | THR | A | 92 | 45.132 | 33.971 | 19.349 | 1.00 | 13.31 |
| ATOM | 693 | O | THR | A | 92 | 44.530 | 33.582 | 20.391 | 1.00 | 13.08 |
| ATOM | 694 | CB | THR | A | 92 | 47.340 | 32.987 | 18.626 | 1.00 | 12.64 |
| ATOM | 695 | OG1 | THR | A | 92 | 47.132 | 31.797 | 19.427 | 1.00 | 16.06 |
| ATOM | 696 | CG2 | THR | A | 92 | 48.849 | 33.212 | 18.472 | 1.00 | 13.80 |
| ATOM | 697 | N | MET | A | 93 | 44.412 | 34.267 | 18.224 | 1.00 | 11.69 |
| ATOM | 698 | CA | MET | A | 93 | 42.951 | 34.108 | 18.147 | 1.00 | 11.35 |
| ATOM | 699 | C | MET | A | 93 | 42.609 | 34.143 | 16.641 | 1.00 | 14.45 |
| ATOM | 700 | O | MET | A | 93 | 43.429 | 34.572 | 15.835 | 1.00 | 13.44 |
| ATOM | 701 | CB | MET | A | 93 | 42.224 | 35.317 | 18.831 | 1.00 | 12.85 |
| ATOM | 702 | CG | MET | A | 93 | 42.628 | 36.660 | 18.178 | 1.00 | 13.91 |
| ATOM | 703 | SD | MET | A | 93 | 42.084 | 38.126 | 19.099 | 1.00 | 14.46 |
| ATOM | 704 | CE | MET | A | 93 | 43.261 | 37.982 | 20.500 | 1.00 | 14.10 |
| ATOM | 705 | N | PRO | A | 94 | 41.440 | 33.664 | 16.331 | 1.00 | 12.36 |
| ATOM | 706 | CA | PRO | A | 94 | 40.994 | 33.662 | 14.921 | 1.00 | 12.35 |
| ATOM | 707 | C | PRO | A | 94 | 40.927 | 35.119 | 14.384 | 1.00 | 15.66 |
| ATOM | 708 | O | PRO | A | 94 | 40.708 | 36.116 | 15.069 | 1.00 | 14.35 |
| ATOM | 709 | CB | PRO | A | 94 | 39.592 | 33.150 | 15.005 | 1.00 | 13.86 |
| ATOM | 710 | CG | PRO | A | 94 | 39.606 | 32.186 | 16.204 | 1.00 | 15.72 |
| ATOM | 711 | CD | PRO | A | 94 | 40.405 | 33.060 | 17.191 | 1.00 | 12.82 |
| ATOM | 712 | N | ASP | A | 95 | 41.040 | 35.223 | 13.035 | 1.00 | 14.03 |
| ATOM | 713 | CA | ASP | A | 95 | 40.966 | 36.538 | 12.434 | 1.00 | 15.39 |
| ATOM | 714 | C | ASP | A | 95 | 39.760 | 37.423 | 12.789 | 1.00 | 16.06 |
| ATOM | 715 | O | ASP | A | 95 | 39.886 | 38.651 | 12.959 | 1.00 | 16.29 |
| ATOM | 716 | CB | ASP | A | 95 | 40.998 | 36.355 | 10.903 | 1.00 | 15.44 |
| ATOM | 717 | CG | ASP | A | 95 | 41.147 | 37.685 | 10.168 | 1.00 | 15.85 |
| ATOM | 718 | CD1 | ASP | A | 95 | 42.199 | 38.354 | 10.289 | 1.00 | 14.33 |
| ATOM | 719 | OD2 | ASP | A | 95 | 40.178 | 38.088 | 9.441 | 1.00 | 18.70 |
| ATOM | 720 | N | GLU | A | 96 | 38.571 | 36.831 | 12.864 | 1.00 | 15.70 |
| ATOM | 721 | CA | GLU | A | 96 | 37.389 | 37.631 | 13.182 | 1.00 | 14.32 |
| ATOM | 722 | C | GLU | A | 96 | 37.468 | 38.304 | 14.550 | 1.00 | 18.35 |
| ATOM | 723 | O | GLU | A | 96 | 37.196 | 39.487 | 14.686 | 1.00 | 17.78 |
| ATOM | 724 | CB | GLU | A | 96 | 36.102 | 36.828 | 12.995 | 1.00 | 16.31 |
| ATOM | 725 | CG | GLU | A | 96 | 34.860 | 37.623 | 13.365 | 1.00 | 22.63 |
| ATOM | 726 | CD | GLU | A | 96 | 33.526 | 36.880 | 13.068 | 1.00 | 23.98 |
| ATOM | 727 | CE1 | GLU | A | 96 | 33.559 | 35.704 | 12.706 | 1.00 | 25.84 |
| ATOM | 728 | OE2 | GLU | A | 96 | 32.461 | 37.497 | 13.246 | 1.00 | 30.53 |
| ATOM | 729 | N | GLU | A | 97 | 37.863 | 37.514 | 15.545 | 1.00 | 15.16 |
| ATOM | 730 | CA | GLU | A | 97 | 37.999 | 38.111 | 16.875 | 1.00 | 15.52 |
| ATOM | 731 | C | GLU | A | 97 | 39.128 | 39.177 | 16.850 | 1.00 | 13.99 |
| ATOM | 732 | O | GLU | A | 97 | 39.028 | 40.206 | 17.493 | 1.00 | 16.67 |

-continued

Data Lists

| | | | | | | | | | |
|---|---|---|---|---|---|---|---|---|---|
| ATOM | 733 | CB | GLU | A | 97 | 38.338 | 36.990 | 17.857 | 1.00 | 15.35 |
| ATOM | 734 | OG | GLU | A | 97 | 38.566 | 37.525 | 19.290 | 1.00 | 17.59 |
| ATOM | 735 | CD | GLU | A | 97 | 38.814 | 36.394 | 20.261 | 1.00 | 22.36 |
| ATOM | 736 | CE1 | GLU | A | 97 | 38.899 | 35.209 | 19.850 | 1.00 | 17.71 |
| ATOM | 737 | OE2 | GLU | A | 97 | 38.890 | 36.747 | 21.481 | 1.00 | 22.62 |
| ATOM | 738 | N | ALA | A | 98 | 40.228 | 38.917 | 16.123 | 1.00 | 13.03 |
| ATOM | 739 | CA | ALA | A | 98 | 41.349 | 39.850 | 16.036 | 1.00 | 12.71 |
| ATOM | 740 | C | ALA | A | 98 | 40.957 | 41.219 | 15.463 | 1.00 | 15.63 |
| ATOM | 741 | O | ALA | A | 98 | 41.496 | 42.253 | 15.834 | 1.00 | 14.36 |
| ATOM | 742 | CB | ALA | A | 98 | 42.463 | 39.223 | 15.190 | 1.00 | 14.85 |
| ATOM | 743 | N | ARG | A | 99 | 39.959 | 41.235 | 14.534 | 1.00 | 14.05 |
| ATOM | 744 | CA | ARG | A | 99 | 39.565 | 42.490 | 13.944 | 1.00 | 15.96 |
| ATOM | 745 | C | ARG | A | 99 | 38.883 | 43.474 | 14.862 | 1.00 | 17.44 |
| ATOM | 746 | O | ARG | A | 99 | 38.845 | 44.666 | 14.535 | 1.00 | 21.21 |
| ATOM | 747 | CB | ARG | A | 99 | 38.743 | 42.259 | 12.633 | 1.00 | 17.37 |
| ATOM | 748 | CG | ARG | A | 99 | 39.630 | 41.725 | 11.515 | 1.00 | 16.32 |
| ATOM | 749 | CD | ARG | A | 99 | 38.869 | 41.511 | 10.154 | 1.00 | 16.45 |
| ATOM | 750 | NE | ARG | A | 99 | 38.150 | 40.252 | 10.074 | 1.00 | 14.75 |
| ATOM | 751 | CZ | ARG | A | 99 | 36.851 | 40.106 | 10.202 | 1.00 | 13.61 |
| ATOM | 752 | NH1 | ARG | A | 99 | 36.084 | 41.162 | 10.415 | 1.00 | 16.09 |
| ATOM | 753 | NH2 | ARG | A | 99 | 36.306 | 38.906 | 10.083 | 1.00 | 18.40 |
| ATOM | 754 | N | THR | A | 100 | 38.364 | 43.021 | 15.998 | 1.00 | 16.42 |
| ATOM | 755 | CA | THR | A | 100 | 37.753 | 43.988 | 16.917 | 1.00 | 16.33 |
| ATOM | 756 | C | THR | A | 100 | 38.350 | 43.803 | 18.317 | 1.00 | 19.97 |
| ATOM | 757 | O | THR | A | 100 | 37.735 | 44.220 | 19.329 | 1.00 | 20.03 |
| ATOM | 758 | CB | THR | A | 100 | 36.246 | 43.908 | 17.014 | 1.00 | 21.91 |
| ATOM | 759 | OG1 | THR | A | 100 | 35.822 | 42.556 | 17.266 | 1.00 | 20.66 |
| ATOM | 760 | CG2 | THR | A | 100 | 35.626 | 44.354 | 15.658 | 1.00 | 22.68 |
| ATOM | 761 | N | TRP | A | 101 | 39.533 | 43.203 | 18.349 | 1.00 | 17.87 |
| ATOM | 762 | CA | TRP | A | 101 | 40.199 | 42.981 | 19.671 | 1.00 | 16.71 |
| ATOM | 763 | C | TRP | A | 101 | 40.710 | 44.288 | 20.258 | 1.00 | 19.04 |
| ATOM | 764 | O | TRP | A | 101 | 41.247 | 45.135 | 19.540 | 1.00 | 17.05 |
| ATOM | 765 | CB | TRP | A | 101 | 41.390 | 42.038 | 19.455 | 1.00 | 14.65 |
| ATOM | 766 | CG | TRP | A | 101 | 42.311 | 41.932 | 20.694 | 1.00 | 14.16 |
| ATOM | 767 | CD1 | TRP | A | 101 | 43.528 | 42.444 | 20.800 | 1.00 | 16.31 |
| ATOM | 768 | CD2 | TRP | A | 101 | 42.034 | 41.196 | 21.899 | 1.00 | 16.31 |
| ATOM | 769 | NE1 | TRP | A | 101 | 44.070 | 42.124 | 22.085 | 1.00 | 15.49 |
| ATOM | 770 | CE2 | TRP | A | 101 | 43.151 | 41.365 | 22.743 | 1.00 | 17.23 |
| ATOM | 771 | CE3 | TRP | A | 101 | 40.944 | 40.448 | 22.362 | 1.00 | 19.60 |
| ATOM | 772 | CZ2 | TRP | A | 101 | 43.211 | 40.796 | 24.037 | 1.00 | 18.02 |
| ATOM | 773 | CZ3 | TRP | A | 101 | 41.013 | 39.854 | 23.639 | 1.00 | 21.23 |
| ATOM | 774 | CH2 | TRP | A | 101 | 42.136 | 40.045 | 24.443 | 1.00 | 21.41 |
| ATOM | 775 | N | ARG | A | 102 | 40.563 | 44.465 | 21.612 | 1.00 | 15.76 |
| ATOM | 776 | CA | ARG | A | 102 | 41.070 | 45.703 | 22.235 | 1.00 | 16.64 |
| ATOM | 777 | C | ARG | A | 102 | 42.180 | 45.344 | 23.275 | 1.00 | 14.79 |
| ATOM | 778 | O | ARG | A | 102 | 41.838 | 44.748 | 24.316 | 1.00 | 17.03 |
| ATOM | 779 | CB | ARG | A | 102 | 39.943 | 46.431 | 22.963 | 1.00 | 17.42 |
| ATOM | 780 | CG | ARG | A | 102 | 38.775 | 46.821 | 22.058 | 1.00 | 24.67 |
| ATOM | 781 | CD | ARG | A | 102 | 39.285 | 47.662 | 20.922 | 1.00 | 40.94 |
| ATOM | 782 | NE | ARG | A | 102 | 38.215 | 47.967 | 19.971 | 1.00 | 58.76 |
| ATOM | 783 | CZ | ARG | A | 102 | 38.246 | 47.668 | 18.668 | 1.00 | 65.94 |
| ATOM | 784 | NH1 | ARG | A | 102 | 39.307 | 47.043 | 18.135 | 1.00 | 46.00 |
| ATOM | 785 | NH2 | ARG | A | 102 | 37.211 | 47.987 | 17.896 | 1.00 | 52.57 |
| ATOM | 786 | N | PRO | A | 103 | 43.422 | 45.671 | 22.999 | 1.00 | 15.12 |
| ATOM | 787 | CA | PRO | A | 103 | 44.515 | 45.313 | 23.948 | 1.00 | 13.53 |
| ATOM | 788 | C | PRO | A | 103 | 44.329 | 46.058 | 25.274 | 1.00 | 15.29 |
| ATOM | 789 | O | PRO | A | 103 | 43.749 | 47.117 | 25.309 | 1.00 | 16.02 |
| ATOM | 790 | CB | PRO | A | 103 | 45.770 | 45.786 | 23.270 | 1.00 | 14.34 |
| ATOM | 791 | CG | PRO | A | 103 | 45.386 | 45.801 | 21.717 | 1.00 | 18.46 |
| ATOM | 792 | CD | PRO | A | 103 | 43.942 | 46.250 | 21.748 | 1.00 | 15.59 |
| ATOM | 793 | N | ASN | A | 104 | 44.884 | 45.445 | 26.347 | 1.00 | 14.28 |
| ATOM | 794 | CA | ASN | A | 104 | 44.836 | 46.034 | 27.698 | 1.00 | 13.04 |
| ATOM | 795 | C | ASN | A | 104 | 46.119 | 46.863 | 27.862 | 1.00 | 14.43 |
| ATOM | 796 | O | ASN | A | 104 | 47.217 | 46.296 | 28.125 | 1.00 | 13.98 |
| ATOM | 797 | CB | ASN | A | 104 | 44.760 | 44.875 | 28.655 | 1.00 | 12.98 |
| ATOM | 798 | CG | ASN | A | 104 | 43.490 | 44.121 | 28.510 | 1.00 | 15.09 |
| ATOM | 799 | OD1 | ASN | A | 104 | 42.398 | 44.706 | 28.655 | 1.00 | 17.92 |
| ATOM | 800 | ND2 | ASN | A | 104 | 43.569 | 42.842 | 28.158 | 1.00 | 16.93 |
| ATOM | 801 | N | VAL | A | 105 | 46.019 | 48.179 | 27.673 | 1.00 | 14.40 |
| ATOM | 802 | CA | VAL | A | 105 | 47.150 | 49.048 | 27.734 | 1.00 | 15.19 |
| ATOM | 803 | C | VAL | A | 105 | 47.164 | 49.895 | 28.992 | 1.00 | 18.79 |
| ATOM | 804 | O | VAL | A | 105 | 46.172 | 50.559 | 29.309 | 1.00 | 20.46 |
| ATOM | 805 | CB | VAL | A | 105 | 47.188 | 50.005 | 26.534 | 1.00 | 18.28 |
| ATOM | 806 | CG1 | VAL | A | 105 | 48.423 | 50.904 | 26.591 | 1.00 | 20.67 |
| ATOM | 807 | CG2 | VAL | A | 105 | 47.223 | 49.166 | 25.186 | 1.00 | 17.51 |
| ATOM | 808 | N | ALA | A | 106 | 48.297 | 49.853 | 29.683 | 1.00 | 16.66 |
| ATOM | 809 | CA | ALA | A | 106 | 48.457 | 50.694 | 30.921 | 1.00 | 16.75 |

-continued

Data Lists

| ATOM | 810 | C | ALA | A | 106 | 49.647 | 51.596 | 30.665 | 1.00 | 15.84 |
|---|---|---|---|---|---|---|---|---|---|---|
| ATOM | 811 | O | ALA | A | 106 | 50.711 | 51.115 | 30.266 | 1.00 | 16.27 |
| ATOM | 812 | CB | ALA | A | 106 | 48.672 | 49.807 | 32.141 | 1.00 | 17.32 |
| ATOM | 813 | N | TYR | A | 107 | 49.475 | 52.911 | 30.905 | 1.00 | 15.99 |
| ATOM | 814 | CA | TYR | A | 107 | 50.474 | 53.931 | 30.697 | 1.00 | 15.93 |
| ATOM | 815 | C | TYR | A | 107 | 51.037 | 54.390 | 32.046 | 1.00 | 18.71 |
| ATOM | 816 | O | TYR | A | 107 | 50.287 | 54.506 | 33.007 | 1.00 | 20.84 |
| ATOM | 817 | CB | TYR | A | 107 | 49.901 | 55.154 | 29.951 | 1.00 | 19.26 |
| ATOM | 818 | CG | TYR | A | 107 | 49.419 | 54.812 | 28.533 | 1.00 | 21.14 |
| ATOM | 819 | CD1 | TYR | A | 107 | 50.291 | 54.819 | 27.490 | 1.00 | 21.91 |
| ATOM | 820 | CD2 | TYR | A | 107 | 48.106 | 54.510 | 28.307 | 1.00 | 23.16 |
| ATOM | 821 | CE1 | TYR | A | 107 | 49.861 | 54.497 | 26.190 | 1.00 | 24.59 |
| ATOM | 822 | CE2 | TYR | A | 107 | 47.672 | 54.182 | 27.007 | 1.00 | 24.09 |
| ATOM | 823 | CZ | TYR | A | 107 | 48.571 | 54.197 | 25.992 | 1.00 | 27.50 |
| ATOM | 824 | OH | TYR | A | 107 | 48.200 | 53.880 | 24.685 | 1.00 | 29.66 |
| ATOM | 825 | N | PHE | A | 108 | 52.340 | 54.609 | 32.042 | 1.00 | 15.42 |
| ATOM | 826 | CA | PHE | A | 108 | 53.049 | 55.012 | 33.297 | 1.00 | 15.71 |
| ATOM | 827 | C | PHE | A | 108 | 53.868 | 56.249 | 33.162 | 1.00 | 19.91 |
| ATOM | 828 | O | PHE | A | 108 | 54.268 | 56.703 | 32.071 | 1.00 | 19.12 |
| ATOM | 829 | CB | PHE | A | 108 | 53.974 | 53.876 | 33.723 | 1.00 | 16.87 |
| ATOM | 830 | CG | PHE | A | 108 | 53.258 | 52.651 | 34.125 | 1.00 | 16.76 |
| ATOM | 831 | CD1 | PHE | A | 108 | 52.842 | 51.702 | 33.160 | 1.00 | 17.17 |
| ATOM | 832 | CD2 | PHE | A | 108 | 52.940 | 52.381 | 35.481 | 1.00 | 17.45 |
| ATOM | 833 | CE1 | PHE | A | 108 | 52.147 | 50.577 | 33.546 | 1.00 | 19.62 |
| ATOM | 834 | CE2 | PHE | A | 108 | 52.242 | 51.243 | 35.867 | 1.00 | 20.41 |
| ATOM | 835 | CZ | PHE | A | 108 | 51.838 | 50.301 | 34.901 | 1.00 | 19.54 |
| ATOM | 836 | N | GLU | A | 109 | 54.193 | 56.830 | 34.342 | 1.00 | 17.02 |
| ATOM | 837 | CA | GLU | A | 109 | 55.053 | 58.009 | 34.382 | 1.00 | 17.21 |
| ATOM | 838 | C | GLU | A | 109 | 55.561 | 58.104 | 35.858 | 1.00 | 15.89 |
| ATOM | 839 | O | GLU | A | 109 | 55.062 | 57.376 | 36.696 | 1.00 | 16.10 |
| ATOM | 840 | CB | GLU | A | 109 | 54.259 | 59.300 | 34.091 | 1.00 | 18.77 |
| ATOM | 841 | CG | GLU | A | 109 | 53.234 | 59.595 | 35.166 | 1.00 | 19.64 |
| ATOM | 842 | CD | GLU | A | 109 | 52.394 | 60.875 | 34.948 | 1.00 | 21.63 |
| ATOM | 843 | OE1 | GLU | A | 109 | 52.761 | 61.761 | 34.165 | 1.00 | 24.76 |
| ATOM | 844 | OE2 | GLU | A | 109 | 51.361 | 60.960 | 35.616 | 1.00 | 28.24 |
| ATOM | 845 | N | GLY | A | 110 | 56.507 | 59.001 | 36.063 | 1.00 | 15.85 |
| ATOM | 846 | CA | GLY | A | 110 | 57.054 | 59.240 | 37.466 | 1.00 | 17.20 |
| ATOM | 847 | C | GLY | A | 110 | 57.499 | 57.968 | 38.164 | 1.00 | 16.93 |
| ATOM | 848 | O | GLY | A | 110 | 58.272 | 57.157 | 37.598 | 1.00 | 16.26 |
| ATOM | 849 | N | ASP | A | 111 | 57.047 | 57.749 | 39.423 | 1.00 | 14.38 |
| ATOM | 850 | CA | ASP | A | 111 | 57.455 | 56.568 | 40.177 | 1.00 | 14.84 |
| ATOM | 851 | C | ASP | A | 111 | 56.588 | 55.369 | 39.865 | 1.00 | 14.72 |
| ATOM | 852 | O | ASP | A | 111 | 55.888 | 54.753 | 40.690 | 1.00 | 14.34 |
| ATOM | 853 | CB | ASP | A | 111 | 57.356 | 56.953 | 41.689 | 1.00 | 17.05 |
| ATOM | 854 | CG | ASP | A | 111 | 57.812 | 55.841 | 42.614 | 1.00 | 19.59 |
| ATOM | 855 | OD1 | ASP | A | 111 | 58.707 | 55.034 | 42.277 | 1.00 | 20.52 |
| ATOM | 856 | OD2 | ASP | A | 111 | 57.219 | 55.731 | 43.714 | 1.00 | 19.81 |
| ATOM | 857 | N | ASN | A | 112 | 56.617 | 54.987 | 38.573 | 1.00 | 14.68 |
| ATOM | 858 | CA | ASN | A | 112 | 55.763 | 53.835 | 38.157 | 1.00 | 16.14 |
| ATOM | 859 | C | ASN | A | 112 | 54.291 | 54.049 | 38.569 | 1.00 | 13.02 |
| ATOM | 860 | O | ASN | A | 112 | 53.609 | 53.111 | 39.049 | 1.00 | 14.89 |
| ATOM | 861 | CB | ASN | A | 112 | 56.322 | 52.431 | 38.503 | 1.00 | 16.17 |
| ATOM | 862 | CG | ASN | A | 112 | 57.541 | 52.089 | 37.656 | 1.00 | 18.78 |
| ATOM | 863 | OD1 | ASN | A | 112 | 57.742 | 52.728 | 36.605 | 1.00 | 17.25 |
| ATOM | 864 | ND2 | ASN | A | 112 | 58.332 | 51.112 | 38.079 | 1.00 | 15.61 |
| ATOM | 865 | N | GLU | A | 113 | 53.814 | 55.286 | 38.317 | 1.00 | 14.05 |
| ATOM | 866 | CA | GLU | A | 113 | 52.440 | 55.685 | 38.605 | 1.00 | 15.74 |
| ATOM | 867 | C | GLU | A | 113 | 51.602 | 55.432 | 37.349 | 1.00 | 18.95 |
| ATOM | 868 | O | GLU | A | 113 | 51.844 | 56.053 | 36.325 | 1.00 | 19.58 |
| ATOM | 869 | CB | GLU | A | 113 | 52.402 | 57.167 | 38.952 | 1.00 | 17.38 |
| ATOM | 870 | CG | GLU | A | 113 | 51.034 | 57.648 | 39.454 | 1.00 | 20.91 |
| ATOM | 871 | CD | GLU | A | 113 | 50.594 | 57.002 | 40.802 | 1.00 | 24.09 |
| ATOM | 872 | OE1 | GLU | A | 113 | 51.358 | 56.979 | 41.779 | 1.00 | 30.10 |
| ATOM | 873 | OE2 | GLU | A | 113 | 49.450 | 56.530 | 40.862 | 1.00 | 36.71 |
| ATOM | 874 | N | MET | A | 114 | 50.624 | 54.554 | 37.470 | 1.00 | 18.64 |
| ATOM | 875 | CA | MET | A | 114 | 49.757 | 54.212 | 36.305 | 1.00 | 20.88 |
| ATOM | 876 | C | MET | A | 114 | 48.811 | 55.341 | 36.028 | 1.00 | 27.67 |
| ATOM | 877 | O | MET | A | 114 | 48.090 | 55.775 | 36.930 | 1.00 | 27.90 |
| ATOM | 878 | CB | MET | A | 114 | 48.991 | 52.925 | 36.584 | 1.00 | 23.89 |
| ATOM | 879 | CG | MET | A | 114 | 48.173 | 52.424 | 35.345 | 1.00 | 26.69 |
| ATOM | 880 | SD | MET | A | 114 | 47.345 | 50.879 | 35.650 | 1.00 | 29.33 |
| ATOM | 881 | CE | MET | A | 114 | 48.738 | 49.883 | 36.101 | 1.00 | 23.75 |
| ATOM | 882 | N | LYS | A | 115 | 48.790 | 55.846 | 34.789 | 1.00 | 25.26 |
| ATOM | 883 | CA | LYS | A | 115 | 47.883 | 56.943 | 34.440 | 1.00 | 30.27 |
| ATOM | 884 | C | LYS | A | 115 | 46.430 | 56.485 | 34.405 | 1.00 | 36.08 |
| ATOM | 885 | O | LYS | A | 115 | 45.545 | 57.363 | 34.605 | 1.00 | 41.29 |
| ATOM | 886 | CB | LYS | A | 115 | 48.251 | 57.602 | 33.112 | 1.00 | 31.52 |

-continued

Data Lists

| | | | | | | | | | |
|---|---|---|---|---|---|---|---|---|---|
| ATOM | 887 | CG | LYS | A | 115 | 49.665 | 58.100 | 32.995 | 1.00 | 29.39 |
| ATOM | 888 | CD | LYS | A | 115 | 49.830 | 58.930 | 31.710 | 1.00 | 35.11 |
| ATOM | 889 | CE | LYS | A | 115 | 51.281 | 59.149 | 31.351 | 1.00 | 39.16 |
| ATOM | 890 | NZ | LYS | A | 115 | 51.445 | 60.206 | 30.288 | 1.00 | 41.83 |
| ATOM | 892 | N | MET | B | 1 | 49.295 | 18.983 | 11.961 | 1.00 | 17.87 |
| ATOM | 893 | CA | MET | B | 1 | 50.088 | 19.983 | 12.674 | 1.00 | 15.77 |
| ATOM | 894 | C | MET | B | 1 | 49.867 | 21.364 | 12.128 | 1.00 | 18.38 |
| ATOM | 895 | O | MET | B | 1 | 49.270 | 21.493 | 11.014 | 1.00 | 16.03 |
| ATOM | 896 | CB | MET | B | 1 | 51.505 | 19.597 | 12.960 | 1.00 | 18.15 |
| ATOM | 897 | CG | MET | B | 1 | 52.312 | 19.036 | 11.858 | 1.00 | 21.69 |
| ATOM | 898 | SD | MET | B | 1 | 52.465 | 20.286 | 10.552 | 1.00 | 24.50 |
| ATOM | 899 | CE | MET | B | 1 | 53.497 | 19.234 | 9.256 | 1.00 | 19.90 |
| ATOM | 900 | N | ILE | B | 2 | 50.273 | 22.378 | 12.874 | 1.00 | 13.90 |
| ATOM | 901 | CA | ILE | B | 2 | 50.019 | 23.771 | 12.510 | 1.00 | 12.73 |
| ATOM | 902 | C | ILE | B | 2 | 51.265 | 24.482 | 12.069 | 1.00 | 15.11 |
| ATOM | 903 | O | ILE | B | 2 | 52.322 | 24.450 | 12.698 | 1.00 | 13.08 |
| ATOM | 904 | CB | ILE | B | 2 | 49.400 | 24.499 | 13.757 | 1.00 | 12.91 |
| ATOM | 905 | CG1 | ILE | B | 2 | 48.119 | 23.792 | 14.267 | 1.00 | 14.95 |
| ATOM | 906 | CG2 | ILE | B | 2 | 49.218 | 25.945 | 13.547 | 1.00 | 13.31 |
| ATOM | 907 | CD1 | ILE | B | 2 | 46.943 | 23.904 | 13.276 | 1.00 | 19.87 |
| ATOM | 908 | N | ARG | B | 3 | 51.138 | 25.131 | 10.910 | 1.00 | 11.64 |
| ATOM | 909 | CA | ARG | B | 3 | 52.229 | 25.868 | 10.327 | 1.00 | 9.38 |
| ATOM | 910 | C | ARG | B | 3 | 52.150 | 27.383 | 10.524 | 1.00 | 8.16 |
| ATOM | 911 | O | ARG | B | 3 | 51.039 | 27.931 | 10.673 | 1.00 | 9.82 |
| ATOM | 912 | CB | ARG | B | 3 | 52.082 | 25.697 | 8.760 | 1.00 | 11.91 |
| ATOM | 913 | CG | ARG | B | 3 | 52.248 | 24.258 | 8.287 | 1.00 | 12.07 |
| ATOM | 914 | CD | ARG | B | 3 | 53.705 | 23.876 | 8.003 | 1.00 | 12.41 |
| ATOM | 915 | NE | ARG | B | 3 | 53.758 | 22.596 | 7.334 | 1.00 | 12.53 |
| ATOM | 916 | CZ | ARG | B | 3 | 54.867 | 21.986 | 6.901 | 1.00 | 11.34 |
| ATOM | 917 | NH1 | ARG | B | 3 | 56.094 | 22.483 | 7.125 | 1.00 | 11.49 |
| ATOM | 918 | NH2 | ARG | B | 3 | 54.748 | 20.841 | 6.167 | 1.00 | 11.64 |
| ATOM | 919 | N | THR | B | 4 | 53.317 | 28.048 | 10.501 | 1.00 | 11.35 |
| ATOM | 920 | CA | THR | B | 4 | 53.417 | 29.519 | 10.576 | 1.00 | 10.99 |
| ATOM | 921 | C | THR | B | 4 | 53.769 | 29.941 | 9.093 | 1.00 | 9.80 |
| ATOM | 922 | O | THR | B | 4 | 54.789 | 29.551 | 8.631 | 1.00 | 10.46 |
| ATOM | 923 | CB | THR | B | 4 | 54.502 | 29.963 | 11.507 | 1.00 | 13.30 |
| ATOM | 924 | OG1 | THR | B | 4 | 54.145 | 29.451 | 12.826 | 1.00 | 12.86 |
| ATOM | 925 | CG2 | THR | B | 4 | 54.597 | 31.446 | 11.593 | 1.00 | 11.07 |
| ATOM | 926 | N | MET | B | 5 | 52.897 | 30.764 | 8.525 | 1.00 | 10.61 |
| ATOM | 927 | CA | MET | B | 5 | 53.045 | 31.215 | 7.092 | 1.00 | 10.17 |
| ATOM | 928 | C | MET | B | 5 | 53.023 | 32.709 | 6.987 | 1.00 | 13.79 |
| ATOM | 929 | O | MET | B | 5 | 52.333 | 33.412 | 7.759 | 1.00 | 12.14 |
| ATOM | 930 | CB | MET | B | 5 | 51.799 | 30.698 | 6.391 | 1.00 | 10.85 |
| ATOM | 931 | CG | MET | B | 5 | 51.655 | 29.138 | 6.389 | 1.00 | 13.35 |
| ATOM | 932 | SD | MET | B | 5 | 52.937 | 28.173 | 5.793 | 1.00 | 12.31 |
| ATOM | 933 | CE | MET | B | 5 | 52.760 | 28.465 | 3.924 | 1.00 | 9.06 |
| ATOM | 934 | N | LEU | B | 6 | 53.705 | 33.229 | 5.939 | 1.00 | 11.48 |
| ATOM | 935 | CA | LEU | B | 6 | 53.676 | 34.675 | 5.698 | 1.00 | 11.70 |
| ATOM | 936 | C | LEU | B | 6 | 52.227 | 35.093 | 5.344 | 1.00 | 15.58 |
| ATOM | 937 | O | LEU | B | 6 | 51.621 | 34.549 | 4.376 | 1.00 | 12.84 |
| ATOM | 938 | CB | LEU | B | 6 | 54.595 | 34.999 | 4.516 | 1.00 | 11.07 |
| ATOM | 939 | CG | LEU | B | 6 | 54.561 | 36.468 | 4.141 | 1.00 | 10.79 |
| ATOM | 940 | CD1 | LEU | B | 6 | 55.327 | 37.415 | 5.158 | 1.00 | 12.32 |
| ATOM | 941 | CD2 | LEU | B | 6 | 55.228 | 36.692 | 2.748 | 1.00 | 12.20 |
| ATOM | 942 | N | GLN | B | 7 | 51.608 | 36.000 | 6.115 | 1.00 | 11.50 |
| ATOM | 943 | CA | GLN | B | 7 | 50.275 | 36.439 | 5.854 | 1.00 | 12.08 |
| ATOM | 944 | C | GLN | B | 7 | 50.283 | 37.543 | 4.772 | 1.00 | 13.00 |
| ATOM | 945 | O | GLN | B | 7 | 49.368 | 37.573 | 3.878 | 1.00 | 13.76 |
| ATOM | 946 | CB | GLN | B | 7 | 49.614 | 37.046 | 7.144 | 1.00 | 13.70 |
| ATOM | 947 | CG | GLN | B | 7 | 48.181 | 37.402 | 7.017 | 1.00 | 13.52 |
| ATOM | 948 | CD | GLN | B | 7 | 47.882 | 38.740 | 6.256 | 1.00 | 15.62 |
| ATOM | 949 | OE1 | GLN | B | 7 | 46.810 | 38.816 | 5.553 | 1.00 | 14.96 |
| ATOM | 950 | NE2 | GLN | B | 7 | 48.745 | 39.780 | 6.431 | 1.00 | 13.51 |
| ATOM | 951 | N | GLY | B | 8 | 51.235 | 38.442 | 4.850 | 1.00 | 12.82 |
| ATOM | 952 | CA | GLY | B | 8 | 51.318 | 39.567 | 3.907 | 1.00 | 13.57 |
| ATOM | 953 | C | GLY | B | 8 | 52.519 | 40.435 | 4.210 | 1.00 | 17.33 |
| ATOM | 954 | O | GLY | B | 8 | 53.154 | 40.314 | 5.278 | 1.00 | 16.12 |
| ATOM | 955 | N | LYS | B | 9 | 52.917 | 41.301 | 3.271 | 1.00 | 13.73 |
| ATOM | 956 | CA | LYS | B | 9 | 54.045 | 42.162 | 3.517 | 1.00 | 14.09 |
| ATOM | 957 | C | LYS | B | 9 | 53.980 | 43.423 | 2.693 | 1.00 | 17.41 |
| ATOM | 958 | O | LYS | B | 9 | 53.290 | 43.474 | 1.636 | 1.00 | 16.23 |
| ATOM | 959 | CB | LYS | B | 9 | 55.357 | 41.484 | 3.338 | 1.00 | 17.25 |
| ATOM | 960 | CG | LYS | B | 9 | 55.685 | 41.165 | 1.849 | 1.00 | 16.41 |
| ATOM | 961 | CD | LYS | B | 9 | 57.128 | 40.757 | 1.590 | 1.00 | 16.11 |
| ATOM | 962 | CE | LYS | B | 9 | 57.413 | 40.363 | 0.083 | 1.00 | 20.64 |
| ATOM | 963 | NZ | LYS | B | 9 | 58.845 | 40.122 | −0.219 | 1.00 | 24.09 |
| ATOM | 964 | N | LEU | B | 10 | 54.623 | 44.438 | 3.206 | 1.00 | 14.37 |

-continued

| | | | | | | | | | |
|---|---|---|---|---|---|---|---|---|---|
| \multicolumn{10}{c}{Data Lists} |
| ATOM | 965 | CA | LEU | B | 10 | 54.793 | 45.753 | 2.541 | 1.00 | 13.07 |
| ATOM | 966 | C | LEU | B | 10 | 56.264 | 45.671 | 2.117 | 1.00 | 17.74 |
| ATOM | 967 | O | LEU | B | 10 | 57.211 | 45.651 | 2.922 | 1.00 | 15.88 |
| ATOM | 968 | CB | LEU | B | 10 | 54.531 | 46.942 | 3.473 | 1.00 | 12.64 |
| ATOM | 969 | CG | LEU | B | 10 | 53.125 | 47.012 | 4.065 | 1.00 | 16.69 |
| ATOM | 970 | CD1 | LEU | B | 10 | 52.972 | 48.183 | 5.050 | 1.00 | 19.95 |
| ATOM | 971 | CD2 | LEU | B | 10 | 51.998 | 47.113 | 2.952 | 1.00 | 18.21 |
| ATOM | 972 | N | HIS | B | 11 | 56.532 | 45.559 | 0.795 | 1.00 | 15.41 |
| ATOM | 973 | CA | HIS | B | 11 | 57.852 | 45.410 | 0.342 | 1.00 | 15.54 |
| ATOM | 974 | C | HIS | B | 11 | 58.554 | 46.680 | −0.107 | 1.00 | 20.36 |
| ATOM | 975 | O | HIS | B | 11 | 58.088 | 47.329 | −1.109 | 1.00 | 19.27 |
| ATOM | 976 | CB | HIS | B | 11 | 57.855 | 44.396 | −0.897 | 1.00 | 17.02 |
| ATOM | 977 | CG | HIS | B | 11 | 59.222 | 43.925 | −1.277 | 1.00 | 20.52 |
| ATOM | 978 | ND1 | HIS | B | 11 | 59.891 | 42.946 | −0.575 | 1.00 | 23.10 |
| ATOM | 979 | CD2 | HIS | B | 11 | 60.067 | 44.321 | −2.265 | 1.00 | 23.01 |
| ATOM | 980 | CE1 | HIS | B | 11 | 61.084 | 42.750 | −1.109 | 1.00 | 22.29 |
| ATOM | 981 | NE2 | HIS | B | 11 | 61.218 | 43.579 | −2.141 | 1.00 | 22.03 |
| ATOM | 982 | N | ARG | B | 12 | 59.636 | 47.041 | 0.577 | 1.00 | 17.66 |
| ATOM | 983 | CA | ARG | B | 12 | 60.427 | 48.202 | 0.273 | 1.00 | 17.87 |
| ATOM | 984 | C | ARG | B | 12 | 59.755 | 49.542 | 0.461 | 1.00 | 21.36 |
| ATOM | 985 | O | ARG | B | 12 | 59.858 | 50.465 | −0.401 | 1.00 | 21.72 |
| ATOM | 986 | CB | ARG | B | 12 | 61.185 | 48.082 | −1.105 | 1.00 | 17.27 |
| ATOM | 987 | CG | ARG | B | 12 | 62.150 | 46.920 | −1.155 | 1.00 | 16.85 |
| ATOM | 988 | CD | ARG | B | 12 | 62.849 | 46.746 | −2.537 | 1.00 | 21.64 |
| ATOM | 989 | NE | ARG | B | 12 | 63.541 | 47.993 | −2.907 | 1.00 | 26.91 |
| ATOM | 990 | CZ | ARG | B | 12 | 64.818 | 48.252 | −2.642 | 1.00 | 32.28 |
| ATOM | 991 | NH1 | ARG | B | 12 | 65.345 | 49.421 | −3.011 | 1.00 | 32.70 |
| ATOM | 992 | NH2 | ARG | B | 12 | 65.573 | 47.367 | −2.015 | 1.00 | 23.04 |
| ATOM | 993 | N | VAL | B | 13 | 59.082 | 49.737 | 1.613 | 1.00 | 16.36 |
| ATOM | 994 | CA | VAL | B | 13 | 58.476 | 51.010 | 1.919 | 1.00 | 16.81 |
| ATOM | 995 | C | VAL | B | 13 | 59.568 | 51.825 | 2.625 | 1.00 | 19.79 |
| ATOM | 996 | O | VAL | B | 13 | 60.555 | 51.259 | 3.103 | 1.00 | 21.56 |
| ATOM | 997 | CB | VAL | B | 13 | 57.262 | 50.903 | 2.868 | 1.00 | 20.87 |
| ATOM | 998 | CG1 | VAL | B | 13 | 56.117 | 50.340 | 2.233 | 1.00 | 22.00 |
| ATOM | 999 | CG2 | VAL | B | 13 | 57.614 | 50.095 | 4.174 | 1.00 | 19.93 |
| ATOM | 1000 | N | LYS | B | 14 | 59.429 | 53.148 | 2.658 | 1.00 | 17.58 |
| ATOM | 1001 | CA | LYS | B | 14 | 60.462 | 53.955 | 3.313 | 1.00 | 18.29 |
| ATOM | 1002 | C | LYS | B | 14 | 59.955 | 54.558 | 4.631 | 1.00 | 17.32 |
| ATOM | 1003 | O | LYS | B | 14 | 58.811 | 54.965 | 4.720 | 1.00 | 17.18 |
| ATOM | 1004 | CB | LYS | B | 14 | 60.958 | 55.077 | 2.370 | 1.00 | 21.96 |
| ATOM | 1005 | CG | LYS | B | 14 | 61.928 | 54.568 | 1.327 | 1.00 | 29.69 |
| ATOM | 1006 | CD | LYS | B | 14 | 62.379 | 55.718 | 0.374 | 1.00 | 27.98 |
| ATOM | 1007 | CE | LYS | B | 14 | 63.251 | 55.192 | −0.769 | 1.00 | 33.09 |
| ATOM | 1008 | NZ | LYS | B | 14 | 62.422 | 54.676 | −1.901 | 1.00 | 36.70 |
| ATOM | 1009 | N | VAL | B | 15 | 60.836 | 54.550 | 5.641 | 1.00 | 17.61 |
| ATOM | 1010 | CA | VAL | B | 15 | 60.462 | 55.122 | 6.942 | 1.00 | 15.98 |
| ATOM | 1011 | C | VAL | B | 15 | 60.291 | 56.648 | 6.751 | 1.00 | 18.36 |
| ATOM | 1012 | O | VAL | B | 15 | 61.155 | 57.284 | 6.183 | 1.00 | 20.10 |
| ATOM | 1013 | CB | VAL | B | 15 | 61.537 | 54.823 | 7.986 | 1.00 | 18.17 |
| ATOM | 1014 | CG1 | VAL | B | 15 | 61.172 | 55.554 | 9.332 | 1.00 | 19.48 |
| ATOM | 1015 | CG2 | VAL | B | 15 | 61.579 | 53.284 | 8.219 | 1.00 | 18.97 |
| ATOM | 1016 | N | THR | B | 16 | 59.195 | 57.208 | 7.241 | 1.00 | 16.59 |
| ATOM | 1017 | CA | THR | B | 16 | 58.949 | 58.657 | 7.071 | 1.00 | 18.46 |
| ATOM | 1018 | C | THR | B | 16 | 59.061 | 59.479 | 8.337 | 1.00 | 23.98 |
| ATOM | 1019 | O | THR | B | 16 | 59.187 | 60.728 | 8.286 | 1.00 | 23.98 |
| ATOM | 1020 | CB | THR | B | 16 | 57.537 | 58.906 | 6.438 | 1.00 | 20.68 |
| ATOM | 1021 | OG1 | THR | B | 16 | 56.495 | 58.483 | 7.322 | 1.00 | 20.66 |
| ATOM | 1022 | CG2 | THR | B | 16 | 57.407 | 58.134 | 5.067 | 1.00 | 20.82 |
| ATOM | 1023 | N | HIS | B | 17 | 59.034 | 58.811 | 9.484 | 1.00 | 21.79 |
| ATOM | 1024 | CA | HIS | B | 17 | 59.102 | 59.539 | 10.776 | 1.00 | 23.09 |
| ATOM | 1025 | C | HIS | B | 17 | 59.580 | 58.582 | 11.852 | 1.00 | 25.64 |
| ATOM | 1026 | O | HIS | B | 17 | 59.398 | 57.358 | 11.739 | 1.00 | 20.59 |
| ATOM | 1027 | CB | HIS | B | 17 | 57.630 | 59.960 | 11.101 | 1.00 | 25.73 |
| ATOM | 1028 | CG | HIS | B | 17 | 57.436 | 60.783 | 12.353 | 1.00 | 31.57 |
| ATOM | 1029 | ND1 | HIS | B | 17 | 56.596 | 60.377 | 13.379 | 1.00 | 34.88 |
| ATOM | 1030 | CD2 | HIS | B | 17 | 57.919 | 62.000 | 12.724 | 1.00 | 34.96 |
| ATOM | 1031 | CE1 | HIS | B | 17 | 56.589 | 61.293 | 14.335 | 1.00 | 35.01 |
| ATOM | 1032 | NE2 | HIS | B | 17 | 57.383 | 62.290 | 13.966 | 1.00 | 35.08 |
| ATOM | 1033 | N | ALA | B | 18 | 60.189 | 59.139 | 12.893 | 1.00 | 25.07 |
| ATOM | 1034 | CA | ALA | B | 18 | 60.673 | 58.327 | 14.027 | 1.00 | 25.93 |
| ATOM | 1035 | C | ALA | B | 18 | 60.235 | 59.122 | 15.285 | 1.00 | 31.11 |
| ATOM | 1036 | O | ALA | B | 18 | 60.376 | 60.360 | 15.314 | 1.00 | 33.50 |
| ATOM | 1037 | CB | ALA | B | 18 | 62.157 | 58.146 | 13.972 | 1.00 | 27.54 |
| ATOM | 1038 | N | ASP | B | 19 | 59.643 | 58.456 | 16.281 | 1.00 | 24.42 |
| ATOM | 1039 | CA | ASP | B | 19 | 59.162 | 59.161 | 17.502 | 1.00 | 24.78 |
| ATOM | 1040 | C | ASP | B | 19 | 59.503 | 58.342 | 18.739 | 1.00 | 27.05 |
| ATOM | 1041 | O | ASP | B | 19 | 58.658 | 57.595 | 19.257 | 1.00 | 24.71 |

-continued

Data Lists

| | | | | | | | | | |
|---|---|---|---|---|---|---|---|---|---|
| ATOM | 1042 | CB | ASP | B | 19 | 57.647 | 59.409 | 17.384 | 1.00 | 25.96 |
| ATOM | 1043 | CG | ASP | B | 19 | 57.052 | 60.183 | 18.572 | 1.00 | 34.10 |
| ATOM | 1044 | OD1 | ASP | B | 19 | 57.807 | 60.624 | 19.466 | 1.00 | 34.04 |
| ATOM | 1045 | OD2 | ASP | B | 19 | 55.800 | 60.351 | 18.593 | 1.00 | 38.22 |
| ATOM | 1046 | N | LEU | B | 20 | 60.742 | 58.494 | 19.199 | 1.00 | 25.80 |
| ATOM | 1047 | CA | LEU | B | 20 | 61.238 | 57.779 | 20.364 | 1.00 | 24.85 |
| ATOM | 1048 | C | LEU | B | 20 | 60.390 | 57.962 | 21.616 | 1.00 | 27.59 |
| ATOM | 1049 | O | LEU | B | 20 | 60.129 | 56.981 | 22.335 | 1.00 | 26.06 |
| ATOM | 1050 | CB | LEU | B | 20 | 62.689 | 58.208 | 20.666 | 1.00 | 25.72 |
| ATOM | 1051 | CG | LEU | B | 20 | 63.459 | 57.525 | 21.809 | 1.00 | 29.24 |
| ATOM | 1052 | CD1 | LEU | B | 20 | 63.844 | 56.100 | 21.431 | 1.00 | 28.84 |
| ATOM | 1053 | CD2 | LEU | B | 20 | 64.720 | 58.345 | 22.159 | 1.00 | 29.15 |
| ATOM | 1054 | N | HIS | B | 21 | 59.981 | 59.207 | 21.878 | 1.00 | 28.61 |
| ATOM | 1055 | CA | HIS | B | 21 | 59.155 | 59.572 | 23.074 | 1.00 | 30.90 |
| ATOM | 1056 | C | HIS | B | 21 | 57.680 | 59.351 | 23.007 | 1.00 | 36.12 |
| ATOM | 1057 | O | HIS | B | 21 | 56.915 | 59.806 | 23.896 | 1.00 | 35.00 |
| ATOM | 1058 | CB | HIS | B | 21 | 59.509 | 60.991 | 23.549 | 1.00 | 32.76 |
| ATOM | 1059 | CG | HIS | B | 21 | 60.950 | 61.157 | 23.845 | 1.00 | 36.81 |
| ATOM | 1060 | ND1 | HIS | B | 21 | 61.792 | 61.941 | 23.086 | 1.00 | 39.48 |
| ATOM | 1061 | CD2 | HIS | B | 21 | 61.731 | 60.556 | 24.776 | 1.00 | 38.76 |
| ATOM | 1062 | CE1 | HIS | B | 21 | 63.025 | 61.847 | 23.564 | 1.00 | 38.26 |
| ATOM | 1063 | NE2 | HIS | B | 21 | 63.014 | 61.014 | 24.588 | 1.00 | 38.36 |
| ATOM | 1064 | N | TYR | B | 22 | 57.270 | 58.641 | 21.975 | 1.00 | 33.13 |
| ATOM | 1065 | CA | TYR | B | 22 | 55.874 | 58.333 | 21.767 | 1.00 | 33.14 |
| ATOM | 1066 | C | TYR | B | 22 | 55.136 | 57.743 | 22.985 | 1.00 | 37.60 |
| ATOM | 1067 | O | TYR | B | 22 | 55.697 | 56.936 | 23.774 | 1.00 | 32.76 |
| ATOM | 1068 | CB | TYR | B | 22 | 55.794 | 57.254 | 20.681 | 1.00 | 33.35 |
| ATOM | 1069 | CG | TYR | B | 22 | 54.410 | 57.005 | 20.169 | 1.00 | 35.03 |
| ATOM | 1070 | CD1 | TYR | B | 22 | 53.728 | 58.003 | 19.481 | 1.00 | 36.82 |
| ATOM | 1071 | CD2 | TYR | B | 22 | 53.772 | 55.794 | 20.385 | 1.00 | 35.58 |
| ATOM | 1072 | CE1 | TYR | B | 22 | 52.442 | 57.795 | 19.013 | 1.00 | 37.35 |
| ATOM | 1073 | CE2 | TYR | B | 22 | 52.491 | 55.577 | 19.914 | 1.00 | 36.01 |
| ATOM | 1074 | CZ | TYR | B | 22 | 51.834 | 56.569 | 19.229 | 1.00 | 42.70 |
| ATOM | 1075 | OH | TYR | B | 22 | 50.542 | 56.288 | 18.772 | 1.00 | 46.65 |
| ATOM | 1076 | N | GLU | B | 23 | 53.877 | 58.126 | 23.092 | 1.00 | 39.24 |
| ATOM | 1077 | CA | GLU | B | 23 | 52.991 | 57.636 | 24.122 | 1.00 | 42.44 |
| ATOM | 1078 | C | GLU | B | 23 | 51.673 | 57.203 | 23.428 | 1.00 | 47.01 |
| ATOM | 1079 | O | GLU | B | 23 | 50.884 | 58.032 | 23.017 | 1.00 | 48.53 |
| ATOM | 1080 | CB | GLU | B | 23 | 52.723 | 58.677 | 25.211 | 1.00 | 44.81 |
| ATOM | 1081 | CG | GLU | B | 23 | 51.620 | 58.234 | 26.155 | 1.00 | 53.00 |
| ATOM | 1082 | CD | GLU | B | 23 | 51.690 | 58.900 | 27.515 | 1.00 | 63.57 |
| ATOM | 1083 | OE1 | GLU | B | 23 | 52.173 | 60.058 | 27.596 | 1.00 | 70.57 |
| ATOM | 1084 | OE2 | GLU | B | 23 | 51.237 | 58.268 | 28.501 | 1.00 | 49.95 |
| ATOM | 1085 | N | GLY | B | 24 | 51.453 | 55.900 | 23.305 | 1.00 | 43.35 |
| ATOM | 1086 | CA | GLY | B | 24 | 50.234 | 55.411 | 22.678 | 1.00 | 47.63 |
| ATOM | 1087 | C | GLY | B | 24 | 50.321 | 53.939 | 22.257 | 1.00 | 49.81 |
| ATOM | 1088 | O | GLY | B | 24 | 50.860 | 53.127 | 23.028 | 1.00 | 43.71 |
| ATOM | 1089 | OH | GLY | B | 24 | 49.852 | 53.595 | 21.143 | 1.00 | 78.26 |
| ATOM | 1090 | C | PVL | B | 25 | 55.590 | 51.160 | 16.243 | 1.00 | 18.29 |
| ATOM | 1091 | O | PVL | B | 25 | 56.587 | 51.766 | 16.023 | 1.00 | 21.21 |
| ATOM | 1092 | CA | PVL | B | 25 | 55.340 | 50.687 | 17.625 | 1.00 | 27.46 |
| ATOM | 1093 | CB | PVL | B | 25 | 54.143 | 49.829 | 17.834 | 1.00 | 25.35 |
| ATOM | 1094 | ON | PVL | B | 25 | 56.135 | 50.957 | 18.541 | 1.00 | 33.71 |
| ATOM | 1095 | N | CYS | B | 26 | 54.735 | 50.714 | 15.217 | 1.00 | 15.60 |
| ATOM | 1096 | CA | CYS | B | 26 | 54.985 | 51.203 | 13.855 | 1.00 | 16.64 |
| ATOM | 1097 | CB | CYS | B | 26 | 55.756 | 50.146 | 13.029 | 1.00 | 14.30 |
| ATOM | 1098 | SG | CYS | B | 26 | 56.010 | 50.798 | 11.325 | 1.00 | 18.05 |
| ATOM | 1099 | C | CYS | B | 26 | 53.636 | 51.600 | 13.281 | 1.00 | 14.55 |
| ATOM | 1100 | O | CYS | B | 26 | 52.716 | 50.778 | 13.121 | 1.00 | 16.28 |
| ATOM | 1101 | N | ALA | B | 27 | 53.472 | 52.925 | 13.012 | 1.00 | 15.46 |
| ATOM | 1102 | CA | ALA | B | 27 | 52.197 | 53.479 | 12.457 | 1.00 | 15.63 |
| ATOM | 1103 | C | ALA | B | 27 | 52.328 | 53.470 | 10.917 | 1.00 | 15.10 |
| ATOM | 1104 | O | ALA | B | 27 | 53.303 | 53.924 | 10.380 | 1.00 | 15.77 |
| ATOM | 1105 | CB | ALA | B | 27 | 51.919 | 54.908 | 12.948 | 1.00 | 16.71 |
| ATOM | 1106 | N | ILE | B | 28 | 51.301 | 52.924 | 10.300 | 1.00 | 14.23 |
| ATOM | 1107 | CA | ILE | B | 28 | 51.286 | 52.712 | 8.846 | 1.00 | 14.71 |
| ATOM | 1108 | C | ILE | B | 28 | 49.989 | 53.151 | 8.224 | 1.00 | 17.41 |
| ATOM | 1109 | O | ILE | B | 28 | 48.913 | 52.880 | 8.714 | 1.00 | 16.90 |
| ATOM | 1110 | CB | ILE | B | 28 | 51.404 | 51.141 | 8.665 | 1.00 | 16.58 |
| ATOM | 1111 | CG1 | ILE | B | 28 | 52.699 | 50.640 | 9.314 | 1.00 | 16.36 |
| ATOM | 1112 | CG2 | ILE | B | 28 | 51.329 | 50.765 | 7.154 | 1.00 | 15.52 |
| ATOM | 1113 | CD1 | ILE | B | 28 | 52.708 | 49.114 | 9.667 | 1.00 | 18.68 |
| ATOM | 1114 | N | ASP | B | 29 | 50.128 | 53.872 | 7.090 | 1.00 | 16.97 |
| ATOM | 1115 | CA | ASP | B | 29 | 48.943 | 54.364 | 6.337 | 1.00 | 18.01 |
| ATOM | 1116 | C | ASP | B | 29 | 47.927 | 53.186 | 6.186 | 1.00 | 17.51 |
| ATOM | 1117 | O | ASP | B | 29 | 48.339 | 52.095 | 5.725 | 1.00 | 15.93 |
| ATOM | 1118 | CB | ASP | B | 29 | 49.481 | 54.766 | 4.949 | 1.00 | 18.64 |

-continued

Data Lists

| ATOM | 1119 | CG  | ASP | B | 29 | 48.383 | 55.304 | 3.960  | 1.00 | 21.55 |
| ATOM | 1120 | OD1 | ASP | B | 29 | 47.171 | 55.003 | 4.082  | 1.00 | 21.30 |
| ATOM | 1121 | OD2 | ASP | B | 29 | 48.831 | 56.051 | 3.034  | 1.00 | 22.85 |
| ATOM | 1122 | N   | GLN | B | 30 | 46.665 | 53.404 | 6.579  | 1.00 | 17.64 |
| ATOM | 1123 | CA  | GLN | B | 30 | 45.593 | 52.389 | 6.498  | 1.00 | 16.64 |
| ATOM | 1124 | C   | GLN | B | 30 | 45.497 | 51.773 | 5.101  | 1.00 | 20.42 |
| ATOM | 1125 | O   | GLN | B | 30 | 45.212 | 50.578 | 4.991  | 1.00 | 19.64 |
| ATOM | 1126 | CB  | GLN | B | 30 | 44.231 | 52.918 | 6.947  | 1.00 | 19.10 |
| ATOM | 1127 | CG  | GLN | B | 30 | 43.138 | 51.881 | 6.990  | 1.00 | 20.18 |
| ATOM | 1128 | CD  | GLN | B | 30 | 43.422 | 50.807 | 8.020  | 1.00 | 24.27 |
| ATOM | 1129 | CE1 | GLN | B | 30 | 43.624 | 51.129 | 9.221  | 1.00 | 20.83 |
| ATOM | 1130 | NE2 | GLN | B | 30 | 43.418 | 49.525 | 7.584  | 1.00 | 20.72 |
| ATOM | 1131 | N   | ASP | B | 31 | 45.765 | 52.541 | 4.034  | 1.00 | 19.98 |
| ATOM | 1132 | CA  | ASP | B | 31 | 45.692 | 51.922 | 2.700  | 1.00 | 20.52 |
| ATOM | 1133 | C   | ASP | B | 31 | 46.711 | 50.794 | 2.519  | 1.00 | 19.87 |
| ATOM | 1134 | O   | ASP | B | 31 | 46.458 | 49.781 | 1.783  | 1.00 | 20.49 |
| ATOM | 1135 | CB  | ASP | B | 31 | 45.971 | 52.970 | 1.621  | 1.00 | 20.56 |
| ATOM | 1136 | CG  | ASP | B | 31 | 44.751 | 53.787 | 1.281  | 1.00 | 27.59 |
| ATOM | 1137 | CD1 | ASP | B | 31 | 43.596 | 53.382 | 1.538  | 1.00 | 27.63 |
| ATOM | 1138 | CD2 | ASP | B | 31 | 44.990 | 54.926 | 0.798  | 1.00 | 25.47 |
| ATOM | 1139 | N   | PHE | B | 32 | 47.886 | 50.935 | 3.170  | 1.00 | 17.26 |
| ATOM | 1140 | CA  | PHE | B | 32 | 48.951 | 49.962 | 3.088  | 1.00 | 16.13 |
| ATOM | 1141 | C   | PHE | B | 32 | 48.525 | 48.723 | 3.890  | 1.00 | 15.84 |
| ATOM | 1142 | O   | PHE | B | 32 | 48.690 | 47.554 | 3.430  | 1.00 | 15.43 |
| ATOM | 1143 | CB  | PHE | B | 32 | 50.278 | 50.479 | 3.670  | 1.00 | 17.62 |
| ATOM | 1144 | CG  | PHE | B | 32 | 50.847 | 51.723 | 2.976  | 1.00 | 18.64 |
| ATOM | 1145 | CD1 | PHE | B | 32 | 50.236 | 52.299 | 1.842  | 1.00 | 20.38 |
| ATOM | 1146 | CD2 | PHE | B | 32 | 52.019 | 52.292 | 3.473  | 1.00 | 21.28 |
| ATOM | 1147 | CE1 | PHE | B | 32 | 50.828 | 53.473 | 1.249  | 1.00 | 21.62 |
| ATOM | 1148 | CE2 | PHE | B | 32 | 52.587 | 53.413 | 2.908  | 1.00 | 24.06 |
| ATOM | 1149 | CZ  | PHE | B | 32 | 51.988 | 54.006 | 1.779  | 1.00 | 22.14 |
| ATOM | 1150 | N   | LEU | B | 33 | 47.989 | 48.981 | 5.086  | 1.00 | 15.62 |
| ATOM | 1151 | CA  | LEU | B | 33 | 47.526 | 47.856 | 5.919  | 1.00 | 15.62 |
| ATOM | 1152 | C   | LEU | B | 33 | 46.481 | 47.031 | 5.124  | 1.00 | 14.56 |
| ATOM | 1153 | O   | LEU | B | 33 | 46.534 | 45.810 | 5.106  | 1.00 | 15.50 |
| ATOM | 1154 | CB  | LEU | B | 33 | 46.899 | 48.361 | 7.221  | 1.00 | 15.46 |
| ATOM | 1155 | CG  | LEU | B | 33 | 47.899 | 49.072 | 8.189  | 1.00 | 17.68 |
| ATOM | 1156 | CD1 | LEU | B | 33 | 47.114 | 49.554 | 9.450  | 1.00 | 18.11 |
| ATOM | 1157 | CD2 | LEU | B | 33 | 48.993 | 48.086 | 8.627  | 1.00 | 17.59 |
| ATOM | 1158 | N   | ASP | B | 34 | 45.530 | 47.724 | 4.466  | 1.00 | 15.47 |
| ATOM | 1159 | CA  | ASP | B | 34 | 44.461 | 47.090 | 3.695  | 1.00 | 15.42 |
| ATOM | 1160 | C   | ASP | B | 34 | 45.018 | 46.177 | 2.609  | 1.00 | 15.50 |
| ATOM | 1161 | O   | ASP | B | 34 | 44.542 | 45.082 | 2.444  | 1.00 | 16.94 |
| ATOM | 1162 | CB  | ASP | B | 34 | 43.604 | 48.177 | 3.031  | 1.00 | 16.78 |
| ATOM | 1163 | CG  | ASP | B | 34 | 42.649 | 48.846 | 3.990  | 1.00 | 21.53 |
| ATOM | 1164 | OD1 | ASP | B | 34 | 42.574 | 48.461 | 5.192  | 1.00 | 22.41 |
| ATOM | 1165 | OD2 | ASP | B | 34 | 41.944 | 49.809 | 3.549  | 1.00 | 24.39 |
| ATOM | 1166 | N   | ALA | B | 35 | 46.013 | 46.650 | 1.875  | 1.00 | 15.30 |
| ATOM | 1167 | CA  | ALA | B | 35 | 46.623 | 45.864 | 0.804  | 1.00 | 16.57 |
| ATOM | 1168 | C   | ALA | B | 35 | 47.378 | 44.636 | 1.289  | 1.00 | 18.73 |
| ATOM | 1169 | O   | ALA | B | 35 | 47.387 | 43.587 | 0.644  | 1.00 | 19.02 |
| ATOM | 1170 | CB  | ALA | B | 35 | 47.576 | 46.726 | −0.042 | 1.00 | 18.18 |
| ATOM | 1171 | N   | ALA | B | 36 | 48.063 | 44.784 | 2.448  | 1.00 | 15.77 |
| ATOM | 1172 | CA  | ALA | B | 36 | 48.818 | 43.688 | 2.949  | 1.00 | 14.01 |
| ATOM | 1173 | C   | ALA | B | 36 | 48.015 | 42.756 | 3.920  | 1.00 | 12.66 |
| ATOM | 1174 | O   | ALA | B | 36 | 48.612 | 41.710 | 4.327  | 1.00 | 15.97 |
| ATOM | 1175 | CB  | ALA | B | 36 | 50.083 | 44.221 | 3.681  | 1.00 | 15.98 |
| ATOM | 1176 | N   | GLY | B | 37 | 46.798 | 43.130 | 4.266  | 1.00 | 12.31 |
| ATOM | 1177 | CA  | GLY | B | 37 | 45.973 | 42.352 | 5.150  | 1.00 | 12.99 |
| ATOM | 1178 | C   | GLY | B | 37 | 46.496 | 42.432 | 6.606  | 1.00 | 13.99 |
| ATOM | 1179 | O   | GLY | B | 37 | 46.069 | 41.557 | 7.415  | 1.00 | 13.49 |
| ATOM | 1180 | N   | ILE | B | 38 | 47.307 | 43.444 | 6.904  | 1.00 | 13.30 |
| ATOM | 1181 | CA  | ILE | B | 38 | 47.864 | 43.618 | 8.310  | 1.00 | 11.90 |
| ATOM | 1182 | C   | ILE | B | 38 | 46.839 | 44.382 | 9.121  | 1.00 | 13.73 |
| ATOM | 1183 | O   | ILE | B | 38 | 46.308 | 45.399 | 8.700  | 1.00 | 13.87 |
| ATOM | 1184 | CB  | ILE | B | 38 | 49.184 | 44.279 | 8.258  | 1.00 | 12.06 |
| ATOM | 1185 | CG1 | ILE | B | 38 | 50.228 | 43.360 | 7.542  | 1.00 | 13.02 |
| ATOM | 1186 | CG2 | ILE | B | 38 | 49.697 | 44.582 | 9.755  | 1.00 | 11.46 |
| ATOM | 1187 | CD1 | ILE | B | 38 | 51.570 | 43.996 | 7.284  | 1.00 | 14.92 |
| ATOM | 1188 | N   | LEU | B | 39 | 46.564 | 43.916 | 10.371 | 1.00 | 11.75 |
| ATOM | 1189 | CA  | LEU | B | 39 | 45.578 | 44.546 | 11.229 | 1.00 | 11.57 |
| ATOM | 1190 | C   | LEU | B | 39 | 46.194 | 45.436 | 12.297 | 1.00 | 13.60 |
| ATOM | 1191 | O   | LEU | B | 39 | 47.314 | 45.212 | 12.681 | 1.00 | 12.83 |
| ATOM | 1192 | CB  | LEU | B | 39 | 44.793 | 43.478 | 11.979 | 1.00 | 11.62 |
| ATOM | 1193 | CG  | LEU | B | 39 | 44.184 | 42.300 | 11.176 | 1.00 | 13.66 |
| ATOM | 1194 | CD1 | LEU | B | 39 | 43.446 | 41.373 | 12.104 | 1.00 | 15.79 |
| ATOM | 1195 | CD2 | LEU | B | 39 | 43.241 | 42.956 | 10.120 | 1.00 | 15.29 |

-continued

| | | | | | | | | | |
|---|---|---|---|---|---|---|---|---|---|
| ATOM | 1196 | N | GLU | B | 40 | 45.452 | 46.455 | 12.667 | 1.00 | 14.52 |
| ATOM | 1197 | CA | GLU | B | 40 | 45.908 | 47.316 | 13.786 | 1.00 | 14.56 |
| ATOM | 1198 | C | GLU | B | 40 | 46.034 | 46.318 | 14.996 | 1.00 | 14.90 |
| ATOM | 1199 | O | GLU | B | 40 | 45.194 | 45.428 | 15.204 | 1.00 | 13.14 |
| ATOM | 1200 | CB | GLU | B | 40 | 44.819 | 48.341 | 14.096 | 1.00 | 17.43 |
| ATOM | 1201 | CG | GLU | B | 40 | 45.175 | 49.769 | 13.693 | 1.00 | 36.71 |
| ATOM | 1202 | CD | GLU | B | 40 | 44.728 | 50.776 | 14.770 | 1.00 | 43.99 |
| ATOM | 1203 | OE1 | GLU | B | 40 | 43.514 | 50.732 | 15.112 | 1.00 | 33.64 |
| ATOM | 1204 | OE2 | GLU | B | 40 | 45.573 | 51.603 | 15.285 | 1.00 | 23.74 |
| ATOM | 1205 | N | ASN | B | 41 | 47.136 | 46.514 | 15.758 | 1.00 | 12.38 |
| ATOM | 1206 | CA | ASN | B | 41 | 47.457 | 45.691 | 16.951 | 1.00 | 12.93 |
| ATOM | 1207 | C | ASN | B | 41 | 48.019 | 44.334 | 16.656 | 1.00 | 15.81 |
| ATOM | 1208 | O | ASN | B | 41 | 48.283 | 43.527 | 17.534 | 1.00 | 13.21 |
| ATOM | 1209 | CB | ASN | B | 41 | 46.298 | 45.648 | 17.922 | 1.00 | 14.28 |
| ATOM | 1210 | CG | ASN | B | 41 | 45.966 | 47.041 | 18.493 | 1.00 | 12.10 |
| ATOM | 1211 | OD1 | ASN | B | 41 | 46.860 | 47.804 | 18.856 | 1.00 | 16.64 |
| ATOM | 1212 | ND2 | ASN | B | 41 | 44.680 | 47.382 | 18.491 | 1.00 | 15.27 |
| ATOM | 1213 | N | GLU | B | 42 | 48.244 | 44.017 | 15.384 | 1.00 | 10.98 |
| ATOM | 1214 | CA | GLU | B | 42 | 48.831 | 42.744 | 15.033 | 1.00 | 9.74 |
| ATOM | 1215 | C | GLU | B | 42 | 50.356 | 42.767 | 15.148 | 1.00 | 9.74 |
| ATOM | 1216 | O | GLU | B | 42 | 51.026 | 43.784 | 14.869 | 1.00 | 10.17 |
| ATOM | 1217 | CB | GLU | B | 42 | 48.499 | 42.388 | 13.482 | 1.00 | 10.40 |
| ATOM | 1218 | CG | GLU | B | 42 | 48.990 | 40.990 | 13.056 | 1.00 | 10.03 |
| ATOM | 1219 | CD | GLU | B | 42 | 48.652 | 40.661 | 11.573 | 1.00 | 13.25 |
| ATOM | 1220 | OE1 | GLU | B | 42 | 48.260 | 41.628 | 10.893 | 1.00 | 15.16 |
| ATOM | 1221 | OE2 | GLU | B | 42 | 48.788 | 39.493 | 11.198 | 1.00 | 12.03 |
| ATOM | 1222 | N | ALA | B | 43 | 50.947 | 41.634 | 15.574 | 1.00 | 9.51 |
| ATOM | 1223 | CA | ALA | B | 43 | 52.384 | 41.493 | 15.647 | 1.00 | 10.88 |
| ATOM | 1224 | C | ALA | B | 43 | 52.996 | 41.666 | 14.214 | 1.00 | 10.85 |
| ATOM | 1225 | O | ALA | B | 43 | 52.435 | 41.054 | 13.263 | 1.00 | 11.54 |
| ATOM | 1226 | CB | ALA | B | 43 | 52.772 | 40.069 | 16.175 | 1.00 | 12.49 |
| ATOM | 1227 | N | ILE | B | 44 | 54.041 | 42.408 | 14.075 | 1.00 | 11.86 |
| ATOM | 1228 | CA | ILE | B | 44 | 54.719 | 42.557 | 12.737 | 1.00 | 11.02 |
| ATOM | 1229 | C | ILE | B | 44 | 56.251 | 42.437 | 12.901 | 1.00 | 13.51 |
| ATOM | 1230 | O | ILE | B | 44 | 56.824 | 42.780 | 13.996 | 1.00 | 13.63 |
| ATOM | 1231 | CB | ILE | B | 44 | 54.386 | 43.905 | 12.029 | 1.00 | 12.21 |
| ATOM | 1232 | CG1 | ILE | B | 44 | 54.727 | 45.106 | 12.987 | 1.00 | 12.04 |
| ATOM | 1233 | CG2 | ILE | B | 44 | 52.925 | 43.894 | 11.585 | 1.00 | 14.58 |
| ATOM | 1234 | CD1 | ILE | B | 44 | 54.477 | 46.487 | 12.346 | 1.00 | 12.27 |
| ATOM | 1235 | N | ASP | B | 45 | 56.970 | 41.986 | 11.865 | 1.00 | 10.42 |
| ATOM | 1236 | CA | ASP | B | 45 | 58.401 | 41.882 | 11.844 | 1.00 | 10.06 |
| ATOM | 1237 | C | ASP | B | 45 | 58.826 | 42.973 | 10.843 | 1.00 | 14.23 |
| ATOM | 1238 | O | ASP | B | 45 | 58.174 | 43.130 | 9.772 | 1.00 | 14.99 |
| ATOM | 1239 | CB | ASP | B | 45 | 58.893 | 40.494 | 11.379 | 1.00 | 12.39 |
| ATOM | 1240 | CG | ASP | B | 45 | 58.410 | 39.394 | 12.277 | 1.00 | 15.51 |
| ATOM | 1241 | OD1 | ASP | B | 45 | 58.325 | 39.655 | 13.536 | 1.00 | 15.80 |
| ATOM | 1242 | OD2 | ASP | B | 45 | 58.044 | 38.297 | 11.812 | 1.00 | 15.67 |
| ATOM | 1243 | N | ILE | B | 46 | 59.874 | 43.711 | 11.152 | 1.00 | 10.63 |
| ATOM | 1244 | CA | ILE | B | 46 | 60.402 | 44.798 | 10.315 | 1.00 | 10.58 |
| ATOM | 1245 | C | ILE | B | 46 | 61.845 | 44.462 | 10.039 | 1.00 | 14.80 |
| ATOM | 1246 | O | ILE | B | 46 | 62.670 | 44.242 | 10.926 | 1.00 | 13.14 |
| ATOM | 1247 | CB | ILE | B | 46 | 60.237 | 46.173 | 10.981 | 1.00 | 12.68 |
| ATOM | 1248 | CG1 | ILE | B | 46 | 58.759 | 46.398 | 11.267 | 1.00 | 11.97 |
| ATOM | 1249 | CG2 | ILE | B | 46 | 60.843 | 47.266 | 10.035 | 1.00 | 14.01 |
| ATOM | 1250 | CD1 | ILE | B | 46 | 58.431 | 47.842 | 11.715 | 1.00 | 17.51 |
| ATOM | 1251 | N | TRP | B | 47 | 62.185 | 44.361 | 8.719 | 1.00 | 11.09 |
| ATOM | 1252 | CA | TRP | B | 47 | 63.488 | 43.982 | 8.256 | 1.00 | 12.91 |
| ATOM | 1253 | C | TRP | B | 47 | 64.025 | 45.208 | 7.488 | 1.00 | 18.14 |
| ATOM | 1254 | O | TRP | B | 47 | 63.436 | 45.628 | 6.467 | 1.00 | 16.83 |
| ATOM | 1255 | CB | TRP | B | 47 | 63.352 | 42.731 | 7.340 | 1.00 | 12.75 |
| ATOM | 1256 | CG | TRP | B | 47 | 62.711 | 41.546 | 8.024 | 1.00 | 12.68 |
| ATOM | 1257 | CD1 | TRP | B | 47 | 62.891 | 41.157 | 9.370 | 1.00 | 13.80 |
| ATOM | 1258 | CD2 | TRP | B | 47 | 61.810 | 40.606 | 7.470 | 1.00 | 12.97 |
| ATOM | 1259 | NE1 | TRP | B | 47 | 62.133 | 40.068 | 9.635 | 1.00 | 12.97 |
| ATOM | 1260 | CE2 | TRP | B | 47 | 61.449 | 39.686 | 8.500 | 1.00 | 14.42 |
| ATOM | 1261 | CE3 | TRP | B | 47 | 61.195 | 40.476 | 6.207 | 1.00 | 14.96 |
| ATOM | 1262 | CZ2 | TRP | B | 47 | 60.573 | 38.635 | 8.298 | 1.00 | 14.53 |
| ATOM | 1263 | CZ3 | TRP | B | 47 | 60.351 | 39.440 | 5.994 | 1.00 | 16.02 |
| ATOM | 1264 | CH2 | TRP | B | 47 | 60.033 | 38.509 | 7.012 | 1.00 | 16.49 |
| ATOM | 1265 | N | ASN | B | 48 | 65.081 | 45.816 | 8.024 | 1.00 | 15.37 |
| ATOM | 1266 | CA | ASN | B | 48 | 65.648 | 47.056 | 7.466 | 1.00 | 15.56 |
| ATOM | 1267 | C | ASN | B | 48 | 66.662 | 46.765 | 6.393 | 1.00 | 16.84 |
| ATOM | 1268 | O | ASN | B | 48 | 67.746 | 46.284 | 6.662 | 1.00 | 15.08 |
| ATOM | 1269 | CB | ASN | B | 48 | 66.293 | 47.841 | 8.654 | 1.00 | 14.22 |
| ATOM | 1270 | CG | ASN | B | 48 | 66.594 | 49.267 | 8.309 | 1.00 | 19.83 |
| ATOM | 1271 | OD1 | ASN | B | 48 | 67.100 | 49.532 | 7.211 | 1.00 | 17.68 |
| ATOM | 1272 | ND2 | ASN | B | 48 | 66.291 | 50.207 | 9.205 | 1.00 | 18.60 |

-continued

Data Lists

| | | | | | | | | | |
|---|---|---|---|---|---|---|---|---|---|
| ATOM | 1273 | N | VAL | B | 49 | 66.292 | 47.051 | 5.125 | 1.00 | 16.35 |
| ATOM | 1274 | CA | VAL | B | 49 | 67.188 | 46.806 | 4.002 | 1.00 | 16.91 |
| ATOM | 1275 | C | VAL | B | 49 | 68.418 | 47.753 | 4.002 | 1.00 | 18.54 |
| ATOM | 1276 | O | VAL | B | 49 | 69.539 | 47.390 | 3.566 | 1.00 | 19.45 |
| ATOM | 1277 | CB | VAL | B | 49 | 66.442 | 47.003 | 2.694 | 1.00 | 20.06 |
| ATOM | 1278 | CG1 | VAL | B | 49 | 67.380 | 46.691 | 1.524 | 1.00 | 21.67 |
| ATOM | 1279 | CG2 | VAL | B | 49 | 65.196 | 46.106 | 2.650 | 1.00 | 18.68 |
| ATOM | 1280 | N | THR | B | 50 | 68.196 | 48.964 | 4.504 | 1.00 | 17.72 |
| ATOM | 1281 | CA | THR | B | 50 | 69.290 | 49.926 | 4.552 | 1.00 | 18.92 |
| ATOM | 1282 | C | THR | B | 50 | 70.403 | 49.565 | 5.528 | 1.00 | 20.97 |
| ATOM | 1283 | O | THR | B | 50 | 71.593 | 49.537 | 5.172 | 1.00 | 20.06 |
| ATOM | 1284 | CB | THR | B | 50 | 68.764 | 51.325 | 4.851 | 1.00 | 19.40 |
| ATOM | 1285 | OG1 | THR | B | 50 | 67.798 | 51.708 | 3.856 | 1.00 | 19.82 |
| ATOM | 1286 | CG2 | THR | B | 50 | 69.931 | 52.390 | 4.950 | 1.00 | 21.30 |
| ATOM | 1287 | N | ASN | B | 51 | 70.022 | 49.279 | 6.788 | 1.00 | 17.46 |
| ATOM | 1288 | CA | ASN | B | 51 | 71.032 | 48.962 | 7.814 | 1.00 | 18.39 |
| ATOM | 1289 | C | ASN | B | 51 | 71.132 | 47.525 | 8.327 | 1.00 | 19.48 |
| ATOM | 1290 | O | ASN | B | 51 | 71.970 | 47.226 | 9.183 | 1.00 | 19.00 |
| ATOM | 1291 | CB | ASN | B | 51 | 70.913 | 49.949 | 8.998 | 1.00 | 18.51 |
| ATOM | 1292 | CG | ASN | B | 51 | 69.679 | 49.690 | 9.874 | 1.00 | 22.35 |
| ATOM | 1293 | OD1 | ASN | B | 51 | 69.028 | 48.659 | 9.772 | 1.00 | 17.21 |
| ATOM | 1294 | ND2 | ASN | B | 51 | 69.349 | 50.649 | 10.715 | 1.00 | 21.24 |
| ATOM | 1295 | N | GLY | B | 52 | 70.282 | 46.636 | 7.807 | 1.00 | 15.50 |
| ATOM | 1296 | CA | GLY | B | 52 | 70.231 | 45.232 | 8.164 | 1.00 | 14.95 |
| ATOM | 1297 | C | GLY | B | 52 | 69.601 | 44.846 | 9.523 | 1.00 | 14.04 |
| ATOM | 1298 | O | GLY | B | 52 | 69.541 | 43.629 | 9.815 | 1.00 | 16.62 |
| ATOM | 1299 | N | LYS | B | 53 | 69.153 | 45.837 | 10.279 | 1.00 | 14.08 |
| ATOM | 1300 | CA | LYS | B | 53 | 68.540 | 45.457 | 11.593 | 1.00 | 14.38 |
| ATOM | 1301 | C | LYS | B | 53 | 67.239 | 44.729 | 11.349 | 1.00 | 15.94 |
| ATOM | 1302 | O | LYS | B | 53 | 66.565 | 44.973 | 10.344 | 1.00 | 16.45 |
| ATOM | 1303 | CB | LYS | B | 53 | 68.311 | 46.698 | 12.463 | 1.00 | 14.22 |
| ATOM | 1304 | CG | LYS | B | 53 | 69.654 | 47.303 | 12.877 | 1.00 | 16.49 |
| ATOM | 1305 | CD | LYS | B | 53 | 69.457 | 48.540 | 13.748 | 1.00 | 19.28 |
| ATOM | 1306 | CE | LYS | B | 53 | 70.801 | 49.177 | 14.108 | 1.00 | 26.70 |
| ATOM | 1307 | NZ | LYS | B | 53 | 70.585 | 50.475 | 14.799 | 1.00 | 29.14 |
| ATOM | 1308 | N | ARG | B | 54 | 66.839 | 43.849 | 12.303 | 1.00 | 12.88 |
| ATOM | 1309 | CA | ARG | B | 54 | 65.612 | 43.091 | 12.229 | 1.00 | 11.93 |
| ATOM | 1310 | C | ARG | B | 54 | 64.954 | 43.162 | 13.592 | 1.00 | 14.91 |
| ATOM | 1311 | O | ARG | B | 54 | 65.646 | 42.907 | 14.590 | 1.00 | 15.98 |
| ATOM | 1312 | CB | ARG | B | 54 | 65.862 | 41.628 | 11.855 | 1.00 | 13.59 |
| ATOM | 1313 | CG | ARG | B | 54 | 66.751 | 41.516 | 10.564 | 1.00 | 14.24 |
| ATOM | 1314 | CD | ARG | B | 54 | 67.058 | 40.054 | 10.159 | 1.00 | 13.75 |
| ATOM | 1315 | NE | ARG | B | 54 | 65.931 | 39.313 | 9.621 | 1.00 | 13.94 |
| ATOM | 1316 | CZ | ARG | B | 54 | 65.562 | 39.372 | 8.330 | 1.00 | 16.69 |
| ATOM | 1317 | NH1 | ARG | B | 54 | 66.281 | 40.180 | 7.510 | 1.00 | 13.80 |
| ATOM | 1318 | NH2 | ARG | B | 54 | 64.520 | 38.644 | 7.857 | 1.00 | 13.52 |
| ATOM | 1319 | N | PHE | B | 55 | 63.707 | 43.548 | 13.634 | 1.00 | 12.40 |
| ATOM | 1320 | CA | PHE | B | 55 | 63.013 | 43.648 | 14.924 | 1.00 | 13.30 |
| ATOM | 1321 | C | PHE | B | 55 | 61.564 | 43.314 | 14.815 | 1.00 | 18.51 |
| ATOM | 1322 | O | PHE | B | 55 | 61.017 | 43.231 | 13.703 | 1.00 | 16.08 |
| ATOM | 1323 | CB | PHE | B | 55 | 63.302 | 44.986 | 15.586 | 1.00 | 13.02 |
| ATOM | 1324 | CG | PHE | B | 55 | 62.735 | 46.165 | 14.864 | 1.00 | 14.95 |
| ATOM | 1325 | CD1 | PHE | B | 55 | 63.436 | 46.742 | 13.782 | 1.00 | 15.75 |
| ATOM | 1326 | CD2 | PHE | B | 55 | 61.514 | 46.740 | 15.273 | 1.00 | 15.13 |
| ATOM | 1327 | CE1 | PHE | B | 55 | 62.892 | 47.912 | 13.106 | 1.00 | 17.56 |
| ATOM | 1328 | CE2 | PHE | B | 55 | 60.996 | 47.844 | 14.615 | 1.00 | 17.23 |
| ATOM | 1329 | CZ | PHE | B | 55 | 61.713 | 48.427 | 13.528 | 1.00 | 16.09 |
| ATOM | 1330 | N | SER | B | 56 | 60.880 | 43.095 | 15.940 | 1.00 | 12.78 |
| ATOM | 1331 | CA | SER | B | 56 | 59.482 | 42.752 | 15.962 | 1.00 | 12.18 |
| ATOM | 1332 | C | SER | B | 56 | 58.741 | 43.706 | 16.846 | 1.00 | 15.48 |
| ATOM | 1333 | O | SER | B | 56 | 59.258 | 44.045 | 17.916 | 1.00 | 14.26 |
| ATOM | 1334 | CB | SER | B | 56 | 59.222 | 41.336 | 16.394 | 1.00 | 13.68 |
| ATOM | 1335 | OG | SER | B | 56 | 59.880 | 40.377 | 15.532 | 1.00 | 18.10 |
| ATOM | 1336 | N | THR | B | 57 | 57.570 | 44.140 | 16.428 | 1.00 | 11.29 |
| ATOM | 1337 | CA | THR | B | 57 | 56.749 | 45.129 | 17.169 | 1.00 | 11.02 |
| ATOM | 1338 | C | THR | B | 57 | 55.256 | 44.860 | 16.831 | 1.00 | 11.10 |
| ATOM | 1339 | O | THR | B | 57 | 54.854 | 43.697 | 16.649 | 1.00 | 10.41 |
| ATOM | 1340 | CB | THR | B | 57 | 57.270 | 46.560 | 16.849 | 1.00 | 13.63 |
| ATOM | 1341 | OG1 | THR | B | 57 | 56.492 | 47.529 | 17.575 | 1.00 | 16.82 |
| ATOM | 1342 | CG2 | THR | B | 57 | 57.073 | 46.896 | 15.328 | 1.00 | 16.40 |
| ATOM | 1343 | N | TYR | B | 58 | 54.424 | 45.890 | 16.747 | 1.00 | 11.85 |
| ATOM | 1344 | CA | TYR | B | 58 | 52.995 | 45.709 | 16.405 | 1.00 | 11.66 |
| ATOM | 1345 | C | TYR | B | 58 | 52.572 | 46.896 | 15.567 | 1.00 | 14.10 |
| ATOM | 1346 | O | TYR | B | 58 | 53.194 | 47.962 | 15.639 | 1.00 | 12.80 |
| ATOM | 1347 | CB | TYR | B | 58 | 52.072 | 45.475 | 17.632 | 1.00 | 13.66 |
| ATOM | 1348 | CG | TYR | B | 58 | 51.879 | 46.659 | 18.537 | 1.00 | 14.03 |
| ATOM | 1349 | CD1 | TYR | B | 58 | 52.768 | 46.908 | 19.611 | 1.00 | 14.60 |

-continued

Data Lists

| | | | | | | | | | |
|---|---|---|---|---|---|---|---|---|---|
| ATOM | 1350 | CD2 | TYR | B | 58 | 50.836 | 47.529 | 18.362 | 1.00 | 14.69 |
| ATOM | 1351 | CE1 | TYR | B | 58 | 52.596 | 48.015 | 20.420 | 1.00 | 14.59 |
| ATOM | 1352 | CE2 | TYR | B | 58 | 50.645 | 48.649 | 19.199 | 1.00 | 16.85 |
| ATOM | 1353 | CZ | TYR | B | 58 | 51.546 | 48.875 | 20.222 | 1.00 | 21.58 |
| ATOM | 1354 | OH | TYR | B | 58 | 51.493 | 49.934 | 21.108 | 1.00 | 22.59 |
| ATOM | 1355 | N | ALA | B | 59 | 51.536 | 46.705 | 14.748 | 1.00 | 12.25 |
| ATOM | 1356 | CA | ALA | B | 59 | 51.078 | 47.769 | 13.891 | 1.00 | 12.10 |
| ATOM | 1357 | C | ALA | B | 59 | 50.067 | 48.702 | 14.494 | 1.00 | 14.08 |
| ATOM | 1358 | O | ALA | B | 59 | 49.190 | 48.297 | 15.241 | 1.00 | 13.85 |
| ATOM | 1359 | CB | ALA | B | 59 | 50.435 | 47.110 | 12.626 | 1.00 | 13.24 |
| ATOM | 1360 | N | ILE | B | 60 | 50.148 | 49.990 | 14.096 | 1.00 | 15.08 |
| ATOM | 1361 | CA | ILE | B | 60 | 49.231 | 51.025 | 14.514 | 1.00 | 17.01 |
| ATOM | 1362 | C | ILE | B | 60 | 48.729 | 51.687 | 13.195 | 1.00 | 16.03 |
| ATOM | 1363 | O | ILE | B | 60 | 49.522 | 51.850 | 12.286 | 1.00 | 16.17 |
| ATOM | 1364 | CB | ILE | B | 60 | 50.004 | 52.105 | 15.349 | 1.00 | 20.97 |
| ATOM | 1365 | CG1 | ILE | B | 60 | 50.363 | 51.533 | 16.724 | 1.00 | 23.49 |
| ATOM | 1366 | CG2 | ILE | B | 60 | 49.155 | 53.362 | 15.569 | 1.00 | 23.18 |
| ATOM | 1367 | CD1 | ILE | B | 60 | 51.454 | 52.337 | 17.451 | 1.00 | 26.91 |
| ATOM | 1368 | N | ALA | B | 61 | 47.449 | 52.016 | 13.107 | 1.00 | 16.21 |
| ATOM | 1369 | CA | ALA | B | 61 | 46.948 | 52.655 | 11.878 | 1.00 | 17.99 |
| ATOM | 1370 | C | ALA | B | 61 | 47.328 | 54.129 | 11.847 | 1.00 | 20.83 |
| ATOM | 1371 | O | ALA | B | 61 | 47.221 | 54.819 | 12.875 | 1.00 | 20.99 |
| ATOM | 1372 | CB | ALA | B | 61 | 45.481 | 52.541 | 11.804 | 1.00 | 19.35 |
| ATOM | 1373 | N | ALA | B | 62 | 47.721 | 54.613 | 10.665 | 1.00 | 17.91 |
| ATOM | 1374 | CA | ALA | B | 62 | 48.040 | 56.043 | 10.407 | 1.00 | 17.67 |
| ATOM | 1375 | C | ALA | B | 62 | 46.962 | 56.453 | 9.380 | 1.00 | 23.91 |
| ATOM | 1376 | O | ALA | B | 62 | 46.335 | 55.614 | 8.745 | 1.00 | 22.36 |
| ATOM | 1377 | CB | ALA | B | 62 | 49.400 | 56.238 | 9.833 | 1.00 | 13.45 |
| ATOM | 1378 | N | GLU | B | 63 | 46.756 | 57.756 | 9.246 | 1.00 | 22.90 |
| ATOM | 1379 | CA | GLU | B | 63 | 45.759 | 58.312 | 8.358 | 1.00 | 23.71 |
| ATOM | 1380 | C | GLU | B | 63 | 45.824 | 57.781 | 6.943 | 1.00 | 23.19 |
| ATOM | 1381 | O | GLU | B | 63 | 46.894 | 57.737 | 6.345 | 1.00 | 22.01 |
| ATOM | 1382 | CB | GLU | B | 63 | 45.919 | 59.835 | 8.343 | 1.00 | 25.20 |
| ATOM | 1333 | CG | GLU | B | 63 | 44.902 | 60.517 | 7.444 | 1.00 | 31.69 |
| ATOM | 1384 | CD | GLU | B | 63 | 44.852 | 61.991 | 7.708 | 1.00 | 54.65 |
| ATOM | 1385 | OE1 | GLU | B | 63 | 44.033 | 62.414 | 8.559 | 1.00 | 50.68 |
| ATOM | 1386 | OE2 | GLU | B | 63 | 45.642 | 62.719 | 7.072 | 1.00 | 49.85 |
| ATOM | 1387 | N | ARG | B | 64 | 44.657 | 57.412 | 6.411 | 1.00 | 23.54 |
| ATOM | 1388 | CA | ARG | B | 64 | 44.564 | 56.896 | 5.065 | 1.00 | 24.49 |
| ATOM | 1389 | C | ARG | B | 64 | 45.068 | 57.940 | 4.059 | 1.00 | 29.91 |
| ATOM | 1390 | O | ARG | B | 64 | 44.635 | 59.103 | 4.101 | 1.00 | 30.10 |
| ATOM | 1391 | CB | ARG | B | 64 | 43.116 | 56.548 | 4.739 | 1.00 | 24.54 |
| ATOM | 1392 | CG | ARG | B | 64 | 42.977 | 55.708 | 3.502 | 1.00 | 33.44 |
| ATOM | 1393 | CD | ARG | B | 64 | 41.521 | 55.461 | 3.169 | 1.00 | 30.76 |
| ATOM | 1394 | NE | ARG | B | 64 | 40.824 | 54.612 | 4.127 | 1.00 | 27.92 |
| ATOM | 1395 | CZ | ARG | B | 64 | 41.003 | 53.288 | 4.241 | 1.00 | 30.52 |
| ATOM | 1396 | NH1 | ARG | B | 64 | 41.878 | 52.653 | 3.470 | 1.00 | 26.37 |
| ATOM | 1397 | NH2 | ARG | B | 64 | 40.302 | 52.609 | 5.131 | 1.00 | 30.42 |
| ATOM | 1398 | N | GLY | B | 65 | 45.967 | 57.544 | 3.177 | 1.00 | 27.07 |
| ATOM | 1399 | CA | GLY | B | 65 | 46.485 | 58.475 | 2.170 | 1.00 | 26.85 |
| ATOM | 1400 | C | GLY | B | 65 | 47.687 | 59.292 | 2.603 | 1.00 | 30.69 |
| ATOM | 1401 | O | GLY | B | 65 | 48.287 | 59.983 | 1.789 | 1.00 | 31.19 |
| ATOM | 1402 | N | SER | B | 66 | 48.069 | 59.183 | 3.874 | 1.00 | 25.88 |
| ATOM | 1403 | CA | SER | B | 66 | 49.215 | 59.916 | 4.387 | 1.00 | 24.31 |
| ATOM | 1404 | C | SER | B | 66 | 50.565 | 59.353 | 3.903 | 1.00 | 28.10 |
| ATOM | 1405 | O | SER | B | 66 | 51.589 | 60.044 | 3.898 | 1.00 | 29.06 |
| ATOM | 1406 | CB | SER | B | 66 | 49.182 | 59.888 | 5.929 | 1.00 | 25.33 |
| ATOM | 1407 | OG | SER | B | 66 | 49.450 | 58.548 | 6.422 | 1.00 | 25.27 |
| ATOM | 1408 | N | ARG | B | 67 | 50.576 | 58.055 | 3.539 | 1.00 | 21.92 |
| ATOM | 1409 | CA | ARG | B | 67 | 51.780 | 57.368 | 3.106 | 1.00 | 20.64 |
| ATOM | 1410 | C | ARG | B | 67 | 52.867 | 57.306 | 4.205 | 1.00 | 21.33 |
| ATOM | 1411 | O | ARG | B | 67 | 54.033 | 57.113 | 3.932 | 1.00 | 23.88 |
| ATOM | 1412 | CB | ARG | B | 67 | 52.272 | 57.896 | 1.753 | 1.00 | 24.90 |
| ATOM | 1413 | CG | ARG | B | 67 | 51.094 | 57.832 | 0.749 | 1.00 | 34.18 |
| ATOM | 1414 | CD | ARG | B | 67 | 51.498 | 57.942 | −0.692 | 1.00 | 41.97 |
| ATOM | 1415 | NE | ARG | B | 67 | 51.642 | 59.344 | −1.083 | 1.00 | 42.73 |
| ATOM | 1416 | CZ | ARG | B | 67 | 50.665 | 60.252 | −1.300 | 1.00 | 50.11 |
| ATOM | 1417 | NH1 | ARG | B | 67 | 49.347 | 60.005 | −1.191 | 1.00 | 32.87 |
| ATOM | 1418 | NH2 | ARG | B | 67 | 51.053 | 61.472 | −1.652 | 1.00 | 35.89 |
| ATOM | 1419 | N | ILE | B | 68 | 52.404 | 57.413 | 5.449 | 1.00 | 20.99 |
| ATOM | 1420 | CA | ILE | B | 68 | 53.313 | 57.374 | 6.590 | 1.00 | 19.82 |
| ATOM | 1421 | C | ILE | B | 68 | 53.722 | 55.943 | 7.025 | 1.00 | 18.74 |
| ATOM | 1422 | O | ILE | B | 68 | 52.928 | 54.964 | 6.944 | 1.00 | 18.59 |
| ATOM | 1423 | CB | ILE | B | 68 | 52.613 | 58.021 | 7.843 | 1.00 | 22.72 |
| ATOM | 1424 | CG1 | ILE | B | 68 | 52.569 | 59.567 | 7.775 | 1.00 | 22.79 |
| ATOM | 1425 | CG2 | ILE | B | 68 | 53.272 | 57.570 | 9.182 | 1.00 | 23.66 |
| ATOM | 1426 | CD1 | ILE | B | 68 | 51.511 | 60.133 | 8.696 | 1.00 | 24.22 |

-continued

| | | | | Data Lists | | | | | |
|---|---|---|---|---|---|---|---|---|---|
| ATOM | 1427 | N | ILE | B | 69 | 54.953 | 55.877 | 7.455 | 1.00 | 17.03 |
| ATOM | 1428 | CA | ILE | B | 69 | 55.592 | 54.662 | 8.057 | 1.00 | 16.07 |
| ATOM | 1429 | C | ILE | B | 69 | 56.398 | 55.328 | 9.218 | 1.00 | 18.47 |
| ATOM | 1430 | O | ILE | B | 69 | 57.495 | 55.875 | 9.001 | 1.00 | 19.41 |
| ATOM | 1431 | CB | ILE | B | 69 | 56.579 | 53.927 | 7.167 | 1.00 | 17.97 |
| ATOM | 1432 | CG1 | ILE | B | 69 | 55.861 | 53.307 | 5.925 | 1.00 | 17.84 |
| ATOM | 1433 | CG2 | ILE | B | 69 | 57.274 | 52.750 | 7.990 | 1.00 | 14.87 |
| ATOM | 1434 | CD1 | ILE | B | 69 | 54.757 | 52.283 | 6.267 | 1.00 | 16.76 |
| ATOM | 1435 | N | SER | B | 70 | 55.833 | 55.293 | 10.427 | 1.00 | 16.82 |
| ATOM | 1436 | CA | SER | B | 70 | 56.501 | 55.939 | 11.600 | 1.00 | 16.67 |
| ATOM | 1437 | C | SER | B | 70 | 56.965 | 54.905 | 12.627 | 1.00 | 16.91 |
| ATOM | 1438 | O | SER | B | 70 | 56.147 | 54.102 | 13.128 | 1.00 | 17.58 |
| ATOM | 1439 | CB | SER | B | 70 | 55.507 | 56.879 | 12.249 | 1.00 | 19.85 |
| ATOM | 1440 | OG | SER | B | 70 | 56.106 | 57.626 | 13.304 | 1.00 | 22.39 |
| ATOM | 1441 | N | VAL | B | 71 | 58.251 | 54.930 | 12.921 | 1.00 | 16.01 |
| ATOM | 1442 | CA | VAL | B | 71 | 58.827 | 53.962 | 13.933 | 1.00 | 17.80 |
| ATOM | 1443 | C | VAL | B | 71 | 58.832 | 54.719 | 15.270 | 1.00 | 22.32 |
| ATOM | 1444 | O | VAL | B | 71 | 59.512 | 55.723 | 15.417 | 1.00 | 23.49 |
| ATOM | 1445 | CB | VAL | B | 71 | 60.163 | 53.404 | 13.523 | 1.00 | 22.83 |
| ATOM | 1446 | CG1 | VAL | B | 71 | 59.967 | 52.567 | 12.214 | 1.00 | 21.98 |
| ATOM | 1447 | CG2 | VAL | B | 71 | 61.222 | 54.501 | 13.387 | 1.00 | 24.06 |
| ATOM | 1448 | N | ASN | B | 72 | 58.010 | 54.232 | 16.202 | 1.00 | 20.48 |
| ATOM | 1449 | CA | ASN | B | 72 | 57.806 | 54.878 | 17.519 | 1.00 | 20.13 |
| ATOM | 1450 | C | ASN | B | 72 | 58.320 | 54.086 | 18.687 | 1.00 | 22.39 |
| ATOM | 1451 | O | ASN | B | 72 | 58.488 | 52.863 | 18.621 | 1.00 | 22.18 |
| ATOM | 1452 | CB | ASN | B | 72 | 56.296 | 55.038 | 17.753 | 1.00 | 21.77 |
| ATOM | 1453 | CG | ASN | B | 72 | 55.591 | 55.775 | 16.621 | 1.00 | 30.59 |
| ATOM | 1454 | OD1 | ASN | B | 72 | 56.228 | 56.530 | 15.869 | 1.00 | 25.69 |
| ATOM | 1455 | ND2 | ASN | B | 72 | 54.279 | 55.529 | 16.469 | 1.00 | 26.90 |
| ATOM | 1456 | N | GLY | B | 73 | 58.520 | 54.790 | 19.792 | 1.00 | 20.53 |
| ATOM | 1457 | CA | GLY | B | 73 | 58.998 | 54.092 | 20.992 | 1.00 | 19.66 |
| ATOM | 1458 | C | GLY | B | 73 | 60.428 | 53.605 | 20.792 | 1.00 | 20.18 |
| ATOM | 1459 | O | GLY | B | 73 | 61.239 | 54.232 | 20.080 | 1.00 | 19.03 |
| ATOM | 1460 | N | ALA | B | 74 | 60.758 | 52.473 | 21.443 | 1.00 | 16.73 |
| ATOM | 1461 | CA | ALA | B | 74 | 62.107 | 51.908 | 21.352 | 1.00 | 16.27 |
| ATOM | 1462 | C | ALA | B | 74 | 62.580 | 51.614 | 19.912 | 1.00 | 17.37 |
| ATOM | 1463 | O | ALA | B | 74 | 63.776 | 51.649 | 19.637 | 1.00 | 18.06 |
| ATOM | 1464 | CB | ALA | B | 74 | 62.278 | 50.633 | 22.256 | 1.00 | 17.59 |
| ATOM | 1465 | N | ALA | B | 75 | 61.592 | 51.305 | 19.057 | 1.00 | 17.95 |
| ATOM | 1466 | CA | ALA | B | 75 | 61.873 | 50.961 | 17.639 | 1.00 | 17.42 |
| ATOM | 1467 | C | ALA | B | 75 | 62.567 | 52.115 | 16.916 | 1.00 | 19.91 |
| ATOM | 1468 | O | ALA | B | 75 | 63.215 | 51.889 | 15.889 | 1.00 | 19.81 |
| ATOM | 1469 | CB | ALA | B | 75 | 60.630 | 50.577 | 16.959 | 1.00 | 18.30 |
| ATOM | 1470 | N | ALA | B | 76 | 62.467 | 53.348 | 17.441 | 1.00 | 16.78 |
| ATOM | 1471 | CA | ALA | B | 76 | 63.152 | 54.470 | 16.804 | 1.00 | 18.31 |
| ATOM | 1472 | C | ALA | B | 76 | 64.688 | 54.276 | 16.795 | 1.00 | 18.92 |
| ATOM | 1473 | O | ALA | B | 76 | 65.409 | 54.921 | 16.046 | 1.00 | 19.50 |
| ATOM | 1474 | CB | ALA | B | 76 | 62.747 | 55.786 | 17.477 | 1.00 | 19.95 |
| ATOM | 1475 | N | HIS | B | 77 | 65.225 | 53.369 | 17.637 | 1.00 | 16.41 |
| ATOM | 1476 | CA | HIS | B | 77 | 66.629 | 53.103 | 17.671 | 1.00 | 17.43 |
| ATOM | 1477 | C | HIS | B | 77 | 67.082 | 52.158 | 16.543 | 1.00 | 18.10 |
| ATOM | 1478 | O | HIS | B | 77 | 68.280 | 51.967 | 16.351 | 1.00 | 20.06 |
| ATOM | 1479 | CB | HIS | B | 77 | 66.975 | 52.307 | 18.995 | 1.00 | 19.37 |
| ATOM | 1480 | CG | HIS | B | 77 | 67.026 | 53.149 | 20.241 | 1.00 | 22.65 |
| ATOM | 1481 | ND1 | HIS | B | 77 | 68.174 | 53.787 | 20.649 | 1.00 | 25.27 |
| ATOM | 1482 | CD2 | HIS | B | 77 | 66.090 | 53.421 | 21.181 | 1.00 | 22.98 |
| ATOM | 1483 | CE1 | HIS | B | 77 | 67.944 | 54.431 | 21.784 | 1.00 | 24.52 |
| ATOM | 1484 | NE2 | HIS | B | 77 | 66.688 | 54.230 | 22.129 | 1.00 | 23.17 |
| ATOM | 1485 | N | CYS | B | 78 | 66.107 | 51.548 | 15.846 | 1.00 | 17.70 |
| ATOM | 1486 | CA | CYS | B | 78 | 66.400 | 50.536 | 14.812 | 1.00 | 18.05 |
| ATOM | 1487 | C | CYS | B | 78 | 66.195 | 50.986 | 13.386 | 1.00 | 21.51 |
| ATOM | 1488 | O | CYS | B | 78 | 66.497 | 50.233 | 12.465 | 1.00 | 21.14 |
| ATOM | 1489 | CB | CYS | B | 78 | 65.489 | 49.332 | 15.033 | 1.00 | 19.61 |
| ATOM | 1490 | SG | CYS | B | 78 | 65.663 | 48.553 | 16.688 | 1.00 | 25.07 |
| ATOM | 1491 | N | ALA | B | 79 | 65.673 | 52.190 | 13.200 | 1.00 | 20.09 |
| ATOM | 1492 | CA | ALA | B | 79 | 65.471 | 52.690 | 11.843 | 1.00 | 19.73 |
| ATOM | 1493 | C | ALA | B | 79 | 65.477 | 54.201 | 11.864 | 1.00 | 25.47 |
| ATOM | 1494 | O | ALA | B | 79 | 65.094 | 54.811 | 12.852 | 1.00 | 23.97 |
| ATOM | 1495 | CB | ALA | B | 79 | 64.173 | 52.190 | 11.274 | 1.00 | 20.06 |
| ATOM | 1496 | N | SER | B | 80 | 65.895 | 54.802 | 10.750 | 1.00 | 21.56 |
| ATOM | 1497 | CA | SER | B | 80 | 65.935 | 56.270 | 10.595 | 1.00 | 22.17 |
| ATOM | 1498 | C | SER | B | 80 | 65.082 | 56.677 | 9.407 | 1.00 | 23.37 |
| ATOM | 1499 | O | SER | B | 80 | 64.831 | 55.862 | 8.511 | 1.00 | 21.62 |
| ATOM | 1500 | CB | SER | B | 80 | 67.335 | 56.763 | 10.301 | 1.00 | 25.03 |
| ATOM | 1501 | OG | SER | B | 80 | 68.302 | 56.327 | 11.243 | 1.00 | 28.26 |
| ATOM | 1502 | N | VAL | B | 81 | 64.652 | 57.936 | 9.398 | 1.00 | 18.88 |
| ATOM | 1503 | CA | VAL | B | 81 | 63.839 | 58.463 | 8.295 | 1.00 | 19.13 |

-continued

Data Lists

| | | | | | | | | | |
|---|---|---|---|---|---|---|---|---|---|
| ATOM | 1504 | C | VAL | B | 81 | 64.647 | 58.216 | 7.017 | 1.00 | 21.75 |
| ATOM | 1505 | O | VAL | B | 81 | 65.878 | 58.452 | 6.967 | 1.00 | 20.90 |
| ATOM | 1506 | CB | VAL | B | 81 | 63.576 | 59.970 | 8.514 | 1.00 | 21.73 |
| ATOM | 1507 | CG1 | VAL | B | 81 | 63.015 | 60.599 | 7.224 | 1.00 | 22.57 |
| ATOM | 1508 | CG2 | VAL | B | 81 | 62.555 | 60.148 | 9.631 | 1.00 | 21.80 |
| ATOM | 1509 | N | GLY | B | 82 | 63.961 | 57.728 | 5.988 | 1.00 | 18.71 |
| ATOM | 1510 | CA | GLY | B | 82 | 64.654 | 57.428 | 4.731 | 1.00 | 18.70 |
| ATOM | 1511 | C | GLY | B | 82 | 65.071 | 55.972 | 4.552 | 1.00 | 22.87 |
| ATOM | 1512 | O | GLY | B | 82 | 65.361 | 55.545 | 3.448 | 1.00 | 22.78 |
| ATOM | 1513 | N | ASP | B | 83 | 65.157 | 55.182 | 5.641 | 1.00 | 16.66 |
| ATOM | 1514 | CA | ASP | B | 83 | 65.546 | 53.791 | 5.481 | 1.00 | 16.76 |
| ATOM | 1515 | C | ASP | B | 83 | 64.461 | 53.003 | 4.716 | 1.00 | 16.77 |
| ATOM | 1516 | O | ASP | B | 83 | 63.257 | 53.256 | 4.890 | 1.00 | 17.18 |
| ATOM | 1517 | CB | ASP | B | 83 | 65.668 | 53.149 | 6.878 | 1.00 | 18.79 |
| ATOM | 1518 | CG | ASP | B | 83 | 66.945 | 53.556 | 7.622 | 1.00 | 22.59 |
| ATOM | 1519 | OD1 | ASP | B | 83 | 67.788 | 54.320 | 7.106 | 1.00 | 20.93 |
| ATOM | 1520 | OD2 | ASP | B | 83 | 67.141 | 53.058 | 8.771 | 1.00 | 21.88 |
| ATOM | 1521 | N | ILE | B | 84 | 64.912 | 52.031 | 3.926 | 1.00 | 17.58 |
| ATOM | 1522 | CA | ILE | B | 84 | 63.979 | 51.167 | 3.183 | 1.00 | 17.77 |
| ATOM | 1523 | C | ILE | B | 84 | 63.804 | 49.904 | 4.035 | 1.00 | 17.52 |
| ATOM | 1524 | O | ILE | B | 84 | 64.819 | 49.318 | 4.435 | 1.00 | 16.51 |
| ATOM | 1525 | CB | ILE | B | 84 | 64.627 | 50.788 | 1.851 | 1.00 | 21.87 |
| ATOM | 1526 | CG1 | ILE | B | 84 | 64.840 | 52.071 | 1.020 | 1.00 | 22.20 |
| ATOM | 1527 | CG2 | ILE | B | 84 | 63.771 | 49.760 | 1.060 | 1.00 | 22.70 |
| ATOM | 1528 | CD1 | ILE | B | 84 | 65.694 | 51.766 | −0.225 | 1.00 | 27.68 |
| ATOM | 1529 | N | VAL | B | 85 | 62.549 | 49.558 | 4.289 | 1.00 | 16.68 |
| ATOM | 1530 | CA | VAL | B | 85 | 62.253 | 48.361 | 5.100 | 1.00 | 14.93 |
| ATOM | 1531 | C | VAL | B | 85 | 61.196 | 47.462 | 4.460 | 1.00 | 18.77 |
| ATOM | 1532 | O | VAL | B | 85 | 60.487 | 47.874 | 3.522 | 1.00 | 18.51 |
| ATOM | 1533 | CB | VAL | B | 85 | 61.774 | 48.796 | 6.520 | 1.00 | 15.49 |
| ATOM | 1534 | CG1 | VAL | B | 85 | 61.754 | 49.740 | 7.159 | 1.00 | 16.44 |
| ATOM | 1535 | CG2 | VAL | B | 85 | 60.456 | 49.420 | 6.480 | 1.00 | 14.40 |
| ATOM | 1536 | N | ILE | B | 86 | 61.088 | 46.220 | 4.979 | 1.00 | 14.77 |
| ATOM | 1537 | CA | ILE | B | 86 | 60.101 | 45.258 | 4.557 | 1.00 | 15.52 |
| ATOM | 1538 | C | ILE | B | 86 | 59.318 | 44.987 | 5.853 | 1.00 | 15.28 |
| ATOM | 1539 | O | ILE | B | 86 | 59.977 | 44.736 | 6.887 | 1.00 | 15.56 |
| ATOM | 1540 | CB | ILE | B | 86 | 60.708 | 43.982 | 4.000 | 1.00 | 18.22 |
| ATOM | 1541 | CG1 | ILE | B | 86 | 61.392 | 44.270 | 2.628 | 1.00 | 19.52 |
| ATOM | 1542 | CG2 | ILE | B | 86 | 59.635 | 42.934 | 3.810 | 1.00 | 18.36 |
| ATOM | 1543 | CD1 | ILE | B | 86 | 62.446 | 43.260 | 2.291 | 1.00 | 25.25 |
| ATOM | 1544 | N | ILE | B | 87 | 58.027 | 45.119 | 5.832 | 1.00 | 11.80 |
| ATOM | 1545 | CA | ILE | B | 87 | 57.150 | 44.909 | 7.039 | 1.00 | 11.37 |
| ATOM | 1546 | C | ILE | B | 87 | 56.294 | 43.697 | 6.765 | 1.00 | 16.80 |
| ATOM | 1547 | O | ILE | B | 87 | 55.535 | 43.669 | 5.743 | 1.00 | 15.75 |
| ATOM | 1548 | CB | ILE | B | 87 | 56.290 | 46.133 | 7.310 | 1.00 | 14.04 |
| ATOM | 1549 | CG1 | ILE | B | 87 | 57.201 | 47.385 | 7.461 | 1.00 | 14.68 |
| ATOM | 1550 | CG2 | ILE | B | 87 | 55.352 | 45.915 | 8.585 | 1.00 | 16.46 |
| ATOM | 1551 | CD1 | ILE | B | 87 | 56.479 | 48.706 | 7.825 | 1.00 | 16.93 |
| ATOM | 1552 | N | ALA | B | 88 | 56.344 | 42.673 | 7.625 | 1.00 | 13.54 |
| ATOM | 1553 | CA | ALA | B | 88 | 55.573 | 41.433 | 7.389 | 1.00 | 12.01 |
| ATOM | 1554 | C | ALA | B | 88 | 54.747 | 40.989 | 8.570 | 1.00 | 15.27 |
| ATOM | 1555 | O | ALA | B | 88 | 55.124 | 41.315 | 9.709 | 1.00 | 14.13 |
| ATOM | 1556 | CB | ALA | B | 88 | 56.578 | 40.310 | 7.103 | 1.00 | 12.68 |
| ATOM | 1557 | N | SER | B | 89 | 53.681 | 40.257 | 8.354 | 1.00 | 11.75 |
| ATOM | 1558 | CA | SER | B | 89 | 52.915 | 39.648 | 9.450 | 1.00 | 9.22 |
| ATOM | 1559 | C | SER | B | 89 | 52.832 | 38.161 | 9.095 | 1.00 | 13.85 |
| ATOM | 1560 | O | SER | B | 89 | 52.842 | 37.761 | 7.892 | 1.00 | 12.02 |
| ATOM | 1561 | CB | SER | B | 89 | 51.576 | 40.264 | 9.748 | 1.00 | 13.00 |
| ATOM | 1562 | OG | SER | B | 89 | 50.496 | 39.710 | 8.999 | 1.00 | 13.68 |
| ATOM | 1563 | N | PHE | B | 90 | 52.719 | 37.289 | 10.096 | 1.00 | 9.51 |
| ATOM | 1564 | CA | PHE | B | 90 | 52.623 | 35.844 | 9.949 | 1.00 | 10.69 |
| ATOM | 1565 | C | PHE | B | 90 | 51.374 | 35.318 | 10.617 | 1.00 | 14.12 |
| ATOM | 1566 | O | PHE | B | 90 | 50.966 | 35.838 | 11.662 | 1.00 | 13.43 |
| ATOM | 1567 | CB | PHE | B | 90 | 53.867 | 35.159 | 10.575 | 1.00 | 9.99 |
| ATOM | 1568 | CG | PHE | B | 90 | 55.113 | 35.353 | 9.734 | 1.00 | 8.63 |
| ATOM | 1569 | CD1 | PHE | B | 90 | 55.859 | 36.535 | 9.814 | 1.00 | 12.75 |
| ATOM | 1570 | CD2 | PHE | B | 90 | 55.522 | 34.331 | 8.843 | 1.00 | 9.84 |
| ATOM | 1571 | CE1 | PHE | B | 90 | 57.025 | 36.701 | 9.041 | 1.00 | 12.66 |
| ATOM | 1572 | CE2 | PHE | B | 90 | 56.641 | 34.530 | 8.034 | 1.00 | 11.34 |
| ATOM | 1573 | CZ | PHE | B | 90 | 57.402 | 35.653 | 8.117 | 1.00 | 11.79 |
| ATOM | 1574 | N | VAL | B | 91 | 50.758 | 34.290 | 10.053 | 1.00 | 11.04 |
| ATOM | 1575 | CA | VAL | B | 91 | 49.550 | 33.671 | 10.631 | 1.00 | 8.97 |
| ATOM | 1576 | C | VAL | B | 91 | 49.759 | 32.182 | 10.733 | 1.00 | 12.88 |
| ATOM | 1577 | O | VAL | B | 91 | 50.664 | 31.609 | 10.051 | 1.00 | 13.37 |
| ATOM | 1578 | CB | VAL | B | 91 | 48.248 | 33.943 | 9.847 | 1.00 | 11.62 |
| ATOM | 1579 | CG1 | VAL | B | 91 | 47.808 | 35.362 | 9.981 | 1.00 | 11.91 |
| ATOM | 1580 | CG2 | VAL | B | 91 | 48.467 | 33.557 | 8.297 | 1.00 | 13.43 |

-continued

Data Lists

| | | | | | | | | | |
|---|---|---|---|---|---|---|---|---|---|
| ATOM | 1581 | N | THR | B | 92 | 48.950 | 31.506 | 11.576 | 1.00 | 11.67 |
| ATOM | 1582 | CA | THR | B | 92 | 49.050 | 30.076 | 11.700 | 1.00 | 9.61 |
| ATOM | 1583 | C | THR | B | 92 | 47.768 | 29.379 | 11.153 | 1.00 | 8.31 |
| ATOM | 1584 | O | THR | B | 92 | 46.695 | 29.929 | 11.140 | 1.00 | 11.35 |
| ATOM | 1585 | CB | THR | B | 92 | 49.410 | 29.637 | 13.156 | 1.00 | 12.02 |
| ATOM | 1586 | OG1 | THR | B | 92 | 48.375 | 30.148 | 14.048 | 1.00 | 17.42 |
| ATOM | 1587 | CG2 | THR | B | 92 | 50.764 | 30.137 | 13.517 | 1.00 | 11.07 |
| ATOM | 1588 | N | MET | B | 93 | 47.931 | 28.135 | 10.727 | 1.00 | 10.31 |
| ATOM | 1589 | CA | MET | B | 93 | 46.813 | 27.363 | 10.119 | 1.00 | 10.55 |
| ATOM | 1590 | C | MET | B | 93 | 47.283 | 25.922 | 9.940 | 1.00 | 10.55 |
| ATOM | 1591 | O | MET | B | 93 | 48.489 | 25.635 | 9.886 | 1.00 | 11.69 |
| ATOM | 1592 | CB | MET | B | 93 | 46.433 | 27.950 | 8.677 | 1.00 | 11.27 |
| ATOM | 1593 | CG | MET | B | 93 | 47.606 | 27.775 | 7.732 | 1.00 | 11.07 |
| ATOM | 1594 | SD | MET | B | 93 | 47.367 | 28.740 | 6.145 | 1.00 | 13.35 |
| ATOM | 1595 | CE | MET | B | 93 | 47.673 | 30.365 | 6.821 | 1.00 | 13.30 |
| ATOM | 1596 | N | PRO | B | 94 | 46.310 | 25.017 | 9.819 | 1.00 | 10.89 |
| ATOM | 1597 | CA | PRO | B | 94 | 46.643 | 23.597 | 9.614 | 1.00 | 10.92 |
| ATOM | 1598 | C | PRO | B | 94 | 47.476 | 23.350 | 8.341 | 1.00 | 13.89 |
| ATOM | 1599 | O | PRO | B | 94 | 47.320 | 24.098 | 7.342 | 1.00 | 13.64 |
| ATOM | 1600 | CB | PRO | B | 94 | 45.279 | 22.924 | 9.495 | 1.00 | 15.15 |
| ATOM | 1601 | CG | PRO | B | 94 | 44.323 | 23.877 | 10.157 | 1.00 | 18.73 |
| ATOM | 1602 | CD | PRO | B | 94 | 44.883 | 25.258 | 9.963 | 1.00 | 13.59 |
| ATOM | 1603 | N | ASP | B | 95 | 48.342 | 22.360 | 8.373 | 1.00 | 12.77 |
| ATOM | 1604 | CA | ASP | B | 95 | 49.212 | 22.008 | 7.262 | 1.00 | 11.85 |
| ATOM | 1605 | C | ASP | B | 95 | 48.393 | 21.914 | 5.939 | 1.00 | 12.73 |
| ATOM | 1606 | O | ASP | B | 95 | 48.870 | 22.437 | 4.868 | 1.00 | 14.23 |
| ATOM | 1607 | CB | ASP | B | 95 | 49.866 | 20.644 | 7.529 | 1.00 | 13.88 |
| ATOM | 1608 | CG | ASP | B | 95 | 50.845 | 20.258 | 6.464 | 1.00 | 16.93 |
| ATOM | 1609 | OD1 | ASP | B | 95 | 51.845 | 20.951 | 6.229 | 1.00 | 15.12 |
| ATOM | 1610 | OD2 | ASP | B | 95 | 50.556 | 19.245 | 5.782 | 1.00 | 25.27 |
| ATOM | 1611 | N | GLU | B | 96 | 47.243 | 21.265 | 6.009 | 1.00 | 11.92 |
| ATOM | 1612 | CA | GLU | B | 96 | 46.390 | 21.080 | 4.780 | 1.00 | 13.09 |
| ATOM | 1613 | C | GLU | B | 96 | 46.038 | 22.401 | 4.116 | 1.00 | 17.50 |
| ATOM | 1614 | O | GLU | B | 96 | 46.007 | 22.470 | 2.870 | 1.00 | 17.59 |
| ATOM | 1615 | CB | GLU | B | 96 | 45.127 | 20.359 | 5.163 | 1.00 | 15.73 |
| ATOM | 1616 | CG | GLU | B | 96 | 44.284 | 19.936 | 3.967 | 1.00 | 27.44 |
| ATOM | 1617 | CD | GLU | B | 96 | 43.202 | 20.920 | 3.636 | 1.00 | 46.48 |
| ATOM | 1618 | OE1 | GLU | B | 96 | 42.841 | 21.740 | 4.488 | 1.00 | 32.53 |
| ATOM | 1619 | OE2 | GLU | B | 96 | 42.694 | 20.865 | 2.486 | 1.00 | 50.29 |
| ATOM | 1620 | N | GLU | B | 97 | 45.759 | 23.446 | 4.888 | 1.00 | 13.12 |
| ATOM | 1621 | CA | GLU | B | 97 | 45.427 | 24.755 | 4.311 | 1.00 | 11.58 |
| ATOM | 1622 | C | GLU | B | 97 | 46.740 | 25.459 | 3.880 | 1.00 | 14.13 |
| ATOM | 1623 | O | GLU | B | 97 | 46.819 | 26.229 | 2.912 | 1.00 | 14.05 |
| ATOM | 1624 | CB | GLU | B | 97 | 44.687 | 25.646 | 5.357 | 1.00 | 10.79 |
| ATOM | 1625 | CG | GLU | B | 97 | 43.358 | 25.155 | 5.736 | 1.00 | 12.84 |
| ATOM | 1626 | CD | GLU | B | 97 | 42.625 | 26.039 | 6.749 | 1.00 | 16.10 |
| ATOM | 1627 | OE1 | GLU | B | 97 | 43.205 | 27.015 | 7.351 | 1.00 | 17.56 |
| ATOM | 1628 | OE2 | GLU | B | 97 | 41.424 | 25.785 | 6.889 | 1.00 | 19.58 |
| ATOM | 1629 | N | ALA | B | 98 | 47.825 | 25.307 | 4.639 | 1.00 | 11.26 |
| ATOM | 1630 | CA | ALA | B | 98 | 49.073 | 25.952 | 4.345 | 1.00 | 12.13 |
| ATOM | 1631 | C | ALA | B | 98 | 49.676 | 25.620 | 2.956 | 1.00 | 12.78 |
| ATOM | 1632 | O | ALA | B | 98 | 50.385 | 26.476 | 2.363 | 1.00 | 12.87 |
| ATOM | 1633 | CB | ALA | B | 98 | 50.090 | 25.538 | 5.483 | 1.00 | 13.93 |
| ATOM | 1634 | N | ARG | B | 99 | 49.379 | 24.371 | 2.518 | 1.00 | 13.12 |
| ATOM | 1635 | CA | ARG | B | 99 | 49.910 | 23.918 | 1.252 | 1.00 | 13.91 |
| ATOM | 1636 | C | ARG | B | 99 | 49.405 | 24.782 | 0.094 | 1.00 | 15.52 |
| ATOM | 1637 | O | ARG | B | 99 | 50.124 | 24.819 | −0.929 | 1.00 | 16.74 |
| ATOM | 1638 | CB | ARG | B | 99 | 49.565 | 22.459 | 1.069 | 1.00 | 13.81 |
| ATOM | 1639 | CG | ARG | B | 99 | 50.400 | 21.628 | 2.049 | 1.00 | 21.54 |
| ATOM | 1640 | CD | ARG | B | 99 | 50.114 | 20.193 | 2.018 | 1.00 | 31.31 |
| ATOM | 1641 | NE | ARG | B | 99 | 50.922 | 19.539 | 3.049 | 1.00 | 34.14 |
| ATOM | 1642 | CZ | ARG | B | 99 | 52.233 | 19.293 | 2.966 | 1.00 | 39.78 |
| ATOM | 1643 | NH1 | ARG | B | 99 | 52.927 | 19.613 | 1.874 | 1.00 | 39.29 |
| ATOM | 1644 | NH2 | ARG | B | 99 | 52.860 | 18.698 | 3.965 | 1.00 | 34.68 |
| ATOM | 1645 | N | THR | B | 100 | 48.273 | 25.465 | 0.233 | 1.00 | 12.99 |
| ATOM | 1646 | CA | THR | B | 100 | 47.765 | 26.311 | −0.888 | 1.00 | 13.08 |
| ATOM | 1647 | C | THR | B | 100 | 47.681 | 27.801 | −0.521 | 1.00 | 15.62 |
| ATOM | 1648 | O | THR | B | 100 | 47.191 | 28.652 | −1.282 | 1.00 | 16.66 |
| ATOM | 1649 | CB | THR | B | 100 | 46.391 | 25.798 | −1.313 | 1.00 | 15.79 |
| ATOM | 1650 | OG1 | THR | B | 100 | 45.503 | 25.711 | −0.202 | 1.00 | 14.58 |
| ATOM | 1651 | CG2 | THR | B | 100 | 46.501 | 24.357 | −1.922 | 1.00 | 15.05 |
| ATOM | 1652 | N | TRP | B | 101 | 48.179 | 28.176 | 0.681 | 1.00 | 14.25 |
| ATOM | 1653 | CA | TRP | B | 101 | 48.083 | 29.565 | 1.087 | 1.00 | 13.12 |
| ATOM | 1654 | C | TRP | B | 101 | 48.843 | 30.513 | 0.232 | 1.00 | 15.17 |
| ATOM | 1655 | O | TRP | B | 101 | 49.947 | 30.182 | −0.256 | 1.00 | 16.82 |
| ATOM | 1656 | CB | TRP | B | 101 | 48.617 | 29.632 | 2.595 | 1.00 | 11.79 |
| ATOM | 1657 | CG | TRP | B | 101 | 48.657 | 31.026 | 3.110 | 1.00 | 10.50 |

-continued

Data Lists

| | | | | | | | | | |
|---|---|---|---|---|---|---|---|---|---|
| ATOM | 1658 | CD1 | TRP | B | 101 | 49.734 | 31.812 | 3.259 | 1.00 | 12.40 |
| ATOM | 1659 | CD2 | TRP | B | 101 | 47.519 | 31.822 | 3.403 | 1.00 | 12.89 |
| ATOM | 1660 | NE1 | TRP | B | 101 | 49.344 | 33.048 | 3.665 | 1.00 | 12.65 |
| ATOM | 1661 | CE2 | TRP | B | 101 | 47.998 | 33.095 | 3.786 | 1.00 | 13.88 |
| ATOM | 1662 | CE3 | TRP | B | 101 | 46.141 | 31.580 | 3.424 | 1.00 | 15.74 |
| ATOM | 1663 | CZ2 | TRP | B | 101 | 47.158 | 34.140 | 4.162 | 1.00 | 16.20 |
| ATOM | 1664 | CZ3 | TRP | B | 101 | 45.272 | 32.635 | 3.777 | 1.00 | 19.25 |
| ATOM | 1665 | CH2 | TRP | B | 101 | 45.792 | 33.914 | 4.137 | 1.00 | 19.62 |
| ATOM | 1666 | N | ARG | B | 102 | 48.283 | 31.722 | 0.072 | 1.00 | 15.08 |
| ATOM | 1667 | CA | ARG | B | 102 | 48.934 | 32.768 | −0.695 | 1.00 | 15.90 |
| ATOM | 1668 | C | ARG | B | 102 | 48.968 | 34.063 | 0.149 | 1.00 | 11.33 |
| ATOM | 1669 | O | ARG | B | 102 | 47.928 | 34.506 | 0.584 | 1.00 | 14.41 |
| ATOM | 1670 | CB | ARG | B | 102 | 48.114 | 33.078 | −1.993 | 1.00 | 18.89 |
| ATOM | 1671 | CG | ARG | B | 102 | 48.011 | 31.878 | −2.994 | 1.00 | 24.40 |
| ATOM | 1672 | CD | ARG | B | 102 | 47.276 | 32.241 | −4.310 | 1.00 | 22.77 |
| ATOM | 1673 | NE | ARG | B | 102 | 47.968 | 33.268 | −5.060 | 1.00 | 27.18 |
| ATOM | 1674 | CZ | ARG | B | 102 | 48.980 | 33.060 | −5.903 | 1.00 | 28.35 |
| ATOM | 1675 | NH1 | ARG | B | 102 | 49.464 | 31.849 | −6.107 | 1.00 | 23.60 |
| ATOM | 1676 | NH2 | ARG | B | 102 | 49.523 | 34.086 | −6.528 | 1.00 | 31.92 |
| ATOM | 1677 | N | PRO | B | 103 | 50.154 | 34.655 | 0.289 | 1.00 | 12.26 |
| ATOM | 1678 | CA | PRO | B | 103 | 50.259 | 35.917 | 0.065 | 1.00 | 13.54 |
| ATOM | 1679 | C | PRO | B | 103 | 49.796 | 37.123 | 0.286 | 1.00 | 17.32 |
| ATOM | 1680 | O | PRO | B | 103 | 49.731 | 37.056 | −1.006 | 1.00 | 16.83 |
| ATOM | 1681 | CB | PRO | B | 103 | 51.763 | 36.065 | 1.280 | 1.00 | 14.38 |
| ATOM | 1682 | CG | PRO | B | 103 | 52.386 | 35.452 | 0.019 | 1.00 | 22.25 |
| ATOM | 1683 | CD | PRO | B | 103 | 51.461 | 34.218 | −0.225 | 1.00 | 16.38 |
| ATOM | 1684 | N | ASN | B | 104 | 49.507 | 38.228 | 1.005 | 1.00 | 13.82 |
| ATOM | 1685 | CA | ASN | B | 104 | 49.083 | 39.495 | 0.409 | 1.00 | 12.48 |
| ATOM | 1686 | C | ASN | B | 104 | 50.317 | 40.372 | 0.282 | 1.00 | 19.52 |
| ATOM | 1687 | O | ASN | B | 104 | 50.868 | 40.809 | 1.326 | 1.00 | 16.91 |
| ATOM | 1688 | CB | ASN | B | 104 | 48.000 | 40.183 | 1.247 | 1.00 | 13.72 |
| ATOM | 1689 | CG | ASN | B | 104 | 46.823 | 39.329 | 1.441 | 1.00 | 19.91 |
| ATOM | 1690 | OD1 | ASN | B | 104 | 46.218 | 38.875 | 0.448 | 1.00 | 17.05 |
| ATOM | 1691 | ND2 | ASN | B | 104 | 46.460 | 39.032 | 2.699 | 1.00 | 20.70 |
| ATOM | 1692 | N | VAL | B | 105 | 50.789 | 40.668 | −0.936 | 1.00 | 17.67 |
| ATOM | 1693 | CA | VAL | B | 105 | 51.984 | 41.447 | −1.064 | 1.00 | 16.36 |
| ATOM | 1694 | C | VAL | B | 105 | 51.762 | 42.755 | −1.760 | 1.00 | 21.93 |
| ATOM | 1695 | O | VAL | B | 105 | 51.102 | 42.783 | −2.816 | 1.00 | 22.45 |
| ATOM | 1696 | CB | VAL | B | 105 | 53.090 | 40.681 | −1.848 | 1.00 | 18.76 |
| ATOM | 1697 | CG1 | VAL | B | 105 | 54.343 | 41.495 | −1.957 | 1.00 | 19.86 |
| ATOM | 1698 | CG2 | VAL | B | 105 | 53.336 | 39.231 | −1.253 | 1.00 | 19.00 |
| ATOM | 1699 | N | ALA | B | 106 | 52.287 | 43.832 | −1.188 | 1.00 | 20.08 |
| ATOM | 1700 | CA | ALA | B | 106 | 52.199 | 45.188 | −1.794 | 1.00 | 19.28 |
| ATOM | 1701 | C | ALA | B | 106 | 53.617 | 45.637 | −2.080 | 1.00 | 22.54 |
| ATOM | 1702 | O | ALA | B | 106 | 54.491 | 45.558 | −1.214 | 1.00 | 20.02 |
| ATOM | 1703 | CB | ALA | B | 106 | 51.533 | 46.151 | −0.903 | 1.00 | 19.59 |
| ATOM | 1704 | N | TYR | B | 107 | 53.895 | 46.128 | −3.312 | 1.00 | 21.77 |
| ATOM | 1705 | CA | TYR | B | 107 | 55.244 | 46.571 | −3.683 | 1.00 | 22.90 |
| ATOM | 1706 | C | TYR | B | 107 | 55.292 | 48.084 | −3.760 | 1.00 | 25.98 |
| ATOM | 1707 | O | TYR | B | 107 | 54.300 | 48.712 | −4.096 | 1.00 | 25.22 |
| ATOM | 1708 | CB | TYR | B | 107 | 55.668 | 45.972 | −5.032 | 1.00 | 25.00 |
| ATOM | 1709 | CG | TYR | B | 107 | 55.904 | 44.492 | −4.966 | 1.00 | 24.25 |
| ATOM | 1710 | CD1 | TYR | B | 107 | 57.129 | 43.980 | −4.544 | 1.00 | 26.30 |
| ATOM | 1711 | CD2 | TYR | B | 107 | 54.888 | 43.600 | −5.316 | 1.00 | 25.93 |
| ATOM | 1712 | CE1 | TYR | B | 107 | 57.342 | 42.629 | −4.484 | 1.00 | 29.13 |
| ATOM | 1713 | CE2 | TYR | B | 107 | 55.100 | 42.234 | −5.270 | 1.00 | 25.26 |
| ATOM | 1714 | CZ | TYR | B | 107 | 56.326 | 41.757 | −4.872 | 1.00 | 31.88 |
| ATOM | 1715 | OH | TYR | B | 107 | 56.524 | 40.388 | −4.808 | 1.00 | 35.96 |
| ATOM | 1716 | N | PHE | B | 108 | 56.446 | 48.652 | −3.408 | 1.00 | 26.53 |
| ATOM | 1717 | CA | PHE | B | 108 | 56.584 | 50.098 | −3.399 | 1.00 | 25.71 |
| ATOM | 1718 | C | PHE | B | 108 | 57.894 | 50.568 | −4.005 | 1.00 | 31.22 |
| ATOM | 1719 | O | PHE | B | 108 | 58.893 | 49.844 | −4.074 | 1.00 | 28.62 |
| ATOM | 1720 | CB | PHE | B | 108 | 56.572 | 50.645 | −1.933 | 1.00 | 25.29 |
| ATOM | 1721 | CG | PHE | B | 108 | 55.293 | 50.411 | −1.188 | 1.00 | 21.78 |
| ATOM | 1722 | CD1 | PHE | B | 108 | 55.033 | 49.174 | −0.571 | 1.00 | 19.05 |
| ATOM | 1723 | CD2 | PHE | B | 108 | 54.354 | 51.421 | −1.064 | 1.00 | 20.20 |
| ATOM | 1724 | CE1 | PHE | B | 108 | 53.856 | 48.967 | 0.111 | 1.00 | 19.07 |
| ATOM | 1725 | CE2 | PHE | B | 108 | 53.187 | 51.237 | −0.377 | 1.00 | 22.77 |
| ATOM | 1726 | CZ | PHE | B | 108 | 52.950 | 49.952 | 0.240 | 1.00 | 20.24 |
| ATOM | 1727 | N | GLU | B | 109 | 57.864 | 51.828 | −4.412 | 1.00 | 30.97 |
| ATOM | 1728 | CA | GLU | B | 109 | 59.012 | 52.499 | −5.011 | 1.00 | 32.90 |
| ATOM | 1729 | C | GLU | B | 109 | 58.921 | 53.977 | −4.680 | 1.00 | 33.93 |
| ATOM | 1730 | O | GLU | B | 109 | 57.889 | 54.468 | −4.269 | 1.00 | 30.42 |
| ATOM | 1731 | CB | GLU | B | 109 | 58.916 | 52.388 | −6.540 | 1.00 | 35.17 |
| ATOM | 1732 | CG | GLU | B | 109 | 57.721 | 53.172 | −7.089 | 1.00 | 44.89 |
| ATOM | 1733 | CD | GLU | B | 109 | 57.496 | 52.955 | −8.566 | 1.00 | 68.70 |
| ATOM | 1734 | OE1 | GLU | B | 109 | 58.416 | 52.425 | −9.234 | 1.00 | 58.38 |

-continued

| | | | | | | | | | |
|---|---|---|---|---|---|---|---|---|---|
| ATOM | 1735 | OE2 | GLU | B | 109 | 56.391 | 53.305 | −9.056 | 1.00 | 66.11 |
| ATOM | 1736 | N | GLY | B | 110 | 60.008 | 54.705 | −4.916 | 1.00 | 33.06 |
| ATOM | 1737 | CA | GLY | B | 110 | 60.007 | 56.135 | −4.668 | 1.00 | 32.35 |
| ATOM | 1738 | C | GLY | B | 110 | 59.545 | 56.486 | −3.270 | 1.00 | 35.50 |
| ATOM | 1739 | O | GLY | B | 110 | 60.045 | 55.920 | −2.286 | 1.00 | 35.53 |
| ATOM | 1740 | N | ASP | B | 111 | 58.646 | 57.449 | −3.185 | 1.00 | 29.97 |
| ATOM | 1741 | CA | ASP | B | 111 | 58.151 | 57.917 | −1.907 | 1.00 | 31.05 |
| ATOM | 1742 | C | ASP | B | 111 | 56.884 | 57.180 | −1.499 | 1.00 | 30.82 |
| ATOM | 1743 | O | ASP | B | 111 | 55.761 | 57.743 | −1.439 | 1.00 | 28.67 |
| ATOM | 1744 | CB | ASP | B | 111 | 57.984 | 59.438 | −1.931 | 1.00 | 33.49 |
| ATOM | 1745 | CG | ASP | B | 111 | 57.207 | 59.966 | −0.755 | 1.00 | 44.31 |
| ATOM | 1746 | OD1 | ASP | B | 111 | 57.431 | 59.473 | 0.386 | 1.00 | 46.12 |
| ATOM | 1747 | OD2 | ASP | B | 111 | 56.359 | 60.857 | −0.974 | 1.00 | 41.60 |
| ATOM | 1748 | N | ASN | B | 112 | 57.084 | 55.909 | −1.181 | 1.00 | 27.75 |
| ATOM | 1749 | CA | ASN | B | 112 | 55.987 | 55.068 | −0.770 | 1.00 | 25.85 |
| ATOM | 1750 | C | ASN | B | 112 | 54.870 | 55.008 | −1.770 | 1.00 | 28.56 |
| ATOM | 1751 | O | ASN | B | 112 | 53.695 | 55.087 | −1.425 | 1.00 | 24.07 |
| ATOM | 1752 | CB | ASN | B | 112 | 55.512 | 55.413 | 0.637 | 1.00 | 25.14 |
| ATOM | 1753 | CG | ASN | B | 112 | 56.544 | 55.084 | 1.628 | 1.00 | 19.48 |
| ATOM | 1754 | OD1 | ASN | B | 112 | 57.512 | 54.410 | 1.275 | 1.00 | 22.70 |
| ATOM | 1755 | ND2 | ASN | B | 112 | 56.399 | 55.582 | 2.868 | 1.00 | 21.36 |
| ATOM | 1756 | N | GLU | B | 113 | 55.271 | 54.857 | −3.032 | 1.00 | 27.11 |
| ATOM | 1757 | CA | GLU | B | 113 | 54.288 | 54.748 | −4.114 | 1.00 | 28.84 |
| ATOM | 1758 | C | GLU | B | 113 | 54.071 | 53.286 | −4.361 | 1.00 | 27.72 |
| ATOM | 1759 | O | GLU | B | 113 | 55.024 | 52.572 | −4.769 | 1.00 | 26.82 |
| ATOM | 1760 | CB | GLU | B | 113 | 54.752 | 55.441 | −5.391 | 1.00 | 30.87 |
| ATOM | 1761 | CG | GLU | B | 113 | 54.797 | 56.958 | −5.306 | 1.00 | 37.93 |
| ATOM | 1762 | CD | GLU | B | 113 | 53.442 | 57.703 | −5.230 | 1.00 | 59.74 |
| ATOM | 1763 | OE1 | GLU | B | 113 | 52.345 | 57.089 | −5.096 | 1.00 | 46.50 |
| ATOM | 1764 | OE2 | GLU | B | 113 | 53.517 | 58.956 | −5.296 | 1.00 | 59.60 |
| ATOM | 1765 | N | MET | B | 114 | 52.842 | 52.856 | −4.080 | 1.00 | 27.25 |
| ATOM | 1766 | CA | MET | B | 114 | 52.436 | 51.459 | −4.226 | 1.00 | 32.32 |
| ATOM | 1767 | C | MET | B | 114 | 52.272 | 51.103 | −5.666 | 1.00 | 39.86 |
| ATOM | 1768 | O | MET | B | 114 | 51.463 | 51.727 | −6.359 | 1.00 | 40.94 |
| ATOM | 1769 | CB | MET | B | 114 | 51.094 | 51.203 | −3.533 | 1.00 | 34.33 |
| ATOM | 1770 | CG | MET | B | 114 | 50.808 | 49.728 | −3.412 | 1.00 | 36.77 |
| ATOM | 1771 | SD | MET | B | 114 | 49.151 | 49.352 | −2.940 | 1.00 | 39.76 |
| ATOM | 1772 | CE | MET | B | 114 | 49.252 | 49.698 | −1.017 | 1.00 | 31.31 |
| ATOM | 1773 | N | LYS | B | 115 | 53.006 | 50.104 | −6.129 | 1.00 | 37.37 |
| ATOM | 1774 | CA | LYS | B | 115 | 52.918 | 49.687 | −7.538 | 1.00 | 38.95 |
| ATOM | 1775 | C | LYS | B | 115 | 51.644 | 48.899 | −7.836 | 1.00 | 54.19 |
| ATOM | 1776 | O | LYS | B | 115 | 51.157 | 48.178 | −6.919 | 1.00 | 51.66 |
| ATOM | 1777 | CB | LYS | B | 115 | 54.114 | 48.851 | −7.929 | 1.00 | 41.43 |
| ATOM | 1778 | CG | LYS | B | 115 | 55.452 | 49.572 | −7.954 | 1.00 | 47.27 |
| ATOM | 1779 | CD | LYS | B | 115 | 56.543 | 48.571 | −8.255 | 1.00 | 43.78 |
| ATOM | 1780 | CE | LYS | B | 115 | 57.915 | 49.055 | −7.874 | 1.00 | 55.99 |
| ATOM | 1781 | NZ | LYS | B | 115 | 58.975 | 48.255 | −8.577 | 1.00 | 62.59 |
| ATOM | 1 | N | MET | C | 1 | 48.433 | 20.814 | 26.350 | 1.00 | 25.25 |
| ATOM | 2 | CA | MET | C | 1 | 49.028 | 22.003 | 25.752 | 1.00 | 23.37 |
| ATOM | 3 | C | MET | C | 1 | 49.715 | 21.688 | 24.462 | 1.00 | 22.04 |
| ATOM | 4 | O | MET | C | 1 | 49.875 | 20.523 | 24.092 | 1.00 | 22.16 |
| ATOM | 5 | CB | MET | C | 1 | 49.850 | 22.851 | 26.665 | 1.00 | 26.58 |
| ATOM | 6 | CG | MET | C | 1 | 50.670 | 22.110 | 27.510 | 1.00 | 29.48 |
| ATOM | 7 | SD | MET | C | 1 | 51.965 | 21.246 | 26.703 | 1.00 | 32.96 |
| ATOM | 8 | CE | MET | C | 1 | 52.813 | 20.920 | 28.227 | 1.00 | 23.68 |
| ATOM | 9 | N | ILE | C | 2 | 50.100 | 22.747 | 23.803 | 1.00 | 14.33 |
| ATOM | 10 | CA | ILE | C | 2 | 50.686 | 22.664 | 22.441 | 1.00 | 12.86 |
| ATOM | 11 | C | ILE | C | 2 | 52.160 | 22.979 | 22.400 | 1.00 | 13.27 |
| ATOM | 12 | O | ILE | C | 2 | 52.627 | 24.031 | 22.948 | 1.00 | 12.60 |
| ATOM | 13 | CB | ILE | C | 2 | 49.882 | 23.673 | 21.576 | 1.00 | 15.76 |
| ATOM | 14 | CG1 | ILE | C | 2 | 48.390 | 23.281 | 21.509 | 1.00 | 18.95 |
| ATOM | 15 | CG2 | ILE | C | 2 | 50.477 | 23.802 | 20.155 | 1.00 | 15.91 |
| ATOM | 16 | CD1 | ILE | C | 2 | 48.150 | 22.002 | 20.809 | 1.00 | 30.84 |
| ATOM | 17 | N | ARG | C | 3 | 52.927 | 22.092 | 21.751 | 1.00 | 11.28 |
| ATOM | 18 | CA | ARG | C | 3 | 54.380 | 22.286 | 21.644 | 1.00 | 10.27 |
| ATOM | 19 | C | ARG | C | 3 | 54.824 | 22.880 | 20.295 | 1.00 | 12.97 |
| ATOM | 20 | O | ARG | C | 3 | 54.091 | 22.691 | 19.313 | 1.00 | 11.98 |
| ATOM | 21 | CB | ARG | C | 3 | 55.085 | 20.920 | 21.683 | 1.00 | 11.24 |
| ATOM | 22 | CG | ARG | C | 3 | 54.887 | 20.123 | 23.057 | 1.00 | 11.07 |
| ATOM | 23 | CD | ARG | C | 3 | 55.885 | 20.640 | 24.091 | 1.00 | 14.19 |
| ATOM | 24 | NE | ARG | C | 3 | 55.755 | 19.688 | 25.224 | 1.00 | 12.85 |
| ATOM | 25 | CZ | ARG | C | 3 | 56.624 | 19.664 | 26.235 | 1.00 | 13.01 |
| ATOM | 26 | NH1 | ARG | C | 3 | 57.564 | 20.552 | 26.371 | 1.00 | 11.87 |
| ATOM | 27 | NH2 | ARG | C | 3 | 56.424 | 18.698 | 27.173 | 1.00 | 15.42 |
| ATOM | 28 | N | THR | C | 4 | 55.967 | 23.542 | 20.295 | 1.00 | 10.90 |
| ATOM | 29 | CA | THR | C | 4 | 56.599 | 24.104 | 19.048 | 1.00 | 8.73 |
| ATOM | 30 | C | THR | C | 4 | 57.765 | 23.120 | 18.793 | 1.00 | 12.54 |

-continued

Data Lists

| | | | | | | | | | |
|---|---|---|---|---|---|---|---|---|---|
| ATOM | 31 | O | THR | C | 4 | 58.739 | 23.023 | 19.649 | 1.00 | 11.96 |
| ATOM | 32 | CB | THR | C | 4 | 57.080 | 25.498 | 19.237 | 1.00 | 10.20 |
| ATOM | 33 | OG1 | THR | C | 4 | 55.949 | 26.331 | 19.490 | 1.00 | 12.29 |
| ATOM | 34 | CG2 | THR | C | 4 | 57.908 | 26.008 | 17.930 | 1.00 | 12.13 |
| ATOM | 35 | N | MET | C | 5 | 57.701 | 22.369 | 17.637 | 1.00 | 10.12 |
| ATOM | 36 | CA | MET | C | 5 | 58.676 | 21.370 | 17.349 | 1.00 | 10.31 |
| ATOM | 37 | C | MET | C | 5 | 59.356 | 21.600 | 16.015 | 1.00 | 13.52 |
| ATOM | 38 | O | MET | C | 5 | 58.720 | 22.172 | 15.112 | 1.00 | 14.15 |
| ATOM | 39 | CB | MET | C | 5 | 57.978 | 20.006 | 17.214 | 1.00 | 13.06 |
| ATOM | 40 | CG | MET | C | 5 | 57.123 | 19.561 | 18.416 | 1.00 | 11.30 |
| ATOM | 41 | SD | MET | C | 5 | 58.165 | 19.333 | 19.918 | 1.00 | 13.37 |
| ATOM | 42 | CE | MET | C | 5 | 59.104 | 17.873 | 19.482 | 1.00 | 14.97 |
| ATOM | 43 | N | LEU | C | 6 | 60.600 | 21.155 | 15.915 | 1.00 | 10.44 |
| ATOM | 44 | CA | LEU | C | 6 | 61.345 | 21.255 | 14.605 | 1.00 | 11.49 |
| ATOM | 45 | C | LEU | C | 6 | 60.559 | 20.378 | 13.639 | 1.00 | 13.65 |
| ATOM | 46 | O | LEU | C | 6 | 60.436 | 19.139 | 13.800 | 1.00 | 12.95 |
| ATOM | 47 | CB | LEU | C | 6 | 62.722 | 20.660 | 14.786 | 1.00 | 11.43 |
| ATOM | 48 | CG | LEU | C | 6 | 63.587 | 20.673 | 13.484 | 1.00 | 12.67 |
| ATOM | 49 | CD1 | LEU | C | 6 | 64.038 | 22.096 | 13.201 | 1.00 | 13.37 |
| ATOM | 50 | CD2 | LEU | C | 6 | 64.839 | 19.829 | 13.742 | 1.00 | 14.36 |
| ATOM | 51 | N | GLN | C | 7 | 60.049 | 21.016 | 12.552 | 1.00 | 12.16 |
| ATOM | 52 | CA | GLN | C | 7 | 59.313 | 20.301 | 11.511 | 1.00 | 11.30 |
| ATOM | 53 | C | GLN | C | 7 | 60.333 | 19.599 | 10.566 | 1.00 | 12.23 |
| ATOM | 54 | O | GLN | C | 7 | 60.125 | 18.449 | 10.136 | 1.00 | 11.94 |
| ATOM | 55 | CB | GLN | C | 7 | 58.544 | 21.330 | 10.679 | 1.00 | 12.62 |
| ATOM | 56 | CG | GLN | C | 7 | 57.590 | 20.710 | 9.638 | 1.00 | 14.99 |
| ATOM | 57 | CD | GLN | C | 7 | 58.349 | 20.221 | 8.351 | 1.00 | 12.25 |
| ATOM | 58 | OE1 | GLN | C | 7 | 58.036 | 19.083 | 7.865 | 1.00 | 14.42 |
| ATOM | 59 | NE2 | GLN | C | 7 | 59.299 | 21.005 | 7.831 | 1.00 | 13.59 |
| ATOM | 60 | N | GLY | C | 8 | 61.406 | 20.329 | 10.295 | 1.00 | 12.10 |
| ATOM | 61 | CA | GLY | C | 8 | 62.459 | 19.795 | 9.406 | 1.00 | 12.14 |
| ATOM | 62 | C | GLY | C | 8 | 63.526 | 20.838 | 9.181 | 1.00 | 11.21 |
| ATOM | 63 | O | GLY | C | 8 | 63.403 | 22.022 | 9.565 | 1.00 | 12.25 |
| ATOM | 64 | N | LYS | C | 9 | 64.617 | 20.409 | 8.526 | 1.00 | 11.80 |
| ATOM | 65 | CA | LYS | C | 9 | 65.690 | 21.351 | 8.271 | 1.00 | 12.75 |
| ATOM | 66 | C | LYS | C | 9 | 66.604 | 20.908 | 7.117 | 1.00 | 12.69 |
| ATOM | 67 | O | LYS | C | 9 | 66.658 | 19.711 | 6.780 | 1.00 | 14.09 |
| ATOM | 68 | CB | LYS | C | 9 | 66.597 | 21.557 | 9.528 | 1.00 | 16.31 |
| ATOM | 69 | CG | LYS | C | 9 | 67.451 | 20.367 | 9.927 | 1.00 | 16.10 |
| ATOM | 70 | CD | LYS | C | 9 | 68.486 | 20.654 | 11.059 | 1.00 | 15.95 |
| ATOM | 71 | CE | LYS | C | 9 | 69.247 | 19.377 | 11.363 | 1.00 | 20.48 |
| ATOM | 72 | NZ | LYS | C | 9 | 70.409 | 19.689 | 12.260 | 1.00 | 22.05 |
| ATOM | 73 | N | LEU | C | 10 | 67.301 | 21.896 | 6.578 | 1.00 | 13.44 |
| ATOM | 74 | CA | LEU | C | 10 | 68.300 | 21.680 | 5.503 | 1.00 | 13.72 |
| ATOM | 75 | C | LEU | C | 10 | 69.586 | 21.951 | 6.258 | 1.00 | 14.03 |
| ATOM | 76 | O | LEU | C | 10 | 69.859 | 23.078 | 6.661 | 1.00 | 15.46 |
| ATOM | 77 | CB | LEU | C | 10 | 68.111 | 22.719 | 4.364 | 1.00 | 13.59 |
| ATOM | 78 | CC | LEU | C | 10 | 66.761 | 22.626 | 3.674 | 1.00 | 14.77 |
| ATOM | 79 | CD1 | LEU | C | 10 | 66.548 | 23.780 | 2.652 | 1.00 | 18.67 |
| ATOM | 80 | CD2 | LEU | C | 10 | 66.545 | 21.240 | 2.957 | 1.00 | 15.75 |
| ATOM | 81 | N | HIS | C | 11 | 70.365 | 20.925 | 6.451 | 1.00 | 14.06 |
| ATOM | 82 | CA | HIS | C | 11 | 71.591 | 21.029 | 7.244 | 1.00 | 14.41 |
| ATOM | 83 | C | HIS | C | 11 | 72.871 | 21.241 | 6.448 | 1.00 | 18.20 |
| ATOM | 84 | O | HIS | C | 11 | 73.258 | 20.362 | 5.684 | 1.00 | 16.24 |
| ATOM | 85 | CB | HIS | C | 11 | 71.710 | 19.803 | 8.172 | 1.00 | 17.29 |
| ATOM | 86 | CG | HIS | C | 11 | 72.805 | 19.913 | 9.185 | 1.00 | 18.36 |
| ATOM | 87 | ND1 | HIS | C | 11 | 72.634 | 20.553 | 10.405 | 1.00 | 20.19 |
| ATOM | 88 | CD2 | HIS | C | 11 | 74.087 | 19.464 | 9.174 | 1.00 | 19.36 |
| ATOM | 89 | CE1 | HIS | C | 11 | 73.769 | 20.514 | 11.075 | 1.00 | 19.59 |
| ATOM | 90 | NE2 | HIS | C | 11 | 74.667 | 19.854 | 10.354 | 1.00 | 18.93 |
| ATOM | 91 | N | ARG | C | 12 | 73.488 | 22.401 | 6.662 | 1.00 | 15.16 |
| ATOM | 92 | CA | ARG | C | 12 | 74.713 | 22.792 | 6.029 | 1.00 | 15.13 |
| ATOM | 93 | C | ARG | C | 12 | 74.613 | 22.974 | 4.525 | 1.00 | 16.37 |
| ATOM | 94 | O | ARG | C | 12 | 75.468 | 22.446 | 3.763 | 1.00 | 18.19 |
| ATOM | 95 | CB | ARG | C | 12 | 75.855 | 21.874 | 6.378 | 1.00 | 15.43 |
| ATOM | 96 | CG | ARG | C | 12 | 76.247 | 21.969 | 7.868 | 1.00 | 17.33 |
| ATOM | 97 | CD | ARG | C | 12 | 77.390 | 21.001 | 8.248 | 1.00 | 17.26 |
| ATOM | 98 | NE | ARG | C | 12 | 78.587 | 21.294 | 7.454 | 1.00 | 19.17 |
| ATOM | 99 | CZ | ARG | C | 12 | 79.529 | 22.164 | 7.760 | 1.00 | 24.65 |
| ATOM | 100 | NH1 | ARG | C | 12 | 79.495 | 22.858 | 8.879 | 1.00 | 21.82 |
| ATOM | 101 | NH2 | ARG | C | 12 | 80.545 | 22.350 | 6.912 | 1.00 | 28.03 |
| ATOM | 102 | N | VAL | C | 13 | 73.610 | 23.681 | 4.119 | 1.00 | 15.70 |
| ATOM | 103 | CA | VAL | C | 13 | 73.518 | 23.999 | 2.680 | 1.00 | 14.78 |
| ATOM | 104 | C | VAL | C | 13 | 74.416 | 25.241 | 2.524 | 1.00 | 18.42 |
| ATOM | 105 | O | VAL | C | 13 | 74.709 | 26.004 | 3.506 | 1.00 | 15.58 |
| ATOM | 106 | CB | VAL | C | 13 | 72.143 | 24.332 | 2.183 | 1.00 | 16.79 |
| ATOM | 107 | CG1 | VAL | C | 13 | 71.318 | 23.094 | 2.020 | 1.00 | 18.88 |

-continued

Data Lists

| | | | | | | | | | |
|---|---|---|---|---|---|---|---|---|---|
| ATOM | 108 | CG2 | VAL | C | 13 | 71.441 | 25.456 | 3.067 | 1.00 | 16.41 |
| ATOM | 109 | N | LYS | C | 14 | 74.877 | 25.500 | 1.273 | 1.00 | 15.68 |
| ATOM | 110 | CA | LYS | C | 14 | 75.726 | 26.646 | 0.997 | 1.00 | 16.45 |
| ATOM | 111 | C | LYS | C | 14 | 74.946 | 27.738 | 0.258 | 1.00 | 16.56 |
| ATOM | 112 | O | LYS | C | 14 | 74.116 | 27.432 | −0.670 | 1.00 | 16.75 |
| ATOM | 113 | CB | LYS | C | 14 | 76.910 | 26.216 | 0.127 | 1.00 | 17.97 |
| ATOM | 114 | CG | LYS | C | 14 | 77.913 | 27.344 | −0.094 | 1.00 | 20.97 |
| ATOM | 115 | CD | LYS | C | 14 | 79.173 | 26.878 | −0.788 | 1.00 | 29.18 |
| ATOM | 116 | CE | LYS | C | 14 | 80.063 | 26.092 | 0.120 | 1.00 | 32.48 |
| ATOM | 117 | NZ | LYS | C | 14 | 81.181 | 25.545 | −0.697 | 1.00 | 33.64 |
| ATOM | 118 | N | VAL | C | 15 | 75.161 | 29.013 | 0.665 | 1.00 | 13.79 |
| ATOM | 119 | CA | VAL | C | 15 | 74.467 | 30.142 | 0.040 | 1.00 | 14.02 |
| ATOM | 120 | C | VAL | C | 15 | 75.067 | 30.312 | −1.393 | 1.00 | 14.49 |
| ATOM | 121 | O | VAL | C | 15 | 76.279 | 30.376 | −1.536 | 1.00 | 14.91 |
| ATOM | 122 | CB | VAL | C | 15 | 74.678 | 31.451 | 0.826 | 1.00 | 14.72 |
| ATOM | 123 | CG1 | VAL | C | 15 | 74.032 | 32.595 | 0.091 | 1.00 | 15.47 |
| ATOM | 124 | CG2 | VAL | C | 15 | 74.013 | 31.273 | 2.287 | 1.00 | 15.44 |
| ATOM | 125 | N | THR | C | 16 | 74.182 | 30.292 | −2.386 | 1.00 | 14.68 |
| ATOM | 126 | CA | THR | C | 16 | 74.627 | 30.393 | −3.796 | 1.00 | 16.18 |
| ATOM | 127 | C | THR | C | 16 | 74.478 | 31.743 | −4.444 | 1.00 | 19.63 |
| ATOM | 128 | O | THR | C | 16 | 75.143 | 31.995 | −5.472 | 1.00 | 18.35 |
| ATOM | 129 | CB | THR | C | 16 | 73.869 | 29.362 | −4.630 | 1.00 | 14.13 |
| ATOM | 130 | OG1 | THR | C | 16 | 72.510 | 29.698 | −4.778 | 1.00 | 17.95 |
| ATOM | 131 | CG2 | THR | C | 16 | 74.103 | 27.943 | −4.087 | 1.00 | 18.04 |
| ATOM | 132 | N | HIS | C | 17 | 73.636 | 32.604 | −3.913 | 1.00 | 14.05 |
| ATOM | 133 | CA | HIS | C | 17 | 73.411 | 33.927 | −4.456 | 1.00 | 15.34 |
| ATOM | 134 | C | HIS | C | 17 | 72.897 | 34.888 | −3.343 | 1.00 | 19.86 |
| ATOM | 135 | O | HIS | C | 17 | 72.249 | 34.434 | −2.351 | 1.00 | 17.90 |
| ATOM | 136 | CB | HIS | C | 17 | 72.332 | 33.779 | −5.554 | 1.00 | 18.53 |
| ATOM | 137 | CG | HIS | C | 17 | 72.007 | 35.052 | −6.293 | 1.00 | 22.33 |
| ATOM | 138 | ND1 | HIS | C | 17 | 70.836 | 35.746 | −6.083 | 1.00 | 25.17 |
| ATOM | 139 | CD2 | HIS | C | 17 | 72.665 | 35.724 | −7.285 | 1.00 | 24.77 |
| ATOM | 140 | CE1 | HIS | C | 17 | 70.797 | 36.809 | −6.865 | 1.00 | 25.62 |
| ATOM | 141 | NE2 | HIS | C | 17 | 71.889 | 36.822 | −7.610 | 1.00 | 24.55 |
| ATOM | 142 | N | ALA | C | 18 | 73.134 | 36.180 | −3.515 | 1.00 | 16.82 |
| ATOM | 143 | CA | ALA | C | 18 | 72.649 | 37.211 | −2.563 | 1.00 | 18.95 |
| ATOM | 144 | C | ALA | C | 18 | 72.073 | 38.366 | −3.404 | 1.00 | 25.44 |
| ATOM | 145 | O | ALA | C | 18 | 72.647 | 38.737 | −4.442 | 1.00 | 26.69 |
| ATOM | 146 | CB | ALA | C | 18 | 73.758 | 37.674 | −1.645 | 1.00 | 21.19 |
| ATOM | 147 | N | ASP | C | 19 | 70.925 | 38.880 | −3.029 | 1.00 | 21.26 |
| ATOM | 148 | CA | ASP | C | 19 | 70.290 | 39.955 | −3.794 | 1.00 | 20.73 |
| ATOM | 149 | C | ASP | C | 19 | 69.612 | 40.957 | −2.869 | 1.00 | 21.60 |
| ATOM | 150 | O | ASP | C | 19 | 68.413 | 40.890 | −2.634 | 1.00 | 20.10 |
| ATOM | 151 | CB | ASP | C | 19 | 69.267 | 39.317 | −4.767 | 1.00 | 21.77 |
| ATOM | 152 | CG | ASP | C | 19 | 68.692 | 40.307 | −5.798 | 1.00 | 27.20 |
| ATOM | 153 | OD1 | ASP | C | 19 | 69.092 | 41.478 | −5.831 | 1.00 | 27.06 |
| ATOM | 154 | OD2 | ASP | C | 19 | 67.785 | 39.862 | −6.570 | 1.00 | 28.93 |
| ATOM | 155 | N | LEU | C | 20 | 70.393 | 41.917 | −2.414 | 1.00 | 21.47 |
| ATOM | 156 | CA | LEU | C | 20 | 69.874 | 42.953 | −1.551 | 1.00 | 21.15 |
| ATOM | 157 | C | LEU | C | 20 | 68.714 | 43.709 | −2.138 | 1.00 | 25.20 |
| ATOM | 158 | O | LEU | C | 20 | 67.771 | 44.028 | −1.426 | 1.00 | 24.39 |
| ATOM | 159 | CB | LEU | C | 20 | 70.997 | 43.944 | −1.181 | 1.00 | 21.58 |
| ATOM | 160 | CG | LEU | C | 20 | 70.700 | 45.069 | −0.209 | 1.00 | 24.50 |
| ATOM | 161 | CD1 | LEU | C | 20 | 70.505 | 44.452 | 1.236 | 1.00 | 22.31 |
| ATOM | 162 | CD2 | LEU | C | 20 | 71.937 | 46.004 | −0.224 | 1.00 | 24.07 |
| ATOM | 163 | N | HIS | C | 21 | 68.786 | 44.010 | −3.448 | 1.00 | 23.99 |
| ATOM | 164 | CA | HIS | C | 21 | 67.733 | 44.767 | −4.147 | 1.00 | 26.08 |
| ATOM | 165 | C | HIS | C | 21 | 66.608 | 43.995 | −4.713 | 1.00 | 29.17 |
| ATOM | 166 | O | HIS | C | 21 | 65.847 | 44.534 | −5.516 | 1.00 | 29.91 |
| ATOM | 167 | CB | HIS | C | 21 | 68.393 | 45.692 | −5.187 | 1.00 | 29.07 |
| ATOM | 168 | CG | HIS | C | 21 | 69.496 | 46.484 | −4.609 | 1.00 | 34.17 |
| ATOM | 169 | ND1 | HIS | C | 21 | 69.283 | 47.347 | −3.561 | 1.00 | 37.06 |
| ATOM | 170 | CD2 | HIS | C | 21 | 70.836 | 46.468 | −4.819 | 1.00 | 37.54 |
| ATOM | 171 | CE1 | HIS | C | 21 | 70.433 | 47.875 | −3.181 | 1.00 | 36.64 |
| ATOM | 172 | NE2 | HIS | C | 21 | 71.394 | 47.358 | −3.926 | 1.00 | 37.19 |
| ATOM | 173 | N | TYR | C | 22 | 66.495 | 42.726 | −4.309 | 1.00 | 26.33 |
| ATOM | 174 | CA | TYR | C | 22 | 65.413 | 41.864 | −4.797 | 1.00 | 27.04 |
| ATOM | 175 | C | TYR | C | 22 | 64.087 | 42.615 | −4.779 | 1.00 | 33.24 |
| ATOM | 176 | O | TYR | C | 22 | 63.709 | 43.265 | −3.775 | 1.00 | 26.75 |
| ATOM | 177 | CB | TYR | C | 22 | 65.294 | 40.643 | −3.890 | 1.00 | 28.34 |
| ATOM | 178 | CG | TYR | C | 22 | 64.348 | 39.561 | −4.368 | 1.00 | 30.64 |
| ATOM | 179 | CD1 | TYR | C | 22 | 64.555 | 38.917 | −5.581 | 1.00 | 31.96 |
| ATOM | 180 | CD2 | TYR | C | 22 | 63.290 | 39.162 | −3.575 | 1.00 | 32.31 |
| ATOM | 181 | CE1 | TYR | C | 22 | 63.697 | 37.898 | −6.009 | 1.00 | 32.16 |
| ATOM | 182 | CE2 | TYR | C | 22 | 62.421 | 38.161 | −3.993 | 1.00 | 32.82 |
| ATOM | 183 | CZ | TYR | C | 22 | 62.641 | 37.525 | −5.201 | 1.00 | 36.63 |
| ATOM | 184 | OH | TYR | C | 22 | 61.767 | 36.526 | −5.622 | 1.00 | 38.85 |

-continued

Data Lists

| | | | | | | | | | |
|---|---|---|---|---|---|---|---|---|---|
| ATOM | 185 | N | GLU | C | 23 | 63.378 | 42.561 | −5.883 | 1.00 | 34.58 |
| ATOM | 186 | CA | GLU | C | 23 | 62.134 | 43.254 | −5.953 | 1.00 | 37.52 |
| ATOM | 187 | C | GLU | C | 23 | 60.863 | 42.459 | −5.743 | 1.00 | 42.30 |
| ATOM | 188 | O | GLU | C | 23 | 59.798 | 43.013 | −5.859 | 1.00 | 40.71 |
| ATOM | 189 | CB | GLU | C | 23 | 62.051 | 44.110 | −7.214 | 1.00 | 39.74 |
| ATOM | 190 | CG | GLU | C | 23 | 63.078 | 45.231 | −7.233 | 1.00 | 50.28 |
| ATOM | 191 | CD | GLU | C | 23 | 62.519 | 46.537 | −6.691 | 1.00 | 61.64 |
| ATOM | 192 | OE1 | GLU | C | 23 | 61.445 | 46.515 | −6.046 | 1.00 | 62.40 |
| ATOM | 193 | OE2 | GLU | C | 23 | 63.152 | 47.594 | −6.923 | 1.00 | 61.54 |
| ATOM | 194 | N | GLY | C | 24 | 60.956 | 41.158 | −5.438 | 1.00 | 39.86 |
| ATOM | 195 | CA | GLY | C | 24 | 59.736 | 40.345 | −5.222 | 1.00 | 43.77 |
| ATOM | 196 | C | GLY | C | 24 | 59.575 | 39.938 | −3.749 | 1.00 | 49.67 |
| ATOM | 197 | O | GLY | C | 24 | 58.617 | 39.195 | −3.402 | 1.00 | 54.64 |
| ATOM | 198 | OH | GLY | C | 24 | 60.410 | 40.339 | −2.920 | 1.00 | 73.31 |
| ATOM | 199 | C | PVL | C | 25 | 64.534 | 35.324 | 1.332 | 1.00 | 17.73 |
| ATOM | 200 | O | PVL | C | 25 | 65.693 | 35.692 | 1.200 | 1.00 | 21.35 |
| ATOM | 201 | CA | PVL | C | 25 | 63.465 | 36.333 | 1.535 | 1.00 | 26.99 |
| ATOM | 202 | CB | PVL | C | 25 | 62.040 | 35.836 | 1.629 | 1.00 | 26.50 |
| ATOM | 203 | ON | PVL | C | 25 | 63.738 | 37.533 | 1.769 | 1.00 | 32.90 |
| ATOM | 204 | N | CYS | C | 26 | 64.218 | 33.987 | 1.203 | 1.00 | 13.65 |
| ATOM | 205 | CA | CYS | C | 26 | 65.226 | 32.982 | 0.870 | 1.00 | 13.69 |
| ATOM | 206 | CB | CYS | C | 26 | 65.775 | 32.194 | 2.112 | 1.00 | 19.50 |
| ATOM | 207 | SG | CYS | C | 26 | 67.153 | 31.117 | 1.678 | 1.00 | 17.42 |
| ATOM | 208 | C | CYS | C | 26 | 64.643 | 32.011 | −0.140 | 1.00 | 17.14 |
| ATOM | 209 | O | CYS | C | 26 | 63.688 | 31.289 | 0.138 | 1.00 | 16.98 |
| ATOM | 210 | N | ALA | C | 27 | 65.174 | 32.063 | −1.414 | 1.00 | 14.97 |
| ATOM | 211 | CA | ALA | C | 27 | 64.691 | 31.198 | −2.478 | 1.00 | 14.51 |
| ATOM | 212 | C | ALA | C | 27 | 65.506 | 29.930 | −2.416 | 1.00 | 11.29 |
| ATOM | 213 | O | ALA | C | 27 | 66.742 | 29.944 | −2.313 | 1.00 | 13.77 |
| ATOM | 214 | CB | ALA | C | 27 | 64.903 | 31.930 | −3.823 | 1.00 | 14.33 |
| ATOM | 215 | N | ILE | C | 28 | 64.784 | 28.821 | −2.436 | 1.00 | 12.96 |
| ATOM | 216 | CA | ILE | C | 28 | 65.324 | 27.513 | −2.268 | 1.00 | 12.54 |
| ATOM | 217 | C | ILE | C | 28 | 64.763 | 26.465 | −3.281 | 1.00 | 13.11 |
| ATOM | 218 | O | ILE | C | 28 | 63.573 | 26.396 | −3.512 | 1.00 | 14.34 |
| ATOM | 219 | CB | ILE | C | 28 | 64.901 | 26.977 | −0.773 | 1.00 | 13.91 |
| ATOM | 220 | CG1 | ILE | C | 28 | 65.435 | 27.945 | 0.261 | 1.00 | 15.23 |
| ATOM | 221 | CG2 | ILE | C | 28 | 65.386 | 25.518 | −0.497 | 1.00 | 16.36 |
| ATOM | 222 | CD1 | ILE | C | 28 | 64.647 | 27.772 | 1.637 | 1.00 | 17.00 |
| ATOM | 223 | N | ASP | C | 29 | 65.689 | 25.727 | −3.865 | 1.00 | 15.10 |
| ATOM | 224 | CA | ASP | C | 29 | 65.333 | 24.657 | −4.850 | 1.00 | 14.57 |
| ATOM | 225 | C | ASP | C | 29 | 64.130 | 23.862 | −4.288 | 1.00 | 17.57 |
| ATOM | 226 | O | ASP | C | 29 | 64.177 | 23.354 | −3.130 | 1.00 | 15.63 |
| ATOM | 227 | CB | ASP | C | 29 | 66.532 | 23.782 | −5.032 | 1.00 | 14.77 |
| ATOM | 228 | CG | ASP | C | 29 | 66.330 | 22.610 | −6.002 | 1.00 | 14.70 |
| ATOM | 229 | OD1 | ASP | C | 29 | 65.209 | 22.105 | −6.198 | 1.00 | 15.75 |
| ATOM | 230 | OD2 | ASP | C | 29 | 67.364 | 22.123 | −6.453 | 1.00 | 16.77 |
| ATOM | 231 | N | GLN | C | 30 | 63.048 | 23.784 | −5.055 | 1.00 | 15.71 |
| ATOM | 232 | CA | GLN | C | 30 | 61.846 | 23.040 | −4.628 | 1.00 | 16.19 |
| ATOM | 233 | C | GLN | C | 30 | 62.169 | 21.606 | −4.152 | 1.00 | 17.73 |
| ATOM | 234 | O | GLN | C | 30 | 61.462 | 21.048 | −3.271 | 1.00 | 17.08 |
| ATOM | 235 | CB | GLN | C | 30 | 60.850 | 22.897 | −5.808 | 1.00 | 17.85 |
| ATOM | 236 | CG | GLN | C | 30 | 59.579 | 22.183 | −5.414 | 1.00 | 23.42 |
| ATOM | 237 | CD | GLN | C | 30 | 58.789 | 22.951 | −4.362 | 1.00 | 23.06 |
| ATOM | 238 | OE1 | GLN | C | 30 | 58.361 | 24.110 | −4.575 | 1.00 | 21.11 |
| ATOM | 239 | NE2 | GLN | C | 30 | 58.574 | 22.285 | −3.172 | 1.00 | 20.59 |
| ATOM | 240 | N | ASP | C | 31 | 63.168 | 20.935 | −4.730 | 1.00 | 16.44 |
| ATOM | 241 | CA | ASP | C | 31 | 63.520 | 19.575 | −4.314 | 1.00 | 16.57 |
| ATOM | 242 | C | ASP | C | 31 | 63.960 | 19.625 | −2.820 | 1.00 | 17.31 |
| ATOM | 243 | O | ASP | C | 31 | 63.633 | 18.679 | −2.057 | 1.00 | 17.32 |
| ATOM | 244 | CB | ASP | C | 31 | 64.705 | 18.996 | −5.106 | 1.00 | 19.02 |
| ATOM | 245 | CG | ASP | C | 31 | 64.300 | 18.460 | −6.508 | 1.00 | 24.47 |
| ATOM | 246 | OD1 | ASP | C | 31 | 63.131 | 18.037 | −6.702 | 1.00 | 24.53 |
| ATOM | 247 | OD2 | ASP | C | 31 | 65.223 | 18.456 | −7.380 | 1.00 | 22.76 |
| ATOM | 248 | N | PHE | C | 32 | 64.716 | 20.662 | −2.468 | 1.00 | 14.02 |
| ATOM | 249 | CA | PHE | C | 32 | 65.221 | 20.820 | −1.075 | 1.00 | 13.65 |
| ATOM | 250 | C | PHE | C | 32 | 64.028 | 21.048 | −0.164 | 1.00 | 16.12 |
| ATOM | 251 | O | PHE | C | 32 | 63.971 | 20.408 | 0.948 | 1.00 | 14.39 |
| ATOM | 252 | CB | PHE | C | 32 | 66.186 | 21.980 | −0.940 | 1.00 | 13.80 |
| ATOM | 253 | CG | PHE | C | 32 | 67.460 | 21.862 | −1.736 | 1.00 | 14.18 |
| ATOM | 254 | CD1 | PHE | C | 32 | 67.825 | 20.722 | −2.462 | 1.00 | 15.47 |
| ATOM | 255 | CD2 | PHE | C | 32 | 68.314 | 22.951 | −1.731 | 1.00 | 15.29 |
| ATOM | 256 | CE1 | PHE | C | 32 | 69.105 | 20.705 | −3.202 | 1.00 | 16.12 |
| ATOM | 257 | CE2 | PHE | C | 32 | 69.515 | 22.950 | −2.452 | 1.00 | 16.29 |
| ATOM | 258 | CZ | PHE | C | 32 | 69.911 | 21.821 | −3.177 | 1.00 | 15.53 |
| ATOM | 259 | N | LEU | C | 33 | 63.106 | 21.911 | −0.561 | 1.00 | 15.49 |
| ATOM | 260 | CA | LEU | C | 33 | 61.887 | 22.193 | 0.225 | 1.00 | 13.34 |
| ATOM | 261 | C | LEU | C | 33 | 61.184 | 20.847 | 0.455 | 1.00 | 17.57 |

-continued

Data Lists

| | | | | | | | | | |
|---|---|---|---|---|---|---|---|---|---|
| ATOM | 262 | O | LEU | C | 33 | 60.783 | 20.497 | 1.591 | 1.00 | 16.65 |
| ATOM | 263 | CB | LEU | C | 33 | 60.926 | 23.160 | −0.496 | 1.00 | 14.40 |
| ATOM | 264 | CG | LEU | C | 33 | 61.494 | 24.560 | −0.722 | 1.00 | 17.89 |
| ATOM | 265 | CD1 | LEU | C | 33 | 60.412 | 25.420 | −1.418 | 1.00 | 15.16 |
| ATOM | 266 | CD2 | LEU | C | 33 | 61.823 | 25.176 | 0.693 | 1.00 | 17.59 |
| ATOM | 267 | N | ASP | C | 34 | 61.007 | 20.035 | −0.596 | 1.00 | 15.41 |
| ATOM | 268 | CA | ASP | C | 34 | 60.313 | 18.744 | −0.431 | 1.00 | 16.06 |
| ATOM | 269 | C | ASP | C | 34 | 61.016 | 17.848 | 0.617 | 1.00 | 18.00 |
| ATOM | 270 | O | ASP | C | 34 | 60.349 | 17.195 | 1.433 | 1.00 | 18.35 |
| ATOM | 271 | CB | ASP | C | 34 | 60.390 | 17.921 | −1.770 | 1.00 | 18.61 |
| ATOM | 272 | CG | ASP | C | 34 | 59.489 | 18.458 | −2.875 | 1.00 | 24.34 |
| ATOM | 273 | OD1 | ASP | C | 34 | 58.649 | 19.342 | −2.651 | 1.00 | 22.17 |
| ATOM | 274 | OD2 | ASP | C | 34 | 59.666 | 17.915 | −4.029 | 1.00 | 28.71 |
| ATOM | 275 | N | ALA | C | 35 | 62.335 | 17.746 | 0.547 | 1.00 | 13.94 |
| ATOM | 276 | CA | ALA | C | 35 | 63.094 | 16.855 | 1.437 | 1.00 | 15.72 |
| ATOM | 277 | C | ALA | C | 35 | 62.964 | 17.259 | 2.887 | 1.00 | 17.50 |
| ATOM | 278 | O | ALA | C | 35 | 62.925 | 16.383 | 3.783 | 1.00 | 18.53 |
| ATOM | 279 | CB | ALA | C | 35 | 64.546 | 16.791 | 1.044 | 1.00 | 16.40 |
| ATOM | 280 | N | ALA | C | 36 | 62.923 | 18.572 | 3.109 | 1.00 | 13.80 |
| ATOM | 281 | CA | ALA | C | 36 | 62.826 | 19.066 | 4.512 | 1.00 | 14.07 |
| ATOM | 282 | C | ALA | C | 36 | 61.369 | 19.265 | 4.931 | 1.00 | 16.21 |
| ATOM | 283 | O | ALA | C | 36 | 61.109 | 19.675 | 6.096 | 1.00 | 16.15 |
| ATOM | 284 | CB | ALA | C | 36 | 63.652 | 20.361 | 4.722 | 1.00 | 14.23 |
| ATOM | 285 | N | GLY | C | 37 | 60.408 | 19.012 | 4.067 | 1.00 | 14.27 |
| ATOM | 286 | CA | GLY | C | 37 | 59.006 | 19.193 | 4.375 | 1.00 | 12.78 |
| ATOM | 287 | C | GLY | C | 37 | 58.621 | 20.712 | 4.515 | 1.00 | 11.55 |
| ATOM | 288 | O | GLY | C | 37 | 57.511 | 21.019 | 5.022 | 1.00 | 13.36 |
| ATOM | 289 | N | ILE | C | 38 | 59.459 | 21.637 | 3.998 | 1.00 | 13.57 |
| ATOM | 290 | CA | ILE | C | 38 | 59.227 | 23.079 | 4.058 | 1.00 | 13.98 |
| ATOM | 291 | C | ILE | C | 38 | 58.350 | 23.496 | 2.908 | 1.00 | 16.32 |
| ATOM | 292 | O | ILE | C | 38 | 58.538 | 22.975 | 1.764 | 1.00 | 16.77 |
| ATOM | 293 | CB | ILE | C | 38 | 60.556 | 23.845 | 4.057 | 1.00 | 15.34 |
| ATOM | 294 | CG1 | ILE | C | 38 | 61.360 | 23.434 | 5.316 | 1.00 | 14.55 |
| ATOM | 295 | CG2 | ILE | C | 38 | 60.360 | 25.362 | 4.098 | 1.00 | 15.27 |
| ATOM | 296 | CD1 | ILE | C | 38 | 62.741 | 24.006 | 5.393 | 1.00 | 19.63 |
| ATOM | 297 | N | LEU | C | 39 | 57.410 | 24.363 | 3.195 | 1.00 | 12.96 |
| ATOM | 298 | CA | LEU | C | 39 | 56.438 | 24.870 | 2.188 | 1.00 | 11.40 |
| ATOM | 299 | C | LEU | C | 39 | 56.789 | 26.256 | 1.685 | 1.00 | 14.26 |
| ATOM | 300 | O | LEU | C | 39 | 57.351 | 27.091 | 2.351 | 1.00 | 13.15 |
| ATOM | 301 | CB | LEU | C | 39 | 55.018 | 24.940 | 2.745 | 1.00 | 12.16 |
| ATOM | 302 | CG | LEU | C | 39 | 54.409 | 23.724 | 3.459 | 1.00 | 13.32 |
| ATOM | 303 | CD1 | LEU | C | 39 | 53.029 | 23.936 | 3.991 | 1.00 | 13.99 |
| ATOM | 304 | CD2 | LEU | C | 39 | 54.450 | 22.512 | 2.442 | 1.00 | 17.01 |
| ATOM | 305 | N | GLU | C | 40 | 56.438 | 26.515 | 0.401 | 1.00 | 14.46 |
| ATOM | 306 | CA | GLU | C | 40 | 56.668 | 27.856 | −0.077 | 1.00 | 15.39 |
| ATOM | 307 | C | GLU | C | 40 | 55.766 | 28.802 | 0.813 | 1.00 | 13.93 |
| ATOM | 308 | O | GLU | C | 40 | 54.630 | 28.488 | 1.146 | 1.00 | 13.92 |
| ATOM | 309 | CB | GLU | C | 40 | 56.149 | 27.962 | −1.564 | 1.00 | 17.33 |
| ATOM | 310 | CG | GLU | C | 40 | 56.299 | 29.405 | −2.092 | 1.00 | 22.86 |
| ATOM | 311 | CD | GLU | C | 40 | 56.447 | 29.500 | −3.609 | 1.00 | 37.57 |
| ATOM | 312 | OE1 | GLU | C | 40 | 55.722 | 28.731 | −4.258 | 1.00 | 29.60 |
| ATOM | 313 | OE2 | GLU | C | 40 | 57.284 | 30.327 | −4.101 | 1.00 | 24.74 |
| ATOM | 314 | N | ASN | C | 41 | 56.349 | 29.944 | 1.163 | 1.00 | 12.53 |
| ATOM | 315 | CA | ASN | C | 41 | 55.781 | 31.000 | 1.960 | 1.00 | 12.52 |
| ATOM | 316 | C | ASN | C | 41 | 55.812 | 30.629 | 3.468 | 1.00 | 13.84 |
| ATOM | 317 | O | ASN | C | 41 | 55.228 | 31.397 | 4.263 | 1.00 | 13.31 |
| ATOM | 318 | CB | ASN | C | 41 | 54.414 | 31.386 | 1.563 | 1.00 | 14.21 |
| ATOM | 319 | CG | ASN | C | 41 | 54.377 | 31.980 | 0.096 | 1.00 | 18.26 |
| ATOM | 320 | OD1 | ASN | C | 41 | 55.127 | 32.868 | −0.218 | 1.00 | 19.96 |
| ATOM | 321 | ND2 | ASN | C | 41 | 53.502 | 31.428 | −0.735 | 1.00 | 23.65 |
| ATOM | 322 | N | GLU | C | 42 | 56.433 | 29.507 | 3.815 | 1.00 | 12.49 |
| ATOM | 323 | CA | GLU | C | 42 | 56.487 | 29.138 | 5.281 | 1.00 | 11.09 |
| ATOM | 324 | C | GLU | C | 42 | 57.541 | 29.977 | 5.920 | 1.00 | 12.61 |
| ATOM | 325 | O | GLU | C | 42 | 58.596 | 30.268 | 5.373 | 1.00 | 13.32 |
| ATOM | 326 | CB | GLU | C | 42 | 56.868 | 27.701 | 5.408 | 1.00 | 11.37 |
| ATOM | 327 | CG | GLU | C | 42 | 56.806 | 27.190 | 6.899 | 1.00 | 13.79 |
| ATOM | 328 | CD | GLU | C | 42 | 57.022 | 25.698 | 6.958 | 1.00 | 16.86 |
| ATOM | 329 | OE1 | GLU | C | 42 | 57.443 | 25.053 | 5.978 | 1.00 | 14.48 |
| ATOM | 330 | OE2 | GLU | C | 42 | 56.821 | 25.073 | 8.083 | 1.00 | 11.57 |
| ATOM | 331 | N | ALA | C | 43 | 57.338 | 30.294 | 7.232 | 1.00 | 11.23 |
| ATOM | 332 | CA | ALA | C | 43 | 58.354 | 30.979 | 7.973 | 1.00 | 11.52 |
| ATOM | 333 | C | ALA | C | 43 | 59.543 | 29.996 | 8.219 | 1.00 | 12.62 |
| ATOM | 334 | O | ALA | C | 43 | 59.345 | 28.779 | 8.496 | 1.00 | 11.29 |
| ATOM | 335 | CB | ALA | C | 43 | 57.767 | 31.316 | 9.366 | 1.00 | 11.84 |
| ATOM | 336 | N | ILE | C | 44 | 60.755 | 30.514 | 8.084 | 1.00 | 10.61 |
| ATOM | 337 | CA | ILE | C | 44 | 61.976 | 29.726 | 8.293 | 1.00 | 9.63 |
| ATOM | 338 | C | ILE | C | 44 | 62.989 | 30.509 | 9.135 | 1.00 | 11.21 |

-continued

Data Lists

| | | | | | | | | | |
|---|---|---|---|---|---|---|---|---|---|
| ATOM | 339 | O | ILE | C | 44 | 63.038 | 31.761 | 9.090 | 1.00 | 11.77 |
| ATOM | 340 | CB | ILE | C | 44 | 62.638 | 29.285 | 6.929 | 1.00 | 11.13 |
| ATOM | 341 | CG1 | ILE | C | 44 | 62.868 | 30.534 | 6.052 | 1.00 | 12.75 |
| ATOM | 342 | CG2 | ILE | C | 44 | 61.738 | 28.241 | 6.300 | 1.00 | 11.62 |
| ATOM | 343 | CD1 | ILE | C | 44 | 63.700 | 30.215 | 4.745 | 1.00 | 16.57 |
| ATOM | 344 | N | ASP | C | 45 | 63.791 | 29.766 | 9.892 | 1.00 | 11.18 |
| ATOM | 345 | CA | ASP | C | 45 | 64.856 | 30.353 | 10.646 | 1.00 | 10.11 |
| ATOM | 346 | C | ASP | C | 45 | 66.187 | 29.921 | 9.981 | 1.00 | 11.65 |
| ATOM | 347 | O | ASP | C | 45 | 66.334 | 28.745 | 9.564 | 1.00 | 12.76 |
| ATOM | 348 | CB | ASP | C | 45 | 64.832 | 29.780 | 12.104 | 1.00 | 11.49 |
| ATOM | 349 | CG | ASP | C | 45 | 63.597 | 30.185 | 12.832 | 1.00 | 12.09 |
| ATOM | 350 | OD1 | ASP | C | 45 | 63.012 | 31.295 | 12.643 | 1.00 | 13.27 |
| ATOM | 351 | OD2 | ASP | C | 45 | 63.146 | 29.292 | 13.666 | 1.00 | 16.15 |
| ATOM | 352 | N | ILE | C | 46 | 67.120 | 30.860 | 9.819 | 1.00 | 12.45 |
| ATOM | 353 | CA | ILE | C | 46 | 68.411 | 30.563 | 9.169 | 1.00 | 11.69 |
| ATOM | 354 | C | ILE | C | 46 | 69.494 | 30.864 | 10.146 | 1.00 | 13.15 |
| ATOM | 355 | O | ILE | C | 46 | 69.566 | 31.982 | 10.710 | 1.00 | 13.26 |
| ATOM | 356 | CB | ILE | C | 46 | 68.536 | 31.422 | 7.883 | 1.00 | 13.14 |
| ATOM | 357 | CG1 | ILE | C | 46 | 67.338 | 31.096 | 7.003 | 1.00 | 12.28 |
| ATOM | 358 | CG2 | ILE | C | 46 | 69.920 | 31.132 | 7.208 | 1.00 | 13.37 |
| ATOM | 359 | CD1 | ILE | C | 46 | 67.524 | 31.730 | 5.488 | 1.00 | 14.34 |
| ATOM | 360 | N | TRP | C | 47 | 70.322 | 29.841 | 10.406 | 1.00 | 12.56 |
| ATOM | 361 | CA | TRP | C | 47 | 71.414 | 29.944 | 11.387 | 1.00 | 11.59 |
| ATOM | 362 | C | TRP | C | 47 | 72.717 | 29.812 | 10.545 | 1.00 | 12.65 |
| ATOM | 363 | O | TRP | C | 47 | 72.955 | 28.776 | 9.937 | 1.00 | 13.30 |
| ATOM | 364 | CB | TRP | C | 47 | 71.265 | 28.791 | 12.381 | 1.00 | 11.85 |
| ATOM | 365 | CG | TRP | C | 47 | 69.917 | 28.832 | 13.078 | 1.00 | 11.21 |
| ATOM | 366 | CD1 | TRP | C | 47 | 69.254 | 29.942 | 13.487 | 1.00 | 12.57 |
| ATOM | 367 | CD2 | TRP | C | 47 | 69.125 | 27.705 | 13.456 | 1.00 | 12.14 |
| ATOM | 368 | NE1 | TRP | C | 47 | 68.053 | 29.581 | 14.123 | 1.00 | 11.88 |
| ATOM | 369 | CE2 | TRP | C | 47 | 67.960 | 28.215 | 14.112 | 1.00 | 10.79 |
| ATOM | 370 | CE3 | TRP | C | 47 | 69.264 | 26.331 | 13.261 | 1.00 | 14.11 |
| ATOM | 371 | CZ2 | TRP | C | 47 | 66.930 | 27.369 | 14.579 | 1.00 | 11.66 |
| ATOM | 372 | CZ3 | TRP | C | 47 | 68.235 | 25.465 | 13.766 | 1.00 | 14.28 |
| ATOM | 373 | CH2 | TRP | C | 47 | 67.080 | 26.038 | 14.410 | 1.00 | 14.15 |
| ATOM | 374 | N | ASN | C | 48 | 73.512 | 30.856 | 10.577 | 1.00 | 12.67 |
| ATOM | 375 | CA | ASN | C | 48 | 74.730 | 30.931 | 9.784 | 1.00 | 14.84 |
| ATOM | 376 | C | ASN | C | 48 | 75.898 | 30.311 | 10.503 | 1.00 | 14.53 |
| ATOM | 377 | O | ASN | C | 48 | 76.456 | 30.916 | 11.495 | 1.00 | 15.46 |
| ATOM | 378 | CB | ASN | C | 48 | 74.966 | 32.379 | 9.370 | 1.00 | 13.17 |
| ATOM | 379 | CG | ASN | C | 48 | 75.984 | 32.520 | 8.231 | 1.00 | 12.09 |
| ATOM | 380 | OD1 | ASN | C | 48 | 76.997 | 31.892 | 8.252 | 1.00 | 14.55 |
| ATOM | 381 | ND2 | ASN | C | 48 | 75.728 | 33.481 | 7.353 | 1.00 | 14.53 |
| ATOM | 382 | N | VAL | C | 49 | 76.306 | 29.138 | 10.060 | 1.00 | 13.24 |
| ATOM | 383 | CA | VAL | C | 49 | 77.416 | 28.477 | 10.667 | 1.00 | 13.19 |
| ATOM | 384 | C | VAL | C | 49 | 78.741 | 29.222 | 10.464 | 1.00 | 18.14 |
| ATOM | 385 | O | VAL | C | 49 | 79.658 | 29.202 | 11.306 | 1.00 | 19.15 |
| ATOM | 386 | CB | VAL | C | 49 | 77.568 | 27.013 | 10.155 | 1.00 | 15.64 |
| ATOM | 387 | CG1 | VAL | C | 49 | 78.718 | 26.315 | 10.879 | 1.00 | 17.34 |
| ATOM | 388 | CG2 | VAL | C | 49 | 76.256 | 26.221 | 10.313 | 1.00 | 15.21 |
| ATOM | 389 | N | THR | C | 50 | 78.884 | 29.888 | 9.312 | 1.00 | 14.80 |
| ATOM | 390 | CA | THR | C | 50 | 80.115 | 30.592 | 9.059 | 1.00 | 14.70 |
| ATOM | 391 | C | THR | C | 50 | 80.332 | 31.856 | 9.917 | 1.00 | 15.83 |
| ATOM | 392 | O | THR | C | 50 | 81.434 | 32.032 | 10.464 | 1.00 | 18.87 |
| ATOM | 393 | CB | THR | C | 50 | 80.206 | 30.952 | 7.521 | 1.00 | 18.21 |
| ATOM | 394 | OG1 | THR | C | 50 | 80.146 | 29.742 | 6.790 | 1.00 | 15.78 |
| ATOM | 395 | CG2 | THR | C | 50 | 81.513 | 31.639 | 7.236 | 1.00 | 16.82 |
| ATOM | 396 | N | ASN | C | 51 | 79.334 | 32.710 | 10.014 | 1.00 | 14.06 |
| ATOM | 397 | CA | ASN | C | 51 | 79.492 | 33.962 | 10.776 | 1.00 | 15.31 |
| ATOM | 398 | C | ASN | C | 51 | 78.715 | 34.092 | 12.098 | 1.00 | 17.85 |
| ATOM | 399 | O | ASN | C | 51 | 78.807 | 35.115 | 12.755 | 1.00 | 17.40 |
| ATOM | 400 | CB | ASN | C | 51 | 79.229 | 35.187 | 9.877 | 1.00 | 18.14 |
| ATOM | 401 | CG | ASN | C | 51 | 77.756 | 35.329 | 9.477 | 1.00 | 20.44 |
| ATOM | 402 | OD1 | ASN | C | 51 | 76.879 | 34.705 | 10.085 | 1.00 | 16.68 |
| ATOM | 403 | ND2 | ASN | C | 51 | 77.462 | 36.172 | 8.454 | 1.00 | 16.78 |
| ATOM | 404 | N | GLY | C | 52 | 77.954 | 33.059 | 12.436 | 1.00 | 15.39 |
| ATOM | 405 | CA | GLY | C | 52 | 77.169 | 33.081 | 13.693 | 1.00 | 16.35 |
| ATOM | 406 | C | GLY | C | 52 | 75.868 | 33.855 | 13.678 | 1.00 | 18.04 |
| ATOM | 407 | O | GLY | C | 52 | 75.109 | 33.788 | 14.680 | 1.00 | 15.14 |
| ATOM | 408 | N | LYS | C | 53 | 75.528 | 34.597 | 12.606 | 1.00 | 13.62 |
| ATOM | 409 | CA | LYS | C | 53 | 74.279 | 35.346 | 12.571 | 1.00 | 13.33 |
| ATOM | 410 | C | LYS | C | 53 | 73.078 | 34.419 | 12.525 | 1.00 | 13.70 |
| ATOM | 411 | O | LYS | C | 53 | 73.156 | 33.312 | 11.988 | 1.00 | 13.57 |
| ATOM | 412 | CB | LYS | C | 53 | 74.226 | 36.376 | 11.407 | 1.00 | 15.27 |
| ATOM | 413 | CG | LYS | C | 53 | 75.408 | 37.304 | 11.460 | 1.00 | 16.18 |
| ATOM | 414 | CD | LYS | C | 53 | 75.235 | 38.411 | 10.445 | 1.00 | 18.83 |
| ATOM | 415 | CE | LYS | C | 53 | 76.538 | 39.222 | 10.332 | 1.00 | 24.88 |

-continued

Data Lists

| | | | | | | | | | |
|---|---|---|---|---|---|---|---|---|---|
| ATOM | 416 | NZ  | LYS | C | 53 | 76.488 | 40.240 | 9.151 | 1.00 | 24.28 |
| ATOM | 417 | N   | ARG | C | 54 | 71.957 | 34.851 | 13.130 | 1.00 | 12.69 |
| ATOM | 418 | CA  | ARG | C | 54 | 70.720 | 34.077 | 13.202 | 1.00 | 11.88 |
| ATOM | 419 | C   | ARG | C | 54 | 69.563 | 35.017 | 12.837 | 1.00 | 14.37 |
| ATOM | 420 | O   | ARG | C | 54 | 69.422 | 36.109 | 13.368 | 1.00 | 13.79 |
| ATOM | 421 | CB  | ARG | C | 54 | 70.513 | 33.544 | 14.658 | 1.00 | 11.58 |
| ATOM | 422 | CG  | ARG | C | 54 | 71.674 | 32.735 | 15.081 | 1.00 | 12.91 |
| ATOM | 423 | CD  | ARG | C | 54 | 71.473 | 32.182 | 16.577 | 1.00 | 13.98 |
| ATOM | 424 | NE  | ARG | C | 54 | 70.621 | 31.016 | 16.648 | 1.00 | 15.65 |
| ATOM | 425 | CZ  | ARG | C | 54 | 71.030 | 29.772 | 16.432 | 1.00 | 13.20 |
| ATOM | 426 | NH1 | ARG | C | 54 | 72.320 | 29.537 | 16.081 | 1.00 | 13.97 |
| ATOM | 427 | NH2 | ARG | C | 54 | 70.206 | 28.733 | 16.554 | 1.00 | 12.47 |
| ATOM | 428 | N   | PHE | C | 55 | 68.708 | 34.614 | 11.897 | 1.00 | 13.21 |
| ATOM | 429 | CA  | PHE | C | 55 | 67.605 | 35.481 | 11.482 | 1.00 | 11.72 |
| ATOM | 430 | C   | PHE | C | 55 | 66.418 | 34.634 | 11.006 | 1.00 | 12.09 |
| ATOM | 431 | O   | PHE | C | 55 | 66.591 | 33.396 | 10.737 | 1.00 | 14.53 |
| ATOM | 432 | CB  | PHE | C | 55 | 68.046 | 36.473 | 10.368 | 1.00 | 12.81 |
| ATOM | 433 | CG  | PHE | C | 55 | 68.562 | 35.804 | 9.087 | 1.00 | 14.26 |
| ATOM | 434 | CD1 | PHE | C | 55 | 69.846 | 35.318 | 9.008 | 1.00 | 15.91 |
| ATOM | 435 | CD2 | PHE | C | 55 | 67.757 | 35.761 | 7.976 | 1.00 | 16.89 |
| ATOM | 436 | CE1 | PHE | C | 55 | 70.335 | 34.741 | 7.814 | 1.00 | 18.73 |
| ATOM | 437 | CE2 | PHE | C | 55 | 68.244 | 35.194 | 6.797 | 1.00 | 18.14 |
| ATOM | 438 | CZ  | PHE | C | 55 | 69.487 | 34.707 | 6.724 | 1.00 | 16.81 |
| ATOM | 439 | N   | SER | C | 56 | 65.271 | 35.285 | 10.899 | 1.00 | 12.30 |
| ATOM | 440 | CA  | SER | C | 56 | 64.027 | 34.624 | 10.507 | 1.00 | 11.60 |
| ATOM | 441 | C   | SER | C | 56 | 63.434 | 35.336 | 9.280 | 1.00 | 13.08 |
| ATOM | 442 | O   | SER | C | 56 | 63.432 | 36.539 | 9.216 | 1.00 | 12.92 |
| ATOM | 443 | CB  | SER | C | 56 | 63.017 | 34.612 | 11.646 | 1.00 | 14.04 |
| ATOM | 444 | OG  | SER | C | 56 | 63.603 | 33.905 | 12.760 | 1.00 | 17.74 |
| ATOM | 445 | N   | THR | C | 57 | 62.982 | 34.543 | 8.325 | 1.00 | 12.51 |
| ATOM | 446 | CA  | THR | C | 57 | 62.408 | 35.094 | 7.083 | 1.00 | 15.14 |
| ATOM | 447 | C   | THR | C | 57 | 61.340 | 34.103 | 6.578 | 1.00 | 16.57 |
| ATOM | 448 | O   | THR | C | 57 | 60.653 | 33.469 | 7.397 | 1.00 | 13.36 |
| ATOM | 449 | CB  | THR | C | 57 | 63.513 | 35.345 | 6.067 | 1.00 | 17.35 |
| ATOM | 450 | OG1 | THR | C | 57 | 62.937 | 36.006 | 4.924 | 1.00 | 17.51 |
| ATOM | 451 | CG2 | THR | C | 57 | 64.314 | 34.105 | 5.666 | 1.00 | 19.79 |
| ATOM | 452 | N   | TYR | C | 58 | 61.118 | 33.960 | 5.247 | 1.00 | 13.07 |
| ATOM | 453 | CA  | TYR | C | 58 | 60.120 | 33.001 | 4.744 | 1.00 | 11.86 |
| ATOM | 454 | C   | TYR | C | 58 | 60.721 | 32.381 | 3.453 | 1.00 | 14.46 |
| ATOM | 455 | O   | TYR | C | 58 | 61.629 | 32.949 | 2.879 | 1.00 | 14.80 |
| ATOM | 456 | CB  | TYR | C | 58 | 58.762 | 33.591 | 4.472 | 1.00 | 11.64 |
| ATOM | 457 | CG  | TYR | C | 58 | 58.754 | 34.679 | 3.414 | 1.00 | 14.08 |
| ATOM | 458 | CD1 | TYR | C | 58 | 59.116 | 35.983 | 3.729 | 1.00 | 14.47 |
| ATOM | 459 | CD2 | TYR | C | 58 | 58.407 | 34.360 | 2.083 | 1.00 | 16.79 |
| ATOM | 460 | CE1 | TYR | C | 58 | 59.123 | 36.982 | 2.767 | 1.00 | 19.79 |
| ATOM | 461 | CE2 | TYR | C | 58 | 58.408 | 35.385 | 1.101 | 1.00 | 15.79 |
| ATOM | 462 | CZ  | TYR | C | 58 | 58.772 | 36.658 | 1.465 | 1.00 | 22.24 |
| ATOM | 463 | OH  | TYR | C | 58 | 58.773 | 37.582 | 0.406 | 1.00 | 23.11 |
| ATOM | 464 | N   | ALA | C | 59 | 60.236 | 31.199 | 3.113 | 1.00 | 11.72 |
| ATOM | 465 | CA  | ALA | C | 59 | 60.747 | 30.471 | 1.952 | 1.00 | 12.72 |
| ATOM | 466 | C   | ALA | C | 59 | 60.040 | 30.828 | 0.681 | 1.00 | 12.49 |
| ATOM | 467 | O   | ALA | C | 59 | 58.820 | 30.922 | 0.629 | 1.00 | 13.37 |
| ATOM | 468 | CB  | ALA | C | 59 | 60.532 | 28.933 | 2.179 | 1.00 | 13.81 |
| ATOM | 469 | N   | ILE | C | 60 | 60.887 | 30.962 | −0.360 | 1.00 | 15.14 |
| ATOM | 470 | CA  | ILE | C | 60 | 60.387 | 31.207 | −1.760 | 1.00 | 16.33 |
| ATOM | 471 | C   | ILE | C | 60 | 60.878 | 29.978 | −2.563 | 1.00 | 16.77 |
| ATOM | 472 | O   | ILE | C | 60 | 62.007 | 29.525 | −2.396 | 1.00 | 14.68 |
| ATOM | 473 | CB  | ILE | C | 60 | 61.069 | 32.427 | −2.340 | 1.00 | 18.30 |
| ATOM | 474 | CG1 | ILE | C | 60 | 60.607 | 33.708 | −1.635 | 1.00 | 19.09 |
| ATOM | 475 | CG2 | ILE | C | 60 | 60.811 | 32.500 | −3.911 | 1.00 | 21.06 |
| ATOM | 476 | CD1 | ILE | C | 60 | 61.497 | 34.913 | −1.895 | 1.00 | 26.31 |
| ATOM | 477 | N   | ALA | C | 61 | 60.014 | 29.412 | −3.422 | 1.00 | 15.66 |
| ATOM | 478 | CA  | ALA | C | 61 | 60.493 | 28.249 | −4.180 | 1.00 | 15.73 |
| ATOM | 479 | C   | ALA | C | 61 | 61.328 | 28.696 | −5.413 | 1.00 | 18.47 |
| ATOM | 480 | O   | ALA | C | 61 | 60.970 | 29.648 | −6.096 | 1.00 | 23.19 |
| ATOM | 481 | CB  | ALA | C | 61 | 59.337 | 27.383 | −4.642 | 1.00 | 17.99 |
| ATOM | 482 | N   | ALA | C | 62 | 62.430 | 28.006 | −5.607 | 1.00 | 14.95 |
| ATOM | 483 | CA  | ALA | C | 62 | 63.342 | 28.198 | −6.774 | 1.00 | 14.55 |
| ATOM | 484 | C   | ALA | C | 62 | 63.068 | 26.946 | −7.605 | 1.00 | 18.92 |
| ATOM | 485 | O   | ALA | C | 62 | 62.551 | 25.909 | −7.178 | 1.00 | 17.86 |
| ATOM | 486 | CB  | ALA | C | 62 | 64.817 | 28.259 | −6.403 | 1.00 | 13.98 |
| ATOM | 487 | N   | GLU | C | 63 | 63.424 | 27.072 | −8.904 | 1.00 | 17.78 |
| ATOM | 488 | CA  | GLU | C | 63 | 63.220 | 25.977 | −9.834 | 1.00 | 19.52 |
| ATOM | 489 | C   | GLU | C | 63 | 63.779 | 24.635 | −9.365 | 1.00 | 19.81 |
| ATOM | 490 | O   | GLU | C | 63 | 64.894 | 24.571 | −8.868 | 1.00 | 17.13 |
| ATOM | 491 | CB  | GLU | C | 63 | 63.968 | 26.354 | −11.140 | 1.00 | 21.37 |
| ATOM | 492 | CG  | GLU | C | 63 | 63.779 | 25.342 | −12.296 | 1.00 | 29.86 |

-continued

Data Lists

| | | | | | | | | | |
|---|---|---|---|---|---|---|---|---|---|
| ATOM | 493 | CD | GLU | C | 63 | 64.980 | 25.283 | −13.255 | 1.00 | 53.22 |
| ATOM | 494 | OE1 | GLU | C | 63 | 65.920 | 26.108 | −13.149 | 1.00 | 44.04 |
| ATOM | 495 | OE2 | GLU | C | 63 | 64.964 | 24.394 | −14.129 | 1.00 | 43.79 |
| ATOM | 496 | N | ARG | C | 64 | 63.012 | 23.575 | −9.561 | 1.00 | 16.26 |
| ATOM | 497 | CA | ARG | C | 64 | 63.425 | 22.245 | −9.201 | 1.00 | 16.34 |
| ATOM | 498 | C | ARG | C | 64 | 64.723 | 21.863 | −9.911 | 1.00 | 21.13 |
| ATOM | 499 | O | ARG | C | 64 | 64.809 | 21.970 | −11.168 | 1.00 | 20.36 |
| ATOM | 500 | CB | ARG | C | 64 | 62.326 | 21.232 | −9.503 | 1.00 | 19.26 |
| ATOM | 501 | CG | ARG | C | 64 | 62.635 | 19.890 | −8.963 | 1.00 | 26.38 |
| ATOM | 502 | CD | ARG | C | 64 | 61.521 | 18.875 | −9.196 | 1.00 | 27.64 |
| ATOM | 503 | NE | ARG | C | 64 | 60.171 | 19.286 | −8.819 | 1.00 | 26.53 |
| ATOM | 504 | CZ | ARG | C | 64 | 59.662 | 19.154 | −7.585 | 1.00 | 41.54 |
| ATOM | 505 | NH1 | ARG | C | 64 | 60.408 | 18.669 | −6.578 | 1.00 | 23.51 |
| ATOM | 506 | NH2 | ARG | C | 64 | 58.421 | 19.526 | −7.351 | 1.00 | 30.75 |
| ATOM | 507 | N | GLY | C | 65 | 65.728 | 21.436 | −9.177 | 1.00 | 17.09 |
| ATOM | 508 | CA | GLY | C | 65 | 67.000 | 21.022 | −9.721 | 1.00 | 17.60 |
| ATOM | 509 | C | GLY | C | 65 | 68.038 | 22.140 | −9.853 | 1.00 | 18.83 |
| ATOM | 510 | O | GLY | C | 65 | 69.192 | 21.885 | −10.218 | 1.00 | 20.21 |
| ATOM | 511 | N | SER | C | 66 | 67.650 | 23.380 | −9.543 | 1.00 | 16.18 |
| ATOM | 512 | CA | SER | C | 66 | 68.539 | 24.515 | −9.627 | 1.00 | 15.57 |
| ATOM | 513 | C | SER | C | 66 | 69.606 | 24.577 | −8.516 | 1.00 | 19.13 |
| ATOM | 514 | O | SER | C | 66 | 70.673 | 25.179 | −8.654 | 1.00 | 18.34 |
| ATOM | 515 | CB | SER | C | 66 | 67.764 | 25.795 | −9.596 | 1.00 | 18.61 |
| ATOM | 516 | OG | SER | C | 66 | 67.136 | 26.006 | −8.280 | 1.00 | 17.83 |
| ATOM | 517 | N | ARG | C | 67 | 69.272 | 23.904 | −7.390 | 1.00 | 16.53 |
| ATOM | 518 | CA | ARG | C | 67 | 70.164 | 23.877 | −6.187 | 1.00 | 17.76 |
| ATOM | 519 | C | ARG | C | 67 | 70.423 | 25.285 | −5.633 | 1.00 | 14.93 |
| ATOM | 520 | O | ARG | C | 67 | 71.423 | 25.507 | −4.998 | 1.00 | 16.56 |
| ATOM | 521 | CB | ARG | C | 67 | 71.476 | 23.153 | −6.456 | 1.00 | 15.58 |
| ATOM | 522 | CG | ARG | C | 67 | 71.298 | 21.685 | −6.865 | 1.00 | 14.91 |
| ATOM | 523 | CD | ARG | C | 67 | 72.533 | 20.909 | −6.767 | 1.00 | 13.81 |
| ATOM | 524 | NE | ARG | C | 67 | 72.322 | 19.522 | −7.249 | 1.00 | 16.78 |
| ATOM | 525 | CZ | ARG | C | 67 | 73.219 | 18.551 | −7.123 | 1.00 | 18.26 |
| ATOM | 526 | NH1 | ARG | C | 67 | 74.395 | 18.751 | −6.546 | 1.00 | 18.16 |
| ATOM | 527 | NH2 | ARG | C | 67 | 72.944 | 17.336 | −7.609 | 1.00 | 19.31 |
| ATOM | 528 | N | ILE | C | 68 | 69.503 | 26.201 | −5.884 | 1.00 | 13.92 |
| ATOM | 529 | CA | ILE | C | 68 | 69.659 | 27.584 | −5.447 | 1.00 | 13.11 |
| ATOM | 530 | C | ILE | C | 68 | 69.325 | 27.709 | −3.918 | 1.00 | 14.96 |
| ATOM | 531 | O | ILE | C | 68 | 68.385 | 27.063 | −3.430 | 1.00 | 16.08 |
| ATOM | 532 | CB | ILE | C | 68 | 68.680 | 28.483 | −6.228 | 1.00 | 16.07 |
| ATOM | 533 | CG1 | ILE | C | 68 | 69.177 | 28.633 | −7.743 | 1.00 | 15.43 |
| ATOM | 534 | CG2 | ILE | C | 68 | 68.517 | 29.887 | −5.539 | 1.00 | 14.91 |
| ATOM | 535 | CD1 | ILE | C | 68 | 68.162 | 29.265 | −8.585 | 1.00 | 17.12 |
| ATOM | 536 | N | ILE | C | 69 | 70.116 | 28.547 | −3.278 | 1.00 | 15.79 |
| ATOM | 537 | CA | ILE | C | 69 | 69.921 | 29.021 | −1.887 | 1.00 | 14.43 |
| ATOM | 538 | C | ILE | C | 69 | 70.273 | 30.521 | −2.099 | 1.00 | 12.91 |
| ATOM | 539 | O | ILE | C | 69 | 71.469 | 30.897 | −2.053 | 1.00 | 16.10 |
| ATOM | 540 | CB | ILE | C | 69 | 70.826 | 28.392 | −0.867 | 1.00 | 14.38 |
| ATOM | 541 | CG1 | ILE | C | 69 | 70.632 | 26.859 | −0.742 | 1.00 | 14.18 |
| ATOM | 542 | CG2 | ILE | C | 69 | 70.524 | 29.042 | 0.545 | 1.00 | 14.77 |
| ATOM | 543 | CD1 | ILE | C | 69 | 69.240 | 26.399 | −0.207 | 1.00 | 13.25 |
| ATOM | 544 | N | SER | C | 70 | 69.266 | 31.361 | −2.315 | 1.00 | 12.61 |
| ATOM | 545 | CA | SER | C | 70 | 69.474 | 32.776 | −2.545 | 1.00 | 12.79 |
| ATOM | 546 | C | SER | C | 70 | 68.897 | 33.612 | −1.365 | 1.00 | 16.65 |
| ATOM | 547 | O | SER | C | 70 | 67.703 | 33.574 | −1.101 | 1.00 | 16.44 |
| ATOM | 548 | CB | SER | C | 70 | 68.786 | 33.187 | −3.877 | 1.00 | 17.19 |
| ATOM | 549 | OG | SER | C | 70 | 69.055 | 34.583 | −4.178 | 1.00 | 19.28 |
| ATOM | 550 | N | VAL | C | 71 | 69.763 | 34.375 | −0.735 | 1.00 | 16.77 |
| ATOM | 551 | CA | VAL | C | 71 | 69.353 | 35.237 | 0.411 | 1.00 | 16.54 |
| ATOM | 552 | C | VAL | C | 71 | 69.046 | 36.611 | −0.216 | 1.00 | 18.47 |
| ATOM | 553 | O | VAL | C | 71 | 69.938 | 37.276 | −0.785 | 1.00 | 20.32 |
| ATOM | 554 | CB | VAL | C | 71 | 70.489 | 35.218 | 1.485 | 1.00 | 21.34 |
| ATOM | 555 | CG1 | VAL | C | 71 | 70.168 | 36.151 | 2.628 | 1.00 | 23.85 |
| ATOM | 556 | CG2 | VAL | C | 71 | 70.601 | 33.816 | 2.075 | 1.00 | 21.90 |
| ATOM | 557 | N | ASN | C | 72 | 67.793 | 37.013 | −0.156 | 1.00 | 17.21 |
| ATOM | 558 | CA | ASN | C | 72 | 67.310 | 38.229 | −0.774 | 1.00 | 18.06 |
| ATOM | 559 | C | ASN | C | 72 | 66.822 | 39.292 | 0.185 | 1.00 | 22.03 |
| ATOM | 560 | O | ASN | C | 72 | 66.550 | 38.985 | 1.364 | 1.00 | 20.77 |
| ATOM | 561 | CB | ASN | C | 72 | 66.111 | 37.862 | −1.684 | 1.00 | 15.71 |
| ATOM | 562 | CG | ASN | C | 72 | 66.479 | 36.805 | −2.771 | 1.00 | 21.14 |
| ATOM | 563 | OD1 | ASN | C | 72 | 67.625 | 36.673 | −3.142 | 1.00 | 22.76 |
| ATOM | 564 | ND2 | ASN | C | 72 | 65.471 | 36.043 | −3.192 | 1.00 | 26.84 |
| ATOM | 565 | N | GLY | C | 73 | 66.680 | 40.519 | −0.296 | 1.00 | 17.96 |
| ATOM | 566 | CA | GLY | C | 73 | 66.191 | 41.609 | 0.547 | 1.00 | 17.13 |
| ATOM | 567 | C | GLY | C | 73 | 67.152 | 41.925 | 1.662 | 1.00 | 17.10 |
| ATOM | 568 | O | GLY | C | 73 | 68.358 | 41.772 | 1.548 | 1.00 | 17.56 |
| ATOM | 569 | N | ALA | C | 74 | 66.585 | 42.379 | 2.783 | 1.00 | 16.81 |

-continued

Data Lists

| | | | | | | | | | |
|---|---|---|---|---|---|---|---|---|---|
| ATOM | 570 | CA | ALA | C | 74 | 67.448 | 42.743 | 3.926 | 1.00 | 16.63 |
| ATOM | 571 | C | ALA | C | 74 | 68.307 | 41.588 | 4.409 | 1.00 | 17.98 |
| ATOM | 572 | O | ALA | C | 74 | 69.403 | 41.809 | 4.948 | 1.00 | 17.87 |
| ATOM | 573 | CB | ALA | C | 74 | 66.585 | 43.261 | 5.083 | 1.00 | 16.76 |
| ATOM | 574 | N | ALA | C | 75 | 67.829 | 40.348 | 4.210 | 1.00 | 16.77 |
| ATOM | 575 | CA | ALA | C | 75 | 68.603 | 39.156 | 4.626 | 1.00 | 17.69 |
| ATOM | 576 | C | ALA | C | 75 | 70.019 | 39.079 | 3.999 | 1.00 | 17.68 |
| ATOM | 577 | O | ALA | C | 75 | 70.898 | 38.411 | 4.507 | 1.00 | 16.79 |
| ATOM | 578 | CB | ALA | C | 75 | 67.861 | 37.907 | 4.282 | 1.00 | 20.55 |
| ATOM | 579 | N | ALA | C | 76 | 70.216 | 39.775 | 2.856 | 1.00 | 16.67 |
| ATOM | 580 | CA | ALA | C | 76 | 71.535 | 39.737 | 2.230 | 1.00 | 17.52 |
| ATOM | 581 | C | ALA | C | 76 | 72.644 | 40.382 | 3.121 | 1.00 | 17.22 |
| ATOM | 582 | O | ALA | C | 76 | 73.840 | 40.202 | 2.886 | 1.00 | 18.09 |
| ATOM | 583 | CB | ALA | C | 76 | 71.482 | 40.359 | 0.797 | 1.00 | 18.29 |
| ATOM | 584 | N | HIS | C | 77 | 72.232 | 41.101 | 4.193 | 1.00 | 15.19 |
| ATOM | 585 | CA | HIS | C | 77 | 73.203 | 41.686 | 5.120 | 1.00 | 16.72 |
| ATOM | 586 | C | HIS | C | 77 | 73.627 | 40.623 | 6.163 | 1.00 | 16.17 |
| ATOM | 587 | O | HIS | C | 77 | 74.587 | 40.860 | 6.914 | 1.00 | 18.25 |
| ATOM | 588 | CB | HIS | C | 77 | 72.502 | 42.778 | 5.963 | 1.00 | 18.31 |
| ATOM | 589 | CG | HIS | C | 77 | 72.336 | 44.077 | 5.261 | 1.00 | 21.21 |
| ATOM | 590 | ND1 | HIS | C | 77 | 73.368 | 44.963 | 5.118 | 1.00 | 25.21 |
| ATOM | 591 | CD2 | HIS | C | 77 | 71.258 | 44.654 | 4.687 | 1.00 | 22.31 |
| ATOM | 592 | CE1 | HIS | C | 77 | 72.940 | 46.030 | 4.463 | 1.00 | 23.74 |
| ATOM | 593 | NE2 | HIS | C | 77 | 71.663 | 45.876 | 4.200 | 1.00 | 22.33 |
| ATOM | 594 | N | CYS | C | 78 | 72.921 | 39.495 | 6.201 | 1.00 | 14.86 |
| ATOM | 595 | CA | CYS | C | 78 | 73.192 | 38.449 | 7.199 | 1.00 | 16.42 |
| ATOM | 596 | C | CYS | C | 78 | 73.868 | 37.192 | 6.701 | 1.00 | 16.96 |
| ATOM | 597 | O | CYS | C | 78 | 74.290 | 36.294 | 7.516 | 1.00 | 16.97 |
| ATOM | 598 | CB | CYS | C | 78 | 71.873 | 38.018 | 7.877 | 1.00 | 16.76 |
| ATOM | 599 | SG | CYS | C | 78 | 70.910 | 39.411 | 8.622 | 1.00 | 22.74 |
| ATOM | 600 | N | ALA | C | 79 | 73.983 | 37.044 | 5.346 | 1.00 | 14.78 |
| ATOM | 601 | CA | ALA | C | 79 | 74.626 | 35.854 | 4.795 | 1.00 | 14.85 |
| ATOM | 602 | C | ALA | C | 79 | 75.204 | 36.282 | 3.435 | 1.00 | 15.30 |
| ATOM | 603 | O | ALA | C | 79 | 74.676 | 37.213 | 2.822 | 1.00 | 16.51 |
| ATOM | 604 | CB | ALA | C | 79 | 73.652 | 34.707 | 4.608 | 1.00 | 15.77 |
| ATOM | 605 | N | SER | C | 80 | 76.281 | 35.597 | 3.082 | 1.00 | 13.90 |
| ATOM | 606 | CA | SER | C | 80 | 77.009 | 35.855 | 1.804 | 1.00 | 13.46 |
| ATOM | 607 | C | SER | C | 80 | 77.182 | 34.588 | 1.039 | 1.00 | 17.54 |
| ATOM | 608 | O | SER | C | 80 | 77.156 | 33.497 | 1.573 | 1.00 | 16.85 |
| ATOM | 609 | CB | SER | C | 80 | 78.368 | 36.434 | 2.130 | 1.00 | 17.79 |
| ATOM | 610 | OG | SER | C | 80 | 78.214 | 37.661 | 2.852 | 1.00 | 18.84 |
| ATOM | 611 | N | VAL | C | 81 | 77.403 | 34.738 | −0.290 | 1.00 | 15.99 |
| ATOM | 612 | CA | VAL | C | 81 | 77.636 | 33.575 | −1.121 | 1.00 | 14.74 |
| ATOM | 613 | C | VAL | C | 81 | 78.865 | 32.845 | −0.571 | 1.00 | 14.78 |
| ATOM | 614 | O | VAL | C | 81 | 79.915 | 33.417 | −0.317 | 1.00 | 15.81 |
| ATOM | 615 | CB | VAL | C | 81 | 77.941 | 34.058 | −2.623 | 1.00 | 14.01 |
| ATOM | 616 | CG1 | VAL | C | 81 | 78.354 | 32.825 | −3.456 | 1.00 | 15.95 |
| ATOM | 617 | CG2 | VAL | C | 81 | 76.706 | 34.650 | −3.234 | 1.00 | 15.67 |
| ATOM | 618 | N | GLY | C | 82 | 78.740 | 31.543 | −0.346 | 1.00 | 14.65 |
| ATOM | 619 | CA | GLY | C | 82 | 79.809 | 30.766 | 0.200 | 1.00 | 14.30 |
| ATOM | 620 | C | GLY | C | 82 | 79.558 | 30.358 | 1.673 | 1.00 | 16.91 |
| ATOM | 621 | O | GLY | C | 82 | 80.116 | 29.368 | 2.122 | 1.00 | 15.50 |
| ATOM | 622 | N | ASP | C | 83 | 78.746 | 31.145 | 2.355 | 1.00 | 14.93 |
| ATOM | 623 | CA | ASP | C | 83 | 78.465 | 30.803 | 3.792 | 1.00 | 13.74 |
| ATOM | 624 | C | ASP | C | 83 | 77.699 | 29.490 | 3.879 | 1.00 | 14.63 |
| ATOM | 625 | O | ASP | C | 83 | 76.858 | 29.163 | 3.011 | 1.00 | 15.91 |
| ATOM | 626 | CB | ASP | C | 83 | 77.586 | 31.900 | 4.467 | 1.00 | 13.28 |
| ATOM | 627 | CG | ASP | C | 83 | 78.339 | 33.192 | 4.782 | 1.00 | 12.11 |
| ATOM | 628 | OD1 | ASP | C | 83 | 79.600 | 33.269 | 4.679 | 1.00 | 15.32 |
| ATOM | 629 | OD2 | ASP | C | 83 | 77.591 | 34.161 | 5.119 | 1.00 | 15.76 |
| ATOM | 630 | N | ILE | C | 84 | 77.970 | 28.743 | 4.968 | 1.00 | 14.29 |
| ATOM | 631 | CA | ILE | C | 84 | 77.296 | 27.473 | 5.239 | 1.00 | 13.65 |
| ATOM | 632 | C | ILE | C | 84 | 76.184 | 27.799 | 6.282 | 1.00 | 13.60 |
| ATOM | 633 | O | ILE | C | 84 | 76.469 | 28.474 | 7.272 | 1.00 | 15.62 |
| ATOM | 634 | CB | ILE | C | 84 | 78.287 | 26.496 | 5.913 | 1.00 | 16.83 |
| ATOM | 635 | CG1 | ILE | C | 84 | 79.463 | 26.115 | 4.939 | 1.00 | 17.52 |
| ATOM | 636 | CG2 | ILE | C | 84 | 77.560 | 25.231 | 6.346 | 1.00 | 19.25 |
| ATOM | 637 | CD1 | ILE | C | 84 | 78.981 | 25.389 | 3.679 | 1.00 | 21.07 |
| ATOM | 638 | N | VAL | C | 85 | 74.976 | 27.392 | 6.001 | 1.00 | 12.41 |
| ATOM | 639 | CA | VAL | C | 85 | 73.864 | 27.713 | 6.910 | 1.00 | 12.94 |
| ATOM | 640 | C | VAL | C | 85 | 72.991 | 26.532 | 7.153 | 1.00 | 15.89 |
| ATOM | 641 | O | VAL | C | 85 | 73.039 | 25.474 | 6.469 | 1.00 | 14.01 |
| ATOM | 642 | CB | VAL | C | 85 | 72.979 | 28.838 | 6.312 | 1.00 | 14.37 |
| ATOM | 643 | CG1 | VAL | C | 85 | 73.501 | 30.088 | 5.901 | 1.00 | 13.95 |
| ATOM | 644 | CG2 | VAL | C | 85 | 72.180 | 28.356 | 5.045 | 1.00 | 14.77 |
| ATOM | 645 | N | ILE | C | 86 | 72.116 | 26.676 | 8.178 | 1.00 | 13.28 |
| ATOM | 646 | CA | ILE | C | 86 | 71.158 | 25.631 | 8.523 | 1.00 | 13.39 |

-continued

| | | | | | | | | | |
|---|---|---|---|---|---|---|---|---|---|
| ATOM | 647 | C | ILE | C | 86 | 69.809 | 26.347 | 8.420 | 1.00 | 14.02 |
| ATOM | 648 | O | ILE | C | 86 | 69.643 | 27.39 | 8.961 | 1.00 | 13.98 |
| ATOM | 649 | CB | ILE | C | 86 | 71.391 | 25.081 | 9.985 | 1.00 | 13.99 |
| ATOM | 650 | CG1 | ILE | C | 86 | 72.703 | 24.242 | 10.022 | 1.00 | 17.59 |
| ATOM | 651 | CG2 | ILE | C | 86 | 70.181 | 24.220 | 10.367 | 1.00 | 15.22 |
| ATOM | 652 | CD1 | ILE | C | 86 | 73.325 | 24.108 | 11.423 | 1.00 | 22.03 |
| ATOM | 653 | N | ILE | C | 87 | 68.861 | 25.804 | 7.637 | 1.00 | 12.05 |
| ATOM | 654 | CA | ILE | C | 87 | 67.560 | 26.410 | 7.449 | 1.00 | 11.27 |
| ATOM | 655 | C | ILE | C | 87 | 66.521 | 25.488 | 8.056 | 1.00 | 12.08 |
| ATOM | 656 | O | ILE | C | 87 | 66.411 | 24.300 | 7.711 | 1.00 | 13.19 |
| ATOM | 657 | CB | ILE | C | 87 | 67.259 | 26.629 | 5.881 | 1.00 | 12.91 |
| ATOM | 658 | CG1 | ILE | C | 87 | 68.381 | 27.458 | 5.331 | 1.00 | 14.33 |
| ATOM | 659 | CG2 | ILE | C | 87 | 65.903 | 27.272 | 5.724 | 1.00 | 14.68 |
| ATOM | 660 | CD1 | ILE | C | 87 | 68.240 | 27.670 | 3.726 | 1.00 | 14.91 |
| ATOM | 661 | N | ALA | C | 88 | 65.718 | 26.045 | 9.004 | 1.00 | 11.17 |
| ATOM | 662 | CA | ALA | C | 88 | 64.724 | 25.224 | 9.662 | 1.00 | 11.51 |
| ATOM | 663 | C | ALA | C | 88 | 63.339 | 25.757 | 9.674 | 1.00 | 11.06 |
| ATOM | 664 | O | ALA | C | 88 | 63.146 | 26.990 | 9.596 | 1.00 | 12.85 |
| ATOM | 665 | CB | ALA | C | 88 | 65.208 | 25.134 | 11.204 | 1.00 | 12.18 |
| ATOM | 666 | N | SER | C | 89 | 62.321 | 24.892 | 9.833 | 1.00 | 11.32 |
| ATOM | 667 | CA | SER | C | 89 | 60.945 | 25.386 | 10.017 | 1.00 | 11.17 |
| ATOM | 668 | C | SER | C | 89 | 60.407 | 24.644 | 11.248 | 1.00 | 11.44 |
| ATOM | 669 | O | SER | C | 89 | 60.891 | 23.539 | 11.573 | 1.00 | 11.04 |
| ATOM | 670 | CB | SER | C | 89 | 59.986 | 25.246 | 8.807 | 1.00 | 14.68 |
| ATOM | 671 | OG | SER | C | 89 | 59.409 | 23.939 | 8.749 | 1.00 | 13.56 |
| ATOM | 672 | N | PHE | C | 90 | 59.489 | 25.340 | 11.926 | 1.00 | 11.58 |
| ATOM | 673 | CA | PHE | C | 90 | 58.878 | 24.772 | 13.154 | 1.00 | 10.03 |
| ATOM | 674 | C | PHE | C | 90 | 57.391 | 24.743 | 13.006 | 1.00 | 11.41 |
| ATOM | 675 | O | PHE | C | 90 | 56.780 | 25.662 | 12.350 | 1.00 | 12.95 |
| ATOM | 676 | CB | PHE | C | 90 | 59.257 | 25.677 | 14.348 | 1.00 | 10.86 |
| ATOM | 677 | CG | PHE | C | 90 | 60.681 | 25.536 | 14.776 | 1.00 | 11.25 |
| ATOM | 678 | CD1 | PHE | C | 90 | 61.724 | 26.266 | 14.169 | 1.00 | 12.54 |
| ATOM | 679 | CD2 | PHE | C | 90 | 61.016 | 24.612 | 15.810 | 1.00 | 13.88 |
| ATOM | 680 | CE1 | PHE | C | 90 | 63.094 | 26.079 | 14.613 | 1.00 | 12.35 |
| ATOM | 681 | CE2 | PHE | C | 90 | 62.289 | 24.431 | 16.247 | 1.00 | 13.61 |
| ATOM | 682 | CZ | PHE | C | 90 | 63.373 | 25.138 | 15.672 | 1.00 | 12.98 |
| ATOM | 683 | N | VAL | C | 91 | 56.768 | 23.720 | 13.608 | 1.00 | 9.83 |
| ATOM | 684 | CA | VAL | C | 91 | 55.315 | 23.572 | 13.573 | 1.00 | 10.22 |
| ATOM | 685 | C | VAL | C | 91 | 54.795 | 23.312 | 14.993 | 1.00 | 14.03 |
| ATOM | 686 | O | VAL | C | 91 | 55.606 | 22.962 | 15.893 | 1.00 | 13.50 |
| ATOM | 687 | CB | VAL | C | 91 | 54.804 | 22.401 | 12.688 | 1.00 | 13.62 |
| ATOM | 688 | CG1 | VAL | C | 91 | 55.015 | 22.757 | 11.190 | 1.00 | 15.08 |
| ATOM | 689 | CG2 | VAL | C | 91 | 55.481 | 21.082 | 13.064 | 1.00 | 13.05 |
| ATOM | 690 | N | THR | C | 92 | 53.528 | 23.542 | 15.175 | 1.00 | 12.76 |
| ATOM | 691 | CA | THR | C | 92 | 52.916 | 23.289 | 16.511 | 1.00 | 11.56 |
| ATOM | 692 | C | THR | C | 92 | 51.985 | 22.099 | 16.437 | 1.00 | 13.31 |
| ATOM | 693 | O | THR | C | 92 | 51.347 | 21.772 | 15.395 | 1.00 | 13.08 |
| ATOM | 694 | CB | THR | C | 92 | 52.237 | 24.503 | 17.160 | 1.00 | 12.64 |
| ATOM | 695 | OG1 | THR | C | 92 | 51.102 | 24.918 | 16.359 | 1.00 | 16.06 |
| ATOM | 696 | CG2 | THR | C | 92 | 53.186 | 25.697 | 17.314 | 1.00 | 13.80 |
| ATOM | 697 | N | MET | C | 93 | 51.881 | 21.327 | 17.562 | 1.00 | 11.69 |
| ATOM | 698 | CA | MET | C | 93 | 51.013 | 20.142 | 17.639 | 1.00 | 11.35 |
| ATOM | 699 | C | MET | C | 93 | 50.872 | 19.828 | 19.145 | 1.00 | 14.45 |
| ATOM | 700 | O | MET | C | 93 | 51.654 | 20.324 | 19.951 | 1.00 | 13.44 |
| ATOM | 701 | CB | MET | C | 93 | 51.697 | 18.907 | 16.955 | 1.00 | 12.85 |
| ATOM | 702 | CG | MET | C | 93 | 53.062 | 18.586 | 17.608 | 1.00 | 13.91 |
| ATOM | 703 | SD | MET | C | 93 | 54.059 | 17.382 | 16.687 | 1.00 | 14.46 |
| ATOM | 704 | CE | MET | C | 93 | 54.523 | 18.473 | 15.286 | 1.00 | 14.10 |
| ATOM | 705 | N | PRO | C | 94 | 49.873 | 19.055 | 19.455 | 1.00 | 12.36 |
| ATOM | 706 | CA | PRO | C | 94 | 49.648 | 18.670 | 20.865 | 1.00 | 12.35 |
| ATOM | 707 | C | PRO | C | 94 | 50.877 | 17.883 | 21.402 | 1.00 | 15.66 |
| ATOM | 708 | O | PRO | C | 94 | 51.630 | 17.195 | 20.717 | 1.00 | 14.35 |
| ATOM | 709 | CB | PRO | C | 94 | 48.504 | 17.712 | 20.781 | 1.00 | 13.86 |
| ATOM | 710 | CG | PRO | C | 94 | 47.676 | 18.206 | 19.582 | 1.00 | 15.72 |
| ATOM | 711 | CD | PRO | C | 94 | 48.832 | 18.461 | 18.595 | 1.00 | 12.82 |
| ATOM | 712 | N | ASP | C | 95 | 51.023 | 17.929 | 22.751 | 1.00 | 14.03 |
| ATOM | 713 | CA | ASP | C | 95 | 52.125 | 17.208 | 23.352 | 1.00 | 15.39 |
| ATOM | 714 | C | ASP | C | 95 | 52.288 | 15.721 | 22.997 | 1.00 | 16.06 |
| ATOM | 715 | O | ASP | C | 95 | 53.415 | 15.216 | 22.827 | 1.00 | 16.29 |
| ATOM | 716 | CB | ASP | C | 95 | 51.982 | 17.327 | 24.883 | 1.00 | 15.44 |
| ATOM | 717 | CG | ASP | C | 95 | 53.209 | 16.791 | 25.618 | 1.00 | 15.85 |
| ATOM | 718 | OD1 | ASP | C | 95 | 54.314 | 17.367 | 25.497 | 1.00 | 14.33 |
| ATOM | 719 | OD2 | ASP | C | 95 | 53.073 | 15.750 | 26.345 | 1.00 | 18.70 |
| ATOM | 720 | N | GLU | C | 96 | 51.181 | 14.987 | 22.922 | 1.00 | 15.70 |
| ATOM | 721 | CA | GLU | C | 96 | 51.283 | 13.563 | 22.604 | 1.00 | 14.32 |
| ATOM | 722 | C | GLU | C | 96 | 51.905 | 13.295 | 21.236 | 1.00 | 18.35 |
| ATOM | 723 | O | GLU | C | 96 | 52.794 | 12.468 | 21.100 | 1.00 | 17.78 |

-continued

Data Lists

| | | | | | | | | | |
|---|---|---|---|---|---|---|---|---|---|
| ATOM | 724 | CB | GLU | C | 96 | 49.944 | 12.850 | 22.791 | 1.00 | 16.31 |
| ATOM | 725 | CG | GLU | C | 96 | 50.012 | 11.377 | 22.421 | 1.00 | 22.63 |
| ATOM | 726 | CD | GLU | C | 96 | 48.701 | 10.594 | 22.718 | 1.00 | 23.98 |
| ATOM | 727 | OE1 | GLU | C | 96 | 47.699 | 11.210 | 23.080 | 1.00 | 25.84 |
| ATOM | 728 | OE2 | GLU | C | 96 | 48.703 | 9.363 | 22.540 | 1.00 | 30.53 |
| ATOM | 729 | N | GLU | C | 97 | 51.419 | 14.032 | 20.241 | 1.00 | 15.16 |
| ATOM | 730 | CA | GLU | C | 97 | 52.004 | 13.852 | 18.911 | 1.00 | 15.52 |
| ATOM | 731 | C | GLU | C | 97 | 53.491 | 14.296 | 18.936 | 1.00 | 13.99 |
| ATOM | 732 | O | GLU | C | 97 | 54.332 | 13.695 | 18.293 | 1.00 | 16.67 |
| ATOM | 733 | CB | GLU | C | 97 | 51.202 | 14.706 | 17.929 | 1.00 | 15.35 |
| ATOM | 734 | CG | GLU | C | 97 | 51.780 | 14.636 | 16.496 | 1.00 | 17.59 |
| ATOM | 735 | CD | GLU | C | 97 | 50.924 | 15.416 | 15.525 | 1.00 | 22.36 |
| ATOM | 736 | OE1 | GLU | C | 97 | 43.940 | 16.082 | 15.936 | 1.00 | 17.71 |
| ATOM | 737 | OE2 | GLU | C | 97 | 51.268 | 15.305 | 14.305 | 1.00 | 22.62 |
| ATOM | 738 | N | ALA | C | 98 | 53.816 | 15.379 | 19.663 | 1.00 | 13.03 |
| ATOM | 739 | CA | ALA | C | 98 | 55.185 | 15.883 | 19.750 | 1.00 | 12.71 |
| ATOM | 740 | C | ALA | C | 98 | 56.174 | 14.859 | 20.323 | 1.00 | 15.63 |
| ATOM | 741 | O | ALA | C | 98 | 57.339 | 14.809 | 19.952 | 1.00 | 14.36 |
| ATOM | 742 | CB | ALA | C | 98 | 55.199 | 17.161 | 20.596 | 1.00 | 14.85 |
| ATOM | 743 | N | ARG | C | 99 | 55.689 | 13.987 | 21.252 | 1.00 | 14.05 |
| ATOM | 744 | CA | ARG | C | 99 | 56.579 | 13.018 | 21.842 | 1.00 | 15.96 |
| ATOM | 745 | C | ARG | C | 99 | 57.090 | 11.936 | 20.924 | 1.00 | 17.44 |
| ATOM | 746 | O | ARG | C | 99 | 58.103 | 11.307 | 21.251 | 1.00 | 21.21 |
| ATOM | 747 | CB | ARG | C | 99 | 55.968 | 12.422 | 23.153 | 1.00 | 17.37 |
| ATOM | 748 | CG | ARG | C | 99 | 55.949 | 13.457 | 24.271 | 1.00 | 16.32 |
| ATOM | 749 | CD | ARG | C | 99 | 55.383 | 12.905 | 25.632 | 1.00 | 16.45 |
| ATOM | 750 | NE | ARG | C | 99 | 53.933 | 12.912 | 25.712 | 1.00 | 14.75 |
| ATOM | 751 | CZ | ARG | C | 99 | 53.157 | 11.860 | 25.584 | 1.00 | 13.61 |
| ATOM | 752 | NH1 | ARG | C | 99 | 53.688 | 10.668 | 25.371 | 1.00 | 16.09 |
| ATOM | 753 | NH2 | ARG | C | 99 | 51.846 | 11.988 | 25.703 | 1.00 | 18.40 |
| ATOM | 754 | N | THR | C | 100 | 56.438 | 11.713 | 19.788 | 1.00 | 16.42 |
| ATOM | 755 | CA | THR | C | 100 | 56.970 | 10.700 | 18.869 | 1.00 | 16.33 |
| ATOM | 756 | C | THR | C | 100 | 57.108 | 11.310 | 17.469 | 1.00 | 19.97 |
| ATOM | 757 | O | THR | C | 100 | 57.162 | 10.569 | 16.457 | 1.00 | 20.03 |
| ATOM | 758 | CB | THR | C | 100 | 56.147 | 9.435 | 18.772 | 1.00 | 21.91 |
| ATOM | 759 | OG1 | THR | C | 100 | 54.764 | 9.744 | 18.520 | 1.00 | 20.66 |
| ATOM | 760 | CG2 | THR | C | 100 | 56.224 | 8.675 | 20.128 | 1.00 | 22.68 |
| ATOM | 761 | N | TRP | C | 101 | 57.180 | 12.634 | 17.437 | 1.00 | 17.87 |
| ATOM | 762 | CA | TRP | C | 101 | 57.321 | 13.322 | 16.115 | 1.00 | 16.71 |
| ATOM | 763 | C | TRP | C | 101 | 58.708 | 13.111 | 15.528 | 1.00 | 19.04 |
| ATOM | 764 | O | TRP | C | 101 | 59.710 | 13.152 | 16.246 | 1.00 | 17.05 |
| ATOM | 765 | CB | TRP | C | 101 | 57.100 | 14.825 | 16.331 | 1.00 | 14.65 |
| ATOM | 766 | CG | TRP | C | 101 | 57.469 | 15.675 | 15.092 | 1.00 | 14.16 |
| ATOM | 767 | CD1 | TRP | C | 101 | 58.521 | 16.473 | 14.986 | 1.00 | 16.31 |
| ATOM | 768 | CD2 | TRP | C | 101 | 56.693 | 15.803 | 13.887 | 1.00 | 16.31 |
| ATOM | 769 | NE1 | TRP | C | 101 | 58.514 | 17.103 | 13.701 | 1.00 | 15.49 |
| ATOM | 770 | CE2 | TRP | C | 101 | 57.398 | 16.686 | 13.043 | 1.00 | 17.23 |
| ATOM | 771 | CE3 | TRP | C | 101 | 55.500 | 15.234 | 13.424 | 1.00 | 19.60 |
| ATOM | 772 | CZ2 | TRP | C | 101 | 56.935 | 17.023 | 11.749 | 1.00 | 18.02 |
| ATOM | 773 | CZ3 | TRP | C | 101 | 55.020 | 15.590 | 12.147 | 1.00 | 21.23 |
| ATOM | 774 | CH2 | TRP | C | 101 | 55.747 | 16.467 | 11.343 | 1.00 | 21.41 |
| ATOM | 775 | N | ARG | C | 102 | 58.788 | 12.895 | 14.174 | 1.00 | 15.76 |
| ATOM | 776 | CA | ARG | C | 102 | 60.114 | 12.715 | 13.551 | 1.00 | 16.64 |
| ATOM | 777 | C | ARG | C | 102 | 60.358 | 13.856 | 12.511 | 1.00 | 14.79 |
| ATOM | 778 | O | ARG | C | 102 | 59.671 | 13.858 | 11.470 | 1.00 | 17.03 |
| ATOM | 779 | CB | ARG | C | 102 | 60.181 | 11.375 | 12.823 | 1.00 | 17.42 |
| ATOM | 780 | CG | ARG | C | 102 | 59.934 | 10.169 | 13.728 | 1.00 | 24.67 |
| ATOM | 781 | CD | ARG | C | 102 | 60.918 | 10.190 | 14.864 | 1.00 | 40.94 |
| ATOM | 782 | NE | ARG | C | 102 | 60.647 | 9.111 | 15.815 | 1.00 | 58.76 |
| ATOM | 783 | CZ | ARG | C | 102 | 60.403 | 9.287 | 17.118 | 1.00 | 65.94 |
| ATOM | 784 | NH1 | ARG | C | 102 | 60.393 | 10.518 | 17.651 | 1.00 | 46.00 |
| ATOM | 785 | NH2 | ARG | C | 102 | 60.162 | 8.231 | 17.890 | 1.00 | 52.57 |
| ATOM | 786 | N | PRO | C | 103 | 61.262 | 14.768 | 12.787 | 1.00 | 15.12 |
| ATOM | 787 | CA | PRO | C | 103 | 61.499 | 15.893 | 11.838 | 1.00 | 13.53 |
| ATOM | 788 | C | PRO | C | 103 | 62.051 | 15.360 | 10.512 | 1.00 | 15.29 |
| ATOM | 789 | O | PRO | C | 103 | 62.678 | 14.328 | 10.477 | 1.00 | 16.02 |
| ATOM | 790 | CB | PRO | C | 103 | 62.536 | 16.744 | 12.516 | 1.00 | 14.34 |
| ATOM | 791 | CG | PRO | C | 103 | 62.357 | 16.404 | 14.069 | 1.00 | 18.46 |
| ATOM | 792 | CD | PRO | C | 103 | 62.024 | 14.929 | 14.038 | 1.00 | 15.59 |
| ATOM | 793 | N | ASN | C | 104 | 61.797 | 16.147 | 9.439 | 1.00 | 14.28 |
| ATOM | 794 | CA | ASN | C | 104 | 62.283 | 15.811 | 8.088 | 1.00 | 13.04 |
| ATOM | 795 | C | ASN | C | 104 | 63.643 | 16.508 | 7.924 | 1.00 | 14.43 |
| ATOM | 796 | O | ASN | C | 104 | 63.701 | 17.742 | 7.661 | 1.00 | 13.98 |
| ATOM | 797 | CB | ASN | C | 104 | 61.242 | 16.325 | 7.131 | 1.00 | 12.98 |
| ATOM | 798 | CG | ASN | C | 104 | 59.954 | 15.602 | 7.276 | 1.00 | 15.09 |
| ATOM | 799 | OD1 | ASN | C | 104 | 59.914 | 14.364 | 7.131 | 1.00 | 17.92 |
| ATOM | 800 | ND2 | ASN | C | 104 | 58.886 | 16.310 | 7.628 | 1.00 | 16.93 |

-continued

Data Lists

| | | | | | | | | | |
|---|---|---|---|---|---|---|---|---|---|
| ATOM | 801 | N | VAL | C | 105 | 64.733 | 15.763 | 8.113 | 1.00 | 14.40 |
| ATOM | 802 | CA | VAL | C | 105 | 66.051 | 16.308 | 8.052 | 1.00 | 15.19 |
| ATOM | 803 | C | VAL | C | 105 | 66.791 | 15.897 | 6.794 | 1.00 | 18.79 |
| ATOM | 804 | O | VAL | C | 105 | 66.870 | 14.705 | 6.477 | 1.00 | 20.46 |
| ATOM | 805 | CB | VAL | C | 105 | 66.898 | 15.862 | 9.252 | 1.00 | 18.28 |
| ATOM | 806 | CG1 | VAL | C | 105 | 68.294 | 16.482 | 9.195 | 1.00 | 20.67 |
| ATOM | 807 | CG2 | VAL | C | 105 | 66.189 | 16.312 | 10.600 | 1.00 | 17.51 |
| ATOM | 808 | N | ALA | C | 106 | 67.321 | 16.899 | 6.103 | 1.00 | 16.66 |
| ATOM | 809 | CA | ALA | C | 106 | 68.130 | 16.617 | 4.865 | 1.00 | 16.75 |
| ATOM | 810 | C | ALA | C | 106 | 69.506 | 17.196 | 5.121 | 1.00 | 15.84 |
| ATOM | 811 | O | ALA | C | 106 | 69.621 | 18.358 | 5.520 | 1.00 | 16.27 |
| ATOM | 812 | CB | ALA | C | 106 | 67.469 | 17.246 | 3.645 | 1.00 | 17.32 |
| ATOM | 813 | N | TYR | C | 107 | 70.558 | 16.390 | 4.881 | 1.00 | 15.99 |
| ATOM | 814 | CA | TYR | C | 107 | 71.941 | 16.745 | 5.089 | 1.00 | 15.93 |
| ATOM | 815 | C | TYR | C | 107 | 72.620 | 17.003 | 3.740 | 1.00 | 18.71 |
| ATOM | 816 | O | TYR | C | 107 | 72.346 | 16.296 | 2.779 | 1.00 | 20.84 |
| ATOM | 817 | CB | TYR | C | 107 | 72.714 | 15.637 | 5.835 | 1.00 | 19.26 |
| ATOM | 818 | CG | TYR | C | 107 | 72.177 | 15.391 | 7.253 | 1.00 | 21.14 |
| ATOM | 819 | CD1 | TYR | C | 107 | 72.619 | 16.143 | 8.296 | 1.00 | 21.91 |
| ATOM | 820 | CD2 | TYR | C | 107 | 71.259 | 14.405 | 7.479 | 1.00 | 23.16 |
| ATOM | 821 | CE1 | TYR | C | 107 | 72.125 | 15.931 | 9.596 | 1.00 | 24.59 |
| ATOM | 822 | CE2 | TYR | C | 107 | 70.758 | 14.193 | 8.779 | 1.00 | 24.09 |
| ATOM | 823 | CZ | TYR | C | 107 | 71.220 | 14.964 | 9.794 | 1.00 | 27.50 |
| ATOM | 824 | OH | TYR | C | 107 | 70.760 | 14.801 | 11.101 | 1.00 | 29.66 |
| ATOM | 825 | N | PHE | C | 108 | 73.461 | 18.022 | 3.744 | 1.00 | 15.42 |
| ATOM | 826 | CA | PHE | C | 108 | 74.165 | 18.434 | 2.489 | 1.00 | 15.71 |
| ATOM | 827 | C | PHE | C | 108 | 75.646 | 18.525 | 2.624 | 1.00 | 19.91 |
| ATOM | 828 | O | PHE | C | 108 | 76.239 | 18.645 | 3.715 | 1.00 | 19.12 |
| ATOM | 829 | CB | PHE | C | 108 | 73.644 | 19.803 | 2.063 | 1.00 | 16.87 |
| ATOM | 830 | CG | PHE | C | 108 | 72.225 | 19.796 | 1.661 | 1.00 | 16.76 |
| ATOM | 831 | CD1 | PHE | C | 108 | 71.195 | 19.910 | 2.626 | 1.00 | 17.17 |
| ATOM | 832 | CD2 | PHE | C | 108 | 71.832 | 19.656 | 0.305 | 1.00 | 17.45 |
| ATOM | 833 | CE1 | PHE | C | 108 | 69.873 | 19.871 | 2.240 | 1.00 | 19.62 |
| ATOM | 834 | CE2 | PHE | C | 108 | 70.497 | 19.620 | −0.081 | 1.00 | 20.41 |
| ATOM | 835 | CZ | PHE | C | 108 | 69.480 | 19.741 | 0.885 | 1.00 | 19.54 |
| ATOM | 836 | N | GLU | C | 109 | 76.311 | 18.516 | 1.444 | 1.00 | 17.02 |
| ATOM | 837 | CA | GLU | C | 109 | 77.762 | 18.671 | 1.404 | 1.00 | 17.21 |
| ATOM | 838 | C | GLU | C | 109 | 78.099 | 19.064 | −0.072 | 1.00 | 15.89 |
| ATOM | 839 | O | GLU | C | 109 | 77.219 | 18.996 | −0.910 | 1.00 | 16.10 |
| ATOM | 840 | CB | GLU | C | 109 | 78.483 | 17.338 | 1.695 | 1.00 | 18.77 |
| ATOM | 841 | CG | GLU | C | 109 | 78.226 | 16.303 | 0.620 | 1.00 | 19.64 |
| ATOM | 842 | CD | GLU | C | 109 | 78.915 | 14.936 | 0.838 | 1.00 | 21.63 |
| ATOM | 843 | OE1 | GLU | C | 109 | 79.866 | 14.811 | 1.621 | 1.00 | 24.76 |
| ATOM | 844 | OE2 | GLU | C | 109 | 78.472 | 13.999 | 0.170 | 1.00 | 28.24 |
| ATOM | 845 | N | GLY | C | 110 | 79.348 | 19.435 | −0.277 | 1.00 | 15.85 |
| ATOM | 846 | CA | GLY | C | 110 | 79.829 | 19.789 | −1.680 | 1.00 | 17.20 |
| ATOM | 847 | C | GLY | C | 110 | 78.950 | 20.810 | −2.378 | 1.00 | 16.93 |
| ATOM | 848 | O | GLY | C | 110 | 78.634 | 21.885 | −1.812 | 1.00 | 16.26 |
| ATOM | 849 | N | ASP | C | 111 | 78.534 | 20.528 | −3.637 | 1.00 | 14.38 |
| ATOM | 850 | CA | ASP | C | 111 | 77.715 | 21.472 | −4.391 | 1.00 | 14.84 |
| ATOM | 851 | C | ASP | C | 111 | 76.244 | 21.321 | −4.079 | 1.00 | 14.72 |
| ATOM | 852 | O | ASP | C | 111 | 75.360 | 21.023 | −4.904 | 1.00 | 14.34 |
| ATOM | 853 | CB | ASP | C | 111 | 77.999 | 21.194 | −5.903 | 1.00 | 17.05 |
| ATOM | 854 | CG | ASP | C | 111 | 77.264 | 22.145 | −6.828 | 1.00 | 19.59 |
| ATOM | 855 | OD1 | ASP | C | 111 | 77.013 | 23.323 | −6.491 | 1.00 | 20.52 |
| ATOM | 856 | OD2 | ASP | C | 111 | 76.873 | 21.686 | −7.928 | 1.00 | 19.81 |
| ATOM | 857 | N | ASN | C | 112 | 75.927 | 21.537 | −2.787 | 1.00 | 14.68 |
| ATOM | 858 | CA | ASN | C | 112 | 74.503 | 21.373 | −2.371 | 1.00 | 16.14 |
| ATOM | 859 | C | ASN | C | 112 | 73.952 | 19.992 | −2.783 | 1.00 | 13.02 |
| ATOM | 860 | O | ASN | C | 112 | 72.799 | 19.870 | −3.263 | 1.00 | 14.89 |
| ATOM | 861 | CB | ASN | C | 112 | 73.566 | 22.559 | −2.717 | 1.00 | 16.17 |
| ATOM | 862 | CG | ASN | C | 112 | 73.880 | 23.786 | −1.870 | 1.00 | 18.78 |
| ATOM | 863 | OD1 | ASN | C | 112 | 74.533 | 23.641 | −0.819 | 1.00 | 17.25 |
| ATOM | 864 | ND2 | ASN | C | 112 | 73.429 | 24.960 | −2.293 | 1.00 | 15.61 |
| ATOM | 865 | N | GLU | C | 113 | 74.785 | 18.960 | −2.531 | 1.00 | 14.05 |
| ATOM | 866 | CA | GLU | C | 113 | 74.443 | 17.571 | −2.819 | 1.00 | 15.74 |
| ATOM | 867 | C | GLU | C | 113 | 73.805 | 16.971 | −1.563 | 1.00 | 18.95 |
| ATOM | 868 | O | GLU | C | 113 | 74.464 | 16.870 | −0.539 | 1.00 | 19.58 |
| ATOM | 869 | CB | GLU | C | 113 | 75.708 | 16.797 | −3.166 | 1.00 | 17.38 |
| ATOM | 870 | CG | GLU | C | 113 | 75.440 | 15.371 | −3.668 | 1.00 | 20.91 |
| ATOM | 871 | CD | GLU | C | 113 | 74.661 | 15.313 | −5.016 | 1.00 | 24.09 |
| ATOM | 872 | OE1 | GLU | C | 113 | 75.023 | 15.987 | −5.993 | 1.00 | 30.10 |
| ATOM | 873 | OE2 | GLU | C | 113 | 73.680 | 14.559 | −5.076 | 1.00 | 36.71 |
| ATOM | 874 | N | MET | C | 114 | 72.556 | 16.563 | −1.684 | 1.00 | 18.64 |
| ATOM | 875 | CA | MET | C | 114 | 71.826 | 15.984 | −0.519 | 1.00 | 20.88 |
| ATOM | 876 | C | MET | C | 114 | 72.331 | 14.600 | −0.242 | 1.00 | 27.67 |
| ATOM | 877 | O | MET | C | 114 | 72.346 | 13.758 | −1.144 | 1.00 | 27.90 |

-continued

Data Lists

| | | | | | | | | | |
|---|---|---|---|---|---|---|---|---|---|
| ATOM | 878 | CB | MET | C | 114 | 70.329 | 15.964 | −0.798 | 1.00 | 23.89 |
| ATOM | 879 | CG | MET | C | 114 | 69.486 | 15.506 | 0.441 | 1.00 | 26.69 |
| ATOM | 880 | SD | MET | C | 114 | 67.734 | 15.561 | 0.136 | 1.00 | 29.33 |
| ATOM | 881 | CE | MET | C | 114 | 67.568 | 17.266 | −0.315 | 1.00 | 23.75 |
| ATOM | 882 | N | LYS | C | 115 | 72.758 | 14.329 | 0.997 | 1.00 | 25.26 |
| ATOM | 883 | CA | LYS | C | 115 | 73.254 | 12.995 | 1.346 | 1.00 | 30.27 |
| ATOM | 884 | C | LYS | C | 115 | 72.131 | 11.966 | 1.381 | 1.00 | 36.08 |
| ATOM | 885 | O | LYS | C | 115 | 72.449 | 10.760 | 1.181 | 1.00 | 41.29 |
| ATOM | 886 | CB | LYS | C | 115 | 74.009 | 12.984 | 2.674 | 1.00 | 31.52 |
| ATOM | 887 | CG | LYS | C | 115 | 75.147 | 13.960 | 2.791 | 1.00 | 29.39 |
| ATOM | 888 | CD | LYS | C | 115 | 75.948 | 13.688 | 4.076 | 1.00 | 35.11 |
| ATOM | 889 | CE | LYS | C | 115 | 76.864 | 14.835 | 4.435 | 1.00 | 39.16 |
| ATOM | 890 | NZ | LYS | C | 115 | 77.861 | 14.448 | 5.498 | 1.00 | 41.83 |
| ATOM | 892 | N | MET | D | 1 | 41.087 | 33.198 | 23.825 | 1.00 | 17.87 |
| ATOM | 893 | CA | MET | D | 1 | 42.349 | 33.385 | 23.112 | 1.00 | 15.77 |
| ATOM | 894 | C | MET | D | 1 | 43.435 | 32.503 | 23.658 | 1.00 | 18.38 |
| ATOM | 895 | O | MET | D | 1 | 43.248 | 31.921 | 24.772 | 1.00 | 16.03 |
| ATOM | 896 | CB | MET | D | 1 | 42.724 | 34.805 | 22.826 | 1.00 | 18.15 |
| ATOM | 897 | CG | MET | D | 1 | 42.641 | 35.784 | 23.928 | 1.00 | 21.69 |
| ATOM | 898 | SD | MET | D | 1 | 43.800 | 35.292 | 25.234 | 1.00 | 24.50 |
| ATOM | 899 | CE | MET | D | 1 | 43.405 | 36.711 | 26.530 | 1.00 | 19.90 |
| ATOM | 900 | N | ILE | D | 2 | 44.516 | 32.347 | 22.912 | 1.00 | 13.90 |
| ATOM | 901 | CA | ILE | D | 2 | 45.595 | 31.431 | 23.276 | 1.00 | 12.73 |
| ATOM | 902 | C | ILE | D | 2 | 46.834 | 32.154 | 23.717 | 1.00 | 15.11 |
| ATOM | 903 | O | ILE | D | 2 | 47.335 | 33.086 | 23.088 | 1.00 | 13.08 |
| ATOM | 904 | CB | ILE | D | 2 | 45.916 | 30.531 | 22.029 | 1.00 | 12.91 |
| ATOM | 905 | CG1 | ILE | D | 2 | 44.663 | 29.775 | 21.519 | 1.00 | 14.95 |
| ATOM | 906 | CG2 | ILE | D | 2 | 47.077 | 29.650 | 22.239 | 1.00 | 13.31 |
| ATOM | 907 | CD1 | ILE | D | 2 | 44.172 | 28.701 | 22.510 | 1.00 | 19.87 |
| ATOM | 908 | N | ARG | D | 3 | 47.332 | 31.720 | 24.876 | 1.00 | 11.64 |
| ATOM | 909 | CA | ARG | D | 3 | 48.516 | 32.296 | 25.459 | 1.00 | 9.38 |
| ATOM | 910 | C | ARG | D | 3 | 49.789 | 31.470 | 25.262 | 1.00 | 8.16 |
| ATOM | 911 | O | ARG | D | 3 | 49.708 | 30.234 | 25.113 | 1.00 | 9.82 |
| ATOM | 912 | CB | ARG | D | 3 | 48.295 | 32.255 | 27.026 | 1.00 | 11.91 |
| ATOM | 913 | CG | ARG | D | 3 | 47.131 | 33.118 | 27.499 | 1.00 | 12.07 |
| ATOM | 914 | CD | ARG | D | 3 | 47.529 | 34.571 | 27.783 | 1.00 | 12.41 |
| ATOM | 915 | NE | ARG | D | 3 | 46.447 | 35.256 | 28.452 | 1.00 | 12.53 |
| ATOM | 916 | CZ | ARG | D | 3 | 46.473 | 36.522 | 28.885 | 1.00 | 11.34 |
| ATOM | 917 | NH1 | ARG | D | 3 | 47.517 | 37.336 | 28.661 | 1.00 | 11.49 |
| ATOM | 918 | NH2 | ARG | D | 3 | 45.422 | 36.991 | 29.619 | 1.00 | 11.64 |
| ATOM | 919 | N | THR | D | 4 | 50.948 | 32.149 | 25.285 | 1.00 | 11.35 |
| ATOM | 920 | CA | THR | D | 4 | 52.272 | 31.500 | 25.210 | 1.00 | 10.99 |
| ATOM | 921 | C | THR | D | 4 | 52.813 | 31.593 | 26.693 | 1.00 | 9.80 |
| ATOM | 922 | O | THR | D | 4 | 52.986 | 32.672 | 27.155 | 1.00 | 10.46 |
| ATOM | 923 | CB | THR | D | 4 | 53.199 | 32.217 | 24.279 | 1.00 | 13.30 |
| ATOM | 924 | OG1 | THR | D | 4 | 52.577 | 32.164 | 22.960 | 1.00 | 12.86 |
| ATOM | 925 | CG2 | THR | D | 4 | 54.531 | 31.558 | 24.193 | 1.00 | 11.07 |
| ATOM | 926 | N | MET | D | 5 | 53.090 | 30.427 | 27.261 | 1.00 | 10.61 |
| ATOM | 927 | CA | MET | D | 5 | 53.555 | 30.329 | 28.694 | 1.00 | 10.17 |
| ATOM | 928 | C | MET | D | 5 | 54.837 | 29.563 | 28.799 | 1.00 | 13.79 |
| ATOM | 929 | O | MET | D | 5 | 55.101 | 28.614 | 28.027 | 1.00 | 12.14 |
| ATOM | 930 | CB | MET | D | 5 | 52.484 | 29.509 | 29.395 | 1.00 | 10.85 |
| ATOM | 931 | CG | MET | D | 5 | 51.061 | 30.164 | 29.397 | 1.00 | 13.35 |
| ATOM | 932 | SD | MET | D | 5 | 50.866 | 31.757 | 29.993 | 1.00 | 12.31 |
| ATOM | 933 | CE | MET | D | 5 | 51.031 | 31.458 | 31.862 | 1.00 | 9.06 |
| ATOM | 934 | N | LEU | D | 6 | 55.629 | 29.894 | 29.847 | 1.00 | 11.48 |
| ATOM | 935 | CA | LEU | D | 6 | 56.867 | 29.146 | 30.088 | 1.00 | 11.70 |
| ATOM | 936 | C | LEU | D | 6 | 56.504 | 27.682 | 30.442 | 1.00 | 15.58 |
| ATOM | 937 | O | LEU | D | 6 | 55.730 | 27.429 | 31.410 | 1.00 | 12.84 |
| ATOM | 938 | CB | LEU | D | 6 | 57.607 | 29.780 | 31.270 | 1.00 | 11.07 |
| ATOM | 939 | CG | LEU | D | 6 | 58.862 | 29.016 | 31.645 | 1.00 | 10.79 |
| ATOM | 940 | CD1 | LEU | D | 6 | 60.065 | 29.206 | 30.628 | 1.00 | 12.32 |
| ATOM | 941 | CD2 | LEU | D | 6 | 59.389 | 29.481 | 33.038 | 1.00 | 12.20 |
| ATOM | 942 | N | GLN | D | 7 | 56.980 | 26.693 | 29.671 | 1.00 | 11.50 |
| ATOM | 943 | CA | GLN | D | 7 | 56.694 | 25.319 | 29.932 | 1.00 | 12.08 |
| ATOM | 944 | C | GLN | D | 7 | 57.654 | 24.774 | 31.014 | 1.00 | 13.00 |
| ATOM | 945 | O | GLN | D | 7 | 57.222 | 23.966 | 31.908 | 1.00 | 13.76 |
| ATOM | 946 | CB | GLN | D | 7 | 56.889 | 24.443 | 28.642 | 1.00 | 13.70 |
| ATOM | 947 | CG | GLN | D | 7 | 56.481 | 23.024 | 28.769 | 1.00 | 13.52 |
| ATOM | 948 | CD | GLN | D | 7 | 57.490 | 22.096 | 29.530 | 1.00 | 15.62 |
| ATOM | 949 | OE1 | GLN | D | 7 | 57.020 | 21.129 | 30.233 | 1.00 | 14.96 |
| ATOM | 950 | NE2 | GLN | D | 7 | 58.822 | 22.323 | 29.355 | 1.00 | 13.51 |
| ATOM | 951 | N | GLY | D | 8 | 58.908 | 25.149 | 30.936 | 1.00 | 12.82 |
| ATOM | 952 | CA | GLY | D | 8 | 59.924 | 24.658 | 31.879 | 1.00 | 13.57 |
| ATOM | 953 | C | GLY | D | 8 | 61.276 | 25.264 | 31.576 | 1.00 | 17.33 |
| ATOM | 954 | O | GLY | D | 8 | 61.489 | 25.874 | 30.508 | 1.00 | 16.12 |
| ATOM | 955 | N | LYS | D | 9 | 62.225 | 25.176 | 32.515 | 1.00 | 13.73 |

-continued

Data Lists

| | | | | | | | | | |
|---|---|---|---|---|---|---|---|---|---|
| ATOM | 956 | CA | LYS | D | 9 | 63.535 | 25.722 | 32.269 | 1.00 | 14.09 |
| ATOM | 957 | C | LYS | D | 9 | 64.594 | 25.035 | 33.093 | 1.00 | 17.41 |
| ATOM | 958 | O | LYS | D | 9 | 64.293 | 24.412 | 34.150 | 1.00 | 16.23 |
| ATOM | 959 | CB | LYS | D | 9 | 63.604 | 27.197 | 32.448 | 1.00 | 17.25 |
| ATOM | 960 | CG | LYS | D | 9 | 63.491 | 27.641 | 33.937 | 1.00 | 16.41 |
| ATOM | 961 | CD | LYS | D | 9 | 63.860 | 29.094 | 34.196 | 1.00 | 16.11 |
| ATOM | 962 | CE | LYS | D | 9 | 63.661 | 29.538 | 35.703 | 1.00 | 20.64 |
| ATOM | 963 | NZ | LYS | D | 9 | 64.168 | 30.899 | 36.005 | 1.00 | 24.09 |
| ATOM | 964 | N | LEU | D | 10 | 65.795 | 25.085 | 32.580 | 1.00 | 14.37 |
| ATOM | 965 | CA | LEU | D | 10 | 67.019 | 24.574 | 33.245 | 1.00 | 13.07 |
| ATOM | 966 | C | LEU | D | 10 | 67.683 | 25.889 | 33.669 | 1.00 | 17.74 |
| ATOM | 967 | O | LEU | D | 10 | 68.139 | 26.719 | 32.864 | 1.00 | 15.88 |
| ATOM | 968 | CB | LEU | D | 10 | 67.917 | 23.753 | 32.313 | 1.00 | 12.64 |
| ATOM | 969 | CG | LEU | D | 10 | 67.275 | 22.500 | 31.721 | 1.00 | 16.69 |
| ATOM | 970 | CD1 | LEU | D | 10 | 68.212 | 21.782 | 30.736 | 1.00 | 19.95 |
| ATOM | 971 | CD2 | LEU | D | 10 | 66.799 | 21.474 | 32.834 | 1.00 | 18.21 |
| ATOM | 972 | N | HIS | D | 11 | 67.720 | 26.177 | 34.991 | 1.00 | 15.41 |
| ATOM | 973 | CA | HIS | D | 11 | 68.251 | 27.395 | 35.444 | 1.00 | 15.54 |
| ATOM | 974 | C | HIS | D | 11 | 69.702 | 27.368 | 35.893 | 1.00 | 20.36 |
| ATOM | 975 | O | HIS | D | 11 | 70.031 | 26.640 | 36.895 | 1.00 | 19.27 |
| ATOM | 976 | CB | HIS | D | 11 | 67.374 | 27.904 | 36.683 | 1.00 | 17.02 |
| ATOM | 977 | CG | HIS | D | 11 | 67.650 | 29.324 | 37.063 | 1.00 | 20.52 |
| ATOM | 978 | ND1 | HIS | D | 11 | 67.137 | 30.393 | 36.361 | 1.00 | 23.10 |
| ATOM | 979 | CD2 | HIS | D | 11 | 68.415 | 29.858 | 38.051 | 1.00 | 23.01 |
| ATOM | 980 | CE1 | HIS | D | 11 | 67.563 | 31.524 | 36.895 | 1.00 | 22.29 |
| ATOM | 981 | NE2 | HIS | D | 11 | 68.348 | 31.225 | 37.927 | 1.00 | 22.03 |
| ATOM | 982 | N | ARG | D | 12 | 70.556 | 28.124 | 35.209 | 1.00 | 17.66 |
| ATOM | 983 | CA | ARG | D | 12 | 71.956 | 28.229 | 35.513 | 1.00 | 17.87 |
| ATOM | 984 | C | ARG | D | 12 | 72.781 | 26.977 | 35.325 | 1.00 | 21.36 |
| ATOM | 985 | O | ARG | D | 12 | 73.632 | 26.605 | 36.187 | 1.00 | 21.72 |
| ATOM | 986 | CB | ARG | D | 12 | 72.232 | 28.945 | 36.891 | 1.00 | 17.27 |
| ATOM | 987 | CG | ARG | D | 12 | 71.708 | 30.362 | 36.941 | 1.00 | 16.85 |
| ATOM | 988 | CD | ARG | D | 12 | 71.907 | 31.054 | 38.323 | 1.00 | 21.64 |
| ATOM | 989 | NE | ARG | D | 12 | 73.332 | 31.030 | 38.693 | 1.00 | 26.91 |
| ATOM | 990 | CZ | ARG | D | 12 | 74.195 | 32.006 | 38.428 | 1.00 | 32.28 |
| ATOM | 991 | NH1 | ARG | D | 12 | 75.471 | 31.878 | 38.797 | 1.00 | 32.70 |
| ATOM | 992 | NH2 | ARG | D | 12 | 73.806 | 33.103 | 37.801 | 1.00 | 23.04 |
| ATOM | 993 | N | VAL | D | 13 | 72.613 | 26.297 | 34.173 | 1.00 | 16.36 |
| ATOM | 994 | CA | VAL | D | 13 | 73.413 | 25.135 | 33.867 | 1.00 | 16.81 |
| ATOM | 995 | C | VAL | D | 13 | 74.664 | 25.673 | 33.161 | 1.00 | 19.79 |
| ATOM | 996 | O | VAL | D | 13 | 74.668 | 26.811 | 32.683 | 1.00 | 21.56 |
| ATOM | 997 | CB | VAL | D | 13 | 72.713 | 24.137 | 32.918 | 1.00 | 20.87 |
| ATOM | 998 | CG1 | VAL | D | 13 | 71.653 | 23.427 | 33.553 | 1.00 | 22.00 |
| ATOM | 999 | CG2 | VAL | D | 13 | 72.189 | 24.846 | 31.612 | 1.00 | 19.93 |
| ATOM | 1000 | N | LYS | D | 14 | 75.741 | 24.892 | 33.128 | 1.00 | 17.58 |
| ATOM | 1001 | CA | LYS | D | 14 | 76.956 | 25.383 | 32.473 | 1.00 | 18.29 |
| ATOM | 1002 | C | LYS | D | 14 | 77.225 | 24.642 | 31.155 | 1.00 | 17.32 |
| ATOM | 1003 | O | LYS | D | 14 | 77.005 | 23.448 | 31.066 | 1.00 | 17.18 |
| ATOM | 1004 | CB | LYS | D | 14 | 78.176 | 25.251 | 33.416 | 1.00 | 21.96 |
| ATOM | 1005 | CG | LYS | D | 14 | 78.220 | 26.346 | 34.459 | 1.00 | 29.69 |
| ATOM | 1006 | CD | LYS | D | 14 | 79.441 | 26.161 | 35.412 | 1.00 | 27.98 |
| ATOM | 1007 | CE | LYS | D | 14 | 79.422 | 27.179 | 36.555 | 1.00 | 33.09 |
| ATOM | 1008 | NZ | LYS | D | 14 | 78.560 | 26.719 | 37.687 | 1.00 | 36.70 |
| ATOM | 1009 | N | VAL | D | 15 | 77.658 | 25.409 | 30.145 | 1.00 | 17.61 |
| ATOM | 1010 | CA | VAL | D | 15 | 77.967 | 24.799 | 28.844 | 1.00 | 15.98 |
| ATOM | 1011 | C | VAL | D | 15 | 79.203 | 23.888 | 29.035 | 1.00 | 18.36 |
| ATOM | 1012 | O | VAL | D | 15 | 80.185 | 24.318 | 29.603 | 1.00 | 20.10 |
| ATOM | 1013 | CB | VAL | D | 15 | 78.245 | 25.880 | 27.800 | 1.00 | 18.17 |
| ATOM | 1014 | CG1 | VAL | D | 15 | 78.696 | 25.198 | 26.454 | 1.00 | 19.48 |
| ATOM | 1015 | CG2 | VAL | D | 15 | 76.933 | 26.685 | 27.567 | 1.00 | 18.97 |
| ATOM | 1016 | N | THR | D | 16 | 79.140 | 22.659 | 28.545 | 1.00 | 16.59 |
| ATOM | 1017 | CA | THR | D | 16 | 80.271 | 21.721 | 28.715 | 1.00 | 18.46 |
| ATOM | 1018 | C | THR | D | 16 | 81.039 | 21.407 | 27.449 | 1.00 | 23.98 |
| ATOM | 1019 | O | THR | D | 16 | 82.184 | 20.892 | 27.500 | 1.00 | 23.98 |
| ATOM | 1020 | CB | THR | D | 16 | 79.781 | 20.374 | 29.348 | 1.00 | 20.68 |
| ATOM | 1021 | OG1 | THR | D | 16 | 78.894 | 19.683 | 28.464 | 1.00 | 20.66 |
| ATOM | 1022 | CG2 | THR | D | 16 | 79.048 | 20.647 | 30.719 | 1.00 | 20.82 |
| ATOM | 1023 | N | HIS | D | 17 | 80.447 | 21.718 | 26.302 | 1.00 | 21.79 |
| ATOM | 1024 | CA | HIS | D | 17 | 81.112 | 21.413 | 25.010 | 1.00 | 23.09 |
| ATOM | 1025 | C | HIS | D | 17 | 80.522 | 22.305 | 23.934 | 1.00 | 25.64 |
| ATOM | 1026 | O | HIS | D | 17 | 79.371 | 22.760 | 24.047 | 1.00 | 20.59 |
| ATOM | 1027 | CB | HIS | D | 17 | 80.740 | 19.928 | 24.685 | 1.00 | 25.73 |
| ATOM | 1028 | CG | HIS | D | 17 | 81.356 | 19.348 | 23.433 | 1.00 | 31.57 |
| ATOM | 1029 | ND1 | HIS | D | 17 | 80.584 | 18.824 | 22.407 | 1.00 | 34.88 |
| ATOM | 1030 | CD2 | HIS | D | 17 | 82.652 | 19.158 | 23.062 | 1.00 | 34.96 |
| ATOM | 1031 | CE1 | HIS | D | 17 | 81.374 | 18.360 | 21.451 | 1.00 | 35.01 |
| ATOM | 1032 | NE2 | HIS | D | 17 | 82.635 | 18.549 | 21.820 | 1.00 | 35.08 |

-continued

| | | | | | | | | | |
|---|---|---|---|---|---|---|---|---|---|
| ATOM | 1033 | N | ALA | D | 18 | 81.309 | 22.554 | 22.893 | 1.00 | 25.07 |
| ATOM | 1034 | CA | ALA | D | 18 | 80.848 | 23.379 | 21.759 | 1.00 | 25.93 |
| ATOM | 1035 | C | ALA | D | 18 | 81.317 | 22.603 | 20.201 | 1.00 | 31.11 |
| ATOM | 1036 | O | ALA | D | 18 | 82.460 | 22.106 | 20.472 | 1.00 | 33.50 |
| ATOM | 1037 | CB | ALA | D | 18 | 81.433 | 24.755 | 21.814 | 1.00 | 27.54 |
| ATOM | 1038 | N | ASP | D | 19 | 80.444 | 22.423 | 19.505 | 1.00 | 24.42 |
| ATOM | 1039 | CA | ASP | D | 19 | 80.814 | 21.654 | 18.284 | 1.00 | 24.78 |
| ATOM | 1040 | C | ASP | D | 19 | 80.276 | 22.359 | 17.047 | 1.00 | 27.05 |
| ATOM | 1041 | O | ASP | D | 19 | 79.206 | 22.000 | 16.529 | 1.00 | 24.71 |
| ATOM | 1042 | CB | ASP | D | 19 | 80.272 | 20.218 | 18.402 | 1.00 | 25.96 |
| ATOM | 1043 | CG | ASP | D | 19 | 80.644 | 19.316 | 17.214 | 1.00 | 34.10 |
| ATOM | 1044 | OD1 | ASP | D | 19 | 81.404 | 19.749 | 16.320 | 1.00 | 34.04 |
| ATOM | 1045 | OD2 | ASP | D | 19 | 80.164 | 18.147 | 17.193 | 1.00 | 38.22 |
| ATOM | 1046 | N | LEU | D | 20 | 81.027 | 23.356 | 16.587 | 1.00 | 25.80 |
| ATOM | 1047 | CA | LEU | D | 20 | 80.656 | 24.143 | 15.422 | 1.00 | 24.85 |
| ATOM | 1048 | C | LEU | D | 20 | 80.390 | 23.317 | 14.170 | 1.00 | 27.59 |
| ATOM | 1049 | O | LEU | D | 20 | 79.410 | 23.581 | 13.451 | 1.00 | 26.06 |
| ATOM | 1050 | CB | LEU | D | 20 | 81.753 | 25.185 | 15.120 | 1.00 | 25.72 |
| ATOM | 1051 | CG | LEU | D | 20 | 81.546 | 26.193 | 13.977 | 1.00 | 29.24 |
| ATOM | 1052 | CD1 | LEU | D | 20 | 80.505 | 27.239 | 14.355 | 1.00 | 28.84 |
| ATOM | 1053 | CD2 | LEU | D | 20 | 82.887 | 26.875 | 13.627 | 1.00 | 29.15 |
| ATOM | 1054 | N | HIS | D | 21 | 81.264 | 22.340 | 13.908 | 1.00 | 28.61 |
| ATOM | 1055 | CA | HIS | D | 21 | 81.167 | 21.442 | 12.712 | 1.00 | 30.90 |
| ATOM | 1056 | C | HIS | D | 21 | 80.238 | 20.275 | 12.779 | 1.00 | 36.12 |
| ATOM | 1057 | O | HIS | D | 21 | 80.249 | 19.385 | 11.890 | 1.00 | 35.00 |
| ATOM | 1058 | CB | HIS | D | 21 | 82.573 | 21.039 | 12.237 | 1.00 | 32.76 |
| ATOM | 1059 | CG | HIS | D | 21 | 83.437 | 22.204 | 11.941 | 1.00 | 36.81 |
| ATOM | 1060 | ND1 | HIS | D | 21 | 84.537 | 22.541 | 12.700 | 1.00 | 39.48 |
| ATOM | 1061 | CD2 | HIS | D | 21 | 83.307 | 23.151 | 11.010 | 1.00 | 38.76 |
| ATOM | 1062 | CE1 | HIS | D | 21 | 85.072 | 23.656 | 12.222 | 1.00 | 38.26 |
| ATOM | 1063 | NE2 | HIS | D | 21 | 84.345 | 24.063 | 11.198 | 1.00 | 38.36 |
| ATOM | 1064 | N | TYR | D | 22 | 79.418 | 20.275 | 13.811 | 1.00 | 33.13 |
| ATOM | 1065 | CA | TYR | D | 22 | 78.453 | 19.220 | 14.019 | 1.00 | 33.14 |
| ATOM | 1066 | C | TYR | D | 22 | 77.573 | 18.876 | 12.801 | 1.00 | 37.60 |
| ATOM | 1067 | O | TYR | D | 22 | 77.155 | 19.766 | 12.012 | 1.00 | 32.76 |
| ATOM | 1068 | CB | TYR | D | 22 | 77.479 | 19.691 | 15.105 | 1.00 | 33.35 |
| ATOM | 1069 | CG | TYR | D | 22 | 76.571 | 18.617 | 15.617 | 1.00 | 35.03 |
| ATOM | 1070 | CD1 | TYR | D | 22 | 77.095 | 17.527 | 16.305 | 1.00 | 36.82 |
| ATOM | 1071 | CD2 | TYR | D | 22 | 75.204 | 18.670 | 15.401 | 1.00 | 35.58 |
| ATOM | 1072 | CE1 | TYR | D | 22 | 76.271 | 16.517 | 16.773 | 1.00 | 37.35 |
| ATOM | 1073 | CE2 | TYR | D | 22 | 74.375 | 17.669 | 15.872 | 1.00 | 36.01 |
| ATOM | 1074 | CZ | TYR | D | 22 | 74.906 | 16.604 | 16.557 | 1.00 | 42.70 |
| ATOM | 1075 | OH | TYR | D | 22 | 74.016 | 15.625 | 17.014 | 1.00 | 46.65 |
| ATOM | 1076 | N | GLU | D | 23 | 77.276 | 17.594 | 12.694 | 1.00 | 39.24 |
| ATOM | 1077 | CA | GLU | D | 23 | 76.408 | 17.072 | 11.664 | 1.00 | 42.44 |
| ATOM | 1078 | C | GLU | D | 23 | 75.374 | 16.147 | 12.358 | 1.00 | 47.01 |
| ATOM | 1079 | O | GLU | D | 23 | 75.698 | 15.050 | 12.769 | 1.00 | 48.53 |
| ATOM | 1080 | CB | GLU | D | 23 | 77.176 | 16.320 | 10.575 | 1.00 | 44.81 |
| ATOM | 1081 | CG | GLU | D | 23 | 76.241 | 15.586 | 9.631 | 1.00 | 53.00 |
| ATOM | 1082 | CD | GLU | D | 23 | 76.852 | 15.314 | 8.271 | 1.00 | 63.57 |
| ATOM | 1083 | OE1 | GLU | D | 23 | 78.097 | 15.153 | 8.190 | 1.00 | 70.57 |
| ATOM | 1084 | OE2 | GLU | D | 23 | 76.079 | 15.237 | 7.285 | 1.00 | 49.95 |
| ATOM | 1085 | N | GLY | D | 24 | 74.136 | 16.608 | 12.481 | 1.00 | 43.35 |
| ATOM | 1086 | CA | GLY | D | 24 | 73.103 | 15.797 | 13.108 | 1.00 | 47.63 |
| ATOM | 1087 | C | GLY | D | 24 | 71.872 | 16.608 | 13.529 | 1.00 | 49.81 |
| ATOM | 1088 | O | GLY | D | 24 | 71.438 | 17.481 | 12.758 | 1.00 | 43.71 |
| ATOM | 1089 | OH | GLY | D | 24 | 71.339 | 16.374 | 14.643 | 1.00 | 78.26 |
| ATOM | 1090 | C | PVL | D | 25 | 72.100 | 22.561 | 19.543 | 1.00 | 18.29 |
| ATOM | 1091 | O | PVL | D | 25 | 73.123 | 23.121 | 19.763 | 1.00 | 21.21 |
| ATOM | 1092 | CA | PVL | D | 25 | 71.565 | 22.581 | 18.161 | 1.00 | 27.46 |
| ATOM | 1093 | CB | PVL | D | 25 | 70.223 | 21.973 | 17.952 | 1.00 | 25.35 |
| ATOM | 1094 | ON | PVL | D | 25 | 72.196 | 23.134 | 17.245 | 1.00 | 33.71 |
| ATOM | 1095 | N | CYS | D | 26 | 71.286 | 22.044 | 20.569 | 1.00 | 15.60 |
| ATOM | 1096 | CA | CYS | D | 26 | 71.834 | 22.016 | 21.931 | 1.00 | 16.64 |
| ATOM | 1097 | CB | CYS | D | 26 | 71.304 | 23.212 | 22.757 | 1.00 | 14.30 |
| ATOM | 1098 | SG | CYS | D | 26 | 71.996 | 23.106 | 24.461 | 1.00 | 18.05 |
| ATOM | 1099 | C | CYS | D | 26 | 71.504 | 20.649 | 22.505 | 1.00 | 14.55 |
| ATOM | 1100 | O | CYS | D | 26 | 70.332 | 20.263 | 22.665 | 1.00 | 16.28 |
| ATOM | 1101 | N | ALA | D | 27 | 72.569 | 19.844 | 22.774 | 1.00 | 15.46 |
| ATOM | 1102 | CA | ALA | D | 27 | 72.411 | 18.463 | 23.329 | 1.00 | 15.63 |
| ATOM | 1103 | C | ALA | D | 27 | 72.469 | 18.581 | 24.869 | 1.00 | 15.10 |
| ATOM | 1104 | O | ALA | D | 27 | 73.350 | 19.198 | 25.406 | 1.00 | 15.77 |
| ATOM | 1105 | CB | ALA | D | 27 | 73.510 | 17.508 | 22.838 | 1.00 | 16.71 |
| ATOM | 1106 | N | ILE | D | 28 | 71.483 | 17.965 | 25.486 | 1.00 | 14.23 |
| ATOM | 1107 | CA | ILE | D | 28 | 71.292 | 18.058 | 26.940 | 1.00 | 14.71 |
| ATOM | 1108 | C | ILE | D | 28 | 71.023 | 16.715 | 27.562 | 1.00 | 17.41 |
| ATOM | 1109 | O | ILE | D | 28 | 70.251 | 15.919 | 27.072 | 1.00 | 16.90 |

-continued

Data Lists

| | | | | | | | | | |
|---|---|---|---|---|---|---|---|---|---|
| ATOM | 1110 | CB | ILE | D | 28 | 69.990 | 18.945 | 27.121 | 1.00 | 16.58 |
| ATOM | 1111 | CG1 | ILE | D | 28 | 70.204 | 20.317 | 26.472 | 1.00 | 16.36 |
| ATOM | 1112 | CG2 | ILE | D | 28 | 69.627 | 19.068 | 28.632 | 1.00 | 15.52 |
| ATOM | 1113 | CD1 | ILE | D | 28 | 68.887 | 21.088 | 26.119 | 1.00 | 18.68 |
| ATOM | 1114 | N | ASP | D | 29 | 71.717 | 16.475 | 28.696 | 1.00 | 16.97 |
| ATOM | 1115 | CA | ASP | D | 29 | 71.551 | 15.203 | 29.449 | 1.00 | 18.01 |
| ATOM | 1116 | C | ASP | D | 29 | 70.023 | 14.912 | 29.600 | 1.00 | 17.51 |
| ATOM | 1117 | O | ASP | D | 29 | 69.284 | 15.814 | 30.061 | 1.00 | 15.93 |
| ATOM | 1118 | CB | ASP | D | 29 | 72.168 | 15.468 | 30.837 | 1.00 | 18.64 |
| ATOM | 1119 | CG | ASP | D | 29 | 72.085 | 14.248 | 31.826 | 1.00 | 21.55 |
| ATOM | 1120 | OD1 | ASP | D | 29 | 71.218 | 13.349 | 31.704 | 1.00 | 21.30 |
| ATOM | 1121 | OD2 | ASP | D | 29 | 72.956 | 14.262 | 32.752 | 1.00 | 22.85 |
| ATOM | 1122 | N | GLN | D | 30 | 69.580 | 13.710 | 29.207 | 1.00 | 17.64 |
| ATOM | 1123 | CA | GLN | D | 30 | 68.165 | 13.289 | 29.288 | 1.00 | 16.64 |
| ATOM | 1124 | C | GLN | D | 30 | 67.584 | 13.514 | 30.685 | 1.00 | 20.42 |
| ATOM | 1125 | O | GLN | D | 30 | 66.407 | 13.865 | 30.795 | 1.00 | 19.64 |
| ATOM | 1126 | CB | GLN | D | 30 | 67.942 | 11.845 | 28.839 | 1.00 | 19.10 |
| ATOM | 1127 | CG | GLN | D | 30 | 66.498 | 11.417 | 28.796 | 1.00 | 20.18 |
| ATOM | 1128 | CD | GLN | D | 30 | 65.710 | 12.200 | 27.766 | 1.00 | 24.27 |
| ATOM | 1129 | OE1 | GLN | D | 30 | 66.090 | 12.214 | 26.565 | 1.00 | 20.83 |
| ATOM | 1130 | NE2 | GLN | D | 30 | 64.598 | 12.837 | 28.202 | 1.00 | 20.72 |
| ATOM | 1131 | N | ASP | D | 31 | 68.383 | 13.362 | 31.752 | 1.00 | 19.98 |
| ATOM | 1132 | CA | ASP | D | 31 | 67.810 | 13.608 | 33.086 | 1.00 | 20.52 |
| ATOM | 1133 | C | ASP | D | 31 | 67.343 | 15.055 | 33.267 | 1.00 | 19.87 |
| ATOM | 1134 | O | ASP | D | 31 | 66.339 | 15.342 | 34.003 | 1.00 | 20.49 |
| ATOM | 1135 | CB | ASP | D | 31 | 68.858 | 13.326 | 34.165 | 1.00 | 20.56 |
| ATOM | 1136 | CG | ASP | D | 31 | 68.955 | 11.861 | 34.505 | 1.00 | 27.59 |
| ATOM | 1137 | OD1 | ASP | D | 31 | 68.027 | 11.063 | 34.248 | 1.00 | 27.63 |
| ATOM | 1138 | OD2 | ASP | D | 31 | 70.061 | 11.498 | 34.988 | 1.00 | 25.47 |
| ATOM | 1139 | N | PHE | D | 32 | 68.053 | 16.002 | 32.616 | 1.00 | 17.26 |
| ATOM | 1140 | CA | PHE | D | 32 | 67.743 | 17.411 | 32.698 | 1.00 | 16.13 |
| ATOM | 1141 | C | PHE | D | 32 | 66.457 | 17.661 | 31.896 | 1.00 | 15.84 |
| ATOM | 1142 | O | PHE | D | 32 | 65.527 | 18.389 | 32.356 | 1.00 | 15.43 |
| ATOM | 1143 | CB | PHE | D | 32 | 68.854 | 18.301 | 32.116 | 1.00 | 17.62 |
| ATOM | 1144 | CG | PHE | D | 32 | 70.216 | 18.172 | 32.810 | 1.00 | 18.64 |
| ATOM | 1145 | CD1 | PHE | D | 32 | 70.409 | 17.355 | 33.944 | 1.00 | 20.38 |
| ATOM | 1146 | CD2 | PHE | D | 32 | 71.294 | 18.902 | 32.313 | 1.00 | 21.28 |
| ATOM | 1147 | CE1 | PHE | D | 32 | 71.722 | 17.281 | 34.537 | 1.00 | 21.62 |
| ATOM | 1148 | CE2 | PHE | D | 32 | 72.549 | 18.834 | 32.878 | 1.00 | 24.06 |
| ATOM | 1149 | CZ | PHE | D | 32 | 72.763 | 18.019 | 34.007 | 1.00 | 22.14 |
| ATOM | 1150 | N | LEU | D | 33 | 66.412 | 17.068 | 30.700 | 1.00 | 15.62 |
| ATOM | 1151 | CA | LEU | D | 33 | 65.206 | 17.230 | 29.867 | 1.00 | 15.62 |
| ATOM | 1152 | C | LEU | D | 33 | 63.969 | 16.737 | 30.662 | 1.00 | 14.56 |
| ATOM | 1153 | O | LEU | D | 33 | 62.938 | 17.393 | 30.680 | 1.00 | 15.50 |
| ATOM | 1154 | CB | LEU | D | 33 | 65.330 | 16.434 | 28.565 | 1.00 | 15.46 |
| ATOM | 1155 | CG | LEU | D | 33 | 66.446 | 16.945 | 27.597 | 1.00 | 17.68 |
| ATOM | 1156 | CD1 | LEU | D | 33 | 66.471 | 16.024 | 26.336 | 1.00 | 18.11 |
| ATOM | 1157 | CD2 | LEU | D | 33 | 66.139 | 18.385 | 27.159 | 1.00 | 17.59 |
| ATOM | 1158 | N | ASP | D | 34 | 64.094 | 15.567 | 31.320 | 1.00 | 15.47 |
| ATOM | 1159 | CA | ASP | D | 34 | 63.010 | 14.958 | 32.091 | 1.00 | 15.42 |
| ATOM | 1160 | C | ASP | D | 34 | 62.498 | 15.897 | 33.177 | 1.00 | 15.50 |
| ATOM | 1161 | O | ASP | D | 34 | 61.312 | 16.032 | 33.342 | 1.00 | 16.94 |
| ATOM | 1162 | CB | ASP | D | 34 | 63.523 | 13.673 | 32.755 | 1.00 | 16.78 |
| ATOM | 1163 | CG | ASP | D | 34 | 63.625 | 12.511 | 31.796 | 1.00 | 21.53 |
| ATOM | 1164 | OD1 | ASP | D | 34 | 63.254 | 12.639 | 30.594 | 1.00 | 22.41 |
| ATOM | 1165 | OD2 | ASP | D | 34 | 64.107 | 11.419 | 32.237 | 1.00 | 24.39 |
| ATOM | 1166 | N | ALA | D | 35 | 63.405 | 16.522 | 33.911 | 1.00 | 15.30 |
| ATOM | 1167 | CA | ALA | D | 35 | 63.030 | 17.444 | 34.982 | 1.00 | 16.57 |
| ATOM | 1168 | C | ALA | D | 35 | 62.344 | 18.711 | 34.497 | 1.00 | 18.73 |
| ATOM | 1169 | O | ALA | D | 35 | 61.440 | 19.244 | 35.142 | 1.00 | 19.02 |
| ATOM | 1170 | CB | ALA | D | 35 | 64.253 | 17.838 | 35.828 | 1.00 | 18.18 |
| ATOM | 1171 | N | ALA | D | 36 | 62.814 | 19.231 | 33.338 | 1.00 | 15.77 |
| ATOM | 1172 | CA | ALA | D | 36 | 62.243 | 20.432 | 32.837 | 1.00 | 14.01 |
| ATOM | 1173 | C | ALA | D | 36 | 61.034 | 20.203 | 31.866 | 1.00 | 12.66 |
| ATOM | 1174 | O | ALA | D | 36 | 60.427 | 21.243 | 31.459 | 1.00 | 15.97 |
| ATOM | 1175 | CB | ALA | D | 36 | 63.337 | 21.261 | 32.105 | 1.00 | 15.98 |
| ATOM | 1176 | N | GLY | D | 37 | 60.750 | 18.962 | 31.520 | 1.00 | 12.31 |
| ATOM | 1177 | CA | GLY | D | 37 | 59.663 | 18.637 | 30.636 | 1.00 | 12.99 |
| ATOM | 1178 | C | GLY | D | 37 | 59.994 | 19.050 | 29.180 | 1.00 | 13.99 |
| ATOM | 1179 | O | GLY | D | 37 | 59.023 | 19.117 | 28.371 | 1.00 | 13.49 |
| ATOM | 1180 | N | ILE | D | 38 | 61.276 | 19.246 | 28.882 | 1.00 | 13.30 |
| ATOM | 1181 | CA | ILE | D | 38 | 61.705 | 19.641 | 27.476 | 1.00 | 11.90 |
| ATOM | 1182 | C | ILE | D | 38 | 61.854 | 18.372 | 26.665 | 1.00 | 13.73 |
| ATOM | 1183 | O | ILE | D | 38 | 62.470 | 17.403 | 27.086 | 1.00 | 13.87 |
| ATOM | 1184 | CB | ILE | D | 38 | 62.938 | 20.454 | 27.528 | 1.00 | 12.06 |
| ATOM | 1185 | CG1 | ILE | D | 38 | 62.664 | 21.817 | 28.244 | 1.00 | 13.02 |
| ATOM | 1186 | CG2 | ILE | D | 38 | 63.457 | 20.747 | 26.031 | 1.00 | 11.46 |

-continued

Data Lists

| | | | | | | | | | |
|---|---|---|---|---|---|---|---|---|---|
| ATOM | 1187 | CD1 | ILE | D | 38 | 63.886 | 22.662 | 28.502 | 1.00 | 14.92 |
| ATOM | 1188 | N | LEU | D | 39 | 61.313 | 18.366 | 25.415 | 1.00 | 11.75 |
| ATOM | 1189 | CA | LEU | D | 39 | 61.366 | 17.198 | 24.557 | 1.00 | 11.57 |
| ATOM | 1190 | C | LEU | D | 39 | 62.445 | 17.286 | 23.489 | 1.00 | 13.60 |
| ATOM | 1191 | O | LEU | D | 39 | 62.811 | 18.368 | 23.105 | 1.00 | 12.83 |
| ATOM | 1192 | CB | LEU | D | 39 | 60.048 | 17.052 | 23.807 | 1.00 | 11.62 |
| ATOM | 1193 | CG | LEU | D | 39 | 58.724 | 17.113 | 24.610 | 1.00 | 13.66 |
| ATOM | 1194 | CD1 | LEU | D | 39 | 57.552 | 16.938 | 23.682 | 1.00 | 15.79 |
| ATOM | 1195 | CD2 | LEU | D | 39 | 58.820 | 15.969 | 25.666 | 1.00 | 15.29 |
| ATOM | 1196 | N | GLU | D | 40 | 62.956 | 16.134 | 23.119 | 1.00 | 14.52 |
| ATOM | 1197 | CA | GLU | D | 40 | 63.930 | 16.098 | 22.000 | 1.00 | 14.56 |
| ATOM | 1198 | C | GLU | D | 40 | 63.128 | 16.706 | 20.790 | 1.00 | 14.90 |
| ATOM | 1199 | O | GLU | D | 40 | 61.938 | 16.424 | 20.582 | 1.00 | 13.14 |
| ATOM | 1200 | CB | GLU | D | 40 | 64.273 | 14.643 | 21.690 | 1.00 | 17.43 |
| ATOM | 1201 | CG | GLU | D | 40 | 65.687 | 14.237 | 22.093 | 1.00 | 36.71 |
| ATOM | 1202 | CD | GLU | D | 40 | 66.336 | 13.346 | 21.016 | 1.00 | 43.99 |
| ATOM | 1203 | OE1 | GLU | D | 40 | 65.691 | 12.317 | 20.674 | 1.00 | 33.64 |
| ATOM | 1204 | OE2 | GLU | D | 40 | 67.475 | 13.665 | 20.501 | 1.00 | 23.74 |
| ATOM | 1205 | N | ASN | D | 41 | 63.849 | 17.563 | 20.028 | 1.00 | 12.38 |
| ATOM | 1206 | CA | ASN | D | 41 | 63.297 | 18.252 | 18.835 | 1.00 | 12.93 |
| ATOM | 1207 | C | ASN | D | 41 | 62.403 | 19.417 | 19.130 | 1.00 | 15.81 |
| ATOM | 1208 | O | ASN | D | 41 | 61.836 | 20.050 | 18.252 | 1.00 | 13.21 |
| ATOM | 1209 | CB | ASN | D | 41 | 62.680 | 17.270 | 17.864 | 1.00 | 14.28 |
| ATOM | 1210 | CG | ASN | D | 41 | 63.721 | 16.286 | 17.293 | 1.00 | 12.10 |
| ATOM | 1211 | OD1 | ASN | D | 41 | 64.828 | 16.679 | 16.930 | 1.00 | 16.64 |
| ATOM | 1212 | ND2 | ASN | D | 41 | 63.373 | 15.002 | 17.295 | 1.00 | 15.27 |
| ATOM | 1213 | N | GLU | D | 42 | 62.241 | 19.771 | 20.402 | 1.00 | 10.98 |
| ATOM | 1214 | CA | GLU | D | 42 | 61.432 | 20.916 | 20.753 | 1.00 | 9.74 |
| ATOM | 1215 | C | GLU | D | 42 | 62.214 | 22.225 | 20.638 | 1.00 | 9.74 |
| ATOM | 1216 | O | GLU | D | 42 | 63.430 | 22.297 | 20.917 | 1.00 | 10.17 |
| ATOM | 1217 | CB | GLU | D | 42 | 60.958 | 20.806 | 22.304 | 1.00 | 10.40 |
| ATOM | 1218 | CG | GLU | D | 42 | 59.992 | 21.930 | 22.730 | 1.00 | 10.03 |
| ATOM | 1219 | CD | GLU | D | 42 | 59.538 | 21.802 | 24.213 | 1.00 | 13.25 |
| ATOM | 1220 | OE1 | GLU | D | 42 | 60.180 | 20.979 | 24.893 | 1.00 | 15.16 |
| ATOM | 1221 | OE2 | GLU | D | 42 | 58.595 | 22.504 | 24.588 | 1.00 | 12.03 |
| ATOM | 1222 | N | ALA | D | 43 | 61.529 | 23.303 | 20.212 | 1.00 | 9.51 |
| ATOM | 1223 | CA | ALA | D | 43 | 62.125 | 24.618 | 20.139 | 1.00 | 10.88 |
| ATOM | 1224 | C | ALA | D | 43 | 62.581 | 25.062 | 21.572 | 1.00 | 10.85 |
| ATOM | 1225 | O | ALA | D | 43 | 61.770 | 24.882 | 22.523 | 1.00 | 11.54 |
| ATOM | 1226 | CB | ALA | D | 43 | 61.086 | 25.666 | 19.611 | 1.00 | 12.49 |
| ATOM | 1227 | N | ILE | D | 44 | 63.746 | 25.596 | 21.711 | 1.00 | 11.86 |
| ATOM | 1228 | CA | ILE | D | 44 | 64.214 | 26.108 | 23.049 | 1.00 | 11.02 |
| ATOM | 1229 | C | ILE | D | 44 | 64.876 | 27.495 | 22.885 | 1.00 | 13.51 |
| ATOM | 1230 | O | ILE | D | 44 | 65.459 | 27.820 | 21.790 | 1.00 | 13.63 |
| ATOM | 1231 | CB | ILE | D | 44 | 65.215 | 25.146 | 23.757 | 1.00 | 12.21 |
| ATOM | 1232 | CG1 | ILE | D | 44 | 66.425 | 24.841 | 22.799 | 1.00 | 12.04 |
| ATOM | 1233 | CG2 | ILE | D | 44 | 64.475 | 23.886 | 24.201 | 1.00 | 14.58 |
| ATOM | 1234 | CD1 | ILE | D | 44 | 67.496 | 23.934 | 23.440 | 1.00 | 12.27 |
| ATOM | 1235 | N | ASP | D | 45 | 64.845 | 28.343 | 23.921 | 1.00 | 10.42 |
| ATOM | 1236 | CA | ASP | D | 45 | 65.470 | 29.634 | 23.942 | 1.00 | 10.06 |
| ATOM | 1237 | C | ASP | D | 45 | 66.628 | 29.457 | 24.943 | 1.00 | 14.23 |
| ATOM | 1238 | O | ASP | D | 45 | 66.438 | 28.814 | 26.014 | 1.00 | 14.99 |
| ATOM | 1239 | CB | ASP | D | 45 | 64.514 | 30.754 | 24.407 | 1.00 | 12.39 |
| ATOM | 1240 | CG | ASP | D | 45 | 63.320 | 30.886 | 23.509 | 1.00 | 15.51 |
| ATOM | 1241 | OD1 | ASP | D | 45 | 63.504 | 30.682 | 22.250 | 1.00 | 15.80 |
| ATOM | 1242 | OD2 | ASP | D | 45 | 62.187 | 31.118 | 23.974 | 1.00 | 15.67 |
| ATOM | 1243 | N | ILE | D | 46 | 67.791 | 29.995 | 24.634 | 1.00 | 10.63 |
| ATOM | 1244 | CA | ILE | D | 46 | 68.996 | 29.909 | 25.471 | 1.00 | 10.58 |
| ATOM | 1245 | C | ILE | D | 46 | 69.427 | 31.327 | 25.747 | 1.00 | 14.80 |
| ATOM | 1246 | O | ILE | D | 46 | 69.649 | 32.151 | 24.860 | 1.00 | 13.14 |
| ATOM | 1247 | CB | ILE | D | 46 | 70.104 | 29.079 | 24.805 | 1.00 | 12.68 |
| ATOM | 1248 | CG1 | ILE | D | 46 | 69.560 | 27.686 | 24.519 | 1.00 | 11.97 |
| ATOM | 1249 | CG2 | ILE | D | 46 | 71.354 | 29.057 | 25.751 | 1.00 | 14.01 |
| ATOM | 1250 | CD1 | ILE | D | 46 | 70.647 | 26.680 | 24.071 | 1.00 | 17.51 |
| ATOM | 1251 | N | TRP | D | 47 | 69.509 | 31.672 | 27.067 | 1.00 | 11.09 |
| ATOM | 1252 | CA | TRP | D | 47 | 69.832 | 32.990 | 27.530 | 1.00 | 12.91 |
| ATOM | 1253 | C | TRP | D | 47 | 71.163 | 32.842 | 28.298 | 1.00 | 18.14 |
| ATOM | 1254 | O | TRP | D | 47 | 71.232 | 32.122 | 29.319 | 1.00 | 16.83 |
| ATOM | 1255 | CB | TRP | D | 47 | 68.681 | 33.497 | 28.446 | 1.00 | 12.75 |
| ATOM | 1256 | CG | TRP | D | 47 | 67.334 | 33.535 | 27.762 | 1.00 | 12.68 |
| ATOM | 1257 | CD1 | TRP | D | 47 | 67.087 | 33.885 | 26.416 | 1.00 | 13.80 |
| ATOM | 1258 | CD2 | TRP | D | 47 | 66.070 | 33.224 | 28.316 | 1.00 | 12.97 |
| ATOM | 1259 | NE1 | TRP | D | 47 | 65.765 | 33.773 | 26.151 | 1.00 | 12.97 |
| ATOM | 1260 | CE2 | TRP | D | 47 | 65.093 | 33.372 | 27.286 | 1.00 | 14.42 |
| ATOM | 1261 | CE3 | TRP | D | 47 | 65.650 | 32.757 | 29.579 | 1.00 | 14.96 |
| ATOM | 1262 | CZ2 | TRP | D | 47 | 63.744 | 33.139 | 27.488 | 1.00 | 14.53 |
| ATOM | 1263 | CZ3 | TRP | D | 47 | 64.331 | 32.544 | 29.792 | 1.00 | 16.02 |

-continued

Data Lists

| | | | | | | | | | |
|---|---|---|---|---|---|---|---|---|---|
| ATOM | 1264 | CH2 | TRP | D | 47 | 63.365 | 32.734 | 28.774 | 1.00 | 16.49 |
| ATOM | 1265 | N | ASN | D | 48 | 72.217 | 33.452 | 27.762 | 1.00 | 15.37 |
| ATOM | 1266 | CA | ASN | D | 48 | 73.574 | 33.323 | 28.320 | 1.00 | 15.56 |
| ATOM | 1267 | C | ASN | D | 48 | 73.829 | 34.347 | 29.393 | 1.00 | 16.84 |
| ATOM | 1268 | O | ASN | D | 48 | 73.955 | 35.526 | 29.124 | 1.00 | 15.08 |
| ATOM | 1269 | CB | ASN | D | 48 | 74.577 | 33.489 | 27.132 | 1.00 | 14.22 |
| ATOM | 1270 | CG | ASN | D | 48 | 75.962 | 33.037 | 27.477 | 1.00 | 19.83 |
| ATOM | 1271 | OD1 | ASN | D | 48 | 76.445 | 33.343 | 28.575 | 1.00 | 17.68 |
| ATOM | 1272 | ND2 | ASN | D | 48 | 76.625 | 32.305 | 26.581 | 1.00 | 18.60 |
| ATOM | 1273 | N | VAL | D | 49 | 73.892 | 33.883 | 30.661 | 1.00 | 16.35 |
| ATOM | 1274 | CA | VAL | D | 49 | 74.128 | 34.782 | 31.784 | 1.00 | 16.91 |
| ATOM | 1275 | C | VAL | D | 49 | 75.563 | 35.373 | 31.784 | 1.00 | 18.54 |
| ATOM | 1276 | O | VAL | D | 49 | 75.809 | 36.526 | 32.220 | 1.00 | 19.45 |
| ATOM | 1277 | CB | VAL | D | 49 | 73.926 | 34.037 | 33.092 | 1.00 | 20.06 |
| ATOM | 1278 | CG1 | VAL | D | 49 | 74.124 | 35.006 | 34.262 | 1.00 | 21.67 |
| ATOM | 1279 | CG2 | VAL | D | 49 | 72.526 | 33.407 | 33.136 | 1.00 | 18.68 |
| ATOM | 1280 | N | THR | D | 50 | 76.501 | 34.576 | 31.282 | 1.00 | 17.72 |
| ATOM | 1281 | CA | THR | D | 50 | 77.881 | 35.042 | 31.234 | 1.00 | 18.92 |
| ATOM | 1282 | C | THR | D | 50 | 78.125 | 36.187 | 30.258 | 1.00 | 20.97 |
| ATOM | 1283 | O | THR | D | 50 | 78.696 | 37.231 | 30.614 | 1.00 | 20.06 |
| ATOM | 1284 | CB | THR | D | 50 | 78.829 | 33.887 | 30.935 | 1.00 | 19.40 |
| ATOM | 1285 | OG1 | THR | D | 50 | 78.678 | 32.859 | 31.930 | 1.00 | 19.82 |
| ATOM | 1286 | CG2 | THR | D | 50 | 80.335 | 34.365 | 30.836 | 1.00 | 21.30 |
| ATOM | 1287 | N | ASN | D | 51 | 77.687 | 36.000 | 28.998 | 1.00 | 17.46 |
| ATOM | 1288 | CA | ASN | D | 51 | 77.917 | 37.033 | 27.972 | 1.00 | 18.39 |
| ATOM | 1289 | C | ASN | D | 51 | 76.723 | 37.838 | 27.459 | 1.00 | 19.48 |
| ATOM | 1290 | O | ASN | D | 51 | 76.883 | 38.713 | 26.603 | 1.00 | 19.00 |
| ATOM | 1291 | CB | ASN | D | 51 | 78.712 | 36.436 | 26.788 | 1.00 | 18.51 |
| ATOM | 1292 | CG | ASN | D | 51 | 77.871 | 35.497 | 25.912 | 1.00 | 22.35 |
| ATOM | 1293 | OD1 | ASN | D | 51 | 76.653 | 35.449 | 26.014 | 1.00 | 17.21 |
| ATOM | 1294 | ND2 | ASN | D | 51 | 78.537 | 34.732 | 25.071 | 1.00 | 21.24 |
| ATOM | 1295 | N | GLY | D | 52 | 75.528 | 37.546 | 27.979 | 1.00 | 15.50 |
| ATOM | 1296 | CA | GLY | D | 52 | 74.286 | 38.204 | 27.622 | 1.00 | 14.95 |
| ATOM | 1297 | C | GLY | D | 52 | 73.637 | 37.851 | 26.263 | 1.00 | 14.04 |
| ATOM | 1298 | O | GLY | D | 52 | 72.553 | 38.408 | 25.971 | 1.00 | 16.62 |
| ATOM | 1299 | N | LYS | D | 53 | 74.271 | 36.968 | 25.507 | 1.00 | 14.08 |
| ATOM | 1300 | CA | LYS | D | 53 | 73.636 | 36.627 | 24.193 | 1.00 | 14.38 |
| ATOM | 1301 | C | LYS | D | 53 | 72.355 | 35.864 | 24.437 | 1.00 | 15.94 |
| ATOM | 1302 | O | LYS | D | 53 | 72.229 | 35.159 | 25.442 | 1.00 | 16.45 |
| ATOM | 1303 | CB | LYS | D | 53 | 74.596 | 35.808 | 23.323 | 1.00 | 14.22 |
| ATOM | 1304 | CG | LYS | D | 53 | 75.791 | 36.669 | 22.909 | 1.00 | 16.49 |
| ATOM | 1305 | CD | LYS | D | 53 | 76.764 | 35.880 | 22.038 | 1.00 | 19.28 |
| ATOM | 1306 | CE | LYS | D | 53 | 77.988 | 36.725 | 21.678 | 1.00 | 26.70 |
| ATOM | 1307 | NZ | LYS | D | 53 | 79.004 | 35.889 | 20.987 | 1.00 | 29.14 |
| ATOM | 1308 | N | ARG | D | 54 | 71.393 | 35.958 | 23.483 | 1.00 | 12.88 |
| ATOM | 1309 | CA | ARG | D | 54 | 70.123 | 35.274 | 23.557 | 1.00 | 11.93 |
| ATOM | 1310 | C | ARG | D | 54 | 69.855 | 34.669 | 22.194 | 1.00 | 14.91 |
| ATOM | 1311 | O | ARG | D | 54 | 69.980 | 35.396 | 21.196 | 1.00 | 15.98 |
| ATOM | 1312 | CB | ARG | D | 54 | 68.981 | 36.222 | 23.931 | 1.00 | 13.59 |
| ATOM | 1313 | CG | ARG | D | 54 | 69.328 | 37.048 | 25.222 | 1.00 | 14.24 |
| ATOM | 1314 | CD | ARG | D | 54 | 68.216 | 38.045 | 25.627 | 1.00 | 13.75 |
| ATOM | 1315 | NE | ARG | D | 54 | 67.011 | 37.440 | 26.165 | 1.00 | 13.94 |
| ATOM | 1316 | CZ | ARG | D | 54 | 66.877 | 37.091 | 27.456 | 1.00 | 16.69 |
| ATOM | 1317 | NH1 | ARG | D | 54 | 67.936 | 37.309 | 28.276 | 1.00 | 13.80 |
| ATOM | 1318 | NH2 | ARG | D | 54 | 65.726 | 36.552 | 27.929 | 1.00 | 13.52 |
| ATOM | 1319 | N | PHE | D | 55 | 69.566 | 33.396 | 22.152 | 1.00 | 12.40 |
| ATOM | 1320 | CA | PHE | D | 55 | 69.306 | 32.745 | 20.862 | 1.00 | 13.30 |
| ATOM | 1321 | C | PHE | D | 55 | 68.292 | 31.657 | 20.971 | 1.00 | 18.51 |
| ATOM | 1322 | O | PHE | D | 55 | 67.947 | 31.225 | 22.083 | 1.00 | 16.08 |
| ATOM | 1323 | CB | PHE | D | 55 | 70.609 | 32.327 | 20.200 | 1.00 | 13.02 |
| ATOM | 1324 | CG | PHE | D | 55 | 71.346 | 31.246 | 20.922 | 1.00 | 14.95 |
| ATOM | 1325 | CD1 | PHE | D | 55 | 72.197 | 31.565 | 22.004 | 1.00 | 15.75 |
| ATOM | 1326 | CD2 | PHE | D | 55 | 71.234 | 29.901 | 20.513 | 1.00 | 15.13 |
| ATOM | 1327 | CE1 | PHE | D | 55 | 72.938 | 30.508 | 22.680 | 1.00 | 17.56 |
| ATOM | 1328 | CE2 | PHE | D | 55 | 71.931 | 28.901 | 21.171 | 1.00 | 17.23 |
| ATOM | 1329 | CZ | PHE | D | 55 | 72.794 | 29.230 | 22.258 | 1.00 | 16.09 |
| ATOM | 1330 | N | SER | D | 56 | 67.760 | 31.175 | 19.846 | 1.00 | 12.78 |
| ATOM | 1331 | CA | SER | D | 56 | 66.764 | 30.135 | 19.824 | 1.00 | 12.18 |
| ATOM | 1332 | C | SER | D | 56 | 67.220 | 29.017 | 18.940 | 1.00 | 15.48 |
| ATOM | 1333 | O | SER | D | 56 | 67.772 | 29.295 | 17.870 | 1.00 | 14.26 |
| ATOM | 1334 | CB | SER | D | 56 | 65.408 | 30.618 | 19.392 | 1.00 | 13.68 |
| ATOM | 1335 | OG | SER | D | 56 | 64.906 | 31.668 | 20.254 | 1.00 | 18.10 |
| ATOM | 1336 | N | THR | D | 57 | 67.010 | 27.786 | 19.358 | 1.00 | 11.29 |
| ATOM | 1337 | CA | THR | D | 57 | 67.456 | 26.580 | 18.617 | 1.00 | 11.02 |
| ATOM | 1338 | C | THR | D | 57 | 66.477 | 25.422 | 18.955 | 1.00 | 11.10 |
| ATOM | 1339 | O | THR | D | 57 | 65.269 | 25.655 | 19.137 | 1.00 | 10.41 |
| ATOM | 1340 | CB | THR | D | 57 | 68.956 | 26.316 | 18.937 | 1.00 | 13.63 |

-continued

Data Lists

| ATOM | 1341 | OG1 | THR | D | 57 | 69.406 | 25.158 | 18.211 | 1.00 | 16.82 |
| --- | --- | --- | --- | --- | --- | --- | --- | --- | --- | --- |
| ATOM | 1342 | CG2 | THR | D | 57 | 69.148 | 25.977 | 20.458 | 1.00 | 16.40 |
| ATOM | 1343 | N | TYR | D | 58 | 66.953 | 24.186 | 19.039 | 1.00 | 11.85 |
| ATOM | 1344 | CA | TYR | D | 58 | 66.081 | 23.039 | 19.381 | 1.00 | 11.66 |
| ATOM | 1345 | C | TYR | D | 58 | 66.898 | 22.079 | 20.219 | 1.00 | 14.10 |
| ATOM | 1346 | O | TYR | D | 58 | 68.132 | 22.085 | 20.147 | 1.00 | 12.80 |
| ATOM | 1347 | CB | TYR | D | 58 | 65.417 | 22.357 | 18.154 | 1.00 | 13.66 |
| ATOM | 1348 | CG | TYR | D | 58 | 66.346 | 21.598 | 17.249 | 1.00 | 14.03 |
| ATOM | 1349 | CD1 | TYR | D | 58 | 67.006 | 22.243 | 16.175 | 1.00 | 14.60 |
| ATOM | 1350 | CD2 | TYR | D | 58 | 66.578 | 20.259 | 17.424 | 1.00 | 14.69 |
| ATOM | 1351 | CE1 | TYR | D | 58 | 67.879 | 21.541 | 15.366 | 1.00 | 14.59 |
| ATOM | 1352 | CE2 | TYR | D | 58 | 67.453 | 19.534 | 16.587 | 1.00 | 16.85 |
| ATOM | 1353 | CZ | TYR | D | 58 | 68.099 | 20.201 | 15.564 | 1.00 | 21.58 |
| ATOM | 1354 | OH | TYR | D | 58 | 68.989 | 19.626 | 14.678 | 1.00 | 22.59 |
| ATOM | 1355 | N | ALA | D | 59 | 66.215 | 21.278 | 21.038 | 1.00 | 12.25 |
| ATOM | 1356 | CA | ALA | D | 59 | 66.907 | 20.349 | 21.895 | 1.00 | 12.10 |
| ATOM | 1357 | C | ALA | D | 59 | 67.209 | 19.007 | 21.292 | 1.00 | 14.08 |
| ATOM | 1358 | O | ALA | D | 59 | 66.420 | 18.450 | 20.545 | 1.00 | 13.85 |
| ATOM | 1359 | CB | ALA | D | 59 | 66.015 | 20.122 | 23.160 | 1.00 | 13.24 |
| ATOM | 1360 | N | ILE | D | 60 | 68.365 | 18.433 | 21.690 | 1.00 | 15.08 |
| ATOM | 1361 | CA | ILE | D | 60 | 68.803 | 17.122 | 21.272 | 1.00 | 17.01 |
| ATOM | 1362 | C | ILE | D | 60 | 69.125 | 16.356 | 22.591 | 1.00 | 16.03 |
| ATOM | 1363 | O | ILE | D | 60 | 69.663 | 16.961 | 23.500 | 1.00 | 16.17 |
| ATOM | 1364 | CB | ILE | D | 60 | 70.125 | 17.251 | 20.437 | 1.00 | 20.97 |
| ATOM | 1365 | CG1 | ILE | D | 60 | 69.809 | 17.848 | 19.062 | 1.00 | 23.49 |
| ATOM | 1366 | CG2 | ILE | D | 60 | 70.789 | 15.887 | 20.217 | 1.00 | 23.18 |
| ATOM | 1367 | CD1 | ILE | D | 60 | 71.051 | 18.391 | 18.335 | 1.00 | 26.91 |
| ATOM | 1368 | N | ALA | D | 61 | 68.770 | 15.083 | 22.679 | 1.00 | 16.21 |
| ATOM | 1369 | CA | ALA | D | 61 | 69.073 | 14.329 | 23.908 | 1.00 | 17.99 |
| ATOM | 1370 | C | ALA | D | 61 | 70.540 | 13.922 | 23.939 | 1.00 | 20.83 |
| ATOM | 1371 | O | ALA | D | 61 | 71.084 | 13.484 | 22.911 | 1.00 | 20.99 |
| ATOM | 1372 | CB | ALA | D | 61 | 68.241 | 13.116 | 23.982 | 1.00 | 19.35 |
| ATOM | 1373 | N | ALA | D | 62 | 71.155 | 14.020 | 25.121 | 1.00 | 17.91 |
| ATOM | 1374 | CA | ALA | D | 62 | 72.553 | 13.581 | 25.379 | 1.00 | 17.67 |
| ATOM | 1375 | C | ALA | D | 62 | 72.369 | 12.443 | 26.406 | 1.00 | 23.91 |
| ATOM | 1376 | O | ALA | D | 62 | 71.329 | 12.319 | 27.041 | 1.00 | 22.36 |
| ATOM | 1377 | CB | ALA | D | 62 | 73.402 | 14.661 | 25.953 | 1.00 | 18.45 |
| ATOM | 1378 | N | GLU | D | 63 | 73.395 | 11.613 | 26.540 | 1.00 | 22.90 |
| ATOM | 1379 | CA | GLU | D | 63 | 73.378 | 10.471 | 27.428 | 1.00 | 23.71 |
| ATOM | 1380 | C | GLU | D | 63 | 72.950 | 10.793 | 28.843 | 1.00 | 23.19 |
| ATOM | 1381 | O | GLU | D | 63 | 73.447 | 11.742 | 29.441 | 1.00 | 22.01 |
| ATOM | 1382 | CB | GLU | D | 63 | 74.777 | 9.848 | 27.443 | 1.00 | 25.20 |
| ATOM | 1383 | CG | GLU | D | 63 | 74.859 | 8.627 | 28.342 | 1.00 | 31.69 |
| ATOM | 1384 | CD | GLU | D | 63 | 76.110 | 7.846 | 28.078 | 1.00 | 54.65 |
| ATOM | 1385 | OE1 | GLU | D | 63 | 76.067 | 6.926 | 27.227 | 1.00 | 50.68 |
| ATOM | 1386 | OE2 | GLU | D | 63 | 77.136 | 8.166 | 28.714 | 1.00 | 49.85 |
| ATOM | 1387 | N | ARG | D | 64 | 72.047 | 9.967 | 29.375 | 1.00 | 23.54 |
| ATOM | 1388 | CA | ARG | D | 64 | 71.554 | 10.144 | 30.721 | 1.00 | 24.49 |
| ATOM | 1389 | C | ARG | D | 64 | 72.710 | 10.059 | 31.727 | 1.00 | 29.91 |
| ATOM | 1390 | O | ARG | D | 64 | 73.501 | 9.102 | 31.685 | 1.00 | 30.10 |
| ATOM | 1391 | CB | ARG | D | 64 | 70.529 | 9.064 | 31.047 | 1.00 | 24.54 |
| ATOM | 1392 | CG | ARG | D | 64 | 69.732 | 9.364 | 32.284 | 1.00 | 33.44 |
| ATOM | 1393 | CD | ARG | D | 64 | 68.790 | 8.227 | 32.617 | 1.00 | 30.76 |
| ATOM | 1394 | NE | ARG | D | 64 | 67.706 | 8.048 | 31.659 | 1.00 | 27.92 |
| ATOM | 1395 | CZ | ARG | D | 64 | 66.649 | 8.865 | 31.545 | 1.00 | 30.52 |
| ATOM | 1396 | NH1 | ARG | D | 64 | 66.536 | 9.940 | 32.316 | 1.00 | 26.37 |
| ATOM | 1397 | NH2 | ARG | D | 64 | 65.710 | 8.597 | 30.655 | 1.00 | 30.42 |
| ATOM | 1398 | N | GLY | D | 65 | 72.817 | 11.035 | 32.609 | 1.00 | 27.07 |
| ATOM | 1399 | CA | GLY | D | 65 | 73.882 | 11.019 | 33.616 | 1.00 | 26.85 |
| ATOM | 1400 | C | GLY | D | 65 | 75.190 | 11.651 | 33.183 | 1.00 | 30.69 |
| ATOM | 1401 | O | GLY | D | 65 | 76.089 | 11.825 | 33.997 | 1.00 | 31.19 |
| ATOM | 1402 | N | SER | D | 66 | 75.287 | 12.036 | 31.912 | 1.00 | 25.88 |
| ATOM | 1403 | CA | SER | D | 66 | 76.495 | 12.662 | 31.399 | 1.00 | 24.31 |
| ATOM | 1404 | C | SER | D | 66 | 76.682 | 14.113 | 31.883 | 1.00 | 28.10 |
| ATOM | 1405 | O | SER | D | 66 | 77.793 | 14.654 | 31.888 | 1.00 | 29.06 |
| ATOM | 1406 | CB | SER | D | 66 | 76.454 | 12.648 | 29.857 | 1.00 | 25.33 |
| ATOM | 1407 | OG | SER | D | 66 | 75.428 | 13.550 | 29.364 | 1.00 | 25.27 |
| ATOM | 1408 | N | ARG | D | 67 | 75.564 | 14.771 | 32.247 | 1.00 | 21.92 |
| ATOM | 1409 | CA | ARG | D | 67 | 75.571 | 16.157 | 32.680 | 1.00 | 20.64 |
| ATOM | 1410 | C | ARG | D | 67 | 76.060 | 17.130 | 31.581 | 1.00 | 21.33 |
| ATOM | 1411 | O | ARG | D | 67 | 76.476 | 18.236 | 31.854 | 1.00 | 23.88 |
| ATOM | 1412 | CB | ARG | D | 67 | 76.274 | 16.320 | 34.033 | 1.00 | 24.90 |
| ATOM | 1413 | CG | ARG | D | 67 | 75.630 | 15.331 | 35.037 | 1.00 | 34.18 |
| ATOM | 1414 | CD | ARG | D | 67 | 75.927 | 15.626 | 36.478 | 1.00 | 41.97 |
| ATOM | 1415 | NE | ARG | D | 67 | 77.213 | 15.050 | 36.869 | 1.00 | 42.73 |
| ATOM | 1416 | CZ | ARG | D | 67 | 77.511 | 13.750 | 37.086 | 1.00 | 50.11 |
| ATOM | 1417 | NH1 | ARG | D | 67 | 76.638 | 12.732 | 36.977 | 1.00 | 32.87 |

-continued

| | | | | | | | | | |
|---|---|---|---|---|---|---|---|---|---|
| ATOM | 1418 | NH2 | ARG | D | 67 | 78.761 | 13.476 | 37.438 | 1.00 | 35.89 |
| ATOM | 1419 | N | ILE | D | 68 | 75.922 | 16.675 | 30.337 | 1.00 | 20.99 |
| ATOM | 1420 | CA | ILE | D | 68 | 76.342 | 17.482 | 29.196 | 1.00 | 19.82 |
| ATOM | 1421 | C | ILE | D | 68 | 75.308 | 18.552 | 28.761 | 1.00 | 18.74 |
| ATOM | 1422 | O | ILE | D | 68 | 74.063 | 18.354 | 28.842 | 1.00 | 18.59 |
| ATOM | 1423 | CB | ILE | D | 68 | 76.553 | 16.552 | 27.943 | 1.00 | 22.72 |
| ATOM | 1424 | CG1 | ILE | D | 68 | 77.870 | 15.741 | 28.011 | 1.00 | 22.79 |
| ATOM | 1425 | CG2 | ILE | D | 68 | 76.492 | 17.349 | 26.604 | 1.00 | 23.66 |
| ATOM | 1426 | CD1 | ILE | D | 68 | 77.831 | 14.542 | 27.090 | 1.00 | 24.22 |
| ATOM | 1427 | N | ILE | D | 69 | 75.866 | 19.651 | 28.331 | 1.00 | 17.03 |
| ATOM | 1428 | CA | ILE | D | 69 | 75.133 | 20.812 | 27.729 | 1.00 | 16.07 |
| ATOM | 1429 | C | ILE | D | 69 | 76.113 | 21.177 | 26.568 | 1.00 | 18.47 |
| ATOM | 1430 | O | ILE | D | 69 | 77.135 | 21.853 | 26.785 | 1.00 | 19.41 |
| ATOM | 1431 | CB | ILE | D | 69 | 74.990 | 22.034 | 28.619 | 1.00 | 17.97 |
| ATOM | 1432 | CG1 | ILE | D | 69 | 74.094 | 21.722 | 29.861 | 1.00 | 17.84 |
| ATOM | 1433 | CG2 | ILE | D | 69 | 74.318 | 23.224 | 27.796 | 1.00 | 14.87 |
| ATOM | 1434 | CD1 | ILE | D | 69 | 72.656 | 21.278 | 29.519 | 1.00 | 16.76 |
| ATOM | 1435 | N | SER | D | 70 | 75.800 | 20.705 | 25.359 | 1.00 | 16.82 |
| ATOM | 1436 | CA | SER | D | 70 | 76.694 | 20.960 | 24.186 | 1.00 | 16.67 |
| ATOM | 1437 | C | SER | D | 70 | 76.030 | 21.879 | 23.159 | 1.00 | 16.91 |
| ATOM | 1438 | O | SER | D | 70 | 74.926 | 21.572 | 22.658 | 1.00 | 17.58 |
| ATOM | 1439 | CB | SER | D | 70 | 77.011 | 9.630 | 23.537 | 1.00 | 19.85 |
| ATOM | 1440 | OG | SER | D | 70 | 77.957 | 19.775 | 22.482 | 1.00 | 22.39 |
| ATOM | 1441 | N | VAL | D | 71 | 76.695 | 22.980 | 22.865 | 1.00 | 16.01 |
| ATOM | 1442 | CA | VAL | D | 71 | 76.145 | 23.963 | 21.853 | 1.00 | 17.80 |
| ATOM | 1443 | C | VAL | D | 71 | 76.803 | 23.589 | 20.516 | 1.00 | 22.32 |
| ATOM | 1444 | O | VAL | D | 71 | 78.012 | 23.676 | 20.369 | 1.00 | 23.49 |
| ATOM | 1445 | CB | VAL | D | 71 | 76.329 | 25.399 | 22.263 | 1.00 | 22.83 |
| ATOM | 1446 | CG1 | VAL | D | 71 | 75.507 | 25.648 | 23.572 | 1.00 | 21.98 |
| ATOM | 1447 | CG2 | VAL | D | 71 | 77.809 | 25.768 | 22.399 | 1.00 | 24.06 |
| ATOM | 1448 | N | ASN | D | 72 | 75.970 | 23.121 | 19.584 | 1.00 | 20.48 |
| ATOM | 1449 | CA | ASN | D | 72 | 76.427 | 22.621 | 18.267 | 1.00 | 20.13 |
| ATOM | 1450 | C | ASN | D | 72 | 75.998 | 23.462 | 17.099 | 1.00 | 22.39 |
| ATOM | 1451 | O | ASN | D | 72 | 75.023 | 24.219 | 17.165 | 1.00 | 22.18 |
| ATOM | 1452 | CB | ASN | D | 72 | 75.811 | 21.233 | 18.033 | 1.00 | 21.77 |
| ATOM | 1453 | CG | ASN | D | 72 | 76.097 | 20.254 | 19.165 | 1.00 | 30.59 |
| ATOM | 1454 | OD1 | ASN | D | 72 | 77.069 | 20.428 | 19.917 | 1.00 | 25.69 |
| ATOM | 1455 | ND2 | ASN | D | 72 | 75.228 | 19.241 | 19.317 | 1.00 | 26.90 |
| ATOM | 1456 | N | GLY | D | 73 | 76.708 | 23.283 | 15.994 | 1.00 | 20.53 |
| ATOM | 1457 | CA | GLY | D | 73 | 76.343 | 24.046 | 14.794 | 1.00 | 19.66 |
| ATOM | 1458 | C | GLY | D | 73 | 76.636 | 25.528 | 14.994 | 1.00 | 20.18 |
| ATOM | 1459 | O | GLY | D | 73 | 77.584 | 25.917 | 15.706 | 1.00 | 19.03 |
| ATOM | 1460 | N | ALA | D | 74 | 75.821 | 26.380 | 14.343 | 1.00 | 16.73 |
| ATOM | 1461 | CA | ALA | D | 74 | 76.006 | 27.831 | 14.434 | 1.00 | 16.27 |
| ATOM | 1462 | C | ALA | D | 74 | 75.988 | 28.387 | 15.874 | 1.00 | 17.37 |
| ATOM | 1463 | O | ALA | D | 74 | 76.616 | 29.406 | 16.149 | 1.00 | 18.06 |
| ATOM | 1464 | CB | ALA | D | 74 | 74.987 | 28.616 | 13.530 | 1.00 | 17.59 |
| ATOM | 1465 | N | ALA | D | 75 | 75.226 | 27.686 | 16.729 | 1.00 | 17.95 |
| ATOM | 1466 | CA | ALA | D | 75 | 75.069 | 28.102 | 18.147 | 1.00 | 17.42 |
| ATOM | 1467 | C | ALA | D | 75 | 76.415 | 28.126 | 18.870 | 1.00 | 19.91 |
| ATOM | 1468 | O | ALA | D | 75 | 76.543 | 28.800 | 19.897 | 1.00 | 19.81 |
| ATOM | 1469 | CB | ALA | D | 75 | 74.115 | 27.217 | 18.827 | 1.00 | 18.30 |
| ATOM | 1470 | N | ALA | D | 76 | 77.433 | 27.422 | 18.345 | 1.00 | 16.78 |
| ATOM | 1471 | CA | ALA | D | 76 | 78.747 | 27.455 | 18.982 | 1.00 | 18.31 |
| ATOM | 1472 | C | ALA | D | 76 | 79.347 | 28.882 | 18.991 | 1.00 | 18.92 |
| ATOM | 1473 | O | ALA | D | 76 | 80.266 | 29.184 | 19.740 | 1.00 | 19.50 |
| ATOM | 1474 | CB | ALA | D | 76 | 79.684 | 26.446 | 18.309 | 1.00 | 19.95 |
| ATOM | 1475 | N | HIS | D | 77 | 78.830 | 29.800 | 18.149 | 1.00 | 16.41 |
| ATOM | 1476 | CA | HIS | D | 77 | 79.302 | 31.149 | 18.115 | 1.00 | 17.43 |
| ATOM | 1477 | C | HIS | D | 77 | 78.710 | 32.014 | 19.243 | 1.00 | 18.10 |
| ATOM | 1478 | O | HIS | D | 77 | 79.143 | 33.147 | 19.435 | 1.00 | 20.06 |
| ATOM | 1479 | CB | HIS | D | 77 | 78.785 | 31.847 | 16.791 | 1.00 | 19.37 |
| ATOM | 1480 | CG | HIS | D | 77 | 79.540 | 31.470 | 15.545 | 1.00 | 22.65 |
| ATOM | 1481 | ND1 | HIS | D | 77 | 80.667 | 32.145 | 15.137 | 1.00 | 25.27 |
| ATOM | 1482 | CD2 | HIS | D | 77 | 79.308 | 30.523 | 14.605 | 1.00 | 22.98 |
| ATOM | 1483 | CE1 | HIS | D | 77 | 81.109 | 31.624 | 14.002 | 1.00 | 24.52 |
| ATOM | 1484 | NE2 | HIS | D | 77 | 80.307 | 30.637 | 13.657 | 1.00 | 23.17 |
| ATOM | 1485 | N | CYS | D | 78 | 77.694 | 31.475 | 19.940 | 1.00 | 17.70 |
| ATOM | 1486 | CA | CYS | D | 78 | 76.964 | 32.234 | 20.974 | 1.00 | 18.05 |
| ATOM | 1487 | C | CYS | D | 78 | 77.251 | 31.832 | 22.400 | 1.00 | 21.51 |
| ATOM | 1488 | O | CYS | D | 78 | 76.750 | 32.470 | 23.321 | 1.00 | 21.14 |
| ATOM | 1489 | CB | CYS | D | 78 | 75.466 | 32.047 | 20.753 | 1.00 | 19.61 |
| ATOM | 1490 | SG | CYS | D | 78 | 74.878 | 32.588 | 19.098 | 1.00 | 25.07 |
| ATOM | 1491 | N | ALA | D | 79 | 78.033 | 30.778 | 22.586 | 1.00 | 20.09 |
| ATOM | 1492 | CA | ALA | D | 79 | 78.365 | 30.353 | 23.943 | 1.00 | 19.73 |
| ATOM | 1493 | C | ALA | D | 79 | 79.677 | 29.603 | 23.922 | 1.00 | 25.47 |
| ATOM | 1494 | O | ALA | D | 79 | 80.013 | 28.966 | 22.934 | 1.00 | 23.97 |

-continued

Data Lists

| ATOM | 1495 | CB  | ALA | D | 79 | 77.283 | 29.479 | 24.512 | 1.00 | 20.06 |
| --- | --- | --- | --- | --- | --- | --- | --- | --- | --- | --- |
| ATOM | 1496 | N   | SER | D | 80 | 80.406 | 29.664 | 25.036 | 1.00 | 21.56 |
| ATOM | 1497 | CA  | SER | D | 80 | 81.697 | 28.965 | 25.191 | 1.00 | 22.17 |
| ATOM | 1498 | C   | SER | D | 80 | 81.623 | 28.023 | 26.379 | 1.00 | 23.37 |
| ATOM | 1499 | O   | SER | D | 80 | 80.792 | 28.213 | 27.275 | 1.00 | 21.62 |
| ATOM | 1500 | CB  | SER | D | 80 | 82.824 | 29.931 | 25.485 | 1.00 | 25.03 |
| ATOM | 1501 | OG  | SER | D | 80 | 82.930 | 30.986 | 24.543 | 1.00 | 28.26 |
| ATOM | 1502 | N   | VAL | D | 81 | 82.499 | 27.021 | 26.388 | 1.00 | 18.88 |
| ATOM | 1503 | CA  | VAL | D | 81 | 82.548 | 26.053 | 27.491 | 1.00 | 19.13 |
| ATOM | 1504 | C   | VAL | D | 81 | 82.739 | 26.876 | 28.769 | 1.00 | 21.75 |
| ATOM | 1505 | O   | VAL | D | 81 | 83.558 | 27.824 | 28.819 | 1.00 | 20.90 |
| ATOM | 1506 | CB  | VAL | D | 81 | 83.722 | 25.072 | 27.272 | 1.00 | 21.73 |
| ATOM | 1507 | CG1 | VAL | D | 81 | 83.986 | 24.271 | 28.562 | 1.00 | 22.57 |
| ATOM | 1508 | CG2 | VAL | D | 81 | 83.366 | 24.099 | 26.155 | 1.00 | 21.80 |
| ATOM | 1509 | N   | GLY | D | 82 | 81.973 | 26.526 | 29.798 | 1.00 | 18.71 |
| ATOM | 1510 | CA  | GLY | D | 82 | 82.060 | 27.276 | 31.055 | 1.00 | 18.70 |
| ATOM | 1511 | C   | GLY | D | 82 | 81.007 | 28.365 | 31.234 | 1.00 | 22.87 |
| ATOM | 1512 | O   | GLY | D | 82 | 80.782 | 28.830 | 32.338 | 1.00 | 22.78 |
| ATOM | 1513 | N   | ASP | D | 83 | 80.366 | 28.835 | 30.145 | 1.00 | 16.66 |
| ATOM | 1514 | CA  | ASP | D | 83 | 79.356 | 29.867 | 30.305 | 1.00 | 16.76 |
| ATOM | 1515 | C   | ASP | D | 83 | 78.131 | 29.322 | 31.070 | 1.00 | 16.77 |
| ATOM | 1516 | O   | ASP | D | 83 | 77.748 | 28.153 | 30.896 | 1.00 | 17.18 |
| ATOM | 1517 | CB  | ASP | D | 83 | 78.861 | 30.294 | 28.908 | 1.00 | 18.79 |
| ATOM | 1518 | CG  | ASP | D | 83 | 79.852 | 31.196 | 28.164 | 1.00 | 22.59 |
| ATOM | 1519 | OD1 | ASP | D | 83 | 80.935 | 31.544 | 28.680 | 1.00 | 20.93 |
| ATOM | 1520 | OD2 | ASP | D | 83 | 79.519 | 31.615 | 27.015 | 1.00 | 21.88 |
| ATOM | 1521 | N   | ILE | D | 84 | 77.515 | 30.198 | 31.860 | 1.00 | 17.58 |
| ATOM | 1522 | CA  | ILE | D | 84 | 76.300 | 29.822 | 32.603 | 1.00 | 17.77 |
| ATOM | 1523 | C   | ILE | D | 84 | 75.119 | 30.302 | 31.751 | 1.00 | 17.52 |
| ATOM | 1524 | O   | ILE | D | 84 | 75.119 | 31.474 | 31.351 | 1.00 | 16.51 |
| ATOM | 1525 | CB  | ILE | D | 84 | 76.296 | 30.573 | 33.935 | 1.00 | 21.87 |
| ATOM | 1526 | CG1 | ILE | D | 84 | 77.513 | 30.116 | 34.766 | 1.00 | 22.20 |
| ATOM | 1527 | CG2 | ILE | D | 84 | 74.978 | 30.346 | 34.726 | 1.00 | 22.70 |
| ATOM | 1528 | CD1 | ILE | D | 84 | 77.676 | 31.008 | 36.011 | 1.00 | 27.68 |
| ATOM | 1529 | N   | VAL | D | 85 | 74.192 | 29.388 | 31.497 | 1.00 | 16.68 |
| ATOM | 1530 | CA  | VAL | D | 85 | 73.007 | 29.731 | 30.686 | 1.00 | 14.93 |
| ATOM | 1531 | C   | VAL | D | 85 | 71.700 | 29.265 | 31.326 | 1.00 | 18.77 |
| ATOM | 1532 | O   | VAL | D | 85 | 71.702 | 28.445 | 32.264 | 1.00 | 18.51 |
| ATOM | 1533 | CB  | VAL | D | 85 | 73.144 | 29.098 | 29.266 | 1.00 | 15.49 |
| ATOM | 1534 | CG1 | VAL | D | 85 | 74.452 | 29.475 | 28.627 | 1.00 | 16.44 |
| ATOM | 1535 | CG2 | VAL | D | 85 | 73.026 | 27.645 | 29.306 | 1.00 | 14.40 |
| ATOM | 1536 | N   | ILE | D | 86 | 70.571 | 29.792 | 30.807 | 1.00 | 14.77 |
| ATOM | 1537 | CA  | ILE | D | 86 | 69.244 | 29.418 | 31.229 | 1.00 | 15.52 |
| ATOM | 1538 | C   | ILE | D | 86 | 68.618 | 28.876 | 29.933 | 1.00 | 15.28 |
| ATOM | 1539 | O   | ILE | D | 86 | 68.730 | 29.572 | 28.899 | 1.00 | 15.56 |
| ATOM | 1540 | CB  | ILE | D | 86 | 68.442 | 30.582 | 31.786 | 1.00 | 18.22 |
| ATOM | 1541 | CG1 | ILE | D | 86 | 69.034 | 31.030 | 33.158 | 1.00 | 19.52 |
| ATOM | 1542 | CG2 | ILE | D | 86 | 66.998 | 30.177 | 31.976 | 1.00 | 18.36 |
| ATOM | 1543 | CD1 | ILE | D | 86 | 68.686 | 32.448 | 33.495 | 1.00 | 25.25 |
| ATOM | 1544 | N   | ILE | D | 87 | 68.087 | 27.692 | 29.954 | 1.00 | 11.80 |
| ATOM | 1545 | CA  | ILE | D | 87 | 67.466 | 27.037 | 28.747 | 1.00 | 11.37 |
| ATOM | 1546 | C   | ILE | D | 87 | 65.989 | 26.902 | 29.021 | 1.00 | 16.80 |
| ATOM | 1547 | O   | ILE | D | 87 | 65.585 | 26.259 | 30.043 | 1.00 | 15.75 |
| ATOM | 1548 | CB  | ILE | D | 87 | 68.096 | 25.681 | 28.476 | 1.00 | 14.04 |
| ATOM | 1549 | CG1 | ILE | D | 87 | 69.636 | 25.844 | 28.325 | 1.00 | 14.68 |
| ATOM | 1550 | CG2 | ILE | D | 87 | 67.438 | 24.977 | 27.201 | 1.00 | 16.46 |
| ATOM | 1551 | CD1 | ILE | D | 87 | 70.419 | 24.558 | 27.961 | 1.00 | 16.93 |
| ATOM | 1552 | N   | ALA | D | 88 | 65.127 | 27.457 | 28.161 | 1.00 | 13.54 |
| ATOM | 1553 | CA  | ALA | D | 88 | 63.667 | 27.410 | 28.397 | 1.00 | 12.01 |
| ATOM | 1554 | C   | ALA | D | 88 | 62.870 | 26.916 | 27.216 | 1.00 | 15.27 |
| ATOM | 1555 | O   | ALA | D | 88 | 63.341 | 27.080 | 26.077 | 1.00 | 14.13 |
| ATOM | 1556 | CB  | ALA | D | 88 | 63.197 | 28.842 | 28.683 | 1.00 | 12.68 |
| ATOM | 1557 | N   | SER | D | 89 | 61.703 | 26.359 | 27.432 | 1.00 | 11.75 |
| ATOM | 1558 | CA  | SER | D | 89 | 60.793 | 26.000 | 26.336 | 1.00 |  9.22 |
| ATOM | 1559 | C   | SER | D | 89 | 59.463 | 26.672 | 26.691 | 1.00 | 13.85 |
| ATOM | 1560 | O   | SER | D | 89 | 59.122 | 26.881 | 27.894 | 1.00 | 12.02 |
| ATOM | 1561 | CB  | SER | D | 89 | 60.657 | 24.533 | 26.038 | 1.00 | 13.00 |
| ATOM | 1562 | OG  | SER | D | 89 | 59.637 | 23.875 | 26.787 | 1.00 | 13.68 |
| ATOM | 1563 | N   | PHE | D | 90 | 58.652 | 27.010 | 25.690 | 1.00 |  9.51 |
| ATOM | 1564 | CA  | PHE | D | 90 | 57.352 | 27.650 | 25.837 | 1.00 | 10.69 |
| ATOM | 1565 | C   | PHE | D | 90 | 56.272 | 26.831 | 25.169 | 1.00 | 14.12 |
| ATOM | 1566 | O   | PHE | D | 90 | 56.519 | 26.218 | 24.124 | 1.00 | 13.43 |
| ATOM | 1567 | CB  | PHE | D | 90 | 57.381 | 29.069 | 25.211 | 1.00 |  9.99 |
| ATOM | 1568 | CG  | PHE | D | 90 | 58.172 | 30.051 | 26.052 | 1.00 |  8.63 |
| ATOM | 1569 | CD1 | PHE | D | 90 | 59.569 | 30.106 | 25.972 | 1.00 | 12.75 |
| ATOM | 1570 | CD2 | PHE | D | 90 | 57.492 | 30.917 | 26.943 | 1.00 |  9.84 |
| ATOM | 1571 | CE1 | PHE | D | 90 | 60.296 | 31.033 | 26.745 | 1.00 | 12.66 |

-continued

Data Lists

| | | | | | | | | | |
|---|---|---|---|---|---|---|---|---|---|
| ATOM | 1572 | CE2 | PHE | D | 90 | 58.223 | 31.786 | 27.752 | 1.00 | 11.34 |
| ATOM | 1573 | CZ | PHE | D | 90 | 59.576 | 31.884 | 27.669 | 1.00 | 11.79 |
| ATOM | 1574 | N | VAL | D | 91 | 55.074 | 26.811 | 25.733 | 1.00 | 11.04 |
| ATOM | 1575 | CA | VAL | D | 91 | 53.934 | 26.075 | 25.155 | 1.00 | 8.97 |
| ATOM | 1576 | C | VAL | D | 91 | 52.749 | 27.000 | 25.053 | 1.00 | 12.88 |
| ATOM | 1577 | O | VAL | D | 91 | 52.705 | 28.071 | 25.735 | 1.00 | 13.37 |
| ATOM | 1578 | CB | VAL | D | 91 | 53.519 | 24.811 | 25.939 | 1.00 | 11.62 |
| ATOM | 1579 | CG1 | VAL | D | 91 | 54.527 | 23.721 | 25.805 | 1.00 | 11.91 |
| ATOM | 1580 | CG2 | VAL | D | 91 | 53.294 | 25.194 | 27.489 | 1.00 | 13.43 |
| ATOM | 1581 | N | THR | D | 92 | 51.759 | 26.638 | 24.210 | 1.00 | 11.67 |
| ATOM | 1582 | CA | THR | D | 92 | 50.571 | 27.439 | 24.086 | 1.00 | 9.61 |
| ATOM | 1583 | C | THR | D | 92 | 49.326 | 26.678 | 24.633 | 1.00 | 8.31 |
| ATOM | 1584 | O | THR | D | 92 | 49.266 | 25.473 | 24.646 | 1.00 | 11.35 |
| ATOM | 1585 | CB | THR | D | 92 | 50.371 | 27.971 | 22.630 | 1.00 | 12.02 |
| ATOM | 1586 | OG1 | THR | D | 92 | 50.296 | 26.819 | 21.738 | 1.00 | 17.42 |
| ATOM | 1587 | CG2 | THR | D | 92 | 51.481 | 28.893 | 22.269 | 1.00 | 11.07 |
| ATOM | 1588 | N | MET | D | 93 | 48.330 | 27.441 | 25.059 | 1.00 | 10.31 |
| ATOM | 1589 | CA | MET | D | 93 | 47.103 | 26.859 | 25.667 | 1.00 | 10.55 |
| ATOM | 1590 | C | MET | D | 93 | 46.090 | 27.986 | 25.846 | 1.00 | 10.55 |
| ATOM | 1591 | O | MET | D | 93 | 46.444 | 29.174 | 25.900 | 1.00 | 11.69 |
| ATOM | 1592 | CB | MET | D | 93 | 47.421 | 26.236 | 27.109 | 1.00 | 11.27 |
| ATOM | 1593 | CG | MET | D | 93 | 47.856 | 27.339 | 28.054 | 1.00 | 11.07 |
| ATOM | 1594 | SD | MET | D | 93 | 48.572 | 26.650 | 29.641 | 1.00 | 13.35 |
| ATOM | 1595 | CE | MET | D | 93 | 50.133 | 26.102 | 28.965 | 1.00 | 13.30 |
| ATOM | 1596 | N | PRO | D | 94 | 44.820 | 27.596 | 25.967 | 1.00 | 10.89 |
| ATOM | 1597 | CA | PRO | D | 94 | 43.757 | 28.594 | 26.172 | 1.00 | 10.92 |
| ATOM | 1598 | C | PRO | D | 94 | 43.959 | 29.439 | 27.445 | 1.00 | 13.89 |
| ATOM | 1599 | O | PRO | D | 94 | 44.529 | 28.930 | 28.444 | 1.00 | 13.64 |
| ATOM | 1600 | CB | PRO | D | 94 | 42.492 | 27.750 | 26.291 | 1.00 | 15.15 |
| ATOM | 1601 | CG | PRO | D | 94 | 42.839 | 26.445 | 25.629 | 1.00 | 18.73 |
| ATOM | 1602 | CD | PRO | D | 94 | 44.315 | 26.240 | 25.823 | 1.00 | 13.59 |
| ATOM | 1603 | N | ASP | D | 95 | 43.535 | 30.684 | 27.413 | 1.00 | 12.77 |
| ATOM | 1604 | CA | ASP | D | 95 | 43.665 | 31.614 | 28.524 | 1.00 | 11.85 |
| ATOM | 1605 | C | ASP | D | 95 | 43.174 | 30.951 | 29.847 | 1.00 | 12.73 |
| ATOM | 1606 | O | ASP | D | 95 | 43.865 | 31.103 | 30.918 | 1.00 | 14.23 |
| ATOM | 1607 | CB | ASP | D | 95 | 42.811 | 32.862 | 28.257 | 1.00 | 13.88 |
| ATOM | 1608 | CG | ASP | D | 95 | 42.966 | 33.903 | 29.322 | 1.00 | 16.93 |
| ATOM | 1609 | OD1 | ASP | D | 95 | 44.066 | 34.422 | 29.557 | 1.00 | 15.12 |
| ATOM | 1610 | OD2 | ASP | D | 95 | 41.944 | 34.159 | 30.004 | 1.00 | 25.27 |
| ATOM | 1611 | N | GLU | D | 96 | 42.037 | 30.280 | 29.777 | 1.00 | 11.92 |
| ATOM | 1612 | CA | GLU | D | 96 | 41.450 | 29.634 | 31.006 | 1.00 | 13.09 |
| ATOM | 1613 | C | GLU | D | 96 | 42.418 | 28.668 | 31.670 | 1.00 | 17.50 |
| ATOM | 1614 | O | GLU | D | 96 | 42.463 | 28.607 | 32.916 | 1.00 | 17.59 |
| ATOM | 1615 | CB | GLU | D | 96 | 40.194 | 28.900 | 30.623 | 1.00 | 15.73 |
| ATOM | 1616 | CG | GLU | D | 96 | 39.407 | 28.382 | 31.819 | 1.00 | 27.44 |
| ATOM | 1617 | CD | GLU | D | 96 | 39.718 | 26.953 | 32.150 | 1.00 | 46.48 |
| ATOM | 1618 | OE1 | GLU | D | 96 | 40.247 | 26.230 | 31.298 | 1.00 | 32.53 |
| ATOM | 1619 | OE2 | GLU | D | 96 | 39.416 | 26.541 | 33.300 | 1.00 | 50.29 |
| ATOM | 1620 | N | GLU | D | 97 | 43.184 | 27.904 | 30.898 | 1.00 | 13.12 |
| ATOM | 1621 | CA | GLU | D | 97 | 44.151 | 26.962 | 31.475 | 1.00 | 11.58 |
| ATOM | 1622 | C | GLU | D | 97 | 45.417 | 27.747 | 31.906 | 1.00 | 14.13 |
| ATOM | 1623 | O | GLU | D | 97 | 46.124 | 27.431 | 32.874 | 1.00 | 14.05 |
| ATOM | 1624 | CB | GLU | D | 97 | 44.553 | 25.876 | 30.429 | 1.00 | 10.79 |
| ATOM | 1625 | CG | GLU | D | 97 | 43.463 | 24.971 | 30.050 | 1.00 | 12.84 |
| ATOM | 1626 | CD | GLU | D | 97 | 43.862 | 23.894 | 29.037 | 1.00 | 16.10 |
| ATOM | 1627 | OE1 | GLU | D | 97 | 44.997 | 23.908 | 28.435 | 1.00 | 17.56 |
| ATOM | 1628 | OE2 | GLU | D | 97 | 43.042 | 22.981 | 28.897 | 1.00 | 19.58 |
| ATOM | 1629 | N | ALA | D | 98 | 45.828 | 28.763 | 31.147 | 1.00 | 11.26 |
| ATOM | 1630 | CA | ALA | D | 98 | 47.011 | 29.521 | 31.441 | 1.00 | 12.13 |
| ATOM | 1631 | C | ALA | D | 98 | 47.025 | 30.209 | 32.830 | 1.00 | 12.78 |
| ATOM | 1632 | O | ALA | D | 98 | 48.121 | 30.395 | 33.423 | 1.00 | 12.87 |
| ATOM | 1633 | CB | ALA | D | 98 | 47.161 | 30.609 | 30.303 | 1.00 | 13.93 |
| ATOM | 1634 | N | ARG | D | 99 | 45.795 | 30.577 | 33.268 | 1.00 | 13.12 |
| ATOM | 1635 | CA | ARG | D | 99 | 45.668 | 31.263 | 34.534 | 1.00 | 13.91 |
| ATOM | 1636 | C | ARG | D | 99 | 46.164 | 30.394 | 35.692 | 1.00 | 15.52 |
| ATOM | 1637 | O | ARG | D | 99 | 46.555 | 30.998 | 36.715 | 1.00 | 16.74 |
| ATOM | 1638 | CB | ARG | D | 99 | 44.232 | 31.694 | 34.717 | 1.00 | 13.81 |
| ATOM | 1639 | CG | ARG | D | 99 | 43.930 | 32.832 | 33.737 | 1.00 | 21.54 |
| ATOM | 1640 | CD | ARG | D | 99 | 42.544 | 33.302 | 33.768 | 1.00 | 31.31 |
| ATOM | 1641 | NE | ARG | D | 99 | 42.382 | 34.329 | 32.737 | 1.00 | 34.14 |
| ATOM | 1642 | CZ | ARG | D | 99 | 42.824 | 35.587 | 32.820 | 1.00 | 39.78 |
| ATOM | 1643 | NH1 | ARG | D | 99 | 43.448 | 36.028 | 33.912 | 1.00 | 39.29 |
| ATOM | 1644 | NH2 | ARG | D | 99 | 42.622 | 36.428 | 31.821 | 1.00 | 34.68 |
| ATOM | 1645 | N | THR | D | 100 | 46.189 | 29.072 | 35.553 | 1.00 | 12.99 |
| ATOM | 1646 | CA | THR | D | 100 | 46.668 | 28.209 | 36.674 | 1.00 | 13.08 |
| ATOM | 1647 | C | THR | D | 100 | 47.916 | 27.391 | 36.307 | 1.00 | 15.62 |
| ATOM | 1648 | O | THR | D | 100 | 48.408 | 26.541 | 37.068 | 1.00 | 16.66 |

-continued

Data Lists

| ATOM | 1649 | CB | THR | D | 100 | 45.537 | 27.276 | 37.099 | 1.00 | 15.79 |
|------|------|-----|-----|---|-----|--------|--------|--------|------|-------|
| ATOM | 1650 | OG1 | THR | D | 100 | 45.017 | 26.550 | 35.988 | 1.00 | 14.58 |
| ATOM | 1651 | CG2 | THR | D | 100 | 44.344 | 28.091 | 37.708 | 1.00 | 15.05 |
| ATOM | 1652 | N | TRP | D | 101 | 48.490 | 27.635 | 35.105 | 1.00 | 14.25 |
| ATOM | 1653 | CA | TRP | D | 101 | 49.645 | 26.857 | 34.699 | 1.00 | 13.12 |
| ATOM | 1654 | C | TRP | D | 101 | 50.846 | 27.042 | 35.554 | 1.00 | 15.17 |
| ATOM | 1655 | O | TRP | D | 101 | 51.111 | 28.163 | 36.042 | 1.00 | 16.82 |
| ATOM | 1656 | CB | TRP | D | 101 | 49.970 | 27.286 | 33.191 | 1.00 | 11.79 |
| ATOM | 1657 | CG | TRP | D | 101 | 51.197 | 26.624 | 32.676 | 1.00 | 10.50 |
| ATOM | 1658 | CD1 | TRP | D | 101 | 52.416 | 27.164 | 32.527 | 1.00 | 12.40 |
| ATOM | 1659 | CD2 | TRP | D | 101 | 51.317 | 25.240 | 32.383 | 1.00 | 12.89 |
| ATOM | 1660 | NE1 | TRP | D | 101 | 53.292 | 26.208 | 32.121 | 1.00 | 12.65 |
| ATOM | 1661 | CE2 | TRP | D | 101 | 52.659 | 25.019 | 32.000 | 1.00 | 13.88 |
| ATOM | 1662 | CE3 | TRP | D | 101 | 50.419 | 24.168 | 32.362 | 1.00 | 15.74 |
| ATOM | 1663 | CZ2 | TRP | D | 101 | 53.144 | 23.769 | 31.624 | 1.00 | 16.20 |
| ATOM | 1664 | CZ3 | TRP | D | 101 | 50.898 | 22.888 | 32.009 | 1.00 | 19.25 |
| ATOM | 1665 | CH2 | TRP | D | 101 | 52.266 | 22.699 | 31.649 | 1.00 | 19.62 |
| ATOM | 1666 | N | ARG | D | 102 | 51.613 | 25.952 | 35.714 | 1.00 | 15.08 |
| ATOM | 1667 | CA | ARG | D | 102 | 52.844 | 25.993 | 36.481 | 1.00 | 15.90 |
| ATOM | 1668 | C | ARG | D | 102 | 53.983 | 25.375 | 35.637 | 1.00 | 11.33 |
| ATOM | 1669 | O | ARG | D | 102 | 53.846 | 24.253 | 35.202 | 1.00 | 14.41 |
| ATOM | 1670 | CB | ARG | D | 102 | 52.703 | 25.128 | 37.779 | 1.00 | 18.89 |
| ATOM | 1671 | CG | ARG | D | 102 | 51.612 | 25.639 | 38.780 | 1.00 | 24.40 |
| ATOM | 1672 | CD | ARG | D | 102 | 51.559 | 24.821 | 40.096 | 1.00 | 22.77 |
| ATOM | 1673 | NE | ARG | D | 102 | 52.794 | 24.906 | 40.846 | 1.00 | 27.18 |
| ATOM | 1674 | CZ | ARG | D | 102 | 53.120 | 25.887 | 41.689 | 1.00 | 28.35 |
| ATOM | 1675 | NH1 | ARG | D | 102 | 52.313 | 26.911 | 41.893 | 1.00 | 23.60 |
| ATOM | 1676 | NH2 | ARG | D | 102 | 54.280 | 25.844 | 42.314 | 1.00 | 31.92 |
| ATOM | 1677 | N | PRO | D | 103 | 55.088 | 26.106 | 35.497 | 1.00 | 12.26 |
| ATOM | 1678 | CA | PRO | D | 103 | 56.234 | 25.566 | 34.721 | 1.00 | 13.54 |
| ATOM | 1679 | C | PRO | D | 103 | 57.047 | 24.562 | 35.500 | 1.00 | 17.32 |
| ATOM | 1680 | O | PRO | D | 103 | 56.956 | 24.539 | 36.792 | 1.00 | 16.83 |
| ATOM | 1681 | CB | PRO | D | 103 | 57.114 | 26.794 | 34.506 | 1.00 | 14.38 |
| ATOM | 1682 | CG | PRO | D | 103 | 56.894 | 27.640 | 35.767 | 1.00 | 22.25 |
| ATOM | 1683 | CD | PRO | D | 103 | 55.363 | 27.456 | 36.011 | 1.00 | 16.38 |
| ATOM | 1684 | N | ASN | D | 104 | 57.859 | 23.759 | 34.781 | 1.00 | 13.82 |
| ATOM | 1685 | CA | ASN | D | 104 | 58.744 | 22.758 | 35.377 | 1.00 | 12.48 |
| ATOM | 1686 | C | ASN | D | 104 | 60.121 | 23.389 | 35.504 | 1.00 | 19.52 |
| ATOM | 1687 | O | ASN | D | 104 | 60.775 | 23.647 | 34.460 | 1.00 | 16.91 |
| ATOM | 1688 | CB | ASN | D | 104 | 58.798 | 21.477 | 34.539 | 1.00 | 13.72 |
| ATOM | 1689 | CG | ASN | D | 104 | 57.470 | 20.884 | 34.345 | 1.00 | 19.91 |
| ATOM | 1690 | OD1 | ASN | D | 104 | 56.775 | 20.587 | 35.338 | 1.00 | 17.05 |
| ATOM | 1691 | ND2 | ASN | D | 104 | 57.032 | 20.718 | 33.087 | 1.00 | 20.70 |
| ATOM | 1692 | N | VAL | D | 105 | 60.613 | 23.649 | 36.722 | 1.00 | 17.67 |
| ATOM | 1693 | CA | VAL | D | 105 | 61.885 | 24.295 | 36.850 | 1.00 | 16.36 |
| ATOM | 1694 | C | VAL | D | 105 | 62.907 | 23.448 | 37.546 | 1.00 | 21.93 |
| ATOM | 1695 | O | VAL | D | 105 | 62.601 | 22.863 | 38.602 | 1.00 | 22.45 |
| ATOM | 1696 | CB | VAL | D | 105 | 61.775 | 25.635 | 37.634 | 1.00 | 18.76 |
| ATOM | 1697 | CG1 | VAL | D | 105 | 63.106 | 26.314 | 37.743 | 1.00 | 19.86 |
| ATOM | 1698 | CG2 | VAL | D | 105 | 60.642 | 26.573 | 37.039 | 1.00 | 19.00 |
| ATOM | 1699 | N | ALA | D | 106 | 64.102 | 23.365 | 36.974 | 1.00 | 20.08 |
| ATOM | 1700 | CA | ALA | D | 106 | 65.232 | 22.610 | 37.580 | 1.00 | 19.28 |
| ATOM | 1701 | C | ALA | D | 106 | 66.330 | 23.614 | 37.866 | 1.00 | 22.54 |
| ATOM | 1702 | O | ALA | D | 106 | 66.699 | 24.410 | 37.000 | 1.00 | 20.02 |
| ATOM | 1703 | CB | ALA | D | 106 | 65.733 | 21.552 | 36.689 | 1.00 | 19.59 |
| ATOM | 1704 | N | TYR | D | 107 | 66.894 | 23.609 | 39.098 | 1.00 | 21.77 |
| ATOM | 1705 | CA | TYR | D | 107 | 67.952 | 24.556 | 39.469 | 1.00 | 22.90 |
| ATOM | 1706 | C | TYR | D | 107 | 69.287 | 23.841 | 39.546 | 1.00 | 25.98 |
| ATOM | 1707 | O | TYR | D | 107 | 69.335 | 22.668 | 39.882 | 1.00 | 25.22 |
| ATOM | 1708 | CB | TYR | D | 107 | 67.646 | 25.222 | 40.818 | 1.00 | 25.00 |
| ATOM | 1709 | CG | TYR | D | 107 | 66.482 | 26.167 | 40.752 | 1.00 | 24.25 |
| ATOM | 1710 | CD1 | TYR | D | 107 | 66.651 | 27.484 | 40.330 | 1.00 | 26.30 |
| ATOM | 1711 | CD2 | TYR | D | 107 | 65.202 | 25.733 | 41.102 | 1.00 | 25.93 |
| ATOM | 1712 | CE1 | TYR | D | 107 | 65.588 | 28.344 | 40.270 | 1.00 | 29.13 |
| ATOM | 1713 | CE2 | TYR | D | 107 | 64.125 | 26.600 | 41.056 | 1.00 | 25.26 |
| ATOM | 1714 | CZ | TYR | D | 107 | 64.325 | 27.900 | 40.658 | 1.00 | 31.88 |
| ATOM | 1715 | OH | TYR | D | 107 | 63.238 | 28.756 | 40.594 | 1.00 | 35.96 |
| ATOM | 1716 | N | PHE | D | 108 | 70.356 | 24.556 | 39.194 | 1.00 | 26.53 |
| ATOM | 1717 | CA | PHE | D | 108 | 71.677 | 23.953 | 39.185 | 1.00 | 25.71 |
| ATOM | 1718 | C | PHE | D | 108 | 72.739 | 24.852 | 39.791 | 1.00 | 31.22 |
| ATOM | 1719 | O | PHE | D | 108 | 72.611 | 26.079 | 39.860 | 1.00 | 28.62 |
| ATOM | 1720 | CB | PHE | D | 108 | 72.145 | 23.669 | 37.719 | 1.00 | 25.29 |
| ATOM | 1721 | CG | PHE | D | 108 | 71.302 | 22.678 | 36.974 | 1.00 | 21.78 |
| ATOM | 1722 | CD1 | PHE | D | 108 | 70.101 | 23.072 | 36.357 | 1.00 | 19.05 |
| ATOM | 1723 | CD2 | PHE | D | 108 | 71.708 | 21.360 | 36.850 | 1.00 | 20.20 |
| ATOM | 1724 | CE1 | PHE | D | 108 | 69.333 | 22.156 | 35.675 | 1.00 | 19.07 |
| ATOM | 1725 | CE2 | PHE | D | 108 | 70.965 | 20.441 | 36.163 | 1.00 | 22.77 |

-continued

Data Lists

| ATOM | 1726 | CZ | PHE | D | 108 | 69.733 | 20.879 | 35.546 | 1.00 | 20.24 |
|------|------|------|-----|---|-----|--------|--------|--------|------|-------|
| ATOM | 1727 | N | GLU | D | 109 | 73.815 | 24.196 | 40.198 | 1.00 | 30.97 |
| ATOM | 1728 | CA | GLU | D | 109 | 74.970 | 24.855 | 40.797 | 1.00 | 32.90 |
| ATOM | 1729 | C | GLU | D | 109 | 76.205 | 24.037 | 40.466 | 1.00 | 33.93 |
| ATOM | 1730 | O | GLU | D | 109 | 76.114 | 22.898 | 40.055 | 1.00 | 30.42 |
| ATOM | 1731 | CB | GLU | D | 109 | 74.826 | 24.827 | 42.326 | 1.00 | 35.17 |
| ATOM | 1732 | CG | GLU | D | 109 | 74.907 | 23.400 | 42.875 | 1.00 | 44.89 |
| ATOM | 1733 | CD | GLU | D | 109 | 74.607 | 23.314 | 44.352 | 1.00 | 68.70 |
| ATOM | 1734 | OE1 | GLU | D | 109 | 74.608 | 24.376 | 45.020 | 1.00 | 58.38 |
| ATOM | 1735 | OE2 | GLU | D | 109 | 74.358 | 22.182 | 44.842 | 1.00 | 66.11 |
| ATOM | 1736 | N | GLY | D | 110 | 77.379 | 24.614 | 40.702 | 1.00 | 33.06 |
| ATOM | 1737 | CA | GLY | D | 110 | 78.616 | 23.899 | 40.454 | 1.00 | 32.35 |
| ATOM | 1738 | C | GLY | D | 110 | 78.689 | 23.323 | 39.056 | 1.00 | 35.50 |
| ATOM | 1739 | O | GLY | D | 110 | 78.449 | 24.039 | 38.072 | 1.00 | 35.53 |
| ATOM | 1740 | N | ASP | D | 111 | 79.074 | 22.063 | 38.971 | 1.00 | 29.97 |
| ATOM | 1741 | CA | ASP | D | 111 | 79.232 | 21.400 | 37.693 | 1.00 | 31.05 |
| ATOM | 1742 | C | ASP | D | 111 | 77.960 | 20.672 | 37.285 | 1.00 | 30.82 |
| ATOM | 1743 | O | ASP | D | 111 | 77.886 | 19.418 | 37.225 | 1.00 | 28.67 |
| ATOM | 1744 | CB | ASP | D | 111 | 80.465 | 20.495 | 37.717 | 1.00 | 33.49 |
| ATOM | 1745 | CG | ASP | D | 111 | 80.534 | 19.558 | 36.541 | 1.00 | 44.31 |
| ATOM | 1746 | OD1 | ASP | D | 111 | 80.219 | 19.999 | 35.400 | 1.00 | 46.12 |
| ATOM | 1747 | OD2 | ASP | D | 111 | 80.882 | 18.378 | 36.760 | 1.00 | 41.60 |
| ATOM | 1748 | N | ASN | D | 112 | 76.959 | 21.480 | 36.967 | 1.00 | 27.75 |
| ATOM | 1749 | CA | ASN | D | 112 | 75.682 | 20.951 | 36.556 | 1.00 | 25.85 |
| ATOM | 1750 | C | ASN | D | 112 | 75.072 | 20.013 | 37.556 | 1.00 | 28.56 |
| ATOM | 1751 | O | ASN | D | 112 | 74.553 | 18.956 | 37.211 | 1.00 | 24.07 |
| ATOM | 1752 | CB | ASN | D | 112 | 75.744 | 20.367 | 35.149 | 1.00 | 25.14 |
| ATOM | 1753 | CG | ASN | D | 112 | 75.975 | 21.425 | 34.158 | 1.00 | 19.48 |
| ATOM | 1754 | OD1 | ASN | D | 112 | 75.875 | 22.600 | 34.511 | 1.00 | 22.70 |
| ATOM | 1755 | ND2 | ASN | D | 112 | 76.334 | 21.051 | 32.918 | 1.00 | 21.36 |
| ATOM | 1756 | N | GLU | D | 413 | 75.142 | 20.436 | 38.818 | 1.00 | 27.11 |
| ATOM | 1757 | CA | GLU | D | 113 | 74.556 | 19.639 | 39.900 | 1.00 | 28.84 |
| ATOM | 1758 | C | GLU | D | 113 | 73.181 | 20.182 | 40.147 | 1.00 | 27.72 |
| ATOM | 1759 | O | GLU | D | 113 | 73.039 | 21.365 | 40.555 | 1.00 | 26.82 |
| ATOM | 1760 | CB | GLU | D | 113 | 75.388 | 19.695 | 41.177 | 1.00 | 30.87 |
| ATOM | 1761 | CG | GLU | D | 113 | 76.724 | 18.975 | 41.092 | 1.00 | 37.93 |
| ATOM | 1762 | CD | GLU | D | 113 | 76.692 | 17.429 | 41.016 | 1.00 | 59.74 |
| ATOM | 1763 | OE1 | GLU | D | 113 | 75.612 | 16.786 | 40.882 | 1.00 | 46.50 |
| ATOM | 1764 | OE2 | GLU | D | 113 | 77.814 | 16.868 | 41.082 | 1.00 | 59.60 |
| ATOM | 1765 | N | MET | D | 114 | 72.194 | 19.333 | 39.866 | 1.00 | 27.25 |
| ATOM | 1766 | CA | MET | D | 114 | 70.781 | 19.680 | 40.012 | 1.00 | 32.32 |
| ATOM | 1767 | C | MET | D | 114 | 70.391 | 19.716 | 41.452 | 1.00 | 39.86 |
| ATOM | 1768 | O | MET | D | 114 | 70.527 | 18.703 | 42.145 | 1.00 | 40.94 |
| ATOM | 1769 | CB | MET | D | 114 | 69.889 | 18.646 | 39.319 | 1.00 | 34.33 |
| ATOM | 1770 | CG | MET | D | 114 | 68.468 | 19.136 | 39.198 | 1.00 | 36.77 |
| ATOM | 1771 | SD | MET | D | 114 | 67.314 | 17.889 | 38.726 | 1.00 | 39.76 |
| ATOM | 1772 | CE | MET | D | 114 | 67.664 | 17.803 | 36.803 | 1.00 | 31.31 |
| ATOM | 1773 | N | LYS | D | 115 | 69.893 | 20.851 | 41.915 | 1.00 | 37.37 |
| ATOM | 1774 | CA | LYS | D | 115 | 69.488 | 20.983 | 43.324 | 1.00 | 38.95 |
| ATOM | 1775 | C | LYS | D | 115 | 68.169 | 20.274 | 43.622 | 1.00 | 54.19 |
| ATOM | 1776 | O | LYS | D | 115 | 67.301 | 20.213 | 42.705 | 1.00 | 51.66 |
| ATOM | 1777 | CB | LYS | D | 115 | 69.362 | 22.437 | 43.715 | 1.00 | 41.43 |
| ATOM | 1778 | CG | LYS | D | 115 | 70.655 | 23.235 | 43.740 | 1.00 | 47.27 |
| ATOM | 1779 | CD | LYS | D | 115 | 70.334 | 24.681 | 44.041 | 1.00 | 43.78 |
| ATOM | 1780 | CE | LYS | D | 115 | 71.439 | 25.627 | 43.660 | 1.00 | 55.99 |
| ATOM | 1781 | NZ | LYS | D | 115 | 71.276 | 26.945 | 44.363 | 1.00 | 62.59 |
| ATOM | 1783 | OW0 | WAT | G | 1 | 50.690 | 34.966 | 25.739 | 1.00 | 12.46 |
| ATOM | 1784 | OW0 | WAT | G | 2 | 65.358 | 37.341 | 23.976 | 1.00 | 14.50 |
| ATOM | 1785 | OW0 | WAT | G | 3 | 53.112 | 36.553 | 25.090 | 1.00 | 12.96 |
| ATOM | 1786 | OW0 | WAT | G | 4 | 59.501 | 34.869 | 25.680 | 1.00 | 16.21 |
| ATOM | 1787 | OW0 | WAT | G | 5 | 42.457 | 44.697 | 14.900 | 1.00 | 16.96 |
| ATOM | 1788 | OW0 | WAT | G | 6 | 62.264 | 42.848 | 18.466 | 1.00 | 12.78 |
| ATOM | 1789 | OW0 | WAT | G | 7 | 60.346 | 41.648 | 20.211 | 1.00 | 14.43 |
| ATOM | 1790 | OW0 | WAT | G | 8 | 49.376 | 37.618 | 12.957 | 1.00 | 11.87 |
| ATOM | 1791 | OW0 | WAT | G | 9 | 43.082 | 43.742 | 4.464 | 1.00 | 15.75 |
| ATOM | 1792 | OW0 | WAT | G | 10 | 57.736 | 40.739 | 19.570 | 1.00 | 18.14 |
| ATOM | 1793 | OW0 | WAT | G | 11 | 53.768 | 31.148 | 15.023 | 1.00 | 18.49 |
| ATOM | 1794 | OW0 | WAT | G | 12 | 46.397 | 19.640 | 8.284 | 1.00 | 20.49 |
| ATOM | 1795 | OW0 | WAT | G | 13 | 49.398 | 32.153 | 35.416 | 1.00 | 15.58 |
| ATOM | 1796 | OW0 | WAT | G | 14 | 52.292 | 38.335 | 12.919 | 1.00 | 12.77 |
| ATOM | 1797 | OW0 | WAT | G | 15 | 55.884 | 41.199 | 17.565 | 1.00 | 17.15 |
| ATOM | 1798 | OW0 | WAT | G | 16 | 68.646 | 41.874 | 7.890 | 1.00 | 18.45 |
| ATOM | 1799 | OW0 | WAT | G | 17 | 60.172 | 36.501 | 11.568 | 1.00 | 20.08 |
| ATOM | 1800 | OW0 | WAT | G | 18 | 52.295 | 33.705 | 18.070 | 1.00 | 19.24 |
| ATOM | 1801 | OW0 | WAT | G | 19 | 43.878 | 46.628 | 8.547 | 1.00 | 18.83 |
| ATOM | 1802 | OW0 | WAT | G | 20 | 44.503 | 23.424 | 0.796 | 1.00 | 17.45 |
| ATOM | 1803 | OW0 | WAT | G | 21 | 64.440 | 48.899 | 19.979 | 1.00 | 18.93 |

-continued

Data Lists

| ATOM | 1804 | OW0 | WAT | G | 22 | 71.193 | 48.088 | 36.959 | 1.00 | 16.89 |
|------|------|-----|-----|---|----|--------|--------|--------|------|-------|
| ATOM | 1805 | OW0 | WAT | G | 23 | 49.349 | 33.334 | 14.599 | 1.00 | 20.32 |
| ATOM | 1806 | OW0 | WAT | G | 24 | 71.024 | 49.740 | 30.410 | 1.00 | 19.88 |
| ATOM | 1807 | OW0 | WAT | G | 25 | 42.979 | 46.992 | 11.153 | 1.00 | 17.12 |
| ATOM | 1808 | OW0 | WAT | G | 26 | 38.559 | 42.979 | 23.184 | 1.00 | 21.81 |
| ATOM | 1809 | OW0 | WAT | G | 27 | 53.263 | 26.900 | 13.822 | 1.00 | 15.81 |
| ATOM | 1810 | OW0 | WAT | G | 28 | 71.768 | 47.157 | 29.190 | 1.00 | 21.31 |
| ATOM | 1811 | OW0 | WAT | G | 29 | 50.910 | 52.836 | 39.909 | 1.00 | 21.20 |
| ATOM | 1812 | OW0 | WAT | G | 30 | 51.612 | 34.739 | 20.749 | 1.00 | 21.50 |
| ATOM | 1813 | OW0 | WAT | G | 31 | 47.760 | 55.722 | 0.508  | 1.00 | 26.79 |
| ATOM | 1814 | OW0 | WAT | G | 32 | 57.250 | 54.959 | 34.792 | 1.00 | 18.33 |
| ATOM | 1815 | OW0 | WAT | G | 33 | 65.008 | 51.887 | 42.170 | 1.00 | 21.45 |
| ATOM | 1816 | OW0 | WAT | G | 34 | 71.716 | 46.104 | 34.998 | 1.00 | 19.77 |
| ATOM | 1817 | OW0 | WAT | G | 35 | 56.789 | 36.428 | 13.221 | 1.00 | 19.13 |
| ATOM | 1818 | OW0 | WAT | G | 36 | 69.004 | 52.586 | 13.271 | 1.00 | 25.88 |
| ATOM | 1819 | OW0 | WAT | G | 37 | 36.912 | 40.900 | 19.049 | 1.00 | 24.35 |
| ATOM | 1820 | OW0 | WAT | G | 38 | 37.939 | 34.172 | 11.858 | 1.00 | 21.53 |
| ATOM | 1821 | OW0 | WAT | G | 39 | 50.673 | 48.829 | 42.462 | 1.00 | 17.05 |
| ATOM | 1822 | OW0 | WAT | G | 40 | 40.211 | 49.838 | 5.952  | 1.00 | 26.29 |
| ATOM | 1823 | OW0 | WAT | G | 41 | 46.904 | 53.941 | 31.892 | 1.00 | 26.19 |
| ATOM | 1824 | OW0 | WAT | G | 42 | 69.397 | 54.598 | 32.144 | 1.00 | 21.59 |
| ATOM | 1825 | OW0 | WAT | G | 43 | 42.745 | 49.698 | 11.329 | 1.00 | 28.13 |
| ATOM | 1826 | OW0 | WAT | G | 44 | 69.038 | 43.121 | 14.087 | 1.00 | 27.79 |
| ATOM | 1827 | OW0 | WAT | G | 45 | 37.919 | 36.710 | 9.225  | 1.00 | 22.42 |
| ATOM | 1828 | OW0 | WAT | G | 46 | 62.878 | 47.097 | 42.928 | 1.00 | 24.58 |
| ATOM | 1829 | OW0 | WAT | G | 47 | 39.794 | 32.943 | 21.142 | 1.00 | 24.59 |
| ATOM | 1830 | OW0 | WAT | G | 48 | 45.700 | 54.348 | 15.115 | 1.00 | 34.46 |
| ATOM | 1831 | OW0 | WAT | G | 49 | 59.403 | 48.140 | 46.193 | 1.00 | 20.52 |
| ATOM | 1832 | OW0 | WAT | G | 50 | 60.684 | 31.160 | 37.777 | 1.00 | 29.82 |
| ATOM | 1833 | OW0 | WAT | G | 51 | 49.475 | 50.666 | 40.460 | 1.00 | 22.18 |
| ATOM | 1834 | OW0 | WAT | G | 52 | 39.653 | 24.604 | 5.289  | 1.00 | 17.35 |
| ATOM | 1835 | OW0 | WAT | G | 53 | 59.252 | 56.969 | 34.916 | 1.00 | 19.50 |
| ATOM | 1836 | OW0 | WAT | G | 54 | 69.096 | 53.771 | 10.568 | 1.00 | 27.87 |
| ATOM | 1837 | OW0 | WAT | G | 55 | 66.440 | 38.568 | 14.149 | 1.00 | 30.16 |
| ATOM | 1838 | OW0 | WAT | G | 56 | 65.406 | 57.383 | 14.154 | 1.00 | 26.01 |
| ATOM | 1839 | OW0 | WAT | G | 57 | 41.137 | 23.132 | 3.518  | 1.00 | 23.54 |
| ATOM | 1840 | OW0 | WAT | G | 58 | 49.156 | 50.953 | 21.456 | 1.00 | 30.99 |
| ATOM | 1841 | OW0 | WAT | G | 59 | 57.860 | 36.323 | 24.017 | 1.00 | 20.83 |
| ATOM | 1842 | OW0 | WAT | G | 60 | 57.496 | 33.962 | 11.899 | 1.00 | 21.39 |
| ATOM | 1843 | OW0 | WAT | G | 61 | 66.579 | 48.294 | 43.413 | 1.00 | 24.77 |
| ATOM | 1844 | OW0 | WAT | G | 62 | 54.871 | 38.598 | 18.657 | 1.00 | 25.45 |
| ATOM | 1845 | OW0 | WAT | G | 63 | 50.967 | 51.195 | 43.999 | 1.00 | 22.75 |
| ATOM | 1846 | OW0 | WAT | G | 64 | 44.140 | 29.593 | 6.643  | 1.00 | 21.96 |
| ATOM | 1847 | OW0 | WAT | G | 65 | 43.548 | 39.803 | 29.673 | 1.00 | 26.57 |
| ATOM | 1848 | OW0 | WAT | G | 66 | 36.492 | 44.150 | 10.666 | 1.00 | 24.57 |
| ATOM | 1849 | OW0 | WAT | G | 67 | 72.566 | 46.343 | 31.771 | 1.00 | 22.95 |
| ATOM | 1850 | OW0 | WAT | G | 68 | 48.293 | 59.724 | 10.894 | 1.00 | 26.76 |
| ATOM | 1851 | OW0 | WAT | G | 69 | 62.460 | 39.930 | 21.422 | 1.00 | 26.61 |
| ATOM | 1852 | OW0 | WAT | G | 70 | 56.208 | 39.397 | 15.274 | 1.00 | 20.01 |
| ATOM | 1853 | OW0 | WAT | G | 71 | 72.875 | 42.561 | 38.908 | 1.00 | 36.97 |
| ATOM | 1854 | OW0 | WAT | G | 72 | 68.365 | 44.087 | 20.849 | 1.00 | 29.26 |
| ATOM | 1855 | OW0 | WAT | G | 73 | 43.058 | 49.160 | 23.577 | 1.00 | 29.45 |
| ATOM | 1856 | OW0 | WAT | G | 74 | 70.366 | 27.891 | 40.490 | 1.00 | 33.14 |
| ATOM | 1857 | OW0 | WAT | G | 75 | 37.060 | 33.614 | 18.493 | 1.00 | 25.03 |
| ATOM | 1858 | OW0 | WAT | G | 76 | 43.652 | 50.031 | 19.379 | 1.00 | 36.34 |
| ATOM | 1859 | OW0 | WAT | G | 77 | 70.513 | 54.847 | 7.916  | 1.00 | 33.66 |
| ATOM | 1860 | OW0 | WAT | G | 78 | 74.648 | 42.946 | 34.418 | 1.00 | 46.06 |
| ATOM | 1861 | OW0 | WAT | G | 79 | 44.747 | 49.850 | -0.304 | 1.00 | 26.95 |
| ATOM | 1862 | OW0 | WAT | G | 80 | 40.824 | 41.298 | 27.887 | 1.00 | 25.17 |
| ATOM | 1863 | OW0 | WAT | G | 81 | 41.107 | 45.630 | 12.507 | 1.00 | 25.41 |
| ATOM | 1864 | OW0 | WAT | G | 82 | 57.806 | 41.126 | 45.667 | 1.00 | 28.19 |
| ATOM | 1865 | OW0 | WAT | G | 83 | 51.183 | 54.617 | -2.727 | 1.00 | 32.75 |
| ATOM | 1866 | OW0 | WAT | G | 84 | 43.186 | 49.347 | 27.882 | 1.00 | 28.33 |
| ATOM | 1867 | OW0 | WAT | G | 85 | 61.540 | 49.575 | -4.582 | 1.00 | 35.95 |
| ATOM | 1868 | OW0 | WAT | G | 86 | 50.267 | 17.542 | 8.910  | 1.00 | 30.16 |
| ATOM | 1869 | OW0 | WAT | G | 87 | 36.217 | 32.811 | 13.941 | 1.00 | 28.34 |
| ATOM | 1870 | OW0 | WAT | G | 88 | 72.058 | 52.836 | 10.622 | 1.00 | 45.57 |
| ATOM | 1871 | OW0 | WAT | G | 89 | 61.348 | 58.887 | 3.805  | 1.00 | 30.95 |
| ATOM | 1872 | OW0 | WAT | G | 90 | 48.622 | 56.983 | 14.003 | 1.00 | 31.75 |
| ATOM | 1873 | OW0 | WAT | G | 91 | 51.936 | 33.480 | 13.709 | 1.00 | 26.64 |
| ATOM | 1874 | OW0 | WAT | G | 92 | 51.875 | 46.258 | -5.376 | 1.00 | 34.61 |
| ATOM | 1875 | OW0 | WAT | G | 93 | 42.359 | 53.407 | 10.255 | 1.00 | 30.41 |
| ATOM | 1876 | OW0 | WAT | G | 94 | 52.890 | 57.749 | 15.136 | 1.00 | 30.22 |
| ATOM | 1877 | OW0 | WAT | G | 95 | 58.430 | 56.302 | 24.467 | 1.00 | 26.47 |
| ATOM | 1878 | OW0 | WAT | G | 96 | 37.197 | 41.147 | 21.811 | 1.00 | 24.52 |
| ATOM | 1879 | OW0 | WAT | G | 97 | 52.686 | 23.652 | -1.094 | 1.00 | 25.58 |
| ATOM | 1880 | OW0 | WAT | G | 98 | 43.317 | 41.529 | 34.451 | 1.00 | 35.83 |

-continued

Data Lists

| | | | | | | | | | |
|---|---|---|---|---|---|---|---|---|---|
| ATOM | 1881 | OW0 | WAT | G | 99 | 50.916 | 40.421 | 46.697 | 1.00 | 31.62 |
| ATOM | 1882 | OW0 | WAT | G | 100 | 59.444 | 53.045 | −1.297 | 1.00 | 35.13 |
| ATOM | 1883 | OW0 | WAT | G | 101 | 54.344 | 37.059 | 14.071 | 1.00 | 25.37 |
| ATOM | 1884 | OW0 | WAT | G | 102 | 39.161 | 35.171 | 23.645 | 1.00 | 22.49 |
| ATOM | 1885 | OW0 | WAT | G | 103 | 48.196 | 28.696 | 16.212 | 1.00 | 22.74 |
| ATOM | 1886 | OW0 | WAT | G | 104 | 51.803 | 31.025 | 19.010 | 1.00 | 23.17 |
| ATOM | 1887 | OW0 | WAT | G | 105 | 50.671 | 37.681 | 42.927 | 1.00 | 29.64 |
| ATOM | 1888 | OW0 | WAT | G | 106 | 62.180 | 51.664 | −1.624 | 1.00 | 34.04 |
| ATOM | 1889 | OW0 | WAT | G | 107 | 52.524 | 59.538 | 42.266 | 1.00 | 35.09 |
| ATOM | 1890 | OW0 | WAT | G | 108 | 46.932 | 49.006 | 21.391 | 1.00 | 25.94 |
| ATOM | 1891 | OW0 | WAT | G | 109 | 37.499 | 38.570 | 22.800 | 1.00 | 26.50 |
| ATOM | 1892 | OW0 | WAT | G | 110 | 72.898 | 50.305 | 27.829 | 1.00 | 30.56 |
| ATOM | 1893 | OW0 | WAT | G | 111 | 67.993 | 56.760 | 5.901 | 1.00 | 29.70 |
| ATOM | 1894 | OW0 | WAT | G | 112 | 48.644 | 53.571 | −1.398 | 1.00 | 35.84 |
| ATOM | 1895 | OW0 | WAT | G | 113 | 58.963 | 38.275 | 42.967 | 1.00 | 30.25 |
| ATOM | 1896 | OW0 | WAT | G | 114 | 48.644 | 29.728 | 18.792 | 1.00 | 30.45 |
| ATOM | 1897 | OW0 | WAT | G | 115 | 42.373 | 28.434 | 9.504 | 1.00 | 30.65 |
| ATOM | 1898 | OW0 | WAT | G | 116 | 48.337 | 17.998 | 4.927 | 1.00 | 26.85 |
| ATOM | 1899 | OW0 | WAT | G | 117 | 43.367 | 57.024 | 0.108 | 1.00 | 36.26 |
| ATOM | 1900 | OW0 | WAT | G | 118 | 55.991 | 35.183 | 42.088 | 1.00 | 33.36 |
| ATOM | 1901 | OW0 | WAT | G | 119 | 55.166 | 18.825 | 3.751 | 1.00 | 39.06 |
| ATOM | 1902 | OW0 | WAT | G | 120 | 36.538 | 34.658 | 16.002 | 1.00 | 23.39 |
| ATOM | 1903 | OW0 | WAT | G | 121 | 38.971 | 45.277 | 10.960 | 1.00 | 32.00 |
| ATOM | 1904 | OW0 | WAT | G | 122 | 45.394 | 39.705 | 40.673 | 1.00 | 28.95 |
| ATOM | 1905 | OW0 | WAT | G | 123 | 64.660 | 56.850 | 28.096 | 1.00 | 31.43 |
| ATOM | 1906 | OW0 | WAT | G | 124 | 31.495 | 39.706 | 12.940 | 1.00 | 30.11 |
| ATOM | 1907 | OW0 | WAT | G | 125 | 66.898 | 41.660 | 19.788 | 1.00 | 37.52 |
| ATOM | 1908 | OW0 | WAT | G | 126 | 59.279 | 62.353 | 6.022 | 1.00 | 30.85 |
| ATOM | 1909 | OW0 | WAT | G | 127 | 54.862 | 34.329 | 17.654 | 1.00 | 28.43 |
| ATOM | 1910 | OW0 | WAT | G | 128 | 46.944 | 36.876 | −2.147 | 1.00 | 28.17 |
| ATOM | 1911 | OW0 | WAT | G | 129 | 47.374 | 18.007 | 2.535 | 1.00 | 36.60 |
| ATOM | 1912 | OW0 | WAT | G | 130 | 44.808 | 50.361 | 22.031 | 1.00 | 29.95 |
| ATOM | 1913 | OW0 | WAT | G | 131 | 56.071 | 58.293 | 30.768 | 1.00 | 29.87 |
| ATOM | 1914 | OW0 | WAT | G | 132 | 39.948 | 33.299 | 8.889 | 1.00 | 43.00 |
| ATOM | 1917 | OW0 | WAT | G | 135 | 62.136 | 38.451 | 12.117 | 1.00 | 15.27 |
| ATOM | 1918 | OW0 | WAT | G | 136 | 57.446 | 61.036 | 34.612 | 1.00 | 23.04 |
| ATOM | 1919 | OW0 | WAT | G | 137 | 55.835 | 37.709 | 21.070 | 1.00 | 20.63 |
| ATOM | 1920 | OW0 | WAT | G | 138 | 62.428 | 40.009 | 14.530 | 1.00 | 34.20 |
| ATOM | 1921 | OW0 | WAT | G | 139 | 62.638 | 59.963 | 30.173 | 1.00 | 31.10 |
| ATOM | 1922 | OW0 | WAT | G | 140 | 55.220 | 36.878 | 16.564 | 1.00 | 26.78 |
| ATOM | 1923 | OW0 | WAT | G | 141 | 53.791 | 35.442 | 22.528 | 1.00 | 28.89 |
| ATOM | 1924 | OW0 | WAT | G | 142 | 64.950 | 39.916 | 20.459 | 1.00 | 30.25 |
| ATOM | 1925 | OW0 | WAT | G | 143 | 60.864 | 56.504 | 38.809 | 1.00 | 27.10 |
| ATOM | 1926 | OW0 | WAT | G | 144 | 50.834 | 36.062 | −3.236 | 1.00 | 24.20 |
| ATOM | 1927 | OW0 | WAT | G | 145 | 57.988 | 31.870 | 13.658 | 1.00 | 27.16 |
| ATOM | 1928 | OW0 | WAT | G | 146 | 59.420 | 50.371 | 43.012 | 1.00 | 27.11 |
| ATOM | 1929 | OW0 | WAT | G | 147 | 41.507 | 31.122 | 20.116 | 1.00 | 27.47 |
| ATOM | 1930 | OW0 | WAT | G | 148 | 60.586 | 52.675 | 43.032 | 1.00 | 29.71 |
| ATOM | 1931 | OW0 | WAT | G | 149 | 46.395 | 26.704 | 16.386 | 1.00 | 36.67 |
| ATOM | 1932 | OW0 | WAT | G | 150 | 65.273 | 33.456 | 33.695 | 1.00 | 30.16 |
| ATOM | 1933 | OW0 | WAT | G | 151 | 64.591 | 41.448 | 18.391 | 1.00 | 28.63 |
| ATOM | 1934 | OW0 | WAT | G | 152 | 48.864 | 29.166 | −5.087 | 1.00 | 26.64 |
| ATOM | 1935 | OW0 | WAT | G | 153 | 62.622 | 58.231 | 27.208 | 1.00 | 34.13 |
| ATOM | 1936 | OW0 | WAT | G | 154 | 61.506 | 38.693 | 18.376 | 1.00 | 48.10 |
| ATOM | 1937 | OW0 | WAT | G | 155 | 56.258 | 32.027 | 15.818 | 1.00 | 40.67 |
| ATOM | 1938 | OW0 | WAT | G | 156 | 58.824 | 38.296 | 18.235 | 1.00 | 34.94 |
| ATOM | 1939 | OW0 | WAT | G | 157 | 53.978 | 29.606 | 39.376 | 1.00 | 38.68 |
| ATOM | 1940 | OW0 | WAT | G | 158 | 53.182 | 56.416 | 29.461 | 1.00 | 25.79 |
| ATOM | 1941 | OW0 | WAT | G | 159 | 49.085 | 39.844 | −3.201 | 1.00 | 29.14 |
| ATOM | 1942 | OW0 | WAT | G | 160 | 60.344 | 34.232 | 21.770 | 1.00 | 38.25 |
| ATOM | 1943 | OW0 | WAT | G | 161 | 51.797 | 60.535 | −5.207 | 1.00 | 32.32 |
| ATOM | 1944 | OW0 | WAT | G | 162 | 48.186 | 38.211 | 36.506 | 1.00 | 28.29 |
| ATOM | 1945 | OW0 | WAT | G | 163 | 58.462 | 37.470 | 15.660 | 1.00 | 45.25 |
| ATOM | 1946 | OW0 | WAT | G | 164 | 45.851 | 29.690 | 18.302 | 1.00 | 28.59 |
| ATOM | 1947 | OW0 | WAT | G | 165 | 64.873 | 40.315 | 16.036 | 1.00 | 36.40 |
| ATOM | 1948 | OW0 | WAT | G | 166 | 59.897 | 58.114 | 1.470 | 1.00 | 36.57 |
| ATOM | 1949 | OW0 | WAT | G | 167 | 55.910 | 60.828 | 8.749 | 1.00 | 35.99 |
| ATOM | 1950 | OW0 | WAT | G | 168 | 58.826 | 36.800 | 21.280 | 1.00 | 46.77 |
| ATOM | 1951 | OW0 | WAT | G | 169 | 73.241 | 44.114 | 36.191 | 1.00 | 28.55 |
| ATOM | 1952 | OW0 | WAT | G | 170 | 62.716 | 53.030 | 41.277 | 1.00 | 28.32 |
| ATOM | 1953 | OW0 | WAT | G | 171 | 71.215 | 34.038 | 37.383 | 1.00 | 27.69 |
| ATOM | 1954 | OW0 | WAT | G | 172 | 62.192 | 37.635 | 14.596 | 1.00 | 50.53 |
| ATOM | 1955 | OW0 | WAT | G | 173 | 65.616 | 56.974 | 1.251 | 1.00 | 31.26 |
| ATOM | 1956 | OW0 | WAT | G | 174 | 76.080 | 34.843 | 37.370 | 1.00 | 35.85 |
| ATOM | 1957 | OW0 | WAT | G | 175 | 73.299 | 43.407 | 25.575 | 1.00 | 36.58 |
| ATOM | 1958 | OW0 | WAT | G | 176 | 65.884 | 43.263 | 17.413 | 1.00 | 40.37 |
| ATOM | 1959 | OW0 | WAT | G | 177 | 67.452 | 40.654 | 15.215 | 1.00 | 42.76 |

-continued

Data Lists

| | | | | | | | | | |
|---|---|---|---|---|---|---|---|---|---|
| ATOM | 1960 | OW0 | WAT | G | 178 | 54.648 | 62.290 | 32.413 | 1.00 | 53.70 |
| ATOM | 1961 | OW0 | WAT | G | 179 | 51.497 | 49.736 | 48.977 | 1.00 | 29.11 |
| ATOM | 1962 | OW0 | WAT | G | 180 | 44.613 | 37.553 | 5.661 | 1.00 | 33.03 |
| ATOM | 1963 | OW0 | WAT | G | 181 | 70.015 | 49.056 | 17.242 | 1.00 | 35.32 |
| ATOM | 1964 | OW0 | WAT | G | 182 | 67.847 | 54.823 | 14.616 | 1.00 | 27.00 |
| ATOM | 1965 | OW0 | WAT | G | 183 | 75.622 | 47.339 | 26.201 | 1.00 | 39.70 |
| ATOM | 1966 | OW0 | WAT | G | 184 | 58.156 | 30.750 | 37.764 | 1.00 | 43.06 |
| ATOM | 1967 | OW0 | WAT | G | 185 | 63.117 | 44.122 | 43.660 | 1.00 | 32.67 |
| ATOM | 1968 | OW0 | WAT | G | 186 | 70.428 | 46.037 | 20.380 | 1.00 | 37.29 |
| ATOM | 1969 | OW0 | WAT | G | 187 | 65.215 | 59.373 | 12.091 | 1.00 | 28.47 |
| ATOM | 1970 | OW0 | WAT | G | 188 | 67.748 | 44.609 | 18.032 | 1.00 | 53.73 |
| ATOM | 1971 | OW0 | WAT | G | 189 | 40.492 | 30.145 | 11.606 | 1.00 | 64.58 |
| ATOM | 1972 | OW0 | WAT | G | 190 | 67.625 | 60.042 | 8.441 | 1.00 | 33.03 |
| ATOM | 1973 | OW0 | WAT | G | 191 | 50.314 | 57.576 | 44.671 | 1.00 | 50.98 |
| ATOM | 1974 | OW0 | WAT | G | 192 | 52.073 | 26.847 | −2.175 | 1.00 | 30.83 |
| ATOM | 1975 | OW0 | WAT | G | 193 | 46.545 | 20.307 | 1.167 | 1.00 | 32.08 |
| ATOM | 1976 | OW0 | WAT | G | 194 | 73.086 | 39.913 | 40.981 | 1.00 | 33.57 |
| ATOM | 1977 | OW0 | WAT | G | 195 | 45.430 | 39.245 | −2.273 | 1.00 | 37.02 |
| ATOM | 1978 | OW0 | WAT | G | 196 | 52.037 | 58.706 | 12.556 | 1.00 | 43.96 |
| ATOM | 1979 | OW0 | WAT | G | 197 | 57.543 | 61.063 | 30.828 | 1.00 | 37.03 |
| ATOM | 1980 | OW0 | WAT | G | 198 | 61.990 | 41.753 | 42.998 | 1.00 | 33.81 |
| ATOM | 1981 | OW0 | WAT | G | 199 | 43.339 | 30.612 | 18.051 | 1.00 | 41.32 |
| ATOM | 1982 | OW0 | WAT | G | 200 | 67.423 | 56.983 | 24.190 | 1.00 | 29.95 |
| ATOM | 1983 | OW0 | WAT | G | 201 | 63.945 | 61.652 | 12.824 | 1.00 | 34.11 |
| ATOM | 1984 | OW0 | WAT | G | 202 | 63.921 | 52.785 | 39.204 | 1.00 | 38.19 |
| ATOM | 1985 | OW0 | WAT | G | 203 | 52.495 | 20.862 | −0.923 | 1.00 | 33.05 |
| ATOM | 1986 | OW0 | WAT | G | 204 | 53.126 | 35.768 | −3.356 | 1.00 | 51.51 |
| ATOM | 1987 | OW0 | WAT | G | 205 | 42.327 | 41.556 | 31.448 | 1.00 | 30.36 |
| ATOM | 1988 | OW0 | WAT | G | 206 | 42.439 | 21.980 | 7.095 | 1.00 | 40.12 |
| ATOM | 1989 | OW0 | WAT | G | 207 | 72.241 | 46.621 | 16.496 | 1.00 | 54.53 |
| ATOM | 1990 | OW0 | WAT | G | 208 | 74.161 | 48.453 | 34.505 | 1.00 | 32.75 |
| ATOM | 1991 | OW0 | WAT | G | 209 | 48.098 | 26.277 | −4.627 | 1.00 | 41.33 |
| ATOM | 1992 | OW0 | WAT | G | 210 | 70.983 | 44.677 | 42.814 | 1.00 | 43.40 |
| ATOM | 1993 | OW0 | WAT | G | 211 | 47.557 | 20.513 | −1.605 | 1.00 | 40.08 |
| ATOM | 1994 | OW0 | WAT | G | 212 | 61.375 | 59.056 | −0.566 | 1.00 | 39.28 |
| ATOM | 1995 | OW0 | WAT | G | 213 | 72.365 | 48.660 | 2.612 | 1.00 | 35.85 |
| ATOM | 1996 | OW0 | WAT | G | 214 | 42.447 | 46.142 | 17.219 | 1.00 | 28.95 |
| ATOM | 1997 | OW0 | WAT | G | 215 | 70.417 | 41.828 | 12.236 | 1.00 | 60.99 |
| ATOM | 1998 | OW0 | WAT | G | 216 | 65.658 | 40.114 | 42.603 | 1.00 | 38.52 |
| ATOM | 1999 | OW0 | WAT | G | 217 | 61.676 | 48.645 | 44.176 | 1.00 | 39.02 |
| ATOM | 2000 | OW0 | WAT | G | 218 | 40.044 | 49.688 | 1.595 | 1.00 | 34.19 |
| ATOM | 2001 | OW0 | WAT | G | 219 | 40.202 | 42.880 | 25.589 | 1.00 | 32.08 |
| ATOM | 2002 | OW0 | WAT | G | 220 | 70.759 | 53.406 | 19.605 | 1.00 | 41.25 |
| ATOM | 2003 | OW0 | WAT | G | 221 | 34.228 | 33.047 | 11.879 | 1.00 | 38.87 |
| ATOM | 2004 | OW0 | WAT | G | 222 | 60.879 | 55.070 | 40.559 | 1.00 | 33.10 |
| ATOM | 2005 | OW0 | WAT | G | 223 | 58.520 | 33.967 | 42.655 | 1.00 | 52.56 |
| ATOM | 2006 | OW0 | WAT | G | 224 | 47.130 | 35.676 | −4.383 | 1.00 | 40.47 |
| ATOM | 2007 | OW0 | WAT | G | 225 | 42.291 | 57.764 | 7.951 | 1.00 | 34.20 |
| ATOM | 2008 | OW0 | WAT | G | 226 | 51.783 | 38.556 | −5.023 | 1.00 | 54.27 |
| ATOM | 2009 | OW0 | WAT | G | 227 | 63.204 | 39.780 | 41.589 | 1.00 | 26.92 |
| ATOM | 2010 | OW0 | WAT | G | 228 | 70.115 | 41.265 | 21.543 | 1.00 | 54.51 |
| ATOM | 2011 | OW0 | WAT | G | 229 | 35.142 | 41.094 | 15.033 | 1.00 | 26.43 |
| ATOM | 2012 | OW0 | WAT | G | 230 | 49.437 | 28.507 | −7.487 | 1.00 | 36.06 |
| ATOM | 2013 | OW0 | WAT | G | 231 | 48.186 | 58.600 | 27.989 | 1.00 | 47.86 |
| ATOM | 2014 | OW0 | WAT | G | 232 | 43.227 | 57.642 | 34.042 | 1.00 | 64.53 |
| ATOM | 2015 | OW0 | WAT | G | 233 | 44.435 | 45.324 | 40.354 | 1.00 | 38.94 |
| ATOM | 2016 | OW0 | WAT | G | 234 | 68.332 | 40.178 | 22.530 | 1.00 | 41.49 |
| ATOM | 2017 | OW0 | WAT | G | 235 | 41.021 | 47.384 | 26.519 | 1.00 | 32.18 |
| ATOM | 2018 | OW0 | WAT | G | 236 | 67.943 | 34.804 | 44.311 | 1.00 | 40.51 |
| ATOM | 2019 | OW0 | WAT | G | 237 | 54.009 | 33.505 | 14.576 | 1.00 | 38.62 |
| ATOM | 2020 | OW0 | WAT | G | 238 | 69.128 | 52.076 | 1.540 | 1.00 | 44.17 |
| ATOM | 2021 | OW0 | WAT | G | 239 | 48.173 | 55.704 | 43.334 | 1.00 | 38.16 |
| ATOM | 2022 | OW0 | WAT | G | 240 | 43.506 | 19.874 | 8.570 | 1.00 | 34.50 |
| ATOM | 2023 | OW0 | WAT | G | 241 | 46.783 | 19.606 | 10.993 | 1.00 | 33.70 |
| ATOM | 2024 | OW0 | WAT | G | 242 | 62.052 | 46.130 | 46.425 | 1.00 | 52.48 |
| ATOM | 2025 | OW0 | WAT | G | 243 | 34.174 | 43.821 | 10.769 | 1.00 | 40.93 |
| ATOM | 2026 | OW0 | WAT | G | 244 | 39.585 | 37.127 | 26.006 | 1.00 | 35.75 |
| ATOM | 2027 | OW0 | WAT | G | 245 | 70.915 | 52.471 | 29.511 | 1.00 | 46.35 |
| ATOM | 2028 | OW0 | WAT | G | 246 | 50.280 | 28.842 | −2.906 | 1.00 | 34.56 |
| ATOM | 2029 | OW0 | WAT | G | 247 | 45.574 | 23.804 | −6.012 | 1.00 | 54.66 |
| ATOM | 2030 | OW0 | WAT | G | 248 | 50.575 | 41.649 | −5.114 | 1.00 | 37.19 |
| ATOM | 2031 | OW0 | WAT | G | 249 | 46.284 | 60.877 | −0.658 | 1.00 | 48.34 |
| ATOM | 2032 | OW0 | WAT | G | 250 | 69.052 | 41.253 | 44.563 | 1.00 | 41.98 |
| ATOM | 2033 | OW0 | WAT | G | 251 | 76.192 | 44.065 | 31.740 | 1.00 | 39.19 |
| ATOM | 2034 | OW0 | WAT | G | 252 | 55.206 | 59.668 | 2.632 | 1.00 | 44.08 |
| ATOM | 2035 | OW0 | WAT | G | 253 | 46.669 | 36.720 | 40.608 | 1.00 | 50.14 |
| ATOM | 2036 | OW0 | WAT | G | 254 | 59.034 | 52.468 | 41.277 | 1.00 | 35.99 |

-continued

Data Lists

| | | | | | | | | | |
|---|---|---|---|---|---|---|---|---|---|
| ATOM | 2037 | OW0 | WAT | G | 255 | 52.334 | 63.688 | 32.421 | 1.00 | 64.26 |
| ATOM | 2038 | OW0 | WAT | G | 256 | 45.249 | 20.912 | 12.682 | 1.00 | 45.78 |
| ATOM | 2039 | OW0 | WAT | G | 257 | 45.580 | 47.063 | 38.611 | 1.00 | 32.72 |
| ATOM | 2040 | OW0 | WAT | G | 258 | 60.934 | 36.503 | 20.702 | 1.00 | 58.02 |
| ATOM | 2041 | OW0 | WAT | G | 259 | 47.948 | 47.662 | 45.709 | 1.00 | 33.97 |
| ATOM | 2042 | OW0 | WAT | G | 260 | 60.178 | 62.958 | 9.683 | 1.00 | 36.71 |
| ATOM | 2043 | OW0 | WAT | G | 261 | 55.919 | 30.766 | 39.029 | 1.00 | 61.42 |
| ATOM | 2044 | OW0 | WAT | G | 262 | 58.188 | 56.854 | 32.396 | 1.00 | 36.54 |
| ATOM | 2045 | OW0 | WAT | G | 263 | 56.797 | 37.074 | 18.930 | 1.00 | 61.43 |
| ATOM | 2046 | OW0 | WAT | G | 264 | 54.847 | 38.394 | −5.215 | 1.00 | 61.42 |
| ATOM | 2047 | OW0 | WAT | G | 265 | 74.299 | 44.365 | 9.183 | 1.00 | 48.11 |
| ATOM | 2048 | OW0 | WAT | G | 266 | 68.666 | 37.135 | 44.386 | 1.00 | 49.26 |
| ATOM | 2049 | OW0 | WAT | G | 267 | 48.423 | 62.166 | 9.434 | 1.00 | 37.66 |
| ATOM | 2050 | OW0 | WAT | G | 268 | 42.729 | 27.614 | 12.002 | 1.00 | 46.39 |
| ATOM | 2051 | OW0 | WAT | G | 269 | 53.863 | 61.181 | 11.430 | 1.00 | 60.41 |
| ATOM | 2052 | OW0 | WAT | G | 270 | 65.415 | 58.143 | 25.828 | 1.00 | 41.48 |
| ATOM | 2053 | OW0 | WAT | G | 271 | 51.875 | 32.393 | −8.603 | 1.00 | 53.80 |
| ATOM | 2054 | OW0 | WAT | G | 272 | 60.962 | 61.993 | 12.376 | 1.00 | 29.89 |
| ATOM | 2055 | OW0 | WAT | G | 273 | 40.308 | 32.786 | 11.451 | 1.00 | 35.54 |
| ATOM | 2056 | OW0 | WAT | G | 274 | 62.383 | 60.257 | 17.773 | 1.00 | 38.70 |
| ATOM | 2057 | OW0 | WAT | G | 275 | 37.093 | 30.464 | 14.199 | 1.00 | 47.27 |
| ATOM | 2058 | OW0 | WAT | G | 276 | 53.952 | 61.207 | −1.317 | 1.00 | 46.85 |
| ATOM | 2059 | OW0 | WAT | G | 277 | 51.860 | 29.501 | 0.746 | 1.00 | 37.36 |
| ATOM | 2060 | OW0 | WAT | G | 278 | 50.151 | 63.360 | 7.446 | 1.00 | 45.00 |
| ATOM | 2061 | OW0 | WAT | G | 279 | 69.694 | 43.050 | 22.397 | 1.00 | 68.19 |
| ATOM | 2062 | OW0 | WAT | G | 280 | 49.754 | 37.037 | −4.944 | 1.00 | 69.60 |
| ATOM | 2063 | OW0 | WAT | G | 281 | 50.342 | 25.060 | −3.761 | 1.00 | 44.24 |
| ATOM | 2064 | OW0 | WAT | G | 282 | 54.321 | 59.856 | 16.427 | 1.00 | 35.71 |
| ATOM | 2065 | OW0 | WAT | G | 283 | 63.746 | 59.693 | 0.468 | 1.00 | 55.15 |
| ATOM | 2066 | OW0 | WAT | G | 284 | 43.389 | 46.275 | 36.615 | 1.00 | 37.96 |
| ATOM | 2067 | OW0 | WAT | G | 285 | 59.808 | 40.715 | 43.590 | 1.00 | 33.32 |
| ATOM | 2068 | OW0 | WAT | G | 286 | 43.995 | 23.232 | 16.324 | 1.00 | 38.95 |
| ATOM | 2069 | OW0 | WAT | G | 287 | 43.552 | 24.401 | 13.416 | 1.00 | 61.34 |
| ATOM | 2070 | OW0 | WAT | G | 288 | 71.661 | 53.820 | 27.764 | 1.00 | 45.96 |
| ATOM | 2071 | OW0 | WAT | G | 289 | 48.871 | 35.713 | 37.068 | 1.00 | 21.32 |
| ATOM | 2072 | OW0 | WAT | G | 290 | 39.975 | 49.726 | 8.734 | 1.00 | 46.02 |
| ATOM | 2074 | OW0 | WAT | G | 292 | 65.526 | 33.873 | 35.894 | 1.00 | 37.27 |
| ATOM | 2075 | OW0 | WAT | G | 293 | 48.218 | 18.217 | 9.649 | 1.00 | 32.19 |
| ATOM | 1783 | OW0 | WAT | H | 1 | 55.626 | 26.415 | 10.047 | 1.00 | 12.46 |
| ATOM | 1784 | OW0 | WAT | H | 2 | 65.016 | 37.930 | 11.810 | 1.00 | 14.50 |
| ATOM | 1785 | OW0 | WAT | H | 3 | 58.211 | 27.718 | 10.696 | 1.00 | 12.96 |
| ATOM | 1786 | OW0 | WAT | H | 4 | 59.947 | 34.093 | 10.106 | 1.00 | 16.21 |
| ATOM | 1787 | OW0 | WAT | H | 5 | 59.936 | 14.419 | 20.886 | 1.00 | 16.96 |
| ATOM | 1788 | OW0 | WAT | H | 6 | 68.238 | 32.497 | 17.320 | 1.00 | 12.78 |
| ATOM | 1789 | OW0 | WAT | H | 7 | 66.240 | 31.436 | 15.575 | 1.00 | 14.43 |
| ATOM | 1790 | OW0 | WAT | H | 8 | 57.265 | 23.951 | 22.829 | 1.00 | 11.87 |
| ATOM | 1791 | OW0 | WAT | H | 9 | 59.422 | 15.438 | 31.322 | 1.00 | 15.75 |
| ATOM | 1792 | OW0 | WAT | H | 10 | 84.148 | 29.630 | 16.216 | 1.00 | 18.14 |
| ATOM | 1793 | OW0 | WAT | H | 11 | 53.858 | 30.989 | 20.763 | 1.00 | 18.49 |
| ATOM | 1794 | OW0 | WAT | H | 12 | 40.207 | 30.360 | 27.502 | 1.00 | 20.49 |
| ATOM | 1795 | OW0 | WAT | H | 13 | 52.543 | 26.702 | 0.370 | 1.00 | 15.58 |
| ATOM | 1796 | OW0 | WAT | H | 14 | 59.344 | 26.117 | 22.867 | 1.00 | 12.77 |
| ATOM | 1797 | OW0 | WAT | H | 15 | 63.620 | 27.796 | 18.221 | 1.00 | 17.15 |
| ATOM | 1798 | OW0 | WAT | H | 16 | 70.586 | 38.510 | 27.896 | 1.00 | 18.45 |
| ATOM | 1799 | OW0 | WAT | H | 17 | 61.696 | 33.858 | 24.218 | 1.00 | 20.08 |
| ATOM | 1800 | OW0 | WAT | H | 18 | 55.336 | 28.435 | 17.716 | 1.00 | 19.24 |
| ATOM | 1801 | OW0 | WAT | H | 19 | 62.319 | 14.684 | 27.239 | 1.00 | 18.83 |
| ATOM | 1802 | OW0 | WAT | H | 20 | 42.537 | 26.828 | 34.990 | 1.00 | 17.45 |
| ATOM | 1803 | OW0 | WAT | H | 21 | 74.567 | 31.356 | 15.807 | 1.00 | 18.93 |
| ATOM | 1804 | OW0 | WAT | H | 22 | 77.241 | 37.609 | −1.173 | 1.00 | 16.89 |
| ATOM | 1805 | OW0 | WAT | H | 23 | 53.542 | 26.069 | 21.187 | 1.00 | 20.32 |
| ATOM | 1806 | OW0 | WAT | H | 24 | 78.587 | 36.637 | 5.376 | 1.00 | 19.88 |
| ATOM | 1807 | OW0 | WAT | H | 25 | 62.185 | 13.724 | 24.633 | 1.00 | 17.12 |
| ATOM | 1808 | OW0 | WAT | H | 26 | 56.499 | 11.903 | 12.602 | 1.00 | 21.81 |
| ATOM | 1809 | OW0 | WAT | H | 27 | 49.927 | 32.676 | 21.964 | 1.00 | 15.81 |
| ATOM | 1810 | OW0 | WAT | H | 28 | 76.722 | 38.573 | 6.596 | 1.00 | 21.31 |
| ATOM | 1811 | OW0 | WAT | H | 29 | 71.211 | 17.670 | −4.123 | 1.00 | 21.20 |
| ATOM | 1812 | OW0 | WAT | H | 30 | 55.890 | 27.326 | 15.037 | 1.00 | 21.50 |
| ATOM | 1813 | OW0 | WAT | H | 31 | 72.135 | 13.499 | 35.278 | 1.00 | 26.79 |
| ATOM | 1814 | OW0 | WAT | H | 32 | 76.219 | 22.099 | 0.994 | 1.00 | 18.33 |
| ATOM | 1815 | OW0 | WAT | H | 33 | 77.438 | 30.353 | −6.384 | 1.00 | 21.45 |
| ATOM | 1816 | OW0 | WAT | H | 34 | 75.784 | 39.054 | 0.788 | 1.00 | 19.77 |
| ATOM | 1817 | OW0 | WAT | H | 35 | 59.941 | 30.965 | 22.565 | 1.00 | 19.13 |
| ATOM | 1818 | OW0 | WAT | H | 36 | 80.041 | 33.464 | 22.515 | 1.00 | 25.88 |
| ATOM | 1819 | OW0 | WAT | H | 37 | 53.875 | 11.516 | 16.737 | 1.00 | 24.35 |
| ATOM | 1820 | OW0 | WAT | H | 38 | 48.562 | 15.769 | 23.928 | 1.00 | 21.53 |
| ATOM | 1821 | OW0 | WAT | H | 39 | 67.622 | 19.468 | −6.676 | 1.00 | 17.05 |

-continued

| | | | | | | | | | |
|---|---|---|---|---|---|---|---|---|---|
| ATOM | 1822 | OW0 | WAT | H | 40 | 63.265 | 9.904 | 29.834 | 1.00 | 26.29 |
| ATOM | 1823 | OW0 | WAT | H | 41 | 70.165 | 13.648 | 3.894 | 1.00 | 26.19 |
| ATOM | 1824 | OW0 | WAT | H | 42 | 81.980 | 32.799 | 3.642 | 1.00 | 21.59 |
| ATOM | 1825 | OW0 | WAT | H | 43 | 64.411 | 12.168 | 24.457 | 1.00 | 28.13 |
| ATOM | 1826 | OW0 | WAT | H | 44 | 71.862 | 38.226 | 21.699 | 1.00 | 27.79 |
| ATOM | 1827 | OW0 | WAT | H | 45 | 50.750 | 14.483 | 26.561 | 1.00 | 22.42 |
| ATOM | 1828 | OW0 | WAT | H | 46 | 72.225 | 30.904 | −7.142 | 1.00 | 24.58 |
| ATOM | 1829 | OW0 | WAT | H | 47 | 48.426 | 17.990 | 14.644 | 1.00 | 24.59 |
| ATOM | 1830 | OW0 | WAT | H | 48 | 69.915 | 12.402 | 20.671 | 1.00 | 34.46 |
| ATOM | 1831 | OW0 | WAT | H | 49 | 71.391 | 27.373 | −10.407 | 1.00 | 20.52 |
| ATOM | 1832 | OW0 | WAT | H | 50 | 57.327 | 36.972 | −1.991 | 1.00 | 29.82 |
| ATOM | 1833 | OW0 | WAT | H | 51 | 68.614 | 17.512 | −4.674 | 1.00 | 22.18 |
| ATOM | 1834 | OW0 | WAT | H | 52 | 41.134 | 22.037 | 30.497 | 1.00 | 17.35 |
| ATOM | 1835 | OW0 | WAT | H | 53 | 78.961 | 22.828 | 0.870 | 1.00 | 19.50 |
| ATOM | 1836 | OW0 | WAT | H | 54 | 81.114 | 32.952 | 25.218 | 1.00 | 27.87 |
| ATOM | 1837 | OW0 | WAT | H | 55 | 66.620 | 38.253 | 21.637 | 1.00 | 30.16 |
| ATOM | 1838 | OW0 | WAT | H | 56 | 82.397 | 27.950 | 21.632 | 1.00 | 26.01 |
| ATOM | 1839 | OW0 | WAT | H | 57 | 40.601 | 24.059 | 32.268 | 1.00 | 23.54 |
| ATOM | 1840 | OW0 | WAT | H | 58 | 68.703 | 17.093 | 14.330 | 1.00 | 30.99 |
| ATOM | 1841 | OW0 | WAT | H | 59 | 60.386 | 31.945 | 11.769 | 1.00 | 20.83 |
| ATOM | 1842 | OW0 | WAT | H | 60 | 58.159 | 32.811 | 23.887 | 1.00 | 21.39 |
| ATOM | 1843 | OW0 | WAT | H | 61 | 75.112 | 33.510 | −7.627 | 1.00 | 24.77 |
| ATOM | 1844 | OW0 | WAT | H | 62 | 60.861 | 28.219 | 17.129 | 1.00 | 25.45 |
| ATOM | 1845 | OW0 | WAT | H | 63 | 69.818 | 18.540 | −8.213 | 1.00 | 22.75 |
| ATOM | 1846 | OW0 | WAT | H | 64 | 47.698 | 23.429 | 29.143 | 1.00 | 21.96 |
| ATOM | 1847 | OW0 | WAT | H | 65 | 56.243 | 17.811 | 6.113 | 1.00 | 26.57 |
| ATOM | 1848 | OW0 | WAT | H | 66 | 56.480 | 9.527 | 25.120 | 1.00 | 24.57 |
| ATOM | 1849 | OW0 | WAT | H | 67 | 76.416 | 39.671 | 4.015 | 1.00 | 22.95 |
| ATOM | 1850 | OW0 | WAT | H | 68 | 75.867 | 11.960 | 24.892 | 1.00 | 26.76 |
| ATOM | 1851 | OW0 | WAT | H | 69 | 65.809 | 34.125 | 14.364 | 1.00 | 26.61 |
| ATOM | 1852 | OW0 | WAT | H | 70 | 62.222 | 28.978 | 20.512 | 1.00 | 20.01 |
| ATOM | 1853 | OW0 | WAT | H | 71 | 73.295 | 41.829 | −3.122 | 1.00 | 36.97 |
| ATOM | 1854 | OW0 | WAT | H | 72 | 72.362 | 37.161 | 14.937 | 1.00 | 29.26 |
| ATOM | 1855 | OW0 | WAT | H | 73 | 64.102 | 12.708 | 12.209 | 1.00 | 29.45 |
| ATOM | 1856 | OW0 | WAT | H | 74 | 59.337 | 46.991 | −4.704 | 1.00 | 33.14 |
| ATOM | 1857 | OW0 | WAT | H | 75 | 47.640 | 15.287 | 17.293 | 1.00 | 25.03 |
| ATOM | 1858 | OW0 | WAT | H | 76 | 65.153 | 12.787 | 16.407 | 1.00 | 36.34 |
| ATOM | 1859 | OW0 | WAT | H | 77 | 82.754 | 33.641 | 27.870 | 1.00 | 33.66 |
| ATOM | 1860 | OW0 | WAT | H | 78 | 74.515 | 43.172 | 1.368 | 1.00 | 46.06 |
| ATOM | 1861 | OW0 | WAT | H | 79 | 65.544 | 13.826 | 36.090 | 1.00 | 26.95 |
| ATOM | 1862 | OW0 | WAT | H | 80 | 56.176 | 14.705 | 7.899 | 1.00 | 25.17 |
| ATOM | 1863 | OW0 | WAT | H | 81 | 60.069 | 12.784 | 23.279 | 1.00 | 25.41 |
| ATOM | 1864 | OW0 | WAT | H | 82 | 64.518 | 29.497 | −9.881 | 1.00 | 28.19 |
| ATOM | 1865 | OW0 | WAT | H | 83 | 72.890 | 17.016 | 38.513 | 1.00 | 32.75 |
| ATOM | 1866 | OW0 | WAT | H | 84 | 64.327 | 12.726 | 7.904 | 1.00 | 28.33 |
| ATOM | 1867 | OW0 | WAT | H | 85 | 73.702 | 28.506 | 40.368 | 1.00 | 35.95 |
| ATOM | 1868 | OW0 | WAT | H | 86 | 40.325 | 34.760 | 26.876 | 1.00 | 30.16 |
| ATOM | 1869 | OW0 | WAT | H | 87 | 46.523 | 14.958 | 21.845 | 1.00 | 28.34 |
| ATOM | 1870 | OW0 | WAT | H | 88 | 81.785 | 35.984 | 25.164 | 1.00 | 45.57 |
| ATOM | 1871 | OW0 | WAT | H | 89 | 81.670 | 23.684 | 31.981 | 1.00 | 30.95 |
| ATOM | 1872 | OW0 | WAT | H | 90 | 73.658 | 13.615 | 21.783 | 1.00 | 31.75 |
| ATOM | 1873 | OW0 | WAT | H | 91 | 54.962 | 28.237 | 22.077 | 1.00 | 26.64 |
| ATOM | 1874 | OW0 | WAT | H | 92 | 65.997 | 21.795 | 41.162 | 1.00 | 34.61 |
| ATOM | 1875 | OW0 | WAT | H | 93 | 67.430 | 9.979 | 25.531 | 1.00 | 30.41 |
| ATOM | 1876 | OW0 | WAT | H | 94 | 76.456 | 16.928 | 20.650 | 1.00 | 30.22 |
| ATOM | 1877 | OW0 | WAT | H | 95 | 77.973 | 22.449 | 11.319 | 1.00 | 26.47 |
| ATOM | 1878 | OW0 | WAT | H | 96 | 54.232 | 11.639 | 13.975 | 1.00 | 24.52 |
| ATOM | 1879 | OW0 | WAT | H | 97 | 46.826 | 33.800 | 36.880 | 1.00 | 25.58 |
| ATOM | 1880 | OW0 | WAT | H | 98 | 57.623 | 16.748 | 1.335 | 1.00 | 35.83 |
| ATOM | 1881 | OW0 | WAT | H | 99 | 60.463 | 23.883 | −10.911 | 1.00 | 31.62 |
| ATOM | 1882 | OW0 | WAT | H | 100 | 75.659 | 24.956 | 37.083 | 1.00 | 35.13 |
| ATOM | 1883 | OW0 | WAT | H | 101 | 59.265 | 28.532 | 21.715 | 1.00 | 25.37 |
| ATOM | 1884 | OW0 | WAT | H | 102 | 50.039 | 16.328 | 12.141 | 1.00 | 22.49 |
| ATOM | 1885 | OW0 | WAT | H | 103 | 48.949 | 27.390 | 19.574 | 1.00 | 22.74 |
| ATOM | 1886 | OW0 | WAT | H | 104 | 52.769 | 29.349 | 16.776 | 1.00 | 23.17 |
| ATOM | 1887 | OW0 | WAT | H | 105 | 57.967 | 25.041 | −7.141 | 1.00 | 29.64 |
| ATOM | 1888 | OW0 | WAT | H | 106 | 75.831 | 28.016 | 37.410 | 1.00 | 34.04 |
| ATOM | 1889 | OW0 | WAT | H | 107 | 77.822 | 15.717 | −6.480 | 1.00 | 35.09 |
| ATOM | 1890 | OW0 | WAT | H | 108 | 65.905 | 16.140 | 14.395 | 1.00 | 25.94 |
| ATOM | 1891 | OW0 | WAT | H | 109 | 52.151 | 13.189 | 12.986 | 1.00 | 26.50 |
| ATOM | 1892 | OW0 | WAT | H | 110 | 80.013 | 37.977 | 7.957 | 1.00 | 30.56 |
| ATOM | 1893 | OW0 | WAT | H | 111 | 83.151 | 30.502 | 29.885 | 1.00 | 29.70 |
| ATOM | 1894 | OW0 | WAT | H | 112 | 70.714 | 15.340 | 37.184 | 1.00 | 35.84 |
| ATOM | 1895 | OW0 | WAT | H | 113 | 62.628 | 31.924 | −7.181 | 1.00 | 30.25 |
| ATOM | 1896 | OW0 | WAT | H | 114 | 50.066 | 27.262 | 16.994 | 1.00 | 30.45 |
| ATOM | 1897 | OW0 | WAT | H | 115 | 45.810 | 22.478 | 26.282 | 1.00 | 30.65 |
| ATOM | 1898 | OW0 | WAT | H | 116 | 39.755 | 32.861 | 30.859 | 1.00 | 26.85 |

-continued

Data Lists

| | | | | | | | | | |
|---|---|---|---|---|---|---|---|---|---|
| ATOM | 1899 | OW0 | WAT | H | 117 | 71.066 | 9.044 | 35.678 | 1.00 | 36.26 |
| ATOM | 1900 | OW0 | WAT | H | 118 | 58.464 | 30.097 | −6.302 | 1.00 | 33.36 |
| ATOM | 1901 | OW0 | WAT | H | 119 | 43.885 | 38.361 | 32.035 | 1.00 | 39.06 |
| ATOM | 1902 | OW0 | WAT | H | 120 | 48.283 | 14.313 | 19.784 | 1.00 | 23.39 |
| ATOM | 1903 | OW0 | WAT | H | 121 | 58.695 | 11.110 | 24.826 | 1.00 | 32.00 |
| ATOM | 1904 | OW0 | WAT | H | 122 | 57.082 | 19.459 | −4.887 | 1.00 | 28.95 |
| ATOM | 1905 | OW0 | WAT | H | 123 | 81.562 | 27.571 | 7.690 | 1.00 | 31.43 |
| ATOM | 1906 | OW0 | WAT | H | 124 | 50.133 | 7.422 | 22.846 | 1.00 | 30.11 |
| ATOM | 1907 | OW0 | WAT | H | 125 | 69.527 | 37.104 | 15.998 | 1.00 | 37.52 |
| ATOM | 1908 | OW0 | WAT | H | 126 | 83.637 | 20.159 | 29.764 | 1.00 | 30.85 |
| ATOM | 1909 | OW0 | WAT | H | 127 | 57.160 | 30.346 | 18.132 | 1.00 | 28.43 |
| ATOM | 1910 | OW0 | WAT | H | 128 | 55.407 | 22.216 | 37.933 | 1.00 | 28.17 |
| ATOM | 1911 | OW0 | WAT | H | 129 | 39.281 | 32.022 | 33.251 | 1.00 | 36.60 |
| ATOM | 1912 | OW0 | WAT | H | 130 | 66.017 | 13.623 | 13.755 | 1.00 | 29.95 |
| ATOM | 1913 | OW0 | WAT | H | 131 | 78.517 | 19.411 | 5.018 | 1.00 | 29.87 |
| ATOM | 1914 | OW0 | WAT | H | 132 | 48.811 | 17.945 | 26.897 | 1.00 | 43.00 |
| ATOM | 1917 | OW0 | WAT | H | 135 | 64.367 | 34.584 | 23.669 | 1.00 | 15.27 |
| ATOM | 1918 | OW0 | WAT | H | 136 | 81.580 | 19.230 | 1.174 | 1.00 | 23.04 |
| ATOM | 1919 | OW0 | WAT | H | 137 | 60.573 | 29.499 | 14.716 | 1.00 | 20.63 |
| ATOM | 1920 | OW0 | WAT | H | 138 | 65.862 | 34.058 | 21.256 | 1.00 | 34.20 |
| ATOM | 1921 | OW0 | WAT | H | 139 | 83.247 | 24.263 | 5.613 | 1.00 | 31.10 |
| ATOM | 1922 | OW0 | WAT | H | 140 | 59.546 | 29.382 | 19.222 | 1.00 | 26.78 |
| ATOM | 1923 | OW0 | WAT | H | 141 | 57.588 | 28.862 | 13.258 | 1.00 | 28.89 |
| ATOM | 1924 | OW0 | WAT | H | 142 | 67.042 | 36.289 | 15.327 | 1.00 | 30.25 |
| ATOM | 1925 | OW0 | WAT | H | 143 | 79.364 | 24.456 | −3.023 | 1.00 | 27.10 |
| ATOM | 1926 | OW0 | WAT | H | 144 | 56.647 | 25.991 | 39.022 | 1.00 | 24.20 |
| ATOM | 1927 | OW0 | WAT | H | 145 | 56.593 | 34.283 | 22.128 | 1.00 | 27.16 |
| ATOM | 1928 | OW0 | WAT | H | 146 | 73.331 | 26.272 | −7.226 | 1.00 | 27.11 |
| ATOM | 1929 | OW0 | WAT | H | 147 | 47.705 | 20.384 | 15.670 | 1.00 | 27.47 |
| ATOM | 1930 | OW0 | WAT | H | 148 | 75.910 | 26.130 | −7.246 | 1.00 | 29.71 |
| ATOM | 1931 | OW0 | WAT | H | 149 | 46.323 | 26.826 | 19.400 | 1.00 | 36.67 |
| ATOM | 1932 | OW0 | WAT | H | 150 | 61.609 | 39.798 | 2.091 | 1.00 | 30.16 |
| ATOM | 1933 | OW0 | WAT | H | 151 | 68.189 | 35.212 | 17.395 | 1.00 | 28.63 |
| ATOM | 1934 | OW0 | WAT | H | 152 | 49.690 | 27.733 | 40.873 | 1.00 | 26.64 |
| ATOM | 1935 | OW0 | WAT | H | 153 | 81.739 | 25.115 | 8.578 | 1.00 | 34.13 |
| ATOM | 1936 | OW0 | WAT | H | 154 | 64.261 | 33.918 | 17.410 | 1.00 | 48.10 |
| ATOM | 1937 | OW0 | WAT | H | 155 | 55.864 | 32.706 | 19.968 | 1.00 | 40.67 |
| ATOM | 1938 | OW0 | WAT | H | 156 | 62.576 | 31.794 | 17.551 | 1.00 | 34.94 |
| ATOM | 1939 | OW0 | WAT | H | 157 | 52.628 | 31.942 | −3.590 | 1.00 | 38.68 |
| ATOM | 1940 | OW0 | WAT | H | 158 | 75.447 | 17.848 | 6.325 | 1.00 | 25.79 |
| ATOM | 1941 | OW0 | WAT | H | 159 | 59.047 | 22.586 | 38.987 | 1.00 | 29.14 |
| ATOM | 1942 | OW0 | WAT | H | 160 | 59.817 | 35.142 | 14.016 | 1.00 | 38.25 |
| ATOM | 1943 | OW0 | WAT | H | 161 | 78.322 | 14.589 | 40.993 | 1.00 | 32.32 |
| ATOM | 1944 | OW0 | WAT | H | 162 | 57.184 | 22.624 | −0.720 | 1.00 | 28.29 |
| ATOM | 1945 | OW0 | WAT | H | 163 | 61.680 | 31.893 | 20.126 | 1.00 | 45.25 |
| ATOM | 1946 | OW0 | WAT | H | 164 | 48.637 | 24.862 | 17.484 | 1.00 | 28.59 |
| ATOM | 1947 | OW0 | WAT | H | 165 | 67.349 | 36.023 | 19.750 | 1.00 | 36.40 |
| ATOM | 1948 | OW0 | WAT | H | 166 | 80.275 | 22.814 | 34.316 | 1.00 | 36.57 |
| ATOM | 1949 | OW0 | WAT | H | 167 | 80.632 | 18.004 | 27.037 | 1.00 | 35.99 |
| ATOM | 1950 | OW0 | WAT | H | 168 | 61.282 | 32.543 | 14.506 | 1.00 | 46.77 |
| ATOM | 1951 | OW0 | WAT | H | 169 | 74.823 | 41.370 | −0.405 | 1.00 | 28.55 |
| ATOM | 1952 | OW0 | WAT | H | 170 | 77.282 | 27.797 | −5.491 | 1.00 | 28.32 |
| ATOM | 1953 | OW0 | WAT | H | 171 | 65.084 | 44.653 | −1.597 | 1.00 | 27.69 |
| ATOM | 1954 | OW0 | WAT | H | 172 | 63.688 | 35.041 | 21.190 | 1.00 | 50.53 |
| ATOM | 1955 | OW0 | WAT | H | 173 | 82.147 | 28.336 | 34.535 | 1.00 | 31.26 |
| ATOM | 1956 | OW0 | WAT | H | 174 | 68.214 | 48.464 | −1.584 | 1.00 | 35.85 |
| ATOM | 1957 | OW0 | WAT | H | 175 | 74.240 | 41.773 | 10.211 | 1.00 | 36.58 |
| ATOM | 1958 | OW0 | WAT | H | 176 | 70.408 | 35.424 | 18.373 | 1.00 | 40.37 |
| ATOM | 1959 | OW0 | WAT | H | 177 | 68.932 | 38.086 | 20.571 | 1.00 | 42.76 |
| ATOM | 1960 | OW0 | WAT | H | 178 | 81.267 | 16.180 | 3.373 | 1.00 | 53.70 |
| ATOM | 1961 | OW0 | WAT | H | 179 | 68.820 | 19.728 | −13.191 | 1.00 | 29.11 |
| ATOM | 1962 | OW0 | WAT | H | 180 | 54.827 | 19.858 | 30.125 | 1.00 | 33.03 |
| ATOM | 1963 | OW0 | WAT | H | 181 | 77.490 | 36.105 | 18.544 | 1.00 | 35.32 |
| ATOM | 1964 | OW0 | WAT | H | 182 | 81.400 | 31.344 | 21.170 | 1.00 | 27.00 |
| ATOM | 1965 | OW0 | WAT | H | 183 | 78.807 | 41.819 | 9.585 | 1.00 | 39.70 |
| ATOM | 1966 | OW0 | WAT | H | 184 | 55.707 | 34.988 | −1.978 | 1.00 | 43.06 |
| ATOM | 1967 | OW0 | WAT | H | 185 | 69.768 | 32.598 | −7.874 | 1.00 | 32.67 |
| ATOM | 1968 | OW0 | WAT | H | 186 | 75.082 | 37.972 | 15.406 | 1.00 | 37.29 |
| ATOM | 1969 | OW0 | WAT | H | 187 | 84.025 | 26.790 | 23.695 | 1.00 | 28.47 |
| ATOM | 1970 | OW0 | WAT | H | 188 | 72.505 | 36.365 | 17.754 | 1.00 | 53.73 |
| ATOM | 1971 | OW0 | WAT | H | 189 | 46.352 | 19.994 | 24.180 | 1.00 | 64.58 |
| ATOM | 1972 | OW0 | WAT | H | 190 | 85.809 | 28.542 | 27.345 | 1.00 | 33.03 |
| ATOM | 1973 | OW0 | WAT | H | 191 | 75.018 | 14.784 | −8.885 | 1.00 | 50.98 |
| ATOM | 1974 | OW0 | WAT | H | 192 | 49.286 | 31.672 | 37.961 | 1.00 | 30.83 |
| ATOM | 1975 | OW0 | WAT | H | 193 | 40.858 | 30.154 | 34.619 | 1.00 | 32.08 |
| ATOM | 1976 | OW0 | WAT | H | 194 | 71.108 | 43.336 | −5.195 | 1.00 | 33.57 |
| ATOM | 1977 | OW0 | WAT | H | 195 | 56.701 | 19.720 | 38.059 | 1.00 | 37.02 |

-continued

Data Lists

| | | | | | | | | | |
|---|---|---|---|---|---|---|---|---|---|
| ATOM | 1978 | OW0 | WAT | H | 196 | 76.858 | 15.711 | 23.230 | 1.00 | 43.96 |
| ATOM | 1979 | OW0 | WAT | H | 197 | 81.652 | 19.301 | 4.958 | 1.00 | 37.03 |
| ATOM | 1980 | OW0 | WAT | H | 198 | 67.153 | 32.807 | −7.212 | 1.00 | 33.81 |
| ATOM | 1981 | OW0 | WAT | H | 199 | 48.179 | 22.226 | 17.735 | 1.00 | 41.32 |
| ATOM | 1982 | OW0 | WAT | H | 200 | 83.059 | 29.897 | 11.596 | 1.00 | 29.95 |
| ATOM | 1983 | OW0 | WAT | H | 201 | 85.363 | 24.550 | 22.962 | 1.00 | 34.11 |
| ATOM | 1984 | OW0 | WAT | H | 202 | 77.672 | 28.963 | −3.418 | 1.00 | 38.19 |
| ATOM | 1985 | OW0 | WAT | H | 203 | 44.314 | 35.030 | 36.709 | 1.00 | 33.05 |
| ATOM | 1986 | OW0 | WAT | H | 204 | 57.538 | 28.123 | 39.142 | 1.00 | 51.51 |
| ATOM | 1987 | OW0 | WAT | H | 205 | 57.151 | 15.877 | 4.338 | 1.00 | 30.36 |
| ATOM | 1988 | OW0 | WAT | H | 206 | 40.254 | 25.762 | 28.691 | 1.00 | 40.12 |
| ATOM | 1989 | OW0 | WAT | H | 207 | 76.494 | 39.250 | 19.290 | 1.00 | 54.53 |
| ATOM | 1990 | OW0 | WAT | H | 208 | 79.041 | 39.997 | 1.281 | 1.00 | 32.75 |
| ATOM | 1991 | OW0 | WAT | H | 209 | 46.805 | 28.514 | 40.413 | 1.00 | 41.33 |
| ATOM | 1992 | OW0 | WAT | H | 210 | 74.182 | 39.133 | −7.028 | 1.00 | 43.40 |
| ATOM | 1993 | OW0 | WAT | H | 211 | 41.543 | 30.928 | 37.391 | 1.00 | 40.08 |
| ATOM | 1994 | OW0 | WAT | H | 212 | 81.830 | 23.623 | 36.352 | 1.00 | 39.28 |
| ATOM | 1995 | OW0 | WAT | H | 213 | 78.322 | 38.338 | 33.174 | 1.00 | 35.85 |
| ATOM | 1996 | OW0 | WAT | H | 214 | 61.182 | 13.688 | 18.567 | 1.00 | 28.95 |
| ATOM | 1997 | OW0 | WAT | H | 215 | 71.432 | 40.067 | 23.550 | 1.00 | 60.99 |
| ATOM | 1998 | OW0 | WAT | H | 216 | 67.568 | 36.803 | −6.817 | 1.00 | 38.52 |
| ATOM | 1999 | OW0 | WAT | H | 217 | 72.965 | 29.089 | −8.390 | 1.00 | 39.02 |
| ATOM | 2000 | OW0 | WAT | H | 218 | 63.052 | 9.834 | 34.191 | 1.00 | 34.19 |
| ATOM | 2001 | OW0 | WAT | H | 219 | 57.235 | 13.375 | 10.197 | 1.00 | 32.08 |
| ATOM | 2002 | OW0 | WAT | H | 220 | 81.629 | 34.574 | 16.181 | 1.00 | 41.25 |
| ATOM | 2003 | OW0 | WAT | H | 221 | 45.733 | 13.118 | 23.907 | 1.00 | 38.87 |
| ATOM | 2004 | OW0 | WAT | H | 222 | 78.130 | 25.186 | −4.773 | 1.00 | 33.10 |
| ATOM | 2005 | OW0 | WAT | H | 223 | 58.675 | 33.695 | −6.869 | 1.00 | 52.56 |
| ATOM | 2006 | OW0 | WAT | H | 224 | 54.460 | 22.977 | 40.169 | 1.00 | 40.47 |
| ATOM | 2007 | OW0 | WAT | H | 225 | 71.169 | 7.742 | 27.835 | 1.00 | 34.20 |
| ATOM | 2008 | OW0 | WAT | H | 226 | 59.281 | 25.566 | 40.809 | 1.00 | 54.27 |
| ATOM | 2009 | OW0 | WAT | H | 227 | 66.051 | 34.845 | −5.803 | 1.00 | 26.92 |
| ATOM | 2010 | OW0 | WAT | H | 228 | 70.793 | 40.087 | 14.243 | 1.00 | 54.51 |
| ATOM | 2011 | OW0 | WAT | H | 229 | 53.158 | 9.886 | 20.753 | 1.00 | 26.43 |
| ATOM | 2012 | OW0 | WAT | H | 230 | 49.406 | 28.559 | 43.273 | 1.00 | 36.06 |
| ATOM | 2013 | OW0 | WAT | H | 231 | 74.841 | 12.429 | 7.797 | 1.00 | 47.86 |
| ATOM | 2014 | OW0 | WAT | H | 232 | 71.531 | 8.614 | 1.744 | 1.00 | 64.53 |
| ATOM | 2015 | OW0 | WAT | H | 233 | 61.468 | 15.819 | −4.568 | 1.00 | 38.94 |
| ATOM | 2016 | OW0 | WAT | H | 234 | 68.960 | 39.087 | 13.256 | 1.00 | 41.49 |
| ATOM | 2017 | OW0 | WAT | H | 235 | 61.545 | 11.832 | 9.267 | 1.00 | 32.18 |
| ATOM | 2018 | OW0 | WAT | H | 236 | 64.112 | 41.437 | −8.525 | 1.00 | 40.51 |
| ATOM | 2019 | OW0 | WAT | H | 237 | 56.020 | 30.019 | 21.210 | 1.00 | 38.62 |
| ATOM | 2020 | OW0 | WAT | H | 238 | 79.662 | 33.827 | 34.246 | 1.00 | 44.17 |
| ATOM | 2021 | OW0 | WAT | H | 239 | 72.326 | 13.866 | −7.548 | 1.00 | 38.16 |
| ATOM | 2022 | OW0 | WAT | H | 240 | 38.964 | 27.739 | 27.216 | 1.00 | 34.50 |
| ATOM | 2023 | OW0 | WAT | H | 241 | 40.370 | 30.711 | 24.793 | 1.00 | 33.70 |
| ATOM | 2024 | OW0 | WAT | H | 242 | 70.975 | 30.672 | −10.639 | 1.00 | 52.48 |
| ATOM | 2025 | OW0 | WAT | H | 243 | 55.036 | 7.684 | 25.017 | 1.00 | 40.93 |
| ATOM | 2026 | OW0 | WAT | H | 244 | 51.944 | 15.717 | 9.780 | 1.00 | 35.75 |
| ATOM | 2027 | OW0 | WAT | H | 245 | 80.897 | 35.177 | 6.275 | 1.00 | 46.35 |
| ATOM | 2028 | OW0 | WAT | H | 246 | 50.117 | 29.121 | 38.692 | 1.00 | 34.56 |
| ATOM | 2029 | OW0 | WAT | H | 247 | 43.401 | 27.565 | 41.798 | 1.00 | 54.66 |
| ATOM | 2030 | OW0 | WAT | H | 248 | 61.356 | 22.973 | 40.900 | 1.00 | 37.19 |
| ATOM | 2031 | OW0 | WAT | H | 249 | 75.861 | 9.643 | 36.444 | 1.00 | 48.34 |
| ATOM | 2032 | OW0 | WAT | H | 250 | 70.251 | 39.173 | −8.777 | 1.00 | 41.98 |
| ATOM | 2033 | OW0 | WAT | H | 251 | 76.256 | 43.950 | 4.046 | 1.00 | 39.19 |
| ATOM | 2034 | OW0 | WAT | H | 252 | 79.275 | 17.974 | 33.154 | 1.00 | 44.08 |
| ATOM | 2035 | OW0 | WAT | H | 253 | 55.134 | 22.055 | −4.822 | 1.00 | 50.14 |
| ATOM | 2036 | OW0 | WAT | H | 254 | 74.954 | 24.889 | −5.491 | 1.00 | 35.99 |
| ATOM | 2037 | OW0 | WAT | H | 255 | 81.321 | 13.477 | 3.365 | 1.00 | 64.26 |
| ATOM | 2038 | OW0 | WAT | H | 256 | 40.734 | 28.730 | 23.104 | 1.00 | 45.78 |
| ATOM | 2039 | OW0 | WAT | H | 257 | 63.547 | 15.941 | −2.825 | 1.00 | 32.72 |
| ATOM | 2040 | OW0 | WAT | H | 258 | 62.079 | 34.517 | 15.084 | 1.00 | 58.02 |
| ATOM | 2041 | OW0 | WAT | H | 259 | 65.249 | 17.692 | −9.923 | 1.00 | 33.97 |
| ATOM | 2042 | OW0 | WAT | H | 260 | 84.611 | 20.635 | 26.103 | 1.00 | 36.71 |
| ATOM | 2043 | OW0 | WAT | H | 261 | 54.603 | 33.043 | −3.243 | 1.00 | 61.42 |
| ATOM | 2044 | OW0 | WAT | H | 262 | 78.330 | 21.964 | 3.390 | 1.00 | 36.54 |
| ATOM | 2045 | OW0 | WAT | H | 263 | 60.505 | 30.649 | 16.856 | 1.00 | 61.43 |
| ATOM | 2046 | OW0 | WAT | H | 264 | 60.673 | 28.301 | 41.001 | 1.00 | 61.42 |
| ATOM | 2047 | OW0 | WAT | H | 265 | 75.570 | 42.160 | 26.603 | 1.00 | 48.11 |
| ATOM | 2048 | OW0 | WAT | H | 266 | 66.492 | 40.897 | −8.600 | 1.00 | 49.26 |
| ATOM | 2049 | OW0 | WAT | H | 267 | 78.047 | 10.851 | 26.352 | 1.00 | 37.66 |
| ATOM | 2050 | OW0 | WAT | H | 268 | 45.278 | 23.196 | 23.784 | 1.00 | 46.39 |
| ATOM | 2051 | OW0 | WAT | H | 269 | 79.914 | 16.055 | 24.356 | 1.00 | 60.41 |
| ATOM | 2052 | OW0 | WAT | H | 270 | 83.059 | 27.578 | 9.958 | 1.00 | 41.48 |
| ATOM | 2053 | OW0 | WAT | H | 271 | 53.990 | 28.727 | 44.389 | 1.00 | 53.80 |
| ATOM | 2054 | OW0 | WAT | H | 272 | 84.167 | 21.797 | 23.410 | 1.00 | 29.89 |

-continued

Data Lists

| | | | | | | | | | |
|---|---|---|---|---|---|---|---|---|---|
| ATOM | 2055 | OW0 | WAT | H | 273 | 48.547 | 18.514 | 24.335 | 1.00 | 35.54 |
| ATOM | 2056 | OW0 | WAT | H | 274 | 83.374 | 23.895 | 18.013 | 1.00 | 38.70 |
| ATOM | 2057 | OW0 | WAT | H | 275 | 44.928 | 16.891 | 21.587 | 1.00 | 47.27 |
| ATOM | 2058 | OW0 | WAT | H | 276 | 79.981 | 10.119 | 37.103 | 1.00 | 46.85 |
| ATOM | 2059 | OW0 | WAT | H | 277 | 51.478 | 30.160 | 35.040 | 1.00 | 37.36 |
| ATOM | 2060 | OW0 | WAT | H | 278 | 79.945 | 11.751 | 28.340 | 1.00 | 45.00 |
| ATOM | 2061 | OW0 | WAT | H | 279 | 72.128 | 38.830 | 13.389 | 1.00 | 68.19 |
| ATOM | 2062 | OW0 | WAT | H | 280 | 56.951 | 24.568 | 40.730 | 1.00 | 69.60 |
| ATOM | 2063 | OW0 | WAT | H | 281 | 46.873 | 31.066 | 39.547 | 1.00 | 44.24 |
| ATOM | 2064 | OW0 | WAT | H | 282 | 78.996 | 17.114 | 19.359 | 1.00 | 35.71 |
| ATOM | 2065 | OW0 | WAT | H | 283 | 83.567 | 25.358 | 35.318 | 1.00 | 55.15 |
| ATOM | 2066 | OW0 | WAT | H | 284 | 61.769 | 14.437 | −0.829 | 1.00 | 37.96 |
| ATOM | 2067 | OW0 | WAT | H | 285 | 65.163 | 31.436 | −7.804 | 1.00 | 33.32 |
| ATOM | 2068 | OW0 | WAT | H | 286 | 42.116 | 26.484 | 19.462 | 1.00 | 38.95 |
| ATOM | 2069 | OW0 | WAT | H | 287 | 42.907 | 25.516 | 22.370 | 1.00 | 61.34 |
| ATOM | 2070 | OW0 | WAT | H | 288 | 82.439 | 35.148 | 8.022 | 1.00 | 45.96 |
| ATOM | 2071 | OW0 | WAT | H | 289 | 55.363 | 24.466 | −1.282 | 1.00 | 21.32 |
| ATOM | 2072 | OW0 | WAT | H | 290 | 63.050 | 9.755 | 27.052 | 1.00 | 46.02 |
| ATOM | 2074 | OW0 | WAT | H | 292 | 62.097 | 39.809 | −0.108 | 1.00 | 37.27 |
| ATOM | 2075 | OW0 | WAT | H | 293 | 39.885 | 32.648 | 26.137 | 1.00 | 32.19 |

TABLE 2

Binding sites of the ADC binding cavity (the atomic coordinates of the binding sites are provided in Table 1)

| Binding site no. | Amino acid residue | Atom(s) involved | Atom no. in Table 1 | Binding interaction |
|---|---|---|---|---|
| 1 | Tyr22A | $C_{D2}$ | 180 | HI |
| | | $C_{E2}$ | 182 | |
| 2 | Pvl25A | $C_A$ | 201 | CB |
| 3 | Pvl25A | $C_B$ | 202 | HI |
| 4 | Thr57A | $O_{G1}$ | 450 | HB |
| 5 | Tyr58A | $C_G$ | 457 | HI |
| | | $C_{E1}$ | 460 | |
| | | $C_{E2}$ | 461 | |
| | | $C_{D1}$ | 458 | |
| | | $C_{D2}$ | 459 | |
| | | $C_Z$ | 462 | |
| 6 | Ile60A | $C_{G1}$ | 474 | HI |
| | | $C_{G2}$ | 475 | |
| | | $C_{D1}$ | 476 | |
| 7 | Asn72A | O | 560 | HB |
| 8 | Ala75A | N | 574 | HB |
| 9 | Lys9D | $N_Z$ | 963 | HB, II or SMI |
| 10 | Trp47D | $C_G$ | 1256 | π |
| | | $C_{D1}$ | 1257 | |
| | | $C_{D2}$ | 1258 | |
| | | $C_{E2}$ | 1260 | |
| | | $C_{E3}$ | 1261 | |
| | | $C_{Z2}$ | 1262 | |
| | | $C_{Z3}$ | 1263 | |
| | | $C_{H2}$ | 1264 | |
| | | $N_{E1}$ | 1259 | |
| 11 | Arg54D | $N_{H1}$ | 1317 | II |
| | | $N_{H2}$ | 1318 | |

CB = Covalent Bond
HB = Hydrogen Bond
II = Ionic Interaction
HI = Hydrophobic Interaction
π = π Interaction
SMI = Sulphate-Mediated Interaction

TABLE 3

X-ray crystallographic data quality statistics

| | Native | MeAsp | rβAla | isoA | Sbst | Prod |
|---|---|---|---|---|---|---|
| Space group: | $P6_122$ | | | | | |
| Wavelength (Å) | 0.87 | 1.54 | 1.54 | 1.54 | 1.54 | 1.54 |
| Number of frames | 360 | 200 | 90 | 90 | 155 | 138 |
| 2θ angle setting (°) | 0 | 24.3 | 17.8 | 0 | 27.2 | 19 |
| Resolution (Å)[a] | 1.55 | 1.7 | 1.9 | 1.7 | 1.5 | 1.7 |
| Estimated mosaicity (°) | 0.24 | 0.36 | 0.35 | 0.24 | 0.31 | 0.42 |
| No. observed reflexions | 1 025 720 | 298 195 | 107 245 | 158 424 | 103 704 | 143 040 |
| No. unique reflexions | 47 479 | 33 689 | 24 116 | 33 723 | 39 320 | 32 160 |
| Multiplicity | 8.9 | 8.9 | 4.4 | 4.7 | 2.6 | 4.1 |
| Completeness (All data) (%) | 98.9 | 93.6 | 91.9 | 93.7 | 76.9 | 89.2 |
| Completeness (highest resol.) (%) | 91.0 | 88.1 | 81.1 | 69.2 | 63.9 | 57.2 |
| Low resolution limit (Å)[b] | 60 | 22 | 11.5 | 25 | 10.3 | 14.8 |
| No. reflexions missing < 10 Å | 16/247 | 48/244 | 99/246 | 21/245 | 219/246 | 17/246 |
| Average I/σ(I) | 24.9 | 20.5 | 13.1 | 23.0 | 18.7 | 15.3 |
| I/σ(I) (highest resolution shell) | 6.8 | 2.4 | 1.7 | 3.5 | 2.3 | 1.8 |

TABLE 3-continued

X-ray crystallographic data quality statistics

|  | Native | MeAsp | rβAla | isoA | Sbst | Prod |
|---|---|---|---|---|---|---|
| $R_{meas}$[c] | 0.071 | 0.064 | 0.070 | 0.048 | 0.059 | 0.090 |
| $R_{meas}$ (highest resolution shell) | 0.166 | 0.499 | 0.590 | 0.330 | 0.399 | 0.382 |

[a] Judged where $I/\sigma(I) > 2$.
[b] Judged where $I/\sigma(I)$ is largest and $R_{meas}$ lowest.
[c] Multiplicity weighted $R_{sym}$:

$$R_{meas} = \frac{\sum_h \sqrt{\frac{n_h}{n_h - 1}} \sum_i |\hat{I}_h - I_{h,i}|}{\sum_h \sum_i I_{h,i}}, \quad \hat{I}_h = \frac{1}{n_h} \sum_i^{n_0} I_h$$

TABLE 4

Model refinement convergence criteria and parameters, and quality indicators

|  | Nat | MeAsp | IsoA | Prod | Subst | rβAla |
|---|---|---|---|---|---|---|
| Crystallographic refinement | | | | | | |
| No. reflexions for refinement | 44 963 | 32 355 | 32 349 | 30 807 | 37 582 | 21 420 |
| No. test reflexions[a] | 2 395 | 1 360 | 1 348 | 1 266 | 1 620 | 1 657 |
| No. restraints[b] | 6 430 | 6 500 | 6 491 | 6 482 | 6 497 | 6 473 |
| No. parameters | 8 300 | 8 888 | 8 832 | 8 744 | 8 536 | 8 220 |
| Weight for geom. restraints (TN7) | 4 | 3 | 4 | 4 | 4 | 3 |
| Final model parameters | | | | | | |
| Residues | 228 | 228 | 228 | 228 | 228 | 228 |
| Hetero groups | 2 | 4 | 4 | 4 | 4 | 6 |
| No. water molecules | 290 | 422 | 410 | 393 | 336 | 261 |
| No. non-hydrogen atoms | 2 072 | 2 222 | 2 208 | 2 185 | 2 134 | 2 063 |
| Resolution range (Å) | 60–1.55 | 22–1.7 | 11.5–1.7 | 25–1.7 | 10.3–1.5 | 14–1.9 |
| Refinement convergence | | | | | | |
| $R_{free}$[c] | 0.217 | 0.205 | 0.196 | 0.206 | 0.194 | 0.229 |
| $R_{factor}$[d] | 0.198 | 0.176 | 0.167 | 0.172 | 0.177 | 0.182 |
| Average B-factor, | | | | | | |
| subunit A (Å$^2$) | 18.1 | 23.3 | 21.1 | 18.4 | 20.9 | 25.8 |
| subunit B (Å$^2$) | 20.7 | 25.4 | 23.3 | 20.1 | 21.9 | 29.4 |
| waters (Å) | 33.2 | 46.0 | 42.9 | 37.4 | 36.9 | 41.0 |
| Wilson distribution $B_{factor}$ (Å$^2$) | 17.8 | 22.6 | 21.4 | 19.7 | 18.8 | 23.1 |
| Model quality | | | | | | |
| Ramachandran plot: % residues | | | | | | |
| In most favoured region | 91.2 | 90.7 | 90.6 | 91.2 | 90.6 | 90.1 |
| In generously allowed region | 8.8 | 9.3 | 9.4 | 8.8 | 9.4 | 9.9 |
| In disallowed region | 0 | 0 | 0 | 0 | 0 | 0 |
| RMS[e] deviation from deal | | | | | | |
| Covalent bond lengths (Å) | 0.022 | 0.018 | 0.021 | 0.023 | 0.019 | 0.018 |
| Bond angles (°) | 1.8 | 1.6 | 1.9 | 1.6 | 1.7 | 1.5 |
| Planar groups (Å) | 0.013 | 0.015 | 0.016 | 0.011 | 0.012 | 0.012 |
| Procheck criteria | | | | | | |
| Bond length outliers (%) | 5.9 | 2.4 | 5.2 | 6.5 | 3.9 | 2.2 |
| Bond angle outliers (%) | 6.1 | 4.0 | 4.8 | 4.4 | 5.2 | 3.8 |
| Planarity outliers (%) | 2.3 | 0 | 0 | 2.9 | 0 | 0 |

[a] Test set is excluded from refinement for cross-validation (Brunger, 1992).
[b] Restraints in TNT with non-zero weight.
[c] $R_{free}$ calculated using test reflexions.
[d] $R_{factor} = \Sigma_b ||F_{obs}| - |F_{calc}||/\Sigma_b |F_{obs}|$, with test reflexions excluded.
[e] RMS—Root mean square

References

The references listed below are incorporated by reference.

Albert et al., *Nature Structural Biology*, 5, (1998), 289–293.

Allen et al., *J. of Chemical Information and Computer Sciences*, 31, (1991), 187–204.

Berman et al., *Nucleic Acids Research*, 28, (2000), 235–242.

Blundell et al., *Protein Crystallography*, Academic Press, New York, London and San Francisco, (1976).

Bohacek et al., *Medicinal Research Reviews*, 16, (1996), 3–50.

Bricogne, *Methods in Enzymology*, 276, (1993), 361–423.

Brunger et al., *Acta Crystallographica*, D54, (1992), 905–921. Collaborative Computational Project 4.

The CCP4 Suite: Programs for Protein Crystallography, *Acta Crystallographica*, D50, (1994), 760–763.

Dunbrack et al., *Folding and Design*, 2, (1997), 27–42.

Engh et al., *Acta Crystallographica*, A47, (1991) 392–400.

Gill et al., *Analytical Biochemistry*, 182, (1989), 319–326.

Goodford, *J. of Medicinal Chemistry*, 28, (1985), 849–857. Greer et al., *J. of Medicinal Chemistry*, 37, (1994), 1035–1054.

Jones et al., *Acta Crystallography*, A47, (1991), 110–119.

Jones et al. in *Current Opinion in Biotechnology*, 6, (1995), 652–656.

Leslie, *Joint CCP4 and EESF-EACMB Newsletter on Protein Crystallography*, Vol.26, Daresbury Laboratory, UK.

Murshudov et al., *Acta Crystallographica*, D53, (1997), 24–255.

Otwinwski et al., Processing of X-ray diffraction data collected in oscillation mode, in *Methods in Enzymology*, Vol. 276, ed. Carter and Sweet, Academic Press, 1997.

Perrakis et al., *Acta Crystallographica*, D55, (1999), 1765–1770.

Ramjee et al., *J. Biochem.*, 323, (1997), 661–669.

Read, *Acta Crystallographica*, A42, (1986), 140–149.

Sawyer et al., in *Crystallization of Nucleic Acids and Proteins*, ed. Ducroix and Giege, 225–289, John Wiley & Sons, New York, 1992.

Sayle et al., *Trends in Biochemical Sciences*, Vol. 20, (1995), 374.

Schagger et al., *Analytical Biochemistry*, 166, (1987), 368–379.

Tronrud, *Methods in Enzymology*, 277, (1997), 306–319.

Walters et al., *Drug Discovery Today*, Vol.3, No.4, (1998), 160–178.

Westhead et al., *Trends in Biochemical Sciences*, 23, (1998), 35–36.

Williamson et al., *J. Biol. Chem.*, 254, (1979), 8074–8082.

What is claimed is:

1. A method of identifying an agent compound which modulates asparate decarboxylase (ADC) activity comprising the steps of:
   a) providing a model of a binding cavity of ADC, said model including at least one of binding site nos. 1 and 9 defined by Table 2;
   b) providing the structure of a candidate agent compound;
   c) fitting the candidate agent compound to said binding cavity, including determining the interactions between the candidate agent compound and at least one of binding site nos. 1 and 9; and
   d) selecting the fitted candidate agent compound.

2. The method according to claim 1, comprising the further step of:
   e) contacting the candidate agent compound with ADC to determine the ability of the candidate agent compound to interact with ADC.

3. The method according to claim 1, comprising the further steps of:
   e) forming a complex of ADC and said candidate agent compound; and
   f) analysing said complex by X-ray crystallography or NMR spectroscopy to determine the ability of said candidate agent compound to interact with ADC.

4. A crystal of fully processed ADC having a hexagonal space group $P6_122$, and unit cell dimensions of a=71.1 Å, and c=215.8 Å.

5. A crystal of fully processed ADC having the three dimensional atomic coordinates of Table 1.

6. A method of fully processing ADC, comprising the step of forming a solution of ADC, the solution having a pH in the range 6.5–8.5 and an ADC concentration in the range 1–50 mg/ml.

7. A method of testing a candidate agent compound for ability to modulate ADC activity, comprising the step of contacting the candidate agent compound with fully processed ADC to determine the ability of the candidate agent compound to interact with ADC.

8. A method of identifying an agent compound which modulates ADC activity, comprising the steps of:
   a) providing a candidate agent compound;
   b) forming a complex of fully processed ADC and the candidate agent compound; and
   c) analysing said complex by X-ray crystallography or NMR spectroscopy to determine the ability of the candidate agent compound to interact with ADC.

9. A method of analysing a fully processed ADC-ligand complex comprising the step of employing (i) X-ray crystallographic diffraction data from the fully processed ADC-ligand complex and (ii) a three-dimensional structure of fully processed ADC, to generate a difference Fourier electron density map of the complex, the three-dimensional structure being defined by atomic coordinate data according to Table 1.

10. A computer system, intended to generate structures and/or perform rational drug design for ADC or ADC ligand complexes, the system containing either (a) atomic coordinate data according to Table 1, said data defining the three-dimensional structure of fully-processed ADC, or (b) structure factor data for fully-processed ADC, said structure factor data being derivable from the atomic coordinate data of Table 1.

11. Computer readable media with either (a) atomic coordinate data according to Table 1 recorded thereon, said data defining the three-dimensional structure of fully-processed ADC, or (b) structure factor data for fully-processed ADC recorded thereon, the structure factor data being derivable from the atomic coordinate data of Table 1.

* * * * *